United States Patent
Sperandio et al.

(10) Patent No.: US 11,945,785 B2
(45) Date of Patent: Apr. 2, 2024

(54) PYRAZINE COMPOUNDS AS INHIBITORS OF FLT3

(71) Applicant: Biomea Fusion, Inc., Redwood City, CA (US)

(72) Inventors: David Sperandio, San Carlos, CA (US); Xiaodong Wang, Millbrae, CA (US); Thorsten A. Kirschberg, San Carlos, CA (US); James T. Palmer, Warrandyte (AU); Thomas Butler, Redwood City, CA (US); Solomon B. Ungashe, Sunnyvale, CA (US); Neil Howard Squires, San Francisco, CA (US); Nan-Horng Lin, Vernon Hills, IL (US); Ravindra B. Upasani, San Jose, CA (US); Amna Trinity-Turjuman Adam, Mountain View, CA (US); Yongli Su, Foster City, CA (US); Thu Phan, Fremont, CA (US)

(73) Assignee: Biomea Fusion, Inc., Redwood City, CA (US)

( * ) Notice: Subject to any disclaimer, the term of this patent is extended or adjusted under 35 U.S.C. 154(b) by 0 days.

(21) Appl. No.: 18/148,311

(22) Filed: Dec. 29, 2022

(65) Prior Publication Data
US 2023/0339867 A1 Oct. 26, 2023

Related U.S. Application Data

(63) Continuation of application No. PCT/US2022/040953, filed on Aug. 19, 2022.

(60) Provisional application No. 63/295,494, filed on Dec. 30, 2021, provisional application No. 63/316,939, filed on Mar. 4, 2022, provisional application No. 63/364,860, filed on May 17, 2022, provisional application No. 63/386,772, filed on Dec. 9, 2022.

(51) Int. Cl.
*C07D 409/12* (2006.01)
*C07D 241/26* (2006.01)

(52) U.S. Cl.
CPC ........ *C07D 241/26* (2013.01); *C07B 2200/05* (2013.01)

(58) Field of Classification Search
CPC ............... C07D 241/20; C07D 405/12; A61K 31/4965; A61K 31/497
USPC ............... 544/360, 407; 514/253.11, 255.05, 514/255.06
See application file for complete search history.

(56) References Cited

U.S. PATENT DOCUMENTS

| | | | |
|---|---|---|---|
| 6,506,798 B1 | 1/2003 | Barrett et al. | |
| 7,083,668 B2 | 8/2006 | Taguchi et al. | |
| 7,960,546 B2 | 6/2011 | Shroeder et al. | |
| 8,067,593 B2 | 11/2011 | Shroeder et al. | |
| 8,846,928 B2 | 9/2014 | Jia et al. | |
| 8,895,585 B2 | 11/2014 | Fujiwara et al. | |
| 8,969,336 B2 | 3/2015 | Shimada et al. | |
| 9,051,310 B2 | 6/2015 | Fujiwara et al. | |
| 9,085,540 B2 | 7/2015 | Takahiro et al. | |
| 9,145,415 B2 | 9/2015 | Takasaki et al. | |
| 9,340,492 B2 | 5/2016 | Xie et al. | |
| 9,487,491 B2 | 11/2016 | Shimada et al. | |
| 9,650,516 B2 | 5/2017 | Barbieru et al. | |
| 9,695,150 B2 | 7/2017 | Xi et al. | |
| 9,701,644 B2 | 7/2017 | Mizumoto et al. | |
| 9,828,373 B2 | 11/2017 | Liu et al. | |
| 9,920,033 B2 | 3/2018 | Xi et al. | |

(Continued)

FOREIGN PATENT DOCUMENTS

| | | |
|---|---|---|
| AR | 110 273 A1 | 3/2019 |
| CN | 106 083 821 A | 11/2016 |

(Continued)

OTHER PUBLICATIONS

Baska et al., "Discovery and development of extreme selective inhibitors of the ITD and D835Y mutant FLT3 kinases", European Journal of Medicinal Chemistry, vol. 184, Dec. 15, 2019, 111710. DOI: 10.1016/j.ejmech.2019.111710.

(Continued)

*Primary Examiner* — Jeffrey H Murray
(74) *Attorney, Agent, or Firm* — SQUIRE PATTON BOGGS (US)

(57) ABSTRACT

Disclosed herein are heterocyclic compounds, for example, according to the following formula and analogs thereof:

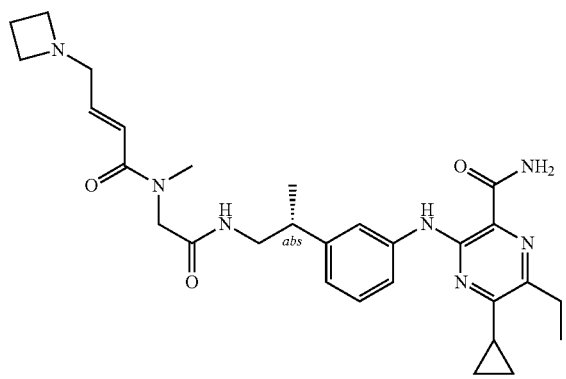

that inhibit the activity of FLT3. Also described are specific covalent inhibitors of FLT3. Also disclosed are pharmaceutical compositions that include the compounds. Methods of using the FLT3 inhibitors are disclosed, alone or in combination with other therapeutic agents, for the treatment of proliferative diseases or conditions, including hematological malignancies and other diseases or conditions dependent on FLT3 activity.

28 Claims, 5 Drawing Sheets

(56) References Cited

U.S. PATENT DOCUMENTS

| | | | |
|---|---|---|---|
| 9,987,278 | B2 | 6/2018 | Naoe et al. |
| 10,065,934 | B2 | 9/2018 | Cheng et al. |
| 10,137,130 | B2 | 11/2018 | Amatangelo et al. |
| 10,179,787 | B2 | 1/2019 | Beck et al. |
| 10,188,737 | B2 | 1/2019 | Tasaki et al. |
| 10,196,365 | B2 | 2/2019 | Hong et al. |
| 10,246,462 | B2 | 4/2019 | Beck et al. |
| 10,308,658 | B2 | 6/2019 | Liu et al. |
| 10,322,128 | B2 | 6/2019 | Vilenchik et al. |
| 10,435,377 | B2 | 10/2019 | Nagato et al. |
| 10,544,223 | B2 | 1/2020 | Van Berkel et al. |
| 10,562,862 | B2 | 2/2020 | Nagato et al. |
| 10,709,687 | B2 | 7/2020 | Valmier |
| 10,744,134 | B2 | 8/2020 | Eguchi et al. |
| 10,786,500 | B2 | 9/2020 | Miyazaki et al. |
| 10,876,176 | B2 | 12/2020 | Tabibiazar et al. |
| 10,927,418 | B2 | 2/2021 | Gordon et al. |
| 10,973,822 | B2 | 4/2021 | Gandhi et al. |
| 11,065,243 | B2 | 7/2021 | Rickard et al. |
| 11,104,676 | B2 | 8/2021 | Hinklin et al. |
| 11,191,771 | B2 | 12/2021 | Arthur et al. |
| 11,247,990 | B1 | 2/2022 | Allen et al. |
| 11,285,154 | B2 | 3/2022 | Habib |
| 11,286,264 | B2 | 3/2022 | Cui et al. |
| 11,291,667 | B2 | 4/2022 | Cui et al. |
| 11,333,659 | B2 | 5/2022 | Laing et al. |
| 11,421,040 | B2 | 8/2022 | Dettling et al. |
| 11,512,074 | B2 | 11/2022 | Wang et al. |
| 11,672,800 | B2 | 6/2023 | Campbell et al. |
| 11,672,801 | B2 | 6/2023 | Habib |
| 11,691,974 | B2 | 7/2023 | Fu et al. |
| 11,702,469 | B2 | 7/2023 | Dorrance et al. |
| 11,712,468 | B2 | 8/2023 | De Haard et al. |
| 11,723,891 | B2 | 8/2023 | Snippert et al. |
| 2006/0009357 | A1 | 1/2006 | Fujiwara et al. |
| 2008/0188595 | A1 | 8/2008 | Deardurff |
| 2016/0339020 | A1 | 11/2016 | Eguchi et al. |
| 2017/0196859 | A1 | 7/2017 | Konagai et al. |
| 2018/0071302 | A1 | 3/2018 | Abella et al. |
| 2018/0344702 | A1 | 12/2018 | Rice et al. |
| 2019/0010158 | A1 | 1/2019 | Ishida |
| 2019/0091205 | A1 | 3/2019 | Stagljar et al. |
| 2019/0091229 | A1 | 3/2019 | Lichenstein et al. |
| 2019/0117649 | A1 | 4/2019 | Bahceci et al. |
| 2019/0262328 | A1 | 8/2019 | Srinivasan et al. |
| 2019/0282569 | A1 | 9/2019 | Sakurai et al. |
| 2019/0298691 | A1 | 10/2019 | Valmier |
| 2020/0147117 | A1 | 5/2020 | Ben Yakar et al. |
| 2020/0171022 | A1 | 6/2020 | Valmier et al. |
| 2020/0197385 | A1 | 6/2020 | Yasuhiro et al. |
| 2020/0208114 | A1 | 7/2020 | Baryawno et al. |
| 2020/0281925 | A1 | 9/2020 | Ferretti et al. |
| 2020/0332369 | A1 | 10/2020 | Sowadski |
| 2020/0390889 | A1 | 12/2020 | Horner et al. |
| 2021/0008047 | A1 | 1/2021 | Marine et al. |
| 2021/0008070 | A1 | 1/2021 | Marine et al. |
| 2021/0060039 | A1 | 3/2021 | Yang et al. |
| 2021/0128545 | A1 | 5/2021 | Buchholz et al. |
| 2021/0220355 | A1 | 7/2021 | Ando et al. |
| 2021/0244730 | A1 | 8/2021 | Oura |
| 2021/0244731 | A1 | 8/2021 | Oura |
| 2021/0244732 | A1 | 8/2021 | Oura |
| 2021/0244733 | A1 | 8/2021 | Oura |
| 2021/0255170 | A1 | 8/2021 | Engelhardt et al. |
| 2021/0260040 | A1 | 8/2021 | Penebre et al. |
| 2021/0301024 | A1 | 9/2021 | Yu et al. |
| 2021/0386763 | A1 | 12/2021 | Guerreiro et al. |
| 2021/0386768 | A1 | 12/2021 | Murao et al. |
| 2021/0401859 | A1 | 12/2021 | Hodgson et al. |
| 2022/0000880 | A1 | 1/2022 | Tong et al. |
| 2022/0017968 | A1 | 1/2022 | Hassane et al. |
| 2022/0040324 | A1 | 2/2022 | Ishii et al. |
| 2022/0047720 | A1 | 2/2022 | Kurisawa et al. |
| 2022/0127206 | A1 | 4/2022 | Miyake et al. |
| 2022/0133715 | A1 | 5/2022 | Tyner et al. |
| 2022/0143049 | A1 | 5/2022 | Bono et al. |
| 2022/0193074 | A1 | 6/2022 | Robichaux et al. |
| 2022/0218682 | A1 | 7/2022 | Amyn et al. |
| 2023/0026907 | A1 | 1/2023 | Zhang et al. |
| 2023/0040637 | A1 | 2/2023 | Jarrett et al. |

FOREIGN PATENT DOCUMENTS

| | | |
|---|---|---|
| CN | 106 267 234 B | 1/2017 |
| CN | 106 589 055 B | 4/2017 |
| CN | 105 439 879 B | 8/2018 |
| CN | 108 392 634 B | 8/2018 |
| CN | 109 251 182 B | 1/2019 |
| CN | 111 558 044 B | 8/2020 |
| CN | 111 760 024 B | 10/2020 |
| CN | 113 861 179 | 12/2021 |
| CN | 111 358 952 B | 3/2022 |
| CN | 111269149 B | 4/2022 |
| CN | 111 808 821 B | 6/2022 |
| CN | 115 429 805 A | 12/2022 |
| CN | 115 710 281 | 2/2023 |
| CN | 112 704 679 B | 6/2023 |
| EP | 2 428 508 A1 | 3/2012 |
| EP | 2 840 080 A1 | 2/2015 |
| EP | 2 868 710 A1 | 5/2015 |
| EP | 3 120 851 A1 | 1/2017 |
| JP | 2002309116 A | 10/2002 |
| JP | 2003221534 A | 8/2003 |
| JP | 2003292859 A | 10/2003 |
| JP | 2004/059687 A | 2/2004 |
| JP | 2004099802 A | 4/2004 |
| JP | 2008013499 A | 1/2008 |
| JP | 2009139810 A | 6/2009 |
| JP | 4406515 B2 | 1/2010 |
| WO | WO 2001/005393 A2 | 1/2001 |
| WO | WO 2002/083795 A2 | 10/2002 |
| WO | WO 2004/016699 A1 | 2/2004 |
| WO | WO 2007/088794 A1 | 8/2007 |
| WO | WO 2010/133748 A1 | 11/2010 |
| WO | WO 2011/034828 A1 | 3/2011 |
| WO | WO 2012/053606 A1 | 4/2012 |
| WO | WO 2015/062929 A1 | 5/2015 |
| WO | WO 2016/015604 A1 | 2/2016 |
| WO | WO 2016/121777 A1 | 8/2016 |
| WO | WO 2016/175252 A1 | 11/2016 |
| WO | WO 2017/013160 A1 | 1/2017 |
| WO | WO 2017/090699 A1 | 6/2017 |
| WO | WO 2017/146795 A1 | 8/2017 |
| WO | WO 2017/218365 A1 | 12/2017 |
| WO | WO 2018/103663 A1 | 6/2018 |
| WO | WO 2018/121228 A1 | 7/2018 |
| WO | WO 2018/167519 A1 | 9/2018 |
| WO | WO 2019/245269 A1 | 12/2019 |
| WO | WO 2020/128892 A1 | 6/2020 |
| WO | WO 2020/128894 A1 | 6/2020 |
| WO | WO 2020/204142 A1 | 10/2020 |
| WO | WO 2020/214824 A1 | 10/2020 |
| WO | WO 2020/257665 A1 | 12/2020 |
| WO | WO 2020/257671 A1 | 12/2020 |
| WO | WO 2021/011871 A1 | 1/2021 |
| WO | WO 2021/030642 A1 | 2/2021 |
| WO | WO 2021/032883 A1 | 2/2021 |
| WO | WO 2021/076985 A1 | 4/2021 |
| WO | WO 2021/079273 A1 | 4/2021 |
| WO | WO 2021/087138 A1 | 5/2021 |
| WO | WO 2021/089791 A1 | 5/2021 |
| WO | WO 2021/092543 A1 | 5/2021 |
| WO | WO 2021/094827 A1 | 5/2021 |
| WO | WO 2021/159993 A1 | 8/2021 |
| WO | WO 2021/180008 A1 | 9/2021 |
| WO | WO 2022/009235 A1 | 1/2022 |
| WO | WO 2022/132936 A1 | 6/2022 |
| WO | WO 2022/158639 A1 | 7/2022 |
| WO | WO 2022/173021 A1 | 8/2022 |
| WO | WO 2023/278483 A1 | 1/2023 |
| WO | WO 2023/027966 A1 | 3/2023 |
| WO | WO 2023/043630 A1 | 3/2023 |

(56) References Cited

FOREIGN PATENT DOCUMENTS

| WO | WO 2023/049829 A2 | 3/2023 |
|----|-------------------|--------|
| WO | WO 2023/116888 A1 | 6/2023 |
| WO | WO 2023/150601 A2 | 8/2023 |

OTHER PUBLICATIONS

Bemsinger et al., "Virtual Screening Identifies Irreversible FMS-like Tyrosine Kinase 3 Inhibitors with Activity towards Resistance-conferring Mutations", *J. Med. Chem.* 2019, 62, 5, 2428-2446. DOI: 10.1021/acs.jmedchem.8b01714.

Chan, P. "Differential signaling of Flt3 activating mutations in acute myeloid leukemia: a working model", Protein Cell 2011, 2(2): 108-115 DOI 10.1007/s13238-011-1020-7.

Dhillon, S., Gilteritinib: First Global Approval. Drugs DOI: 10.1007/s40265-019-1062-3.

Dohner et al., "Acute Myeloid Leukemia", The New England Journal of Medicine, . N Engl J Med 2015;373:1136-52. DOI: 10.1056/NEJMra1406184.

Guo et al., "Enhancing intra cellular accumulation and target engagement of PROTACs with reversible covalent chemistry", *Nature Communications* (2020) 11:4268. DOI: 10.1038/s41467-020-17997-6.

Huang et al., "A Chemoproteomic Approach to Query the Degradable Kinome Using a Multi-kinase Degrader", *Cell Chemical Biology* 25, 88-99, Jan. 18, 2018. DOI: 10.1016/j.chembio1.2017.10.005.

International Search Report and Written Opinion for International Application PCT/US2022/054270, 10 pages, dated Apr. 11, 2023.

International Search Report and Written Opinion for International Application PCT/US2022/040953, 10 pages, dated Oct. 31, 2022.

James et al., "Pharmacokinetic Profle of Gilteritinib: A Novel FLT-3 Tyrosine Kinase Inhibitor", *Clinical Pharmacokinetics* (2020) 59:1273-1290. DOI: 10.1007/s40262-020-00888-w.

Janssen et al., "Drug Discovery Maps, a Machine Learning Model That Visualizes and Predicts Kinome-Inhibitor Interaction Landscapes", *Journal of Chemical Information and Modeling* (2019), 59(3), 1221-1229. DOI: 10.1021/acs.jcim.8b00640.

Kawase et al., "Effect of Fms-like tyrosine kinase 3 (FLT3) ligand (FL) on antitumor activity of gilteritinib, a FLT3 inhibitor, in mice xenografted with FL-overexpressing cells", Oncotarget, 2019, vol. 10, (No. 58), pp. 6111-6123.

Koenig et al., "The Changing Landscape of Treatment in Acute Myeloid Leukemia" 2020 ASCO Educational Book. DOI: 10.1200/EDBK_ 279129.

Kumari et al. "Amide Bond Bioisosteres: Strategies, Synthesis, and Successes", DOI: 10.1021/acs.jmedchem.0c00530.

Leishman et al., "Revisiting the hERG safety margin after 20 years of routine hERG screening", *Journal of Pharmacological and Toxicological Methods* 105 (2020) 106900. DOI: 10.1016/j.vascn.2020.106900.

Levis et al., "Phase I first-in-human study of irreversible FLT3 inhibitor of FF-10101-01 in relapsed or refractory acute myeloid leukemia", *2021 ASCO annual meeting*.

Li et al., "Discovery of AMG 925, a FLT3 and CDK4 Dual Kinase Inhibitor with Preferential Affinity for the Activated State of FLT3", *J. Med. Chem.* 2014, 57, 3430-3449. DOI: 10.1021/jm500118j.

Loh et al., "Tyrosine kinome sequencing of pediatric acute lymphoblastic leukemia: a report from the Children's Oncology Group", TARGET Project. Blood, Jan. 17, 2013, vol. 121, No. 3, 485-488.

Loriaux et al., "High-throughput sequence analysis of the tyrosine kinome in acute myeloid leukemia", Blood, May 1, 2008, vol. 111, No. 9, 4788-4796.

Matheson et al., "2-Arylamino-6-ethynylpurines are cysteine-targeting irreversible inhibitors of Nek2 kinase", *RSC Med. Chem.*, 2020, 11, 707-731. DOI: 10.1039/d0md00074d.

Miao et al., Combinatorial treatment with menin and FLT3 inhibitors induces complete remission in AML models with activating FLT3 mutations. Blood (2020) 136 (25): 2958-2963. DOI: 10.1182/blood.2020006575.

Mizuta et al., "Gilteritinib overcomes lorlatinib resistance in ALK-rearranged cancer", *Nature Communications*, (2021) 12:1261. DOI: 10.1038/s41467-021-21396-w.

Munawar et al., "Experimentally Validated Pharmacoinformatics Approach to Predict hERG Inhibition Potential of New Chemical Entities", *Front. Pharmacol.* 9:1035. DOI: 10.3389/fphar.2018.01035.

Myers et al., "AXL Inhibitors in Cancer: A Medicinal Chemistry Perspective", J. Med. Chem. 2016, 59, 3593-3608. DOI: 10.1021/acs.jmedchem.5b01273.

Orgueira et al., "FLT3 inhibitors in the treatment of acute myeloid leukemia: current status and future perspectives", *Minerva Medica* Oct. 2020; 111(5):427-42. DOI: 10.23736/S0026-4806.20.06989-X.

Perl et al., "Follow-up of patients with R/R FLT3-mutation-positive AML treated with gilteritinib in the phase 3 ADMIRAL trial", Blood 2022 | vol. 139, No. 23, pp. 3366-3375.

Perl. Availability of FLT3 inhibitors: how do we use them? Blood, 2019, vol. 134, No. 9, 741-745.

Perner et al., "Kinomics Screening Identifies Aberrant Phosphorylation of CDC25C in FLT3-ITD-positive AML", *Anticancer Research* 36: 6249-6258 (2016). DOI: 10.21873/anticanres.11219.

Reiter et al., "Tyrosine kinase inhibition increases the cell surface localization of FLT3-ITD and enhances FLT3-directed immunotherapy of acute myeloid leukemia", 0 *Leukemia* (2018) 32, 313-322.

Talele, T., "Acetylene Group, Friend or Foe in Medicinal Chemistry", *Journal of Medicinal Chemistry* 2020, 63, 11, 5625-5663. DOI: 10.1021/acs.jmedchem.9b01617.

Tian et al., "Electronic probing of ketone catalysts for asymmetric epoxidation. Search for more robust catalysts" Organic letters, 2001, 3(5), 715-718. DOI: 10.1021/oI000385q.

Gillet et al., "3.12 Chemoinformatics", University of Sheffield UK, Comprehensive Medicinal Chemistry II, vol. 3, 2007, pp. 235-264.

Wang et al. "Discovery of 1-(4-(4-Amino-3-(4-(2-morpholinoethoxy) phenyl)-1H-pyrazolo[3,4-d]pyrimidin-1-yl) phenyl)-3-(5-(tertbutyl)isoxazol-3-yl) urea (CHMFL-FLT3-213) as a Highly Potent Type II FLT3 Kinase Inhibitor Capable of Overcoming a Variety of FLT3 Kinase Mutants in FLT3-ITD Positive AML", J. Med. Chem. 2017, 60, 8407-8424. DOI: 10.1021/acs.jmedchem.7b00840.

Wang et al., "Discovery of a Potent and Selective FLT3 Inhibitor (Z)-N-(5-((5Fluoro-2-oxoindolin-3-ylidene) methyl)-4-methyl-1H-pyrrol-3-yl)-3(pyrrolidin-1-yl) propenamide with Improved Drug-like Properties and Superior Efficacy in FLT3-ITD-Positive Acute Myeloid Leukemia", J. Med. Chem. 2021, 64, 4870-4890. DOI: 10.1021/acs.jmedchem.0c02247.

Wang et al., Discovery of a potent tyrosine kinase AXL inhibitor bearing the 3-((2,3,4,5-tetrahydro-1H-benzo[d]azepin-7-yl) amino) pyrazine core. *Bioorganic & Medicinal Chemistry Letters* 29 (2019) 836-83.

Wang et al., "FLT3 Inhibitors in Acute Myeloid Leukemia: Challenges and Recent Developments in Overcoming Resistance", *J. Med. Chem.* 2021, 64, 2878-2900. DOI: 10.1021/acs.jmedchem.0c01851.

Wang et al., Discovery of 4-((7H-Pyrrolo[2,3-d] pyrimidin-4-yl) amino)-N-(4-((4-methylpiperazin-1-yl) methyl) phenyl)-1H-pyrazole-3-carboxamide (FN-1501), an FLT3- and CDK-Kinase Inhibitor with Potentially High Efficiency against Acute Myelocytic Leukemia, *Journal of Medicinal Chemistry*, 61, 1499-1518. DOI: 10.1021/acs.jmedchem.7b01261.

Warkenstein et al., "Overcoming myelosuppression due to synthetic lethal toxicity for FLT3-targeted acute myeloid leukemia therapy", Warkentin et al. eLife 2014;3:e03445. DOI: 10.7554/eLife.03445.

Wu et al., "Discovery of a highly potent FLT3 kinase inhibitor for FLT3-ITD-positive AML", *Leukemia* (2016), 30(10), 2112-2116. DOI: 10.1038/leu.2016.151.

Wu et al., "FLT3 inhibitors in acute myeloid leukemia", Wu et al. Journal of Hematology & Oncology (2018) 11:133https://doi.org/10.1186/s13045-018-0675-4.

Xospata® (gilteritinib) tablets, for oral use Initial U.S. Approval: 2018, Xospata Package Information, Adverse Reactions, Highlights of Prescribing Information.

(56) References Cited

OTHER PUBLICATIONS

Yamaura et al., "A novel irreversible FLT3 inhibitor, FF-10101, shows excellent efficacy against AML cells with FLT3 mutations", *Blood*, 2018, vol. 131, No. 4, 426-438. DOI 10.1182/blood-2017-05-786657.

Yu et al., "LT-171-861, a novel FLT3 inhibitor, shows excellent preclinical efficacy for the treatment of FLT3 mutant acute myeloid leukemia", *Theranostics* 2021; 11(1):93-106. DOI: 10.7150/thno.46593.

Zhang et al., UNC2025, a Potent and Orally Bioavailable MER/FLT3 Dual Inhibitor. *J. Med. Chem.* 2014, 57, 7031-7041. DOI: 10.1021/jm500749d.

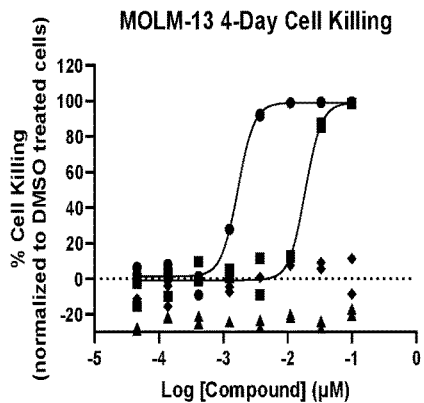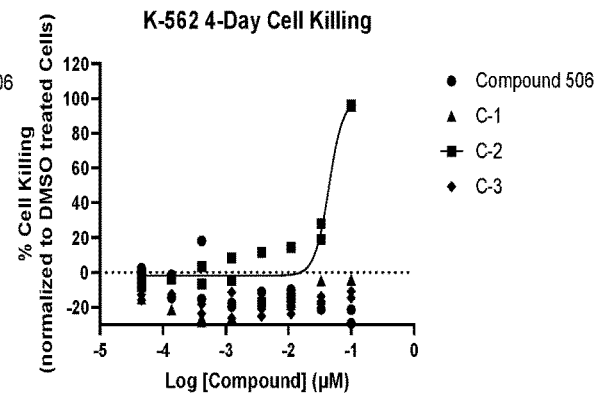
FIG. 2A    FIG. 2B
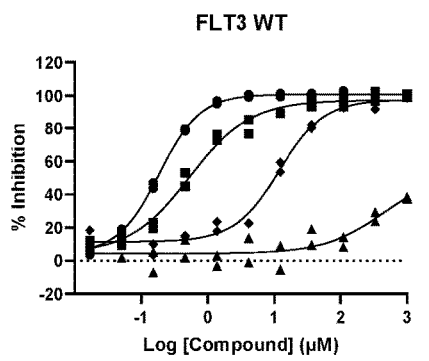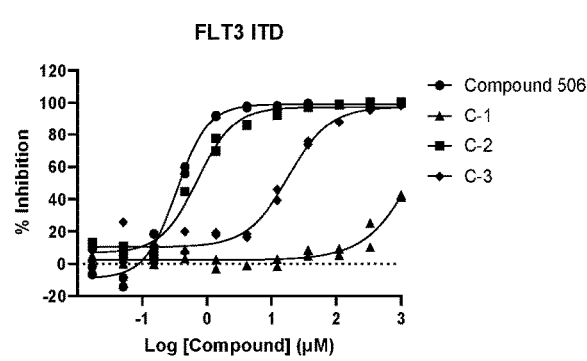
FIG. 2C    FIG. 2D

PYRAZINE COMPOUNDS AS INHIBITORS OF FLT3

CROSS-REFERENCE

The present application claims the benefit of U.S. provisional application Nos. 63/295,494, filed Dec. 30, 2021, 63/316,939, filed Mar. 4, 2022, 63/364,860, filed May 17, 2022, and 63/386,772, filed Dec. 9, 2022, and international application no. PCT/US2022/40953, filed Aug. 19, 2022, and the contents of which are hereby incorporated by reference in their entireties.

FIELD

Described herein are compounds, methods of making such compounds, pharmaceutical compositions, and medicaments containing such compounds, and methods of using such compounds and compositions to inhibit the activity of FLT3.

BACKGROUND

FMS-like tyrosine kinase 3 (FLT3) is a receptor tyrosine kinase that is expressed on normal hematopoietic stem/progenitor cells. Upon its activation by the FLT3 ligand (FL), FLT3 dimerizes and induces many signaling pathways related to hematopoietic cell survival and proliferation.

FLT3 is also often overexpressed in many acute leukemia cells, and mutation of the FLT3 gene is the most frequent generic alteration in acute myeloid leukemia. Activating mutations of the FLT3 gene account for approximately one-third of newly diagnosed AML adult patients (Papaemmanuil et al., 2016, N Engl J Med. 374: 2209) where these mutations cause constitutive FLT3 signaling cascade. Genetic alterations of FLT3 have also been identified in other myeloid malignancies, such as myelodysplastic syndromes (MDS) and acute lymphocytic leukemia (ALL). Activating FLT3 mutations are either internal tandem duplicates (ITD), or point mutations in the tyrosine kinase domain or sometimes combination of both. FLT3-ITD mutations are present in approximately 20% of AML patients, and point mutations are present in approximately 5%-10% of AML patients. Both mutations can constitutively activate FLT3 through ligand-independent autophosphorylation causing increased signaling and cellular proliferation, leading to survival of the leukemia cells (Kennedy et al., 2020, Front. Oncol. 10:612880; Kiyoi et al., 2020, Cancer Science 111: 312). FLT3-ITD mutations are especially associated with a poor prognosis and high rate of relapse, and ITD mutations can be gained or lost during disease progression and/or relapse. For that reason, testing for FLT3-ITD in patients with AML is recommended by both the European Leukemia Net and Cancer Network Guidelines.

Early studied FLT3 inhibitors, referred to as first-generation FLT3 inhibitors, included multi-kinase inhibitors sorafenib, midostaurin, lestaurtinib, sunitinib, and tandutinib. These first-generation inhibitors lacked efficacy as a monotherapy, most likely due in part to their non-specific effects. While many of these first-generation inhibitors have been abandoned as therapeutic agents for AML as monotherapy or in combination with chemotherapy, midostaurin (Rydapt) in combination with chemotherapy received FDA approval in 2017 for the adults with newly diagnosed FTL3-mutated AML.

Second-generation FLT3 inhibitors have greater specificity for FLT3 and are more potent. Second generation inhibitors include gilteritinib, crenolanib, and quizartinib. Gilteritinib and crenolanib are both Type I inhibitors, meaning that they can bind to both the inactive and active conformations of FLT3, while quizartinib is a Type II inhibitor that can only bind to the inactive conformation. In 2018, the FDA approved gilteritinib for relapsed or refractory AML with patients with FLT3 mutation. In a Phase III trial studying the effect of quizartinib in combination with induction or consolidation chemotherapy (QuANTUM-R) in patients with relapsed or refractory FLT3-ITD AML, quizartinib exhibited a survival benefit and a manageable safety profile (Cortes et al., 2019, Lancet Oncol., 20: 984). Currently, crenolanib is being studied in a Phase III clinical trial for the treatment of relapsed or refractory AML in patients with an FLT3 mutation.

An additional inhibitor of FLT3 includes the covalently binding FLT3 inhibitor FF-10101, which has demonstrated activity against quizartinib-resistant AML (Yamaura et al., 2018, Blood, 131: 426) and is currently being studied in clinical trials for relapsed or refractory hematological malignancies, including AML. FF-10101 and other N-phenylpyrimidine-2-amine compounds are described in PCT Application WO 2013/157540 and U.S. Pat. No. 9,145,415 assigned to Fujifilm Corporation. PCT Application WO 2015/056683 and U.S. Pat. No. 9,701,644, also assigned to Fujifilm Corporation, describe crystalline forms of FF-10101. Additional patents and patent applications assigned to Fujifilm Corporation that describe FF-10101 and the use of FF-10101 for certain types of cancer include PCT Applications WO 2016/027904; WO 2020/075838; WO 2020/175629; and U.S. Pat. No. 9,987,278.

Hanmi Pharmaceutical. Co., Ltd describe pyrimidine-containing compounds and the use of these compounds in FLT3-mutated cancers in PCT Applications WO 2020/022600; WO 2020/171646; WO 2020/171649; and WO 2020/262974. The pyrimidine-containing FLT3 inhibitor HM43239 is currently being studied in a Phase 1/2 clinical trial for patients with relapsed or refractory resistant AML (Daver et al. 2019, Blood, 134: 1331).

Genosco and Oscotec, Inc. describe pyridopyrimidine compounds and their use in the treatment of hematological malignancies in PCT Application WO 2013/142382 and U.S. Pat. No. 8,877,763. Crystal forms of the specific FLT3 inhibitor G-749 are described in WO 2020/040467 assigned to Oscotec, Inc. and oral pharmaceutical compositions of G-749 are described in WO 2020/159117 also assigned to Oscotec, Inc.

Biochemically, these inhibitors are reported to block auto-phosphorylation of FLT3 at TYR-589/591 and downstream signaling mediators signal transducer and activator of transcription 5 (STAT5) and extracellular-signal related kinase (ERK) (Wang et al., 2021, J. Med. Chem. 64(8): 4870-4890. Resistance to FLT3 inhibitors has been reported in the clinic through secondary mutations in FLT3 including mutations in the tyrosine kinase domain in prior ITD-only mutant tumors (Heidel et al., 2006, Blood 107(1):293-300, Smith et al., 2012, Nature 485(7397):260-263).

Despite research in this area, there is still a need to deliver effective compounds for the inhibition of FLT3. Therefore, the object of the present invention is to provide inhibitors of FLT3, pharmaceutical compositions thereof, and methods for the inhibition of FLT3. Also of key importance is to develop inhibitors that will overcome the known resistance mechanisms of co-mutations of ITD that re-awaken the autophosphorylation capabilities of FLT3.

SUMMARY

In one aspect, described herein are inhibitors of FLT3. Also described herein are specific heterocyclic inhibitors of FLT3. In some embodiments, the inhibitors of FLT3 are covalent inhibitors. In some embodiments, the inhibitors of FLT3 are non-covalent inhibitors.

In another aspect, described herein are methods for synthesizing such covalent inhibitors, methods for using such covalent inhibitors in the treatment of diseases (including diseases wherein inhibition of FLT3 provides therapeutic benefit to a patient having the disease). Further described are pharmaceutical compositions that comprise an inhibitor of FLT3 and one or more pharmaceutically acceptable carriers, excipients, or diluents. Also, described herein are compounds and methods of use thereof to inhibit FLT3. In certain embodiments, the compounds and pharmaceutical compositions described herein are used for the treatment of hematological malignancies, including but not limited to, acute myeloid leukemia.

In some embodiments, provided herein are compounds according to Formula (P6-I) having the structure:

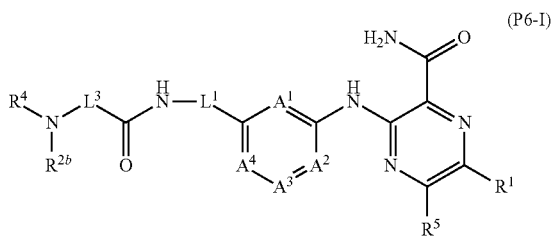

(P6-I)

or a stereoisomer thereof, or a pharmaceutically acceptable salt thereof,
wherein: each $A^1$, $A^2$, $A^3$, and $A^4$ is independently —C($R^7$)=, or —N=; provided no more than two of $A^1$, $A^2$, $A^3$, and $A^4$ is N;
each $L^1$ and $L^3$ is independently substituted or unsubstituted $C_1$-$C_4$ alkylene;
$R^1$ is H, halo, CN, substituted or unsubstituted $C_{1-6}$ alkyl, substituted or unsubstituted alkoxy, substituted or unsubstituted alkenyl, substituted or unsubstituted alkynyl, substituted or unsubstituted cycloalkyl, or substituted or unsubstituted heterocycloalkyl;
$R^{2b}$ is independently H or $C_1$-$C_4$ alkyl;
$R^4$ is i) —C(O)—C($R^{6a}$)=C($R^{6b}$)($R^{6c}$), ii) —S(O)—C($R^{6a}$)=C($R^{6b}$)($R^{6c}$), iii) —S(O)$_2$—C($R^{6a}$)=C($R^{6b}$)($R^{6c}$), or iv) substituted or unsubstituted epoxide;
$R^5$ is H, Cy, CN, halo, substituted or unsubstituted $C_{1-6}$ alkyl, substituted or unsubstituted haloalkyl, substituted or unsubstituted $C_{1-6}$ alkoxy, substituted or unsubstituted haloalkoxy, substituted or unsubstituted alkylamino;
Cy is substituted or unsubstituted cycloalkyl, or substituted or unsubstituted heterocycloalkyl; each $R^{6a}$ and $R^{6b}$ is independently H, halo, CN, or $C_{1-6}$ alkyl; or $R^{6a}$ and $R^{6b}$ are joined together to form a bond; $R^{6c}$ is H, halo, CN, or $C_{1-6}$ alkyl, wherein the $C_{1-6}$ alkyl is unsubstituted or substituted with one or more groups selected from substituted or unsubstituted amino, substituted or unsubstituted hydroxy, and substituted or unsubstituted heterocycloalkyl having 1-2 heteroatoms independently selected from nitrogen, oxygen, and sulfur; and
each $R^7$ is independently H, halo, CN, substituted or unsubstituted $C_{1-6}$ alkyl, substituted or unsubstituted alkoxy, or substituted or unsubstituted heterocycloalkyl.

In some embodiments, provided herein is a compound according to Formula (P6-IIa) or (P6-IIb):

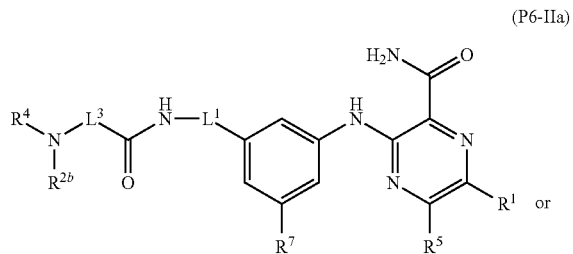

(P6-IIa)

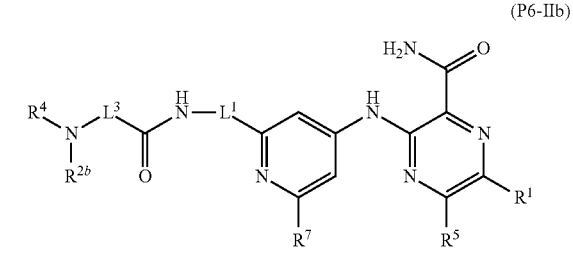

(P6-IIb)

or a stereoisomer thereof, or a pharmaceutically acceptable salt thereof.

In some embodiments, provided herein is a compound according to Formula (P6-IIIa), (P6-IIIb), (P6-IIIc) or (P6-IIId):

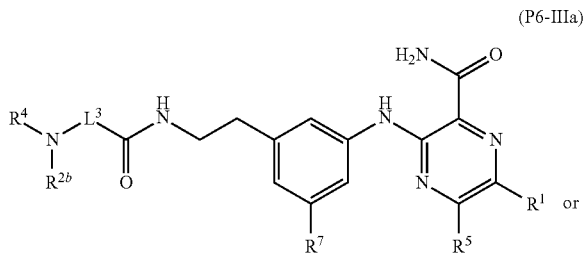

(P6-IIIa)

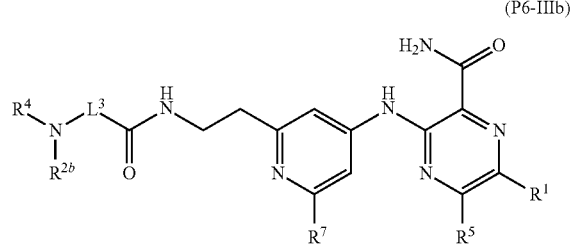

(P6-IIIb)

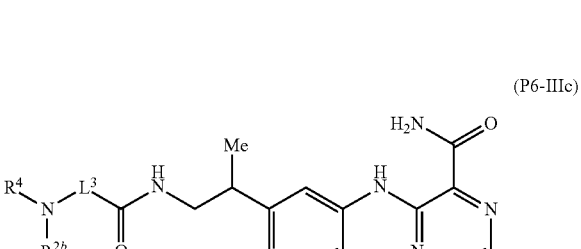

(P6-IIIc)

-continued (P6-IIId)

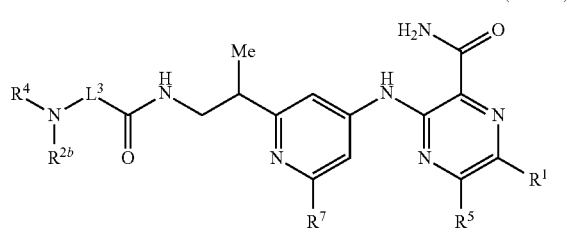

or a stereoisomer thereof, or a pharmaceutically acceptable salt thereof.

In some embodiments, with respect to the compounds of any of the formulas described herein, $R^5$ is H, Cy, CN, halo, $C_{1-6}$ alkyl, $C_{1-6}$ alkoxy, or $C_{1-6}$ alkylamino; Cy is cycloalkyl, or heterocycloalkyl; each of Cy, alkyl, alkoxy, and alkylamino is unsubstituted or substituted with one or more halo, CN, $C_{1-4}$ alkyl, hydroxy, amino, alkylamino, or dialkylamino, substituted or unsubstituted cycloalkyl, substituted or unsubstituted heterocycloalkyl, substituted or unsubstituted aryl, substituted or unsubstituted heteroaryl, or $C_{1-4}$ alkoxy.

In some embodiments, with respect to the compounds of any of the formulas described herein, $R^5$ is Me, Et, n-Pr, i-Pr, i-Bu, cyclopropyl, N,N-dimethyl, N-ethyl-N-methyl, N-isopropylamino, N-isopropyl-N-methylamino, methoxy, ethoxy, or i-propyloxy.

In some embodiments, with respect to the compounds of any of the formulas described herein, $R^4$ is —C(O)—B—C($R^{6a}$)=C($R^{6b}$)—C(O)—$R^{6c}$, —S(O)—B—C($R^{6a}$)=C($R^{6b}$)—C(O)—$R^{6c}$, —S(O)$_2$—B—C($R^{6a}$)=C($R^{6b}$)—C(O)—$R^{6c}$, —B—C($R^{6a}$)=C($R^{6b}$)—C(O)—$R^{6c}$, —B—C($R^{6a}$)=C($R^{6b}$)—S(O)—$R^{6c}$, —B—C($R^{6a}$)=C($R^{6b}$)—S(O)$_2$—$R^{6c}$, —B—C($R^{6a}$)=C($R^{6b}$)—P(O)—$R^{6a}R^{6b}$; or —B—C($R^{6a}$)=C($R^{6b}$)—P(O)—O$R^{6a}$O$R^{6b}$; B is substituted or unsubstituted $C_{1-4}$ alkylene, substituted or unsubstituted cycloalkyl, or substituted or unsubstituted heterocycloalkyl; and $R^{6c}$ is substituted or unsubstituted alkoxy, substituted or unsubstituted amino, substituted or unsubstituted heterocycloalkyl, having 1-2 heteroatoms independently selected from nitrogen, oxygen, and sulfur. In some embodiments, $R^4$ is —CH$_2$—CH=CH—C(O)—N(CH$_3$)$_2$. In some embodiments, $R^4$ is —CH$_2$—C≡CH—C(O)—N(CH$_3$)$_2$.

In certain embodiments, the compound is capable of covalently bonding FLT3. In certain embodiments, the compound comprises a functional group, e.g. at $R^4$, capable of covalently bonding FLT3. In certain embodiments, the compound comprises a linker that facilitates covalently bonding FLT3. While not intending to be bound by any theory of operation, it is believed that the right side (to the right of L1) of the structure P6-I forms a functional group capable of binding a binding pocket of FLT3. The linker of the compounds provided herein provides sufficient length and composition to provide covalent bonding of $R^4$ to a site on FLT3, for instance Cys12. In certain embodiments, the linker comprises L'. In certain embodiments, the linker comprises $L^3$. In certain embodiments, the linker comprises $L^1$ and $L^3$. In certain embodiments, the linker is -$L^1$-N(H)—C(O)-$L^3$-. In certain embodiments, the linker facilitates covalent binding that distinguishes the compounds over compounds known to those of skill, which have linkers of lengths or compositions, or both, insufficient to facilitate sufficient, or any, covalent binding of FLT3.

In certain embodiments, the compound is not any of Compounds 1-41, or any salt thereof.

| Cpd | Structure |
|---|---|
| 1 | ![structure 1] |
| 2 | ![structure 2] |

| Cpd | Structure |
| --- | --- |
| 3 | *N-(3-(3-((3-carbamoyl-5-ethyl-6-((tetrahydro-2H-pyran-4-yl)amino)pyrazin-2-yl)amino)phenoxy)propyl)acrylamide* |
| 4 | *N-(3-(3-((3-carbamoyl-5-ethyl-6-((tetrahydro-2H-pyran-4-yl)amino)pyrazin-2-yl)amino)phenoxy)propyl)ethenesulfonamide* |
| 5 | *N-(4-(3-((3-carbamoyl-5-ethyl-6-((tetrahydro-2H-pyran-4-yl)amino)pyrazin-2-yl)amino)phenoxy)butyl)propiolamide* |
| 6 | *N-(4-(3-((3-carbamoyl-5-ethyl-6-((tetrahydro-2H-pyran-4-yl)amino)pyrazin-2-yl)amino)phenoxy)butyl)but-2-ynamide* |
| 7 | *N-(3-(3-((3-carbamoyl-5-ethyl-6-((tetrahydro-2H-pyran-4-yl)amino)pyrazin-2-yl)amino)phenoxy)propyl)propiolamide* |

-continued
| Cpd | Structure |
|---|---|
| 8 | 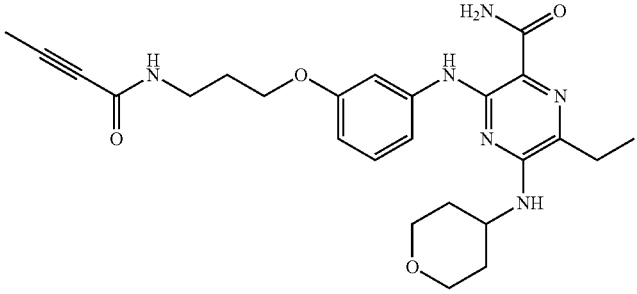 |
| 9 | 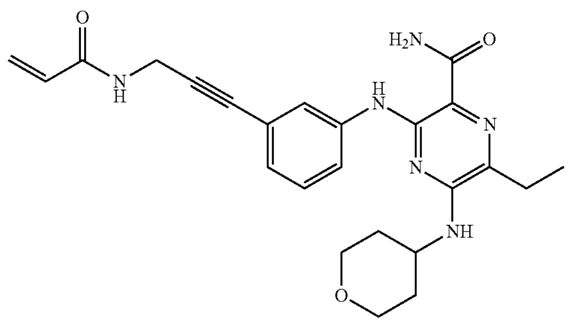 [SMILES: C=CC(=O)NCC#Cc1cccc(Nc2nc(NC3CCOCC3)c(CC)nc2C(N)=O)c1] |
| 10 | 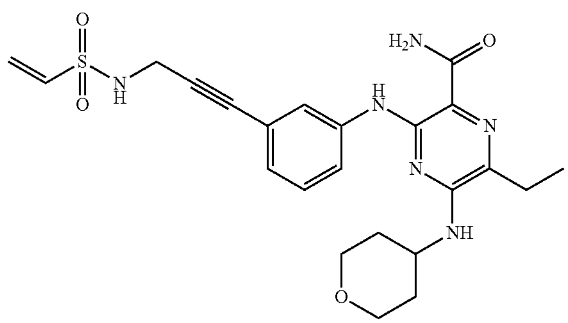 [SMILES: C=CS(=O)(=O)NCC#Cc1cccc(Nc2nc(NC3CCOCC3)c(CC)nc2C(N)=O)c1] |
| 11 | 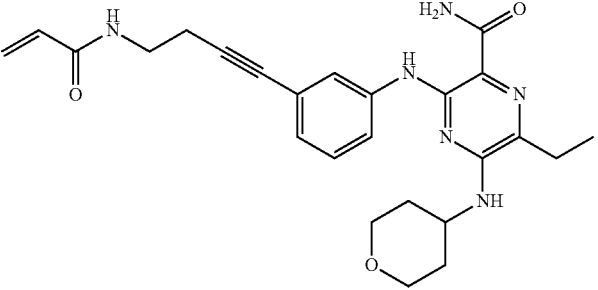 [SMILES: C=CC(=O)NCCC#Cc1cccc(Nc2nc(NC3CCOCC3)c(CC)nc2C(N)=O)c1] |
| 12 | 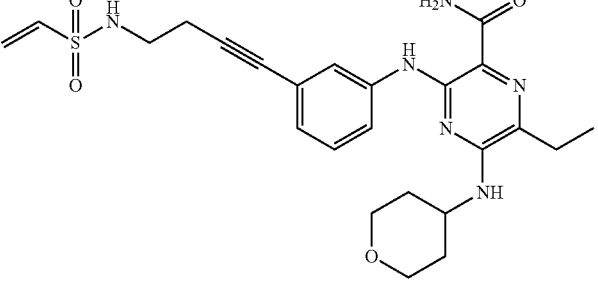 |

-continued

| Cpd | Structure |
|---|---|
| 13 | 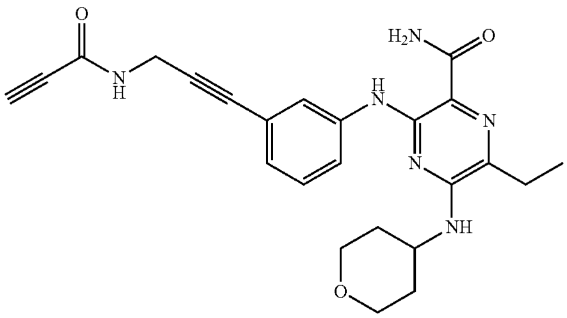 [SMILES: C#CC(=O)NCC#Cc1cccc(Nc2nc(NC3CCOCC3)c(CC)nc2C(N)=O)c1] |
| 14 | 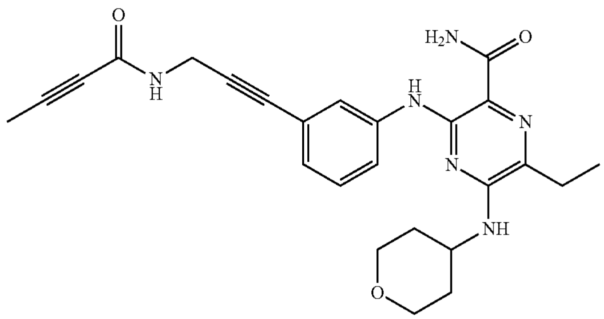 [SMILES: CC#CC(=O)NCC#Cc1cccc(Nc2nc(NC3CCOCC3)c(CC)nc2C(N)=O)c1] |
| 15 | 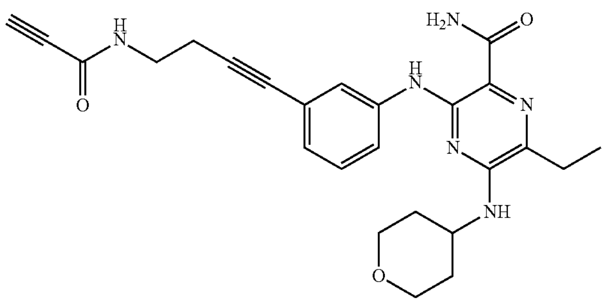 [SMILES: C#CC(=O)NCCC#Cc1cccc(Nc2nc(NC3CCOCC3)c(CC)nc2C(N)=O)c1] |
| 16 | 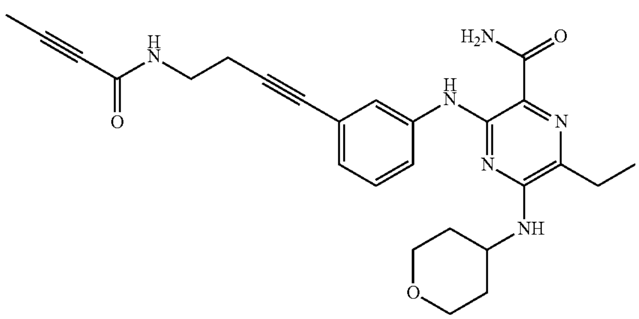 [SMILES: CC#CC(=O)NCCC#Cc1cccc(Nc2nc(NC3CCOCC3)c(CC)nc2C(N)=O)c1] |
| 17 | 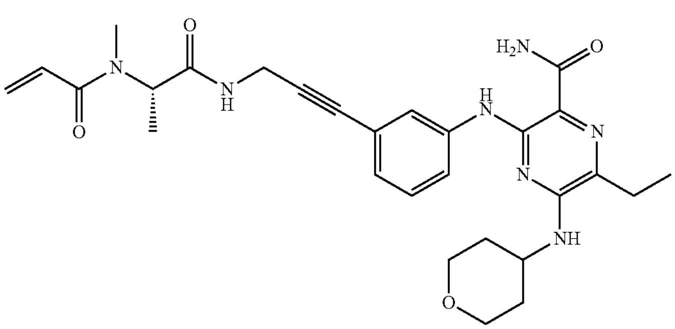 [SMILES: C=CC(=O)N(C)[C@@H](C)C(=O)NCC#Cc1cccc(Nc2nc(NC3CCOCC3)c(CC)nc2C(N)=O)c1] |

-continued
| Cpd | Structure |
|---|---|
| 18 | 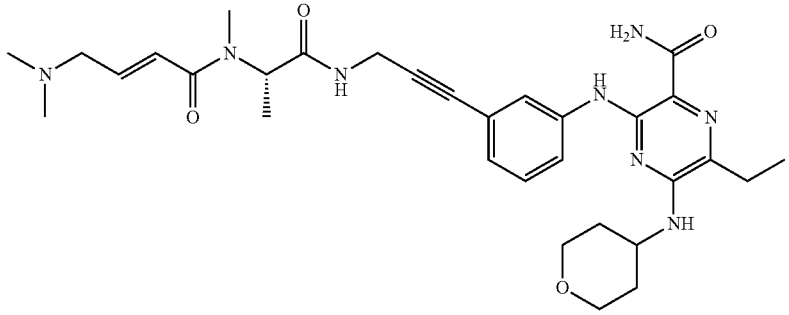 [SMILES: CCc1nc(C(N)=O)c(Nc2cccc(C#CCNC(=O)[C@H](C)N(C)C(=O)/C=C/CN(C)C)c2)nc1NC1CCOCC1] |
| 19 | 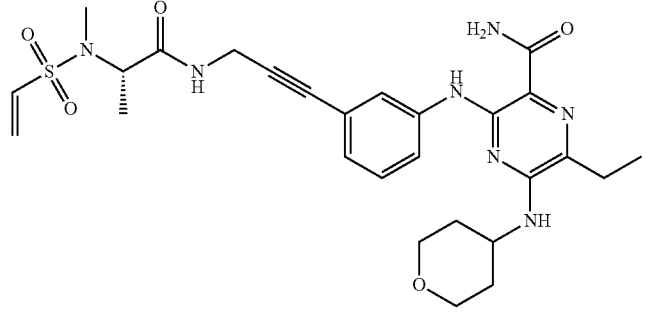 [SMILES: C=CS(=O)(=O)N(C)[C@@H](C)C(=O)NCC#Cc1cccc(Nc2nc(NC3CCOCC3)c(CC)nc2C(N)=O)c1] |
| 20 | 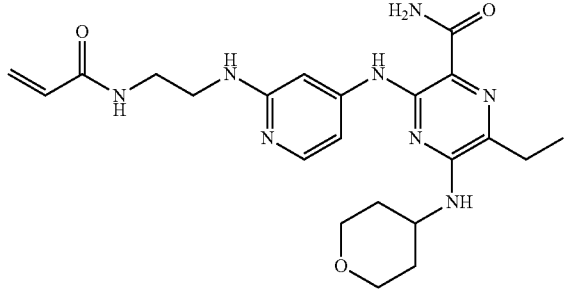 [SMILES: C=CC(=O)NCCNc1cc(Nc2nc(NC3CCOCC3)c(CC)nc2C(N)=O)ccn1] |
| 21 | 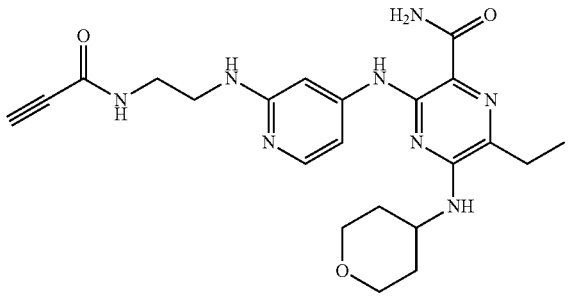 [SMILES: C#CC(=O)NCCNc1cc(Nc2nc(NC3CCOCC3)c(CC)nc2C(N)=O)ccn1] |
| 22 | 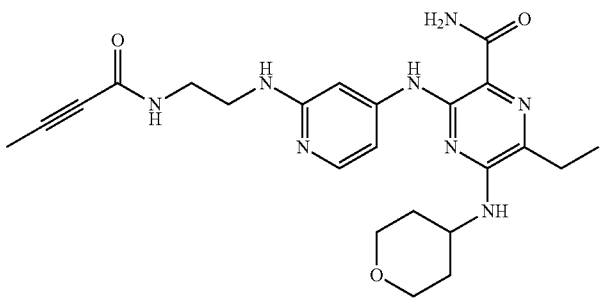 [SMILES: CC#CC(=O)NCCNc1cc(Nc2nc(NC3CCOCC3)c(CC)nc2C(N)=O)ccn1] |

-continued

| Cpd | Structure |
|---|---|
| 23 | 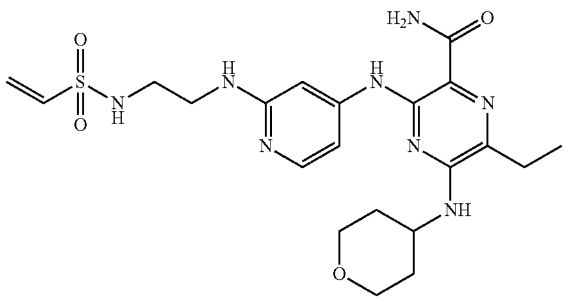 [SMILES: C=CS(=O)(=O)NCCNc1cc(Nc2nc(NC3CCOCC3)c(CC)nc2C(N)=O)ccn1] |
| 24 | 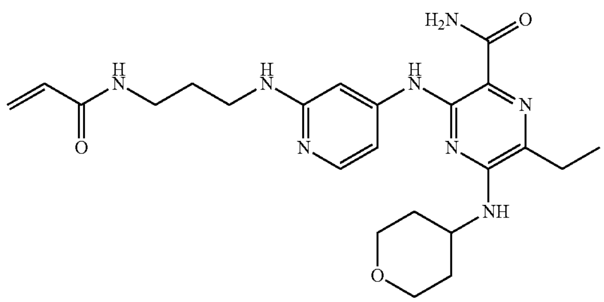 [SMILES: C=CC(=O)NCCCNc1cc(Nc2nc(NC3CCOCC3)c(CC)nc2C(N)=O)ccn1] |
| 25 | 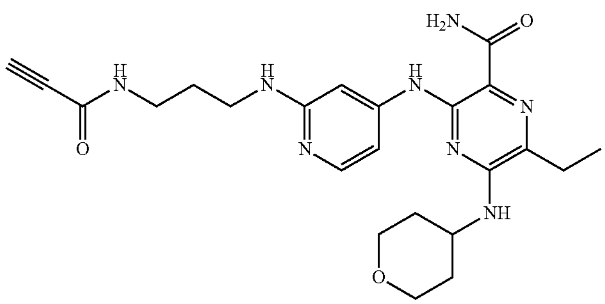 [SMILES: C#CC(=O)NCCCNc1cc(Nc2nc(NC3CCOCC3)c(CC)nc2C(N)=O)ccn1] |
| 26 | 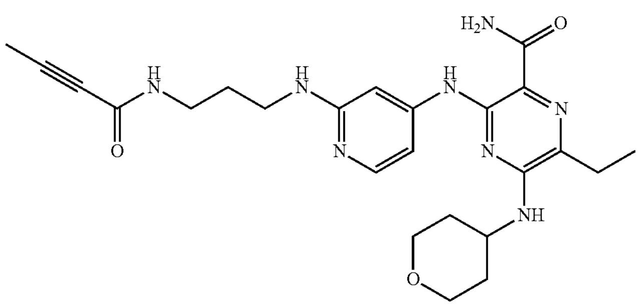 [SMILES: CC#CC(=O)NCCCNc1cc(Nc2nc(NC3CCOCC3)c(CC)nc2C(N)=O)ccn1] |
| 27 | 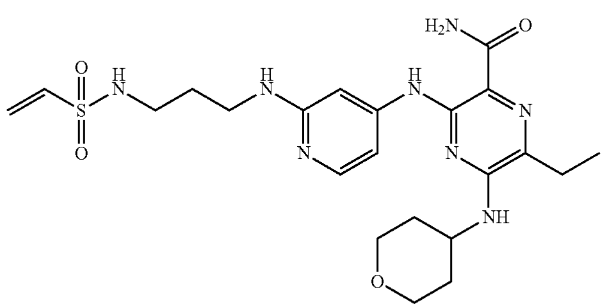 [SMILES: C=CS(=O)(=O)NCCCNc1cc(Nc2nc(NC3CCOCC3)c(CC)nc2C(N)=O)ccn1] |

-continued

| Cpd | Structure |
|---|---|
| 28 | 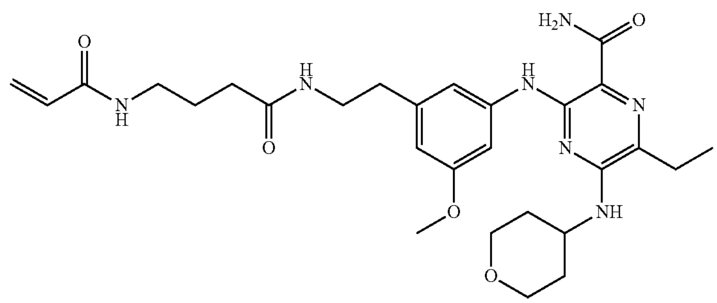 [SMILES: C=CC(=O)NCCCC(=O)NCCc1cc(Nc2nc(NC3CCOCC3)c(CC)nc2C(N)=O)cc(OC)c1] |
| 29 | 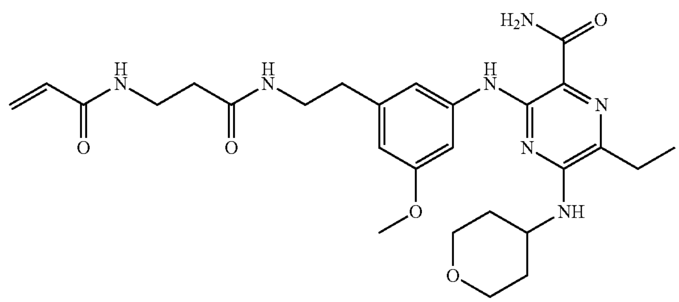 [SMILES: C=CC(=O)NCCC(=O)NCCc1cc(Nc2nc(NC3CCOCC3)c(CC)nc2C(N)=O)cc(OC)c1] |
| 30 | 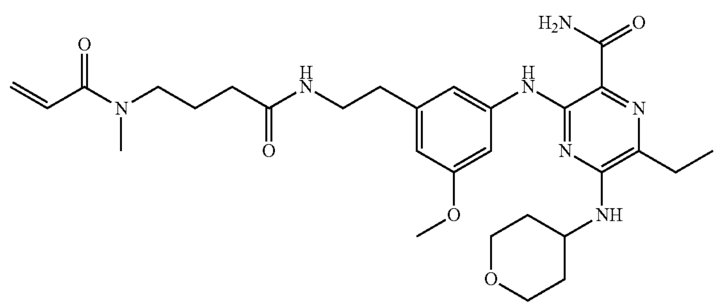 [SMILES: C=CC(=O)N(C)CCCC(=O)NCCc1cc(Nc2nc(NC3CCOCC3)c(CC)nc2C(N)=O)cc(OC)c1] |
| 31 | 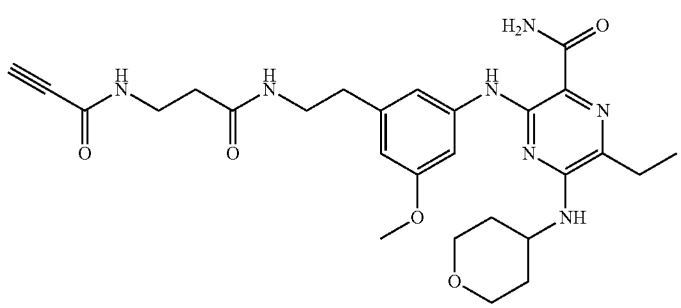 [SMILES: C#CC(=O)NCCC(=O)NCCc1cc(Nc2nc(NC3CCOCC3)c(CC)nc2C(N)=O)cc(OC)c1] |
| 32 | 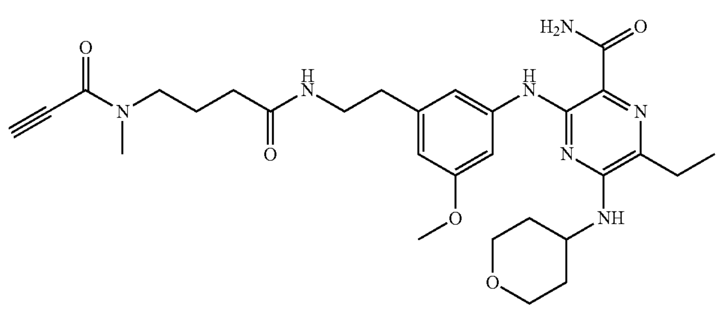 [SMILES: C#CC(=O)N(C)CCCC(=O)NCCc1cc(Nc2nc(NC3CCOCC3)c(CC)nc2C(N)=O)cc(OC)c1] |

-continued

| Cpd | Structure |
|---|---|
| 33 | 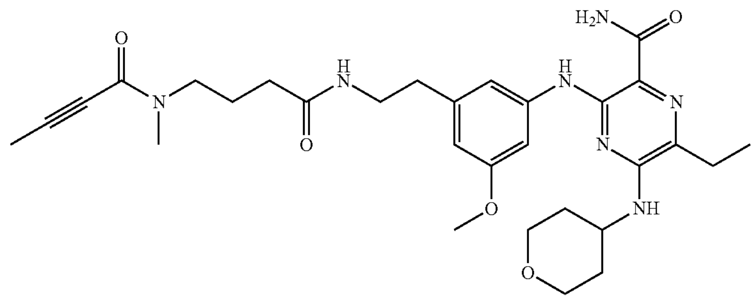 [SMILES: CC#CC(=O)N(C)CCCC(=O)NCCc1cc(Nc2nc(NC3CCOCC3)c(CC)nc2C(N)=O)cc(OC)c1] |
| 34 | 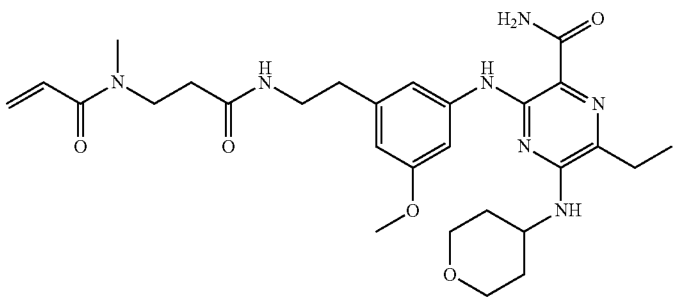 [SMILES: C=CC(=O)N(C)CCC(=O)NCCc1cc(Nc2nc(NC3CCOCC3)c(CC)nc2C(N)=O)cc(OC)c1] |
| 35 | 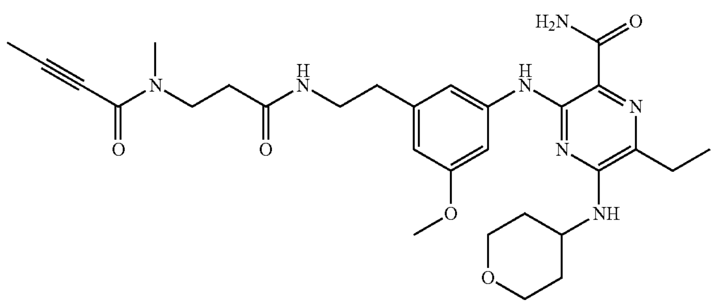 [SMILES: CC#CC(=O)N(C)CCC(=O)NCCc1cc(Nc2nc(NC3CCOCC3)c(CC)nc2C(N)=O)cc(OC)c1] |
| 36 | 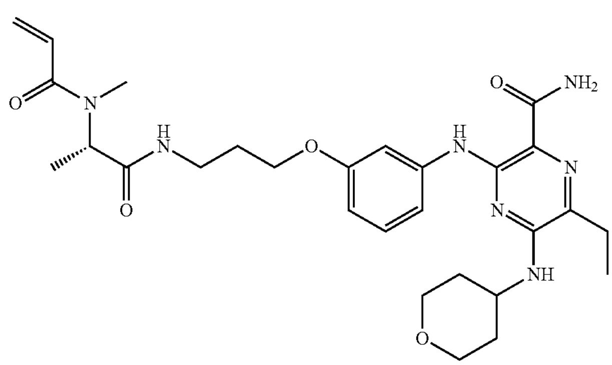 [SMILES: C=CC(=O)N(C)[C@@H](C)C(=O)NCCCOc1cccc(Nc2nc(NC3CCOCC3)c(CC)nc2C(N)=O)c1] |

| Cpd | Structure |
|---|---|
| 37 | 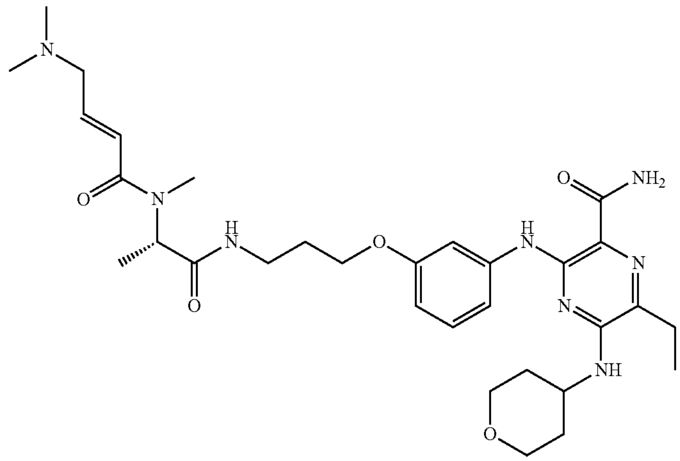 [SMILES: CCc1nc(C(N)=O)c(Nc2cccc(OCCCNC(=O)[C@H](C)N(C)C(=O)/C=C/CN(C)C)c2)nc1NC1CCOCC1] |
| 38 | 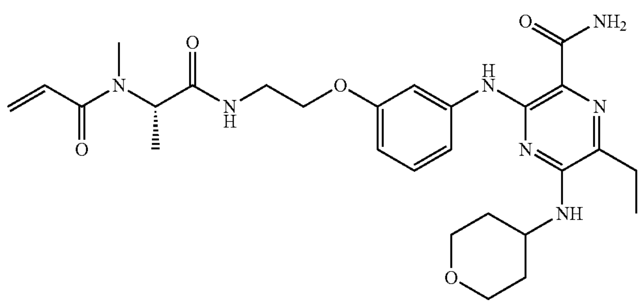 [SMILES: C=CC(=O)N(C)[C@@H](C)C(=O)NCCOc1cccc(Nc2nc(NC3CCOCC3)c(CC)nc2C(N)=O)c1] |
| 39 | 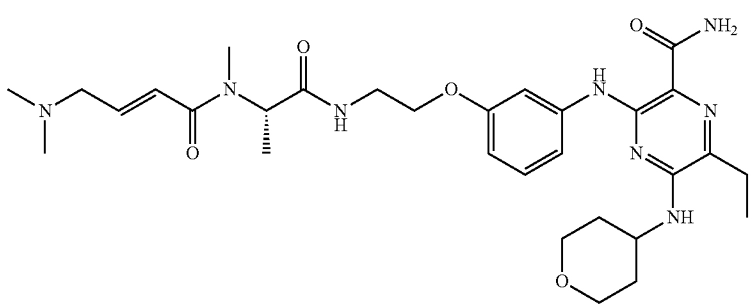 [SMILES: CCc1nc(C(N)=O)c(Nc2cccc(OCCNC(=O)[C@H](C)N(C)C(=O)/C=C/CN(C)C)c2)nc1NC1CCOCC1] |
| 40 | 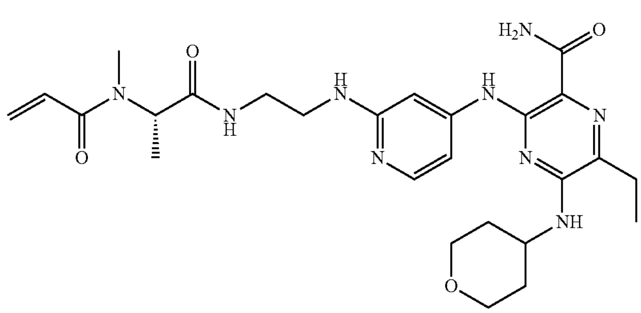 [SMILES: C=CC(=O)N(C)[C@@H](C)C(=O)NCCNc1cc(Nc2nc(NC3CCOCC3)c(CC)nc2C(N)=O)ccn1] |

| Cpd | Structure |
|---|---|
| 41 | 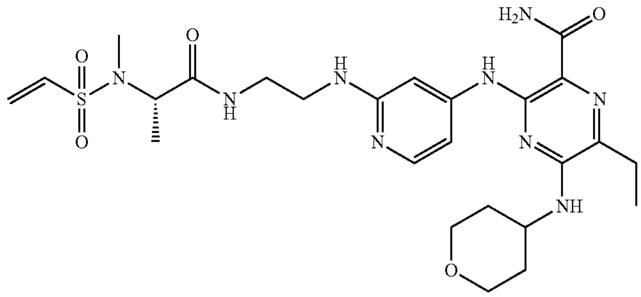 [SMILES: C=CS(=O)(=O)N(C)[C@@H](C)C(=O)NCCNc1cc(Nc2nc(NC3CCOCC3)c(CC)nc2C(N)=O)ccn1] |
In certain embodiments, the compound is not any of Compounds 14-P19, or any salt thereof:
| Cpd | Structure |
|---|---|
| P-14 | 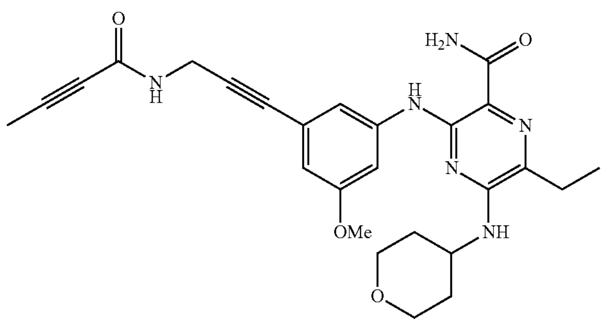 [SMILES: CC#CC(=O)NCC#Cc1cc(Nc2nc(NC3CCOCC3)c(CC)nc2C(N)=O)cc(OC)c1] |
| P-15 | 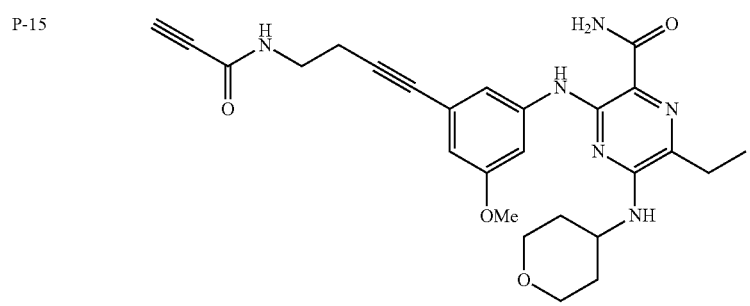 |
| P-16 | 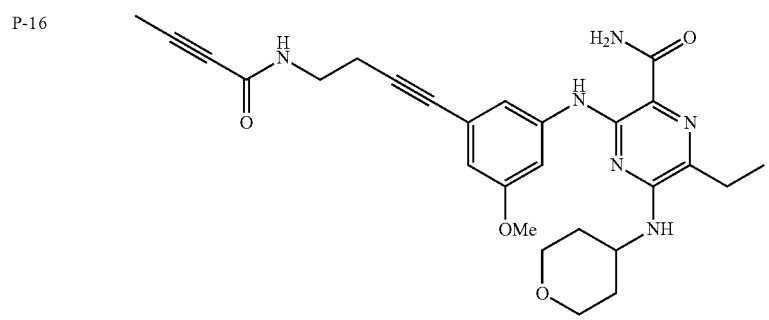 |

| Cpd | Structure |
|---|---|
| P-17 | 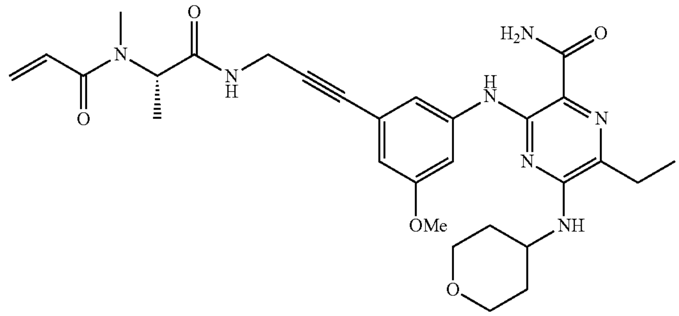 [SMILES: C=CC(=O)N(C)[C@@H](C)C(=O)NCC#Cc1cc(Nc2nc(NC3CCOCC3)c(CC)nc2C(N)=O)cc(OC)c1] |
| P-18 | 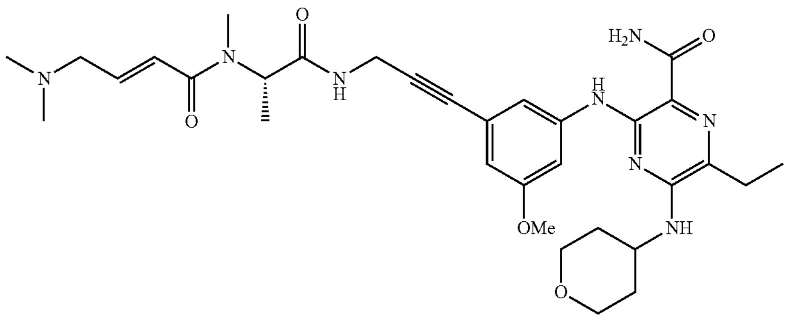 [SMILES: CCc1nc(C(N)=O)c(Nc2cc(C#CCNC(=O)[C@H](C)N(C)C(=O)/C=C/CN(C)C)cc(OC)c2)nc1NC1CCOCC1] |
| P-19 | 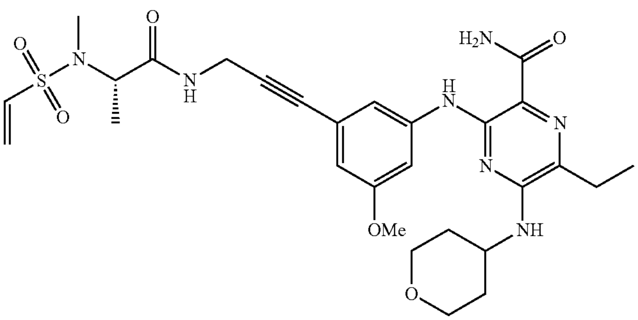 [SMILES: C=CS(=O)(=O)N(C)[C@@H](C)C(=O)NCC#Cc1cc(Nc2nc(NC3CCOCC3)c(CC)nc2C(N)=O)cc(OC)c1] |

Any combination of the groups described above for the various variables is contemplated herein. It is understood that substituents and substitution patterns on the compounds provided herein can be selected by one of ordinary skill in the art to provide compounds that are chemically stable and that can be synthesized by techniques known in the art, as well as those set forth herein.

In some embodiments, provided herein are pharmaceutical compositions, which comprise a therapeutically effective amount of at least one of any of the compounds herein, or a pharmaceutically acceptable salt, pharmaceutically active metabolite, pharmaceutically acceptable prodrug, or pharmaceutically acceptable solvate thereof. In certain embodiments, pharmaceutical compositions provided herein further include a pharmaceutically acceptable carrier, excipient and/or diluent.

Pharmaceutical compositions formulated for administration by an appropriate route and means containing effective concentrations of one or more of the compounds provided herein, or pharmaceutically effective derivatives thereof, that deliver amounts effective for the treatment, prevention, or amelioration of one or more symptoms of diseases, disorders or conditions that are modulated or otherwise affected by FLT3 activity, in which FLT3 activity is implicated, or are characterized by a mutation in the FLT3 gene, are provided. The effective amounts and concentrations are effective for ameliorating any of the symptoms of any of the diseases, disorders or conditions disclosed herein.

In certain embodiments, provided herein is a pharmaceutical composition comprising: i) a pharmaceutically acceptable carrier, diluent, and/or excipient; and ii) one or more compounds provided herein.

In some embodiments, provided herein are pharmaceutical compositions comprising a therapeutically effective amount of a compound selected from Formula (P2-I), Formula (P4-I)-(P4-Vb), Formula (P5-I')-(P5-Vd), and Formula (P6-I)-(P6-IIId) and a pharmaceutically acceptable carrier, excipient, or diluent. In some embodiments, the pharmaceutical composition comprising the compound selected from Formula (P2-I), Formula (P4-I)-(P4-Vb), Formula (P5-I')-(P5-Vd), and Formula (P6-I)-(P6-IIId) is formulated for a route of administration selected from oral administration, parenteral administration, buccal administration, nasal administration, topical administration, and rectal administration.

In some embodiments, provided herein are methods for preventing, treating or ameliorating in a mammal a disease or condition that is related to the aberrant activity of FLT3, which comprises administering to the mammal an effective disease-treating or condition-treating amount of a compound selected from Formula (P2-I), Formula (P4-I)-(P4-Vb), Formula (P5-I')-(P5-Vd), and Formula (P6-I)-(P6-IIId) or a pharmaceutically acceptable salt thereof. In other embodiments, provided herein are methods for preventing, treating or ameliorating in a mammal a disease or condition that is related to a mutation of the FLT3 gene, which comprises administering to the mammal an effective disease-treating or condition-treating amount of a compound selected from Formula (P2-I), Formula (P4-I)-(P4-Vb), Formula (P5-I')-(P5-Vd), and Formula (P6-I)-(P6-IIId) or a pharmaceutically acceptable salt thereof. In certain embodiments, the FLT3 mutation is an internal tandem mutation (FLT3-ITD). In certain embodiments, the FLT3 mutation is a point mutation in the tyrosine kinase domain (FLT3-TKD).

In some embodiments, the disease or condition is a hematologic malignancy, including, but not limited to leukemia, lymphoma, or multiple myeloma. In certain embodiments, the disease or condition is a leukemia, including, but not limited to, acute lymphocytic leukemia (ALL), acute myeloid leukemia (AML), chronic lymphocytic leukemia (CLL), chronic myeloid leukemia (CML), prolymphocytic leukemia (PLL), large granular lymphocytic (LGL), hairy cell leukemia (HCL), mast-cell leukemia (MCL) or myelodysplastic syndrome (MDS).

In certain embodiments, the disease or condition is acute myeloid leukemia (AML). In certain embodiments, the AML is FLT3 mutation-positive. In certain embodiments, the AML is newly diagnosed. In certain embodiments, the AML is FLT3 mutation-positive and newly diagnosed. In certain embodiments, the AML is relapsed or refractory. In certain embodiments, the AML is relapsed or refractory and is FLT3 mutation-positive. In certain embodiments, the patient has an NPM1 mutation.

In certain embodiments, the disease or condition is a lymphoma, including, but not limited to, non-Hodgkin's lymphoma or Hodgkin's lymphoma. In certain embodiments, the disease or condition is multiple myeloma.

In some embodiments, provided herein are compounds selected from Formula (P2-I), Formula (P4-I)-(P4-Vb), Formula (P5-I')-(P5-Vd), and Formula (P6-I)-(P6-IIId) or a pharmaceutically salt thereof for use in therapy. In some embodiments, provided herein are compounds selected from Formula (P2-I), Formula (P4-I)-(P4-Vb), Formula (P5-I')-(P5-Vd), and Formula (P6-I)-(P6-IIId) or a pharmaceutically acceptable salt thereof for use in the treatment of a disease or condition related to the aberrant activity of a FLT3 in vivo. In some embodiments, provided herein are compounds selected from Formula (P2-I), Formula (P4-I)-(P4-Vb), Formula (P5-I')-(P5-Vd), and Formula (P6-I)-(P6-IIId) or a pharmaceutically acceptable salt thereof for use in therapy. In some embodiments, provided herein are compounds selected from Formula (P2-I), Formula (P4-I)-(P4-Vb), Formula (P5-I')-(P5-Vd), and Formula (P6-I)-(P6-IIId) or a pharmaceutically acceptable salt thereof for use in the treatment of a disease or condition related to a mutation in the FLT3 gene in vivo. In some embodiments, provided herein are compounds selected from Formula (P2-I), Formula (P4-I)-(P4-Vb), Formula (P5-I')-(P5-Vd), and Formula (P6-I)-(P6-IIId) or a pharmaceutically acceptable salt thereof for use in the manufacture of a medicament for therapy. In some embodiments, provided herein are compounds selected from Formula (P2-I), Formula (P4-I)-(P4-Vb), Formula (P5-I')-(P5-Vd), and Formula (P6-I)-(P6-IIId) or a pharmaceutically acceptable salt thereof for use in the manufacture of a medicament for the treatment of a disease or condition related to the aberrant activity of FLT3 or related to a mutation of the FLT3 gene. Useful diseases and conditions are described herein.

In some embodiments, provided herein are pharmaceutical compositions comprising a compound selected from Formula (P2-I), Formula (P4-I)-(P4-Vb), Formula (P5-I')-(P5-Vd), and Formula (P6-I)-(P6-IIId) or a pharmaceutically acceptable salt thereof for use in therapy. In some embodiments, provided herein are pharmaceutical compositions comprising a compound selected from Formula (P2-I), Formula (P4-I)-(P4-Vb), Formula (P5-I')-(P5-Vd), and Formula (P6-I)-(P6-IIId) or a pharmaceutically acceptable salt thereof for use in the treatment of a disease or condition related to the aberrant activity of FLT3 or related to a mutation of the FLT3 gene. In some embodiments, provided herein are pharmaceutical compositions comprising a compound selected from Formula (P2-I), Formula (P4-I)-(P4-Vb), Formula (P5-I')-(P5-Vd), and Formula (P6-I)-(P6-IIId) or a pharmaceutically acceptable salt thereof for use in the manufacture of a medicament for therapy. In some embodiments, provided herein are pharmaceutical compositions comprising a compound selected from Formula (P2-I), Formula (P4-I)-(P4-Vb), Formula (P5-I')-(P5-Vd), and Formula (P6-I)-(P6-IIId) or a pharmaceutically acceptable salt thereof for use in the manufacture of a medicament for the treatment of a disease or condition related to the aberrant activity of FLT3 or related to a mutation of the FLT3 gene in vivo. Useful diseases and conditions are described herein.

In any of the aforementioned embodiments are some embodiments in which administration is enteral, parenteral, or both, and wherein (a) an effective amount of a provided compound is systemically administered to the mammal; (b) an effective amount of a provided compound is administered orally to the mammal; (c) an effective amount of a provided compound is intravenously administered to the mammal; (d) an effective amount of a provided compound is administered by inhalation; (e) an effective amount of a provided compound is administered by nasal administration; or (f) an effective amount of a provided compound is administered by injection to the mammal; (g) an effective amount of a provided compound is administered topically (dermal) to the mammal; (h) an effective amount of a provided compound is administered by ophthalmic administration; or (i) an effective amount of a provided compound is administered rectally to the mammal.

In any of the aforementioned embodiments are some embodiments comprising single administrations of an effective amount of a provided compound including some embodiments in which (i) a provided compound is administered once; (ii) a provided compound is administered to the mammal multiple times over the span of one day; (iii) continually; or (iv) continuously.

In any of the aforementioned embodiments are some embodiments comprising multiple administrations of an effective amount of a provided compound, including some embodiments in which (i) a provided compound is administered in a single dose; (ii) the time between multiple administrations is every 6 hours; (iii) a provided compound is administered to the mammal every 8 hours. In some embodiments, the method comprises a drug holiday, wherein the administration of the compound is temporarily suspended or the dose of the compound being administered is temporarily reduced; at the end of the drug holiday, dosing of the compound is resumed. The length of the drug holiday can vary from 2 days to 1 year.

In any of the aforementioned embodiments involving the treatment of proliferative disorders, including cancer, for example, a hematological cancer, are some embodiments comprising administering at least one additional agent selected from the group consisting of alemtuzumab, azacitine, bortezomib, decitabine, everolimus, malademetan, palbociclib, ponatinib, venetoclax, and vorinostat. In other embodiments, the treatment of proliferative disorders, including cancer, for example, a hematological cancer, comprise the administration of at least one additional active agent selected from arsenic trioxide, asparaginase (pegylated or non-), bevacizumab, cetuximab, platinum-based compounds such as cisplatin, cladribine, daunorubicin/doxorubicin/idarubicin, irinotecan, fludarabine, 5-fluorouracil, gemtuzumab, methotrexate, Paclitaxel™, taxol, temozolomide, thioguanine, or classes of drugs including hormones (an antiestrogen, an antiandrogen, or gonadotropin releasing hormone analogues), interferons such as alpha interferon, nitrogen mustards such as busulfan or melphalan or mechlorethamine, retinoids such as tretinoin, topoisomerase irreversible inhibitors such as irinotecan or topotecan, tyrosine kinase irreversible inhibitors such as gefinitinib or imatinib, or agents to treat signs or symptoms induced by such therapy including allopurinol, filgrastim, granisetron/ondansetron/palonosetron, dronabinol.

In certain embodiments, provided herein are articles of manufacture including packaging material, a compound or composition thereof provided herein within the packaging material, and a label that indicates that the compound or composition is administered to treat a disease or condition.

In some embodiments, the compounds of Formula (P2-I), Formula (P4-I)-(P4-Vb), Formula (P5-I')-(P5-Vd), and Formula (P6-I)-(P6-IIId) are covalent inhibitors of FLT3 activity. In certain embodiments, such covalent inhibitors have an $IC_{50}$ below 10 microM in enzyme assay. In some embodiments, a FLT3 inhibitor has an $IC_{50}$ of less than 1 microM, and in some embodiments, less than 0.25 microM or even less than 0.025 microM.

Other objects, features, and advantages of the methods and compositions described herein will become apparent from the following detailed description. It should be understood, however, that the detailed description and the specific examples, while indicating specific embodiments, are given by way of illustration only, since various changes and modifications within the spirit and scope of the present disclosure will become apparent to those skilled in the art from this detailed description. The section headings used herein are for organizational purposes only and are not to be construed as limiting the subject matter described. All documents, or portions of documents, cited in the application including, but not limited to, patents, patent applications, articles, books, manuals, and treatises are hereby expressly incorporated by reference in their entirety for any purpose.

BRIEF DESCRIPTION OF THE FIGURES

FIG. 2A depicts cell-based and biochemical activity of compounds 506, C-1, C-2, and C-3 in MOLM-13 cells.

FIG. 2B depicts cell-based and biochemical activity of compounds 506, C-1, C-2, and C-3 in K-562 cells.

FIG. 2C depicts cell-based and biochemical activity of compounds 506, C-1, C-2, and C-3 in FLT3-WT cells.

FIG. 2D depicts cell-based and biochemical activity of compounds 506, C-1, C-2, and C-3 in FLT3-ITD enzymes.

DETAILED DESCRIPTION OF THE PREFERRED EMBODIMENTS

1. Certain Terminology

Figure 1:
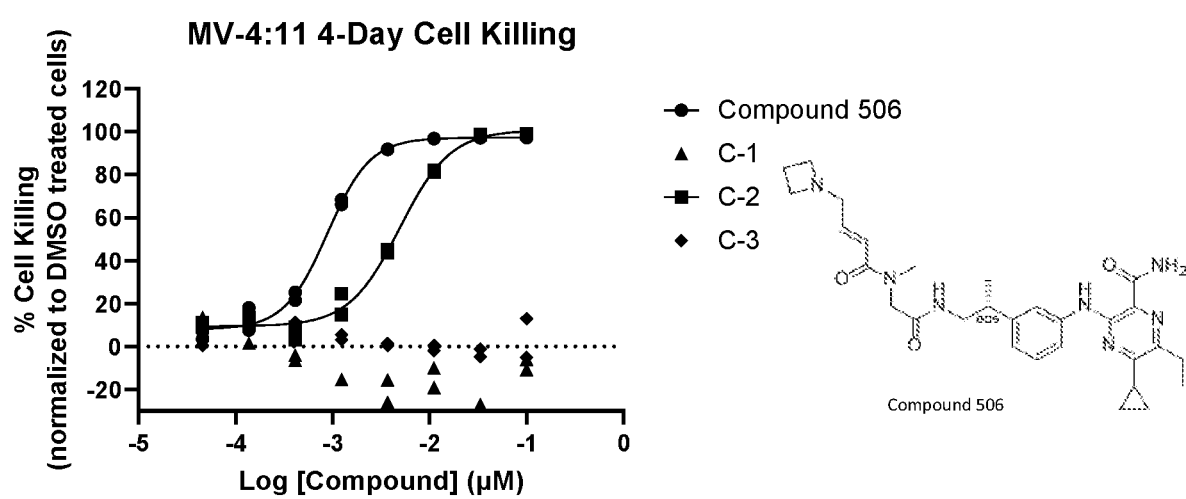
FIG. 1 illustrates cell-based activity of compounds 506, C-1, C-2, and C-3 in MV-4:11 cell lines.

Unless defined otherwise, all technical and scientific terms used herein have the same meaning as is commonly understood by one of skill in the art to which the claimed subject matter belongs. In the event that there are a plurality of definitions for terms herein, those in this section prevail. Where reference is made to a URL or other such identifier or address, it is understood that such identifiers can change and particular information on the internet can come and go, but equivalent information can be found by searching the internet. Reference thereto evidences the availability and public dissemination of such information.

It is to be understood that the foregoing general description and the following detailed description are exemplary and explanatory only and are not restrictive of any subject matter claimed. In this application, the use of the singular includes the plural unless specifically stated otherwise. It must be noted that, as used in the specification and the appended claims, the singular forms "a," "an" and "the" include plural referents unless the context clearly dictates otherwise. Use of the term "including" as well as other forms, such as "include", "includes," and "included," is not limiting. Definition of standard chemistry terms may be found in reference works, including Carey and Sundberg "ADVANCED ORGANIC CHEMISTRY $4^{TH}$ ED." Vols. A (2000) and B (2001), Plenum Press, New York.

Unless otherwise indicated, conventional methods of mass spectroscopy, NMR, HPLC, protein chemistry, biochemistry, recombinant DNA techniques and pharmacology, within the skill of the art are employed. Unless specific definitions are provided, the nomenclature employed in connection with, and the laboratory procedures and techniques of, analytical chemistry, synthetic organic chemistry, and medicinal and pharmaceutical chemistry described herein are those known in the art. Standard techniques can be used for chemical syntheses, chemical analyses, pharmaceutical preparation, formulation, and delivery, and treatment of patients. Standard techniques can be used for recombinant DNA, oligonucleotide synthesis, and tissue culture and transformation (e.g., electroporation, lipofection). Reactions and purification techniques can be performed e.g., using kits of manufacturer's specifications, or as commonly accomplished in the art or as described herein. The foregoing techniques and procedures can be generally performed of conventional methods well known in the art and as described in various general and more specific references that are cited and discussed throughout the present specification.

It is to be understood that the methods and compositions described herein are not limited to the particular methodology, protocols, cell lines, constructs, and reagents described herein and as such may vary. It is also to be understood that the terminology used herein is for the purpose of describing particular embodiments only, and is not intended to limit the scope of the methods and compositions described herein, which will be limited only by the appended claims.

All publications and patents mentioned herein are incorporated herein by reference in their entirety for the purpose of describing and disclosing, for example, the constructs and methodologies that are described in the publications, which might be used in connection with the methods, compositions and compounds described herein. The publications discussed herein are provided solely for their disclosure prior to the filing date of the present application. Nothing herein is to be construed as an admission that the inventors described herein are not entitled to antedate such disclosure by virtue of prior invention or for any other reason.

"Alkyl" refers to a straight or branched hydrocarbon chain radical consisting solely of carbon and hydrogen atoms, containing no unsaturation, having from one to fifteen carbon atoms (e.g., $C_1$-$C_{15}$ alkyl). In certain embodiments, an alkyl comprises one to thirteen carbon atoms (e.g., $C_1$-$C_{13}$ alkyl). In certain embodiments, an alkyl comprises one to eight carbon atoms (e.g., $C_1$-$C_8$ alkyl). In some embodiments, an alkyl comprises five to fifteen carbon atoms (e.g., $C_5$-$C_{15}$ alkyl). In certain embodiments, an alkyl comprises five to eight carbon atoms (e.g., $C_5$-$C_8$ alkyl). The alkyl is attached to the rest of the molecule by a single bond, for example, methyl (Me), ethyl (Et), n-propyl (n-pr), 1-methylethyl (iso-propyl or i-Pr), n-butyl (n-Bu), n-pentyl, 1,1-dimethylethyl (t-butyl, or t-Bu), 3-methylhexyl, 2-methylhexyl, and the like. Unless stated otherwise specifically in the specification, an alkyl group is optionally substituted as defined and described below and herein.

The "alkyl" group could also be a "lower alkyl" having 1 to 6 carbon atoms.

As used herein, $C_1$-$C_x$ includes $C_1$-$C_2$, $C_1$-$C_3$ . . . . $C_1$-$C_x$.

"Alkenyl" refers to a straight or branched hydrocarbon chain radical group consisting solely of carbon and hydrogen atoms, containing at least one double bond, and having from two to twelve carbon atoms. In certain embodiments, an alkenyl comprises two to eight carbon atoms. In some embodiments, an alkenyl comprises two to four carbon atoms. The alkenyl is attached to the rest of the molecule by a single bond, for example, ethenyl (i.e., vinyl), prop-1-enyl (i.e., allyl), but-1-enyl, pent-1-enyl, penta-1,4-dienyl, and the like. Unless stated otherwise specifically in the specification, an alkenyl group is optionally substituted as defined and described below and herein.

"Alkynyl" refers to a straight or branched hydrocarbon chain radical group consisting solely of carbon and hydrogen atoms, containing at least one triple bond, having from two to twelve carbon atoms. In certain embodiments, an alkynyl comprises two to eight carbon atoms. In some embodiments, an alkynyl has two to four carbon atoms. The alkynyl is attached to the rest of the molecule by a single bond, for example, ethynyl, propynyl, butynyl, pentynyl, hexynyl, and the like. Unless stated otherwise specifically in the specification, an alkynyl group is optionally substituted as defined and described below and herein.

"Alkylene" or "alkylene chain" refers to a straight or branched divalent hydrocarbon chain linking the rest of the molecule to a radical group, consisting solely of carbon and hydrogen, containing no unsaturation and having from one to twelve carbon atoms, for example, methylene, ethylene, propylene, n-butylene, and the like. The alkylene chain is attached to the rest of the molecule through a single bond and to the radical group through a single bond. The points of attachment of the alkylene chain to the rest of the molecule and to the radical group can be through one carbon in the alkylene chain or through any two carbons within the chain. Unless stated otherwise specifically in the specification, an alkylene chain is optionally substituted as defined and described below and herein.

"Alkenylene" or "alkenylene chain" refers to a straight or branched divalent hydrocarbon chain linking the rest of the molecule to a radical group, consisting solely of carbon and hydrogen, containing at least one double bond and having from two to twelve carbon atoms, for example, ethenylene, propenylene, n-butenylene, and the like. The alkenylene chain is attached to the rest of the molecule through a double bond or a single bond and to the radical group through a double bond or a single bond. The points of attachment of the alkenylene chain to the rest of the molecule and to the radical group can be through one carbon or any two carbons within the chain. Unless stated otherwise specifically in the specification, an alkenylene chain is optionally substituted as defined and described below and herein.

"Alkynylene" or "alkynylene chain" refers to a straight or branched divalent hydrocarbon chain linking the rest of the molecule to a radical group, consisting solely of carbon and hydrogen, containing at least one triple bond and having from two to twelve carbon atoms, for example, ethyne, propyne, butyne, and the like. The alkenylene chain is attached to the rest of the molecule through a triple bond or a single bond and to the radical group through a triple bond or a single bond. The points of attachment of the alkynylene chain to the rest of the molecule and to the radical group can be through one carbon or any two carbons within the chain. Unless stated otherwise specifically in the specification, an alkynylene chain is optionally substituted as defined and described below and herein.

"Aryl" refers to a radical derived from an aromatic monocyclic or multicyclic hydrocarbon ring system by removing a hydrogen atom from a ring carbon atom. The aromatic monocyclic or multicyclic hydrocarbon ring system contains only hydrogen and carbon from six to eighteen carbon atoms, where at least one of the rings in the ring system is fully unsaturated, i.e., it contains a cyclic, delocalized (4n+2) π-electron system in accordance with the Hückel theory. Aryl groups include, but are not limited to, groups such as phenyl (Ph), fluorenyl, and naphthyl. Unless stated otherwise specifically in the specification, the term "aryl" or the prefix "ar-" (such as in "aralkyl") is meant to include aryl radicals optionally substituted as defined and described below and herein.

"Aralkyl" refers to a radical of the formula —$R^c$-aryl where $R^c$ is an alkylene chain as defined above, for example, benzyl, diphenylmethyl and the like. The alkylene chain part of the aralkyl radical is optionally substituted as described above for an alkylene chain. The aryl part of the aralkyl radical is optionally substituted as described above for an aryl group.

"Aralkenyl" refers to a radical of the formula —R$^d$-aryl where R$^d$ is an alkenylene chain as defined above. The aryl part of the aralkenyl radical is optionally substituted as described above for an aryl group. The alkenylene chain part of the aralkenyl radical is optionally substituted as defined above for an alkenylene group.

"Aralkynyl" refers to a radical of the formula —R$^e$-aryl, where R$^e$ is an alkynylene chain as defined above. The aryl part of the aralkynyl radical is optionally substituted as described above for an aryl group. The alkynylene chain part of the aralkynyl radical is optionally substituted as defined above for an alkynylene chain.

"Carbocyclyl" or "cycloalkyl" refers to a stable non-aromatic monocyclic or polycyclic hydrocarbon radical consisting solely of carbon and hydrogen atoms, which includes fused or bridged ring systems, having from three to fifteen carbon atoms. In certain embodiments, a carbocyclyl comprises three to ten carbon atoms. In some embodiments, a carbocyclyl comprises five to seven carbon atoms. The carbocyclyl is attached to the rest of the molecule by a single bond. Carbocyclyl is optionally saturated, (i.e., containing single C—C bonds only) or unsaturated (i.e., containing one or more double bonds or triple bonds.) A fully saturated carbocyclyl radical is also referred to as "cycloalkyl." Examples of monocyclic cycloalkyls include, e.g., cyclopropyl, cyclobutyl, cyclopentyl, cyclohexyl, cycloheptyl, and cyclooctyl. An unsaturated carbocyclyl is also referred to as "cycloalkenyl." Examples of monocyclic cycloalkenyls include, e.g., cyclopentenyl, cyclohexenyl, cycloheptenyl, and cyclooctenyl. Polycyclic carbocyclyl radicals include, for example, adamantyl, norbornyl (i.e., bicyclo[2.2.1]heptanyl), norbornenyl, decalinyl, 7,7-dimethyl-bicyclo[2.2.1]heptanyl, and the like. Unless otherwise stated specifically in the specification, the term "carbocyclyl" is meant to include carbocyclyl radicals that are optionally substituted as defined and described below and herein.

"Halo" or "halogen" refers to bromo, chloro, fluoro or iodo substituents.

The terms "haloalkyl," "haloalkenyl," "haloalkynyl" and "haloalkoxy" include alkyl, alkenyl, alkynyl and alkoxy structures in which at least one hydrogen is replaced with a halogen atom. In certain embodiments in which two or more hydrogen atoms are replaced with halogen atoms, the halogen atoms are all the same as one another. In some embodiments in which two or more hydrogen atoms are replaced with halogen atoms, the halogen atoms are not all the same as one another.

"Fluoroalkyl" refers to an alkyl radical, as defined above, that is substituted by one or more fluoro radicals, as defined above, for example, trifluoromethyl, difluoromethyl, 2,2,2-trifluoroethyl, 1-fluoromethyl-2-fluoroethyl, and the like. The alkyl part of the fluoroalkyl radical is optionally substituted as defined above for an alkyl group.

As used herein, the term "non-aromatic heterocycle", "heterocycloalkyl" or "heteroalicyclic" refers to a non-aromatic ring wherein one or more atoms forming the ring is a heteroatom. A "non-aromatic heterocycle" or "heterocycloalkyl" group refers to a cycloalkyl group that includes at least one heteroatom selected from nitrogen, oxygen and sulfur. The radicals may be fused with an aryl or heteroaryl. Heterocycloalkyl rings can be formed by three to 14 ring atoms, such as three, four, five, six, seven, eight, nine, or more than nine atoms. Heterocycloalkyl rings can be optionally substituted.

In certain embodiments, non-aromatic heterocycles contain one or more carbonyl or thiocarbonyl groups such as, for example, oxo- and thio-containing groups. Examples of heterocycloalkyls include, but are not limited to, lactams, lactones, cyclic imides, cyclic thioimides, cyclic carbamates, tetrahydrothiopyran, 4H-pyran, tetrahydropyran, piperidine, 1,3-dioxin, 1,3-dioxane, 1,4-dioxin, 1,4-dioxane, piperazine, 1,3-oxathiane, 1,4-oxathiin, 1,4-oxathiane, tetrahydro-1,4-thiazine, 2H-1,2-oxazine, maleimide, succinimide, barbituric acid, thiobarbituric acid, dioxopiperazine, hydantoin, dihydrouracil, morpholine, trioxane, hexahydro-1,3,5-triazine, tetrahydrothiophene, tetrahydrofuran, pyrroline, pyrrolidine, pyrrolidone, pyrrolidione, pyrazoline, pyrazolidine, imidazoline, imidazolidine, 1,3-dioxole, 1,3-dioxolane, 1,3-dithiole, 1,3-dithiolane, isoxazoline, isoxazolidine, oxazoline, oxazolidine, oxazolidinone, thiazoline, thiazolidine, and 1,3-oxathiolane. Illustrative examples of heterocycloalkyl groups, also referred to as non-aromatic heterocycles, include:

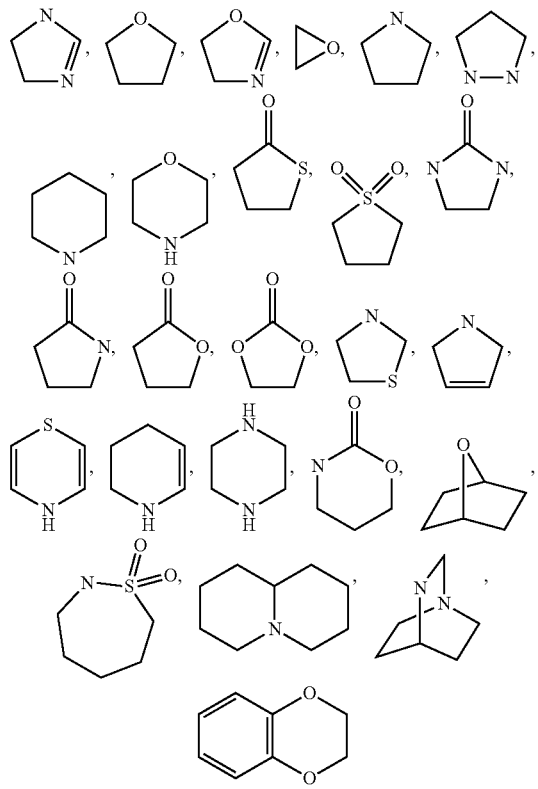

and the like. The term heteroalicyclic also includes all ring forms of the carbohydrates, including but not limited to the monosaccharides, the disaccharides and the oligosaccharides. Depending on the structure, a heterocycloalkyl group can be a monoradical or a diradical (i.e., a heterocycloalkylene group).

"Heteroaryl" refers to a radical derived from a 3- to 18-membered aromatic ring radical that comprises two to seventeen carbon atoms and from one to six heteroatoms selected from nitrogen, oxygen and sulfur. As used herein, the heteroaryl radical is a monocyclic, bicyclic, tricyclic or tetracyclic ring system, wherein at least one of the rings in the ring system is fully unsaturated, i.e., it contains a cyclic, delocalized (4n+2) π-electron system in accordance with the Hückel theory.

Heteroaryl includes fused or bridged ring systems. In some embodiments, heteroaryl rings have five, six, seven, eight, nine, or more than nine ring atoms. The heteroatom(s)

in the heteroaryl radical is optionally oxidized. One or more nitrogen atoms, if present, are optionally quaternized. The heteroaryl is attached to the rest of the molecule through any atom of the ring(s). Examples of heteroaryls include, but are not limited to, azepinyl, acridinyl, benzimidazolyl, benzindolyl, 1,3-benzodioxolyl, benzofuranyl, benzooxazolyl, benzo[d]thiazolyl, benzothiadiazolyl, benzo[b][1,4]dioxepinyl, benzo[b][1,4]oxazinyl, 1,4-benzodioxanyl, benzonaphthofuranyl, benzoxazolyl, benzodioxolyl, benzodioxinyl, benzopyranyl, benzopyranonyl, benzofuranyl, benzofuranonyl, benzothienyl (benzothiophenyl), benzothieno[3,2-d]pyrimidinyl, benzotriazolyl, benzo[4,6]imidazo[1,2-a]pyridinyl, carbazolyl, cinnolinyl, cyclopenta[d]pyrimidinyl, 6,7-dihydro-5H-cyclopenta[4,5]thieno[2,3-d]pyrimidinyl, 5,6-dihydrobenzo[h]quinazolinyl, 5,6-dihydrobenzo[h]cinnolinyl, 6,7-dihydro-5H-benzo[6,7]cyclohepta[1,2-c]pyridazinyl, dibenzofuranyl, dibenzothiophenyl, furanyl, furanonyl, furo[3,2-c]pyridinyl, 5,6,7,8,9,10-hexahydrocycloocta[d]pyrimidinyl, 5,6,7,8,9,10-hexahydrocycloocta[d]pyridazinyl, 5,6,7,8,9,10-hexahydrocycloocta[d]pyridinyl, isothiazolyl, imidazolyl, indazolyl, indolyl, indazolyl, isoindolyl, indolinyl, isoindolinyl, isoquinolyl, indolizinyl, isoxazolyl, 5,8-methano-5,6,7,8-tetrahydroquinazolinyl, naphthyridinyl, 1,6-naphthyridinonyl, oxadiazolyl, 2-oxoazepinyl, oxazolyl, oxiranyl, 5,6,6a,7,8,9,10,10a-octahydrobenzo[h]quinazolinyl, 1-phenyl-1H-pyrrolyl, phenazinyl, phenothiazinyl, phenoxazinyl, phthalazinyl, pteridinyl, purinyl, pyrrolyl, pyrazolyl, pyrazolo[3,4-d]pyrimidinyl, pyridinyl, pyrido[3,2-d]pyrimidinyl, pyrido[3,4-d]pyrimidinyl, pyrazinyl, pyrimidinyl, pyridazinyl, pyrrolyl, quinazolinyl, quinoxalinyl, quinolinyl, isoquinolinyl, tetrahydroquinolinyl, 5,6,7,8-tetrahydroquinazolinyl, 5,6,7,8-tetrahydrobenzo[4,5]thieno[2,3-d]pyrimidinyl, 6,7,8,9-tetrahydro-5H-cyclohepta[4,5]thieno[2,3-d]pyrimidinyl, 5,6,7,8-tetrahydropyrido[4,5-c]pyridazinyl, thiazolyl, thiadiazolyl, triazolyl, tetrazolyl, triazinyl, thieno[2,3-d]pyrimidinyl, thieno[3,2-d]pyrimidinyl, thieno[2,3-c]pridinyl, and thiophenyl (i.e. thienyl). Unless stated otherwise specifically in the specification, the term "heteroaryl" is meant to include heteroaryl radicals as defined above which are optionally substituted as defined and described below and herein.

"N-heteroaryl" refers to a heteroaryl radical as defined above containing at least one nitrogen and where the point of attachment of the heteroaryl radical to the rest of the molecule is through a nitrogen atom in the heteroaryl radical. An N-heteroaryl radical is optionally substituted as described above for heteroaryl radicals.

"C-heteroaryl" refers to a heteroaryl radical as defined above and where the point of attachment of the heteroaryl radical to the rest of the molecule is through a carbon atom in the heteroaryl radical. A C-heteroaryl radical is optionally substituted as described above for heteroaryl radicals.

"Epoxide" refers to a three-membered cyclic ether. The epoxide is optionally substituted as defined and described below and herein.

"Heteroarylalkyl" refers to a radical of the formula —$R^c$-heteroaryl, where $R^c$ is an alkylene chain as defined above. If the heteroaryl is a nitrogen-containing heteroaryl, the heteroaryl is optionally attached to the alkyl radical at the nitrogen atom. The alkylene chain of the heteroarylalkyl radical is optionally substituted as defined above for an alkylene chain. The heteroaryl part of the heteroarylalkyl radical is optionally substituted as defined above for a heteroaryl group.

"Sulfanyl" refers to the —S— radical.
"Sulfinyl" refers to the —S(=O)— radical.
"Sulfonyl" refers to the —S(=O)$_2$— radical.

"Amino" refers to the —NH$_2$ radical.
"Cyano" refers to the —CN radical.
"Nitro" refers to the —NO$_2$ radical.
"Oxa" refers to the —O— radical.
"Oxo" refers to the =O radical.
"Imino" refers to the =NH radical.
"Thioxo" refers to the =S radical.

An "alkoxy" group refers to a (alkyl)O— group, where alkyl is as defined herein.

An "aryloxy" group refers to an (aryl)O— group, where aryl is as defined herein.

"Carbocyclylalkyl" means an alkyl radical, as defined herein, substituted with a carbocyclyl group. "Cycloalkylalkyl" means an alkyl radical, as defined herein, substituted with a cycloalkyl group. Non-limiting cycloalkylalkyl groups include cyclopropylmethyl, cyclobutylmethyl, cyclopentylmethyl, cyclohexylmethyl, and the like.

As used herein, the terms "heteroalkyl," "heteroalkenyl," and "heteroalkynyl" include optionally substituted alkyl, alkenyl and alkynyl radicals in which one or more skeletal chain atoms is a heteroatom, e.g., oxygen, nitrogen, sulfur, silicon, phosphorus or combinations thereof. The heteroatom(s) may be placed at any interior position of the heteroalkyl group or at the position at which the heteroalkyl group is attached to the remainder of the molecule. Examples include, but are not limited to, —CH$_2$—O—CH$_3$, —CH$_2$—CH$_2$—O—CH$_3$, —CH$_2$—NH—CH$_3$, —CH$_2$—CH$_2$—NH—CH$_3$, —CH$_2$—N(CH$_3$)—CH$_3$, —CH$_2$—CH$_2$—NH—CH$_3$, —CH$_2$—CH$_2$—N(CH$_3$)—CH$_3$, —CH$_2$—S—CH$_2$—CH$_3$, —CH$_2$—CH$_2$, —S(O)—CH$_3$, —CH$_2$—CH$_2$—S(O)$_2$—CH$_3$, —CH=CHO—CH$_3$, —Si(CH$_3$)$_3$, —CH$_2$—CH=N—OCH$_3$, and —CH=CH—N(CH$_3$)—CH$_3$. In addition, up to two heteroatoms may be consecutive, such as, by way of example, —CH$_2$—NH—OCH$_3$ and —CH$_2$—O—Si(CH$_3$)$_3$.

The term "heteroatom" refers to an atom other than carbon or hydrogen. Heteroatoms are typically independently selected from among oxygen, sulfur, nitrogen, silicon and phosphorus, but are not limited to these atoms. In embodiments in which two or more heteroatoms are present, the two or more heteroatoms can all be the same as one another, or some or all of the two or more heteroatoms can each be different from the others.

The term "bond," "direct bond" or "single bond" refers to a chemical bond between two atoms, or two moieties when the atoms joined by the bond are considered to be part of larger substructure.

An "isocyanato" group refers to a —NCO group.
An "isothiocyanato" group refers to a —NCS group.

The term "moiety" refers to a specific segment or functional group of a molecule. Chemical moieties are often recognized chemical entities embedded in or appended to a molecule.

A "thioalkoxy" or "alkylthio" group refers to a —S-alkyl group.

A "alkylthioalkyl" group refers to an alkyl group substituted with a —S-alkyl group.

As used herein, the term "acyloxy" refers to a group of formula RC(=O)O—.

"Carboxy" means a —C(O)OH radical.

As used herein, the term "acetyl" refers to a group of formula —C(=O)CH$_3$.

"Acyl" refers to the group —C(O)R.

As used herein, the term "trihalomethanesulfonyl" refers to a group of formula X$_3$CS(=O)$_2$— where X is a halogen.

"Cyanoalkyl" means an alkyl radical, as defined herein, substituted with at least one cyano group.

As used herein, the term "N-sulfonamido" or "sulfonylamino" refers to a group of formula $RS(=O)_2NH—$.

As used herein, the term "O-carbamyl" refers to a group of formula $—OC(=O)NR_2$.

As used herein, the term "N-carbamyl" refers to a group of formula $ROC(=O)NH—$.

As used herein, the term "O-thiocarbamyl" refers to a group of formula $—OC(=S)NR_2$.

As used herein, "N-thiocarbamyl" refers to a group of formula $ROC(=S)NH—$.

As used herein, the term "C-amido" refers to a group of formula $—C(=O)NR_2$.

"Aminocarbonyl" refers to a $—CONH_2$ radical.

As used herein, the term "N-amido" refers to a group of formula $RC(=O)NH—$.

"Hydroxyalkyl" refers to an alkyl radical, as defined herein, substituted with at least one hydroxy group. Non-limiting examples of a hydroxyalkyl include, but are not limited to, hydroxymethyl, 2-hydroxyethyl, 2-hydroxypropyl, 3-hydroxypropyl, 1-(hydroxymethyl)-2-methylpropyl, 2-hydroxybutyl, 3-hydroxybutyl, 4-hydroxybutyl, 2,3-dihydroxypropyl, 1-(hydroxymethyl)-2-hydroxyethyl, 2,3-dihydroxybutyl, 3,4-dihydroxybutyl and 2-(hydroxymethyl)-3-hydroxypropyl.

"Alkoxyalkyl" refers to an alkyl radical, as defined herein, substituted with an alkoxy group, as defined herein.

An "alkenyloxy" group refers to a (alkenyl)O— group, where alkenyl is as defined herein.

The term "alkylamine" refers to the $—N(alkyl)_xH_y$ group, where x and y are selected from among x=1, y=1 and x=2, y=0. When x=2, the alkyl groups, taken together with the N atom to which they are attached, can optionally form a cyclic ring system.

"Alkylaminoalkyl" refers to an alkyl radical, as defined herein, substituted with an alkylamine, as defined herein.

An "amide" is a chemical moiety with the formula $—C(O)NHR$ or $—NHC(O)R$, where R is selected from among alkyl, cycloalkyl, aryl, heteroaryl (bonded through a ring carbon) and heteroalicyclic (bonded through a ring carbon). An amide moiety may form a linkage between an amino acid or a peptide molecule and a compound described herein, thereby forming a prodrug. Any amine, or carboxyl side chain on the compounds described herein can be amidified. The procedures and specific groups to make such amides are known to those of skill in the art and can readily be found in reference sources such as Greene and Wuts, Protective Groups in Organic Synthesis, 3$^{rd}$ Ed., John Wiley & Sons, New York, NY, 1999, which is incorporated herein by reference in its entirety.

The term "ester" refers to a chemical moiety with formula $—COOR$, where R is selected from among alkyl, cycloalkyl, aryl, heteroaryl (bonded through a ring carbon) and heteroalicyclic (bonded through a ring carbon). Any hydroxy, or carboxyl side chain on the compounds described herein can be esterified. The procedures and specific groups to make such esters are known to those of skill in the art and can readily be found in reference sources such as Greene and Wuts, Protective Groups in Organic Synthesis, 3$^{rd}$ Ed., John Wiley & Sons, New York, NY, 1999, which is incorporated herein by reference in its entirety.

As used herein, the term "ring" refers to any covalently closed structure. Rings include, for example, carbocycles (e.g., aryls and cycloalkyls), heterocycles (e.g., heteroaryls and non-aromatic heterocycles), aromatics (e.g. aryls and heteroaryls), and non-aromatics (e.g., cycloalkyls and non-aromatic heterocycles). Rings can be optionally substituted. Rings can be monocyclic or polycyclic.

As used herein, the term "ring system" refers to one, or more than one ring.

The term "membered ring" can embrace any cyclic structure. The term "membered" is meant to denote the number of skeletal atoms that constitute the ring. Thus, for example, cyclohexyl, pyridine, pyran and thiopyran are 6-membered rings and cyclopentyl, pyrrole, furan, and thiophene are 5-membered rings.

The term "fused" refers to structures in which two or more rings share one or more bonds.

As described herein, compounds provided herein may be "optionally substituted". In general, the term "substituted," whether preceded by the term "optionally" or not, means that one or more hydrogens of a designated moiety are replaced with a suitable substituent. Unless otherwise indicated, an "optionally substituted" group may have a suitable substituent at each substitutable position of the group, and when more than one position in any given structure may be substituted with more than one substituent selected from a specified group, the substituent may be either the same or different at every position. Combinations of substituents provided herein are preferably those that result in the formation of stable or chemically feasible compounds. The term "stable," as used herein, refers to compounds that are not substantially altered when subjected to conditions to allow for their production, detection, and, in certain embodiments, their recovery, purification, and use for one or more of the purposes disclosed herein.

Suitable monovalent substituents on a substitutable carbon atom of an "optionally substituted" group are independently halogen; $—(CH_2)_{0-4}R°$; $—(CH_2)_{0-4}OR°$; $—O(CH_2)_{0-4}R°$, $—O—(CH_2)_{0-4}C(O)OR°$; $—(CH_2)_{0-4}CH(OR°)_2$; $—(CH_2)_{0-4}SR°$; $—(CH_2)_{0-4}Ph$, which may be substituted with $R°$; $—(CH_2)_{0-4}O(CH_2)_{0-1}Ph$ which may be substituted with $R°$; $—CH=CHPh$, which may be substituted with $R°$; $—(CH_2)_{0-4}O(CH_2)_{0-1}$-pyridyl which may be substituted with $R°$; $—NO_2$; $—CN$; $—N_3$; $—(CH_2)_{0-4}N(R°)_2$; $—(CH_2)_{0-4}N(R°)C(O)R°$; $—N(R°)C(S)R°$; $—(CH_2)_{0-4}N(R°)C(O)NR°_2$; $—N(R°)C(S)NR°_2$; $—(CH_2)_{0-4}N(R°)C(O)OR°$; $—N(R°)N(R°)C(O)R°$; $—N(R°)N(R°)C(O)NR°_2$; $—N(R°)N(R°)C(O)OR°$; $—(CH_2)_{0-4}C(O)R°$; $—C(S)R°$; $—(CH_2)_{0-4}C(O)OR°$; $—(CH_2)_{0-4}C(O)SR°$; $—(CH_2)_{0-4}C(O)OSiR°_3$; $—(CH_2)_{0-4}OC(O)R°$; $—OC(O)(CH_2)_{0-4}SR—$, $—SC(S)SR°$; $—(CH_2)_{0-4}SC(O)R°$; $—(CH_2)_{0-4}C(O)NR°_2$; $—C(S)NR°_2$; $—C(S)SR°$; $—(CH_2)_{0-4}OC(O)NR°_2$; $—C(O)N(OR°)R°$; $—C(O)C(O)R°$; $—C(O)CH_2C(O)R°$; $—C(NOR°)R°$; $—(CH_2)_{0-4}SSR°$; $—(CH_2)_{0-4}S(O)_2R°$; $—(CH_2)_{0-4}S(O)_2OR°$; $—(CH_2)_{0-4}OS(O)_2R°$; $—S(O)_2NR°_2$; $—(CH_2)_{0-4}S(O)R°$; $—N(R°)S(O)_2NR°_2$; $—N(R°)S(O)_2R°$; $—N(OR°)R°$; $—C(NH)NR°_2$; $—P(O)_2R°$; $—P(O)R°_2$; $—OP(O)R°_2$; $—OP(O)(OR°)_2$; $SiR°_3$; $—(C_{1-4}$ straight or branched alkylene)O$—N(R°)_2$; or $—(C_{1-4}$ straight or branched alkylene)C(O)O$—N(R°)_2$, wherein each $R°$ may be substituted as defined below and is independently hydrogen, $C_{1-6}$ aliphatic, $—CH_2Ph$, $—O(CH_2)_{0-1}Ph$, $—CH_2$-(5-6 membered heteroaryl ring), or a 5-6-membered saturated, partially unsaturated, or aryl ring having 0-4 heteroatoms independently selected from nitrogen, oxygen, or sulfur, or, notwithstanding the definition above, two independent occurrences of $R°$, taken together with their intervening atom(s), form a 3-12-membered saturated, partially unsaturated, or aryl mono- or bicyclic ring having 0-4 heteroatoms independently selected from nitrogen, oxygen, or sulfur, which may be substituted as defined below.

Suitable monovalent substituents on $R°$ (or the ring formed by taking two independent occurrences of $R°$ together with their intervening atoms), are independently halogen, —$(CH_2)_{0-2}R^\bullet$, -(halo$R^\bullet$), —$(CH_2)_{0-2}OH$, —$(CH_2)_{0-2}OR^\bullet$, —$(CH_2)_{0-2}CH(OR^\bullet)_2$; —$O(haloR^\bullet)$, —CN, —$N_3$, —$(CH_2)_{0-2}C(O)R^\bullet$, —$(CH_2)_{0-2}C(O)OH$, —$(CH_2)_{0-2}C(O)OR^\bullet$, —$(CH_2)_{0-2}SR^\bullet$, —$(CH_2)_{0-2}SH$, —$(CH_2)_{0-2}NH_2$, —$(CH_2)_{0-2}NHR^\bullet$, —$(CH_2)_{0-2}NR^\bullet{}_2$, —$NO_2$, —$SiR^\bullet{}_3$, —$OSiR^\bullet{}_3$, —$C(O)SR^\bullet$, —$(C_{1-4}$ straight or branched alkylene)$C(O)OR^\bullet$, or —$SSR^\bullet$ wherein each $R^\bullet$ is unsubstituted or where preceded by "halo" is substituted only with one or more halogens, and is independently selected from $C_{1-4}$ aliphatic, —$CH_2Ph$, —$O(CH_2)_{0-1}Ph$, or a 5-6-membered saturated, partially unsaturated, or aryl ring having 0-4 heteroatoms independently selected from nitrogen, oxygen, or sulfur. Suitable divalent substituents on a saturated carbon atom of $R^\circ$ include =O and =S.

Suitable divalent substituents on a saturated carbon atom of an "optionally substituted" group include the following: =O, =S, =$NNR^*{}_2$, =$NNHC(O)R^*$, =$NNHC(O)OR^*$, =$NNHS(O)_2R^*$, =$NR^*$, =$NOR^*$, —$O(C(R^*{}_2))_{2-3}O$—, or —$S(C(R^*{}_2))_{2-3}S$—, wherein each independent occurrence of $R^*$ is selected from hydrogen, $C_{1-3}$ aliphatic which may be substituted as defined below, or an unsubstituted 5-6-membered saturated, partially unsaturated, or aryl ring having 0-4 heteroatoms independently selected from nitrogen, oxygen, or sulfur. Suitable divalent substituents that are bound to vicinal substitutable carbons of an "optionally substituted" group include: —$O(CR^*{}_2)_{2-3}O$—, wherein each independent occurrence of $R^*$ is selected from hydrogen, $C_{1-6}$ aliphatic which may be substituted as defined below, or an unsubstituted 5-6-membered saturated, partially unsaturated, or aryl ring having 0-4 heteroatoms independently selected from nitrogen, oxygen, or sulfur.

Suitable substituents on the aliphatic group of $R^*$ include halogen, —$R^\bullet$, -(halo$R^\bullet$), —OH, —$OR^\bullet$, —$O(haloR^\bullet)$, —CN, —C(O)OH, —$C(O)OR^\bullet$, —$NH_2$, —$NHR^\bullet$, —$NR^\bullet{}_2$, or —$NO_2$, wherein each $R^\bullet$ is unsubstituted or where preceded by "halo" is substituted only with one or more halogens, and is independently $C_{1-4}$ aliphatic, —$CH_2Ph$, —$O(CH_2)_{0-1}Ph$, or a 5-6-membered saturated, partially unsaturated, or aryl ring having 0-4 heteroatoms independently selected from nitrogen, oxygen, or sulfur.

Suitable substituents on a substitutable nitrogen of an "optionally substituted" group include —$R^\dagger$, —$NR^\dagger{}_2$, —$C(O)R^\dagger$, —$C(O)OR^\dagger$, —$C(O)C(O)R^\dagger$, —$C(O)CH_2C(O)R^\dagger$, —$S(O)_2R^\dagger$, —$S(O)_2NR^\dagger{}_2$, —$C(S)NR^\dagger{}_2$, —$C(NH)NR^\dagger{}_2$, or —$N(R^\dagger)S(O)_2R$; wherein each $R^\dagger$ is independently hydrogen, $C_{1-3}$ aliphatic which may be substituted as defined below, unsubstituted —OPh, or an unsubstituted 5-6-membered saturated, partially unsaturated, or aryl ring having 0-4 heteroatoms independently selected from nitrogen, oxygen, or sulfur, or, notwithstanding the definition above, two independent occurrences of $R^\dagger$, taken together with their intervening atom(s) form an unsubstituted 3-12-membered saturated, partially unsaturated, or aryl mono- or bicyclic ring having 0-4 heteroatoms independently selected from nitrogen, oxygen, or sulfur.

Suitable substituents on the aliphatic group of $R^\dagger$ are independently halogen, —$R^\bullet$, -(halo$R^\bullet$), —OH, —$OR^*$, —$O(haloR^\bullet)$, —CN, —C(O)OH, —$C(O)OR^\bullet$, —$NH_2$, —$NHR^\bullet$, —$NR^\bullet{}_2$, or —$NO_2$, wherein each $R^\bullet$ is unsubstituted or where preceded by "halo" is substituted only with one or more halogens, and is independently $C_{1-4}$ aliphatic, —$CH_2Ph$, —$O(CH_2)_{0-1}Ph$, or a 5-6-membered saturated, partially unsaturated, or aryl ring having 0-4 heteroatoms independently selected from nitrogen, oxygen, or sulfur.

The term "nucleophile" or "nucleophilic" refers to an electron rich compound, or moiety thereof.

The term "electrophile", or "electrophilic" refers to an electron poor or electron deficient molecule, or moiety thereof. Examples of electrophiles include, but in no way are limited to, Michael acceptor moieties.

The term "acceptable" or "pharmaceutically acceptable", with respect to a formulation, composition or ingredient, as used herein, means having no persistent detrimental effect on the general health of the subject being treated or does not abrogate the biological activity or properties of the compound, and is relatively nontoxic.

As used herein, "amelioration" of the symptoms of a particular disease, disorder or condition by administration of a particular compound or pharmaceutical composition refers to any lessening of severity, delay in onset, slowing of progression, or shortening of duration, whether permanent or temporary, lasting or transient that can be attributed to or associated with administration of the compound or composition.

"Bioavailability" refers to the percentage of the weight of compounds disclosed herein, such as, compounds of any of Formula (P2-I), Formula (P4-I)-(P4-Vb), Formula (P5-I')-(P5-Vd), and Formula (P6-I)-(P6-IIId) dosed that is delivered into the general circulation of the animal or human being studied. The total exposure ($AUC_{(0-\infty)}$) of a drug when administered intravenously is usually defined as 100% bioavailable (F %). "Oral bioavailability" refers to the extent to which compounds disclosed herein, such as, compounds of any of Formula (P2-I), Formula (P4-I)-(P4-Vb), Formula (P5-I')-(P5-Vd), and Formula (P6-I)-(P6-IIId) are absorbed into the general circulation when the pharmaceutical composition is taken orally as compared to intravenous injection.

"Blood plasma concentration" refers to the concentration of compounds disclosed herein, such as, compounds of any of Formula (P2-I), Formula (P4-I)-(P4-Vb), Formula (P5-I')-(P5-Vd), and Formula (P6-I)-(P6-IIId) in the plasma component of blood of a subject. It is understood that the plasma concentration of compounds of any of Formula (P2-I), Formula (P4-I)-(P4-Vb), Formula (P5-I')-(P5-Vd), and Formula (P6-I)-(P6-IIId) may vary significantly between subjects, due to variability with respect to metabolism and/or possible interactions with other therapeutic agents. In accordance with some embodiments disclosed herein, the blood plasma concentration of the compounds of any of Formula (P2-I), Formula (P4-I)-(P4-Vb), Formula (P5-I')-(P5-Vd), and Formula (P6-I)-(P6-IIId) may vary from subject to subject. Likewise, values such as maximum plasma concentration ($C_max$) or time to reach maximum plasma concentration ($T_{max}$), or total area under the plasma concentration time curve ($AUC_{(0-\infty)}$) may vary from subject to subject. Due to this variability, the amount necessary to constitute "a therapeutically effective amount" of a compound of any one of Formula (P2-I), Formula (P4-I)-(P4-Vb), Formula (P5-I')-(P5-Vd), and Formula (P6-I)-(P6-IIId) may vary from subject to subject.

The terms "co-administration" or the like, as used herein, are meant to encompass administration of the selected therapeutic agents to a single patient, and are intended to include treatment regimens in which the agents are administered by the same or different route of administration or at the same or different time.

The terms "effective amount" or "therapeutically effective amount," as used herein, refer to a sufficient amount of an agent or a compound being administered which will relieve to some extent one or more of the symptoms of the disease or condition being treated. The result can be reduction and/or alleviation of the signs, symptoms, or causes of a disease, or any other desired alteration of a biological system. For example, an "effective amount" for therapeutic uses is the amount of the composition including a compound as disclosed herein required to provide a clinically significant decrease in disease symptoms without undue adverse side effects. An appropriate "effective amount" in any individual case may be determined using techniques, such as a dose escalation study. The term "therapeutically effective amount" includes, for example, a prophylactically effective amount. An "effective amount" of a compound disclosed herein is an amount effective to achieve a desired pharmacologic effect or therapeutic improvement without undue adverse side effects. It is understood that "an effect amount" or "a therapeutically effective amount" can vary from subject to subject, due to variation in metabolism of the compound of any of Formula (P-I), Formula (I)-Formula (LXIIIb), Formula (P2-I), Formula (P4-I)-(P4-Vb), or Formula (P5-I')-(P5-Vd), age, weight, general condition of the subject, the condition being treated, the severity of the condition being treated, and the judgment of the prescribing physician. By way of example only, therapeutically effective amounts may be determined by routine experimentation, including but not limited to a dose escalation clinical trial.

The terms "enhance" or "enhancing" means to increase or prolong either in potency or duration a desired effect. By way of example, "enhancing" the effect of therapeutic agents refers to the ability to increase or prolong, either in potency or duration, the effect of therapeutic agents on during treatment of a disease, disorder or condition. An "enhancing-effective amount," as used herein, refers to an amount adequate to enhance the effect of a therapeutic agent in the treatment of a disease, disorder or condition. When used in a patient, amounts effective for this use will depend on the severity and course of the disease, disorder or condition, previous therapy, the patient's health status and response to the drugs, and the judgment of the treating physician.

The term "identical," as used herein, refers to two or more sequences or subsequences which are the same. In addition, the term "substantially identical," as used herein, refers to two or more sequences which have a percentage of sequential units which are the same when compared and aligned for maximum correspondence over a comparison window, or designated region as measured using comparison algorithms or by manual alignment and visual inspection. By way of example only, two or more sequences may be "substantially identical" if the sequential units are about 60% identical, about 65% identical, about 70% identical, about 75% identical, about 80% identical, about 85% identical, about 90% identical, or about 95% identical over a specified region. Such percentages to describe the "percent identity" of two or more sequences. The identity of a sequence can exist over a region that is at least about 75-100 sequential units in length, over a region that is about 50 sequential units in length, or, where not specified, across the entire sequence. This definition also refers to the complement of a test sequence. By way of example only, two or more polypeptide sequences are identical when the amino acid residues are the same, while two or more polypeptide sequences are "substantially identical" if the amino acid residues are about 60% identical, about 65% identical, about 70% identical, about 75% identical, about 80% identical, about 85% identical, about 90% identical, or about 95% identical over a specified region. The identity can exist over a region that is at least about 75-100 amino acids in length, over a region that is about 50 amino acids in length, or, where not specified, across the entire sequence of a polypeptide sequence. In addition, by way of example only, two or more polynucleotide sequences are identical when the nucleic acid residues are the same, while two or more polynucleotide sequences are "substantially identical" if the nucleic acid residues are about 60% identical, about 65% identical, about 70% identical, about 75% identical, about 80% identical, about 85% identical, about 90% identical, or about 95% identical over a specified region. The identity can exist over a region that is at least about 75-100 nucleic acids in length, over a region that is about 50 nucleic acids in length, or, where not specified, across the entire sequence of a polynucleotide sequence.

The term "isolated," as used herein, refers to separating and removing a component of interest from components not of interest. Isolated substances can be in either a dry or semi-dry state, or in solution, including but not limited to an aqueous solution. The isolated component can be in a homogeneous state or the isolated component can be a part of a pharmaceutical composition that comprises additional pharmaceutically acceptable carriers and/or excipients. By way of example only, nucleic acids or proteins are "isolated" when such nucleic acids or proteins are free of at least some of the cellular components with which it is associated in the natural state, or that the nucleic acid or protein has been concentrated to a level greater than the concentration of its in vivo or in vitro production. Also, by way of example, a gene is isolated when separated from open reading frames which flank the gene and encode a protein other than the gene of interest.

A "metabolite" of a compound disclosed herein is a derivative of that compound that is formed when the compound is metabolized. The term "active metabolite" refers to a biologically active derivative of a compound that is formed when the compound is metabolized. The term "metabolized," as used herein, refers to the sum of the processes (including, but not limited to, hydrolysis reactions and reactions catalyzed by enzymes, such as, oxidation reactions) by which a particular substance is changed by an organism. Thus, enzymes may produce specific structural alterations to a compound. For example, cytochrome P450 catalyzes a variety of oxidative and reductive reactions while uridine diphosphate glucuronyl transferases catalyze the transfer of an activated glucuronic-acid molecule to aromatic alcohols, aliphatic alcohols, carboxylic acids, amines and free sulfhydryl groups. Further information on metabolism may be obtained from The Pharmacological Basis of Therapeutics, 9th Edition, McGraw-Hill (1996). Metabolites of the compounds disclosed herein can be identified either by administration of compounds to a host and analysis of tissue samples from the host, or by incubation of compounds with hepatic cells in vitro and analysis of the resulting compounds. Both methods are well known in the art. In some embodiments, metabolites of a compound are formed by oxidative processes and correspond to the corresponding hydroxy-containing compound. In some embodiments, a compound is metabolized to pharmacologically active metabolites.

The term "modulate," as used herein, means to interact with a target either directly or indirectly so as to alter the activity of the target, including, by way of example only, to enhance the activity of the target, to inhibit the activity of the target, to limit the activity of the target, or to extend the activity of the target.

As used herein, the term "modulator" refers to a compound that alters an activity of a molecule. For example, a modulator can cause an increase or decrease in the magnitude of a certain activity of a molecule compared to the magnitude of the activity in the absence of the modulator. In certain embodiments, a modulator is an inhibitor, which decreases the magnitude of one or more activities of a molecule. In certain embodiments, an inhibitor completely prevents one or more activities of a molecule. In certain embodiments, a modulator is an activator, which increases the magnitude of at least one activity of a molecule. In certain embodiments the presence of a modulator results in an activity that does not occur in the absence of the modulator.

The term "covalent inhibitor," as used herein, refers to a compound that, upon contact with a target protein (e.g., FLT3) causes the formation of a new covalent bond with or within the protein, whereby one or more of the target protein's biological activities (e.g., phosphotransferase activity) is diminished or abolished notwithstanding the subsequent presence or absence of the covalent inhibitor. In contrast, a non-covalent inhibitor compound upon contact with a target protein does not cause the formation of a new covalent bond with or within the protein and therefore can associate and dissociate from the target protein. In certain embodiments, covalent inhibitors are irreversible. In certain embodiments, non-covalent inhibitors are reversible.

The term "covalent inhibitor of FLT3 protein-protein interaction" as used herein, refers to an inhibitor of FLT3 that can form a covalent bond with an amino acid residue of FLT3. In one embodiment, the covalent inhibitor of FLT3 can form a covalent bond with a Cys residue of FLT3; in particular embodiments, the covalent inhibitor can form a covalent bond with a Cys 12 residue (or a homolog thereof) of FLT3.

The term "prophylactically effective amount," as used herein, refers that amount of a composition applied to a patient that will relieve to some extent one or more of the symptoms of a disease, disease or condition being treated. In such prophylactic applications, such amounts may depend on the patient's state of health, weight, and the like. It is considered well within the skill of the art for one to determine such prophylactically effective amounts by routine experimentation, including, but not limited to, a dose escalation clinical trial.

As used herein, the term "selective binding compound" refers to a compound that selectively binds to any portion of one or more target proteins.

As used herein, the term "selectively binds" refers to the ability of a selective binding compound to bind to a target protein, such as, for example, FLT3, with greater affinity than it binds to a non-target protein. In certain embodiments, specific binding refers to binding to a target with an affinity that is at least 10, 50, 100, 250, 500, 1000 or more times greater than the affinity for a non-target.

As used herein, the term "selective modulator" refers to a compound that selectively modulates a target activity relative to a non-target activity. In certain embodiments, specific modulater refers to modulating a target activity at least 10, 50, 100, 250, 500, 1000 times more than a non-target activity.

The term "substantially purified," as used herein, refers to a component of interest that may be substantially or essentially free of other components which normally accompany or interact with the component of interest prior to purification. By way of example only, a component of interest may be "substantially purified" when the preparation of the component of interest contains less than about 30%, less than about 25%, less than about 20%, less than about 15%, less than about 10%, less than about 5%, less than about 4%, less than about 3%, less than about 2%, or less than about 1% (by dry weight) of contaminating components. Thus, a "substantially purified" component of interest may have a purity level of about 70%, about 75%, about 80%, about 85%, about 90%, about 95%, about 96%, about 97%, about 98%, about 99% or greater.

The term "subject" or "patient" as used herein, refers to an animal which is the object of treatment, observation, or experiment. By way of example only, a subject may be, but is not limited to, a mammal including, but not limited to, a human.

As used herein, the term "target activity" refers to a biological activity capable of being modulated by a selective modulator. Certain exemplary target activities include, but are not limited to, binding affinity, signal transduction, enzymatic activity, tumor growth, inflammation, or inflammation-related processes, and amelioration of one or more symptoms associated with a disease or condition.

As used herein, the term "target protein" refers to a molecule or a portion of a protein capable of being bound by a selective binding compound. In certain embodiments, a target protein is FLT3.

The terms "treat," "treating" or "treatment", as used herein, include alleviating, abating or ameliorating a disease or condition symptoms, preventing additional symptoms, ameliorating or preventing the underlying metabolic causes of symptoms, inhibiting the disease or condition, e.g., arresting the development of the disease or condition, relieving the disease or condition, causing regression of the disease or condition, relieving a condition caused by the disease or condition, or stopping the symptoms of the disease or condition. The terms "treat," "treating" or "treatment", include, but are not limited to, prophylactic and/or therapeutic treatments.

As used herein, the term "FLT3" or "FLT3" refers to fins-like tyrosine kinase 3, gene or protein. Synonyms include CD135, CD135 antigen, fetal liver kinase 2, FL cytokine receptor, FLK-2, FLK2, FLT3_HUMAN, fins-related tyrosine kinase 3, growth factor receptor tyrosine kinase type III, receptor-type tyrosine-protein kinase FLT3, stem cell tyrosine kinase 1, STK-1, and STK1. Human sequences include NM_004119 and NM_004119.2 (mRNA), and NP_004110 and NP_004110.2 (protein). Mouse sequences include NM_010229 and NM_010229.2 (mRNA) and NP_034359 and NP_034359.2 (protein).

As used herein, the $IC_{50}$ refers to an amount, concentration, or dosage of a particular test compound that achieves a 50% inhibition of a maximal response, such as inhibition of FLT3, in an assay that measures such response.

As used herein, $EC_{50}$ refers to a dosage, concentration, or amount of a particular test compound that elicits a dose-dependent response at 50% of maximal expression of a particular response that is induced, provoked or potentiated by the particular test compound.

Methods described herein include administering to a subject in need a composition containing a therapeutically effective amount of one or more FLT3 inhibitor compounds described herein.

In some embodiments, methods described herein can be used to treat a cancer, e.g., B-cell proliferative disorders, which include, but are not limited to diffuse large B cell lymphoma, follicular lymphoma, chronic lymphocytic lymphoma, chronic lymphocytic leukemia, B-cell prolymphocytic leukemia, lymphoplasmacytic lymphoma/Waldenström macroglobulinemia, splenic marginal zone lymphoma, plasma cell myeloma, plasmacytoma, extranodal marginal zone B cell lymphoma, nodal marginal zone B cell lymphoma, mantle cell lymphoma, mediastinal (thymic) large B cell lymphoma, intravascular large B cell lymphoma, primary effusion lymphoma, burkitt lymphoma/leukemia, and lymphomatoid granulomatosis.

Symptoms, diagnostic tests, and prognostic tests for each of the above-mentioned conditions are known in the art. See, e.g., Harrison's Principles of Internal Medicine©," 16th ed., 2004, The McGraw-Hill Companies, Inc. Dey et al. (2006), Cytojournal 3(24), and the "Revised European American Lymphoma" (REAL) classification system (see, e.g., the website maintained by the National Cancer Institute).

A number of animal models of are useful for establishing a range of therapeutically effective doses of FLT3 inhibitor compounds for treating any of the foregoing diseases.

Animal models for treatment of thromboembolic disorders are also known.

The therapeutic efficacy of a provided compound for one of the foregoing diseases can be optimized during a course of treatment. For example, a subject being treated can undergo a diagnostic evaluation to correlate the relief of disease symptoms or pathologies to inhibition of in vivo FLT3 activity achieved by administering a given dose of a FLT3 inhibitor.

2. Compounds

In the following description of FLT3 inhibitor compounds suitable for use in the methods described herein, definitions of referred-to standard chemistry terms may be found in reference works (if not otherwise defined herein), including Carey and Sundberg "Advanced Organic Chemistry 4th Ed." Vols. A (2000) and B (2001), Plenum Press, New York. Unless otherwise indicated, conventional methods of mass spectroscopy, NMR, HPLC, protein chemistry, biochemistry, recombinant DNA techniques and pharmacology, within the ordinary skill of the art are employed. Unless specific definitions are provided, the nomenclature employed in connection with, and the laboratory procedures and techniques of, analytical chemistry, synthetic organic chemistry, and medicinal and pharmaceutical chemistry described herein are those known in the art. Standard techniques can be used for chemical syntheses, chemical analyses, pharmaceutical preparation, formulation, and delivery, and treatment of patients.

FLT3 inhibitor compounds can be used for the manufacture of a medicament for treating any of the foregoing conditions (e.g., hematological malignancies).

In some embodiments, the FLT3 inhibitor compound used for the methods described herein inhibits FLT3 activity with an in vitro $IC_{50}$ of less than about 10 µM (e.g., less than about 1 µM, less than about 0.5 µM, less than about 0.4 µM, less than about 0.3 µM, less than about 0.1 µM, less than about 0.08 µM, less than about 0.06 µM, less than about 0.05 µM, less than about 0.04 µM, less than about 0.03 µM, less than about 0.02 µM, less than about 0.01 µM, less than about 0.008 µM, less than about 0.006 µM, less than about 0.005 µM, less than about 0.004 µM, less than about 0.003 µM, less than about 0.002 µM, less than about 0.001 µM, less than about 0.00099 µM, less than about 0.00098 µM, less than about 0.00097 µM, less than about 0.00096 µM, less than about 0.00095 µM, less than about 0.00094 µM, less than about 0.00093 µM, less than about 0.00092 µM, or less than about 0.00090 µM). In some embodiments, the FLT3 inhibitor is selective for FLT3. In some embodiments, the FLT3 inhibitor is selective for FLT3 over cKit.

Also described herein are methods for synthesizing such covalent inhibitors, methods for using such covalent inhibitors in the treatment of diseases (including diseases wherein inhibition of FLT3 provides therapeutic benefit to a patient having the disease). Further described are pharmaceutical compositions that include an inhibitor of FLT3.

Specifically described herein are covalent inhibitors of FLT3 that form a covalent bond with a cysteine residue on FLT3. Further described herein are covalent inhibitors of FLT3 that form a covalent bond with a Cys12 residue on FLT3. Covalent inhibitor compounds described herein include a Michael acceptor moiety. Also described are pharmaceutical formulations that include an covalent inhibitor of FLT3.

Generally, a non-covalent or covalent inhibitor compound of FLT3 used in the methods described herein is identified or characterized in an in vitro assay, e.g., an acellular biochemical assay or a cellular functional assay. Such assays are useful to determine an in vitro $IC_{50}$ for a non-covalent or covalent FLT3 inhibitor compound.

Further, covalent complex formation between FLT3 and a candidate covalent FLT3 inhibitor is a useful indicator of covalent inhibition of FLT3 that can be readily determined by a number of methods known in the art (e.g., mass spectrometry). For example, some covalent FLT3-inhibitor compounds can form a covalent bond with Cys 12 of FLT3 GC12 (e.g., via a Michael reaction). See S. Xu et al. Angewandte Chemie International Ed. 57(6), 1601-1605 (2017) (incorporated by reference in its entirety).

Described herein are compounds of any of Formula (P-I), Formula (I)-Formula (LXIIIb), Formula (P2-I), Formula (P4-I)-(P4-Vb), and Formula (P5-I')-(P5-Vd). Also described herein are pharmaceutically acceptable salts, pharmaceutically acceptable solvates, pharmaceutically active metabolites, and pharmaceutically acceptable prodrugs of such compounds. Pharmaceutical compositions that include at least one such compound or a pharmaceutically acceptable salt, pharmaceutically acceptable solvate, pharmaceutically active metabolite or pharmaceutically acceptable prodrug of such compound, are provided. In some embodiments, when compounds disclosed herein contain an oxidizable nitrogen atom, the nitrogen atom can be converted to an N-oxide by methods well known in the art. In certain embodiments, isomers and chemically protected forms of compounds having a structure represented by any of Formula (P2-I), Formula (P4-I)-(P4-Vb), Formula (P5-I')-(P5-Vd), and Formula (P6-I)-(P6-IIId) are also provided.

In some embodiments, provided herein are FLT3 covalent inhibitors according to compounds of Formula (P6-I). In some embodiments, provided herein is a compound according to Formula (P6-I) having the structure:

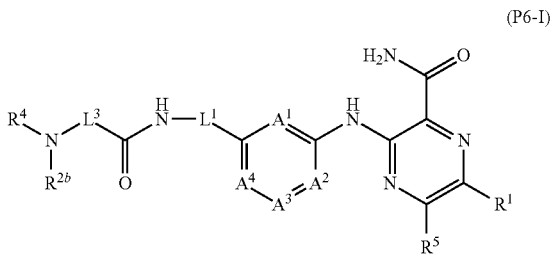

(P6-I)

or a stereoisomer thereof, or a pharmaceutically acceptable salt thereof, wherein: each $A^1$, $A^2$, $A^3$, and $A^4$ is independently —C($R^7$)═, or —N═; provided no more than two of $A^1$, $A^2$, $A^3$, and $A^4$ is N;

each $L^1$ and $L^3$ is independently substituted or unsubstituted $C_1$-$C_4$ alkylene;

R[1] is H, halo, CN, substituted or unsubstituted $C_{1-6}$ alkyl, substituted or unsubstituted alkoxy, substituted or unsubstituted alkenyl, substituted or unsubstituted alkynyl, substituted or unsubstituted cycloalkyl, or substituted or unsubstituted heterocycloalkyl;

$R^{2b}$ is independently H or $C_1$-$C_4$ alkyl;

$R^4$ is i) —C(O)—C($R^{6a}$)=C($R^{6b}$)($R^{6c}$), ii) —S(O)—C($R^{6a}$)=C($R^{6b}$)($R^{6c}$), iii) —S(O)$_2$—C($R^{6a}$)=C($R^{6b}$)($R^{6c}$), or iv) substituted or unsubstituted epoxide;

$R^5$ is H, Cy, CN, halo, substituted or unsubstituted $C_{1-6}$ alkyl, substituted or unsubstituted haloalkyl, substituted or unsubstituted $C_{1-6}$ alkoxy, substituted or unsubstituted haloalkoxy, substituted or unsubstituted alkylamino;

Cy is substituted or unsubstituted cycloalkyl, or substituted or unsubstituted heterocycloalkyl; each $R^{6a}$ and $R^{6b}$ is independently H, halo, CN, or $C_{1-6}$ alkyl; or $R^{6a}$ and $R^{6b}$ are joined together to form a bond; $R^{6c}$ is H, halo, CN, or $C_{1-6}$ alkyl, wherein the $C_{1-6}$ alkyl is unsubstituted or substituted with one or more groups selected from substituted or unsubstituted amino, substituted or unsubstituted hydroxy, and substituted or unsubstituted heterocycloalkyl having 1-2 heteroatoms independently selected from nitrogen, oxygen, and sulfur; and each $R^7$ is independently H, halo, CN, substituted or unsubstituted $C_{1-6}$ alkyl, substituted or unsubstituted alkoxy, or substituted or unsubstituted heterocycloalkyl.

In certain embodiments, the compounds provided herein do not include any of compounds C-1, C-2, or C-3, or any salt thereof:

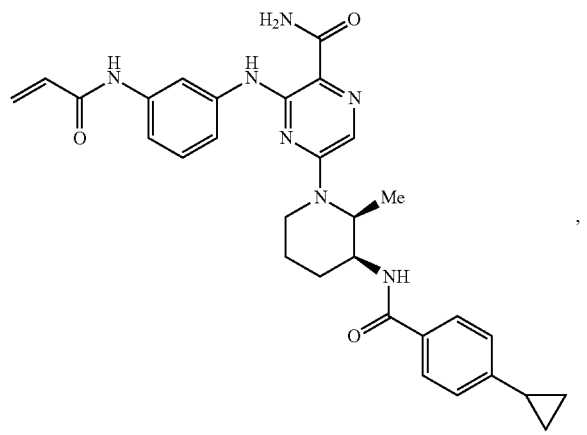

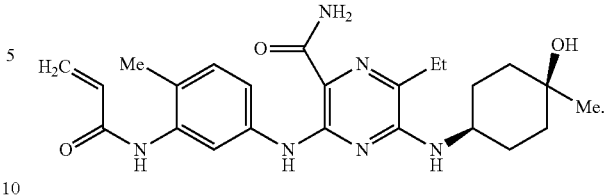

In certain embodiments, one or more compounds provided herein display superior properties compared to or more of C-1, C-2, and C-3. In certain embodiments, one or more compounds provided herein display superior $IC_{50}$ values compared to C-1, C-2, and/or C-3 in cells bearing FLT3-ITD mutations, e.g., MOLM-13 cells. In certain embodiments, one or more compounds provided herein display superior $IC_{50}$ values compared to C-1, C-2, and/or C-3 in cells bearing FLT3-ITD mutations, e.g., MV4-11 cells. In certain embodiments, one or more compounds provided herein display fewer off-target effects compared to C-1, C-2, and/or C-3. In certain embodiments, one or more compounds provided herein display inhibition than compound C-2 in cells bearing no FLT-3 mutations, e.g., K562 cells. In certain embodiments, compound C-1 displayed an $IC_{50}$ of >100 nM and a Ymax of 0% in MOLM-13 cells, an $IC_{50}$ of >100 nM and a Ymax of 9.7% in MV4-11 cells, and an $IC_{50}$ of >100 nM and a Ymax of 0% in K562 cells. In certain embodiments, compound C-2 displayed an $IC_{50}$ of 19.2 nM and a Ymax of 98.6% in MOLM-13 cells, an $IC_{50}$ of 5 nM and a Ymax of 99.1% in MV4-11 cells, and an $IC_{50}$ of 44 nM and a Ymax of 95.8% in K562 cells. The K562 results for compound C-2 indicate effects in cells without FLT3 mutations. In certain embodiments, compound C-3 displayed an $IC_{50}$ of >100 nM and a Ymax of 0% in MOLM-13 cells, an $IC_{50}$ of >100 nM and a Ymax of 6.8% in MV4-11 cells, and an $IC_{50}$ of >100 nM and a Ymax of 0% in K562 cells. These results are comparable to the results in Table 2A of the Examples herein.

In certain embodiments, $R^5$ is Cy. In certain embodiments, $R^5$ is substituted or unsubstituted $C_{1-6}$ alkyl. In certain embodiments, $R^5$ is $C_{1-6}$ alkyl, unsubstituted or substituted with halo, CN, OH, substituted or unsubstituted $C_{1-6}$ alkoxy. In certain embodiments, $R^5$ is $C_{1-6}$ alkyl, substituted with F, CN, OMe, or OEt. In certain embodiments, $R^5$ is $C_{1-6}$ alkoxy, unsubstituted or substituted with halo, CN, OH, substituted or unsubstituted $C_{1-6}$ alkoxy. In certain embodiments, $R^5$ is $C_{1-6}$ alkoxy, substituted with F, CN, OMe, or OEt. In certain embodiments, $R^5$ is alkylamino, unsubstituted or substituted with halo, CN, OH, substituted or unsubstituted $C_{1-6}$ alkoxy. In certain embodiments, $R^5$ is alkylamino, substituted with F, CN, OMe, or OEt. In certain embodiments, $R^5$ is N(H)(Me), N(H)(Et), or N(H)(iPr). In certain embodiments, $R^5$ is dialkylamino, unsubstituted or substituted with halo, CN, OH, substituted or unsubstituted $C_{1-6}$ alkoxy. In certain embodiments, $R^5$ is dialkylamino, substituted with F, CN, OMe, or OEt.

In certain embodiments, $R^5$ is $N(Me)_2$.

In certain embodiments, $R^5$ is Cy. In certain embodiments, $R^5$ is cyclopropyl, cyclobutyl or cyclopentyl.

In certain embodiments, $R^1$ is Me. In particular embodiments, $R^1$ is Et. In certain embodiments, $R^7$ is F, Cl, Me, Et, or OMe. In particular embodiments, $R^7$ is H.

In certain embodiments, $R^4$ is —C(O)—CH=CH$_2$. In particular embodiments, $R^4$ is —C(O)—CH=CH—CH$_2$—NMe$_2$.

alkyl is unsubstituted or substituted with one or more groups selected from substituted or unsubstituted amino, substituted or unsubstituted hydroxy, and In some embodiments, with respect to the compounds of any of the formulas described herein, R$^4$ is —C(O)—B—C(R$^{6a}$)=C(R$^{6b}$)—C(O)—R$^{6c}$, —S(O)— B—C(R$^{6a}$)=C(R$^{6b}$)—C(O)—R$^{6c}$, —S(O)$_2$—B—C(R$^{6a}$)=C(R$^{6b}$)—C(O)—R$^{6c}$, —B—C(R$^{6a}$)=C(R$^{6b}$)—C(O)—R$^{6c}$, —B—C(R$^{6a}$)=C(R$^{6b}$)—S(O)—R$^{6c}$, —B—C(R$^{6a}$)=C(R$^{6b}$)—S(O)$_2$—R$^{6c}$, —B—C(R$^{6a}$)=C(R$^{6b}$)—P(O)—R$^{6a}$R$^{6b}$; or —B—C(R$^{6a}$)=C(R$^{6b}$)—P(O)—OR$^{6a}$OR$^{6b}$; B is substituted or unsubstituted C$_{1-4}$ alkylene, substituted or unsubstituted cycloalkyl, or substituted or unsubstituted heterocycloalkyl; and R$^{6c}$ is substituted or unsubstituted alkoxy, substituted or unsubstituted amino, substituted or unsubstituted heterocycloalkyl, having 1-2 heteroatoms independently selected from nitrogen, oxygen, and sulfur. In some embodiments, R$^4$ is —CH$_2$—CH=CH—C(O)—N(CH$_3$)$_2$. In some embodiments, R$^4$ is —CH$_2$—C≡CH—C(O)—N(CH$_3$)$_2$.

In certain embodiments, one of A$^1$, A$^2$, A$^3$, and A$^4$ is N. In certain embodiments, two of A$^1$, A$^2$, A$^3$, and A$^4$ are N.

In certain embodiments, each of A$^1$, A$^2$, and A$^3$ is independently —C(R$^7$)=; and A$^4$ is C(R$^7$)= or N.

In certain embodiments, A$^4$ is —N=. In certain embodiments, A$^4$ is —C(R$^7$)=; and R$^7$ is H, alkyl, or alkoxy. In certain embodiments, A$^4$ is —C(R$^7$)=; and R$^7$ is substituted or unsubstituted heterocycloalkyl. In certain embodiments, A$^4$ is —C(R$^7$)=; and R$^7$ is substituted or unsubstituted pyrrolidinyl, or piperidinyl. In certain embodiments, A$^4$ is —C(R$^7$)=; and R$^7$ is piperidinyl, unsubstituted or substituted with alkyl, or heterocycloalkyl. In certain embodiments, A$^3$ is —C(R$^7$)=; and R$^7$ is H, alkyl, or alkoxy.

In certain embodiments, Y is —C(R$^{2e}$R$^{2f}$)—. In certain embodiments, Y is —CH$_2$—, —C(Me)H, CMe$_2$, CHF, or CF$_2$. In certain embodiments, Y is —O—. In certain embodiments, Y is —NR$^2$—. In certain embodiments, Y is —NMe-. In certain embodiments, Y is —NH—.

In certain embodiments, each R$^{2c}$ and R$^{2d}$ is independently H or alkyl. In certain embodiments, each R$^{2c}$ and R$^{2d}$ is independently H or Me. In certain embodiments, R$^{2c}$ is H; and R$^{2d}$ is Me. In certain embodiments, R$^{2c}$ and R$^{2d}$ may join together to form a 4-6 membered heterocycloalkyl. In certain embodiments, each R$^{2c}$ and R$^{2d}$ is H.

In certain embodiments, L$^1$ is substituted or unsubstituted C$_2$-C$_4$ alkylene. In certain embodiments, L$^1$ is C$_2$-C$_4$ alkylene, unsubstituted or substituted with halo, hydroxy, or alkyl.

In certain embodiments, L$^1$ is unsubstituted C$_2$-C$_4$ alkylene. In certain embodiments, L$^1$ is —CH$_2$—CH$_2$—, —CH$_2$—CH$_2$—CH$_2$—, or —CH$_2$—CH$_2$—CH$_2$—CH$_2$—. In certain embodiments, L$^1$ is —CH$_2$—CH$_2$—. In certain embodiments, L$^1$ is —CH$_2$—CH$_2$—CH$_2$—. In certain embodiments, L$^1$ is —CH$_2$—CH$_2$—CH$_2$—CH$_2$—.

In certain embodiments, L$^2$ is a single bond. In certain embodiments, L$^2$ is —C(O)-L$^3$-NR$^{2b}$—. In certain embodiments, L$^2$ is —C(O)-L$^3$-NH—. In certain embodiments, L$^2$ is —C(O)-L$^3$-N(CH$_3$)—.

In certain embodiments, L$^1$ is unsubstituted C$_2$-C$_4$ alkylene and L$^2$ is —C(O)-L$^3$-NR$^{2b}$—. In certain embodiments, L$^1$ is unsubstituted C$_2$-C$_4$ alkylene and L$^2$ is —C(O)-L$^3$-NR$^{2b}$—. In certain embodiments, L$^1$ is —CH$_2$—CH$_2$—, —CH$_2$—CH$_2$—CH$_2$—, or —CH$_2$—CH$_2$—CH$_2$—CH$_2$— and L$^2$ is —C(O)—CH(CH$_3$)—NH—.

In certain embodiments the compound is according to Formula (P5-I'):

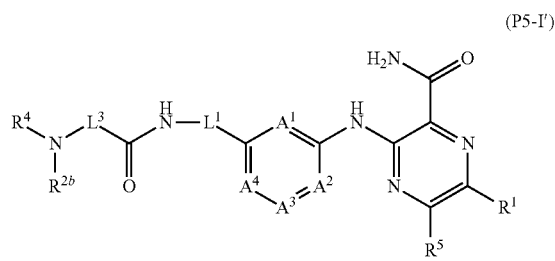

or a stereoisomer thereof, or a pharmaceutically acceptable salt thereof.

In certain embodiments, each of A$^1$, A$^2$, and A$^4$, is CH, and A$^4$ is CR$^7$; and the compound is according to Formula (P4-I):

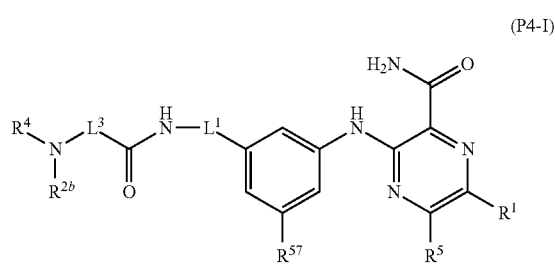

or a stereoisomer thereof, or a pharmaceutically acceptable salt thereof.

In certain embodiments, the compound is according to Formula (P5-Ia), and (P5-Ib):

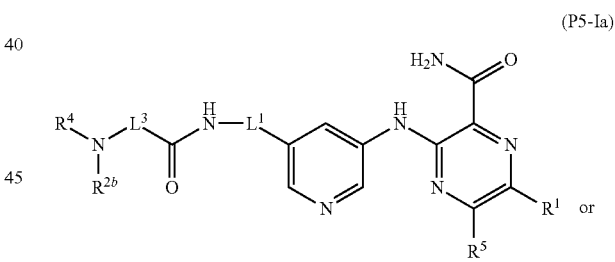

or a stereoisomer thereof, or a pharmaceutically acceptable salt thereof.

In certain embodiments, L$^1$ is substituted or unsubstituted ethylene. In certain embodiments, L$^1$ is unsubstituted ethylene.

In certain embodiments, the compound is according to Formula (P4-II):

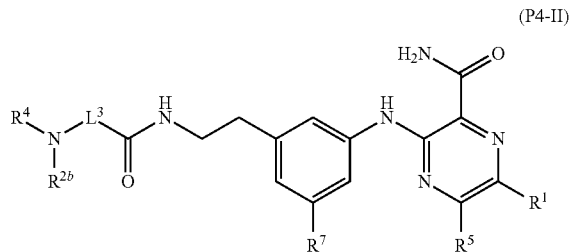
(P4-II)

or a stereoisomer thereof, or a pharmaceutically acceptable salt thereof.

In certain embodiments, the compound is according to Formula (P5-IIa) or (P5-IIb):

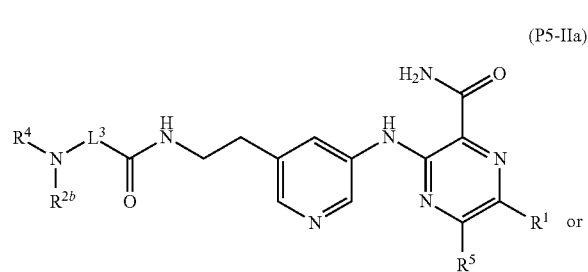
(P5-IIa)

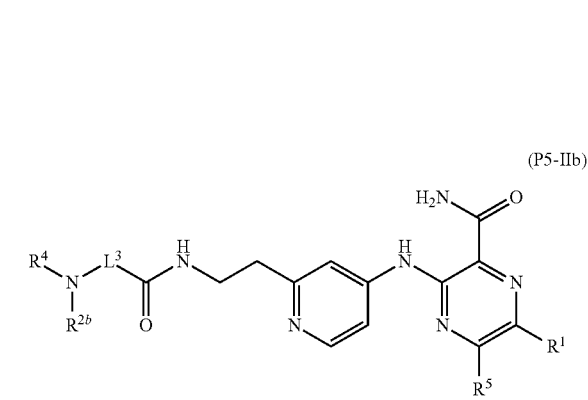
(P5-IIb)

or a stereoisomer thereof, or a pharmaceutically acceptable salt thereof.

In certain embodiments, $L^1$ is ethylene, substituted with Me, Et, i-Pr, dimethyl, OH, or methoxy.

In certain embodiments, the compound is according to (P4-IIIa) or (P4-IIIb):

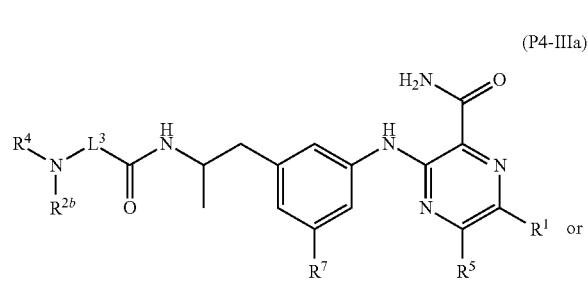
(P4-IIIa)

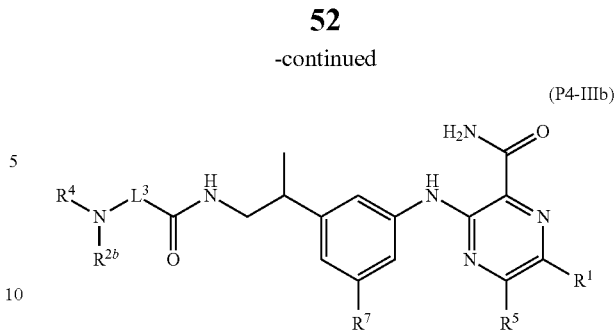
(P4-IIIb)

or a stereoisomer thereof, or a pharmaceutically acceptable salt thereof.

In certain embodiments, the compound is according to (P5-IIIa), (P5-IIIb), (P5-IIIc) or (P5-IIId):

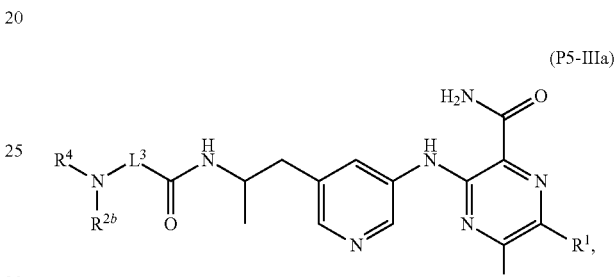
(P5-IIIa)

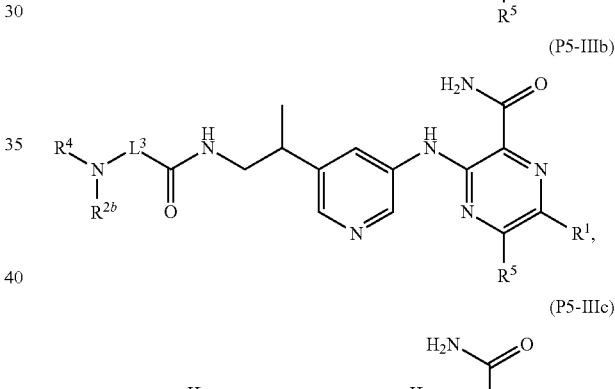
(P5-IIIb)

(P5-IIIc)

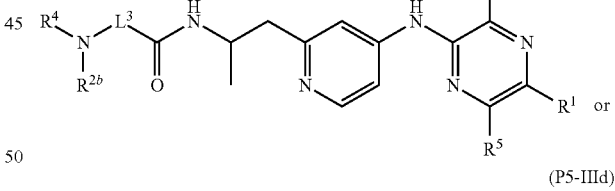
(P5-IIId)

or a stereoisomer thereof, or a pharmaceutically acceptable salt thereof.

In certain embodiments, $L^3$ is —CH$_2$—.

In certain embodiments, the compound is according to Formula (P4-IVa) or (P4-IVb):

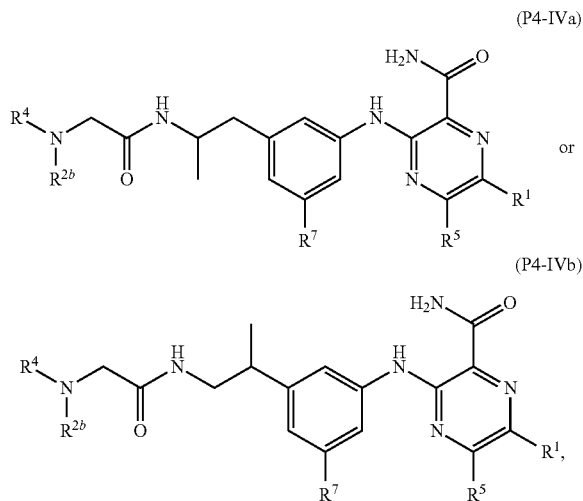

(P4-IVa)

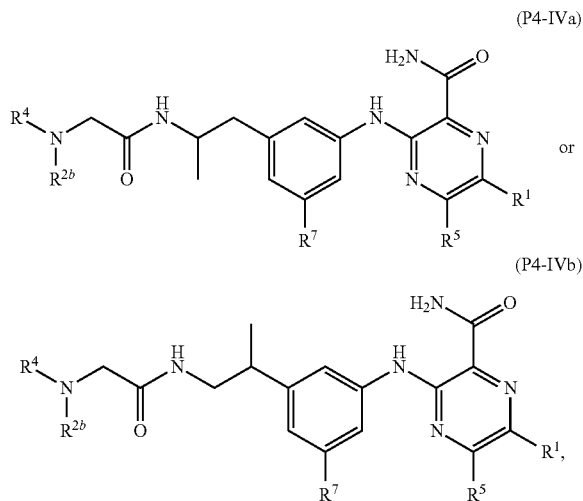

(P4-IVb)

or a stereoisomer thereof, or a pharmaceutically acceptable salt thereof.

In certain embodiments, the compound is according to Formula (P5-IVa), (P5-IVb), (P5-IVc) or (P5-IVd):

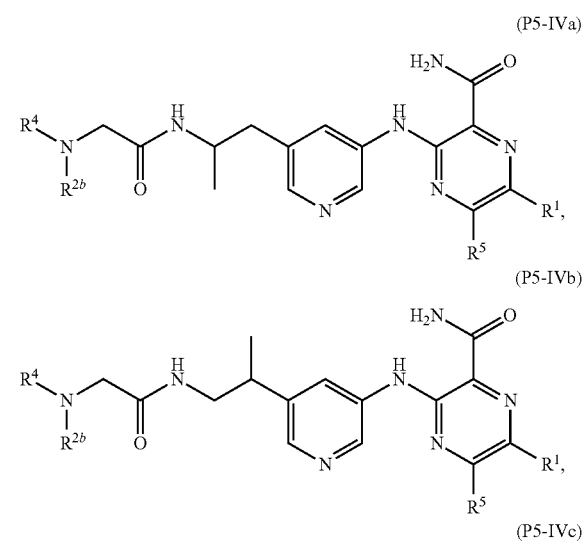

(P5-IVa)

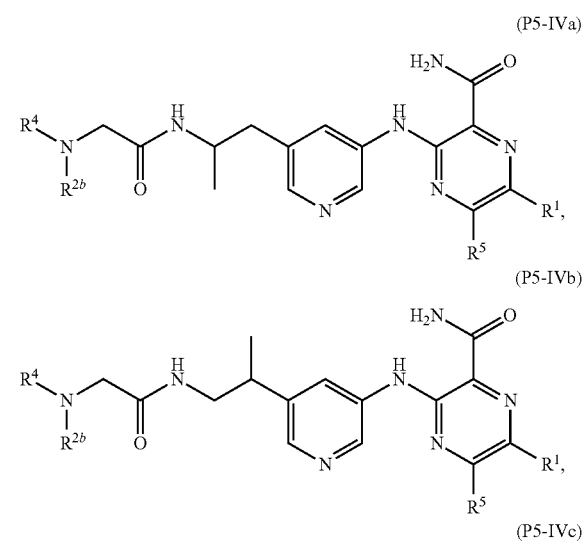

(P5-IVb)

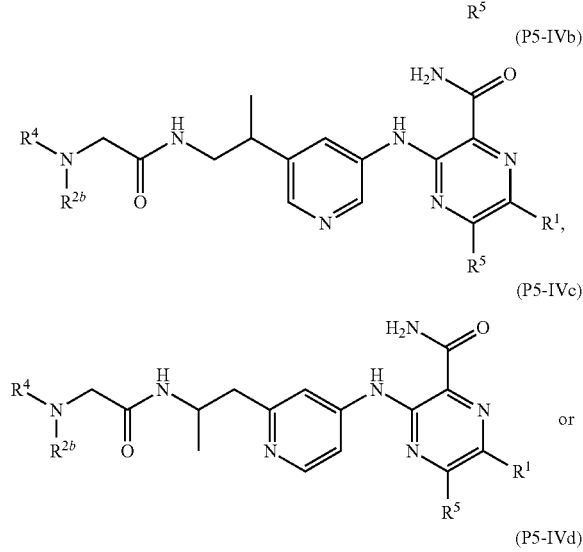

(P5-IVc)

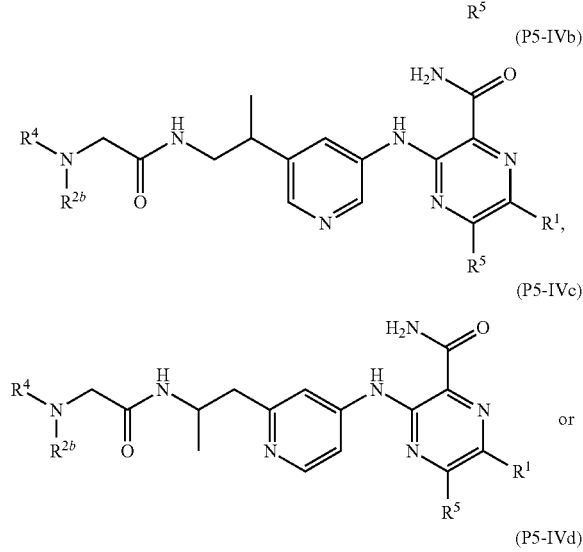

(P5-IVd)

or a stereoisomer thereof, or a pharmaceutically acceptable salt thereof.

In certain embodiments, $L^3$ is —CH(Me)-, or C(Me)$_2$-.

In certain embodiments, the compound is according to Formula (P4-Va) or (P4-Vb):

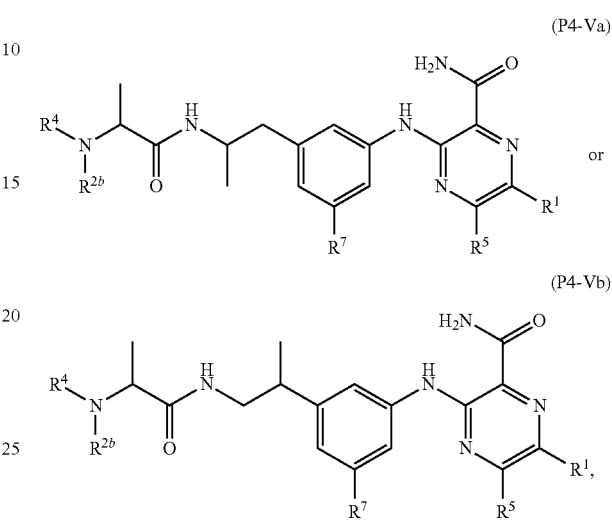

(P4-Va)

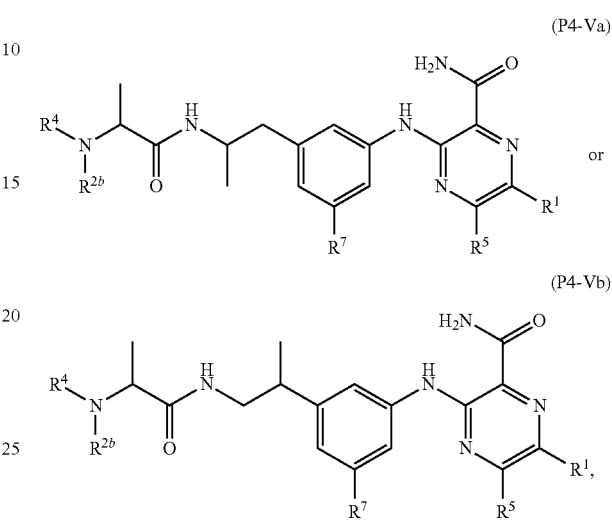

(P4-Vb)

or a stereoisomer thereof, or a pharmaceutically acceptable salt thereof.

In certain embodiments, the compound is according to Formula (P5-Va), (P5-Vb), (P5-Vc) or (P5-Vd):

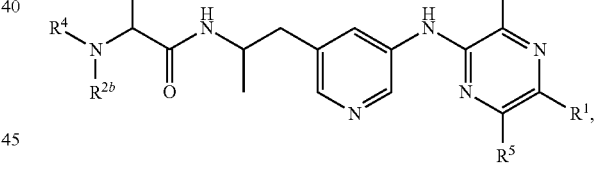

(P5-Va)

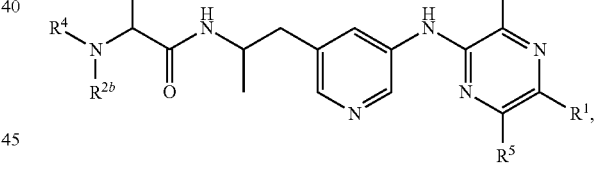

(P5-Vb)

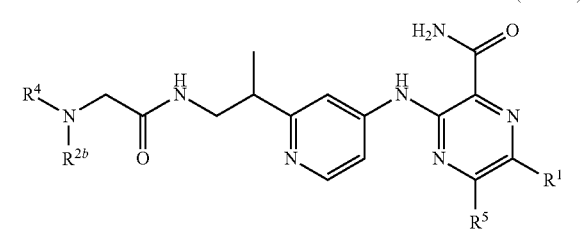

(P5-Vc)

(P5-Vd)


or a stereoisomer thereof, or a pharmaceutically acceptable salt thereof.

In certain embodiments, $R^{2b}$ is H or Me.

In certain embodiments, the compound is according to Formula (P2-I):

(P2-I)


or a stereoisomer thereof, or a pharmaceutically acceptable salt thereof.

In certain embodiments, $R^7$ is H, Me, Et, Cl, F, or OMe. In certain embodiments, $R^7$ is H.

In certain embodiments, $R^1$ is Me or Et. In certain embodiments, $R^5$ is cyclopropyl, Me, Et, N(Me)$_2$, or N(i-Pr)(Me). In certain embodiments, $R^1$ is Me or Et and $R^5$ is cyclopropyl, Me, Et, N(Me)$_2$, or N(i-Pr)(Me). In certain embodiments, $R^1$ is Me or Et, $R^5$ is cyclopropyl, Me, Et, N(Me)$_2$, or N(i-Pr)(Me), and $R^7$ is H.

In certain embodiments, the compound is according to Formula (XLIIIa), (XLIIIb), (XLIIIc) or (XLIIId):

(XLIIIa)

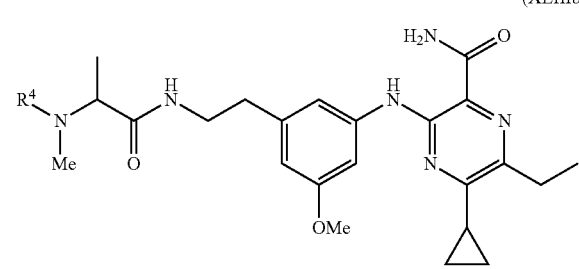

(XLIIIb)

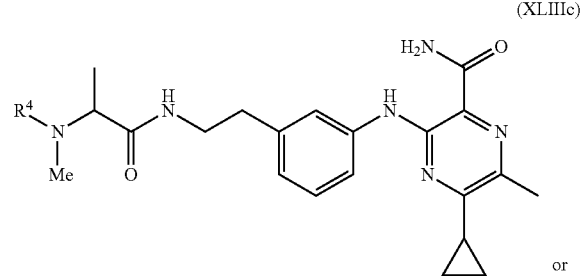

, (XLIIIc)

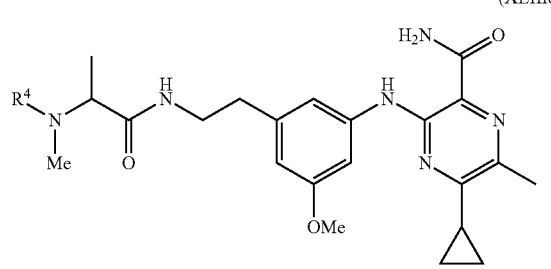

or (XLIIId)

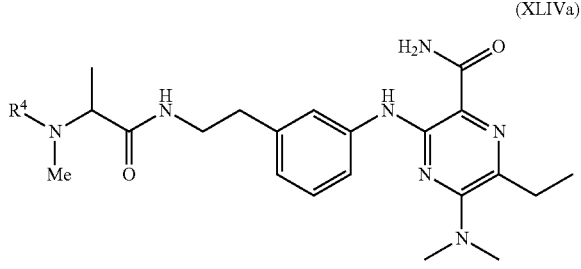

or a stereoisomer thereof, or a pharmaceutically acceptable salt thereof.

In certain embodiments, the compound is according to Formula (XLIVa), (XLIVb), (XLIVc), or (XLIVd):

(XLIVa)

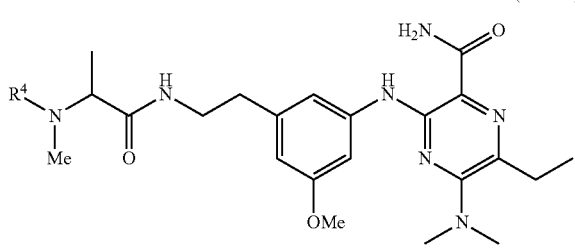

(XLIVb)

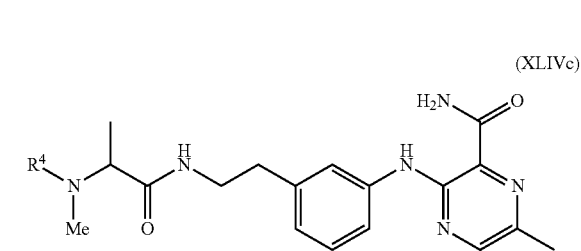

(XLIVc)

(XLIVd)

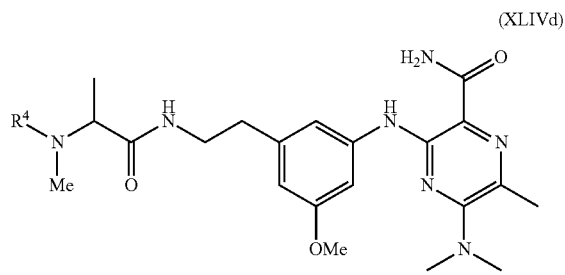

or a stereoisomer thereof, or a pharmaceutically acceptable salt thereof.

In certain embodiments, the compound is according to Formula (XLVIa), (XLVIb), (XLVIc), (XLVId), (XLVIe) or (XLVIf):

(XLVIa)

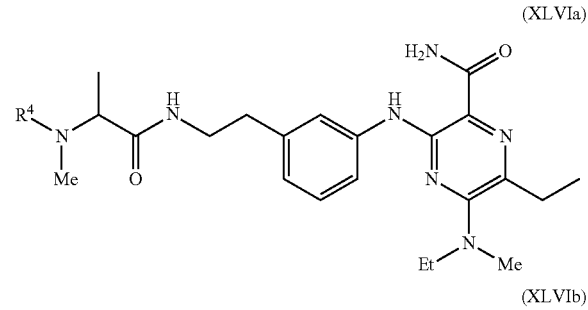

(XLVIb)

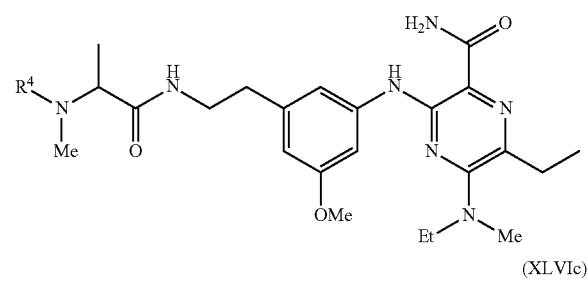

(XLVIc)

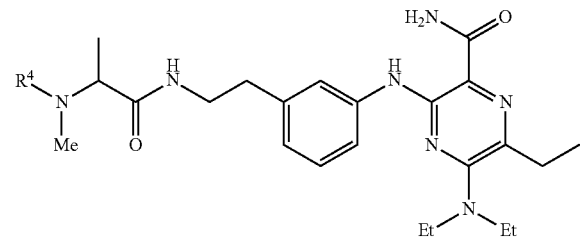

(XLVId)

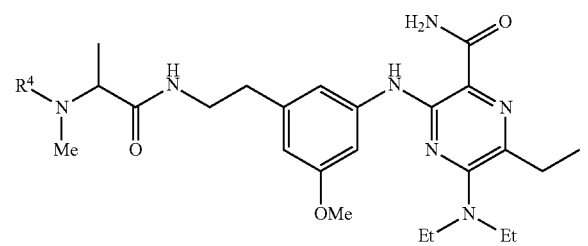

(XLVIe)

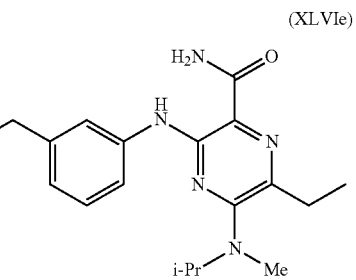

(XLVIf)

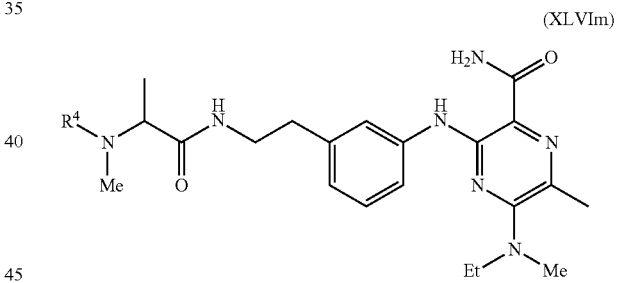

or a stereoisomer thereof, or a pharmaceutically acceptable salt thereof.

In certain embodiments, the compound is according to Formula (XLVIm), (XLVIn), (XLVIo), (XLVIp), (XLVIq) or (XLVIr):

(XLVIm)


(XLVIn)

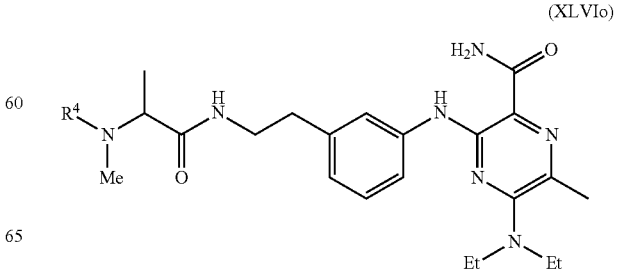

(XLVIo)

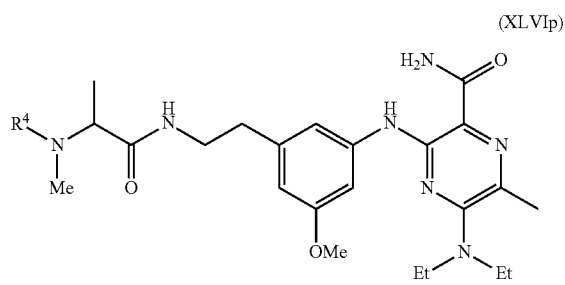

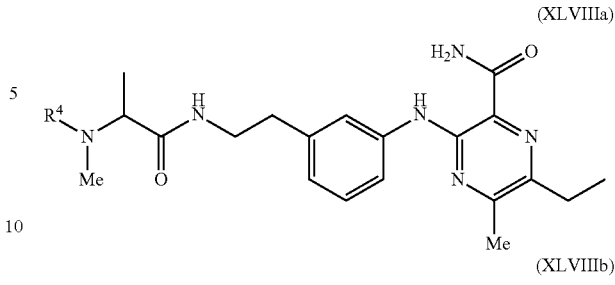

or a stereoisomer thereof, or a pharmaceutically acceptable salt thereof.

In certain embodiments the compound is according to Formula (XLVIIa) or (XLVIIb):

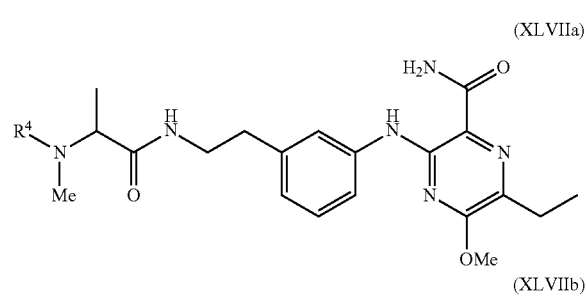

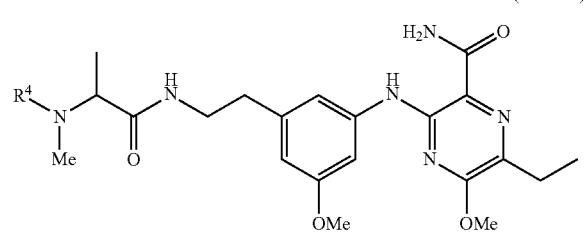

or a stereoisomer thereof, or a pharmaceutically acceptable salt thereof.

In certain embodiments, the compound is according to Formula (XLVIIIa), (XLVIIIb), (XLVIIIc), or (XLVIIId):

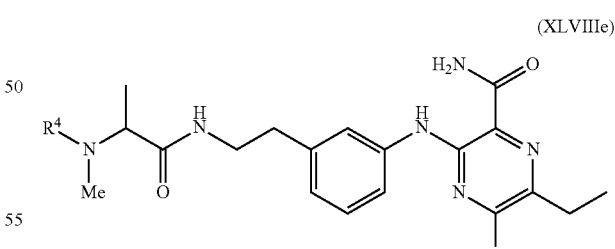

or a stereoisomer thereof, or a pharmaceutically acceptable salt thereof.

In certain embodiments, the compound is according to Formula (XLVIIIe), (XLVIIIf), (XLVIIIg), or (XLVIIIh):

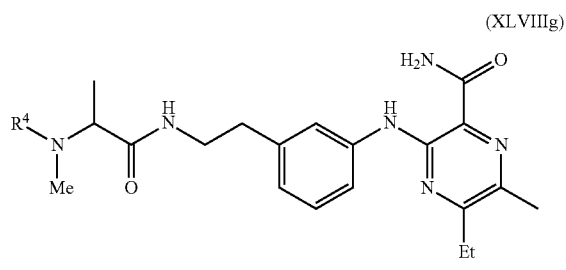

(XLVIIIg)

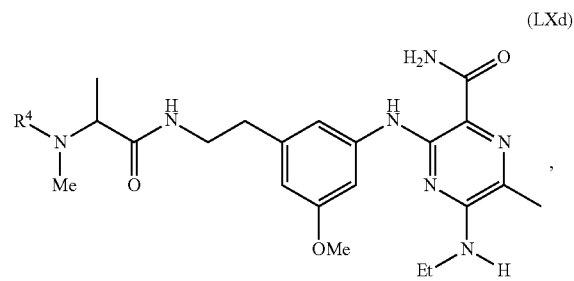

(LXd)

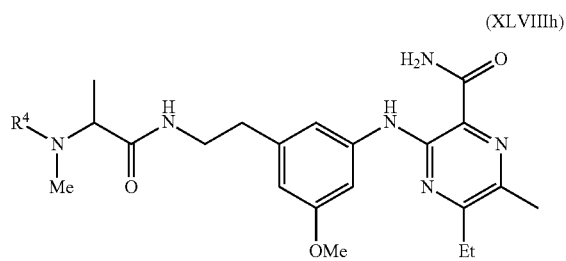

(XLVIIIh)

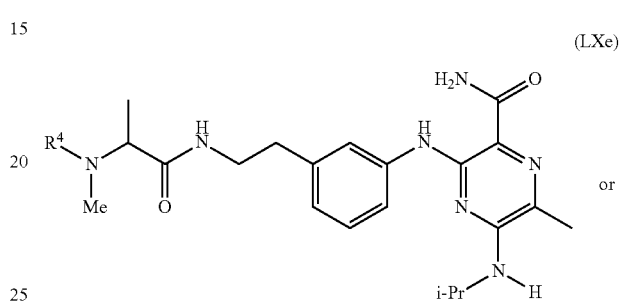

(LXe)

or a stereoisomer thereof, or a pharmaceutically acceptable salt thereof.

In certain embodiments, with respect to formulas Va-LIIf, the Et group, when present, is replaced with Me.

In certain embodiments, the compound is according to Formula (LXa), (LXb), (LXc), (LXd), (LXe) or (LXf):

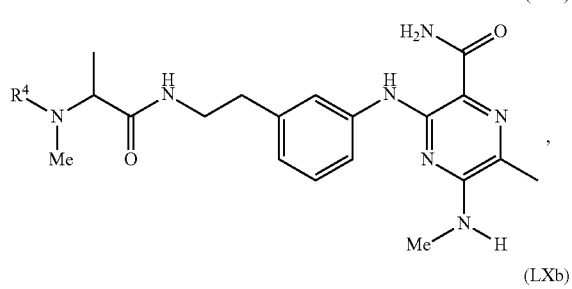

(LXa)

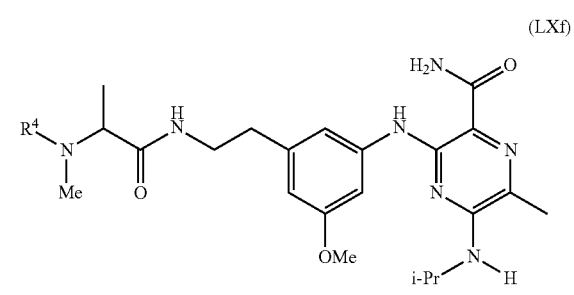

(LXf)

or a stereoisomer thereof, or a pharmaceutically acceptable salt thereof.

In certain embodiments, the compound is according to Formula (LXIa), (LXIb), (LXIc), or (LXId):

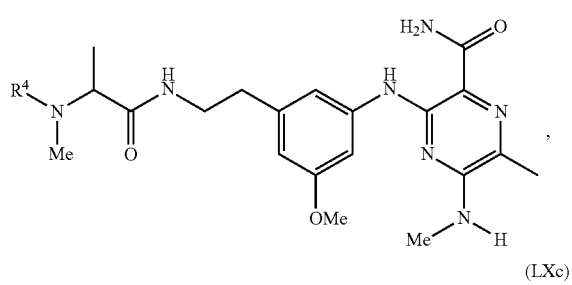

(LXb)

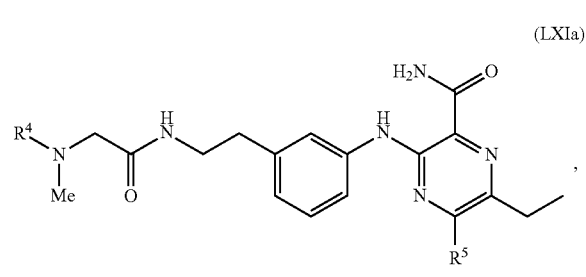

(LXIa)

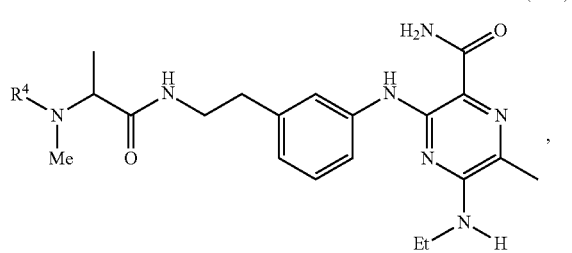

(LXc)

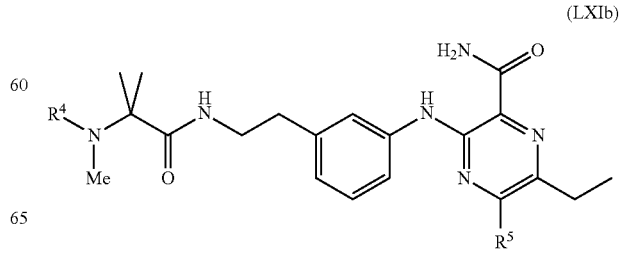

(LXIb)

-continued (LXIc)

(LXId)

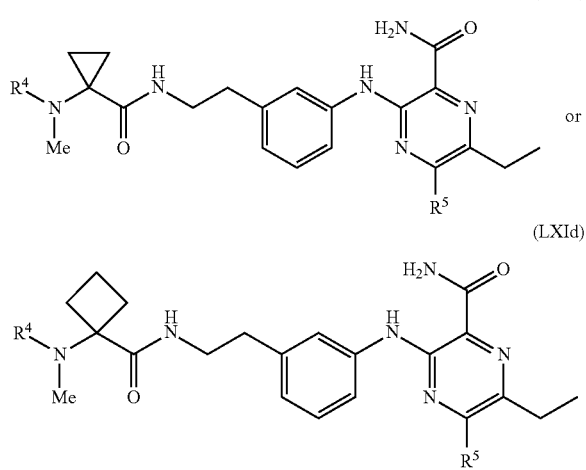

or a stereoisomer thereof, or a pharmaceutically acceptable salt thereof.

In certain embodiments, the compound is according to Formula (LXIIa), (LXIIb), (LXIIc), or (LXIId):

(LXIIa)

(LXIIb)

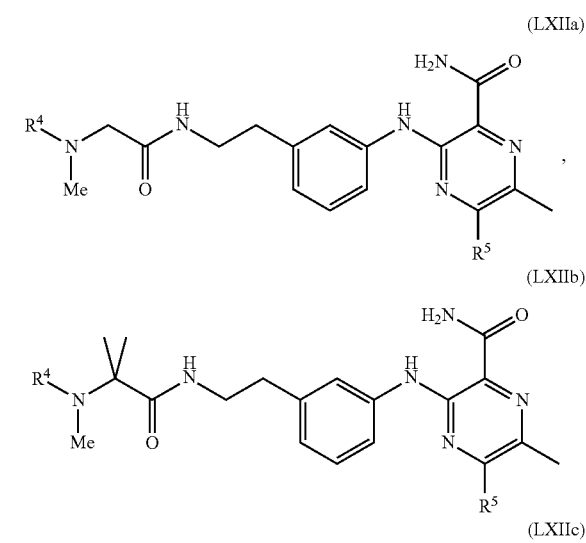

(LXIIc)

(LXIId)

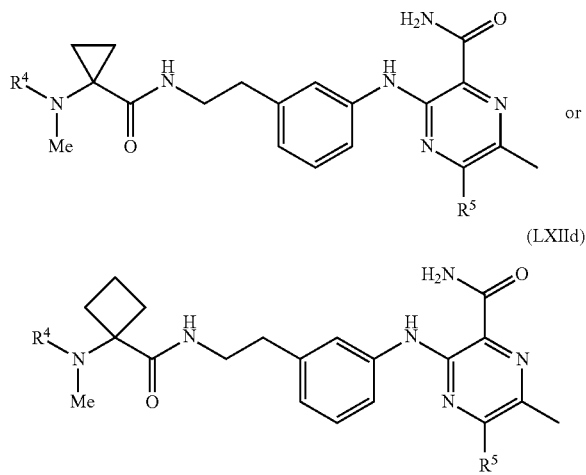

or a stereoisomer thereof, or a pharmaceutically acceptable salt thereof.

In certain embodiments, the compound is according to Formula (LXIIIa), or (LXIIIb):

(LXIIIa)

(LXIIIb)

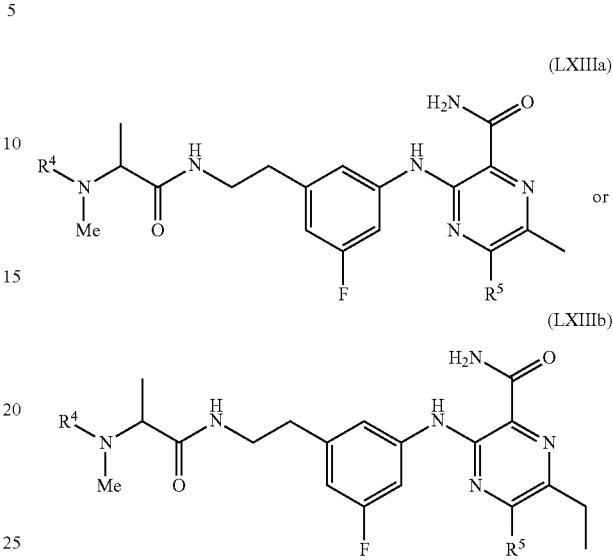

or a stereoisomer thereof, or a pharmaceutically acceptable salt thereof.

In certain embodiments, $R^5$ is as described for Formula P6-I. In certain embodiments, $R^5$ is cyclopropyl, Me, Et, $N(Me)_2$, or $N(i-Pr)(Me)$. In certain embodiments, $R^5$ is NHMe, $NH(CH(CH_2CH_3)_2)$, or NH(cycloalkyl) wherein the cycloalkyl is substituted with 1 or 2 fluoro groups.

In certain embodiments, with respect to Formulas (P-I), (P2-I), (I)-(LXIIIb), (P4-I)-(P4-Vb), and (P5-I')-(P5-Vd), the —$CONH_2$ group is replaced with —CON(H)Me.

Each of the following embodiments described herein, unless specified otherwise, may apply independently to each of Formulas (P-I), (P2-I), (I)-(LXIIIb), (P4-I)-(P4-Vb), and (P5-I')-(P5-Vd), above.

In certain embodiments, X is O. In certain embodiments, X is —$NR^{2a}$—. In certain embodiments, X is —$NR^{2a}$—; and $R^{2a}$ is H, Me, Et, or i-Pr. In certain embodiments, X is —$NR^{2a}$—; and $R^{2a}$ is H. In certain embodiments, X is a single bond.

In certain embodiments, $L^1$ is substituted or unsubstituted $C_1$-$C_4$ alkylene. In certain embodiments, $L^1$ is $C_2$-$C_4$ alkylene, unsubstituted or substituted with halo, hydroxy, or alkyl. In certain embodiments, $L^1$ is unsubstituted $C_1$-$C_4$ alkylene. In certain embodiments, $L^1$ is unsubstituted $C_2$-$C_4$ alkylene. In certain embodiments, $L^1$ is —$CH_2$—$CH_2$—, —$CH_2$—$CH_2$—$CH_2$—, or —$CH_2$—$CH_2$—$CH_2$—$CH_2$—. In certain embodiments, $L^1$ is —$CH_2$—$CH_2$—. In certain embodiments, $L^1$ is —$CH_2$—$CH_2$—$CH_2$—. In certain embodiments, $L^1$ is —$CH_2$—$CH_2$—$CH_2$—$CH_2$—.

In certain embodiments, $L^2$ is a single bond. In certain embodiments, $L^2$ is —$C(O)$-$L^3$-$NR^{2b}$—. In certain embodiments, $L^2$ is —$C(O)$-$L^3$-NH—. In certain embodiments, $L^2$ is —$C(O)$-$L^3$-$N(CH_3)$—.

In certain embodiments, $L^3$ is substituted or unsubstituted $C_1$-$C_4$ alkylene; and the substituents on each of alkylene are independently selected from one or more halo, CN, $C_{1-4}$ alkyl, hydroxy, and $C_{1-4}$ alkoxy. In certain embodiments, $L^3$ is unsubstituted $C_1$-$C_4$alkylene. In certain embodiments, $L^3$ is unsubstituted $C_2$-$C_4$alkylene. In certain embodiments, $L^3$ is unsubstituted $C_1$alkylene. In certain embodiments, $L^3$ is unsubstituted $C_2$alkylene. In certain embodiments, $L^3$ is unsubstituted $C_3$alkylene.

In certain embodiments, $R^{2b}$ is $C_1$-$C_4$alkyl. In certain embodiments, $R^{2b}$ is methyl.

In certain embodiments, $R^4$ is —C(O)—C($R^{6a}$)=C($R^{6b}$)($R^{6c}$. In certain embodiments, $R^4$ is —C(O)—CH=CH$_2$. In certain embodiments, $R^4$ is —S(O)—C($R^{6a}$)=C($R^{6b}$)($R^{6c}$, or —S(O)$_2$—C($R^{6a}$)=C($R^{6b}$)($R^{6c}$) In certain embodiments, $R^4$ is —S(O)$_2$—CH=CH$_2$. In certain embodiments, $R^4$ is —C(O)—C($R^{6a}$)=C($R^{6b}$)($R^{6c}$).

In certain embodiments, $R^4$ is —C(O)—CH=CH$_2$. In certain embodiments, $R^4$ is —S(O)$_2$—C($R^{6a}$)=C($R^{6b}$)($R^{6c}$. In certain embodiments, $R^4$ is —S(O)$_2$—CH=CH$_2$.

In certain embodiments, $R^7$ is hydrogen.

In certain embodiments, each of $R^{6a}$, $R^{6b}$, and $R^{6c}$ is H. In certain embodiments, each of $R^{6a}$ and $R^{6b}$ is H or F; and $R^{6c}$ is substituted or unsubstituted alkyl. In certain embodiments, one of $R^{6a}$ and $R^{6b}$ is CN, the other is H; and $R^{6c}$ is H, or substituted or unsubstituted alkyl. In certain embodiments, each of $R^{6a}$ and $R^{6b}$ is H; and $R^{6c}$ is unsubstituted alkyl. In certain embodiments, each of $R^{6a}$ and $R^{6b}$ is H; and $R^{6c}$ is Me, or Et. In certain embodiments, each of $R^{6a}$ and $R^{6b}$ is H; and $R^{6c}$ is alkyl substituted with amino, alkylamino or dialkylamino. In certain embodiments, each of $R^{6a}$ and $R^{6b}$ is H; and $R^{6c}$ is alkyl substituted with NH$_2$, NHCH$_3$ or N(CH$_3$)$_2$. In certain embodiments, each of $R^{6a}$ and $R^{6b}$ is H; and $R^{6c}$ is alkyl substituted with dimethylamino. In certain embodiments, each of $R^{6a}$ and $R^{6b}$ is H; and $R^{6c}$ is —CH$_2$NMe$_2$. In certain embodiments, $R^{6a}$ and $R^{6b}$ form a bond (thereby forming a triple bond); and $R^{6c}$ is H or substituted or unsubstituted alkyl. In certain embodiments, $R^{6a}$ and $R^{6b}$ form a bond (thereby forming a triple bond); and $R^{6c}$ is Me. In certain embodiments, each of $R^{6a}$ and $R^{6b}$ is H; and $R^{6c}$ is —(CH$_2$)$_q$-heterocycloalkyl; and q is 1, 2, 3, or 4. In certain embodiments, each of $R^{6a}$ and $R^{6b}$ is H; and $R^{6c}$ is —(CH$_2$)$_q$-heterocycloalkyl; and q is 1. In certain embodiments, each of $R^{6a}$ and $R^{6b}$ is H; and $R^{6c}$ is —(CH$_2$)$_q$-heterocycloalkyl; and q is 2. In certain embodiments, each of $R^{6a}$ and $R^{6b}$ is H; and $R^{6c}$ is —(CH$_2$)$_q$-heterocycloalkyl; and q is 3. In certain embodiments, heterocycloalkyl is substituted or unsubstituted azetidinyl, pyrrolidinyl, piperidinyl, or azepinyl. In certain embodiments, heterocycloalkyl is azetidin-1-yl, pyrrolidin-1-yl, piperidin-1-yl, or azepin-1-yl. In certain embodiments, heterocycloalkyl is substituted azetidin-1-yl substituted with 1 or 2 fluoro groups. In certain embodiments, each of $R^{6a}$ and $R^{6b}$ is H or Me; and $R^{6c}$ is —CH$_2$-azetidin-1-yl, —CH$_2$-pyrrolidin-1-yl, or —CH$_2$-piperidin-1-yl. In certain embodiments, each of $R^{6a}$ and $R^{6b}$ is H or Me; and $R^{6c}$ is —CH$_2$-azetidin-1-yl wherein the azetidin-1-yl is substituted with 1 or 2 fluoro groups. In certain embodiments, one of $R^{6a}$, and $R^{6b}$ is F; and $R^{6c}$ is H or unsubstituted alkyl. In certain embodiments, one of $R^{6a}$, and $R^{6b}$ is F; and $R^{6c}$ is Me, or Et. In certain embodiments, one of $R^{6a}$, and $R^{6b}$ is F; and $R^{6c}$ is alkyl substituted with amino, alkylamino or dialkylamino. In certain embodiments, one of $R^{6a}$, and $R^{6b}$ is F; the other is H; and $R^{6c}$ is H. In certain embodiments, $R^{6c}$ is alkyl substituted with substituted amino, and wherein the substitution on amino is selected from alkyl, cycloalkyl or heterocycloalkyl. In certain embodiments, $R^{6c}$ is alkyl substituted with N-cycloalkyl-N-alkyl-amino. In certain embodiments, $R^{6c}$ is alkyl substituted with N-heterocycloalkyl-N-alkyl-amino. In certain embodiments, $R^{6c}$ is alkyl substituted with N-cyclopropyl-N-alkyl-amino. In certain embodiments, $R^{6c}$ is alkyl substituted with N-cyclopropyl-N-methyl-amino. In certain embodiments, $R^{6c}$ is alkyl substituted with N-cyclopropyl-N-ethyl-amino. In certain embodiment with respect to $R^{6c}$ alkyl is methyl or ethyl. In certain embodiments, $R^{6c}$ is methyl substituted with N-cyclopropyl-N-methyl-amino.

In certain embodiments, $R^4$ is —C(O)—CH=CH$_2$, —C(O)—C(F)=CH$_2$, or —S(O)$_2$—CH=CH$_2$.

In certain embodiments, $R^{1a}$ is Me, Et, or i-Pr. In certain embodiments, $R^{1a}$ is Me.

In certain embodiments, $R^4$ is unsubstituted epoxide. In certain embodiments, $R^4$ is epoxide substituted with alkyl. In certain embodiments, $R^4$ is epoxide substituted with Me, Et, i-Pr, or n-Pr.

In certain embodiments, $R^{6a}$ is H. In certain embodiments, $R^{6a}$ is F. In certain embodiments, $R^{6a}$ is CN.

In certain embodiments of Formula (P-I), (P2-I), (I), (LXIa)-(LXIIIb), (P4-I)-(P4-Vb), or (P5-I')-(P5-Vd), $R^4$ is —C(O)—CR$^{6a}$=C($R^{6b}$)$R^{6c}$. In certain embodiments of Formula (P-I), (P2-I), (I), (LXIa)-(LXIIIb), (P4-I)-(P4-Vb), or (P5-I')-(P5-Vd), $R^4$ is —C(O)—CH=C(H)$R^{6c}$. In certain embodiments of Formula (P-I), (P2-I), (I), (LXIa)-(LXIIIb), (P4-I)-(P4-Vb), or (P5-I')-(P5-Vd), $R^4$ is —C(O)— CF=C($R^{6b}$)$R^{6c}$. In certain embodiments, $R^4$ is —C(O)—CF=CH$_2$. In certain embodiments of Formula (P-I), (P2-I), (I), (LXIa)-(LXIIIb), (P4-I)-(P4-Vb), or (P5-I')-(P5-Vd), $R^4$ is —C(O)—CH=CH$_2$. In certain embodiments of Formula (P-I), (P2-I), (I), (LXIa)-(LXIIIb), (P4-I)-(P4-Vb), or (P5-I')-(P5-Vd), $R^4$ is —C(O)—C≡CR$^{6c}$. In certain embodiments of Formula (P-I), (P2-I), (I), (LXIa)-(LXIIIb), (P4-I)-(P4-Vb), or (P5-I')-(P5-Vd), $R^4$ is —C(O)—C≡CH. In certain embodiments of Formula (P-I), (P2-I), (I), (LXIa)-(LXIIIb), (P4-I)-(P4-Vb), or (P5-I')-(P5-Vd), $R^4$ is —C(O)—C≡C—CH$_3$. In certain embodiments of Formula (P-I), (P2-I), (I), (LXIa)-(LXIIIb), (P4-I)-(P4-Vb), or (P5-I')-(P5-Vd), $R^4$ is —C(O)—CH=CH—CH$_2$—NMe$_2$. In certain embodiments of Formula (P-I), (P2-I), (I), (LXIa)-(LXIIIb), (P4-I)-(P4-Vb), or (P5-I')-(P5-Vd), $R^4$ is —C(O)—CH=CH—CH$_2$—NHMe. In certain embodiments of Formula (P-I), (P2-I), (I), (LXIa)-(LXIIIb), (P4-I)-(P4-Vb), or (P5-I')-(P5-Vd), $R^4$ is —C(O)—CH=CH—CH$_2$-heterocycloalkyl wherein the heterocycloalkyl has 1 nitrogen and is optionally substituted. In certain embodiments of Formula (P-I), (P2-I), (I), (LXIa)-(LXIIIb), (P4-I)-(P4-Vb), or (P5-I')-(P5-Vd), $R^4$ is —C(O)—CH=CH—CH$_2$-heterocycloalkyl wherein the heterocycloalkyl is N-linked and is optionally substituted. In certain embodiments of Formula (P-I), (P2-I), (I), (LXIa)-(LXIIIb), (P4-I)-(P4-Vb), or (P5-I')-(P5-Vd), $R^4$ is —C(O)—CH=CH—CH$_2$-heterocycloalkyl having 1 nitrogen. In certain embodiments of Formula (P-I), (P2-I), (I), (LXIa)-(LXIIIb), (P4-I)-(P4-Vb), or (P5-I')-(P5-Vd), $R^4$ is

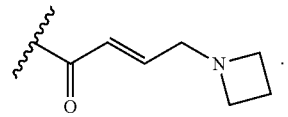 [SMILES: *C(=O)/C=C/CN1CCC1]

In certain embodiments of Formula (P-I), (P2-I), (I), (LXIa)-(LXIIIb), (P4-I)-(P4-Vb), or (P5-I')-(P5-Vd), $R^4$ is

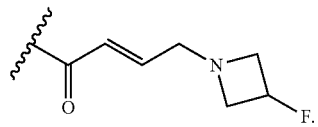 [SMILES: *C(=O)/C=C/CN1CC(F)C1]

In certain embodiments, R⁴ is

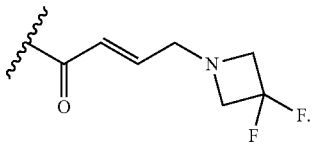 [SMILES: *C(=O)/C=C/CN1CC(F)(F)C1]

In certain embodiments, $R^{6c}$ is H. In certain embodiments, $R^{6c}$ is substituted or unsubstituted alkyl. In certain embodiments, $R^{6c}$ is H, or substituted or unsubstituted alkyl. In certain embodiments, $R^{6c}$ is unsubstituted alkyl. In certain embodiments, $R^{6c}$ is Me, or Et.

In certain embodiments, $R^{6c}$ is alkyl substituted with amino, alkylamino or dialkylamino. In certain embodiments, $R^{6c}$ is alkyl substituted with dimethylamino. In certain embodiments, $R^{6c}$ is —CH₂NMe₂. In certain embodiments, $R^{6c}$ is H or substituted or unsubstituted alkyl. In certain embodiments, $R^{6c}$ is Me. In certain embodiments, $R^{6c}$ is —(CH₂)$_q$-heterocycloalkyl; and q is 1, 2, 3, or 4. In certain embodiments, $R^{6c}$ is —(CH₂)$_q$-heterocycloalkyl; and q is 1. In certain embodiments, $R^{6c}$ is —(CH₂)$_q$-heterocycloalkyl; and q is 2. In certain embodiments, $R^{6c}$ is —(CH₂)$_q$-heterocycloalkyl; and q is 3.

In certain embodiments, the compound is according to Formula (XLIVa) or (XLIVc). In certain embodiments, the compound is according to Formula (XLVIe) or (XLVIq). In certain embodiments, the compound is according to Formula (XLVIIIa) or (XLVIIIc). In certain embodiments, the compound is according to Formula (XLIIIa) or (XLIIIc). In certain embodiments, the compound is according to Formula (XLIVa) or (XLIVc); and R⁴ is —C(O)—CH═CH₂. In certain embodiments, the compound is according to Formula (XLIVa) or (XLIVc); and R⁴ is —C(O)—CH═CHR$^{6c}$. In particular embodiments of Formula (XLIVa) or (XLIVc), R⁴ is —C(O)—CH═CH—CH₂—NMe₂.

In certain embodiments, the compound is according to Formula (XLVIe) or (XLVIq); and R⁴ is —C(O)—CH═CH₂. In certain embodiments, the compound is according to Formula (XLVIe) or (XLVIq); and R⁴ is —C(O)—CH═CHR$^{6c}$. In particular embodiments, of Formula (XLVIe) or (XLVIq), R⁴ is —C(O)—CH═CH—CH₂—NMe₂. In certain embodiments, the compound is according to Formula (XLVIIIa) or (XLVIIIc); and R⁴ is —C(O)—CH═CH₂. In certain embodiments, the compound is according to Formula (XLVIIIa) or (XLVIIIc); and R⁴ is —C(O)—CH═CHR$^{6c}$. In particular embodiments of Formula (XLVIIIa) or (XLVIIIc), R⁴ is —C(O)—CH═CH—CH₂—NMe₂. In certain embodiments, the compound is according to Formula (XLIIIa) or (XLIIIc); and R⁴ is —C(O)—CH═CH₂. In certain embodiments, the compound is according to Formula (XLIIIa) or (XLIIIc); and R⁴ is —C(O)—CH═CHR$^{6c}$. In particular embodiments of Formula (XLIIIa) or (XLIIIc), R⁴ is —C(O)—CH═CH—CH₂—NMe₂.

In some embodiments, with respect to the compounds of Formula (P-I), (P4-I), (P2-I), (XLIIIa), (XLIIIb), (XLIIIc), (XLIIId), (XLIVa), (XLIVb), (XLIVc), (XLIVd), Formula (XLVIa), (XLVIb), (XLVIc), (XLVId), (XLVIe), (XLVIf), (XLVIm), (XLVIn), (XLVIo), (XLVIp), (XLVIq), (XLVIr), (XLVIIIa), (XLVIIIc), (XLVIIIe), (XLVIIIg), (LXa), (LXb), (LXc), (LXd), (LXe), (LXf), (LXIa), (LXIb), (LXIc), (LXId), (LXIIa), (LXIIb), (LXIIc), (LXIId), (LXIIIa), or (LXIIIb), R⁴ is —C(O)— B—C(R$^{6a}$)═C(R$^{6b}$)—C(O)—R$^{6c}$, —S(O)—B—C(R$^{6a}$)═C(R$^{6b}$)—C(O)—R$^{6c}$, —S(O)₂—B—C(R$^{6a}$)═C(R$^{6b}$)—C(O)—R$^{6c}$, —B—C(R$^{6a}$)═C(R$^{6b}$)—C(O)—R$^{6c}$, —B—C(R$^{6a}$)═C(R$^{6b}$)—S(O)—R$^{6c}$, —B—C(R$^{6a}$)═C(R$^{6b}$)—S(O)₂—R$^{6c}$, —B—C(R$^{6a}$)═C(R$^{6b}$)—P(O)—R$^{6a}$R$^{6b}$; or —B—C(R$^{6a}$)═C(R$^{6b}$)—P(O)—OR$^{6a}$OR$^{6b}$; B is substituted or unsubstituted $C_{1-4}$ alkylene, substituted or unsubstituted cycloalkyl, or substituted or unsubstituted heterocycloalkyl; and R$^{6c}$ is substituted or unsubstituted alkoxy, substituted or unsubstituted amino, substituted or unsubstituted heterocycloalkyl, having 1-2 heteroatoms independently selected from nitrogen, oxygen, and sulfur. In certain embodiments, R⁴ is —C(O)—B—C(R$^{6a}$)═C(R$^{6b}$)—C(O)—R$^{6c}$, —S(O)—B—C(R$^{6a}$)═C(R$^{6b}$)—C(O)—R$^{6c}$, or —S(O)₂—B—C(R$^{6a}$)═C(R$^{6b}$)—C(O)—R$^{6c}$. In certain embodiments, R⁴ is —B—C(R$^{6a}$)═C(R$^{6b}$)—C(O)—R$^{6c}$, —B—C(R$^{6a}$)═C(R$^{6b}$)—S(O)—R$^{6c}$, —B—C(R$^{6a}$)═C(R$^{6b}$)—S(O)₂—R$^{6c}$. In certain embodiments, R⁴ is —B—C(R$^{6a}$)═C(R$^{6b}$)—P(O)—R$^{6a}$R$^{6b}$; or —B—C(R$^{6a}$)═C(R$^{6b}$)—P(O)—OR$^{6a}$OR$^{6b}$. In particular embodiments, R⁴ is —B—C(R$^{6a}$)═C(R$^{6b}$)—C(O)—R$^{6c}$. In certain embodiments, R⁴ is —C(O)—CH═CH—CH₂—NMe₂. In certain embodiments, R⁴ is —C(O)—CH═CH—CH₂—NHMe. In certain embodiments, R$^{6c}$ is substituted or unsubstituted alkoxy. In certain embodiments, R$^{6c}$ is substituted or unsubstituted OMe, OEt, O-i-Pr, or O-t-Bu. In certain embodiments, R$^{6c}$ is OMe, OEt, O-i-Pr, or O-t-Bu. In certain embodiments, R$^{6c}$ is substituted or unsubstituted heterocycloalkyl. In certain embodiments, R$^{6c}$ is substituted or unsubstituted azetidinyl, pyrrolidinyl, piperidinyl, or azepinyl. In certain embodiments, R$^{6c}$ is azetidin-1-yl, pyrrolidin-1-yl, piperidin-1-yl, or azepin-1-yl. In certain embodiments, R$^{6c}$ is piperidin-1-yl. In certain embodiments, R$^{6c}$ is substituted or unsubstituted amino. In certain embodiments, R$^{6c}$ is substituted amino. In certain embodiments, R$^{6c}$ is dialkylamino. In certain embodiments, R$^{6c}$ is dimethylamino, diethylamino, N-isopropyl-N-methylamino, or N-isopropyl-N-ethylamino. In certain embodiments, R$^{6c}$ is dimethylamino.

In some preferred embodiments, provided herein is a compound according to Formula (P6-I) having the structure (P6-I):

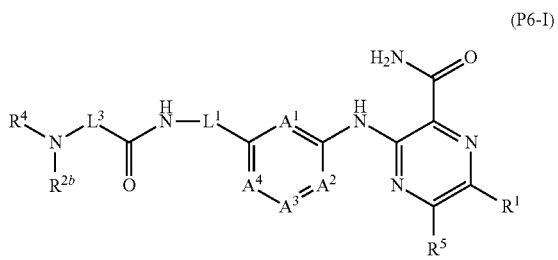

or a stereoisomer thereof, or a pharmaceutically acceptable salt thereof,
wherein: each $A^1$, $A^2$, $A^3$, and $A^4$ is independently —C(R⁷)═, or —N═; provided no more than two of $A^1$, $A^2$, $A^3$, and $A^4$ is N;
each $L^1$ and $L^3$ is independently substituted or unsubstituted $C_1$-$C_4$ alkylene;
$R^1$ is H, halo, CN, substituted or unsubstituted $C_{1-6}$ alkyl, substituted or unsubstituted alkoxy, substituted or unsubstituted alkenyl, substituted or unsubstituted alkynyl, substituted or unsubstituted cycloalkyl, or substituted or unsubstituted heterocycloalkyl;

$R^{2b}$ is independently H or $C_1$-$C_4$ alkyl;

$R^4$ is i) —C(O)—C($R^{6a}$)=C($R^{6b}$)($R^{6c}$), ii) —S(O)—C($R^{6a}$)=C($R^{6b}$)($R^{6c}$), iii) —S(O)$_2$—C($R^{6a}$)=C($R^{6b}$)($R^{6c}$), or iv) substituted or unsubstituted epoxide;

$R^5$ is H, Cy, CN, halo, substituted or unsubstituted $C_{1-6}$ alkyl, substituted or unsubstituted haloalkyl, substituted or unsubstituted $C_{1-6}$ alkoxy, substituted or unsubstituted haloalkoxy, substituted or unsubstituted alkylamino;

Cy is substituted or unsubstituted cycloalkyl, or substituted or unsubstituted heterocycloalkyl;

each $R^{6a}$ and $R^{6b}$ is independently H, halo, CN, or $C_{1-6}$ alkyl; or $R^{6a}$ and $R^{6b}$ are joined together to form a bond; $R^{6c}$ is H, halo, CN, or $C_{1-6}$ alkyl, wherein the $C_{1-6}$ alkyl is unsubstituted or substituted with one or more groups selected from substituted or unsubstituted amino, substituted or unsubstituted hydroxy, and substituted or unsubstituted heterocycloalkyl having 1-2 heteroatoms independently selected from nitrogen, oxygen, and sulfur; and each $R^7$ is independently H, halo, CN, substituted or unsubstituted $C_{1-6}$ alkyl, substituted or unsubstituted alkoxy, or substituted or unsubstituted heterocycloalkyl.

In some embodiments, with respect to the compounds of any of the formulas described herein, R is H, Cy, CN, halo, $C_{1-6}$ alkyl, $C_{1-6}$ alkoxy, or $C_{1-6}$ alkylamino; Cy is cycloalkyl, or heterocycloalkyl; each of Cy, alkyl, alkoxy, and alkylamino is unsubstituted or substituted with one or more halo, CN, $C_{1-4}$ alkyl, hydroxy, amino, alkylamino, or dialkylamino, substituted or unsubstituted cycloalkyl, substituted or unsubstituted heterocycloalkyl, substituted or unsubstituted aryl, substituted or unsubstituted heteroaryl, or $C_{1-4}$ alkoxy. In certain embodiments, the substituents on each cycloalkyl, heterocycloalkyl, aryl, and heteroaryl is selected from one or more halo, CN, $C_{1-4}$ alkyl, hydroxy, and $C_{1-4}$ alkoxy.

In certain embodiments, $R^5$ is substituted $C_{1-6}$ alkyl, substituted $C_{1-6}$ alkoxy, or substituted alkylamino; and the substitution is other than substituted or unsubstituted cycloalkyl or substituted or unsubstituted heterocycloalkyl. In certain embodiments, $R^5$ is unsubstituted cycloalkyl. In certain embodiments, $R^5$ is cycloalkyl is substituted with hydroxy, alkoxy, halo, or $C_1$-$C_6$ alkyl. In certain embodiments, $R^5$ is unsubstituted cycloalkyl. In certain embodiments, $R^5$ is heterocycloalkyl is substituted with hydroxy, alkoxy, halo, or $C_1$-$C_6$ alkyl.

In certain embodiments, $R^5$ is —NHC(O)R; and $R^5$ is $C_1$-$C_6$ alkyl.

In certain embodiments, each of $A^1$, $A^2$, and $A^4$, is CH, and $A^3$ is $CR^7$. In certain embodiments, each of $A^1$, and $A^2$ is CH; $A^3$ is $CR^7$, and $A^4$ is N. In certain embodiments, each of $A^1$, $A^2$, and $A^3$, is CH, and $A^4$ is $CR^7$. In certain embodiments, $A^4$ is $CR^7$; and $R^7$ is H, halo, alkyl, halolalkyl, or alkoxy.

In certain embodiments, $A^4$ is $CR^7$; and $R^7$ is H, F, Me, Et, Cl, $CF_3$, or OMe. In certain embodiments, $A^3$ is $CR^7$; and $R^7$ is H, halo, alkyl, halolalkyl, or alkoxy. In certain embodiments, $A^3$ is $CR^7$; and $R^7$ is H, F, Me, Et, Cl, $CF_3$, or OMe.

In certain embodiments, the compound is according to Formula (P6-IIa) or (P6-IIb):

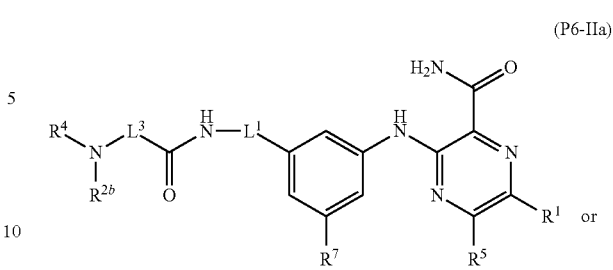

(P6-IIa)

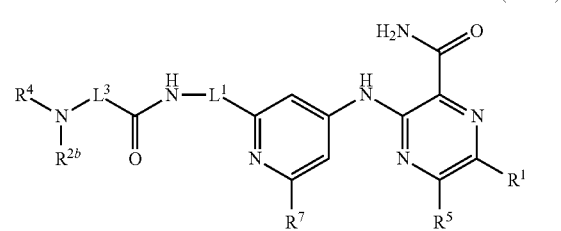

(P6-IIb)

or a stereoisomer thereof, or a pharmaceutically acceptable salt thereof.

In certain embodiments, $L^1$ is substituted or unsubstituted $C_1$-$C_4$ alkylene. In certain embodiments, the substituents on each of alkylene are independently selected from one or more halo, CN, $C_{1-4}$ alkyl, hydroxy, and $C_{1-4}$alkoxy. In certain embodiments, $L^1$ is —CH$_2$—CH$_2$—, —C(Me)H—CH$_2$—, or —CH$_2$—C(Me)H—. In certain embodiments, $L^1$ is —CH$_2$—C(Me)H—.

In certain embodiments, the compound is according to Formula (P6-IIIa), (P6-IIIb), (P6-IIIc) or (P6-IIId):

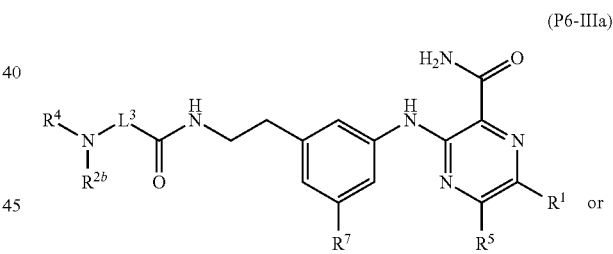

(P6-IIIa)

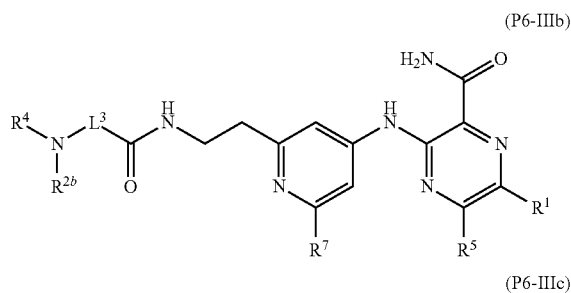

(P6-IIIb)

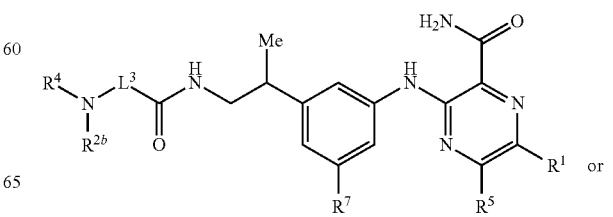

(P6-IIIc)

-continued (P6-IIId)

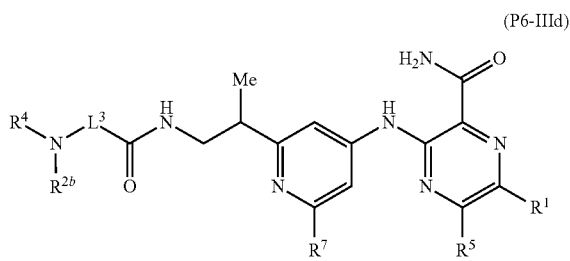

or a stereoisomer thereof, or a pharmaceutically acceptable salt thereof.

In certain embodiments, $R^1$ is H, halo, CN, substituted or unsubstituted $C_{1-6}$ alkyl, substituted or unsubstituted alkoxy, substituted or unsubstituted alkenyl, substituted or unsubstituted alkynyl, substituted or unsubstituted cycloalkyl, or substituted or unsubstituted heterocycloalkyl, having 1-2 heteroatoms independently selected from nitrogen, oxygen, and sulfur. In certain embodiments, the substituents on each of alkyl, alkoxy, alkenyl, alkynyl, cycloalkyl and heterocycloalkyl are selected from one or more halo, CN, $C_{1-4}$ alkyl, hydroxy, and $C_{1-4}$ alkoxy. In certain embodiments, $R^1$ is H, Me, or Et.

In certain embodiments, the compound is according to Formula (P6-IVa), (P6-IVb), (P6-IVc) or (P6-IVd):

(P6-IVa)

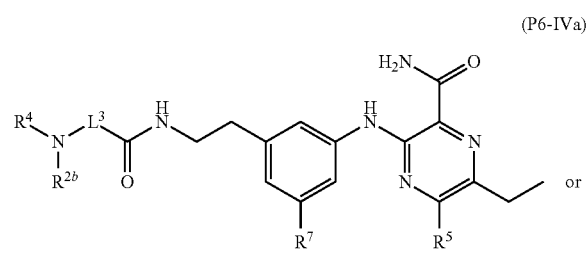

(P6-IVb)

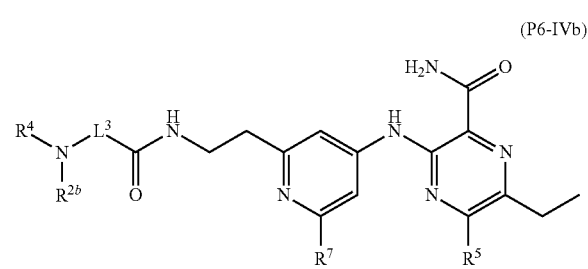

(P6-IVc)

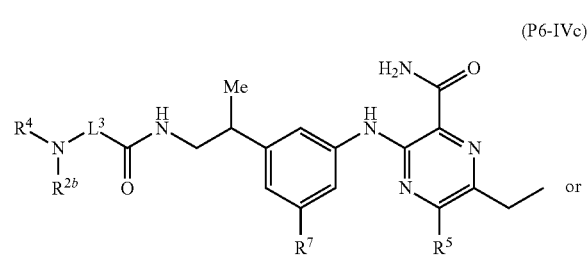

-continued (P6-IVd)

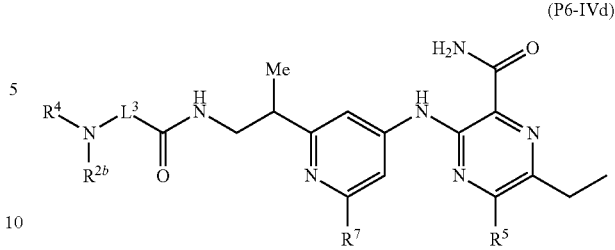

or a stereoisomer thereof, or a pharmaceutically acceptable salt thereof.

In certain embodiments, $L^3$ is substituted or unsubstituted $C_1$-$C_4$ alkylene. In certain embodiments, the substituents on each of alkylene are independently selected from one or more halo, CN, $C_{1-4}$alkyl, hydroxy, and $C_{1-4}$alkoxy. In certain embodiments, $L^3$ is —CH$_2$—, or —C(Me)H—. In certain embodiments, $L^3$ is —C(Me)$_2$-, —CH$_2$—CH$_2$—, —C(Me)H—CH$_2$—, —CH$_2$—C(Me)H—, or

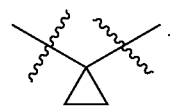

In certain embodiments, $R^{2b}$ is H, or Me.

In certain embodiments, each $R^7$ is independently H, halo, CN, substituted or unsubstituted $C_{1-6}$ alkyl, substituted or unsubstituted alkoxy, or substituted or unsubstituted heterocycloalkyl, having 1-2 heteroatoms independently selected from nitrogen, oxygen, and sulfur. In certain embodiments, the substituents on each of alkyl, alkoxy and heterocycloalkyl are selected from one or more halo, CN, $C_{1-4}$ alkyl, hydroxy, and $C_{1-4}$ alkoxy.

In certain embodiments, $R^7$ is H, F, Me, Et, Cl, CF$_3$, or OMe.

In certain embodiments, $R^5$ is H, Cy, CN, halo, $C_{1-6}$ alkyl, $C_{1-6}$ alkoxy, or $C_{1-6}$ alkylamino; each of Cy, alkyl, alkoxy, and alkylamino is unsubstituted or substituted with one or more halo, CN, $C_{1-4}$ alkyl, hydroxy, amino, alkylamino, dialkylamino, substituted or unsubstituted cycloalkyl, substituted or unsubstituted heterocycloalkyl, having 1-2 heteroatoms independently selected from nitrogen, oxygen, and sulfur; substituted or unsubstituted aryl, substituted or unsubstituted heteroaryl, or $C_{1-4}$ alkoxy. In certain embodiments, the substituents on each of cycloalkyl, heterocycloalkyl, aryl, and heteroaryl are selected from one or more halo, CN, $C_{1-4}$ alkyl, hydroxy, and $C_{1-4}$ alkoxy. In certain embodiments, Cy is cycloalkyl. In certain embodiments, Cy is heterocycloalkyl.

In certain embodiments, $R^5$ is Cy, unsubstituted or substituted with one or more halo, CN, $C_{1-4}$ alkyl, hydroxy, amino, alkylamino, dialkylamino, substituted or unsubstituted cycloalkyl, substituted or unsubstituted heterocycloalkyl, substituted or unsubstituted aryl, substituted or unsubstituted heteroaryl, or $C_{1-4}$ alkoxy. In certain embodiments, the substituents on each of cycloalkyl, heterocycloalkyl, aryl, and heteroaryl are selected from one or more halo, CN, $C_{1-4}$ alkyl, hydroxy, and $C_{1-4}$ alkoxy; and Cy is cycloalkyl, or heterocycloalkyl.

In certain embodiments, $R^5$ is unsubstituted or substituted $C_{1-6}$ alkyl, unsubstituted or substituted $C_{1-6}$ alkoxy, or unsubstituted or substituted alkylamino. In certain embodiments, each of alkyl, alkoxy, and alkylamino is unsubstituted or substituted with one or more halo, CN, $C_{1-4}$ alkyl, hydroxy, amino, alkylamino, dialkylamino, substituted or unsubstituted cycloalkyl, substituted or unsubstituted heterocycloalkyl, substituted or unsubstituted aryl, substituted or unsubstituted heteroaryl, or $C_{1-4}$ alkoxy. In certain embodiments, the substituents on each of cycloalkyl, heterocycloalkyl, aryl, and heteroaryl are selected from one or more halo, CN, $C_{1-4}$ alkyl, hydroxy, and $C_{1-4}$ alkoxy.

In certain embodiments, $R^5$ is Cy, CN, halo, substituted or unsubstituted $C_{1-6}$ alkyl, substituted or unsubstituted haloalkyl, substituted or unsubstituted $C_{1-6}$ alkoxy, substituted or unsubstituted haloalkoxy, or substituted or unsubstituted alkylamino.

In certain embodiments, $R^5$ is Me, Et, i-Pr, n-Pr, n-Bu, i-Bu, t-Bu, sec-Bu, substituted or unsubstituted cyclopropyl, substituted or unsubstituted cyclobutyl, substituted or unsubstituted cyclopentyl, substituted or unsubstituted cyclohexyl, Cl, F, CN, $CF_3$, OMe, OEt, O-i-Pr, —$OCF_3$, N,N-dimethylamino, N,N-diethylamino, N,N-diisopropylamino, N-ethyl-N-methylamino, N-iso-propyl-N-methylamino, N-iso-propyl-N-ethylamino, N-isopropylamino, N-ethylamino, N-methylamino, N-n-propylamino, substituted or unsubstituted 1-azetidinyl, substituted or unsubstituted 1-pyrrolidinyl, substituted or unsubstituted 1-piperidinyl, or substituted or unsubstituted 1-morpholinyl. In certain embodiments, the substituents on each of cyclopropyl, cyclobutyl, cyclopentyl, and cyclohexyl are selected from one or more halo, CN, $C_{1-4}$ alkyl, hydroxy, and $C_{1-4}$ alkoxy.

In certain embodiments, $R^5$ is Me, Et, n-Pr, i-Pr, i-Bu, cyclopropyl, N,N-dimethyl, N-ethyl-N-methyl, N-isopropylamino, N-isopropyl-N-methylamino, methoxy, ethoxy, or i-propyloxy. In certain embodiments, $R^5$ is cyclopropyl. In certain embodiments, $R^5$ is Me. In certain embodiments, $R^5$ is N-isopropyl-N-methylamino.

In certain embodiments, $R^4$ is —C(O)—C($R^{6a}$)=C($R^{6b}$)($R^{6c}$)

In certain embodiments, each $R^{6a}$ and $R^{6b}$ is independently H, halo, CN, or $C_{1-6}$ alkyl; or $R^{6a}$ and $R^{6b}$ are joined together to form a bond; $R^{6c}$ is H, halo, CN, or $C_{1-6}$ alkyl, wherein the $C_{1-6}$ alkyl is unsubstituted or substituted with one or more groups selected from substituted or unsubstituted amino, hydroxy, substituted or unsubstituted $C_{1-6}$ alkoxy, and substituted or unsubstituted heterocycloalkyl having 1-2 heteroatoms independently selected from nitrogen, oxygen, and sulfur. In certain embodiments, the substituents on each of amino, alkoxy and heterocycloalkyl are selected from one or more halo, CN, $C_{1-4}$alkyl, hydroxy, and $C_{1-4}$alkoxy.

In certain embodiments, each of $R^{6a}$, $R^{6b}$, and $R^{6c}$ is H.

In certain embodiments, $R^{6c}$ is alkyl substituted with amino, alkylamino or dialkylamino. In certain embodiments, each of $R^{6a}$ and $R^{6b}$ is H; and $R^{6c}$ is alkyl substituted with amino, alkylamino or dialkylamino.

In certain embodiments, $R^{6a}$ and $R^{6b}$ form a bond; and $R^{6c}$ is H or substituted or unsubstituted alkyl. In certain embodiment, the substituents on alkyl are selected from one or more halo, CN, $C_{1-4}$ alkyl, hydroxy, $C_{1-4}$alkoxy, and heterocycloalkyl, having 1-2 heteroatoms independently selected from nitrogen, oxygen, and sulfur. In certain embodiments, $R^{6a}$ and $R^{6b}$ form a bond; and $R^{6c}$ is Me.

In certain embodiments, each of $R^{6a}$ and $R^{6b}$ is H; and $R^{6c}$ is —$(CH_2)_q$-heterocycloalkyl; and q is 1.

In certain embodiments, heterocycloalkyl is substituted or unsubstituted azetidin-1-yl, substituted or unsubstituted pyrrolidin-1-yl, substituted or unsubstituted piperidin-1-yl, substituted or unsubstituted morpholin-1-yl, or substituted or unsubstituted azepin-1-yl. In certain embodiments, the substituents on each of azetidinyl, pyrrolidinyl, piperidinyl, morpholinyl, and azepinyl are selected from one or more halo, CN, $C_{1-4}$ alkyl, hydroxy, and $C_{1-4}$ alkoxy.

In certain embodiments, each of $R^{6a}$ and $R^{6b}$ is H or Me; and $R^{6c}$ is —$CH_2$-azetidin-1-yl, —$CH_2$-pyrrolidin-1-yl, or —$CH_2$-piperidin-1-yl.

In certain embodiments, $R^4$ is —C(O)—CH=$CH_2$, —C(O)—CH=CH—$CH_2$—NHMe, —C(O)—CH=CH—$CH_2$—$NMe_2$, —C(O)—CH=CH—$CH_2$-azetidin-1-yl, —C(O)—CH=CH—$CH_2$—(3-fluoroazetidin-1-yl), —C(O)—CH=CH—$CH_2$—(3,3-difluoroazetidin-1-yl), —C(O)—C≡CH, —C(O)—C≡C-Me, or —C(O)—C≡C—$CH_2$—$NMe_2$.

In certain embodiments, the compound is selected from any one of the compounds listed in Table 2A, or a pharmaceutically acceptable stereoisomer, salt, or solvate thereof.

In some particular embodiments, the compound is any compound selected from Compound #163, 164, 202, 203, 204, 213, 224, 226, 227, 228, 230, 232, 233, 241, 247, 252, 308, 310, 315, 501-506, 507, 508, 509, 511, 512, 513, 516A, 517, 518, 520, and 605, or a pharmaceutically acceptable salt or solvate or stereoisomer thereof.

In some particular embodiments, the compound is any compound selected from Compound #204, 252, 310, 501-506, 507, 508, 509, 511, 512, 513, 516A, 517, 518, 520, and 605.

In certain embodiments, the compound is selected from Compound ID 204, 252, 310, 509, 511, and 516A.

In certain embodiments, the compound is selected from Compound ID 308, 315, 506, 507, 508, 513, 512, 513, 517, and 520.

In certain embodiments, the compound is selected from Compound ID 515, and 516.

In some particular embodiments, the compound is any compound selected from Compound #156, 158, 159, and 160, or a pharmaceutically acceptable salt or solvate or stereoisomer thereof.

In some particular embodiments, the compound is any compound selected from Compound #142A, 204, 219, 221, 228, 232, and 246 or a pharmaceutically acceptable salt or solvate or stereoisomer thereof. In some particular embodiments, the compound is any compound selected from Compound #142A, 204, 228, and 232 or a pharmaceutically acceptable salt or solvate or stereoisomer thereof.

In some particular embodiments, the compound is Compound #142A, or a pharmaceutically acceptable salt or solvate or stereoisomer thereof. In some particular embodiments, the compound is Compound 228, or a pharmaceutically acceptable salt or solvate or stereoisomer thereof. In certain embodiments, the compound is Compound 204. In certain embodiments, the compound is Compound 506. In certain embodiments, the compound is Compound 516A. In certain embodiments, the compound is Compound ID 252. In certain embodiments, the compound is Compound ID 509. In certain embodiments, the compound is Compound 511.

In some particular embodiments, the compound is any compound selected from Table 2A or Table 2B, or a pharmaceutically acceptable salt or solvate or stereoisomer thereof.

In some particular embodiments, the compound is any of compounds listed below in Table 1, or a pharmaceutically acceptable salt or solvate or stereoisomer thereof:

TABLE 1

| ID | Name |
|---|---|
| 137 | 5-(dimethylamino)-3-[3-[2-[[(2S)-2-[[(E)-4-(dimethylamino)but-2-enoyl]-methyl-amino]propanoyl]amino]ethyl]anilino]-6-ethyl-pyrazine-2-carboxamide; |
| 138 | 5-cyclopropyl-3-[3-[2-[[(2S)-2-[[(E)-4-(dimethylamino)but-2-enoyl]-methyl-amino]propanoyl]amino]ethyl]anilino]-6-ethyl-pyrazine-2-carboxamide; |
| 142A | 3-[3-[2-[[(2S)-2-[[(E)-4-(dimethylamino)but-2-enoyl]-methyl-amino]propanoyl]amino]ethyl]anilino]-6-ethyl-5-methyl-pyrazine-2-carboxamide; |
| 143 | 5-(dimethylamino)-3-[3-[2-[[(2S)-2-[[(E)-4-(dimethylamino)but-2-enoyl]-methyl-amino]propanoyl]amino]ethyl]-5-methoxy-anilino]-6-ethyl-pyrazine-2-carboxamide; |
| 144 | 5-cyclopropyl-3-[3-[2-[[(2S)-2-[[(E)-4-(dimethylamino)but-2-enoyl]-methyl-amino]propanoyl]amino]ethyl]-5-methoxy-anilino]-6-ethyl-pyrazine-2-carboxamide; |
| 156 | 3-[3-[2-[[(2S)-2-[[(E)-4-(azetidin-1-yl)but-2-enoyl]-methyl-amino]propanoyl]amino]ethyl]anilino]-5-(dimethylamino)-6-ethyl-pyrazine-2-carboxamide; |
| 158 | 5-(dimethylamino)-3-[3-[2-[[(2S)-2-[[(E)-4-(dimethylamino)but-2-enoyl]-methyl-amino]propanoyl]amino]ethyl]-5-fluoro-anilino]-6-ethyl-pyrazine-2-carboxamide; |
| 159 | 5-cyclopropyl-3-[3-[2-[[(2S)-2-[[(E)-4-(dimethylamino)but-2-enoyl]-methyl-amino]propanoyl]amino]ethyl]-5-fluoro-anilino]-6-ethyl-pyrazine-2-carboxamide; |
| 160 | 3-[3-[2-[[(2S)-2-[but-2-ynoyl(methyl)amino]propanoyl]amino]ethyl]anilino]-5-(dimethylamino)-6-ethyl-pyrazine-2-carboxamide; |
| 162 | 5-(dimethylamino)-3-[3-[2-[[(2S)-2-[[(Z)-4-(dimethylamino)-2-fluoro-but-2-enoyl]-methyl-amino]propanoylamino]ethyl]anilino]-6-ethyl-pyrazine-2-carboxamide; |
| 163 | 3-[3-[2-[[(2S)-2-[[(E)-4-(dimethylamino)but-2-enoyl]-methyl-amino]propanoyl]amino]ethyl]-5-fluoro-anilino]-6-ethyl-5-methyl-pyrazine-2-carboxamide; |
| 164 | 3-[3-[2-[[(2S)-2-[[(E)-4-[bis(trideuteriomethyl)amino]but-2-enoyl]-methyl-amino]propanoyl]amino]ethyl]anilino]-6-ethyl-5-methyl-pyrazine-2-carboxamide; |
| 202 | 3-[3-[2-[[(2S)-2-[[(E)-4-(azetidin-1-yl)but-2-enoyl]-methyl-amino]propanoyl]amino]ethyl]anilino]-6-ethyl-5-methyl-pyrazine-2-carboxamide; |
| 203 | 5-(dimethylamino)-3-[3-[2-[[(2S)-2-[4-(dimethylamino)but-2-ynoyl-methyl-amino]propanoyl]amino]ethyl]anilino]-6-ethyl-pyrazine-2-carboxamide; |
| 204 | 3-[3-[2-[[(2S)-2-[[(E)-4-(dimethylamino)but-2-enoyl]-methyl-amino]propanoyl]-amino]ethyl]anilino]-6-ethyl-5-[isopropyl(methyl)amino]pyrazine-2-carboxamide; |
| 205 | 3-[3-[2-[[(2S)-2-[[(E)-4-(dimethylamino)but-2-enoyl]-methyl-amino]propanoyl]amino]ethyl]anilino]-6-ethyl-5-(isopropylamino)pyrazine-2-carboxamide; |
| 207 | 3-[3-[2-[[(2S)-2-[[(E)-4-(dimethylamino)but-2-enoyl]-methyl-amino]propanoyl]amino]ethyl]anilino]-5,6-dimethyl-pyrazine-2-carboxamide; |
| 208 | 5-cyclopropyl-6-ethyl-3-[3-[2-[[(2S)-2-[methyl(prop-2-enoyl)amino]propanoyl]amino]ethyl]anilino]pyrazine-2-carboxamide; |
| 209 | 3-[3-[2-[[(2S)-2-[but-2-ynoyl(methyl)amino]propanoyl]amino]ethyl]anilino]-5-cyclopropyl-6-ethyl-pyrazine-2-carboxamide; |
| 211 | 5-cyclopropyl-3-[3-[2-[2-[[(E)-4-(dimethylamino)but-2-enoyl]-methyl-amino]propanoylamino]ethyl]anilino]-6-methyl-pyrazine-2-carboxamide; |
| 213 | 5-(dimethylamino)-6-ethyl-3-[3-[2-[[(2S)-2-[methyl(prop-2-enoyl)amino]propanoyl]amino]ethyl]anilino]pyrazine-2-carboxamide; |
| 214 | 3-[3-[2-[[(2S)-2-[[(E)-4-(azetidin-1-yl)but-2-enoyl]-methyl-amino]propanoyl]amino]ethyl]anilino]-5,6-dimethyl-pyrazine-2-carboxamide; |
| 215 | 5-cyclopropyl-6-ethyl-3-[3-[2-[[(2S)-2-[2-fluoroprop-2-enoyl(methyl)amino]propanoyl]amino]ethyl]anilino]pyrazine-2-carboxamide; |
| 216 | 6-ethyl-5-methyl-3-[3-[2-[[(2S)-2-[methyl(prop-2-enoyl)amino]propanoyl]amino]ethyl]anilino]pyrazine-2-carboxamide; |
| 217 | 3-[3-[2-[[(2S)-2-[but-2-ynoyl(methyl)amino]propanoyl]amino]ethyl]anilino]-5-(dimethylamino)-6-methyl-pyrazine-2-carboxamide; |
| 218 | 5-(dimethylamino)-6-methyl-3-[3-[2-[[(2S)-2-[methyl(prop-2-enoyl)amino]propanoyl]amino]ethyl]anilino]pyrazine-2-carboxamide; |
| 219 | 5-cyclopropyl-3-[3-[2-[2-[[(E)-4-(dimethylamino)but-2-enoyl]-methyl-amino]acetyl]amino]ethyl]anilino]-6-ethyl-pyrazine-2-carboxamide; |
| 220 | 5-cyclopropyl-3-[3-[2-[1-[[(E)-4-(dimethylamino)but-2-enoyl]-methyl-amino]cyclopropanecarbonyl]amino]ethyl]anilino]-6-ethyl-pyrazine-2-carboxamide; |

TABLE 1-continued

| ID | Name |
|---|---|
| 221 | 3-[3-[2-[[(2S)-2-[[(E)-4-(dimethylamino)but-2-enoyl]-methyl-amino]propanoyl]amino]ethyl]anilino]-6-ethyl-5-[ethyl(methyl)amino]pyrazine-2-carboxamide; |
| 222 | 5-cyclopropyl-6-methyl-3-[3-[2-[[(2S)-2-[methyl(prop-2-enoyl)amino]propanoyl]amino]ethyl]anilino]pyrazine-2-carboxamide; |
| 223 | 3-[3-[2-[[1-[[(E)-4-(dimethylamino)but-2-enoyl]-methyl-amino]cyclopropanecarbonyl]amino]ethyl]anilino]-6-ethyl-5-methyl-pyrazine-2-carboxamide; |
| 224 | 5-cyclopropyl-6-ethyl-3-[3-[2-[[(2S)-2-[methyl-[(E)-4-(methylamino)but-2-enoyl]amino]propanoyl]amino]ethyl]anilino]pyrazine-2-carboxamide; |
| 225 | 5-[ethyl(methyl)amino]-6-methyl-3-[3-[2-[[(2S)-2-[methyl(prop-2-enoyl)amino]propanoyl]amino]ethyl]anilino]pyrazine-2-carboxamide; |
| 226 | 3-[3-[2-[[2-[[(E)-4-(dimethylamino)but-2-enoyl]-methyl-amino]acetyl]amino]ethyl]anilino]-6-ethyl-5-methyl-pyrazine-2-carboxamide; |
| 227 | 6-ethyl-5-methyl-3-[3-[2-[[(2S)-2-[methyl-[(E)-4-(methylamino)but-2-enoyl]amino]propanoyl]amino]ethyl]anilino]pyrazine-2-carboxamide; |
| 228 | 5-cyclopropyl-3-[3-[2-[[(2S)-2-[[(E)-4-(dimethylamino)but-2-enoyl]-methyl-amino]propanoyl]amino]ethyl]anilino]-6-methyl-pyrazine-2-carboxamide; |
| 230 | 3-[3-[2-[[(2S)-2-[[(E)-4-(azetidin-1-yl)but-2-enoyl]-methyl-amino]propanoyl]amino]ethyl]anilino]-5-(dimethylamino)-6-methyl-pyrazine-2-carboxamide; |
| 231 | 5-[isopropyl(methyl)amino]-6-methyl-3-[3-[2-[[(2S)-2-[methyl(prop-2-enoyl)amino]propanoyl]amino]ethyl]anilino]pyrazine-2-carboxamide; |
| 232 | 3-[3-[2-[[(2S)-2-[[(E)-4-(dimethylamino)but-2-enoyl]-methyl-amino]propanoyl]amino]ethyl]anilino]-5-[isopropyl(methyl)amino]-6-methyl-pyrazine-2-carboxamide; |
| 233 | 5-(dimethylamino)-3-[3-[2-[[(2S)-2-[[(E)-4-(dimethylamino)but-2-enoyl]-methyl-amino]propanoyl]amino]ethyl]anilino]-6-methyl-pyrazine-2-carboxamide; |
| 234 | 3-[3-[2-[[(2R)-2-[[(E)-4-(dimethylamino)but-2-enoyl]-methyl-amino]propanoyl]amino]ethyl]anilino]-6-ethyl-5-methyl-pyrazine-2-carboxamide; |
| 236 | 5-cyclopropyl-6-ethyl-3-[3-[2-[[(2R)-2-[methyl(prop-2-enoyl)amino]propanoyl]amino]ethyl]anilino]pyrazine-2-carboxamide; |
| 237 | 5-cyclopropyl-6-ethyl-3-[3-[2-[[(2S)-2-[prop-2-enoyl(trideuteriomethyl)amino]propanoyl]amino]ethyl]anilino]pyrazine-2-carboxamide; |
| 238 | 5,6-dimethyl-3-[3-[2-[[(2S)-2-[methyl(prop-2-enoyl)amino]propanoyl]amino]ethyl]anilino]pyrazine-2-carboxamide; |
| 239 | 5-(dimethylamino)-3-[3-[2-[[(2S)-2-[[(E)-4-(dimethylamino)but-2-enoyl]-methyl-amino]propanoyl]amino]ethyl]-5-fluoro-anilino]-6-methyl-pyrazine-2-carboxamide; |
| 240 | 6-ethyl-3-[3-[2-[[(2S)-2-[[(E)-4-(3-fluoroazetidin-1-yl)but-2-enoyl]-methyl-amino]propanoyl]amino]ethyl]anilino]-5-methyl-pyrazine-2-carboxamide; |
| 241 | 5-cyclopropyl-3-[3-[2-[[2-[[(E)-4-(dimethylamino)but-2-enoyl]-methyl-amino]acetyl]amino]ethyl]anilino]-6-methyl-pyrazine-2-carboxamide; |
| 242 | 3-[3-[2-[[(2S)-2-[[(E)-4-(azetidin-1-yl)but-2-enoyl]-methyl-amino]propanoyl]amino]ethyl]anilino]-5-cyclopropyl-6-methyl-pyrazine-2-carboxamide; |
| 243 | 3-[3-[2-[[(2S)-2-[[(E)-4-(dimethylamino)but-2-enoyl]-methyl-amino]propanoyl]amino]ethyl]anilino]-5,6-diethyl-pyrazine-2-carboxamide; |
| 244 | 3-[3-[2-[[(2S)-2-[4-(dimethylamino)but-2-ynoyl-methyl-amino]propanoyl]amino]ethyl]anilino]-6-ethyl-5-methyl-pyrazine-2-carboxamide; |
| 245 | 3-[3-[2-[[(2S)-2-[[(E)-4-(dimethylamino)but-2-enoyl]-methyl-amino]propanoyl]amino]ethyl]-5-fluoro-anilino]-5,6-dimethyl-pyrazine-2-carboxamide; |
| 246 | 3-[3-[2-[[(2S)-2-[[(E)-4-bis(trideuteriomethyl)amino]but-2-enoyl]-methyl-amino]propanoyl]amino]ethyl]anilino]-6-ethyl-5-[ethyl(methyl)amino]pyrazine-2-carboxamide; |
| 247 | 3-[3-[2-[[(2S)-2-[[(E)-4-bis(trideuteriomethyl)amino]but-2-enoyl]-methyl-amino]propanoyl]amino]ethyl]anilino]-5-[isopropyl(methyl)amino]-6-methyl-pyrazine-2-carboxamide; |
| 248 | 3-[3-[2-[[(2S)-2-[[(E)-4-bis(trideuteriomethyl)amino]but-2-enoyl]-methyl-amino]propanoyl]amino]ethyl]anilino]-5-cyclopropyl-6-methyl-pyrazine-2-carboxamide; |
| 249 | 3-[3-[2-[[(2S)-2-[[(E)-4-bis(trideuteriomethyl)amino]but-2-enoyl]-methyl-amino]propanoyl]amino]ethyl]anilino]-6-ethyl-5-[isopropyl(methyl)amino]pyrazine-2-carboxamide; |
| 250 | 3-[3-[2-[[2-[[(E)-4-(dimethylamino)but-2-enoyl]-methyl-amino]acetyl]amino]ethyl]anilino]-5-[isopropyl(methyl)amino]-6-methyl-pyrazine-2-carboxamide; |
| 251 | 3-[3-[2-[[2-[[(E)-4-(dimethylamino)but-2-enoyl]-methyl-amino]acetyl]amino]ethyl]-5-fluoro-anilino]-5,6-dimethyl-pyrazine-2-carboxamide; |

TABLE 1-continued

| ID | Name |
|---|---|
| 252 | 3-[3-[2-[[2-[[(E)-4-(dimethylamino)but-2-enoyl]-methyl-amino]acetyl]amino]ethyl]anilino]-6-ethyl-5-[ethyl(methyl)amino]pyrazine-2-carboxamide; |
| 253 | 3-[3-[2-[[(2S)-2-[[(E)-4-(dimethylamino)but-2-enoyl]-methyl-amino]propanoyl]amino]ethyl]anilino]-5-[ethyl(methyl)amino]-6-methyl-pyrazine-2-carboxamide; |
| 254 | 5-cyclopropyl-3-[3-[2-[[(2S)-2-[[(E)-4-(dimethylamino)but-2-enoyl]-methyl-amino]propanoyl]amino]ethyl]-5-fluoro-anilino]-6-methyl-pyrazine-2-carboxamide; or |
| 255 | 3-[3-[2-[[(2S)-2-[[(E)-4-(dimethylamino)but-2-enoyl]-methyl-amino]propanoyl]amino]ethyl]anilino]-5-ethyl-6-methyl-pyrazine-2-carboxamide; |
| 301 | 3-[3-[2-[[2-[[(E)-4-(dimethylamino)but-2-enoyl]-methyl-amino]acetyl]amino]ethyl]anilino]-5,6-dimethyl-pyrazine-2-carboxamide |
| 302 | 3-[3-[2-[[(2R)-2-[[(E)-4-(dimethylamino)but-2-enoyl]-methyl-amino]propanoyl]amino]ethyl]anilino]-6-ethyl-5-[isopropyl(methyl)amino]pyrazine-2-carboxamide |
| 303 | 6-ethyl-5-(isopropylamino)-3-[3-[2-[[(2S)-2-[methyl-[(E)-4-(methylamino)but-2-enoyl]amino]propanoyl]amino]ethyl]anilino]pyrazine-2-carboxamide |
| 304 | 5-cyclopropyl-3-[[4-[2-[[(2S)-2-[[(E)-4-(dimethylamino)but-2-enoyl]-methyl-amino]propanoyl]amino]ethyl]-2-pyridyl]amino]-6-ethyl-pyrazine-2-carboxamide |
| 305 | 3-[3-[2-[[(2S)-2-[[(E)-4-(dimethylamino)but-2-enoyl]-methyl-amino]propanoyl]amino]ethyl]anilino]-5-isopropyl-6-methyl-pyrazine-2-carboxamide |
| 306 | 5-cyclopropyl-3-[[5-[2-[[(2S)-2-[[(E)-4-(dimethylamino)but-2-enoyl]-methyl-amino]propanoyl]amino]ethyl]-3-pyridyl]amino]-6-ethyl-pyrazine-2-carboxamide |
| 307 | 6-ethyl-5-[isopropyl(methyl)amino]-3-[3-[2-[[(2S)-2-[methyl-[(E)-4-(methylamino)but-2-enoyl]amino]propanoyl]amino]ethyl]anilino]pyrazine-2-carboxamide |
| 308 | 6-ethyl-5-[isopropyl(methyl)amino]-3-[3-[2-[[2-[methyl(prop-2-enoyl)amino]acetyl]amino]ethyl]anilino]pyrazine-2-carboxamide |
| 309 | 5-[isopropyl(methyl)amino]-6-methyl-3-[3-[2-[[2-[methyl(prop-2-enoyl)amino]acetyl]amino]ethyl]anilino]pyrazine-2-carboxamide |
| 310 | 5-cyclopropyl-3-[[2-[2-[[(2S)-2-[[(E)-4-(dimethylamino)but-2-enoyl]-methyl-amino]propanoyl]amino]ethyl]-4-pyridyl]amino]-6-ethyl-pyrazine-2-carboxamide |
| 311 | 3-[3-[(2R)-2-[[2-[[(E)-4-(dimethylamino)but-2-enoyl]-methyl-amino]acetyl]amino]propyl]anilino]-6-ethyl-5-methyl-pyrazine-2-carboxamide |
| 312 | 3-[3-[(2S)-2-[[2-[[(E)-4-(dimethylamino)but-2-enoyl]-methyl-amino]acetyl]amino]propyl]anilino]-6-ethyl-5-methyl-pyrazine-2-carboxamide |
| 313 | 5-cyclopropyl-3-[[6-[2-[[(2S)-2-[[(E)-4-(dimethylamino)but-2-enoyl]-methyl-amino]propanoyl]amino]ethyl]-2-pyridyl]amino]-6-ethyl-pyrazine-2-carboxamide |
| 314 | 3-[3-[(2R)-2-[[(2S)-2-[[(E)-4-(dimethylamino)but-2-enoyl]-methyl-amino]propanoyl]amino]propyl]anilino]-6-ethyl-5-methyl-pyrazine-2-carboxamide |
| 315 | 6-ethyl-5-[isopropyl(methyl)amino]-3-[3-[2-[[(2S)-2-[methyl(prop-2-enoyl)amino]propanoyl]amino]ethyl]anilino]pyrazine-2-carboxamide |
| 316 | 6-cyclopropyl-2-[3-[2-[[(2S)-2-[[(E)-4-(dimethylamino)but-2-enoyl]-methyl-amino]propanoyl]amino]ethyl]anilino]-5-ethyl-pyridine-3-carboxamide |
| 317 | 3-[3-[(2S)-2-[[(2S)-2-[[(E)-4-(dimethylamino)but-2-enoyl]-methyl-amino]propanoyl]amino]propyl]anilino]-6-ethyl-5-methyl-pyrazine-2-carboxamide |
| 318 | 3-[3-[2-[[(2S)-2-[4-(dimethylamino)butanoyl-methyl-amino]propanoyl]amino]ethyl]anilino]-6-ethyl-5-[isopropyl(methyl)amino]pyrazine-2-carboxamide |
| 319 | 6-cyclopropyl-2-[3-[2-[[(2S)-2-[[(E)-4-(dimethylamino)but-2-enoyl]-methyl-amino]propanoyl]amino]ethyl]anilino]-5-methyl-pyridine-3-carboxamide |
| 320 | 6-cyclopropyl-2-[[5-[2-[[(2S)-2-[[(E)-4-(dimethylamino)but-2-enoyl]-methyl-amino]propanoyl]amino]ethyl]-3-pyridyl]amino]-5-ethyl-pyridine-3-carboxamide |
| 321 | 3-[3-[(1R)-2-[[2-[[(E)-4-(dimethylamino)but-2-enoyl]-methyl-amino]acetyl]amino]-1-methyl-ethyl]anilino]-6-ethyl-5-methyl-pyrazine-2-carboxamide |
| 322 | 6-(dimethylamino)-2-[3-[2-[[(2S)-2-[[(E)-4-(dimethylamino)but-2-enoyl]-methyl-amino]propanoyl]amino]ethyl]anilino]-5-ethyl-pyridine-3-carboxamide |
| 323 | 6-cyclopropyl-2-[[5-[2-[[(2S)-2-[[(E)-4-(dimethylamino)but-2-enoyl]-methyl-amino]propanoyl]amino]ethyl]-3-pyridyl]amino]-5-methyl-pyridine-3-carboxamide |

TABLE 1-continued

| ID | Name |
|---|---|
| 324 | 3-[3-[(1S)-2-[[2-[[(E)-4-(dimethylamino)but-2-enoyl]-methyl-amino]acetyl]amino]-1-methyl-ethyl]anilino]-6-ethyl-5-methyl-pyrazine-2-carboxamide |
| 325 | 3-[3-[(1S)-2-[[(2S)-2-[[(E)-4-(dimethylamino)but-2-enoyl]-methyl-amino]propanoyl]amino]-1-methyl-ethyl]anilino]-6-ethyl-5-methyl-pyrazine-2-carboxamide |
| 326 | 3-[3-[(1R)-2-[[(2S)-2-[[(E)-4-(dimethylamino)but-2-enoyl]-methyl-amino]propanoyl]amino]-1-methyl-ethyl]anilino]-6-ethyl-5-methyl-pyrazine-2-carboxamide |
| 327 | 3-[3-[2-[[2-[[(E)-4-(dimethylamino)but-2-enoyl]-methyl-amino]acetyl]amino]ethyl]anilino]-6-ethynyl-5-[isopropyl(methyl)amino]pyrazine-2-carboxamide |
| 328 | 3-[3-[2-[[2-[[(E)-4-(dimethylamino)but-2-enoyl]-methyl-amino]acetyl]amino]ethyl]anilino]-5-[isopropyl(methyl)amino]-6-vinyl-pyrazine-2-carboxamide |
| 501 | 3-[3-[2-[[(2S)-2-[[(E)-4-(dimethylamino)but-2-enoyl]amino]propanoyl]amino]ethyl]anilino]-6-ethyl-5-(isopropylamino)pyrazine-2-carboxamide |
| 502 | 3-[3-[2-[[(2S)-2-[[(E)-4-(dimethylamino)but-2-enoyl]amino]propanoyl]amino]ethyl]anilino]-6-ethyl-5-[isopropyl(methyl)amino]pyrazine-2-carboxamide |
| 503 | 3-[3-[(1R)-2-[[2-[[(E)-4-(dimethylamino)but-2-enoyl]-methyl-amino]acetyl]amino]-1-methyl-ethyl]anilino]-5,6-diethyl-pyrazine-2-carboxamide |
| 504 | 5-cyclopropyl-3-[3-[(1R)-2-[[2-[[(E)-4-(dimethylamino)but-2-enoyl]-methyl-amino]acetyl]amino]-1-methyl-ethyl]anilino]-6-ethyl-pyrazine-2-carboxamide |
| 505 | 3-[3-[2-[[(2S)-2-[[(E)-4-[bis(trideuteriomethyl)amino]but-2-enoyl]-methyl-amino]propanoyl]amino]ethyl]anilino]-6-ethyl-5-(isopropylamino)pyrazine-2-carboxamide |
| 506 | 3-[3-[(1R)-2-[[2-[[(E)-4-(azetidin-1-yl)but-2-enoyl]-methyl-amino]acetyl]amino]-1-methyl-ethyl]anilino]-5-cyclopropyl-6-ethyl-pyrazine-2-carboxamide |
| 507 | 3-[3-[(1R)-2-[[2-[[(E)-4-(azetidin-1-yl)but-2-enoyl]-methyl-amino]acetyl]amino]-1-methyl-ethyl]anilino]-6-ethyl-5-propyl-pyrazine-2-carboxamide |
| 508 | 3-[3-[(1R)-2-[[2-[[(E)-4-(azetidin-1-yl)but-2-enoyl]-methyl-amino]acetyl]amino]-1-methyl-ethyl]anilino]-5,6-diethyl-pyrazine-2-carboxamide |
| 509 | 3-[3-[(1R)-2-[[2-[[(E)-4-(azetidin-1-yl)but-2-enoyl]-methyl-amino]acetyl]amino]-1-methyl-ethyl]anilino]-6-ethyl-5-isopropyl-pyrazine-2-carboxamide |
| 510 | 6-ethyl-5-isobutyl-3-[3-[2-[[2-[[methyl(prop-2-enoyl)amino]acetyl]amino]ethyl]anilino]pyrazine-2-carboxamide |
| 511 | 6-ethyl-5-[ethyl(methyl)amino]-3-[3-[2-[[2-[[methyl(prop-2-enoyl)amino]acetyl]amino]ethyl]anilino]pyrazine-2-carboxamide |
| 512 | 6-ethyl-5-isobutyl-3-[3-[(1R)-1-methyl-2-[[2-[[methyl(prop-2-enoyl)amino]acetyl]amino]ethyl]anilino]pyrazine-2-carboxamide |
| 513 | 6-ethyl-5-[ethyl(methyl)amino]-3-[3-[(1R)-1-methyl-2-[[2-[[methyl(prop-2-enoyl)amino]acetyl]amino]ethyl]anilino]pyrazine-2-carboxamide |
| 514 | 3-[3-[2-[[2-[[(E)-4-(azetidin-1-yl)but-2-enoyl]-methyl-amino]acetyl]amino]ethyl]anilino]-6-ethyl-5-methoxy-pyrazine-2-carboxamide |
| 515 | 3-[3-[2-[[2-[[(E)-4-(azetidin-1-yl)but-2-enoyl]-methyl-amino]acetyl]amino]ethyl]anilino]-5-ethoxy-6-ethyl-pyrazine-2-carboxamide |
| 516 | 3-[3-[2-[[2-[[(E)-4-(azetidin-1-yl)but-2-enoyl]-methyl-amino]acetyl]amino]ethyl]anilino]-6-ethyl-5-isopropoxy-pyrazine-2-carboxamide |
| 516A | 3-[3-[2-[[2-[[(E)-4-(azetidin-1-yl)but-2-enoyl]-methyl-amino]acetyl]amino]ethyl]anilino]-6-ethyl-5-[ethyl(methyl)amino]pyrazine-2-carboxamide |
| 517 | 3-[3-[(1R)-2-[[2-[[(E)-4-(azetidin-1-yl)but-2-enoyl]-methyl-amino]acetyl]amino]-1-methyl-ethyl]anilino]-6-ethyl-5-isobutyl-pyrazine-2-carboxamide |
| 518 | 3-[3-[(1R)-2-[[2-[[(E)-4-(azetidin-1-yl)but-2-enoyl]-methyl-amino]acetyl]amino]-1-methyl-ethyl]anilino]-6-ethyl-5-[ethyl(methyl)amino]pyrazine-2-carboxamide |
| 519 | 3-[3-[(1S)-2-[[2-[[(E)-4-(azetidin-1-yl)but-2-enoyl]-methyl-amino]acetyl]amino]-1-methyl-ethyl]anilino]-5,6-diethyl-pyrazine-2-carboxamide |
| 520 | 3-[[2-[2-[[2-[[(E)-4-(azetidin-1-yl)but-2-enoyl]-methyl-amino]acetyl]amino]ethyl]-4-pyridyl]amino]-5-cyclopropyl-6-ethyl-pyrazine-2-carboxamide |
| 601 | 3-[3-[2-[[2-[[(E)-4-(azetidin-1-yl)but-2-enoyl]-methyl-amino]acetyl]amino]ethyl]anilino]-6-ethyl-5-isobutyl-pyrazine-2-carboxamide |

TABLE 1-continued

| ID | Name |
|---|---|
| 602 | 3-[3-[2-[[2-[[[(E)-4-(azetidin-1-yl)but-2-enoyl]-methyl-amino]acetyl]amino]ethyl]anilino]-5-ethoxy-6-ethyl-pyrazine-2-carboxamide |
| 603 | 3-[3-[2-[[2-[[[(E)-4-(azetidin-1-yl)but-2-enoyl]-methyl-amino]acetyl]amino]ethyl]anilino]-6-ethyl-5-isopropoxy-pyrazine-2-carboxamide |
| 604 | 3-[[2-[2-[[2-[[[(E)-4-(azetidin-1-yl)but-2-enoyl]-methyl-amino]acetyl]amino]ethyl]-4-pyridyl]amino]-6-ethyl-5-isobutyl-pyrazine-2-carboxamide |
| 605 | 3-[[2-[2-[[(2S)-2-[[(E)-4-(dimethylamino)but-2-enoyl]-methyl-amino]propanoyl]amino]ethyl]-4-pyridyl]amino]-6-ethyl-5-[isopropyl(methyl)amino]pyrazine-2-carboxamide |
| 606 | 3-[[2-[2-[[2-[[[(E)-4-(dimethylamino)but-2-enoyl]-methyl-amino]acetyl]amino]ethyl]-4-pyridyl]amino]-6-ethyl-5-[ethyl(methyl)amino]pyrazine-2-carboxamide |
| 607 | 3-[3-[2-[[2-[[[(E)-4-(azetidin-1-yl)but-2-enoyl]-methyl-amino]acetyl]amino]ethyl]-4-fluoro-anilino]-5-cyclopropyl-6-ethyl-pyrazine-2-carboxamide |

In some particular embodiments, the compound is any compound selected from Compound #204, or a pharmaceutically acceptable salt or solvate or stereoisomer thereof.

In some particular embodiments, the compound is any compound selected from Compound #232, or a pharmaceutically acceptable salt or solvate or stereoisomer thereof.

In some particular embodiments, the compound is any one compound selected from:

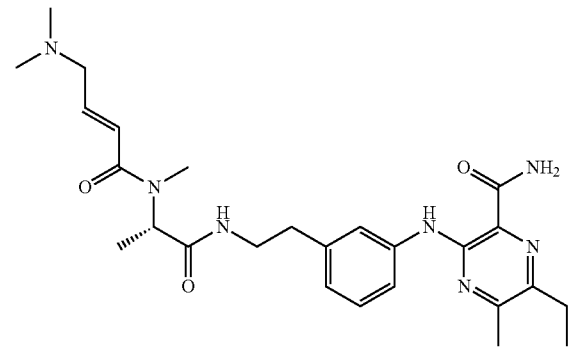

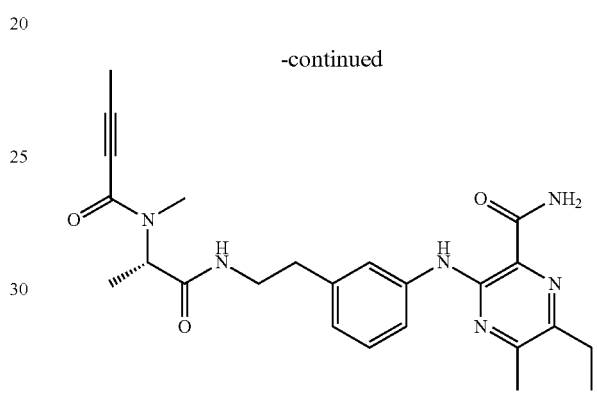

or a pharmaceutically acceptable salt or solvate or stereoisomer thereof.

In some particular embodiments, the compound is any one compound selected from:

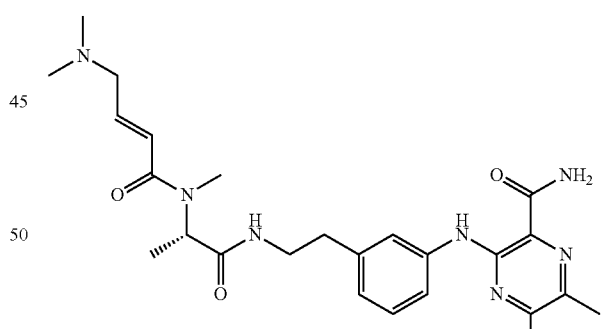

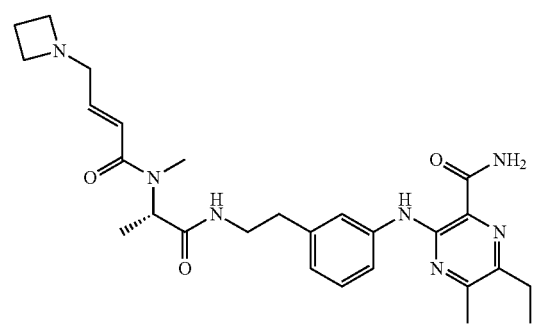

and

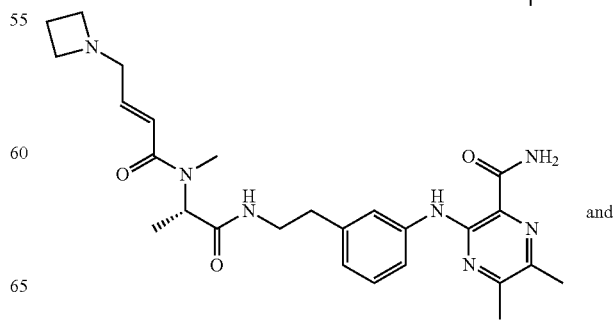

and

-continued

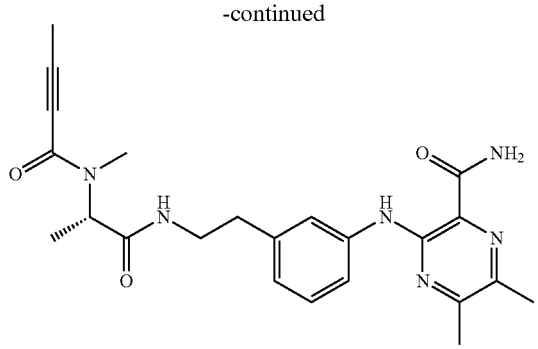

or a pharmaceutically acceptable salt or solvate or stereoisomer thereof.

In some particular embodiments, the compound is:

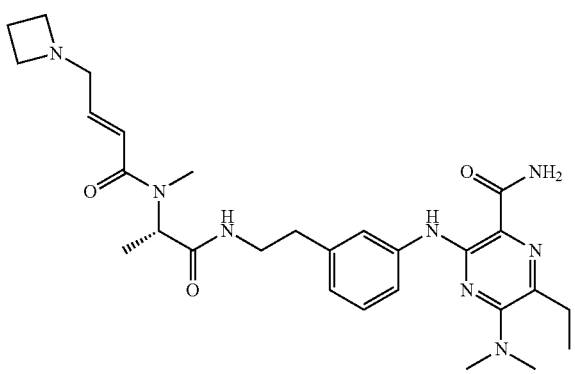

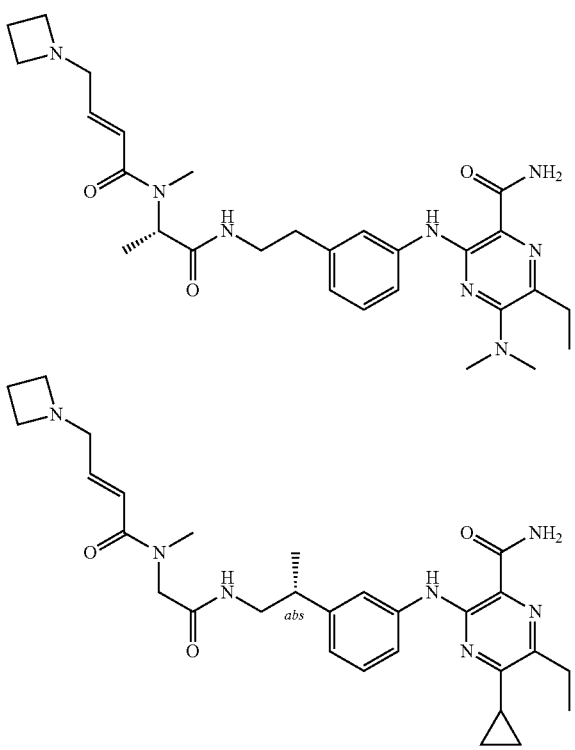

or a pharmaceutically acceptable salt or solvate or stereoisomer thereof.

In some particular embodiments, the compound is:

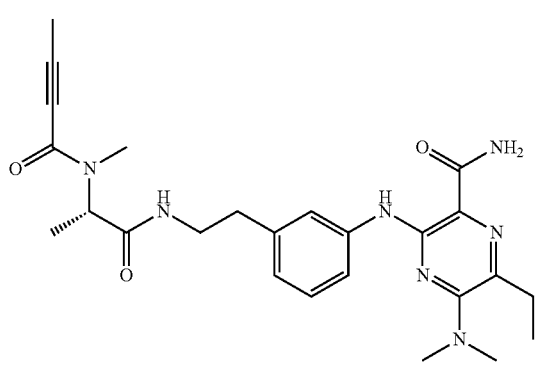 [SMILES: CC#CC(=O)N(C)[C@@H](C)C(=O)NCCc1cccc(Nc2nc(N(C)C)c(CC)nc2C(N)=O)c1]

or a pharmaceutically acceptable salt or solvate or stereoisomer thereof.

In some particular embodiments, the compound is:

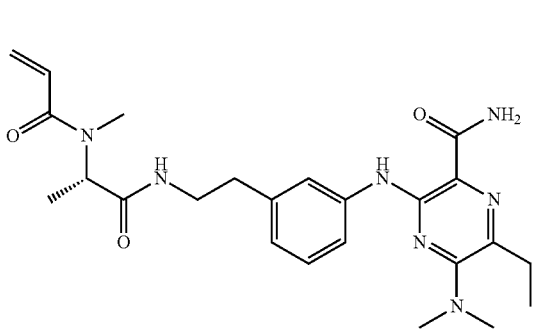 [SMILES: C=CC(=O)N(C)[C@@H](C)C(=O)NCCc1cccc(Nc2nc(N(C)C)c(CC)nc2C(N)=O)c1]

or a pharmaceutically acceptable salt or solvate or stereoisomer thereof.

In some particular embodiments, the compound is:

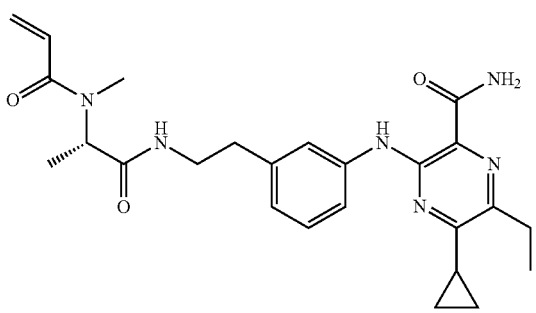 [SMILES: C=CC(=O)N(C)[C@@H](C)C(=O)NCCc1cccc(Nc2nc(C3CC3)c(CC)nc2C(N)=O)c1]

or a pharmaceutically acceptable salt or solvate or stereoisomer thereof.

In some particular embodiments, the compound is:

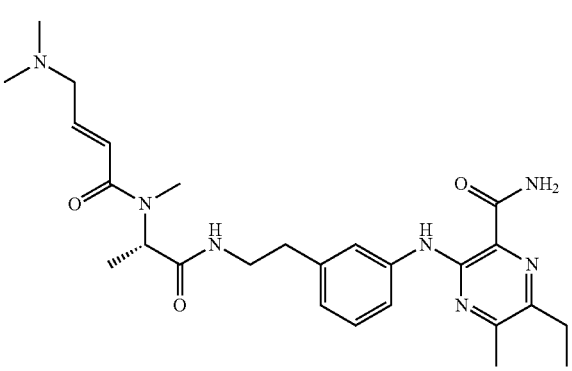 [SMILES: CCc1nc(C(N)=O)c(Nc2cccc(CCNC(=O)[C@H](C)N(C)C(=O)/C=C/CN(C)C)c2)nc1C]

or a pharmaceutically acceptable salt or solvate or stereoisomer thereof.

In some particular embodiments, the compound is:

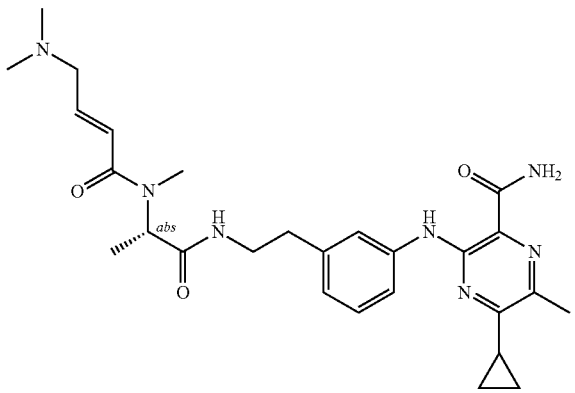

or a pharmaceutically acceptable salt or solvate or stereoisomer thereof.

In some particular embodiments, the compound is:

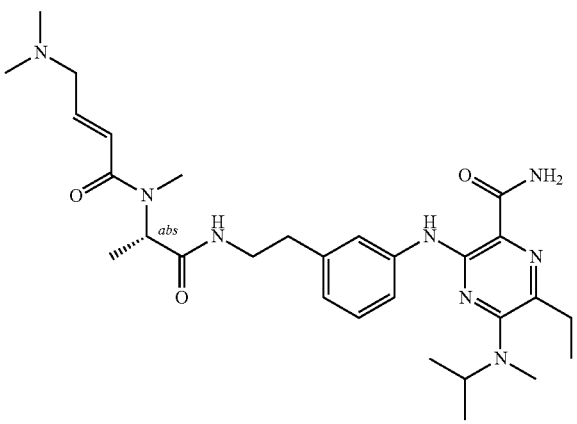

or a pharmaceutically acceptable salt or solvate or stereoisomer thereof.

In some particular embodiments, the compound is:

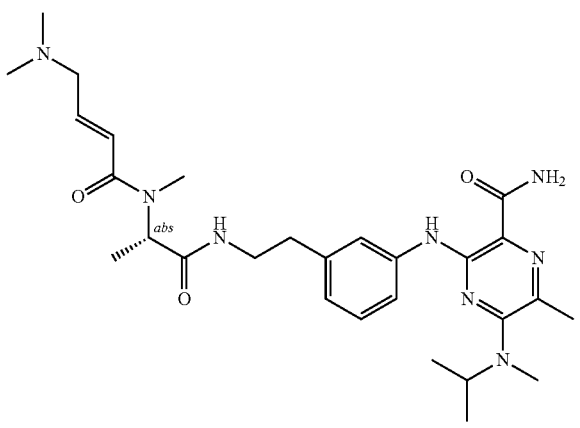

or a pharmaceutically acceptable salt or solvate or stereoisomer thereof.

In some particular embodiments, the compound is:

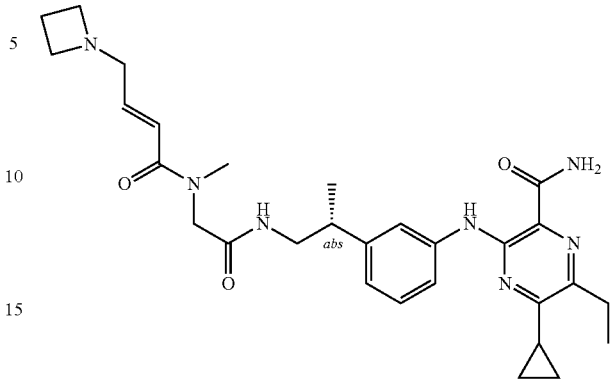

or a pharmaceutically acceptable salt or solvate or stereoisomer thereof.

Certain embodiments of the compounds of Formula (P2-I), Formula (P4-I)-(P4-Vb), Formula (P5-I')-(P5-Vd), and Formula (P6-I)-(P6-IIId) display improved potency against FLT3 with $IC_{50}$ values of as low as less than 1 nM or less than 0.1 nM, and/or high occupancy of active site of FLT3 (e.g., more than 50%, 70% or 90% occupancy) at low dosages of below 5 mg/kg (e.g., at or below 3 mg/kg) when administered in vivo (e.g., in rats).

In some embodiments, provided herein is a pharmaceutical composition comprising a compound selected from Formula (P2-I), Formula (P4-I)-(P4-Vb), Formula (P5-I')-(P5-Vd), and Formula (P6-I)-(P6-IIId) or a pharmaceutically acceptable salt thereof.

In some embodiments, provided herein is a pharmaceutical composition comprising a therapeutically effective amount of a compound of Formula (P-I), Formula (I)-Formula (LXIIIb), Formula (P2-I), Formula (P4-I)-(P4-Vb), and Formula (P5-I')-(P5-Vd), and a pharmaceutically acceptable excipient.

In some embodiments, the pharmaceutical composition is formulated for a route of administration selected from oral administration, parenteral administration, buccal administration, nasal administration, topical administration, or rectal administration.

In some embodiments, provided herein are methods for treating an proliferative disease or condition comprising administering to a patient in need the pharmaceutical composition provided herein.

In certain embodiments, the patient has one or more FLT3 mutations. In certain embodiments, the FLT3 mutation is selected from N676K, F691L, D835H, D835V, D835Y, Y842C, and combinations thereof. In certain embodiments, the FLT3 mutation is N676K. In certain embodiments, the FLT3 mutation is F691L. In certain embodiments, the FLT3 mutation is D835H. In certain embodiments, the FLT3 mutation is D835V. In certain embodiments, the FLT3 mutation is D835Y. In certain embodiments, the FLT3 mutation is Y842C. In certain embodiments, the patient has an NPM1 mutation.

In some embodiments, the autoimmune disease is selected from hematological malignancies.

In some embodiments, provided herein are methods for treating a heteroimmune disease or condition comprising administering to a patient in need the pharmaceutical composition provided herein.

In some embodiments, provided herein are methods for treating a cancer comprising administering to a patient in need the pharmaceutical composition provided herein.

In certain embodiments, the cancer has an ALK (anaplastic lymphoma kinase) mutation. In certain embodiments, the cancer is positive for an ALK fusion. In certain embodiments, the cancer is resistant to an ALK inhibitor. In certain embodiments, the cancer has an ALK mutation selected from the group consisting of T1151K, I1171N, I1171S, I1171T, F1174I, F1174L, F1174V, V1180L, L1196M, L1196Q, L1198F, L1198H, C1156Y, C1159Y, G1202R, D1203N, F1245V, L1256F, G1269A, and combinations thereof.

In some embodiments, the cancer is a hematological malignancy. In some embodiments, the disease or condition is leukemia, lymphoma, or multiple myeloma.

In certain embodiments, the disease or condition is acute lymphocytic leukemia (ALL), acute myeloid leukemia (AML), chronic lymphocytic leukemia (CLL), chronic myeloid leukemia (CML), prolymphocytic leukemia (PLL), large granular lymphocytic (LGL), hairy cell leukemia (HCL), mast-cell leukemia (MCL), or myelodysplastic syndrome (MDS).

In certain embodiments, the disease or condition is acute myeloid leukemia (AML). In certain embodiments, the AML is FLT3 mutation-positive. In certain embodiments, the AML is newly diagnosed. In certain embodiments, the AML is FLT3 mutation-positive and newly diagnosed. In certain embodiments, the AML is relapsed or refractory. In certain embodiments, the AML is relapsed or refractory and is FLT3 mutation-positive. In certain embodiments, the FLT3 mutation is an FLT3-ITD mutation. In certain embodiments, the FLT3 mutation is selected from N676K, F691L, D835H, D835V, D835Y, Y842C, and combinations thereof. In certain embodiments, the FLT3 mutation is N676K. In certain embodiments, the FLT3 mutation is F691L. In certain embodiments, the FLT3 mutation is D835H. In certain embodiments, the FLT3 mutation is D835V. In certain embodiments, the FLT3 mutation is D835Y. In certain embodiments, the FLT3 mutation is Y842C. In certain embodiments, the patient has an NPM1 mutation.

In certain embodiments, the AML is resistant to chemotherapy. In certain embodiments, the AML is resistant to chemotherapy and has developed a FLT3-IND mutation, including, but not limited to at least one mutation selected from N676K, F691L, D835H, D835V, D835Y, Y842C, and combinations thereof.

In certain embodiments, the AML is resistant to a previously administered FLT3 inhibitor. In certain embodiments, the AML is resistant to gilteritinib. In certain embodiments, the AML is resistant to midostaurin.

In some embodiments, provided herein are methods for treating mastocytosis comprising administering to a patient in need a pharmaceutical composition provided herein.

In some embodiments, provided herein are methods for treating osteoporosis or bone resorption disorders comprising administering to a patient in need a pharmaceutical composition provided herein.

In some embodiments, provided herein are methods for treating an inflammatory disease or condition comprising administering to a patient in need a pharmaceutical composition provided herein.

In some embodiments, provided herein are methods for treating lupus comprising administering to a subject in need thereof a composition containing a therapeutically effective amount of a compound that is an inhibitor of FLT3 selected from Formula (P2-I), Formula (P4-I)-(P4-Vb), Formula (P5-I')-(P5-Vd), and Formula (P6-I)-(P6-IIId) or a pharmaceutically acceptable salt thereof.

In some embodiments, provided herein are methods for treating a heteroimmune disease or condition comprising administering to a subject in need thereof a composition containing a therapeutically effective amount of a compound that is an inhibitor of FLT3 selected from Formula (P2-I), Formula (P4-I)-(P4-Vb), Formula (P5-I')-(P5-Vd), and Formula (P6-I)-(P6-IIId) or a pharmaceutically acceptable salt thereof.

In some embodiments provided herein are methods for treating diffuse large B cell lymphoma, follicular lymphoma or chronic lymphocytic leukemia comprising administering to a subject in need thereof a composition containing a therapeutically effective amount of a compound that is an inhibitor of FLT3 selected from Formula (P2-I), Formula (P4-I)-(P4-Vb), Formula (P5-I')-(P5-Vd), and Formula (P6-I)-(P6-IIId) or a pharmaceutically acceptable salt thereof.

In some embodiments, provided herein are methods for treating mastocytosis, comprising administering to a subject in need thereof a composition containing a therapeutically effective amount of a compound that is an inhibitor of FLT3 selected from Formula (P2-I), Formula (P4-I)-(P4-Vb), Formula (P5-I')-(P5-Vd), and Formula (P6-I)-(P6-IIId) or a pharmaceutically acceptable salt thereof.

In some embodiments, provided herein are methods for treating osteoporosis or bone resorption disorders comprising administering to a subject in need thereof a composition containing a therapeutically effective amount of a compound that is an inhibitor of FLT3 selected from Formula (P2-I), Formula (P4-I)-(P4-Vb), Formula (P5-I')-(P5-Vd), and Formula (P6-I)-(P6-IIId) or a pharmaceutically acceptable salt thereof.

In some embodiments, provided herein are methods for treating an inflammatory disease or condition comprising administering to a subject in need thereof a composition containing a therapeutically effective amount of a compound that is an inhibitor of FLT3 selected from Formula (P2-I), Formula (P4-I)-(P4-Vb), Formula (P5-I')-(P5-Vd), and Formula (P6-I)-(P6-IIId) or a pharmaceutically acceptable salt thereof.

In some embodiments, provided herein is a pharmaceutical composition comprising a pharmaceutically acceptable carrier and a pharmaceutically effective amount of a compound according to any one of the formulas described herein. In some embodiments, the compound is according to any one of Formula (P-I), Formula (I)-Formula (LXIIIb), Formula (P2-I), Formula (P4-I)-(P4-Vb), and Formula (P5-I')-(P5-Vd).

In some embodiments, the pharmaceutical composition is formulated for a route of administration selected from oral administration, parenteral administration, buccal administration, nasal administration, topical administration, or rectal administration.

In some embodiments, the carrier is a parenteral carrier. In some embodiments, the carrier is an oral carrier. In some embodiments, the carrier is a topical carrier.

Any combination of the groups described above for the various variables is contemplated herein. It is understood that substituents and substitution patterns on the compounds provided herein can be selected by one of ordinary skill in the art to provide compounds that are chemically stable and that can be synthesized by techniques known in the art, as well as those set forth herein.

Further representative embodiments of compounds of Formula (I), include compounds listed in Table 2A and Table 2B, or a pharmaceutically acceptable salt, solvate, hydrate, or stereoisomer thereof.

Throughout the specification, groups and substituents thereof can be chosen by one skilled in the field to provide stable moieties and compounds.

In some embodiments, the compounds of Formula (P2-I), Formula (P4-I)-(P4-Vb), Formula (P5-I')-(P5-Vd), and Formula (P6-I)-(P6-IIId) inhibit FLT3. In some embodiments, the compounds of Formula (P2-I), Formula (P4-I)-(P4-Vb), Formula (P5-I')-(P5-Vd), and Formula (P6-I)-(P6-IIId) are used to treat patients suffering from FLT3-dependent or FLT3 mediated conditions or diseases, including, but not limited to, proliferative diseases such as hematological malignancies.

In some embodiments, the compounds of Formula (P2-I), Formula (P4-I)-(P4-Vb), Formula (P5-I')-(P5-Vd), and Formula (P6-I)-(P6-IIId) are used to treat patients suffering from FLT-dependent or FLT3 mediated conditions or diseases, including, but not limited to, cancer, e.g., hematological malignancies.

3. Preparation of Compounds

Compounds of any of Formula (P2-I), Formula (P4-I)-(P4-Vb), Formula (P5-I')-(P5-Vd), and Formula (P6-I)-(P6-IIId) may be synthesized using standard synthetic reactions known to those of skill in the art or using methods known in the art. The reactions can be employed in a linear sequence to provide the compounds, or they may be used to synthesize fragments which are subsequently joined by the methods known in the art. Exemplary methods are provided in the Examples herein.

Described herein are compounds that inhibit the activity of FLT3, and processes for their preparation. Also described herein are pharmaceutically acceptable salts, pharmaceutically acceptable solvates, pharmaceutically active metabolites, and pharmaceutically acceptable prodrugs of such compounds. Pharmaceutical compositions that include at least one such compound or a pharmaceutically acceptable salt, pharmaceutically acceptable solvate, pharmaceutically active metabolite or pharmaceutically acceptable prodrug of such compound, are provided.

The starting material used for the synthesis of the compounds described herein may be synthesized or can be obtained from commercial sources, such as, but not limited to, Aldrich Chemical Co. (Milwaukee, Wisconsin), Bachem (Torrance, California), or Sigma Chemical Co. (St. Louis, Mo.).

The compounds described herein, and other related compounds having different substituents can be synthesized using techniques and materials known to those of skill in the art, such as described, for example, in March, ADVANCED ORGANIC CHEMISTRY 4$^{th}$ Ed., (Wiley 1992); Carey and Sundberg, ADVANCED ORGANIC CHEMISTRY 4$^{th}$ Ed., Vols. A and B (Plenum 2000, 2001); Green and Wuts, PROTECTIVE GROUPS IN ORGANIC SYNTHESIS 3$^{rd}$ Ed., (Wiley 1999); Fieser and Fieser's Reagents for Organic Synthesis, Volumes 1-17 (John Wiley and Sons, 1991); Rodd's Chemistry of Carbon Compounds, Volumes 1-5 and Supplementals (Elsevier Science Publishers, 1989); Organic Reactions, Volumes 1-40 (John Wiley and Sons, 1991); and Larock's Comprehensive Organic Transformations (VCH Publishers Inc., 1989). (all of which are incorporated by reference in their entirety). Additional methods for the synthesis of compounds described herein may be found in International Patent Publication No. WO 01/01982901, Arnold et al. Bioorganic & Medicinal Chemistry Letters 10 (2000) 2167-2170; Burchat et al. Bioorganic & Medicinal Chemistry Letters 12 (2002) 1687-1690. General methods for the preparation of compound as disclosed herein may be derived from known reactions in the field, and the reactions may be modified by the use of appropriate reagents and conditions, as would be recognized by the skilled person, for the introduction of the various moieties found in the formulae as provided herein.

The products of the reactions may be isolated and purified, if desired, using conventional techniques, including, but not limited to, filtration, distillation, crystallization, chromatography, and the like. Such materials may be characterized using conventional means, including physical constants and spectral data.

Compounds described herein may be prepared as a single isomer or a mixture of isomers.

In some embodiments, representative compounds of Formula (P6-I) are prepared according to synthetic schemes depicted herein.

4. Further Forms of Compounds

Compounds disclosed herein have a structure of Formula (P-I), Formula (I)-Formula (LXIIIb), Formula (P2-I), Formula (P4-I)-(P4-Vb), or Formula (P5-I')-(P5-Vd). It is understood that when reference is made to compounds described herein, it is meant to include compounds of any of Formula (P2-I), Formula (P4-I)-(P4-Vb), Formula (P5-I')-(P5-Vd), and Formula (P6-I)-(P6-IIId) as well as to all of the specific compounds that fall within the scope of these generic formulae, unless otherwise indicated.

Compounds described herein may possess one or more stereocenters and each center may exist in the R or S configuration. Compounds presented herein include all diastereomeric, enantiomeric, and epimeric forms as well as the appropriate mixtures thereof. Stereoisomers may be obtained, if desired, by methods known in the art as, for example, the separation of stereoisomers by chiral chromatographic columns.

Diastereomeric mixtures can be separated into their individual diastereomers on the basis of their physical chemical differences by methods known, for example, by chromatography and/or fractional crystallization. In some embodiments, enantiomers can be separated by chiral chromatographic columns. In some embodiments, enantiomers can be separated by converting the enantiomeric mixture into a diastereomeric mixture by reaction with an appropriate optically active compound (e.g., alcohol), separating the diastereomers and converting (e.g., hydrolyzing) the individual diastereomers to the corresponding pure enantiomers. All such isomers, including diastereomers, enantiomers, and mixtures thereof are considered as part of the compositions described herein.

Methods and formulations described herein include the use of N-oxides, crystalline forms (also known as polymorphs), or pharmaceutically acceptable salts of compounds described herein, as well as active metabolites of these compounds having the same type of activity. In some situations, compounds may exist as tautomers. All tautomers are included within the scope of the compounds presented herein. In addition, compounds described herein can exist in unsolvated as well as solvated forms with pharmaceutically acceptable solvents such as water, ethanol, and the like. Solvated forms of compounds presented herein are also considered to be disclosed herein.

Compounds of any of Formula (P2-I), Formula (P4-I)-(P4-Vb), Formula (P5-I')-(P5-Vd), and Formula (P6-I)-(P6-IIId) in unoxidized form can be prepared from N-oxides of compounds of any of Formula (P2-I), Formula (P4-I)-(P4-Vb), Formula (P5-I')-(P5-Vd), and Formula (P6-I)-(P6-IIId)

by treating with a reducing agent, such as, but not limited to, sulfur, sulfur dioxide, triphenyl phosphine, lithium borohydride, sodium borohydride, phosphorus trichloride, tribromide, or the like in a suitable inert organic solvent, such as, but not limited to, acetonitrile, ethanol, aqueous dioxane, or the like at 0 to 80° C.

In some embodiments, compounds described herein are prepared as prodrugs. A "prodrug" refers to an agent that is converted into the parent drug in vivo. Prodrugs are often useful because, in some situations, they may be easier to administer than the parent drug. They may, for instance, be bioavailable by oral administration whereas the parent is not. The prodrug may also have improved solubility in pharmaceutical compositions over the parent drug. An example, without limitation, of a prodrug would be a compound described herein, which is administered as an ester (the "prodrug") to facilitate transmittal across a cell membrane where water solubility is detrimental to mobility but which then is metabolically hydrolyzed to the carboxylic acid, the active entity, once inside the cell where water-solubility is beneficial. A further example of a prodrug might be a short peptide (polyaminoacid) bonded to an acid group where the peptide is metabolized to reveal the active moiety. In certain embodiments, upon in vivo administration, a prodrug is chemically converted to the biologically, pharmaceutically, or therapeutically active form of the compound. In certain embodiments, a prodrug is enzymatically metabolized by one or more steps or processes to the biologically, pharmaceutically, or therapeutically active form of the compound. To produce a prodrug, a pharmaceutically active compound is modified such that the active compound will be regenerated upon in vivo administration. The prodrug can be designed to alter the metabolic stability or the transport characteristics of a drug, to mask side effects or toxicity, to improve the flavor of a drug or to alter other characteristics or properties of a drug. By virtue of knowledge of pharmacodynamic processes and drug metabolism in vivo, those of skill in this art, once a pharmaceutically active compound is known, can design prodrugs of the compound. (see, for example, Nogrady (1985) Medicinal Chemistry A Biochemical Approach, Oxford University Press, New York, pages 388-392; Silverman (1992), The Organic Chemistry of Drug Design and Drug Action, Academic Press, Inc., San Diego, pages 352-401, Saulnier et al., (1994), Bioorganic and Medicinal Chemistry Letters, Vol. 4, p. 1985).

Prodrug forms of the herein described compounds, wherein the prodrug is metabolized in vivo to produce a derivative as set forth herein are included within the scope of the claims. In some cases, some of the herein-described compounds may be a prodrug for another derivative or active compound.

Prodrugs are often useful because, in some situations, they may be easier to administer than the parent drug. They may, for instance, be bioavailable by oral administration whereas the parent is not. The prodrug may also have improved solubility in pharmaceutical compositions over the parent drug. Prodrugs may be designed as reversible drug derivatives, for use as modifiers to enhance drug transport to site-specific tissues. In some embodiments, the design of a prodrug increases the effective water solubility. See, e.g., Fedorak et al., Am. J. Physiol., 269:G210-218 (1995); McLeod et al., Gastroenterol, 106:405-413 (1994); Hochhaus et al., Biomed. Chrom., 6:283-286 (1992); J. Larsen and H. Bundgaard, Int. J. Pharmaceutics, 37, 87 (1987); J. Larsen et al., Int. J. Pharmaceutics, 47, 103 (1988); Sinkula et al., J. Pharm. Sci., 64:181-210 (1975); T. Higuchi and V. Stella, Pro-drugs as Novel Delivery Systems, Vol. 14 of the A.C.S. Symposium Series; and Edward B. Roche, Bioreversible Carriers in Drug Design, American Pharmaceutical Association and Pergamon Press, 1987, all incorporated herein in their entirety.

Sites on the aromatic ring portion of compounds of any of Formula (P2-I), Formula (P4-I)-(P4-Vb), Formula (P5-I')-(P5-Vd), and Formula (P6-I)-(P6-IIId) can be susceptible to various metabolic reactions, therefore incorporation of appropriate substituents on the aromatic ring structures, such as, by way of example only, halogens can reduce, minimize or eliminate this metabolic pathway.

Compounds described herein include isotopically-labeled compounds, which are identical to those recited in the various formulas and structures presented herein, but for the fact that one or more atoms are replaced by an atom having an atomic mass or mass number different from the atomic mass or mass number usually found in nature. Examples of isotopes that can be incorporated into the present compounds include isotopes of hydrogen, carbon, nitrogen, oxygen, fluorine and chlorine, such as $^{2}H$, $^{3}H$, $^{13}C$, $^{14}C$, $^{15}N$, $^{18}O$, $^{17}O$, $^{35}S$, $^{18}F$, $^{36}Cl$, respectively. Certain isotopically-labeled compounds described herein, for example those into which radioactive isotopes such as $^{3}H$ and $^{14}C$ are incorporated, are useful in drug and/or substrate tissue distribution assays. Further, substitution with isotopes such as deuterium, i.e., $^{2}H$, can afford certain therapeutic advantages resulting from greater metabolic stability, for example increased in vivo half-life or reduced dosage requirements.

In additional or some embodiments, the compounds described herein are metabolized upon administration to an organism in need to produce a metabolite that is then used to produce a desired effect, including a desired therapeutic effect.

Compounds described herein may be formed as, and/or used as, pharmaceutically acceptable salts. The type of pharmaceutical acceptable salts, include, but are not limited to: (1) acid addition salts, formed by reacting the free base form of the compound with a pharmaceutically acceptable: inorganic acid such as hydrochloric acid, hydrobromic acid, sulfuric acid, nitric acid, phosphoric acid, metaphosphoric acid, and the like; or with an organic acid such as acetic acid, propionic acid, hexanoic acid, cyclopentanepropionic acid, glycolic acid, pyruvic acid, lactic acid, malonic acid, succinic acid, malic acid, maleic acid, fumaric acid, trifluoroacetic acid, tartaric acid, citric acid, benzoic acid, 3-(4-hydroxybenzoyl)benzoic acid, cinnamic acid, mandelic acid, methanesulfonic acid, ethanesulfonic acid, 1,2-ethane-disulfonic acid, 2-hydroxyethanesulfonic acid, benzene-sulfonic acid, toluenesulfonic acid, 2-naphthalenesulfonic acid, 4-methylbicyclo-[2.2.2]oct-2-ene-1-carboxylic acid, glucoheptonic acid, 4,4'-methylenebis-(3-hydroxy-2-ene-1-carboxylic acid), 3-phenylpropionic acid, trimethylacetic acid, tertiary butylacetic acid, lauryl sulfuric acid, gluconic acid, glutamic acid, hydroxynaphthoic acid, salicylic acid, stearic acid, muconic acid, and the like; (2) salts formed when an acidic proton present in the parent compound either is replaced by a metal ion, e.g., an alkali metal ion (e.g. lithium, sodium, potassium), an alkaline earth ion (e.g. magnesium, or calcium), or an aluminum ion; or coordinates with an organic base. Acceptable organic bases include ethanolamine, diethanolamine, triethanolamine, tromethamine, N-methylglucamine, and the like. Acceptable inorganic bases include aluminum hydroxide, calcium hydroxide, potassium hydroxide, sodium carbonate, sodium hydroxide, and the like.

The corresponding counterions of the pharmaceutically acceptable salts may be analyzed and identified using various methods including, but not limited to, ion exchange chromatography, ion chromatography, capillary electrophoresis, inductively coupled plasma, atomic absorption spectroscopy, mass spectrometry, or any combination thereof.

The salts are recovered by using at least one of the following techniques: filtration, precipitation with a non-solvent followed by filtration, evaporation of the solvent, or, in the case of aqueous solutions, lyophilization.

It should be understood that a reference to a pharmaceutically acceptable salt includes the solvent addition forms or crystal forms thereof, particularly solvates or polymorphs. Solvates contain either stoichiometric or non-stoichiometric amounts of a solvent and may be formed during the process of crystallization with pharmaceutically acceptable solvents such as water, ethanol, and the like. Hydrates are formed when the solvent is water, or alcoholates are formed when the solvent is alcohol. Solvates of compounds described herein can be conveniently prepared or formed during the processes described herein. In addition, the compounds provided herein can exist in unsolvated as well as solvated forms. In general, the solvated forms are considered equivalent to the unsolvated forms for the purposes of the compounds and methods provided herein.

It should be understood that a reference to a salt includes the solvent addition forms or crystal forms thereof, particularly solvates or polymorphs. Solvates contain either stoichiometric or non-stoichiometric amounts of a solvent, and are often formed during the process of crystallization with pharmaceutically acceptable solvents such as water, ethanol, and the like. Hydrates are formed when the solvent is water, or alcoholates are formed when the solvent is alcohol. Polymorphs include the different crystal packing arrangements of the same elemental composition of a compound. Polymorphs usually have different X-ray diffraction patterns, infrared spectra, melting points, density, hardness, crystal shape, optical and electrical properties, stability, and solubility. Various factors such as the recrystallization solvent, rate of crystallization, and storage temperature may cause a single crystal form to dominate.

Compounds described herein may be in various forms, including but not limited to, amorphous forms, milled forms and nano-particulate forms. In addition, compounds described herein include crystalline forms, also known as polymorphs. Polymorphs include the different crystal packing arrangements of the same elemental composition of a compound. Polymorphs usually have different X-ray diffraction patterns, infrared spectra, melting points, density, hardness, crystal shape, optical and electrical properties, stability, and solubility. Various factors such as the recrystallization solvent, rate of crystallization, and storage temperature may cause a single crystal form to dominate.

The screening and characterization of the pharmaceutically acceptable salts, polymorphs, and/or solvates may be accomplished using a variety of techniques including, but not limited to, thermal analysis, x-ray diffraction, spectroscopy, vapor sorption, and microscopy. Thermal analysis methods address thermo chemical degradation or thermo physical processes including, but not limited to, polymorphic transitions, and such methods are used to analyze the relationships between polymorphic forms, determine weight loss, to find the glass transition temperature, or for excipient compatibility studies. Such methods include, but are not limited to, Differential scanning calorimetry (DSC), Modulated Differential Scanning Calorimetry (MDCS), Thermogravimetric analysis (TGA), and Thermogravi-metric and Infrared analysis (TG/IR). X-ray diffraction methods include, but are not limited to, single crystal and powder diffractometers and synchrotron sources. The various spectroscopic techniques used include, but are not limited to, Raman, FTIR, UVIS, and NMR (liquid and solid state). The various microscopy techniques include, but are not limited to, polarized light microscopy, Scanning Electron Microscopy (SEM) with Energy Dispersive X-Ray Analysis (EDX), Environmental Scanning Electron Microscopy with EDX (in gas or water vapor atmosphere), IR microscopy, and Raman microscopy.

Throughout the specification, groups and substituents thereof can be chosen by one skilled in the field to provide stable moieties and compounds.

5. Pharmaceutical Composition/Formulation

Pharmaceutical compositions may be formulated in a conventional manner using one or more physiologically acceptable carriers including excipients and auxiliaries which facilitate processing of the active compounds into preparations which can be used pharmaceutically. Proper formulation is dependent upon the route of administration chosen. Any of the well-known techniques, carriers, and excipients may be used as suitable and as understood in the art. A summary of pharmaceutical compositions described herein may be found, for example, in Remington: The Science and Practice of Pharmacy, Nineteenth Ed (Easton, Pa.: Mack Publishing Company, 1995); Hoover, John E., Remington's Pharmaceutical Sciences, Mack Publishing Co., Easton, Pennsylvania 1975; Liberman, H. A. and Lachman, L., Eds., Pharmaceutical Dosage Forms, Marcel Decker, New York, N.Y., 1980; and Pharmaceutical Dosage Forms and Drug Delivery Systems, Seventh Ed. (Lippincott Williams & Wilkins 1999), herein incorporated by reference in their entirety.

A pharmaceutical composition, as used herein, refers to a mixture of a compound described herein, such as, for example, compounds of any of Formula (P2-I), Formula (P4-I)-(P4-Vb), Formula (P5-I')-(P5-Vd), and Formula (P6-I)-(P6-IIId) with other chemical components, such as carriers, stabilizers, diluents, dispersing agents, suspending agents, thickening agents, and/or excipients. The pharmaceutical composition facilitates administration of the compound to an organism. In practicing the methods of treatment or use provided herein, therapeutically effective amounts of compounds described herein are administered in a pharmaceutical composition to a mammal having a disease, disorder, or condition to be treated. Preferably, the mammal is a human. A therapeutically effective amount can vary widely depending on the severity of the disease, the age and relative health of the subject, the potency of the compound used and other factors. The compounds can be used singly or in combination with one or more therapeutic agents as components of mixtures.

In certain embodiments, compositions may also include one or more pH adjusting agents or buffering agents, including acids such as acetic, boric, citric, lactic, phosphoric and hydrochloric acids; bases such as sodium hydroxide, sodium phosphate, sodium borate, sodium citrate, sodium acetate, sodium lactate and tris-hydroxymethylaminomethane; and buffers such as citrate/dextrose, sodium bicarbonate and ammonium chloride. Such acids, bases and buffers are included in an amount required to maintain pH of the composition in an acceptable range.

In some embodiments, compositions may also include one or more salts in an amount required to bring osmolality of the composition into an acceptable range. Such salts include those having sodium, potassium or ammonium cations, and chloride, citrate, ascorbate, borate, phosphate, bicarbonate, sulfate, thiosulfate or bisulfite anions; suitable salts include sodium chloride, potassium chloride, sodium thiosulfate, sodium bisulfite and ammonium sulfate.

The term "pharmaceutical combination" as used herein, means a product that results from the mixing or combining of more than one active ingredient and includes both fixed and non-fixed combinations of the active ingredients. The term "fixed combination" means that the active ingredients, e.g. a compound described herein and a co-agent, are both administered to a patient simultaneously in the form of a single entity or dosage. The term "non-fixed combination" means that the active ingredients, e.g. a compound described herein and a co-agent, are administered to a patient as separate entities either simultaneously, concurrently or sequentially with no specific intervening time limits, wherein such administration provides effective levels of the two compounds in the body of the patient. The latter also applies to cocktail therapy, e.g. the administration of three or more active ingredients.

The pharmaceutical compositions described herein can be administered to a subject by multiple administration routes, including but not limited to, oral, parenteral (e.g., intravenous, subcutaneous, intramuscular), intranasal, buccal, topical, rectal, or transdermal administration routes. The pharmaceutical compositions described herein include, but are not limited to, aqueous liquid dispersions, self-emulsifying dispersions, solid solutions, liposomal dispersions, aerosols, solid dosage forms, powders, immediate release formulations, controlled release formulations, fast melt formulations, tablets, capsules, pills, delayed release formulations, extended release formulations, pulsatile release formulations, multiparticulate formulations, and mixed immediate and controlled release formulations.

Pharmaceutical compositions including a compound described herein may be manufactured in a conventional manner, such as, by way of example only, by means of conventional mixing, dissolving, granulating, dragee-making, levigating, emulsifying, encapsulating, entrapping or compression processes.

The pharmaceutical compositions will include at least one compound described herein, such as, for example, a compound of any one of Formula (P2-I), Formula (P4-I)-(P4-Vb), Formula (P5-I')-(P5-Vd), and Formula (P6-I)-(P6-IIId) as an active ingredient in free-acid or free-base form, or in a pharmaceutically acceptable salt form. In addition, the methods and pharmaceutical compositions described herein include the use of N-oxides, crystalline forms (also known as polymorphs), as well as active metabolites of these compounds having the same type of activity. In some situations, compounds may exist as tautomers. All tautomers are included within the scope of the compounds presented herein. Additionally, the compounds described herein can exist in unsolvated as well as solvated forms with pharmaceutically acceptable solvents such as water, ethanol, and the like. The solvated forms of the compounds presented herein are also considered to be disclosed herein.

"Antifoaming agents" reduce foaming during processing which can result in coagulation of aqueous dispersions, bubbles in the finished film, or generally impair processing. Exemplary anti-foaming agents include silicon emulsions or sorbitan sesquioleate.

"Antioxidants" include, for example, butylated hydroxytoluene (BHT), sodium ascorbate, ascorbic acid, sodium metabisulfite, and tocopherol. In certain embodiments, antioxidants enhance chemical stability where required.

In certain embodiments, compositions provided herein may also include one or more preservatives to inhibit microbial activity. Suitable preservatives include mercury-containing substances such as merfen and thiomersal; stabilized chlorine dioxide; and quaternary ammonium compounds such as benzalkonium chloride, cetyltrimethylammonium bromide and cetylpyridinium chloride.

Formulations described herein may benefit from antioxidants, metal chelating agents, thiol containing compounds and other general stabilizing agents. Examples of such stabilizing agents, include, but are not limited to: (a) about 0.5% to about 2% w/v glycerol, (b) about 0.1% to about 1% w/v methionine, (c) about 0.1% to about 2% w/v monothioglycerol, (d) about 1 mM to about 10 mM EDTA, (e) about 0.01% to about 2% w/v ascorbic acid, (f) 0.003% to about 0.02% w/v polysorbate 80, (g) 0.001% to about 0.05% w/v. polysorbate 20, (h) arginine, (i) heparin, (j) dextran sulfate, (k) cyclodextrins, (1) pentosan polysulfate and other heparinoids, (m) divalent cations such as magnesium and zinc; or (n) combinations thereof.

"Binders" impart cohesive qualities and include, e.g., alginic acid and salts thereof; cellulose derivatives such as carboxymethylcellulose, methylcellulose (e.g., Methocel®), hydroxypropylmethylcellulose, hydroxyethylcellulose, hydroxypropylcellulose (e.g., Klucel®), ethylcellulose (e.g., Ethocel®), and microcrystalline cellulose (e.g., Avicel®); microcrystalline dextrose; amylose; magnesium aluminum silicate; polysaccharide acids; bentonites; gelatin; polyvinylpyrrolidone/vinyl acetate copolymer; crosspovidone; povidone; starch; pregelatinized starch; tragacanth, dextrin, a sugar, such as sucrose (e.g., Dipac®), glucose, dextrose, molasses, mannitol, sorbitol, xylitol (e.g., Xylitab®), and lactose; a natural or synthetic gum such as acacia, tragacanth, ghatti gum, mucilage of isapol husks, polyvinylpyrrolidone (e.g., Polyvidone® CL, Kollidon® CL, Polyplasdone® XL-10), larch arabogalactan, Veegum®, polyethylene glycol, waxes, sodium alginate, and the like.

A "carrier" or "carrier materials" include any commonly used excipients in pharmaceutics and should be selected on the basis of compatibility with compounds disclosed herein, such as, compounds of any one of Formula (P2-I), Formula (P4-I)-(P4-Vb), Formula (P5-I')-(P5-Vd), and Formula (P6-I)-(P6-IIId) and the release profile properties of the desired dosage form. Exemplary carrier materials include, e.g., binders, suspending agents, disintegration agents, filling agents, surfactants, solubilizers, stabilizers, lubricants, wetting agents, diluents, and the like. "Pharmaceutically compatible carrier materials" may include, but are not limited to, acacia, gelatin, colloidal silicon dioxide, calcium glycerophosphate, calcium lactate, maltodextrin, glycerine, magnesium silicate, polyvinylpyrollidone (PVP), cholesterol, cholesterol esters, sodium caseinate, soy lecithin, taurocholic acid, phosphotidylcholine, sodium chloride, tricalcium phosphate, dipotassium phosphate, cellulose and cellulose conjugates, sugars sodium stearoyl lactylate, carrageenan, monoglyceride, diglyceride, pregelatinized starch, and the like. See, e.g., Remington: The Science and Practice of Pharmacy, Nineteenth Ed (Easton, Pa.: Mack Publishing Company, 1995); Hoover, John E., Remington's Pharmaceutical Sciences, Mack Publishing Co., Easton, Pennsylvania 1975; Liberman, H. A. and Lachman, L., Eds., Pharmaceutical Dosage Forms, Marcel Decker, New York, N.Y., 1980; and Pharmaceutical Dosage Forms and Drug Delivery Systems, Seventh Ed. (Lippincott Williams & Wilkins 1999).

"Dispersing agents," and/or "viscosity modulating agents" include materials that control the diffusion and homogeneity of a drug through liquid media or a granulation method or blend method. In some embodiments, these agents also facilitate the effectiveness of a coating or eroding matrix. Exemplary diffusion facilitators/dispersing agents include, e.g., hydrophilic polymers, electrolytes, Tween® 60 or 80, PEG, polyvinylpyrrolidone (PVP; commercially known as Plasdone®), and the carbohydrate-based dispersing agents such as, for example, hydroxypropyl celluloses (e.g., HPC, HPC-SL, and HPC-L), hydroxypropyl methylcelluloses (e.g., HPMC K100, HPMC K4M, HPMC K15M, and HPMC K100M), carboxymethylcellulose sodium, methylcellulose, hydroxyethylcellulose, hydroxypropylcellulose, hydroxypropylmethylcellulose phthalate, hydroxypropylmethylcellulose acetate stearate (HPMCAS), noncrystalline cellulose, magnesium aluminum silicate, triethanolamine, polyvinyl alcohol (PVA), vinyl pyrrolidone/vinyl acetate copolymer (S630), 4-(1,1,3,3-tetramethylbutyl)-phenol polymer with ethylene oxide and formaldehyde (also known as tyloxapol), poloxamers (e.g., Pluronics F68®, F88®, and F108®, which are block copolymers of ethylene oxide and propylene oxide); and poloxamines (e.g., Tetronic 908®, also known as Poloxamine 908®, which is a tetrafunctional block copolymer derived from sequential addition of propylene oxide and ethylene oxide to ethylenediamine (BASF Corporation, Parsippany, N.J.)), polyvinylpyrrolidone K12, polyvinylpyrrolidone K17, polyvinylpyrrolidone K25, or polyvinylpyrrolidone K30, polyvinylpyrrolidone/vinyl acetate copolymer (S-630), polyethylene glycol, e.g., the polyethylene glycol can have a molecular weight of about 300 to about 6000, or about 3350 to about 4000, or about 7000 to about 5400, sodium carboxymethylcellulose, methylcellulose, polysorbate-80, sodium alginate, gums, such as, e.g., gum tragacanth and gum acacia, guar gum, xanthans, including xanthan gum, sugars, cellulosics, such as, e.g., sodium carboxymethylcellulose, methylcellulose, sodium carboxymethylcellulose, polysorbate-80, sodium alginate, polyethoxylated sorbitan monolaurate, polyethoxylated sorbitan monolaurate, povidone, carbomers, polyvinyl alcohol (PVA), alginates, chitosans and combinations thereof. Plasticizers such as cellulose or triethyl cellulose can also be used as dispersing agents. Dispersing agents particularly useful in liposomal dispersions and self-emulsifying dispersions are dimyristoyl phosphatidyl choline, natural phosphatidyl choline from eggs, natural phosphatidyl glycerol from eggs, cholesterol and isopropyl myristate.

Combinations of one or more erosion facilitator with one or more diffusion facilitator can also be used in the present compositions.

The term "diluent" refers to chemical compounds that are used to dilute the compound of interest prior to delivery. Diluents can also be used to stabilize compounds because they can provide a more stable environment. Salts dissolved in buffered solutions (which also can provide pH control or maintenance) are utilized as diluents in the art, including, but not limited to a phosphate buffered saline solution. In certain embodiments, diluents increase bulk of the composition to facilitate compression or create sufficient bulk for homogenous blend for capsule filling. Such compounds include e.g., lactose, starch, mannitol, sorbitol, dextrose, microcrystalline cellulose such as Avicel®; dibasic calcium phosphate, dicalcium phosphate dihydrate; tricalcium phosphate, calcium phosphate; anhydrous lactose, spray-dried lactose; pregelatinized starch, compressible sugar, such as Di-Pac® (Amstar); mannitol, hydroxypropylmethylcellulose, hydroxypropylmethylcellulose acetate stearate, sucrose-based diluents, confectioner's sugar; monobasic calcium sulfate monohydrate, calcium sulfate dihydrate; calcium lactate trihydrate, dextrates; hydrolyzed cereal solids, amylose; powdered cellulose, calcium carbonate; glycine, kaolin; mannitol, sodium chloride; inositol, bentonite, and the like.

The term "disintegrate" includes both the dissolution and dispersion of the dosage form when contacted with gastrointestinal fluid. "Disintegration agents or disintegrants" facilitate the breakup or disintegration of a substance. Examples of disintegration agents include a starch, e.g., a natural starch such as corn starch or potato starch, a pregelatinized starch such as National 1551 or Amijel®, or sodium starch glycolate such as Promogel® or Explotab®, a cellulose such as a wood product, methylcrystalline cellulose, e.g., Avicel®, Avicel® PH101, Avicel® PH102, Avicel® PH105, Elcema® P100, Emcocel®, Vivacel®, Ming Tia®, and Solka-Floc®, methylcellulose, croscarmellose, or a cross-linked cellulose, such as cross-linked sodium carboxymethylcellulose (Ac-Di-Sol®), cross-linked carboxymethylcellulose, or cross-linked croscarmellose, a cross-linked starch such as sodium starch glycolate, a cross-linked polymer such as crosspovidone, a cross-linked polyvinylpyrrolidone, alginate such as alginic acid or a salt of alginic acid such as sodium alginate, a clay such as Veegum® HV (magnesium aluminum silicate), a gum such as agar, guar, locust bean, Karaya, pectin, or tragacanth, sodium starch glycolate, bentonite, a natural sponge, a surfactant, a resin such as a cation-exchange resin, citrus pulp, sodium lauryl sulfate, sodium lauryl sulfate in combination starch, and the like.

"Drug absorption" or "absorption" typically refers to the process of movement of drug from site of administration of a drug across a barrier into a blood vessel or the site of action, e.g., a drug moving from the gastrointestinal tract into the portal vein or lymphatic system.

An "enteric coating" is a substance that remains substantially intact in the stomach but dissolves and releases the drug in the small intestine or colon. Generally, the enteric coating comprises a polymeric material that prevents release in the low pH environment of the stomach but that ionizes at a higher pH, typically a pH of 6 to 7, and thus dissolves sufficiently in the small intestine or colon to release the active agent therein.

"Erosion facilitators" include materials that control the erosion of a particular material in gastrointestinal fluid. Erosion facilitators are generally known to those of ordinary skill in the art. Exemplary erosion facilitators include, e.g., hydrophilic polymers, electrolytes, proteins, peptides, and amino acids.

"Filling agents" include compounds such as lactose, calcium carbonate, calcium phosphate, dibasic calcium phosphate, calcium sulfate, microcrystalline cellulose, cellulose powder, dextrose, dextrates, dextran, starches, pregelatinized starch, sucrose, xylitol, lactitol, mannitol, sorbitol, sodium chloride, polyethylene glycol, and the like.

"Flavoring agents" and/or "sweeteners" useful in the formulations described herein, include, e.g., acacia syrup, acesulfame K, alitame, anise, apple, aspartame, banana, Bavarian cream, berry, black currant, butterscotch, calcium citrate, camphor, caramel, cherry, cherry cream, chocolate, cinnamon, bubble gum, citrus, citrus punch, citrus cream, cotton candy, cocoa, cola, cool cherry, cool citrus, cyclamate, cylamate, dextrose, eucalyptus, eugenol, fructose, fruit punch, ginger, glycyrrhetinate, glycyrrhiza (licorice) syrup, grape, grapefruit, honey, isomalt, lemon, lime, lemon cream, monoammonium glyrrhizinate (MagnaSweet®), maltol, mannitol, maple, marshmallow, menthol, mint cream, mixed berry, neohesperidine DC, neotame, orange, pear, peach, peppermint, peppermint cream, Prosweet® Powder, raspberry, root beer, rum, saccharin, safrole, sorbitol, spearmint, spearmint cream, strawberry, strawberry cream, stevia, sucralose, sucrose, sodium saccharin, saccharin, aspartame, acesulfame potassium, mannitol, talin, sylitol, sucralose, sorbitol, Swiss cream, tagatose, tangerine, thaumatin, tutti fruitti, vanilla, walnut, watermelon, wild cherry, wintergreen, xylitol, or any combination of these flavoring ingredients, e.g., anise-menthol, cherry-anise, cinnamon-orange, cherry-cinnamon, chocolate-mint, honey-lemon, lemon-lime, lemon-mint, menthol-eucalyptus, orange-cream, vanilla-mint, and mixtures thereof.

"Lubricants" and "glidants" are compounds that prevent, reduce or inhibit adhesion or friction of materials. Exemplary lubricants include, e.g., stearic acid, calcium hydroxide, talc, sodium stearyl fumerate, a hydrocarbon such as mineral oil, or hydrogenated vegetable oil such as hydrogenated soybean oil (Sterotex®), higher fatty acids and their alkali-metal and alkaline earth metal salts, such as aluminum, calcium, magnesium, zinc, stearic acid, sodium stearates, glycerol, talc, waxes, Stearowet®, boric acid, sodium benzoate, sodium acetate, sodium chloride, leucine, a polyethylene glycol (e.g., PEG-4000) or a methoxypolyethylene glycol such as Carbowax™, sodium oleate, sodium benzoate, glyceryl behenate, polyethylene glycol, magnesium or sodium lauryl sulfate, colloidal silica such as Syloid™, Cab-O-Sil®, a starch such as corn starch, silicone oil, a surfactant, and the like.

A "measurable serum concentration" or "measurable plasma concentration" describes the blood serum or blood plasma concentration, typically measured in mg, g, or ng of therapeutic agent per ml, dl, or l of blood serum, absorbed into the bloodstream after administration. As used herein, measurable plasma concentrations are typically measured in ng/ml or g/ml.

"Pharmacodynamics" refers to the factors which determine the biologic response observed relative to the concentration of drug at a site of action.

"Pharmacokinetics" refers to the factors which determine the attainment and maintenance of the appropriate concentration of drug at a site of action.

"Plasticizers" are compounds used to soften the microencapsulation material or film coatings to make them less brittle. Suitable plasticizers include, e.g., polyethylene glycols such as PEG 300, PEG 400, PEG 600, PEG 1450, PEG 3350, and PEG 800, stearic acid, propylene glycol, oleic acid, triethyl cellulose and triacetin. In some embodiments, plasticizers can also function as dispersing agents or wetting agents.

"Solubilizers" include compounds such as triacetin, triethylcitrate, ethyl oleate, ethyl caprylate, sodium lauryl sulfate, sodium doccusate, vitamin E TPGS, dimethylacetamide, N-methylpyrrolidone, N-hydroxyethylpyrrolidone, polyvinylpyrrolidone, hydroxypropylmethyl cellulose, hydroxypropyl cyclodextrins, ethanol, n-butanol, isopropyl alcohol, cholesterol, bile salts, polyethylene glycol 200-600, glycofurol, transcutol, propylene glycol, and dimethyl isosorbide and the like.

"Stabilizers" include compounds such as any antioxidation agents, buffers, acids, preservatives and the like.

"Steady state," as used herein, is when the amount of drug administered is equal to the amount of drug eliminated within one dosing interval resulting in a plateau or constant plasma drug exposure.

"Suspending agents" include compounds such as polyvinylpyrrolidone, e.g., polyvinylpyrrolidone K12, polyvinylpyrrolidone K17, polyvinylpyrrolidone K25, or polyvinylpyrrolidone K30, vinyl pyrrolidone/vinyl acetate copolymer (S630), polyethylene glycol, e.g., the polyethylene glycol can have a molecular weight of about 300 to about 6000, or about 3350 to about 4000, or about 7000 to about 5400, sodium carboxymethylcellulose, methylcellulose, hydroxypropylmethylcellulose, hydroxymethylcellulose acetate stearate, polysorbate-80, hydroxyethylcellulose, sodium alginate, gums, such as, e.g., gum tragacanth and gum acacia, guar gum, xanthans, including xanthan gum, sugars, cellulosics, such as, e.g., sodium carboxymethylcellulose, methylcellulose, sodium carboxymethylcellulose, hydroxypropylmethylcellulose, hydroxyethylcellulose, polysorbate-80, sodium alginate, polyethoxylated sorbitan monolaurate, polyethoxylated sorbitan monolaurate, povidone and the like.

"Surfactants" include compounds such as sodium lauryl sulfate, sodium docusate, Tween 60 or 80, triacetin, vitamin E TPGS, sorbitan monooleate, polyoxyethylene sorbitan monooleate, polysorbates, polaxomers, bile salts, glyceryl monostearate, copolymers of ethylene oxide and propylene oxide, e.g., Pluronic® (BASF), and the like. Some other surfactants include polyoxyethylene fatty acid glycerides and vegetable oils, e.g., polyoxyethylene (60) hydrogenated castor oil; and polyoxyethylene alkylethers and alkylphenyl ethers, e.g., octoxynol 10, octoxynol 40. In some embodiments, surfactants may be included to enhance physical stability or for other purposes.

"Viscosity enhancing agents" include, e.g., methyl cellulose, xanthan gum, carboxymethyl cellulose, hydroxypropyl cellulose, hydroxypropylmethyl cellulose, hydroxypropylmethyl cellulose acetate stearate, hydroxypropylmethyl cellulose phthalate, carbomer, polyvinyl alcohol, alginates, acacia, chitosans and combinations thereof.

"Wetting agents" include compounds such as oleic acid, glyceryl monostearate, sorbitan monooleate, sorbitan monolaurate, triethanolamine oleate, polyoxyethylene sorbitan monooleate, polyoxyethylene sorbitan monolaurate, sodium docusate, sodium oleate, sodium lauryl sulfate, sodium doccusate, triacetin, Tween 80, vitamin E TPGS, ammonium salts and the like.

5.1 Dosage Forms

The compositions described herein can be formulated for administration to a subject via any conventional means including, but not limited to, oral, parenteral (e.g., intravenous, subcutaneous, or intramuscular), buccal, intranasal, rectal or transdermal administration routes. As used herein, the term "subject" is used to mean an animal, preferably a mammal, including a human or non-human. The terms patient and subject may be used interchangeably.

Moreover, the pharmaceutical compositions described herein, which include a compound of any one of Formula (P2-I), Formula (P4-I)-(P4-Vb), Formula (P5-I')-(P5-Vd), and Formula (P6-I)-(P6-IIId) can be formulated into any suitable dosage form, including but not limited to, aqueous oral dispersions, liquids, gels, syrups, elixirs, slurries, suspensions and the like, for oral ingestion by a patient to be treated, solid oral dosage forms, aerosols, controlled release formulations, fast melt formulations, effervescent formulations, lyophilized formulations, tablets, powders, pills, dragees, capsules, delayed release formulations, extended release formulations, pulsatile release formulations, multiparticulate formulations, and mixed immediate release and controlled release formulations.

Pharmaceutical preparations for oral use can be obtained by mixing one or more solid excipient with one or more of the compounds described herein, optionally grinding the resulting mixture, and processing the mixture of granules, after adding suitable auxiliaries, if desired, to obtain tablets or dragee cores. Suitable excipients include, for example, fillers such as sugars, including lactose, sucrose, mannitol, or sorbitol; cellulose preparations such as, for example, maize starch, wheat starch, rice starch, potato starch, gelatin, gum tragacanth, methylcellulose, microcrystalline cellulose, hydroxypropylmethylcellulose, sodium carboxymethylcellulose; or others such as: polyvinylpyrrolidone (PVP or povidone) or calcium phosphate. If desired, disintegrating agents may be added, such as the cross-linked croscarmellose sodium, polyvinylpyrrolidone, agar, or alginic acid or a salt thereof such as sodium alginate.

Dragee cores are provided with suitable coatings. For this purpose, concentrated sugar solutions may be used, which may optionally contain gum arabic, talc, polyvinylpyrrolidone, carbopol gel, polyethylene glycol, and/or titanium dioxide, lacquer solutions, and suitable organic solvents or solvent mixtures. Dyestuffs or pigments may be added to the tablets or dragee coatings for identification or to characterize different combinations of active compound doses.

Pharmaceutical preparations which can be used orally include push-fit capsules made of gelatin, as well as soft, sealed capsules made of gelatin and a plasticizer, such as glycerol or sorbitol. The push-fit capsules can contain the active ingredients in admixture with filler such as lactose, binders such as starches, and/or lubricants such as talc or magnesium stearate and, optionally, stabilizers. In soft capsules, the active compounds may be dissolved or suspended in suitable liquids, such as fatty oils, liquid paraffin, or liquid polyethylene glycols. In addition, stabilizers may be added. All formulations for oral administration should be in dosages suitable for such administration.

In some embodiments, the solid dosage forms disclosed herein may be in the form of a tablet, (including a suspension tablet, a fast-melt tablet, a bite-disintegration tablet, a rapid-disintegration tablet, an effervescent tablet, or a caplet), a pill, a powder (including a sterile packaged powder, a dispensable powder, or an effervescent powder) a capsule (including both soft or hard capsules, e.g., capsules made from animal-derived gelatin or plant-derived HPMC, or "sprinkle capsules"), solid dispersion, solid solution, bioerodible dosage form, controlled release formulations, pulsatile release dosage forms, multiparticulate dosage forms, pellets, granules, or an aerosol. In some embodiments, the pharmaceutical composition is in the form of a powder. In some embodiments, the pharmaceutical composition is in the form of a tablet, including but not limited to, a fast-melt tablet. Additionally, pharmaceutical compositions described herein may be administered as a single capsule or in multiple capsule dosage form. In some embodiments, the pharmaceutical composition is administered in two, or three, or four, capsules or tablets.

In some embodiments, solid dosage forms, e.g., tablets, effervescent tablets, and capsules, are prepared by mixing particles of a compound of any one of Formula (P2-I), Formula (P4-I)-(P4-Vb), Formula (P5-I')-(P5-Vd), and Formula (P6-I)-(P6-IIId) with one or more pharmaceutical excipients to form a bulk blend composition. When referring to these bulk blend compositions as homogeneous, it is meant that the particles of the compound of any of Formula (P2-I), Formula (P4-I)-(P4-Vb), Formula (P5-I')-(P5-Vd), and Formula (P6-I)-(P6-IIId) are dispersed evenly throughout the composition so that the composition may be readily subdivided into equally effective unit dosage forms, such as tablets, pills, and capsules. The individual unit dosages may also include film coatings, which disintegrate upon oral ingestion or upon contact with diluent. These formulations can be manufactured by conventional pharmacological techniques.

Conventional pharmacological techniques include, e.g., one or a combination of methods: (1) dry mixing, (2) direct compression, (3) milling, (4) dry or non-aqueous granulation, (5) wet granulation, or (6) fusion. See, e.g., Lachman et al., The Theory and Practice of Industrial Pharmacy (1986). Other methods include, e.g., spray drying, pan coating, melt granulation, granulation, fluidized bed spray drying or coating (e.g., wurster coating), tangential coating, top spraying, tableting, extruding and the like.

The pharmaceutical solid dosage forms described herein can include a compound described herein and one or more pharmaceutically acceptable additives such as a compatible carrier, binder, filling agent, suspending agent, flavoring agent, sweetening agent, disintegrating agent, dispersing agent, surfactant, lubricant, colorant, diluent, solubilizer, moistening agent, plasticizer, stabilizer, penetration enhancer, wetting agent, anti-foaming agent, antioxidant, preservative, or one or more combination thereof. In some embodiments, using standard coating procedures, such as those described in Remington's Pharmaceutical Sciences, 20th Edition (2000), a film coating is provided around the formulation of the compound of Formula (P-I), Formula (I)-Formula (LXIIIb), Formula (P2-I), Formula (P4-I)-(P4-Vb), or Formula (P5-I')-(P5-Vd). In some embodiments, some or all of the particles of the compound of Formula (P-I), Formula (I)-Formula (LXIIIb), Formula (P2-I), Formula (P4-I)-(P4-Vb), or Formula (P5-I')-(P5-Vd) are coated. In some embodiments, some or all of the particles of the compound of Formula (P-I), Formula (I)-Formula (LXIIIb), Formula (P2-I), Formula (P4-I)-(P4-Vb), or Formula (P5-I')-(P5-Vd) are microencapsulated. In still some embodiments, the particles of the compound of Formula (P-I), Formula (I)-Formula (LXIIIb), Formula (P2-I), Formula (P4-I)-(P4-Vb), or Formula (P5-I')-(P5-Vd) are not microencapsulated and are uncoated.

Suitable carriers for use in the solid dosage forms described herein include, but are not limited to, acacia, gelatin, colloidal silicon dioxide, calcium glycerophosphate, calcium lactate, maltodextrin, glycerine, magnesium silicate, sodium caseinate, soy lecithin, sodium chloride, tricalcium phosphate, dipotassium phosphate, sodium stearoyl lactylate, carrageenan, monoglyceride, diglyceride, pregelatinized starch, hydroxypropylmethylcellulose, hydroxypropylmethylcellulose acetate stearate, sucrose, microcrystalline cellulose, lactose, mannitol and the like.

Suitable filling agents for use in the solid dosage forms described herein include, but are not limited to, lactose, calcium carbonate, calcium phosphate, dibasic calcium phosphate, calcium sulfate, microcrystalline cellulose, cellulose powder, dextrose, dextrates, dextran, starches, pregelatinized starch, hydroxypropylmethycellulose (HPMC), hydroxypropylmethycellulose phthalate, hydroxypropylmethylcellulose acetate stearate (HPMCAS), sucrose, xylitol, lactitol, mannitol, sorbitol, sodium chloride, polyethylene glycol, and the like.

In order to release the compound of Formula (P-I), Formula (I)-Formula (LXIIIb), Formula (P2-I), Formula (P4-I)-(P4-Vb), or Formula (P5-I')-(P5-Vd) or a pharmaceutically acceptable salt thereof from a solid dosage form matrix as efficiently as possible, disintegrants are often used in the formulation, especially when the dosage forms are compressed with binder. Disintegrants help rupturing the dosage form matrix by swelling or capillary action when moisture is absorbed into the dosage form. Suitable disintegrants for use in the solid dosage forms described herein include, but are not limited to, natural starch such as corn starch or potato starch, a pregelatinized starch such as National 1551 or Amijel®, or sodium starch glycolate such as Promogel® or Explotab®, a cellulose such as a wood product, methylcrystalline cellulose, e.g., Avicel®, Avicel® PH101, Avicel® PH102, Avicel® PH105, Elcema® P100, Emcocel®, Vivacel®, Ming Tia®, and Solka-Floc®, methylcellulose, croscarmellose, or a cross-linked cellulose, such as cross-linked sodium carboxymethylcellulose (Ac-Di-Sol®), cross-linked carboxymethylcellulose, or cross-linked croscarmellose, a cross-linked starch such as sodium starch glycolate, a cross-linked polymer such as crospovidone, a cross-linked polyvinylpyrrolidone, alginate such as alginic acid or a salt of alginic acid such as sodium alginate, a clay such as Veegum® HV (magnesium aluminum silicate), a gum such as agar, guar, locust bean, Karaya, pectin, or tragacanth, sodium starch glycolate, bentonite, a natural sponge, a surfactant, a resin such as a cation-exchange resin, citrus pulp, sodium lauryl sulfate, sodium lauryl sulfate in combination starch, and the like.

Binders impart cohesiveness to solid oral dosage form formulations: for powder filled capsule formulation, they aid in plug formation that can be filled into soft or hard shell capsules and for tablet formulation, they ensure the tablet remaining intact after compression and help assure blend uniformity prior to a compression or fill step. Materials suitable for use as binders in the solid dosage forms described herein include, but are not limited to, carboxymethylcellulose, methylcellulose (e.g., Methocel®), hydroxypropylmethylcellulose (e.g. Hypromellose USP Pharmacoat-603, hydroxypropylmethylcellulose acetate stearate (Agoate HS-LF and HS), hydroxyethylcellulose, hydroxypropylcellulose (e.g., Klucel®), ethylcellulose (e.g., Ethocel®), and microcrystalline cellulose (e.g., Avicel®), microcrystalline dextrose, amylose, magnesium aluminum silicate, polysaccharide acids, bentonites, gelatin, polyvinylpyrrolidone/vinyl acetate copolymer, crospovidone, povidone, starch, pregelatinized starch, tragacanth, dextrin, a sugar, such as sucrose (e.g., Dipac®), glucose, dextrose, molasses, mannitol, sorbitol, xylitol (e.g., Xylitab®), lactose, a natural or synthetic gum such as acacia, tragacanth, ghatti gum, mucilage of isapol husks, starch, polyvinylpyrrolidone (e.g., Povidone® CL, Kollidon® CL, Polyplasdone® XL-10, and Povidone® K-12), larch arabogalactan, Veegum®, polyethylene glycol, waxes, sodium alginate, and the like.

In general, binder levels of 20-70% are used in powder-filled gelatin capsule formulations. Binder usage level in tablet formulations varies whether direct compression, wet granulation, roller compaction, or usage of other excipients such as fillers which itself can act as moderate binder. Formulators skilled in art can determine the binder level for the formulations, but binder usage level of up to 70% in tablet formulations is common.

Suitable lubricants or glidants for use in the solid dosage forms described herein include, but are not limited to, stearic acid, calcium hydroxide, talc, corn starch, sodium stearyl fumerate, alkali-metal and alkaline earth metal salts, such as aluminum, calcium, magnesium, zinc, stearic acid, sodium stearates, magnesium stearate, zinc stearate, waxes, Stearowet®, boric acid, sodium benzoate, sodium acetate, sodium chloride, leucine, a polyethylene glycol or a methoxypolyethylene glycol such as Carbowax™, PEG 4000, PEG 5000, PEG 6000, propylene glycol, sodium oleate, glyceryl behenate, glyceryl palmitostearate, glyceryl benzoate, magnesium or sodium lauryl sulfate, and the like.

Suitable diluents for use in the solid dosage forms described herein include, but are not limited to, sugars (including lactose, sucrose, and dextrose), polysaccharides (including dextrates and maltodextrin), polyols (including mannitol, xylitol, and sorbitol), cyclodextrins and the like.

The term "non water-soluble diluent" represents compounds typically used in the formulation of pharmaceuticals, such as calcium phosphate, calcium sulfate, starches, modified starches and microcrystalline cellulose, and microcellulose (e.g., having a density of about 0.45 g/cm$^3$, e.g. Avicel, powdered cellulose), and talc.

Suitable wetting agents for use in the solid dosage forms described herein include, for example, oleic acid, glyceryl monostearate, sorbitan monooleate, sorbitan monolaurate, triethanolamine oleate, polyoxyethylene sorbitan monooleate, polyoxyethylene sorbitan monolaurate, quaternary ammonium compounds (e.g., Polyquat 10®), sodium oleate, sodium lauryl sulfate, magnesium stearate, sodium docusate, triacetin, vitamin E TPGS and the like.

Suitable surfactants for use in the solid dosage forms described herein include, for example, sodium lauryl sulfate, sorbitan monooleate, polyoxyethylene sorbitan monooleate, polysorbates, polaxomers, bile salts, glyceryl monostearate, copolymers of ethylene oxide and propylene oxide, e.g., Pluronic® (BASF), and the like.

Suitable suspending agents for use in the solid dosage forms described here include, but are not limited to, polyvinylpyrrolidone, e.g., polyvinylpyrrolidone K12, polyvinylpyrrolidone K17, polyvinylpyrrolidone K25, or polyvinylpyrrolidone K30, polyethylene glycol, e.g., the polyethylene glycol can have a molecular weight of about 300 to about 6000, or about 3350 to about 4000, or about 7000 to about 5400, vinyl pyrrolidone/vinyl acetate copolymer (S630), sodium carboxymethylcellulose, methylcellulose, hydroxy-propylmethylcellulose, polysorbate-80, hydroxyethylcellulose, sodium alginate, gums, such as, e.g., gum tragacanth and gum acacia, guar gum, xanthans, including xanthan gum, sugars, cellulosics, such as, e.g., sodium carboxymethylcellulose, methylcellulose, sodium carboxymethylcellulose, hydroxypropylmethylcellulose, hydroxyethylcellulose, polysorbate-80, sodium alginate, polyethoxylated sorbitan monolaurate, polyethoxylated sorbitan monolaurate, povidone and the like.

Suitable antioxidants for use in the solid dosage forms described herein include, for example, e.g., butylated hydroxytoluene (BHT), sodium ascorbate, and tocopherol.

It should be appreciated that there is considerable overlap between additives used in the solid dosage forms described herein. Thus, the above-listed additives should be taken as merely exemplary, and not limiting, of the types of additives that can be included in solid dosage forms described herein. The amounts of such additives can be readily determined by one skilled in the art, according to the particular properties desired.

In some embodiments, one or more layers of the pharmaceutical composition are plasticized. Illustratively, a plasticizer is generally a high boiling point solid or liquid. Suitable plasticizers can be added from about 0.01% to about 50% by weight (w/w) of the coating composition. Plasticizers include, but are not limited to, diethyl phthalate, citrate esters, polyethylene glycol, glycerol, acetylated glycerides, triacetin, polypropylene glycol, polyethylene glycol, triethyl citrate, dibutyl sebacate, stearic acid, stearol, stearate, and castor oil.

Compressed tablets are solid dosage forms prepared by compacting the bulk blend of the formulations described above. In various embodiments, compressed tablets which are designed to dissolve in the mouth will include one or more flavoring agents. In some embodiments, the compressed tablets will include a film surrounding the final compressed tablet. In some embodiments, the film coating can provide a delayed release of the compound of Formula (P-I), Formula (I)-Formula (LXIIIb), Formula (P2-I), Formula (P4-I)-(P4-Vb), or Formula (P5-I')-(P5-Vd) from the formulation. In some embodiments, the film coating aids in patient compliance (e.g., Opadry® coatings or sugar coating). Film coatings including Opadry® typically range from about 1% to about 3% of the tablet weight. In some embodiments, the compressed tablets include one or more excipients.

A capsule may be prepared, for example, by placing the bulk blend of the formulation of the compound of Formula (P-I), Formula (I)-Formula (LXIIIb), Formula (P2-I), Formula (P4-I)-(P4-Vb), or Formula (P5-I')-(P5-Vd) described above, inside of a capsule. In some embodiments, the formulations (non-aqueous suspensions and solutions) are placed in a soft gelatin capsule. In some embodiments, the formulations are placed in standard gelatin capsules or non-gelatin capsules such as capsules comprising HPMC. In some embodiments, the formulation is placed in a sprinkle capsule, wherein the capsule may be swallowed whole or the capsule may be opened and the contents sprinkled on food prior to eating. In some embodiments, the therapeutic dose is split into multiple (e.g., two, three, or four) capsules. In some embodiments, the entire dose of the formulation is delivered in a capsule form.

In various embodiments, the particles of the compound of Formula (P-I), Formula (I)-Formula (LXIIIb), Formula (P2-I), Formula (P4-I)-(P4-Vb), or Formula (P5-I')-(P5-Vd) and one or more excipients are dry blended and compressed into a mass, such as a tablet, having a hardness sufficient to provide a pharmaceutical composition that substantially disintegrates within less than about 30 minutes, less than about 35 minutes, less than about 40 minutes, less than about 45 minutes, less than about 50 minutes, less than about 55 minutes, or less than about 60 minutes, after oral administration, thereby releasing the formulation into the gastrointestinal fluid.

In some embodiments, dosage forms may include microencapsulated formulations. In some embodiments, one or more other compatible materials are present in the microencapsulation material. Exemplary materials include, but are not limited to, pH modifiers, erosion facilitators, anti-foaming agents, antioxidants, flavoring agents, and carrier materials such as binders, suspending agents, disintegration agents, filling agents, surfactants, solubilizers, stabilizers, lubricants, wetting agents, and diluents.

Materials useful for the microencapsulation described herein include materials compatible with compounds of Formula (P-I), Formula (I)-Formula (LXIIIb), Formula (P2-I), Formula (P4-I)-(P4-Vb), or Formula (P5-I')-(P5-Vd) which sufficiently isolate the compound of Formula (P-I), Formula (I)-Formula (LXIIIb), Formula (P2-I), Formula (P4-I)-(P4-Vb), or Formula (P5-I')-(P5-Vd) from other non-compatible excipients. Materials compatible with compounds of Formula (P-I), Formula (I)-Formula (LXIIIb), Formula (P2-I), Formula (P4-I)-(P4-Vb), or Formula (P5-I')-(P5-Vd) are those that delay the release of the compounds of Formula (P-I), Formula (I)-Formula (LXIIIb), Formula (P2-I), Formula (P4-I)-(P4-Vb), or Formula (P5-I')-(P5-Vd) in vivo.

Exemplary microencapsulation materials useful for delaying the release of the formulations including compounds described herein, include, but are not limited to, hydroxypropyl cellulose ethers (HPC) such as Klucel® or Nisso HPC, low-substituted hydroxypropyl cellulose ethers (L-HPC), hydroxypropyl methyl cellulose ethers (HPMC) such as Seppifilm-LC, Pharmacoat®, Metolose SR, Methocel®-E, Opadry YS, PrimaFlo, Benecel MP824, and Benecel MP843, methylcellulose polymers such as Methocel®-A, hydroxypropylmethylcellulose acetate stearate Aqoat (HF-LS, HF-LG, HF-MS) and Metolose®, Ethylcelluloses (EC) and mixtures thereof such as E461, Ethocel®, Aqualon®-EC, Surelease®, Polyvinyl alcohol (PVA) such as Opadry AMB, hydroxyethylcelluloses such as Natrosol®, carboxymethylcelluloses and salts of carboxymethylcelluloses (CMC) such as Aqualon®-CMC, polyvinyl alcohol and polyethylene glycol co-polymers such as Kollicoat IR®, monoglycerides (Myverol), triglycerides (KLX), polyethylene glycols, modified food starch, acrylic polymers and mixtures of acrylic polymers with cellulose ethers such as Eudragit® EPO, Eudragit® L30D-55, Eudragit® FS 30D Eudragit® L100-55, Eudragit® L100, Eudragit® S100, Eudragit® RD100, Eudragit® E100, Eudragit® L12.5, Eudragit® S12.5, Eudragit® NE30D, and Eudragit® NE 40D, cellulose acetate phthalate, sepifilms such as mixtures of HPMC and stearic acid, cyclodextrins, and mixtures of these materials.

In some embodiments, plasticizers such as polyethylene glycols, e.g., PEG 300, PEG 400, PEG 600, PEG 1450, PEG 3350, and PEG 800, stearic acid, propylene glycol, oleic acid, and triacetin are incorporated into the microencapsulation material. In some embodiments, the microencapsulating material useful for delaying the release of the pharmaceutical compositions is from the USP or the National Formulary (NF). In some embodiments, the microencapsulation material is Klucel. In some embodiments, the microencapsulation material is methocel.

Microencapsulated compounds of any one of Formula (P2-I), Formula (P4-I)-(P4-Vb), Formula (P5-I')-(P5-Vd), and Formula (P6-I)-(P6-IIId) may be formulated by methods known by one of ordinary skill in the art. Such known methods include, e.g., spray drying processes, spinning disk-solvent processes, hot melt processes, spray chilling methods, fluidized bed, electrostatic deposition, centrifugal extrusion, rotational suspension separation, polymerization at liquid-gas or solid-gas interface, pressure extrusion, or spraying solvent extraction bath. In addition to these, several chemical techniques, e.g., complex coacervation, solvent evaporation, polymer-polymer incompatibility, interfacial polymerization in liquid media, in situ polymerization, in-liquid drying, and desolvation in liquid media could also be used. Furthermore, other methods such as roller compaction, extrusion/spheronization, coacervation, or nanoparticle coating may also be used.

In some embodiments, the particles of compounds of any one of Formula (P2-I), Formula (P4-I)-(P4-Vb), Formula (P5-I')-(P5-Vd), and Formula (P6-I)-(P6-IIId) are microencapsulated prior to being formulated into one of the above forms. In still some embodiments, some or most of the particles are coated prior to being further formulated by using standard coating procedures, such as those described in Remington's Pharmaceutical Sciences, 20th Edition (2000).

In some embodiments, the solid dosage formulations of the compounds of any one of Formula (P2-I), Formula (P4-I)-(P4-Vb), Formula (P5-I')-(P5-Vd), and Formula (P6-I)-(P6-IIId) are plasticized (coated) with one or more layers. Illustratively, a plasticizer is generally a high boiling point solid or liquid. Suitable plasticizers can be added from about 0.01% to about 50% by weight (w/w) of the coating composition. Plasticizers include, but are not limited to, diethyl phthalate, citrate esters, polyethylene glycol, glycerol, acetylated glycerides, triacetin, polypropylene glycol, polyethylene glycol, triethyl citrate, dibutyl sebacate, stearic acid, stearol, stearate, and castor oil.

In some embodiments, a powder including the formulations with a compound of any one of Formula (P2-I), Formula (P4-I)-(P4-Vb), Formula (P5-I')-(P5-Vd), and Formula (P6-I)-(P6-IIId) described herein, may be formulated to include one or more pharmaceutical excipients and flavors. Such a powder may be prepared, for example, by mixing the formulation and optional pharmaceutical excipients to form a bulk blend composition. Additional embodiments also include a suspending agent and/or a wetting agent. This bulk blend is uniformly subdivided into unit dosage packaging or multi-dosage packaging units.

In still some embodiments, effervescent powders are also prepared in accordance with the present disclosure. Effervescent salts have been used to disperse medicines in water for oral administration. Effervescent salts are granules or coarse powders containing a medicinal agent in a dry mixture, usually composed of sodium bicarbonate, citric acid, and/or tartaric acid. When salts of the compositions described herein are added to water, the acids and the base react to liberate carbon dioxide gas, thereby causing "effervescence." Examples of effervescent salts include, e.g., the following ingredients: sodium bicarbonate or a mixture of sodium bicarbonate and sodium carbonate, citric acid and/or tartaric acid. Any acid-base combination that results in the liberation of carbon dioxide can be used in place of the combination of sodium bicarbonate and citric and tartaric acids, as long as the ingredients were suitable for pharmaceutical use and result in a pH of about 6.0 or higher.

In some embodiments, the formulations described herein, which include a compound of Formula (P-I), Formula (I)-Formula (LXIIIb), Formula (P2-I), Formula (P4-I)-(P4-Vb), or Formula (P5-I')-(P5-Vd) are solid dispersions. Methods of producing such solid dispersions are known in the art and include, but are not limited to, for example, U.S. Pat. Nos. 4,343,789, 5,340,591, 5,456,923, 5,700,485, 5,723,269, and U.S. Pub. Appl 2004/0013734, each of which is specifically incorporated by reference. In some embodiments, the formulations described herein are solid solutions. Solid solutions incorporate a substance together with the active agent and other excipients such that heating the mixture results in dissolution of the drug and the resulting composition is then cooled to provide a solid blend which can be further formulated or directly added to a capsule or compressed into a tablet. Methods of producing such solid solutions are known in the art and include, but are not limited to, for example, U.S. Pat. Nos. 4,151,273, 5,281,420, and 6,083,518, each of which is specifically incorporated by reference.

The pharmaceutical solid oral dosage forms including formulations described herein, which include a compound of any one of Formula (P-I), Formula (I)-Formula (LXIIIb), Formula (P2-I), Formula (P4-I)-(P4-Vb), and Formula (P5-I')-(P5-Vd), can be further formulated to provide a controlled release of the compound of Formula (P-I), Formula (I)-Formula (LXIIIb), Formula (P2-I), Formula (P4-I)-(P4-Vb), or Formula (P5-I')-(P5-Vd). Controlled release refers to the release of the compound of any one of Formula (P2-I), Formula (P4-I)-(P4-Vb), Formula (P5-I')-(P5-Vd), and Formula (P6-I)-(P6-IIId) from a dosage form in which it is incorporated according to a desired profile over an extended period of time. Controlled release profiles include, for example, sustained release, prolonged release, pulsatile release, and delayed release profiles. In contrast to immediate release compositions, controlled release compositions allow delivery of an agent to a subject over an extended period of time according to a predetermined profile. Such release rates can provide therapeutically effective levels of agent for an extended period of time and thereby provide a longer period of pharmacologic response while minimizing side effects as compared to conventional rapid release dosage forms. Such longer periods of response provide for many inherent benefits that are not achieved with the corresponding short acting, immediate release preparations.

In some embodiments, the solid dosage forms described herein can be formulated as enteric coated delayed release oral dosage forms, i.e., as an oral dosage form of a pharmaceutical composition as described herein which utilizes an enteric coating to affect release in the small intestine of the gastrointestinal tract. The enteric coated dosage form may be a compressed or molded or extruded tablet/mold (coated or uncoated) containing granules, powder, pellets, beads or particles of the active ingredient and/or other composition components, which are themselves coated or uncoated. The enteric coated oral dosage form may also be a capsule (coated or uncoated) containing pellets, beads or granules of the solid carrier or the composition, which are themselves coated or uncoated.

The term "delayed release" as used herein refers to the delivery so that the release can be accomplished at some generally predictable location in the intestinal tract more distal to that which would have been accomplished if there had been no delayed release alterations. In some embodiments the method for delay of release is coating. Any coatings should be applied to a sufficient thickness such that the entire coating does not dissolve in the gastrointestinal fluids at pH below about 5, but does dissolve at pH about 5 and above. It is expected that any anionic polymer exhibiting a pH-dependent solubility profile can be used as an enteric coating in the methods and compositions described herein to achieve delivery to the lower gastrointestinal tract. In some embodiments the polymers described herein are anionic carboxylic polymers. In some embodiments, the polymers and compatible mixtures thereof, and some of their properties, include, but are not limited to:

Shellac, also called purified lac, a refined product obtained from the resinous secretion of an insect. This coating dissolves in media of pH >7;

Acrylic polymers. The performance of acrylic polymers (primarily their solubility in biological fluids) can vary based on the degree and type of substitution. Examples of suitable acrylic polymers include methacrylic acid copolymers and ammonium methacrylate copolymers. The Eudragit series E, L, S, RL, RS, and NE (Rohm Pharma) are available as solubilized in organic solvent, aqueous dispersion, or dry powders. The Eudragit series RL, NE, and RS are insoluble in the gastrointestinal tract but are permeable and are used primarily for colonic targeting. The Eudragit series E dissolve in the stomach. The Eudragit series L, L-30D and S are insoluble in stomach and dissolve in the intestine;

Cellulose Derivatives. Examples of suitable cellulose derivatives are: ethyl cellulose; reaction mixtures of partial acetate esters of cellulose with phthalic anhydride. The performance can vary based on the degree and type of substitution. Cellulose acetate phthalate (CAP) dissolves in pH >6. Aquateric (FMC) is an aqueous based system and is a spray dried CAP psuedolatex with particles <1 m. Other components in Aquateric can include pluronics, Tweens, and acetylated monoglycerides. Other suitable cellulose derivatives include: cellulose acetate trimellitate (Eastman); methylcellulose (Pharmacoat, Methocel); hydroxypropylmethyl cellulose phthalate (HPMCP); hydroxypropylmethyl cellulose succinate (HPMCS); and hydroxypropylmethylcellulose acetate succinate (e.g., AQOAT (Shin Etsu)).

The performance can vary based on the degree and type of substitution. For example, HPMCP such as, HP-50, HP-55, HP-55S, HP-55F grades are suitable. The performance can vary based on the degree and type of substitution. For example, suitable grades of hydroxypropylmethylcellulose acetate succinate include, but are not limited to, AS-LG (LF), which dissolves at pH 5, AS-MG (MF), which dissolves at pH 5.5, and AS-HG (HF), which dissolves at higher pH. These polymers are offered as granules, or as fine powders for aqueous dispersions.

Poly Vinyl Acetate Phthalate (PVAP). PVAP dissolves in pH >5, and it is much less permeable to water vapor and gastric fluids.

In some embodiments, the coating can, and usually does, contain a plasticizer and possibly other coating excipients such as colorants, talc, and/or magnesium stearate, which are well known in the art. Suitable plasticizers include triethyl citrate (Citroflex 2), triacetin (glyceryl triacetate), acetyl triethyl citrate (Citroflec A2), Carbowax 400 (polyethylene glycol 400), diethyl phthalate, tributyl citrate, acetylated monoglycerides, glycerol, fatty acid esters, propylene glycol, and dibutyl phthalate. In particular, anionic carboxylic acrylic polymers usually will contain 10-25% by weight of a plasticizer, especially dibutyl phthalate, polyethylene glycol, triethyl citrate, and triacetin. Conventional coating techniques such as spray or pan coating are employed to apply coatings. The coating thickness must be sufficient to ensure that the oral dosage form remains intact until the desired site of topical delivery in the intestinal tract is reached.

Colorants, detackifiers, surfactants, antifoaming agents, lubricants (e.g., carnuba wax or PEG) may be added to the coatings besides plasticizers to solubilize or disperse the coating material, and to improve coating performance and the coated product.

In some embodiments, the formulations described herein, which include a compound of Formula (P-I), Formula (I)-Formula (LXIIIb), Formula (P2-I), Formula (P4-I)-(P4-Vb), or Formula (P5-I')-(P5-Vd) are delivered using a pulsatile dosage form. A pulsatile dosage form is capable of providing one or more immediate release pulses at predetermined time points after a controlled lag time or at specific sites. Pulsatile dosage forms including the formulations described herein, which include a compound of any one of Formula (P2-I), Formula (P4-I)-(P4-Vb), Formula (P5-I')-(P5-Vd), and Formula (P6-I)-(P6-IIId) may be administered using a variety of pulsatile formulations known in the art. For example, such formulations include, but are not limited to, those described in U.S. Pat. Nos. 5,011,692, 5,017,381, 5,229,135, and 5,840,329, each of which is specifically incorporated by reference. Other pulsatile release dosage forms suitable for use with the present formulations include, but are not limited to, for example, U.S. Pat. Nos. 4,871,549, 5,260,068, 5,260,069, 5,508,040, 5,567,441 and 5,837,284, all of which are specifically incorporated by reference. In some embodiments, the controlled release dosage form is pulsatile release solid oral dosage form including at least two groups of particles, (i.e. multiparticulate) each containing the formulation described herein. The first group of particles provides a substantially immediate dose of the compound of Formula (P-I), Formula (I)-Formula (LXIIIb), Formula (P2-I), Formula (P4-I)-(P4-Vb), or Formula (P5-I')-(P5-Vd) upon ingestion by a mammal. The first group of particles can be either uncoated or include a coating and/or sealant. The second group of particles includes coated particles, which includes from about 2% to about 75%, from about 2.5% to about 70%, or from about 40% to about 70%, by weight of the total dose of the compound of any one of Formula (P2-I), Formula (P4-I)-(P4-Vb), Formula (P5-I')-(P5-Vd), and Formula (P6-I)-(P6-IIId) in said formulation, in admixture with one or more binders. The coating includes a pharmaceutically acceptable ingredient in an amount sufficient to provide a delay of from about 2 hours to about 7 hours following ingestion before release of the second dose. Suitable coatings include one or more differentially degradable coatings such as, by way of example only, pH sensitive coatings (enteric coatings) such as acrylic resins (e.g., Eudragit® EPO, Eudragit® L30D-55, Eudragit® FS 30D Eudragit® L100-55, Eudragit® L100, Eudragit® S100, Eudragit® RD100, Eudragit® E100, Eudragit® L12.5, Eudragit® S12.5, and Eudragit® NE30D, Eudragit® NE 40D®) either alone or blended with cellulose derivatives, e.g., ethylcellulose, or non-enteric coatings having variable thickness to provide differential release of the formulation that includes a compound of any one of Formula (P-I), Formula (I)-Formula (LXIIIb), Formula (P2-I), Formula (P4-I)-(P4-Vb), and Formula (P5-I')-(P5-Vd).

Many other types of controlled release systems known to those of ordinary skill in the art and are suitable for use with the formulations described herein. Examples of such delivery systems include, e.g., polymer-based systems, such as polylactic and polyglycolic acid, plyanhydrides and polycaprolactone; porous matrices, nonpolymer-based systems that are lipids, including sterols, such as cholesterol, cholesterol esters and fatty acids, or neutral fats, such as mono-, di- and triglycerides; hydrogel release systems; silastic systems; peptide-based systems; wax coatings, bioerodible dosage forms, compressed tablets using conventional binders and the like. See, e.g., Liberman et al., Pharmaceutical Dosage Forms, 2 Ed., Vol. 1, pp. 209-214 (1990); Singh et al., Encyclopedia of Pharmaceutical Technology, $2^{nd}$ Ed., pp. 751-753 (2002); U.S. Pat. Nos. 4,327,725, 4,624,848, 4,968,509, 5,461,140, 5,456,923, 5,516,527, 5,622,721, 5,686,105, 5,700,410, 5,977,175, 6,465,014, and 6,932,983, each of which is specifically incorporated by reference.

In some embodiments, pharmaceutical compositions are provided that include particles of the compounds of any one of Formula (P2-I), Formula (P4-I)-(P4-Vb), Formula (P5-I')-(P5-Vd), and Formula (P6-I)-(P6-IIId) described herein and at least one dispersing agent or suspending agent for oral administration to a subject. The formulations may be a powder and/or granules for suspension, and upon admixture with water, a substantially uniform suspension is obtained.

Liquid formulation dosage forms for oral administration can be aqueous suspensions selected from the group including, but not limited to, pharmaceutically acceptable aqueous oral dispersions, emulsions, solutions, elixirs, gels, and syrups. See, e.g., Singh et al., Encyclopedia of Pharmaceutical Technology, $2^{nd}$ Ed., pp. 754-757 (2002). In addition to the particles of a compound of Formula (P-I), Formula (I)-Formula (LXIIIb), Formula (P2-I), Formula (P4-I)-(P4-Vb), or Formula (P5-I')-(P5-Vd) the liquid dosage forms may include additives, such as: (a) disintegrating agents; (b) dispersing agents; (c) wetting agents; (d) at least one preservative, (e) viscosity enhancing agents, (f) at least one sweetening agent, and (g) at least one flavoring agent. In some embodiments, the aqueous dispersions can further include a crystalline inhibitor.

The aqueous suspensions and dispersions described herein can remain in a homogenous state, as defined in The USP Pharmacists' Pharmacopeia (2005 edition, chapter 905), for at least 4 hours. The homogeneity should be determined by a sampling method consistent with regard to determining homogeneity of the entire composition. In some embodiments, an aqueous suspension can be re-suspended into a homogenous suspension by physical agitation lasting less than 1 minute. In some embodiments, an aqueous suspension can be re-suspended into a homogenous suspension by physical agitation lasting less than 45 seconds. In yet some embodiments, an aqueous suspension can be re-suspended into a homogenous suspension by physical agitation lasting less than 30 seconds. In still some embodiments, no agitation is necessary to maintain a homogeneous aqueous dispersion.

Examples of disintegrating agents for use in the aqueous suspensions and dispersions include, but are not limited to, a starch, e.g., a natural starch such as corn starch or potato starch, a pregelatinized starch such as National 1551 or Amijel®, or sodium starch glycolate such as Promogel® or Explotab®; a cellulose such as a wood product, methylcrystalline cellulose, e.g., Avicel®, Avicel® PH101, Avicel® PH102, Avicel® PH105, Elcema® P100, Emcocel®, Vivacel®, Ming Tia®, and Solka-Floc®, methylcellulose, croscarmellose, or a cross-linked cellulose, such as cross-linked sodium carboxymethylcellulose (Ac-Di-Sol®), cross-linked carboxymethylcellulose, or cross-linked croscarmellose; a cross-linked starch such as sodium starch glycolate; a cross-linked polymer such as crospovidone; a cross-linked polyvinylpyrrolidone; alginate such as alginic acid or a salt of alginic acid such as sodium alginate; a clay such as Veegum® HV (magnesium aluminum silicate); a gum such as agar, guar, locust bean, Karaya, pectin, or tragacanth; sodium starch glycolate; bentonite; a natural sponge; a surfactant; a resin such as a cation-exchange resin; citrus pulp; sodium lauryl sulfate; sodium lauryl sulfate in combination starch; and the like.

In some embodiments, the dispersing agents suitable for the aqueous suspensions and dispersions described herein are known in the art and include, for example, hydrophilic polymers, electrolytes, Tween® 60 or 80, PEG, polyvinylpyrrolidone (PVP; commercially known as Plasdone®), and the carbohydrate-based dispersing agents such as, for example, hydroxypropylcellulose and hydroxypropyl cellulose ethers (e.g., HPC, HPC-SL, and HPC-L), hydroxypropyl methylcellulose and hydroxypropyl methylcellulose ethers (e.g. HPMC K100, HPMC K4M, HPMC K15M, and HPMC K100M), carboxymethylcellulose sodium, methylcellulose, hydroxyethylcellulose, hydroxypropylmethyl-cellulose phthalate, hydroxypropylmethyl-cellulose acetate stearate, noncrystalline cellulose, magnesium aluminum silicate, triethanolamine, polyvinyl alcohol (PVA), polyvinylpyrrolidone/vinyl acetate copolymer (Plasdone®, e.g., S-630), 4-(1,1,3,3-tetramethylbutyl)-phenol polymer with ethylene oxide and formaldehyde (also known as tyloxapol), poloxamers (e.g., Pluronics F68®, F88®, and F108®, which are block copolymers of ethylene oxide and propylene oxide); and poloxamines (e.g., Tetronic 908®, also known as Poloxamine 908®, which is a tetrafunctional block copolymer derived from sequential addition of propylene oxide and ethylene oxide to ethylenediamine (BASF Corporation, Parsippany, N.J.)). In some embodiments, the dispersing agent is selected from a group not comprising one of the following agents: hydrophilic polymers; electrolytes; Tween® 60 or 80; PEG; polyvinylpyrrolidone (PVP); hydroxypropylcellulose and hydroxypropyl cellulose ethers (e.g., HPC, HPC-SL, and HPC-L); hydroxypropyl methylcellulose and hydroxypropyl methylcellulose ethers (e.g. HPMC K100, HPMC K4M, HPMC K15M, HPMC K100M, and Pharmacoat® USP 2910 (Shin-Etsu)); carboxymethylcellulose sodium; methylcellulose; hydroxyethylcellulose; hydroxypropylmethyl-cellulose phthalate; hydroxypropylmethylcellulose acetate stearate; noncrystalline cellulose; magnesium aluminum silicate; triethanolamine; polyvinyl alcohol (PVA); 4-(1,1,3,3-tetramethylbutyl)-phenol polymer with ethylene oxide and formaldehyde; poloxamers (e.g., Pluronics F68®, F88®, and F108®, which are block copolymers of ethylene oxide and propylene oxide); or poloxamines (e.g., Tetronic 908®, also known as Poloxamine 908®).

Wetting agents suitable for the aqueous suspensions and dispersions described herein are known in the art and include, but are not limited to, cetyl alcohol, glycerol monostearate, polyoxyethylene sorbitan fatty acid esters (e.g., the commercially available Tweens® such as e.g., Tween 20® and Tween 80® (ICI Specialty Chemicals)), and polyethylene glycols (e.g., Carbowaxs 3350® and 1450®, and Carbopol 934® (Union Carbide)), oleic acid, glyceryl monostearate, sorbitan monooleate, sorbitan monolaurate, triethanolamine oleate, polyoxyethylene sorbitan monooleate, polyoxyethylene sorbitan monolaurate, sodium oleate, sodium lauryl sulfate, sodium docusate, triacetin, vitamin E TPGS, sodium taurocholate, simethicone, phosphotidylcholine and the like Suitable preservatives for the aqueous suspensions or dispersions described herein include, for example, potassium sorbate, parabens (e.g., methylparaben and propylparaben), benzoic acid and its salts, other esters of parahydroxybenzoic acid such as butylparaben, alcohols such as ethyl alcohol or benzyl alcohol, phenolic compounds such as phenol, or quaternary compounds such as benzalkonium chloride. Preservatives, as used herein, are incorporated into the dosage form at a concentration sufficient to inhibit microbial growth.

Suitable viscosity enhancing agents for the aqueous suspensions or dispersions described herein include, but are not limited to, methyl cellulose, xanthan gum, carboxymethyl cellulose, hydroxypropyl cellulose, hydroxypropylmethyl cellulose, Plasdon® S-630, carbomer, polyvinyl alcohol, alginates, acacia, chitosans and combinations thereof. The concentration of the viscosity enhancing agent will depend upon the agent selected and the viscosity desired.

Examples of sweetening agents suitable for the aqueous suspensions or dispersions described herein include, for example, acacia syrup, acesulfame K, alitame, anise, apple, aspartame, banana, Bavarian cream, berry, black currant, butterscotch, calcium citrate, camphor, caramel, cherry, cherry cream, chocolate, cinnamon, bubble gum, citrus, citrus punch, citrus cream, cotton candy, cocoa, cola, cool cherry, cool citrus, cyclamate, cylamate, dextrose, eucalyptus, eugenol, fructose, fruit punch, ginger, glycyrrhetinate, glycyrrhiza (licorice) syrup, grape, grapefruit, honey, isomalt, lemon, lime, lemon cream, monoammonium glyrrhizinate (MagnaSweet®), maltol, mannitol, maple, marshmallow, menthol, mint cream, mixed berry, neohesperidine DC, neotame, orange, pear, peach, peppermint, peppermint cream, Prosweet® Powder, raspberry, root beer, rum, saccharin, safrole, sorbitol, spearmint, spearmint cream, strawberry, strawberry cream, stevia, sucralose, sucrose, sodium saccharin, saccharin, aspartame, acesulfame potassium, mannitol, talin, sucralose, sorbitol, swiss cream, tagatose, tangerine, thaumatin, tutti fruitti, vanilla, walnut, watermelon, wild cherry, wintergreen, xylitol, or any combination of these flavoring ingredients, e.g., anise-menthol, cherry-anise, cinnamon-orange, cherry-cinnamon, chocolate-mint, honey-lemon, lemon-lime, lemon-mint, menthol-eucalyptus, orange-cream, vanilla-mint, and mixtures thereof. In some embodiments, the aqueous liquid dispersion can comprise a sweetening agent or flavoring agent in a concentration ranging from about 0.001% to about 1.0% the volume of the aqueous dispersion. In some embodiments, the aqueous liquid dispersion can comprise a sweetening agent or flavoring agent in a concentration ranging from about 0.005% to about 0.5% the volume of the aqueous dispersion. In yet some embodiments, the aqueous liquid dispersion can comprise a sweetening agent or flavoring agent in a concentration ranging from about 0.010% to about 1.0% the volume of the aqueous dispersion.

In addition to the additives listed above, the liquid formulations can also include inert diluents commonly used in the art, such as water or other solvents, solubilizing agents, and emulsifiers. Exemplary emulsifiers are ethyl alcohol, isopropyl alcohol, ethyl carbonate, ethyl acetate, benzyl alcohol, benzyl benzoate, propyleneglycol, 1,3-butyleneglycol, dimethylformamide, sodium lauryl sulfate, sodium docusate, cholesterol, cholesterol esters, taurocholic acid, phosphotidylcholine, oils, such as cottonseed oil, groundnut oil, corn germ oil, olive oil, castor oil, and sesame oil, glycerol, tetrahydrofurfuryl alcohol, polyethylene glycols, fatty acid esters of sorbitan, or mixtures of these substances, and the like.

In some embodiments, the pharmaceutical compositions described herein can be self-emulsifying drug delivery systems (SEDDS). Emulsions are dispersions of one immiscible phase in another, usually in the form of droplets. Generally, emulsions are created by vigorous mechanical dispersion. SEDDS, as opposed to emulsions or microemulsions, spontaneously form emulsions when added to an excess of water without any external mechanical dispersion or agitation. An advantage of SEDDS is that only gentle mixing is required to distribute the droplets throughout the solution. Additionally, water or the aqueous phase can be added just prior to administration, which ensures stability of an unstable or hydrophobic active ingredient. Thus, the SEDDS provides an effective delivery system for oral and parenteral delivery of hydrophobic active ingredients. SEDDS may provide improvements in the bioavailability of hydrophobic active ingredients. Methods of producing self-emulsifying dosage forms are known in the art and include, but are not limited to, for example, U.S. Pat. Nos. 5,858,401, 6,667,048, and 6,960,563, each of which is specifically incorporated by reference.

It is to be appreciated that there is overlap between the above-listed additives used in the aqueous dispersions or suspensions described herein, since a given additive is often classified differently by different practitioners in the field, or is commonly used for any of several different functions. Thus, the above-listed additives should be taken as merely exemplary, and not limiting, of the types of additives that can be included in formulations described herein. The amounts of such additives can be readily determined by one skilled in the art, according to the particular properties desired.

5.2 Intranasal Formulations

Intranasal formulations are known in the art and are described in, for example, U.S. Pat. Nos. 4,476,116, 5,116, 817, and 6,391,452, each of which is specifically incorporated by reference. Formulations that include a compound of any one of Formula (P2-I), Formula (P4-I)-(P4-Vb), Formula (P5-I')-(P5-Vd), and Formula (P6-I)-(P6-IIId) which are prepared according to these and other techniques well-known in the art are prepared as solutions in saline, employing benzyl alcohol or other suitable preservatives, fluorocarbons, and/or other solubilizing or dispersing agents known in the art. See, for example, Ansel, H. C. et al., Pharmaceutical Dosage Forms and Drug Delivery Systems, Sixth Ed. (1995). Preferably these compositions and formulations are prepared with suitable nontoxic pharmaceutically acceptable ingredients. These ingredients are known to those skilled in the preparation of nasal dosage forms and some of these can be found in REMINGTON: THE SCIENCE AND PRACTICE OF PHARMACY, 21st edition, 2005, a standard reference in the field. The choice of suitable carriers is highly dependent upon the exact nature of the nasal dosage form desired, e.g., solutions, suspensions, ointments, or gels. Nasal dosage forms generally contain large amounts of water in addition to the active ingredient. Minor amounts of other ingredients such as pH adjusters, emulsifiers or dispersing agents, preservatives, surfactants, gelling agents, or buffering and other stabilizing and solubilizing agents may also be present. The nasal dosage form should be isotonic with nasal secretions.

For administration by inhalation, the compounds of any one of Formula (P2-I), Formula (P4-I)-(P4-Vb), Formula (P5-I')-(P5-Vd), and Formula (P6-I)-(P6-IIId) described herein may be in a form as an aerosol, a mist or a powder. Pharmaceutical compositions described herein are conveniently delivered in the form of an aerosol spray presentation from pressurized packs or a nebuliser, with the use of a suitable propellant, e.g., dichlorodifluoromethane, trichlorofluoromethane, dichlorotetrafluoroethane, carbon dioxide or other suitable gas. In the case of a pressurized aerosol, the dosage unit may be determined by providing a valve to deliver a metered amount. Capsules and cartridges of, such as, by way of example only, gelatin for use in an inhaler or insufflator may be formulated containing a powder mix of the compound described herein and a suitable powder base such as lactose or starch.

5.3 Buccal Formulations

Buccal formulations that include compounds of any one of Formula (P2-I), Formula (P4-I)-(P4-Vb), Formula (P5-I')-(P5-Vd), and Formula (P6-I)-(P6-IIId) may be administered using a variety of formulations known in the art. For example, such formulations include, but are not limited to, U.S. Pat. Nos. 4,229,447, 4,596,795, 4,755,386, and 5,739, 136, each of which is specifically incorporated by reference. In addition, the buccal dosage forms described herein can further include a bioerodible (hydrolysable) polymeric carrier that also serves to adhere the dosage form to the buccal mucosa. The buccal dosage form is fabricated so as to erode gradually over a predetermined time period, wherein the delivery of the compound of any one of Formula (P2-I), Formula (P4-I)-(P4-Vb), Formula (P5-I')-(P5-Vd), and Formula (P6-I)-(P6-IIId) is provided essentially throughout. Buccal drug delivery, as will be appreciated by those skilled in the art, avoids the disadvantages encountered with oral drug administration, e.g., slow absorption, degradation of the active agent by fluids present in the gastrointestinal tract and/or first-pass inactivation in the liver. With regard to the bioerodible (hydrolysable) polymeric carrier, it will be appreciated that virtually any such carrier can be used, so long as the desired drug release profile is not compromised, and the carrier is compatible with the compound of any one of Formula (P2-I), Formula (P4-I)-(P4-Vb), Formula (P5-

I')-(P5-Vd), and Formula (P6-I)-(P6-IIId) and any other components that may be present in the buccal dosage unit. Generally, the polymeric carrier comprises hydrophilic (water-soluble and water-swellable) polymers that adhere to the wet surface of the buccal mucosa. Examples of polymeric carriers useful herein include acrylic acid polymers and co, e.g., those known as "carbomers" (Carbopol®, which may be obtained from B.F. Goodrich, is one such polymer). Other components may also be incorporated into the buccal dosage forms described herein include, but are not limited to, disintegrants, diluents, binders, lubricants, flavoring, colorants, preservatives, and the like. For buccal or sublingual administration, the compositions may take the form of tablets, lozenges, or gels formulated in a conventional manner.

5.4 Transdermal Formulations

Transdermal formulations described herein may be administered using a variety of devices which have been described in the art. For example, such devices include, but are not limited to, U.S. Pat. Nos. 3,598,122, 3,598,123, 3,710,795, 3,731,683, 3,742,951, 3,814,097, 3,921,636, 3,972,995, 3,993,072, 3,993,073, 3,996,934, 4,031,894, 4,060,084, 4,069,307, 4,077,407, 4,201,211, 4,230,105, 4,292,299, 4,292,303, 5,336,168, 5,665,378, 5,837,280, 5,869,090, 6,923,983, 6,929,801 and 6,946,144, each of which is specifically incorporated by reference in its entirety.

The transdermal dosage forms described herein may incorporate certain pharmaceutically acceptable excipients which are conventional in the art. In some embodiments, the transdermal formulations described herein include at least three components: (1) a formulation of a compound of any one of Formula (P2-I), Formula (P4-I)-(P4-Vb), Formula (P5-I')-(P5-Vd), and Formula (P6-I)-(P6-IIId) (2) a penetration enhancer; and (3) an aqueous adjuvant. In addition, transdermal formulations can include additional components such as, but not limited to, gelling agents, creams and ointment bases, and the like. In some embodiments, the transdermal formulation can further include a woven or non-woven backing material to enhance absorption and prevent the removal of the transdermal formulation from the skin. In some embodiments, the transdermal formulations described herein can maintain a saturated or supersaturated state to promote diffusion into the skin.

Formulations suitable for transdermal administration of compounds described herein may employ transdermal delivery devices and transdermal delivery patches and can be lipophilic emulsions or buffered, aqueous solutions, dissolved and/or dispersed in a polymer or an adhesive. Such patches may be constructed for continuous, pulsatile, or on demand delivery of pharmaceutical agents. Still further, transdermal delivery of the compounds described herein can be accomplished by means of iontophoretic patches and the like. Additionally, transdermal patches can provide controlled delivery of the compounds of any one of Formula (P-I), Formula (I)-Formula (LXIIIb), Formula (P2-I), Formula (P4-I)-(P4-Vb), and Formula (P5-I')-(P5-Vd). The rate of absorption can be slowed by using rate-controlling membranes or by trapping the compound within a polymer matrix or gel. Conversely, absorption enhancers can be used to increase absorption. An absorption enhancer or carrier can include absorbable pharmaceutically acceptable solvents to assist passage through the skin. For example, transdermal devices are in the form of a bandage comprising a backing member, a reservoir containing the compound optionally with carriers, optionally a rate controlling barrier to deliver the compound to the skin of the host at a controlled and predetermined rate over a prolonged period of time, and means to secure the device to the skin.

5.5 Injectable Formulations

Formulations that include a compound of any one of Formula (P2-I), Formula (P4-I)-(P4-Vb), Formula (P5-I')-(P5-Vd), and Formula (P6-I)-(P6-IIId) suitable for intramuscular, subcutaneous, or intravenous injection may include physiologically acceptable sterile aqueous or non-aqueous solutions, dispersions, suspensions or emulsions, and sterile powders for reconstitution into sterile injectable solutions or dispersions. Examples of suitable aqueous and non-aqueous carriers, diluents, solvents, or vehicles including water, ethanol, polyols (propyleneglycol, polyethylene-glycol, glycerol, cremophor and the like), suitable mixtures thereof, vegetable oils (such as olive oil) and injectable organic esters such as ethyl oleate. Proper fluidity can be maintained, for example, by the use of a coating such as lecithin, by the maintenance of the required particle size in the case of dispersions, and by the use of surfactants. Formulations suitable for subcutaneous injection may also contain additives such as preserving, wetting, emulsifying, and dispensing agents. Prevention of the growth of microorganisms can be ensured by various antibacterial and antifungal agents, such as parabens, chlorobutanol, phenol, sorbic acid, and the like. It may also be desirable to include isotonic agents, such as sugars, sodium chloride, and the like. Prolonged absorption of the injectable pharmaceutical form can be brought about by the use of agents delaying absorption, such as aluminum monostearate and gelatin.

For intravenous injections, compounds described herein may be formulated in aqueous solutions, preferably in physiologically compatible buffers such as Hank's solution, Ringer's solution, or physiological saline buffer. For transmucosal administration, penetrants appropriate to the barrier to be permeated are used in the formulation. Such penetrants are generally known in the art. For other parenteral injections, appropriate formulations may include aqueous or nonaqueous solutions, preferably with physiologically compatible buffers or excipients. Such excipients are generally known in the art.

Parenteral injections may involve bolus injection or continuous infusion. Formulations for injection may be presented in unit dosage form, e.g., in ampoules or in multi-dose containers, with an added preservative. The pharmaceutical composition described herein may be in a form suitable for parenteral injection as a sterile suspensions, solutions, or emulsions in oily or aqueous vehicles, and may contain formulatory agents such as suspending, stabilizing and/or dispersing agents. Pharmaceutical compositions for parenteral administration include aqueous solutions of the active compounds in water-soluble form. Additionally, suspensions of the active compounds may be prepared as appropriate oily injection suspensions. Suitable lipophilic solvents or vehicles include fatty oils such as sesame oil, or synthetic fatty acid esters, such as ethyl oleate or triglycerides, or liposomes. Aqueous injection suspensions may contain substances which increase the viscosity of the suspension, such as sodium carboxymethyl cellulose, sorbitol, or dextran. Optionally, the suspension may also contain suitable stabilizers or agents which increase the solubility of the compounds to allow for the preparation of highly concentrated solutions. Alternatively, the active ingredient may be in powder form for constitution with a suitable vehicle, e.g., sterile pyrogen-free water, before use.

6. Formulations

In certain embodiments, delivery systems for pharmaceutical compounds may be employed, such as, for example, liposomes and emulsions. In certain embodiments, compositions provided herein can also include an mucoadhesive polymer, selected from among, for example, carboxymethylcellulose, carbomer (acrylic acid polymer), poly(methylmethacrylate), polyacrylamide, polycarbophil, acrylic acid/butyl acrylate copolymer, sodium alginate and dextran.

In some embodiments, the compounds described herein may be administered topically and can be formulated into a variety of topically administrable compositions, such as solutions, suspensions, lotions, gels, pastes, medicated sticks, balms, creams, or ointments. Such pharmaceutical compounds can contain solubilizers, stabilizers, tonicity enhancing agents, buffers, and preservatives.

The compounds described herein may also be formulated in rectal compositions such as enemas, rectal gels, rectal foams, rectal aerosols, suppositories, jelly suppositories, or retention enemas, containing conventional suppository bases such as cocoa butter or other glycerides, as well as synthetic polymers such as polyvinylpyrrolidone, PEG, and the like. In suppository forms of the compositions, a low-melting wax such as, but not limited to, a mixture of fatty acid glycerides, optionally in combination with cocoa butter is first melted.

7. Examples of Methods of Dosing and Treatment Regimens

The compounds described herein can be used in the preparation of medicaments for the inhibition of FLT3 or a homolog thereof, or for the treatment of diseases or conditions that would benefit, at least in part, from inhibition of FLT3 or a homolog thereof. In addition, a method for treating any of the diseases or conditions described herein in a subject in need of such treatment, involves administration of pharmaceutical compositions containing at least one compound of any of Formula (P2-I), Formula (P4-I)-(P4-Vb), Formula (P5-I')-(P5-Vd), and Formula (P6-I)-(P6-IIId) described herein, or a pharmaceutically acceptable salt, pharmaceutically acceptable N-oxide, pharmaceutically active metabolite, pharmaceutically acceptable prodrug, or pharmaceutically acceptable solvate thereof, in therapeutically effective amounts to said subject.

The compositions containing the compound(s) described herein can be administered for prophylactic and/or therapeutic treatments. In therapeutic applications, the compositions are administered to a patient already suffering from a disease or condition, in an amount sufficient to cure or at least partially arrest the symptoms of the disease or condition. Amounts effective for this use will depend on the severity and course of the disease or condition, previous therapy, the patient's health status, weight, and response to the drugs, and the judgment of the treating physician. It is considered well within the skill of the art for one to determine such therapeutically effective amounts by routine experimentation (including, but not limited to, a dose escalation clinical trial).

In prophylactic applications, compositions containing the compounds described herein are administered to a patient susceptible to or otherwise at risk of a particular disease, disorder, or condition. Such an amount is defined to be a "prophylactically effective amount or dose." In this use, the precise amounts also depend on the patient's state of health, weight, and the like. It is considered well within the skill of the art for one to determine such prophylactically effective amounts by routine experimentation (e.g., a dose escalation clinical trial). When used in a patient, effective amounts for this use will depend on the severity and course of the disease, disorder or condition, previous therapy, the patient's health status and response to the drugs, and the judgment of the treating physician.

In the case wherein the patient's condition does not improve, upon the doctor's discretion the administration of the compounds may be administered chronically, that is, for an extended period of time, including throughout the duration of the patient's life in order to ameliorate or otherwise control or limit the symptoms of the patient's disease or condition.

In the case wherein the patient's status does improve, upon the doctor's discretion the administration of the compounds may be given continuously; alternatively, the dose of drug being administered may be temporarily reduced or temporarily suspended for a certain length of time (i.e., a "drug holiday"). The length of the drug holiday can vary between 2 days and 1 year, including by way of example only, 2 days, 3 days, 4 days, 5 days, 6 days, 7 days, 10 days, 12 days, 15 days, 20 days, 28 days, 35 days, 50 days, 70 days, 100 days, 120 days, 150 days, 180 days, 200 days, 250 days, 280 days, 300 days, 320 days, 350 days, or 365 days. The dose reduction during a drug holiday may be from 10%-100%, including, by way of example only, 10%, 15%, 20%, 25%, 30%, 35%, 40%, 45%, 50%, 55%, 60%, 65%, 70%, 75%, 80%, 85%, 90%, 95%, or 100%.

Once improvement of the patient's conditions has occurred, a maintenance dose is administered if necessary. Subsequently, the dosage or the frequency of administration, or both, can be reduced, as a function of the symptoms, to a level at which the improved disease, disorder or condition is retained. Patients can, however, require intermittent treatment on a long-term basis upon any recurrence of symptoms.

The amount of a given agent that will correspond to such an amount will vary depending upon factors such as the particular compound, disease or condition and its severity, the identity (e.g., weight) of the subject or host in need of treatment, but can nevertheless be routinely determined in a manner known in the art according to the particular circumstances surrounding the case, including, e.g., the specific agent being administered, the route of administration, the condition being treated, and the subject or host being treated. In general, however, doses employed for adult human treatment will typically be in the range of 0.02-5000 mg per day, or from about 1-1500 mg per day. The desired dose may conveniently be presented in a single dose or as divided doses administered simultaneously (or over a short period of time) or at appropriate intervals, for example as two, three, four or more sub-doses per day.

The pharmaceutical composition described herein may be in unit dosage forms suitable for single administration of precise dosages. In unit dosage form, the formulation is divided into unit doses containing appropriate quantities of one or more compound. The unit dosage may be in the form of a package containing discrete quantities of the formulation. Non-limiting examples are packaged tablets or capsules, and powders in vials or ampoules. Aqueous suspension compositions can be packaged in single-dose non-reclosable containers. Alternatively, multiple-dose reclosable containers can be used, in which case it is typical to include a preservative in the composition. By way of example only, formulations for parenteral injection may be presented in unit dosage form, which include, but are not limited to ampoules, or in multi-dose containers, with an added preservative.

The foregoing ranges are merely suggestive, as the number of variables in regard to an individual treatment regime is large, and considerable excursions from these recommended values are not uncommon. Such dosages may be altered depending on a number of variables, not limited to the activity of the compound used, the disease or condition to be treated, the mode of administration, the requirements of the individual subject, the severity of the disease or condition being treated, and the judgment of the practitioner.

Toxicity and therapeutic efficacy of such therapeutic regimens can be determined by standard pharmaceutical procedures in cell cultures or experimental animals, including, but not limited to, the determination of the $LD_{50}$ (the dose lethal to 50% of the population) and the $ED_{50}$ (the dose therapeutically effective in 50% of the population). The dose ratio between the toxic and therapeutic effects is the therapeutic index and it can be expressed as the ratio between $LD_{50}$ and $ED_{50}$. Compounds exhibiting high therapeutic indices are preferred. The data obtained from cell culture assays and animal studies can be used in formulating a range of dosage for use in human. The dosage of such compounds lies preferably within a range of circulating concentrations that include the $ED_{50}$ with minimal toxicity. The dosage may vary within this range depending upon the dosage form employed and the route of administration utilized

8. Methods of Treatment

In particular embodiments, provided herein are methods of treating, ameliorating, or preventing a disease or condition in a patient in need thereof comprising administering an amount of a compound described herein to treat, ameliorate, or prevent the disease or condition. In particular embodiments, provided herein are methods of treating, ameliorating, or preventing a disease or condition in a patient in need thereof comprising administering an amount of a pharmaceutical composition described herein to treat, ameliorate, or prevent the disease or condition. In certain embodiments, provided herein are any of the compounds described herein for use in therapy. In certain embodiments, provided herein are any of the pharmaceutical compositions described herein for use in therapy. In certain embodiments, provided herein are any of the compounds described herein for use in treating, ameliorating, or preventing a disease or condition in a patient in need thereof. In certain embodiments, provided herein are any of the pharmaceutical compositions described herein for use in treating, ameliorating, or preventing a disease or condition in a patient in need thereof. In certain embodiments, provided herein are any of the compounds described herein for use the manufacture of a medicament for therapy. In certain embodiments, provided herein are any of the pharmaceutical compositions described herein for therapy. In certain embodiments, provided herein are any of the compounds described herein for use the manufacture of a medicament for treating, ameliorating, or preventing a disease or condition in a patient in need thereof. In certain embodiments, provided herein are any of the pharmaceutical compositions described herein for the manufacture of a medicament for treating, ameliorating, or preventing a disease or condition in a patient in need thereof. Useful conditions and disorders are described herein.

In certain embodiments, the disease or condition is associated with FLT3 dysfunction. In certain embodiments, the disease or condition is associated with undesired FLT3 expression. In certain embodiments, the disease or condition is associated with excessive FLT3 expression. In certain embodiments, the disease or condition is associated with undesired FLT3 levels. In certain embodiments, the disease or condition is associated with excessive FLT3 levels. In certain embodiments, the disease or condition is associated with undesired FLT3 activity. In certain embodiments, the disease or condition is associated with excessive FLT3 activity. In certain embodiments, the disease or condition is associated with undesired FLT3-MLL interaction. In certain embodiments, the disease or condition is associated with excessive FLT3-MLL interaction. In certain embodiments, the disease or condition is amenable to treatment by inhibiting FLT3 expression. In certain embodiments, the disease or condition is amenable to treatment by inhibiting excessive FLT3 expression. In certain embodiments, the disease or condition is amenable to treatment by inhibiting FLT3 levels. In certain embodiments, the disease or condition is amenable to treatment by inhibiting excessive FLT3 levels. In certain embodiments, the disease or condition is amenable to treatment by inhibiting undesired FLT3 activity. In certain embodiments, the disease or condition is amenable to treatment by inhibiting excessive FLT3 activity. In certain embodiments, the disease or condition is amenable to treatment by inhibiting FLT3-MLL interaction. In certain embodiments, the disease or condition is amenable to treatment by inhibiting excessive FLT3-MLL interaction.

In certain embodiments, the disease or condition is associated with a mutation in the FLT3 gene. In certain embodiments, the mutation in the FLT3 gene is an internal tandem duplicate mutation (FLT3-IND). In certain embodiments, the FLT3-IND mutation is a D835 mutation. In one embodiment, the FLT3-IND mutation is D835V. In certain embodiments, the FLT3-IND mutation is D835Y. In certain embodiments, the mutation is a point mutation in the tyrosine kinase domain (FLT3-TKD). In certain embodiments, the FLT3 mutation is selected from N676K, F691L, D835H, D835V, D835Y, Y842C, and combinations thereof. In certain embodiments, the FLT3 mutation is N676K. In certain embodiments, the FLT3 mutation is F691L. In certain embodiments, the FLT3 mutation is D835H. In certain embodiments, the FLT3 mutation is D835V. In certain embodiments, the FLT3 mutation is D835Y. In certain embodiments, the FLT3 mutation is Y842C. In certain embodiments, the patient has an NPM1 mutation.

In some embodiments, compounds provided herein are administered to a human.

In some embodiments, compounds provided herein are orally administered.

In some embodiments, the disease or condition is a hematologic malignancy, including, but not limited to, leukemia, lymphoma, or multiple myeloma. In certain embodiments, the disease or condition is a leukemia, including, but not limited to, acute lymphocytic leukemia (ALL), acute myeloid leukemia (AML), chronic lymphocytic leukemia (CLL), chronic myeloid leukemia (CML), prolymphocytic leukemia (PLL), acute prolymphocytic leukemia (APL), large granular lymphocytic (LGL), hairy cell leukemia (HCL), chronic neutrophilic leukemia (CNL), acute undifferentiated leukemia (AUL), anaplastic large cell lymphoma (ALCL), prolymphocytic leukemia (PML), juvenile myelomonocytic leukemia (JMML), adult T cell ALL, or myeloproliferative disorder (MPD), mast-cell lymphoma (MCC), or myelodysplastic syndromes (MDS). In certain embodiments, the disease or condition is acute myeloid leukemia (AML). In certain embodiments, the disease or condition is relapsed or refractory AML.

In certain embodiments, the disease or condition is a lymphoma, including, but not limited to, non-Hodgkin's lymphoma or Hodgkin's lymphoma. In certain embodiments, the disease or condition is non-Hodgkin's lymphoma, including, but not limited to, B-cell lymphoma, diffuse large B-cell lymphoma (DLBCL), T-cell lymphoma, Burkitt's lymphoma, follicular lymphoma (FL), mantle cell lymphoma, primary mediastinal B cell lymphoma, small lymphocytic lymphoma, or Waldenstrom macroglobulinemia (lymphoplasmacytic lymphoma). In certain embodiments, the disease or condition is Hodgkin's lymphoma, including but not limited to, lymphocyte-deleted Hodgkin's disease, lymphocyte-rich Hodgkin's disease, mixed cellularity Hodgkin's disease, nodular lymphocyte-predominant Hodgkin's disease, or nodular sclerosis Hodgkin's lymphoma.

In certain embodiments, the disease or condition is multiple myeloma. In one embodiment, the multiple myeloma is hyperdiploid. In one embodiment, the multiple myeloma is hypodiploid.

In certain embodiments, the disease or condition is relapsed or refractory. In one embodiment, the disease or condition is relapsed or refractory acute myeloid leukemia (AML). In certain embodiments, the disease or condition is newly diagnosed. In one embodiment, the disease or condition is newly diagnosed AML.

9. Combination Treatments

The FLT3 inhibitor compositions described herein can also be used in combination with other well-known therapeutic reagents that are selected for their therapeutic value for the condition to be treated. In general, the compositions described herein and, in embodiments where combinational therapy is employed, other agents do not have to be administered in the same pharmaceutical composition, and may, because of different physical and chemical characteristics, have to be administered by different routes. The determination of the mode of administration and the advisability of administration, where possible, in the same pharmaceutical composition, is well within the knowledge of the skilled clinician. The initial administration can be made according to established protocols known in the art, and then, based upon the observed effects, the dosage, modes of administration and times of administration can be modified by the skilled clinician.

In certain instances, it may be appropriate to administer at least one FLT3 inhibitor compound described herein in combination with another therapeutic agent. By way of example only, if one of the side effects experienced by a patient upon receiving one of the FLT3 inhibitor compounds described herein is nausea, then it may be appropriate to administer an anti-nausea agent in combination with the initial therapeutic agent. Or, by way of example only, the therapeutic effectiveness of one of the compounds described herein may be enhanced by administration of an adjuvant (i.e., by itself the adjuvant may have minimal therapeutic benefit, but in combination with another therapeutic agent, the overall therapeutic benefit to the patient is enhanced). Or, by way of example only, the benefit experienced by a patient may be increased by administering one of the compounds described herein with another therapeutic agent (which also includes a therapeutic regimen) that also has therapeutic benefit. In any case, regardless of the disease, disorder or condition being treated, the overall benefit experienced by the patient may simply be additive of the two therapeutic agents or the patient may experience a synergistic benefit.

The particular choice of compounds used will depend upon the diagnosis of the attending physicians and their judgment of the condition of the patient and the appropriate treatment protocol. The compounds may be administered concurrently (e.g., simultaneously, essentially simultaneously or within the same treatment protocol) or sequentially, depending upon the nature of the disease, disorder, or condition, the condition of the patient, and the actual choice of compounds used. The determination of the order of administration, and the number of repetitions of administration of each therapeutic agent during a treatment protocol, is well within the knowledge of the skilled physician after evaluation of the disease being treated and the condition of the patient.

It is known to those of skill in the art that therapeutically-effective dosages can vary when the drugs are used in treatment combinations. Methods for experimentally determining therapeutically-effective dosages of drugs and other agents for use in combination treatment regimens are described in the literature. For example, the use of metronomic dosing, i.e., providing more frequent, lower doses in order to minimize toxic side effects, has been described extensively in the literature Combination treatment further includes periodic treatments that start and stop at various times to assist with the clinical management of the patient.

For combination therapies described herein, dosages of the co-administered compounds will of course vary depending on the type of co-drug employed, on the specific drug employed, on the disease or condition being treated and so forth. In addition, when co-administered with one or more biologically active agents, the compound provided herein may be administered either simultaneously with the biologically active agent(s), or sequentially. If administered sequentially, the attending physician will decide on the appropriate sequence of administering protein in combination with the biologically active agent(s).

In any case, the multiple therapeutic agents (one of which is a compound of Formula (P-I), Formula (I)-Formula (LXIIIb), Formula (P2-I), Formula (P4-I)-(P4-Vb), or Formula (P5-I')-(P5-Vd) described herein) may be administered in any order or even simultaneously. If simultaneously, the multiple therapeutic agents may be provided in a single, unified form, or in multiple forms (by way of example only, either as a single pill or as two separate pills). One of the therapeutic agents may be given in multiple doses, or both may be given as multiple doses. If not simultaneous, the timing between the multiple doses may vary from more than zero weeks to less than four weeks. In addition, the combination methods, compositions and formulations are not to be limited to the use of only two agents; the use of multiple therapeutic combinations are also envisioned.

It is understood that the dosage regimen to treat, prevent, or ameliorate the condition(s) for which relief is sought, can be modified in accordance with a variety of factors. These factors include the disorder from which the subject suffers, as well as the age, weight, sex, diet, and medical condition of the subject. Thus, the dosage regimen actually employed can vary widely and therefore can deviate from the dosage regimens set forth herein.

The pharmaceutical agents which make up the combination therapy disclosed herein may be a combined dosage form or in separate dosage forms intended for substantially simultaneous administration. The pharmaceutical agents that make up the combination therapy may also be administered sequentially, with either therapeutic compound being administered by a regimen calling for two-step administration. The two-step administration regimen may call for sequential administration of the active agents or spaced-apart administration of the separate active agents. The time period between the multiple administration steps may range from, a few minutes to several hours, depending upon the properties of each pharmaceutical agent, such as potency, solubility, bioavailability, plasma half-life, and kinetic profile of the pharmaceutical agent. Circadian variation of the target molecule concentration may also determine the optimal dose interval.

In addition, the compounds described herein also may be used in combination with procedures that may provide additional or synergistic benefit to the patient. By way of example only, patients are expected to find therapeutic and/or prophylactic benefit in the methods described herein, wherein pharmaceutical composition of a compound disclosed herein and/or combinations with other therapeutics are combined with genetic testing to determine whether that individual is a carrier of a mutant gene that is known to be correlated with certain diseases or conditions.

The compounds described herein and combination therapies can be administered before, during or after the occurrence of a disease or condition, and the timing of administering the composition containing a compound can vary. Thus, for example, the compounds can be used as a prophylactic and can be administered continuously to subjects with a propensity to develop conditions or diseases in order to prevent the occurrence of the disease or condition. The compounds and compositions can be administered to a subject during or as soon as possible after the onset of the symptoms. The administration of the compounds can be initiated within the first 48 hours of the onset of the symptoms, within the first 6 hours of the onset of the symptoms, or within 3 hours of the onset of the symptoms. The initial administration can be via any route practical, such as, for example, an intravenous injection, a bolus injection, infusion over 5 minutes to about 5 hours, a pill, a capsule, transdermal patch, buccal delivery, and the like, or combination thereof. A compound should be administered as soon as is practicable after the onset of a disease or condition is detected or suspected, and for a length of time necessary for the treatment of the disease, such as, for example, from about 1 month to about 3 months. The length of treatment can vary for each subject, and the length can be determined using the known criteria. For example, the compound or a formulation containing the compound can be administered for at least 2 weeks, between about 1 month to about 5 years, or from about 1 month to about 3 years.

10. Exemplary Therapeutic Agents for Use in Combination with a FLT3 Inhibitor Compound Other anti-cancer agents that can be employed in combination with an FLT3 inhibitor compound include Adriamycin, Dactinomycin, Bleomycin, Vinblastine, Cisplatin, acivicin; aclarubicin; acodazole hydrochloride; acronine; adozelesin; aldesleukin; altretamine; ambomycin; ametantrone acetate; aminoglutethimide; amsacrine; anastrozole; anthramycin; asparaginase; asperlin; azacitidine; azetepa; azotomycin; batimastat; benzodepa; bicalutamide; bisantrene hydrochloride; bisnafide dimesylate; bizelesin; bleomycin sulfate; brequinar sodium; bropirimine; busulfan; cactinomycin; calusterone; caracemide; carbetimer; carboplatin; carmustine; carubicin hydrochloride; carzelesin; cedefingol; chlorambucil; cirolemycin; cladribine; crisnatol mesylate; cyclophosphamide; cytarabine; dacarbazine; daunorubicin hydrochloride; decitabine; dexormaplatin; dezaguanine; dezaguanine mesylate; diaziquone; doxorubicin; doxorubicin hydrochloride; droloxifene; droloxifene citrate; dromostanolone propionate; duazomycin; edatrexate; eflornithine hydrochloride; elsamitrucin; enloplatin; enpromate; epipropidine; epirubicin hydrochloride; erbulozole; esorubicin hydrochloride; estramustine; estramustine phosphate sodium; etanidazole; etoposide; etoposide phosphate; etoprine; fadrozole hydrochloride; fazarabine; fenretinide; floxuridine; fludarabine phosphate; fluorouracil; flurocitabine; fosquidone; fostriecin sodium; gemcitabine; gemcitabine hydrochloride; hydroxyurea; idarubicin hydrochloride; ifosfamide; iimofosine; interleukin Il (including recombinant interleukin II, or rIL2), interferon α-2a; interferon α-2b; interferon α-n1; interferon α-n3; interferon β-1a; interferon γ-1b; iproplatin; irinotecan hydrochloride; lanreotide acetate; letrozole; leuprolide acetate; liarozole hydrochloride; lometrexol sodium; lomustine; losoxantrone hydrochloride; masoprocol; maytansine; mechlorethamine hydrochloride; megestrol acetate; melengestrol acetate; melphalan; menogaril; mercaptopurine; methotrexate; methotrexate sodium; metoprine; meturedepa; mitindomide; mitocarcin; mitocromin; mitogillin; mitomalcin; mitomycin; mitosper; mitotane; mitoxantrone hydrochloride; mycophenolic acid; nocodazoie; nogalamycin; ormaplatin; oxisuran; pegaspargase; peliomycin; pentamustine; peplomycin sulfate; perfosfamide; pipobroman; piposulfan; piroxantrone hydrochloride; plicamycin; plomestane; porfimer sodium; porfiromycin; prednimustine; procarbazine hydrochloride; puromycin; puromycin hydrochloride; pyrazofurin; riboprine; rogletimide; safingol; safingol hydrochloride; semustine; simtrazene; sparfosate sodium; sparsomycin; spirogermanium hydrochloride; spiromustine; spiroplatin; streptonigrin; streptozocin; sulofenur; talisomycin; tecogalan sodium; tegafur; teloxantrone hydrochloride; temoporfin; teniposide; teroxirone; testolactone; thiamiprine; thioguanine; thiotepa; tiazofurin; tirapazamine; toremifene citrate; trestolone acetate; triciribine phosphate; trimetrexate; trimetrexate glucuronate; triptorelin; tubulozole hydrochloride; uracil mustard; uredepa; vapreotide; verteporfin; vinblastine sulfate; vincristine sulfate; vindesine; vindesine sulfate; vinepidine sulfate; vinglycinate sulfate; vinleurosine sulfate; vinorelbine tartrate; vinrosidine sulfate; vinzolidine sulfate; vorozole; zeniplatin; zinostatin; zorubicin hydrochloride.

Other anti-cancer agents that can be employed in combination with an FLT3 inhibitor compound include: 20-epi-1, 25 dihydroxyvitamin D3; 5-ethynyluracil; abiraterone; aclarubicin; acylfulvene; adecypenol; adozelesin; aldesleukin; ALL-TK antagonists; altretamine; ambamustine; amidox; amifostine; aminolevulinic acid; amrubicin; amsacrine; anagrelide; anastrozole; andrographolide; angiogenesis irreversible inhibitors; antagonist D; antagonist G; antarelix; anti-dorsalizing morphogenetic protein-1; antiandrogen, prostatic carcinoma; antiestrogen; antineoplaston; antisense oligonucleotides; aphidicolin glycinate; apoptosis gene modulators; apoptosis regulators; apurinic acid; ara-CDP-DL-PTBA; arginine deaminase; asulacrine; atamestane; atrimustine; axinastatin 1; axinastatin 2; axinastatin 3; azasetron; azatoxin; azatyrosine; baccatin III derivatives; balanol; batimastat; BCR/ABL antagonists; benzochlorins; benzoylstaurosporine; beta lactam derivatives; beta-alethine; betaclamycin B; betulinic acid; bFGF inhibitor; bicalutamide; bisantrene; bisaziridinylspermine; bisnafide; bistratene A; bizelesin; breflate; bropirimine; budotitane; buthionine sulfoximine; calcipotriol; calphostin C; camptothecin derivatives; canarypox IL-2; capecitabine; carboxamide-amino-triazole; carboxyamidotriazole; CaRest M3; CARN 700; cartilage derived inhibitor; carzelesin; casein kinase irreversible inhibitors (ICOS); castanospermine; cecropin B; cetrorelix; chlorlns; chloroquinoxaline sulfonamide; cicaprost; cis-porphyrin; cladribine; clomifene analogues; clotrimazole; collismycin A; collismycin B; combretastatin A4; combretastatin analogue; conagenin; crambescidin 816;

crisnatol; cryptophycin 8; cryptophycin A derivatives; curacin A; cyclopentanthraquinones; cycloplatam; cypemycin; cytarabine ocfosfate; cytolytic factor; cytostatin; dacliximab; decitabine; dehydrodidemnin B; deslorelin; dexamethasone; dexifosfamide; dexrazoxane; dexverapamil; diaziquone; didemnin B; didox; diethylnorspermine; dihydro-5-azacytidine; 9-dioxamycin; diphenyl spiromustine; docosanol; dolasetron; doxifluridine; droloxifene; dronabinol; duocarmycin SA; ebselen; ecomustine; edelfosine; edrecolomab; eflornithine; elemene; emitefur; epirubicin; epristeride; estramustine analogue; estrogen agonists; estrogen antagonists; etanidazole; etoposide phosphate; exemestane; fadrozole; fazarabine; fenretinide; filgrastim; finasteride; flavopiridol; flezelastine; fluasterone; fludarabine; fluorodaunorunicin hydrochloride; forfenimex; formestane; fostriecin; fotemustine; gadolinium texaphyrin; gallium nitrate; galocitabine; ganirelix; gelatinase irreversible inhibitors; gemcitabine; glutathione irreversible inhibitors; hepsulfam; heregulin; hexamethylene bisacetamide; hypericin; ibandronic acid; idarubicin; idoxifene; idramantone; ilmofosine; ilomastat; imidazoacridones; imiquimod; immunostimulant peptides; insulin-like growth factor-1 receptor inhibitor; interferon agonists; interferons; interleukins; iobenguane; iododoxorubicin; ipomeanol, 4-; iroplact; irsogladine; isobengazole; isohomohalicondrin B; itasetron; jasplakinolide; kahalalide F; lamellarin-N triacetate; lanreotide; leinamycin; lenograstim; lentinan sulfate; leptolstatin; letrozole; leukemia inhibiting factor; leukocyte alpha interferon; leuprolide+estrogen+progesterone; leuprorelin; levamisole; liarozole; linear polyamine analogue; lipophilic disaccharide peptide; lipophilic platinum compounds; lissoclinamide 7; lobaplatin; lombricine; lometrexol; lonidamine; losoxantrone; lovastatin; loxoribine; lurtotecan; lutetium texaphyrin; lysofylline; lytic peptides; maitansine; mannostatin A; marimastat; masoprocol; maspin; matrilysin irreversible inhibitors; matrix metalloproteinase irreversible inhibitors; menogaril; merbarone; meterelin; methioninase; metoclopramide; MIF inhibitor; mifepristone; miltefosine; mirimostim; mismatched double stranded RNA; mitoguazone; mitolactol; mitomycin analogues; mitonafide; mitotoxin fibroblast growth factor-saporin; mitoxantrone; mofarotene; molgramostim; monoclonal antibody, human chorionic gonadotrophin; monophosphoryl lipid A+myobacterium cell wall sk; mopidamol; multiple drug resistance gene inhibitor; multiple tumor suppressor 1-based therapy; mustard anticancer agent; mycaperoxide B; mycobacterial cell wall extract; myriaporone; N-acetyldinaline; N-substituted benzamides; nafarelin; nagrestip; naloxone+pentazocine; napavin; naphterpin; nartograstim; nedaplatin; nemorubicin; neridronic acid; neutral endopeptidase; nilutamide; nisamycin; nitric oxide modulators; nitroxide antioxidant; nitrullyn; 06-benzylguanine; octreotide; okicenone; oligonucleotides; onapristone; ondansetron; ondansetron; oracin; oral cytokine inducer; ormaplatin; osaterone; oxaliplatin; oxaunomycin; palauamine; palmitoylrhizoxin; pamidronic acid; panaxytriol; panomifene; parabactin; pazelliptine; pegaspargase; peldesine; pentosan polysulfate sodium; pentostatin; pentrozole; perflubron; perfosfamide; perillyl alcohol; phenazinomycin; phenylacetate; phosphatase irreversible inhibitors; picibanil; pilocarpine hydrochloride; pirarubicin; piritrexim; placetin A; placetin B; plasminogen activator inhibitor; platinum complex; platinum compounds; platinum-triamine complex; porfimer sodium; porfiromycin; prednisone; propyl bis-acridone; prostaglandin J2; proteasome irreversible inhibitors; protein A-based immune modulator; protein kinase C inhibitor; protein kinase C irreversible inhibitors, microalgal; protein tyrosine phosphatase irreversible inhibitors; purine nucleoside phosphorylase irreversible inhibitors; purpurins; pyrazoloacridine; pyridoxylated hemoglobin polyoxyethylerie conjugate; raf antagonists; raltitrexed; ramosetron; ras farnesyl protein transferase irreversible inhibitors; ras irreversible inhibitors; ras-GAP inhibitor; retelliptine demethylated; rhenium Re 186 etidronate; rhizoxin; ribozymes; RII retinamide; rogletimide; rohitukine; romurtide; roquinimex; rubiginone B1; ruboxyl; safingol; saintopin; SarCNU; sarcophytol A; sargramostim; Sdi 1 mimetics; semustine; senescence derived inhibitor 1; sense oligonucleotides; signal transduction irreversible inhibitors; signal transduction modulators; single chain antigen-binding protein; sizofiran; sobuzoxane; sodium borocaptate; sodium phenylacetate; solverol; somatomedin binding protein; sonermin; sparfosic acid; spicamycin D; spiromustine; splenopentin; spongistatin 1; squalamine; stem cell inhibitor; stem-cell division irreversible inhibitors; stipiamide; stromelysin irreversible inhibitors; sulfinosine; superactive vasoactive intestinal peptide antagonist; suradista; suramin; swainsonine; synthetic glycosaminoglycans; tallimustine; tamoxifen methiodide; tauromustine; tazarotene; tecogalan sodium; tegafur; tellurapyrylium; telomerase irreversible inhibitors; temoporfin; temozolomide; teniposide; tetrachlorodecaoxide; tetrazomine; thaliblastine; thiocoraline; thrombopoietin; thrombopoietin mimetic; thymalfasin; thymopoietin receptor agonist; thymotrinan; thyroid stimulating hormone; tin ethyl etiopurpurin; tirapazamine; titanocene bichloride; topsentin; toremifene; totipotent stem cell factor; translation irreversible inhibitors; tretinoin; triacetyluridine; triciribine; trimetrexate; triptorelin; tropisetron; turosteride; tyrosine kinase irreversible inhibitors; tyrphostins; UBC irreversible inhibitors; ubenimex; urogenital sinus-derived growth inhibitory factor; urokinase receptor antagonists; vapreotide; variolin B; vector system, erythrocyte gene therapy; velaresol; veramine; verdins; verteporfin; vinorelbine; vinxaltine; vitaxin; vorozole; zanoterone; zeniplatin; zilascorb; and zinostatin stimalamer.

Yet other anticancer agents that can be employed in combination with an FLT3 inhibitor compound include alkylating agents, antimetabolites, natural products, or hormones, e.g., nitrogen mustards (e.g., mechloroethamine, cyclophosphamide, chlorambucil, etc.), alkyl sulfonates (e.g., busulfan), nitrosoureas (e.g., carmustine, lomusitne, etc.), or triazenes (decarbazine, etc.). Examples of antimetabolites include but are not limited to folic acid analog (e.g., methotrexate), or pyrimidine analogs (e.g., Cytarabine), purine analogs (e.g., mercaptopurine, thioguanine, pentostatin).

Yet other anticancer agents that can be employed in combination with an FLT3 inhibitor compound described herein include Menin inhibitors.

Anticancer agents that can be employed in combination with an FLT3 inhibitor compound described herein include WDR5 inhibitors.

Anticancer agents that can be employed in combination with an FLT3 inhibitor compound described herein include KRAS inhibitors.

Yet other anticancer agents that can be employed in combination with an FLT3 inhibitor compound described herein include MEK inhibitors. In one embodiment, the MEK inhibitor is trametinib.

Yet other anticancer agents that can be employed in combination with an FLT3 inhibitor compound described herein include BCL2 inhibitors. In one embodiment, the BCL2 inhibitor is venetoclax.

Examples of natural products useful in combination with an FLT3 inhibitor compound described herein include, but are not limited to, vinca alkaloids (e.g., vinblastin, vincristine), epipodophyllotoxins (e.g., etoposide), antibiotics (e.g., daunorubicin, doxorubicin, bleomycin), enzymes (e.g., L-asparaginase), or biological response modifiers (e.g., interferon alpha).

Examples of alkylating agents that can be employed in combination an FLT3 inhibitor compound described herein include, but are not limited to, nitrogen mustards (e.g., mechloroethamine, cyclophosphamide, chlorambucil, meiphalan, etc.), ethylenimine and methylmelamines (e.g., hexamethlymelamine, thiotepa), alkyl sulfonates (e.g., busulfan), nitrosoureas (e.g., carmustine, lomusitne, semustine, streptozocin, etc.), or triazenes (decarbazine, etc.). Examples of antimetabolites include, but are not limited to folic acid analog (e.g., methotrexate), or pyrimidine analogs (e.g., fluorouracil, floxouridine, Cytarabine), purine analogs (e.g., mercaptopurine, thioguanine, pentostatin.

Examples of hormones and antagonists useful in combination with an FLT3 inhibitor compound described herein include, but are not limited to, adrenocorticosteroids (e.g., prednisone), progestins (e.g., hydroxyprogesterone caproate, megestrol acetate, medroxyprogesterone acetate), estrogens (e.g., diethlystilbestrol, ethinyl estradiol), antiestrogen (e.g., tamoxifen), androgens (e.g., testosterone propionate, fluoxymesterone), antiandrogen (e.g., flutamide), gonadotropin releasing hormone analog (e.g., leuprolide). Other agents that can be used in the methods and compositions described herein for the treatment or prevention of cancer include platinum coordination complexes (e.g., cisplatin, carboblatin), anthracenedione (e.g., mitoxantrone), substituted urea (e.g., hydroxyurea), methyl hydrazine derivative (e.g., procarbazine), adrenocortical suppressant (e.g., mitotane, aminoglutethimide).

Examples of anti-cancer agents which act by arresting cells in the G2-M phases due to stabilized microtubules and which can be used in combination with an FLT3 inhibitor compound described herein include without limitation the following marketed drugs and drugs in development: Erbulozole (also known as R-55104), Dolastatin 10 (also known as DLS-10 and NSC-376128), Mivobulin isethionate (also known as CI-980), Vincristine, NSC-639829, Discodermolide (also known as NVP-XX-A-296), ABT-751 (Abbott, also known as E-7010), Altorhyrtins (such as Altorhyrtin A and Altorhyrtin C), Spongistatins (such as Spongistatin 1, Spongistatin 2, Spongistatin 3, Spongistatin 4, Spongistatin 5, Spongistatin 6, Spongistatin 7, Spongistatin 8, and Spongistatin 9), Cemadotin hydrochloride (also known as LU-103793 and NSC-D-669356), Epothilones (such as Epothilone A, Epothilone B, Epothilone C (also known as desoxyepothilone A or dEpoA), Epothilone D (also referred to as KOS-862, dEpoB, and desoxyepothilone B), Epothilone E, Epothilone F, Epothilone B N-oxide, Epothilone A N-oxide, 16-aza-epothilone B, 21-aminoepothilone B (also known as BMS-310705), 21-hydroxyepothilone D (also known as Desoxyepothilone F and dEpoF), 26-fluoroepothilone), Auristatin PE (also known as NSC-654663), Soblidotin (also known as TZT-1027), LS-4559-P (Pharmacia, also known as LS-4577), LS-4578 (Pharmacia, also known as LS-477-P), LS-4477 (Pharmacia), LS-4559 (Pharmacia), RPR-112378 (Aventis), Vincristine sulfate, DZ-3358 (Daiichi), FR-182877 (Fujisawa, also known as WS-9885B), GS-164 (Takeda), GS-198 (Takeda), KAR-2 (Hungarian Academy of Sciences), BSF-223651 (BASF, also known as ILX-651 and LU-223651), SAH-49960 (Lilly/Novartis), SDZ-268970 (Lilly/Novartis), AM-97 (Armad/Kyowa Hakko), AM-132 (Armad), AM-138 (Armad/Kyowa Hakko), IDN-5005 (Indena), Cryptophycin 52 (also known as LY-355703), AC-7739 (Ajinomoto, also known as AVE-8063A and CS-39.HCI), AC-7700 (Ajinomoto, also known as AVE-8062, AVE-8062A, CS-39-L-Ser.HCI, and RPR-258062A), Vitilevuamide, Tubulysin A, Canadensol, Centaureidin (also known as NSC-106969), T-138067 (Tularik, also known as T-67, TL-138067 and TI-138067), COBRA-1 (Parker Hughes Institute, also known as DDE-261 and WHI-261), H10 (Kansas State University), H16 (Kansas State University), Oncocidin A1 (also known as BTO-956 and DIME), DDE-313 (Parker Hughes Institute), Fijianolide B, Laulimalide, SPA-2 (Parker Hughes Institute), SPA-1 (Parker Hughes Institute, also known as SPIKET-P), 3-IAABU (Cytoskeleton/Mt. Sinai School of Medicine, also known as MF-569), Narcosine (also known as NSC-5366), Nascapine, D-24851 (Asta Medica), A-105972 (Abbott), Hemiasterlin, 3-BAABU (Cytoskeleton/Mt. Sinai School of Medicine, also known as MF-191), TMPN (Arizona State University), Vanadocene acetylacetonate, T-138026 (Tularik), Monsatrol, lnanocine (also known as NSC-698666), 3-lAABE (Cytoskeleton/Mt. Sinai School of Medicine), A-204197 (Abbott), T-607 (Tuiarik, also known as T-900607), RPR-115781 (Aventis), Eleutherobins (such as Desmethyleleutherobin, Desaetyleleutherobin, lsoeleutherobin A, and Z-Eleutherobin), Caribaeoside, Caribaeolin, Halichondrin B, D-64131 (Asta Medica), D-68144 (Asta Medica), Diazonamide A, A-293620 (Abbott), NPI-2350 (Nereus), Taccalonolide A, TUB-245 (Aventis), A-259754 (Abbott), Diozostatin, (–)-Phenylahistin (also known as NSCL-96F037), D-68838 (Asta Medica), D-68836 (Asta Medica), Myoseverin B, D-43411 (Zentaris, also known as D-81862), A-289099 (Abbott), A-318315 (Abbott), HTI-286 (also known as SPA-110, trifluoroacetate salt) (Wyeth), D-82317 (Zentaris), D-82318 (Zentaris), SC-12983 (NCI), Resverastatin phosphate sodium, BPR-OY-007 (National Health Research Institutes), and SSR-250411 (Sanofi).

The FLT3 inhibitors described herein can also be administered in combination with other FLT3 inhibitors, including, but not limited to sorafenib, midostaurin, lestaurtinib, sunitinib, tandutinib, gilteritinib, crenolanib, quizartinib, FF-10101, and HM43239.

11. Kits/Articles of Manufacture

For use in the therapeutic applications described herein, kits and articles of manufacture are also described herein. Such kits can include a carrier, package, or container that is compartmentalized to receive one or more containers such as vials, tubes, and the like, each of the container(s) including one of the separate elements to be used in a method described herein. Suitable containers include, for example, bottles, vials, syringes, and test tubes. The containers can be formed from a variety of materials such as glass or plastic.

The articles of manufacture provided herein contain packaging materials. Packaging materials for use in packaging pharmaceutical products are well known to those of skill in the art. See, e.g., U.S. Pat. Nos. 5,323,907, 5,052,558 and 5,033,252. Examples of pharmaceutical packaging materials include, but are not limited to, blister packs, bottles, tubes, inhalers, pumps, bags, vials, containers, syringes, bottles, and any packaging material suitable for a selected formulation and intended mode of administration and treatment. A wide array of formulations of the compounds and compositions provided herein are contemplated as are a variety of treatments for any disease, disorder, or condition that would benefit by inhibition of FLT3, or in which FLT3 is a mediator or contributor to the symptoms or cause.

For example, the container(s) can include one or more compounds described herein, optionally in a composition or in combination with another agent as disclosed herein. The container(s) optionally have a sterile access port (for example the container can be an intravenous solution bag or a vial having a stopper pierceable by a hypodermic injection needle). Such kits optionally comprising a compound with an identifying description or label or instructions relating to its use in the methods described herein.

A kit will typically include one or more additional containers, each with one or more of various materials (such as reagents, optionally in concentrated form, and/or devices) desirable from a commercial and user standpoint for use of a compound described herein. Non-limiting examples of such materials include, but not limited to, buffers, diluents, filters, needles, syringes; carrier, package, container, vial and/or tube labels listing contents and/or instructions for use, and package inserts with instructions for use. A set of instructions will also typically be included.

A label can be on or associated with the container. A label can be on a container when letters, numbers or other characters forming the label are attached, molded or etched into the container itself; a label can be associated with a container when it is present within a receptacle or carrier that also holds the container, e.g., as a package insert. A label can be used to indicate that the contents are to be used for a specific therapeutic application. The label can also indicate directions for use of the contents, such as in the methods described herein.

In certain embodiments, the pharmaceutical compositions can be presented in a pack or dispenser device which can contain one or more unit dosage forms containing a compound provided herein. The pack can for example contain metal or plastic foil, such as a blister pack. The pack or dispenser device can be accompanied by instructions for administration. The pack or dispenser can also be accompanied with a notice associated with the container in form prescribed by a governmental agency regulating the manufacture, use, or sale of pharmaceuticals, which notice is reflective of approval by the agency of the form of the drug for human or veterinary administration. Such notice, for example, can be the labeling approved by the U.S. Food and Drug Administration for prescription drugs, or the approved product insert. Compositions containing a compound provided herein formulated in a compatible pharmaceutical carrier can also be prepared, placed in an appropriate container, and labeled for treatment of an indicated condition.

EXAMPLES

The following specific and non-limiting examples are to be construed as merely illustrative, and do not limit the present disclosure in any way whatsoever. Without further elaboration, it is believed that one skilled in the art can, based on the description herein, utilize the present disclosure to its fullest extent. All publications cited herein are hereby incorporated by reference in their entirety. Where reference is made to a URL or other such identifier or address, it is understood that such identifiers can change and particular information on the internet can come and go, but equivalent information can be found by searching the internet. Reference thereto evidences the availability and public dissemination of such information.

The examples below as well as throughout the application, the following abbreviations have the following meanings. If not defined, the terms have their generally accepted meanings.

| | |
|---|---|
| aq = | aqueous |
| Boc = | tert-butyloxycarbonyl |
| t-BuOH = | tertiary butanol |
| DCE = | 1,2-dichloroethane |
| DCM = | dichloromethane |
| DIAD = | diisopropyl azodicarboxylate |
| DIEA or DIPEA = | N,N-diisopropylethylamine |
| DMAP = | dimethylaminopyridine |
| DMF = | dimethylformamide |
| DMSO = | dimethylsulfoxide |
| ESI = | electron spray ionization |
| EA = | ethyl acetate |
| g = | gram |
| HCl = | hydrogen chloride |
| HPLC = | high performance liquid chromatography |
| hr = | hour |
| $^1$H NMR = | proton nuclear magnetic resonance |
| IPA = | isopropyl alcohol |
| KOAc = | potassium acetate |
| LC-MS = | liquid chromatography mass spectroscopy |
| M = | molar |
| MeCN = | acetonitrile |
| MeOH = | methanol |
| mg = | milligram |
| min = | minute |
| ml = | milliliter |
| mM = | millimolar |
| mmol = | millimole |
| m.p. = | melting point |
| MS = | mass spectrometry |
| m/z = | mass-to-charge ratio |
| N = | normal |
| NIS = | N-iodosuccinimide |
| nM = | nanomolar |
| nm = | nanometer |
| Pd(dppf)Cl$_2$ = | [1,1'-Bis(diphenylphosphino)ferrocene]dichloropalladium(II) |
| PE = | petroleum ether |
| PyBOP = | benzotriazol-1-yl-oxytripyrrolidinophosphonium hexafluorophosphate |
| quant. = | quantitative |
| RP = | reverse phase |
| rt or r.t. = | room temperature |
| Sat. = | saturated |
| TEA = | triethylamine |
| TFA = | trifluoroacetic acid |
| μL = | microliter |
| μM = | Micromolar |

General Synthetic Scheme I

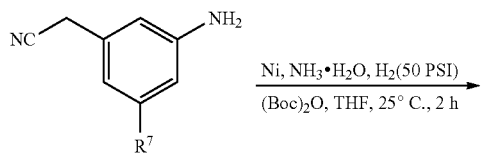

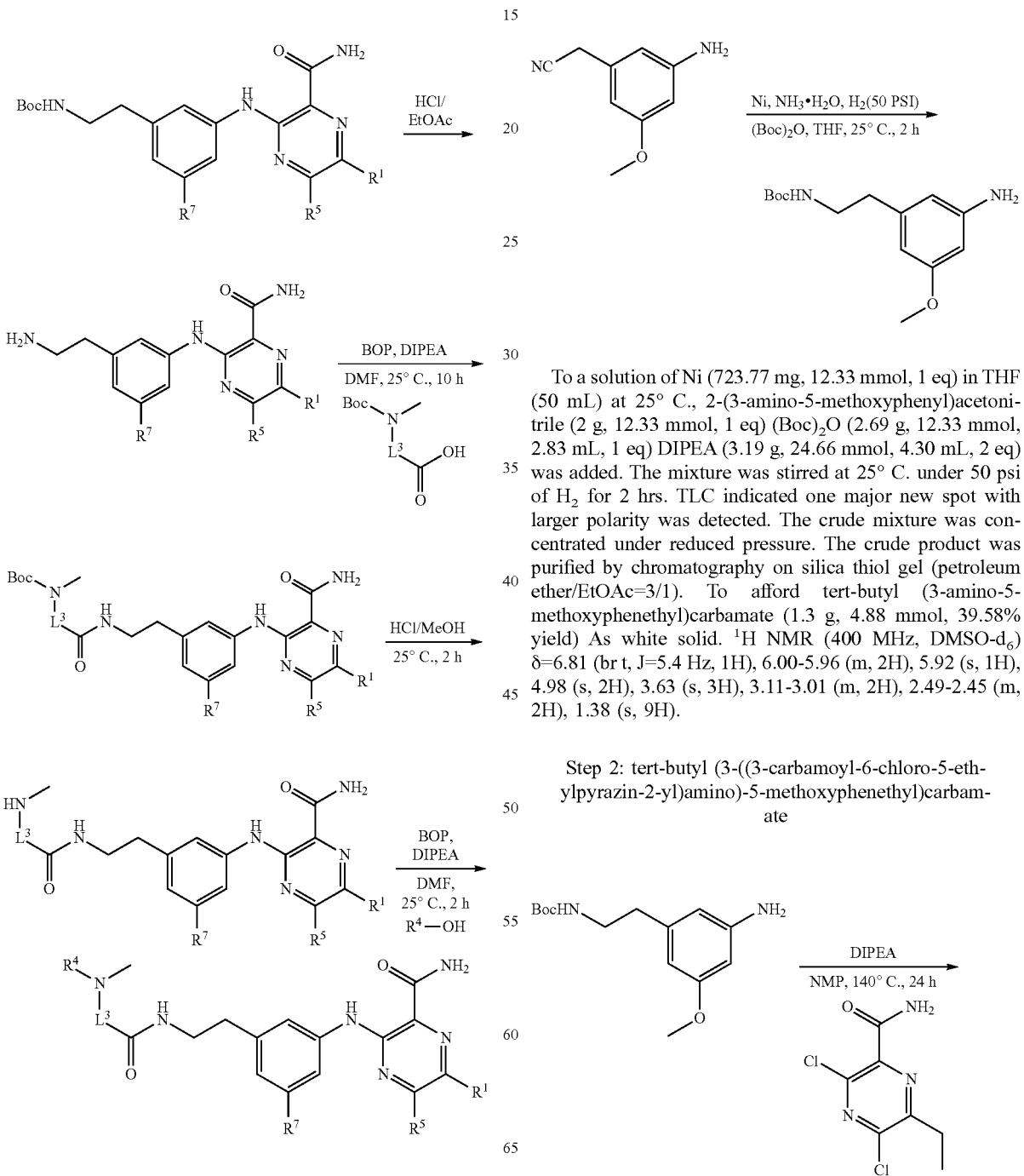

wherein L³, R¹, R⁴, R⁵, and R⁷ are as described herein.

Synthesis of Intermediates

Intermediate 6 tert-butyl (S)-(1-((3-((3-carbamoyl-6-chloro-5-ethylpyrazin-2-yl)amino)-5-methoxyphenethyl)amino)-1-oxopropan-2-yl)(methyl)carbamate Step 1: tert-butyl (3-amino-5-methoxyphenethyl)carbamate

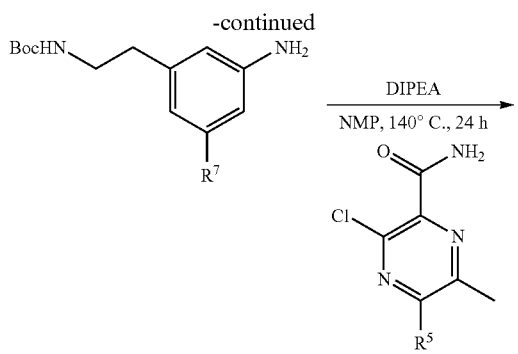

To a solution of Ni (723.77 mg, 12.33 mmol, 1 eq) in THF (50 mL) at 25° C., 2-(3-amino-5-methoxyphenyl)acetonitrile (2 g, 12.33 mmol, 1 eq) (Boc)₂O (2.69 g, 12.33 mmol, 2.83 mL, 1 eq) DIPEA (3.19 g, 24.66 mmol, 4.30 mL, 2 eq) was added. The mixture was stirred at 25° C. under 50 psi of H₂ for 2 hrs. TLC indicated one major new spot with larger polarity was detected. The crude mixture was concentrated under reduced pressure. The crude product was purified by chromatography on silica thiol gel (petroleum ether/EtOAc=3/1). To afford tert-butyl (3-amino-5-methoxyphenethyl)carbamate (1.3 g, 4.88 mmol, 39.58% yield) As white solid. ¹H NMR (400 MHz, DMSO-d₆) δ=6.81 (br t, J=5.4 Hz, 1H), 6.00-5.96 (m, 2H), 5.92 (s, 1H), 4.98 (s, 2H), 3.63 (s, 3H), 3.11-3.01 (m, 2H), 2.49-2.45 (m, 2H), 1.38 (s, 9H).

Step 2: tert-butyl (3-((3-carbamoyl-6-chloro-5-ethylpyrazin-2-yl)amino)-5-methoxyphenethyl)carbamate

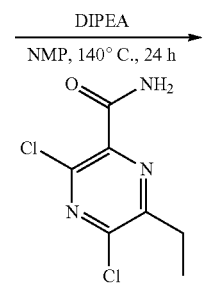

-continued

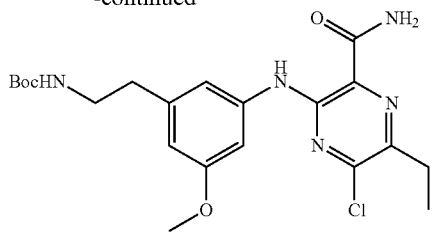

To a solution of tert-butyl (3-amino-5-methoxyphenethyl) carbamate (1.65 g, 7.51 mmol, 1 eq), 3,5-dichloro-6-ethylpyrazine-2-carboxamide (2 g, 7.51 mmol, 1 eq) in 872-50-4 (5 mL) was added DIPEA (19.41 g, 150.19 mmol, 26.16 mL, 20 eq). The mixture was stirred at 140° C. for 24 h under $N_2$ LCMS showed the reaction was completed. The reaction was poured into water (30 mL) and extracted with EtOAc (20 mL*3). The organic layers were combined, washed with water (50 mL*2), sat. brine (100 mL), dried with anhydrous $Na_2SO_4$, filtered and concentrated to give crude product. The crude product was purified by chromatography on silica thiol gel (Petroleum ether/Ethyl acetate/Dichloromethane=2/1/1). To afford tert-butyl (3-((3-carbamoyl-6-chloro-5-ethylpyrazin-2-yl)amino)-5-methoxyphenethyl)carbamate (1.93 g, 4.01 mmol, 53.40% yield) as yellow solid. 1H NMR (400 MHz, DMSO-d6) δ=11.27 (s, 1H), 8.33 (s, 1H), 8.11 (s, 1H), 7.42 (s, 1H), 6.92 (br t, J=5.3 Hz, 1H), 6.86 (s, 1H), 6.54 (s, 1H), 3.81 (s, 3H), 3.21 (q, J=6.6 Hz, 2H), 3.30-3.26 (m, 2H), 2.81-2.79 (m, 2H) 2.50-2.48 (m, 2H), 1.42 (s, 9H), 1.32 (t, J=7.5 Hz, 4H). LC-MS (ES+, m/z): 351.4 [(M+H)$^+$]; Rt=0.824 min.

Step 3: 3-((3-(2-aminoethyl)-5-methoxyphenyl)amino)-5-chloro-6-ethylpyrazine-2-carboxamide

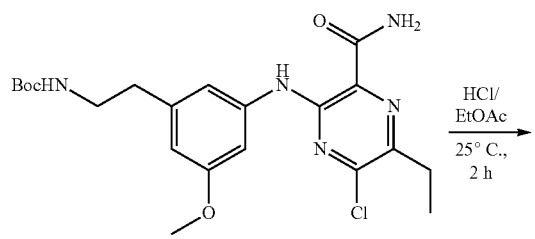

To a solution of tert-butyl (3-((3-carbamoyl-6-chloro-5-ethylpyrazin-2-yl)amino)-5-methoxyphenethyl)carbamate (1.93 g, 3.43 mmol, 80% purity, 1 eq) in HCl/EtOAc (100 mL). The mixture was stirred at 25° C. for 2 h. LCMS showed the reaction was completed. The crude mixture was worked up by filtration. The crude product was purified by re-crystallization from EtOAc (20 mL) at 25° C. to afford 3-((3-(2-aminoethyl)-5-methoxyphenyl)amino)-5-chloro-6-ethylpyrazine-2-carboxamide (1.3 g, 3.30 mmol, 96.11% yield, HCl) as yellow solid. LC-MS (ES+, m/z): 350.1 [(M+H)$^+$]; Rt=0.698 min.

Note: HCl/EtOAc (4 M): HCl was bubbled into a solution EtOAc at 0° C. for 0.5 h. Then, the solution was weighed to obtained the HCl/EtOAc (4 M)

Step 4: tert-butyl (S)-(1-((3-((3-carbamoyl-6-chloro-5-ethylpyrazin-2-yl)amino)-5-methoxyphenethyl)amino)-1-oxopropan-2-yl)(methyl)carbamate

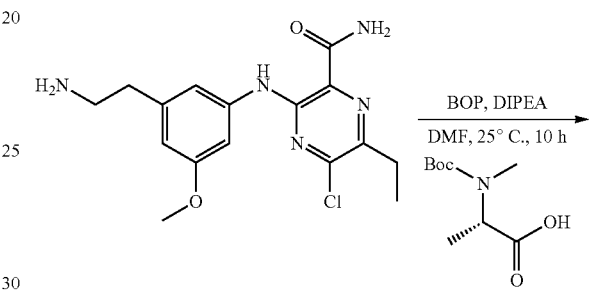

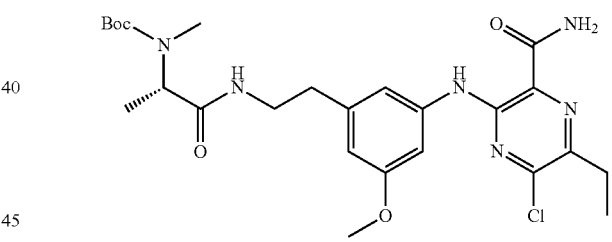

To a solution of 3-((3-(2-aminoethyl)-5-methoxyphenyl)amino)-5-chloro-6-ethylpyrazine-2-carboxamide (1.3 g, 3.65 mmol, 98.2% purity, 1 eq), N-(tert-butoxycarbonyl)-N-methyl-L-alanine (1.11 g, 5.47 mmol, 1.5 eq) in DMF (10 mL) was added BOP (1.54 g, 5.47 mmol, 1.5 eq), DIPEA (3.00 g, 36.49 mmol, 2.91 mL, 10 eq). The mixture was stirred at 25° C. for 10 hrs under $N_2$. LCMS showed the reaction was completed. The crude product was purified by chromatography on silica thiol gel (petroleum ether/EtOAc=1/2). To afford tert-butyl (S)-(1-((3-((3-carbamoyl-6-chloro-5-ethylpyrazin-2-yl)amino)-5-methoxyphenethyl)amino)-1-oxopropan-2-yl)(methyl) carbamate (1.84 g, 2.48 mmol, 67.85% yield) as yellow oil. 1H NMR (400 MHz, DMSO-d6) δ=11.22 (s, 1H), 8.28 (s, 1H), 8.06 (s, 1H), 7.81 (br s, 1H), 7.34 (s, 1H), 6.85 (s, 1H), 6.50 (s, 1H), 4.55-4.52 (m, 1H), 3.76 (s, 3H), 3.30-3.24 (m, 2H), 2.90-2.78 (m, 2H), 2.74-2.66 (m, 5H), 1.36 (br s, 9H), 1.28-1.11 (m, 6H). LC-MS (ES+, m/z): 435.2 [(M+H)$^+$]; Rt=0.884 min; HRMS: 435.1911.

Intermediate 7 tert-butyl (S)-(1-((3-((3-carbamoyl-6-chloro-5-ethylpyrazin-2-yl)amino)phenethyl)amino)-1-oxopropan-2-yl)(methyl)carbamate

Step 1: tert-butyl (3-((3-carbamoyl-6-chloro-5-ethylpyrazin-2-yl)amino)phenethyl)carbamate

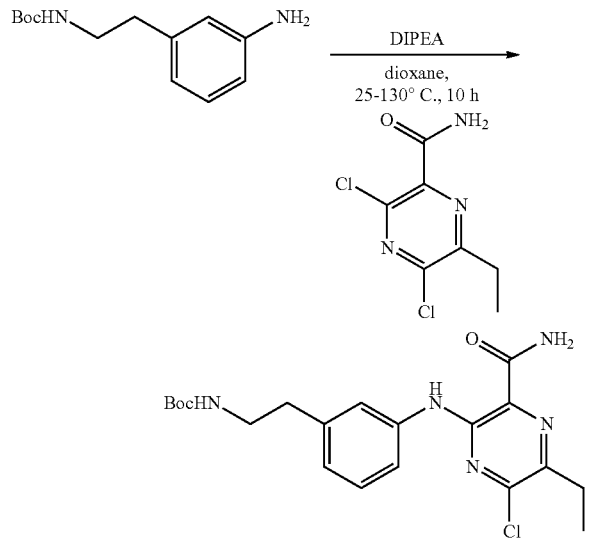

To a solution of tert-butyl (3-aminophenethyl)carbamate (2.25 g, 9.52 mmol, 1 eq) 3,5-dichloro-6-ethylpyrazine-2-carboxamide (2.10 g, 9.52 mmol, 1 eq) in dioxane (20 mL) at 25° C., DIPEA (12.31 g, 95.21 mmol, 16.58 mL, 10 eq) was added. The mixture was stirred at 130° C. for 10 hrs. LCMS indicated the reaction was completed. The mixture was poured into water (40 mL) and extracted with EtOAc (20 mL*2). The organic layers was washed with water (40 mL*2), saturated brine (80 mL*2), dried over anhydrous Na₂SO₄, filtered, concentrated under reduced pressure to give a residue. The crude product was purified by chromatography on silica gel (petroleum ether/EtOAc=1:1) to afford tert-butyl (3-((3-carbamoyl-6-chloro-5-ethylpyrazin-2-yl)amino)phenethyl)carbamate (3 g, 4.79 mmol, 50.27% yield) as yellow oil. LC-MS (ES$^+$, m/z): 420.2 [(M+H)$^+$]; Rt=0.939 min.

Step 2: 3-((3-(2-aminoethyl)phenyl)amino)-5-chloro-6-ethylpyrazine-2-carboxamide

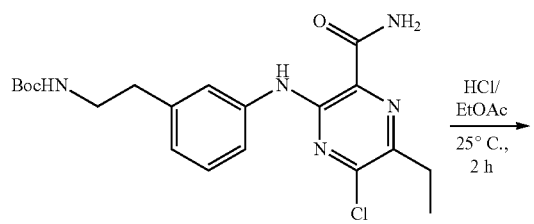

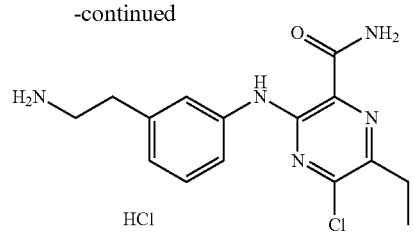

The mixture tert-butyl N-[2-[3-[(3-carbamoyl-6-chloro-5-ethyl-pyrazin-2-yl)amino]phenyl]ethyl]carbamate (2 g, 4.76 mmol, 1 eq) and HCl/EtOAc (4 M, 50 mL, 41.99 eq) was stirred at 25° C. for 2 hrs. LCMS indicated the reaction was completed. The mixture was concentrated under reduced pressure to give a residue. The crude product was purified by chromatography on silica gel (petroleum ether/EtOAc=1:1) to afford 3-((3-(2-aminoethyl)phenyl)amino)-5-chloro-6-ethylpyrazine-2-carboxamide (1.38 g, 4.32 mmol, 90.60% yield) as yellow solid. LC-MS (ES$^+$, m/z): 320.2 [(M+H)$^+$]; Rt=0.671 min.

Note: HCl/EtOAc (4 M): HCl was bubbled into a solution EtOAc at 0° C. for 0.5 h. Then, the solution was weighed to obtained the HCl/EtOAc (4 M)

Step 3: tert-butyl (S)-(1-((3-((3-carbamoyl-6-chloro-5-ethylpyrazin-2-yl)amino)phenethyl)amino)-1-oxopropan-2-yl)(methyl)carbamate

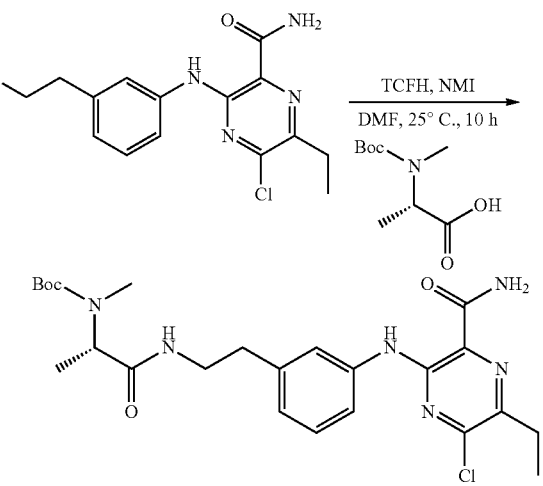

To a solution of 3-((3-(2-aminoethyl)phenyl)amino)-5-chloro-6-ethylpyrazine-2-carboxamide (1.38 g, 4.32 mmol, 1 eq), TCFH (1.82 g, 6.47 mmol, 1.5 eq) NMI (3.54 g, 43.15 mmol, 10 eq) in DMF (15 mL) at 25° C., N-(tert-butoxycarbonyl)-N-methyl-L-alanine (1.32 g, 6.47 mmol, 1.5 eq) was added. The mixture was stirred at 25° C. for 10 hrs. LCMS indicated the reaction was completed. The mixture was poured into water (30 mL) and extracted with EtOAc (15 mL*2). The organic layers was washed with water (30 mL*2), saturated brine (30 mL*2), dried over anhydrous Na₂SO₄, filtered, concentrated under reduced pressure to give a residue. The crude product was purified by chromatography on silica gel (petroleum ether/EtOAc=1:1) to afford tert-butyl N-[(1S)-2-[2-[3-[(3-carbamoyl-6-chloro-5-ethyl-pyrazin-2-yl)amino]phenyl]ethylamino]-1-methyl-2- oxo-ethyl]-N-methyl-carbamate (2.55 g, crude) as yellow oil. LC-MS (ES+, m/z): 505.2 [(M+H)+]; Rt=7.177 min.

Intermediate 8 tert-butyl (S)-(1-((3-((3-carbamoyl-6-chloro-5-ethylpyrazin-2-yl)amino)-5-fluorophenethyl)amino)-1-oxopropan-2-yl)(methyl)carbamate Step 1: (3-bromo-5-fluorophenyl)methanol

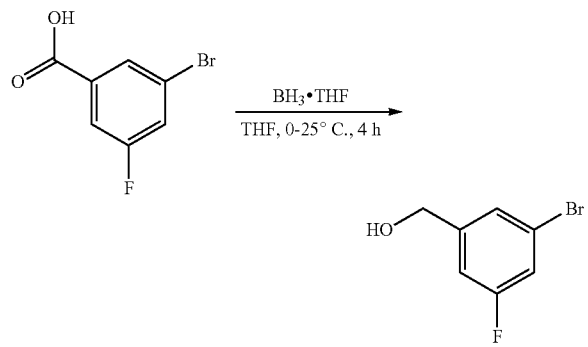

To a solution of 3-bromo-5-fluorobenzoic acid (50 g, 228.30 mmol, 1 eq) in THF (500 mL) at 0° C., BH$_3$·THF (1 M, 570.76 mL, 2.5 eq) was added. The mixture was allowed to warm to 25° C. for 4 hrs. LCMS indicated the reaction was completed. The reaction mixture was slowly added into MeOH (300 mL) at 0° C. Then the combined organic phase was stirred at 70° C. for 1 h, filtered and concentrated in vacuum. The residue was poured into EtOAc (500 mL) and H$_2$O (1 L). The aqueous phase was separated and extracted with ethyl acetate (600 mL*3). The combined organic phase was washed with saturated brine (600 mL*3), dried with anhydrous Na$_2$SO$_4$, filtered and concentrated to give (3-bromo-5-fluoro-phenyl)methanol (50 g, crude) as yellow oil. $^1$H NMR (400 MHz, DMSO-d$_6$) δ=7.49-7.36 (m, 2H), 7.17 (dd, J=1.0, 9.7 Hz, 1H), 5.45 (t, J=5.8 Hz, 1H), 4.52 (d, J=5.8 Hz, 2H). LC-MS (ES+, m/z): 202.9[(M−H)−]; Rt=1.493 min.

Step 2: 1-bromo-3-(bromomethyl)-5-fluorobenzene

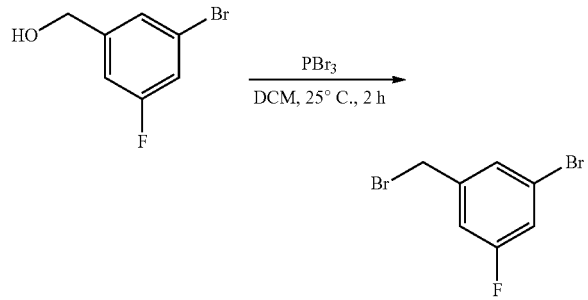

To a solution of (3-bromo-5-fluoro-phenyl)methanol (50 g, 243.87 mmol, 1 eq) in DCM (500 mL) was added PBr$_3$ (132.03 g, 487.75 mmol, 2 eq) The mixture was stirred at 25° C. for 2 hrs under N$_2$ atmosphere. TLC indicated the reaction was completed. The mixture was concentrated. The residue was diluted with saturated NaHCO$_3$ (800 mL) and extracted with EtOAc (800 mL*2). The organic layers were combined, washed with water (800 mL*2), saturated brine (800 mL), dried with anhydrous Na$_2$SO$_4$, filtered and concentrated to give 1-bromo-3-(bromomethyl)-5-fluorobenzene (60 g, crude) as white solid. $^1$H NMR (400 MHz, DMSO-d$_6$) δ=7.47 (s, 1H), 7.46-7.41 (m, 1H), 7.32-7.25 (m, 1H), 4.62 (s, 2H)

Step 3: 2-(3-bromo-5-fluorophenyl)acetonitrile

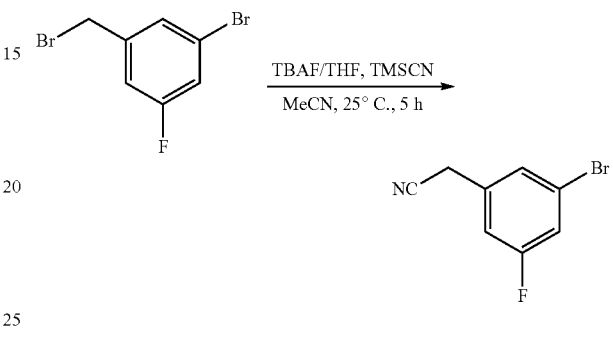

To a solution of 1-bromo-3-(bromomethyl)-5-fluorobenzene (50 g, 186.62 mmol, 1 eq) and TMSCN (24.07 g, 242.61 mmol, 30.35 mL, 1.3 eq) in CH$_3$CN (600 mL) at 25° C., TBAF in THF (1 M, 242.61 mL, 1.3 eq) was added. The mixture was stirred at 25° C. for 5 hrs. TLC indicated the reaction was completed. The mixture was concentrated. The residue was diluted with H$_2$O (1000 mL) and extracted with EtOAc (800 mL*2). The organic layers were combined, washed with water (800 mL*2), saturated brine (800 mL), dried with anhydrous Na$_2$SO$_4$, filtered and concentrated to give crude product. The crude product was purified by chromatography on silica gel (petroleum ether/EtOAc=20/1) to give 2-(3-bromo-5-fluorophenyl)acetonitrile (29.1 g, 135.96 mmol, 72.85% yield) as yellow oil. $^1$H NMR (400 MHz, DMSO-d$_6$) δ=7.54 (td, J=2.0, 8.4 Hz, 1H), 7.46 (s, 1H), 7.28 (br d, J=9.4 Hz, 1H), 4.10 (s, 2H).

Step 4: tert-butyl (3-(cyanomethyl)-5-fluorophenyl)carbamate

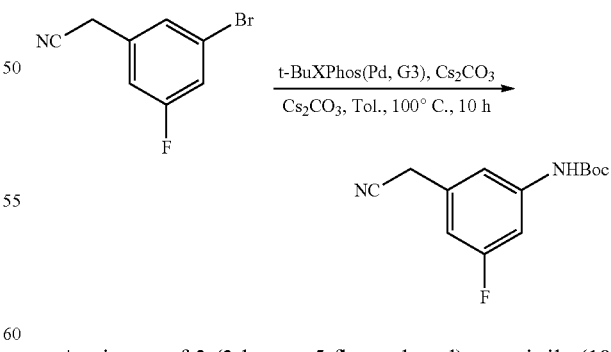

A mixture of 2-(3-bromo-5-fluorophenyl)acetonitrile (10 g, 46.72 mmol, 1 eq), tert-butyl carbamate (8.21 g, 70.08 mmol, 1.5 eq), t-Bu Xphos (991.99 mg, 2.34 mmol, 0.05 eq), tBuXPhos Pd G3 (1.86 g, 2.34 mmol, 0.05 eq) and Cs$_2$CO$_3$ (30.45 g, 93.44 mmol, 2 eq) in toluene (100 mL) was degassed and purged with N$_2$ for 3 times, and then the mixture was stirred at 100° C. for 10 hrs under N$_2$ atmosphere. LC-MS showed the reaction was completed. The reaction mixture was filtered and concentrated under reduced pressure to give a residue. The residue was purified by column chromatography (SiO2, Petroleum ether/Ethyl acetate=10/1 to 1/1) to afford tert-butyl (3-(cyanomethyl)-5-fluorophenyl)carbamate (9 g, 35.96 mmol, 76.97% yield) as yellow solid. 1H NMR (400 MHz, DMSO-d6) δ=9.70 (s, 1H), 7.34 (s, 1H), 7.25 (br d, J=11.5 Hz, 1H), 6.77 (br d, J=8.8 Hz, 1H), 4.03 (s, 2H), 1.48 (s, 9H). LC-MS (ES$^+$, m/z): 251.2 [(M+H)$^+$]; Rt=0.795 min.

Step 5: 2-(3-amino-5-fluorophenyl)acetonitrile

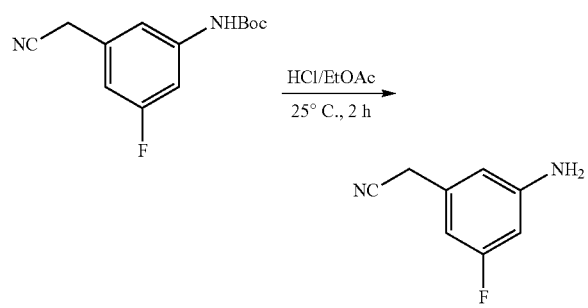

A mixture of tert-butyl N-[3-(cyanomethyl)-5-fluoro-phenyl]carbamate (9 g, 35.96 mmol, 1 eq) in HCl/EtOAc (4 M, 99.96 mL, 11.12 eq) was stirred at 25° C. for 2 hrs. LC-MS showed reaction was completed. The reaction mixture was poured into saturated Na$_2$CO$_3$ (50 mL) and extracted with EA 150 mL (50 mL*3). The combined organic layers were washed with saturated brine 60 mL (20 mL*3), dried over anhydrous Na$_2$SO$_4$, filtered and concentrated under reduced pressure to afford 2-(3-amino-5-fluorophenyl)acetonitrile (4.3 g, crude) as yellow oil. LC-MS (ES$^+$, m/z): 151.2 [(M+H)$^+$]; Rt=0.120 min.

Note: HCl/EtOAc (4 M): HCl was bubbled into a solution EtOAc at 0° C. for 0.5 h. Then, the solution was weighed to obtained the HCl/EtOAc (4 M)

Step 6: 3-(2-aminoethyl)-5-fluoroaniline

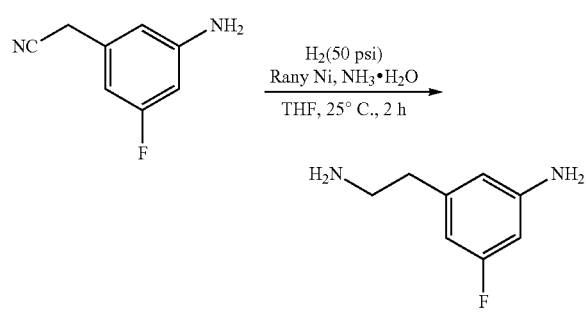

To a solution of 2-(3-amino-5-fluoro-phenyl)acetonitrile (4.3 g, 28.64 mmol, 1 eq) and NH3·H2O (4.55 g, 45.44 mmol, 5.00 mL, 35% purity, 1.59 eq) in THF (100 mL) was added Raney-Ni (15.00 g, 175.08 mmol, 6.11 eq) under N$_2$ atmosphere. The suspension was degassed and purged with H$_2$ for 3 times. The mixture was stirred under 50 Psi of H$_2$ (57.85 mg, 28.64 mmol, 1 eq) at 25° C. for 2 hrs. LC-MS showed reaction was completed. The reaction mixture was filtered and concentrated under reduced pressure to afford 3-(2-aminoethyl)-5-fluoroaniline (4.3 g, crude) as yellow oil. LC-MS (ES$^+$, m/z): 155.1 [(M+H)$^+$]; Rt=0.146 min.

Step 7: tert-butyl (3-amino-5-fluorophenethyl)carbamate

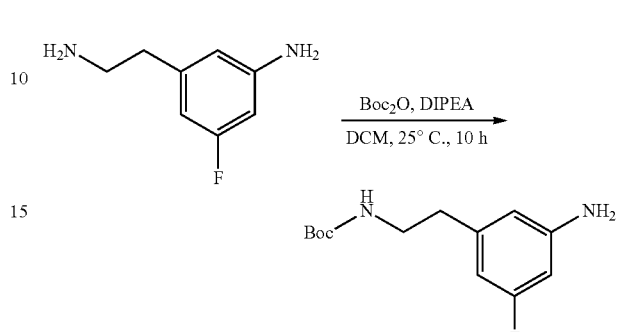

A mixture of 3-(2-aminoethyl)-5-fluoroaniline (4.3 g, 27.89 mmol, 1 eq), (Boc)$_2$O (6.09 g, 27.89 mmol, 6.41 mL, 1 eq), DIPEA (7.21 g, 55.78 mmol, 9.72 mL, 2 eq) in DCM (50 mL) was degassed and purged with N$_2$ for 3 times, and then the mixture was stirred at 25° C. for 10 hrs under N$_2$ atmosphere. LC-MS showed the reaction was completed. The reaction mixture was concentrated under reduced pressure to remove DCM. The residue was diluted with H$_2$O 10 mL and extracted with EA (30 mL*3). The combined organic layers were washed with saturated brine (100 mL*1), dried over anhydrous Na$_2$SO$_4$, filtered and concentrated under reduced pressure to give a residue. The residue was purified by column chromatography (SiO2, Petroleum ether/Ethyl acetate=10/1 to 1/1) to afford tert-butyl N-[2-(3-amino-5-fluoro-phenyl)ethyl]carbamate (3.4 g, 13.37 mmol, 47.94% yield) as yellow oil. 1H NMR (400 MHz, DMSO-d6) δ=6.91-6.76 (m, 1H), 6.24-6.03 (m, 3H), 5.37-5.25 (m, 2H), 3.19-3.15 (d, 1H), 3.11-3.03 (m, 2H), 2.57-2.52 (m, 1H), 1.42-1.34 (m, 9H). LC-MS (ES$^+$, m/z): 155.2 [(M+H-100)$^+$], 199.2 [(M+H-56)$^+$]; Rt=0.666 min.

Step 8: tert-butyl (3-((3-carbamoyl-6-chloro-5-ethylpyrazin-2-yl)amino)-5-fluorophenethyl)carbamate

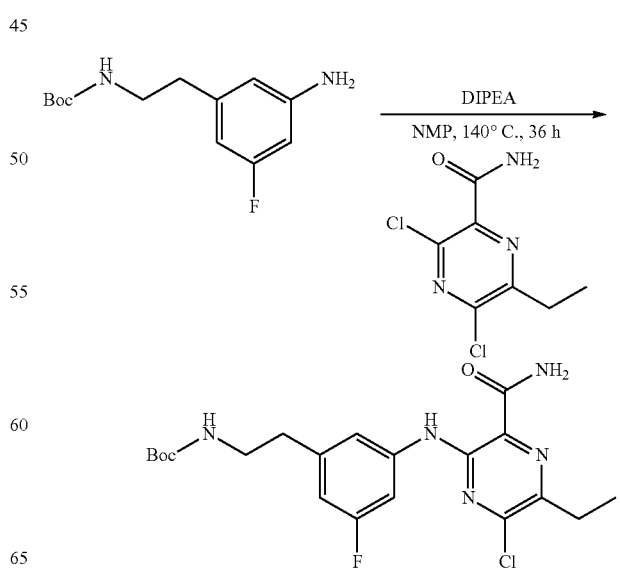

To a solution of tert-butyl (3-amino-5-fluorophenethyl) carbamate (2 g, 7.86 mmol, 1 eq) and 3,5-dichloro-6-ethylpyrazine-2-carboxamide (1.73 g, 7.86 mmol, 1 eq) in NMP (4 mL) was added DIPEA (40.66 g, 314.59 mmol, 54.80 mL, 40 eq). The mixture was stirred at 140° C. for 36 hrs. LC-MS showed the reaction was completed. The reaction mixture was poured into H$_2$O (15 mL), filtered to give a residue. The residue was diluted with EA 15 mL and poured into H$_2$O 15 mL, then extracted with EA (15 mL*3). The organic phase was separated, washed with saturated brine (10 mL*3), dried over anhydrous Na$_2$SO$_4$, filtered and concentrated under reduced pressure to give a residue. The residue was purified by column chromatography (SiO$_2$, Petroleum ether/Ethyl acetate=5/1 to 1/1) to afford tert-butyl (3-((3-carbamoyl-6-chloro-5-ethylpyrazin-2-yl)amino)-5-fluorophenethyl)carbamate (1.78 g, 3.13 mmol, 39.86% yield, 77.12% purity) as yellow oil. $^1$H NMR (400 MHz, DMSO-d6) δ=11.36 (s, 1H), 8.30 (br s, 1H), 8.09 (br s, 1H), 7.65 (br d, J=11.5 Hz, 1H), 6.98 (s, 1H), 6.87 (br t, J=5.0 Hz, 1H), 6.71 (br d, J=9.4 Hz, 1H), 3.19-3.13 (m, 2H), 2.83 (q, J=7.4 Hz, 2H), 2.69 (br t, J=6.9 Hz, 2H), 1.34 (s, 9H), 1.26 (t, J=7.4 Hz, 3H). LC-MS (ES$^+$, m/z): 438.2 [(M+H)$^+$]; Rt=0.914 min; 77.12% purity.

Step 9: 3-((3-(2-aminoethyl)-5-fluorophenyl) amino)-5-chloro-6-ethylpyrazine-2-carboxamide

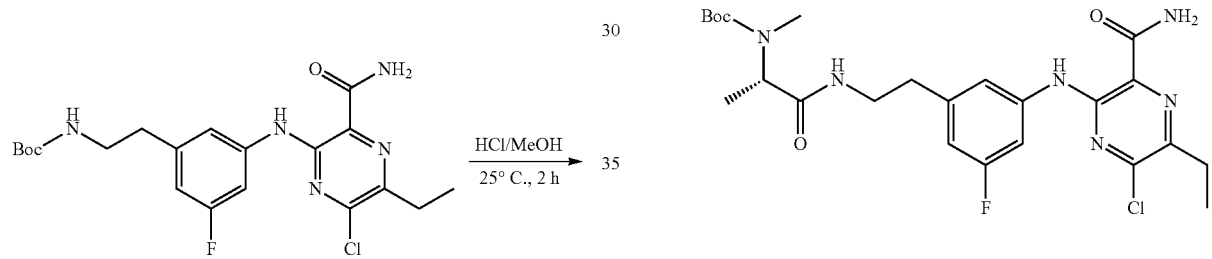

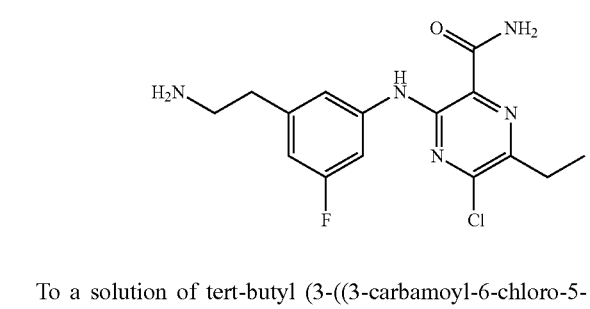

To a solution of tert-butyl (3-((3-carbamoyl-6-chloro-5-ethylpyrazin-2-yl) amino)-5-fluorophenethyl)carbamate (1.3 g, 2.97 mmol, 1 eq) in HCl/MeOH (4 M, 50 mL, 67.37 eq) was stirred at 25° C. for 2 hrs. LC-MS showed the reaction was completed. The reaction mixture was filtered and concentrated under reduced pressure to give a residue to afford 3-((3-(2-aminoethyl)-5-fluorophenyl)amino)-5-chloro-6-ethylpyrazine-2-carboxamide (1 g, crude, HCl) as yellow solid. LC-MS (ES$^+$, m/z): 338.2 [(M+H)$^+$]; Rt=0.710 min.

Note: HCl/MeOH (4 M): HCl was bubbled into a solution MeOH at 0° C. for 0.5 h.

Step 10: tert-butyl (S)-(1-((3-((3-carbamoyl-6-chloro-5-ethylpyrazin-2-yl)amino)-5-fluorophenethyl)amino)-1-oxopropan-2-yl)(methyl)carbamate

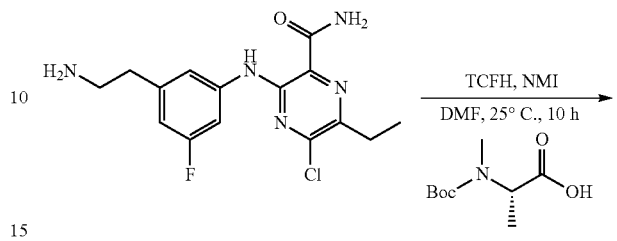

To a solution of 3-((3-(2-aminoethyl)-5-fluorophenyl) amino)-5-chloro-6-ethylpyrazine-2-carboxamide (1 g, 2.96 mmol, 1 eq) and N-(tert-butoxycarbonyl)-N-methyl-L-alanine (902.52 mg, 4.44 mmol, 1.5 eq) in DMF (15 mL) was added 1-methyl-1H-imidazole (2.43 g, 29.61 mmol, 2.36 mL, 10 eq) and chloro-N,N,N',N'-tetramethylformamidinium hexafluorophosphate (1.25 g, 4.44 mmol, 1.5 eq). The mixture was stirred at 25° C. for 10 hrs. LC-MS showed the reaction was completed. The reaction mixture was poured into H$_2$O (15 mL) and extracted with EA (10 mL*3). The combined organic layers were washed with saturated brine (10 mL*3), dried over anhydrous Na$_2$SO$_4$, filtered and concentrated under reduced pressure to give a residue. The residue was purified by column chromatography (SiO2, Petroleum ether/Ethyl acetate=5/1 to 1/5) to afford tert-butyl (S)-(1-((3-((3-carbamoyl-6-chloro-5-ethylpyrazin-2-yl) amino)-5-fluorophenethyl) amino)-1-oxopropan-2-yl) (methyl)carbamate (1.5 g, 2.87 mmol, 96.88% yield) was obtained as a yellow oil. $^1$H NMR (400 MHz, DMSO-d$_6$) δ=11.42-11.35 (m, 1H), 8.38-8.05 (m, 2H), 7.96 (s, 1H), 7.82 (br t, J=5.1 Hz, 1H), 7.70-7.61 (m, 1H), 7.08-7.00 (m, 1H), 6.76-6.70 (m, 1H), 3.32 (s, 3H), 2.89 (s, 2H), 2.87 (s, 2H), 2.73 (s, 2H), 1.35 (br s, 9H), 1.27 (t, J=7.5 Hz, 3H), 1.22-1.16 (m, 3H). LC-MS (ES$^+$, m/z): 415.1 [(M+H)$^+$]; Rt=1.901 min, 99.09% purity; HRMS: 415.2488.

Intermediate 9

3,5-dichloro-6-ethyl-N-methylpyrazine-2-carboxamide

Step 1: methyl 3,5-dichloro-6-ethylpyrazine-2-carboxylate

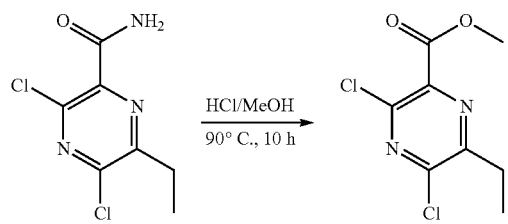

A mixture of 3,5-dichloro-6-ethyl-pyrazine-2-carboxamide (15 g, 68.16 mmol, 1.0 eq), HCl/MeOH (4 M, 350.03 mL, 20.54 eq) was stirred at 90° C. for 10 hrs. LCMS showed the reaction was completed. The mixture was concentrated. The residue was diluted with saturated NaHCO$_3$ (500 mL) and extracted with EtOAc (400 mL*2). The organic layers were combined, washed with water (300 mL*2), sat. saturated brine (300 mL), dried with anhydrous Na2CO3, filtered and concentrated to give crude product. The crude product was purified by chromatography on silica gel (petroleum ether/EtOAc=100/1) TLC (plate1)Rf=0.67) to afford methyl 3,5-dichloro-6-ethyl-pyrazine-2-carboxylate (13 g, 55.30 mmol, 81.13% yield) as a yellow oil. LC-MS (ES$^+$, m/z): 235.1 [(M+H)$^+$]; Rt=0.830 min.

Note: HCl/MeOH (4 M): HCl was bubbled into a solution MeOH at 0° C. for 0.5 h.

Step 2: 3,5-dichloro-6-ethylpyrazine-2-carboxylic acid

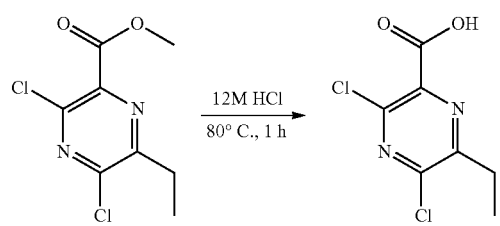

The mixture of methyl 3,5-dichloro-6-ethyl-pyrazine-2-carboxylate (4.8 g, 20.42 mmol, 1.0 eq) in HCl (12 M, 671.40 mL, 131.52 eq). LCMS showed the reaction was completed. The reaction was poured into H$_2$O (100 mL). The aqueous phase was extracted with ethyl acetate (50 mL*3). The combined organic phase was washed with saturated brine (100 mL*1), dried with anhydrous Na$_2$SO$_4$. Filtered and concentrated in vacuum to afford 3,5-dichloro-6-ethyl-pyrazine-2-carboxylic acid (3 g, 13.57 mmol, 66.47% yield) as a yellow solid. LC-MS (ES$^+$, m/z): 221.1 [(M+H)$^+$]; Rt=0.688 min.

Step 3: 3,5-dichloro-6-ethylpyrazine-2-carbonyl chloride

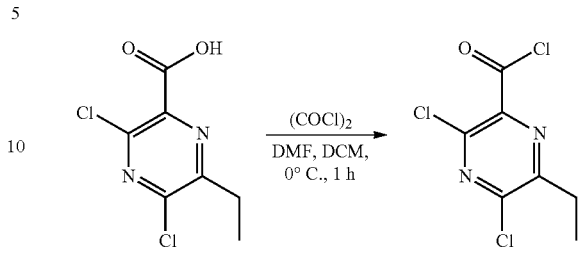

To a mixture of 3,5-dichloro-6-ethyl-pyrazine-2-carboxylic acid (1 g, 4.52 mmol, 1.0 eq) in DCM (10 mL) was added DMF (16.53 mg, 226.20 umol, 0.05 eq) finally added (COCl)$_2$ (1.15 g, 9.05 mmol, 2.0 eq) in one portion at 0° C. under N$_2$ for 1 hr. TLC showed the reaction was completed. The residue was concentrated in vacuum to afford 3,5-dichloro-6-ethyl-pyrazine-2-carbonyl chloride (0.8 g, 3.34 mmol, 73.84% yield) as a yellow solid.

Step 4: 3,5-dichloro-6-ethyl-N-methylpyrazine-2-carboxamide

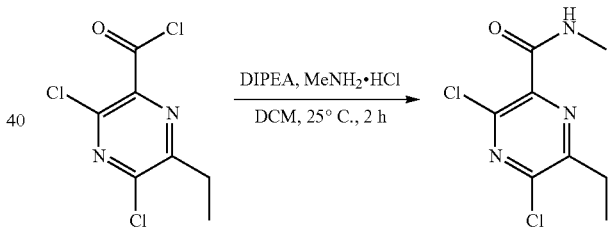

A mixture of 3,5-dichloro-6-ethyl-pyrazine-2-carbonyl chloride (0.8 g, 3.34 mmol, 1.0 eq), methanamine; hydrochloride (451.08 mg, 6.68 mmol, 2.0 eq), and DIPEA (2.16 g, 16.70 mmol, 5.0 eq) in DCM (10 mL). The mixture was stirred at 25° C. for 2 hours. LCMS showed the reaction was completed. The reaction was poured into H$_2$O (50 mL). The aqueous phase was extracted with ethyl acetate (10 mL*3). The combined organic phase was washed with saturated brine (50 mL*1), dried with anhydrous Na$_2$SO$_4$. Filtered and concentrated in vacuum. The residue was purified by silica gel chromatography (column height: 250 mm, diameter: 100 mm, 100-200 mesh silica gel, Petroleum ether/Ethyl acetate=1/1, 10/1) to afford 3,5-dichloro-6-ethyl-N-methyl-pyrazine-2-carboxamide (500 mg, 2.14 mmol, 63.94% yield) as a brown solid. LC-MS (ES$^+$, m/z): 234.1 [(M+H)$^+$]; Rt=0.705 min.

Intermediate 10

(E)-N-(4-(dimethylamino)but-2-enoyl)-N-methyl-L-alanine

Step 1: tert-butyl (E)-N-(4-(dimethylamino)but-2-enoyl)-N-methyl-L-alaninate

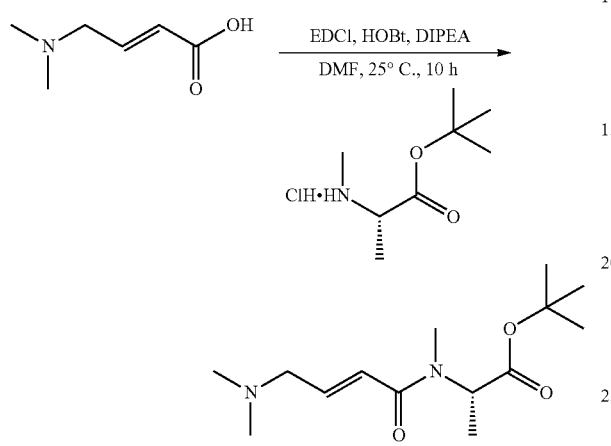

To a solution of tert-butyl methyl-L-alaninate hydrochloride (3 g, 15.33 mmol, 1 eq) (E)-4-(dimethylamino)but-2-enoic acid (2.79 g, 16.86 mmol, 1.1 eq) EDCI (4.41 g, 23.00 mmol, 1.5 eq) HOBt (2.07 g, 15.33 mmol, 1 eq) in DMF (30 mL) at 25° C., DIPEA (19.81 g, 153.31 mmol, 26.70 mL, 10 eq) was added. The mixture was stirred at 25° C. for 10 hrs. LCMS indicated the reaction was completed. The mixture was poured into water (100 mL) and extracted with EtOAc (60 mL*2). The organic layers was washed with water (60 mL*2), saturated brine (60 mL*2), dried over anhydrous Na2SO4, filtered, concentrated under reduced pressure to give a residue. The crude product was purified by chromatography on silica gel (Dichloromethane:Methanol=10:1) to afford tert-butyl (E)-N-(4-(dimethylamino)but-2-enoyl)-N-methyl-L-alaninate (2.75 g, 9.56 mmol, 62.37% yield, 94% purity) as black brown oil. LC-MS (ES+, m/z): 217.3 [(M+H)+]; Rt=0.556 min.

Step 2: (E)-N-(4-(dimethylamino)but-2-enoyl)-N-methyl-L-alanine

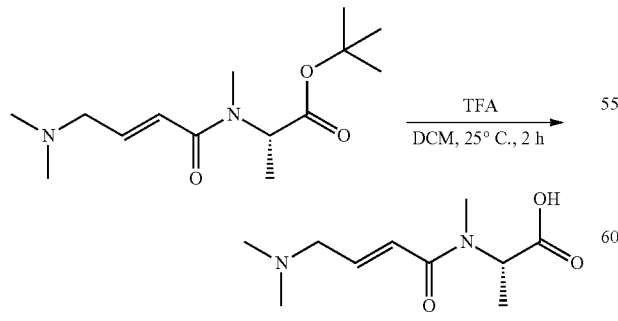

To a solution of tert-butyl (E)-N-(4-(dimethylamino)but-2-enoyl)-N-methyl-L-alaninate (1 g, 3.70 mmol, 1 eq) TFA (7.70 g, 67.53 mmol, 5 mL, 18.26 eq) in DCM (10 mL) at 25° C. The mixture was stirred at 25° C. for 2 hrs. LCMS indicated the reaction was completed. The mixture was a concentrated under reduced pressure to give (E)-N-(4-(dimethylamino)but-2-enoyl)-N-methyl-L-alanine (760 mg, crude) as black brown oil. LC-MS (ES+, m/z): 215.2 [(M+H)+]; Rt=0.339 min.

Intermediate 11

3-((3-(2-aminoethyl)phenyl)amino)-5-(dimethylamino)-6-ethylpyrazine-2-carboxamide.HCl Step 1: tert-butyl (3-((3-carbamoyl-6-(dimethylamino)-5-ethylpyrazin-2-yl)amino)phenethyl)carbamate

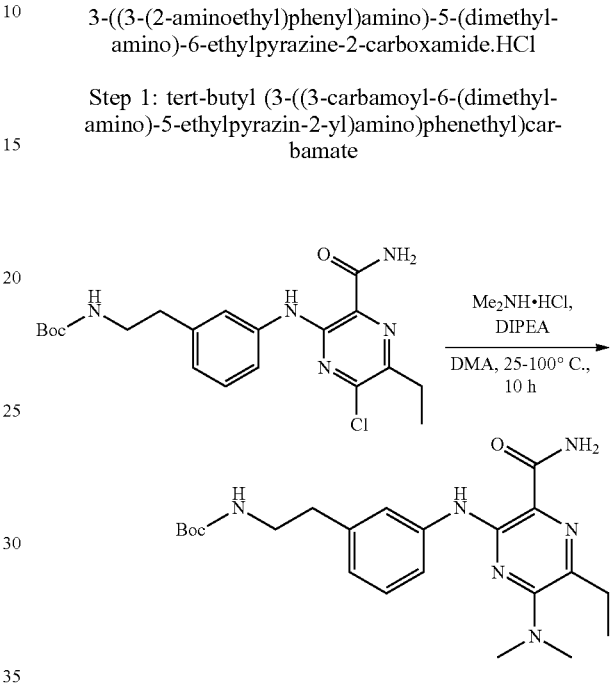

To a solution of tert-butyl (3-((3-carbamoyl-6-chloro-5-ethylpyrazin-2-yl)amino)phenethyl)carbamate (3 g, 7.14 mmol, 1 eq) DIEA (9.23 g, 71.44 mmol, 12.44 mL, 10 eq)N-methylmethanamine (3.22 g, 39.50 mmol, 3.62 mL, 5.53 eq, HCl) and DMA (20 mL) at 25° C., the mixture was stirred at 100° C. for 10 hrs. LCMS indicated the reaction was completed. The reaction was poured into water (50 mL) and extracted with EtOAc (30 mL*3). The organic layers were combined, washed with water (10 mL*2), sat. brine (10 mL), dried with anhydrous Na2SO4, filtered and concentrated to give crude product. The crude product was purified by chromatography on silica thiol gel (petroleum ether/EtOAc=1/1). To give tert-butyl (3-((3-carbamoyl-6-(dimethylamino)-5-ethylpyrazin-2-yl)amino)phenethyl)carbamate (1.34 g, 3.13 mmol, 43.77% yield) as yellow solid. LC-MS (ES+, m/z): 429.3 [(M+H)+]; Rt=0.929 min.

Step 2: 3-((3-(2-aminoethyl)phenyl)amino)-5-(dimethylamino)-6-ethylpyrazine-2-carboxamide

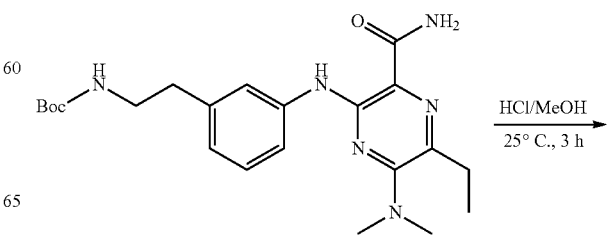

-continued

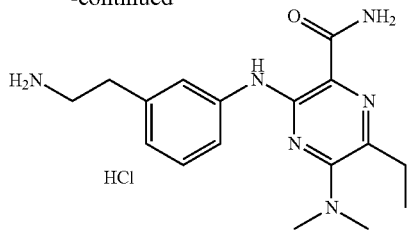

A mixture of tert-butyl (3-((3-carbamoyl-6-(dimethylamino)-5-ethylpyrazin-2-yl)amino)phenethyl)carbamate (1.3 g, 3.03 mmol, 1 eq) HCl/EtOAc (4 M, 30 mL, 39.56 eq) was stirred at 25° C. for 3 hr. LCMS indicated the reaction was completed. The mixture was concentrated under reduced pressure to give 3-((3-(2-aminoethyl)phenyl)amino)-5-(dimethylamino)-6-ethylpyrazine-2-carboxamide (900 mg, crude, HCl) was yellow solid. LC-MS (ES+, m/z): 329.4 [(M+H)+]; Rt=0.641 min.
Note: HCl/MeOH (4 M): HCl gas was bubbled into a solution MeOH at 0° C. for 0.5 h. Then, the solution was weighed to obtained the HCl/MeOH (4 M)

Intermediate 12

(S)-6-ethyl-5-(isopropyl(methyl)amino)-3-((3-(2-(2-(methylamino)propanamido)ethyl)phenyl)amino)pyrazine-2-carboxamide Step 1: tert-butyl (3-((3-carbamoyl-6-chloro-5-ethylpyrazin-2-yl)amino)phenethyl)carbamate

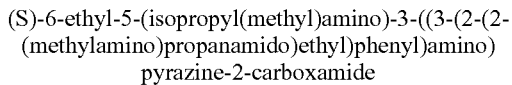

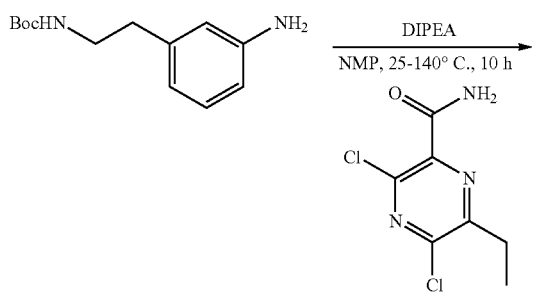

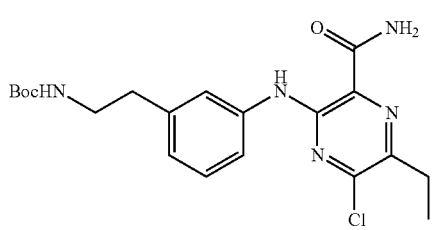

A mixture of tert-butyl (3-aminophenethyl)carbamate (2 g, 8.46 mmol, 1 eq), 3,5-dichloro-6-ethylpyrazine-2-carboxamide (1.86 g, 8.46 mmol, 1 eq) in NMP (5 mL), DIPEA (21.88 g, 169.27 mmol, 29.48 mL, 20 eq) was added at 25° C. The mixture was stirred at 140° C. for 10 hours. LCMS showed the reaction was completed. The reaction was poured into H2O (50 mL). The aqueous phase was extracted with ethyl acetate (20 mL*3). The combined organic phase was washed with saturated brine (50 mL*1), dried with anhydrous Na2SO4. Filtered and concentrated in vacuum. The residue was purified by silica gel chromatography (column height: 250 mm, diameter: 100 mm, 100-200 mesh silica gel, Petroleum ether/Ethyl acetate=1/1, 10/1) to afford tert-butyl (3-((3-carbamoyl-6-chloro-5-ethylpyrazin-2-yl)amino)phenethyl)carbamate (3.5 g, 6.67 mmol, 78.79% yield) as a yellow solid. 1H NMR (400 MHz, DMSO-d6) δ=11.19 (s, 1H), 8.26 (s, 1H), 8.04 (br s, 1H), 7.59 (br d, J=7.9 Hz, 1H), 7.32-7.23 (m, 2H), 6.93-6.83 (m, 2H), 3.16 (q, J=6.5 Hz, 2H), 2.82 (q, J=7.5 Hz, 2H), 2.69 (t, J=7.3 Hz, 2H), 1.36 (s, 9H), 1.28-1.24 (m, 3H) LC-MS (ES+, m/z): 420.3 [(M+H)+]; Rt=0.941 min.

Step 2: tert-butyl (3-((3-carbamoyl-5-ethyl-6-(isopropyl(methyl)amino)pyrazin-2-yl)amino)phenethyl)carbamate

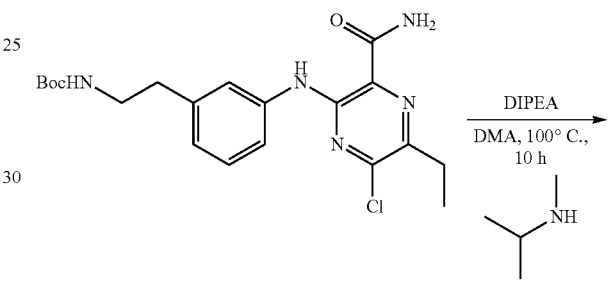

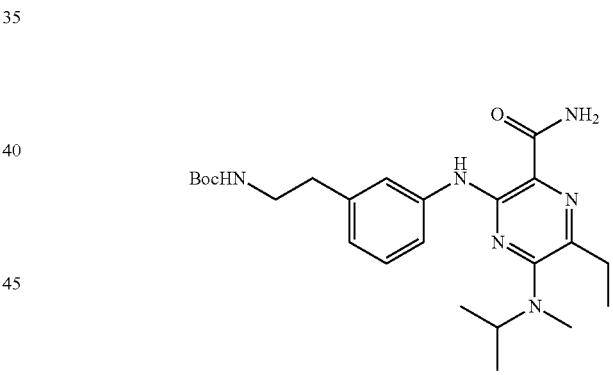

To a solution of tert-butyl (3-((3-carbamoyl-6-chloro-5-ethylpyrazin-2-yl)amino)phenethyl)carbamate (400 mg, 952.60 umol, 1 eq) and N-methylpropan-2-amine (696.70 mg, 9.53 mmol, 992.44 uL, 10 eq) in DMA (10 mL) was added DIPEA (123.12 mg, 952.60 umol, 165.93 uL, 1 eq) at 20° C. The mixture was stirred at 100° C. for 10 hrs in sealed tube. LCMS indicated the reaction was complete. The reaction was poured into water (30 mL) and extracted with EtOAc (30 mL*2). The organic layers were combined, washed with water (15 mL*2), saturated brine (10 mL), dried (Na2SO4), filtered and concentrated to give crude product. The crude product was purified by chromatography on silica thiol gel (petroleum ether/EtOAc=1/2) to give tert-butyl (3-((3-carbamoyl-5-ethyl-6-(isopropyl(methyl)amino)pyrazin-2-yl)amino)phenethyl)carbamate (350 mg, 766.57 umol, 80.47% yield) as yellow solid.

LC-MS (ES+, m/z): 457.5 [(M+H)+]; Rt=0.992 min.

Step 3: 3-((3-(2-aminoethyl)phenyl)amino)-6-ethyl-5-(isopropyl(methyl)amino)pyrazine-2-carboxamide

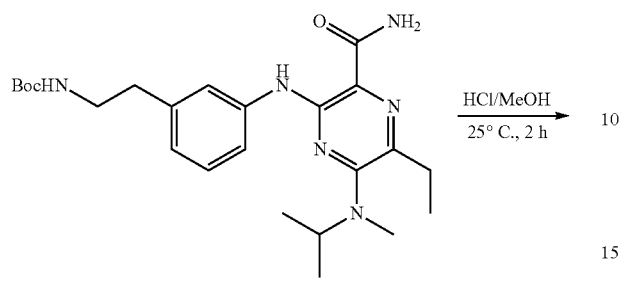

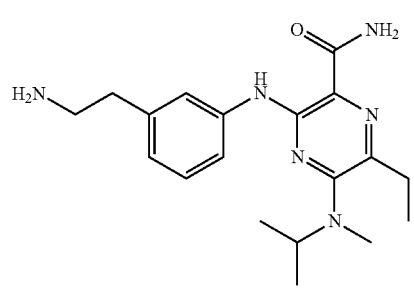

A solution of tert-butyl (3-((3-carbamoyl-5-ethyl-6-(isopropyl(methyl)amino)pyrazin-2-yl)amino)phenethyl)carbamate (350 mg, 766.57 umol, 1 eq) and HCl/MeOH (4 M, 10.94 mL, 57.07 eq) was stirred at 25° C. for 2 hrs. LCMS indicated the reaction was complete. The mixture was concentrated under reduced pressure to give 3-((3-(2-aminoethyl)phenyl)amino)-6-ethyl-5-(isopropyl(methyl)amino)pyrazine-2-carboxamide (260 mg, crude) as yellow solid. LC-MS (ES$^+$, m/z): 357.3 [(M+H)$^+$]; Rt=0.716 min.

Note:

HCl/MeOH (4 M): HCl gas was bubbled into a solution MeOH at 0° C. for 0.5 h. Then, the solution was weighed to obtained the HCl/MeOH (4 M)

Step 4: tert-butyl (S)-(1-((3-((3-carbamoyl-5-ethyl-6-(isopropyl(methyl)amino)pyrazin-2-yl)amino)phenethyl)amino)-1-oxopropan-2-yl)(methyl)carbamate

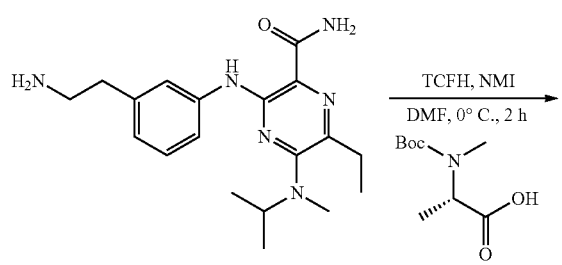

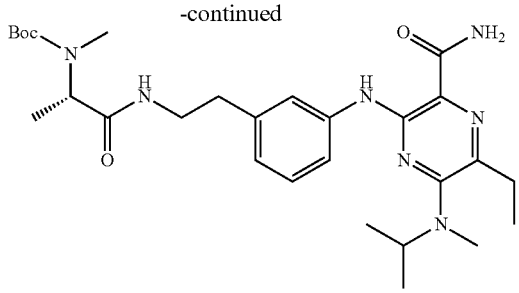

To a solution of 3-((3-(2-aminoethyl)phenyl)amino)-6-ethyl-5-(isopropyl(methyl)amino)pyrazine-2-carboxamide (260 mg, 729.39 umol, 1 eq), NMI (598.85 mg, 7.29 mmol, 581.41 uL, 10 eq), N-(tert-butoxycarbonyl)-N-methyl-L-alanine (222.36 mg, 1.09 mmol, 1.5 eq) in DMF (3 mL), was added TCFH (306.98 mg, 1.09 mmol, 1.5 eq). The mixture was stirred at 0° C. for 2 hrs. LCMS indicated the reaction was complete. The reaction was poured into water (15 mL) and extracted with EtOAc (10 mL*2). The organic layers were combined, washed with water (10 mL*2), saturated brine (5 mL), dried (Na$_2$SO$_4$), filtered and concentrated to give crude product. The crude product was purified by chromatography on silica thiol gel (petroleum ether/EtOAc=1/1) TLC(plate 1 Rf=0.75) to give tert-butyl (S)-(1-((3-((3-carbamoyl-5-ethyl-6-(isopropyl(methyl)amino)pyrazin-2-yl)amino)phenethyl)amino)-1-oxopropan-2-yl)(methyl)carbamate (350 mg, 646.13 umol, 88.59% yield) as yellow solid. LC-MS (ES$^+$, m/z): 542.4 [(M+H)$^+$]; Rt=0.945 min.

Step 5: (S)-6-ethyl-5-(isopropyl(methyl)amino)-3-((3-(2-(2-(methylamino)propanamido)ethyl)phenyl)amino)pyrazine-2-carboxamide

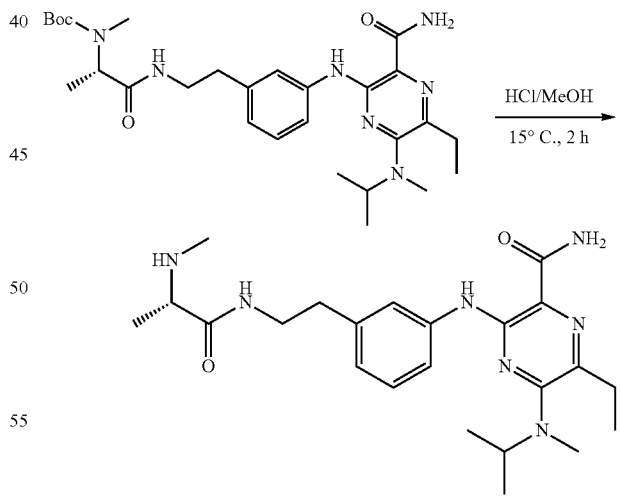

A mixture of tert-butyl (S)-(1-((3-((3-carbamoyl-5-ethyl-6-(isopropyl(methyl)amino)pyrazin-2-yl)amino)phenethyl)amino)-1-oxopropan-2-yl)(methyl)carbamate (350 mg, 646.13 umol, 1 eq) and HCl/MeOH (4 M, 10 mL, 61.91 eq) was stirred at 15° C. for 2 hrs. LCMS indicated the reaction was complete. The mixture was concentrated under reduced pressure to give (S)-6-ethyl-5-(isopropyl(methyl)amino)-3-((3-(2-(2-(methylamino) propanamido)ethyl)phenyl) amino)

pyrazine-2-carboxamide (270 mg, crude) as yellow solid. LC-MS (ES+, m/z): 442.3 [(M+H)+]; Rt=0.726 min.
Note: HCl/MeOH (4 M): HCl gas was bubbled into a solution MeOH at 0° C. for 0.5 h. Then, the solution was weighed to obtained the HCl/MeOH (4 M)

Intermediate 13 tert-butyl (3-((3-carbamoyl-6-chloro-5-methylpyrazin-2-yl)amino)phenethyl)carbamate Step 1: 3,5-dichloro-6-methylpyrazine-2-carboxamide

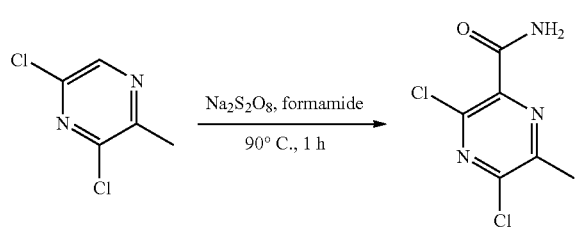

To a solution of 3,5-dichloro-2-methylpyrazine (8 g, 49.08 mmol, 1 eq) in formamide (53.05 g, 1.18 mol, 46.95 mL, 24 eq) at 25° C., $Na_2S_2O_8$ (18.70 g, 78.53 mmol, 17.00 mL, 1.6 eq) was added in batches at 90° C. The mixture was stirred at 90° C. for 1 h. LCMS indicated the reaction was complete. The mixture was poured into water (150 mL) and extracted with DCM (100 mL*2). The organic layers was washed with water (100 mL*2), saturated brine (100 mL*2), dried over $Na_2SO_4$, filtered, concentrated under reduced pressure to give a residue. The crude product was purified by chromatography on silica gel (petroleum ether/EtOAc=3:1) to give 3,5-dichloro-6-methylpyrazine-2-carboxamide (3 g, 14.56 mmol, 29.67% yield) as white solid. $^1$H NMR (400 MHz, DMSO-$d_6$) δ=8.27-8.13 (m, 1H), 8.02 (br s, 1H), 2.67 (s, 3H); LC-MS (ES+, m/z): 206.2 [(M+H)+]. Rt=0.627 min.

Step 2: tert-butyl (3-((3-carbamoyl-6-chloro-5-methylpyrazin-2-yl) amino) phenethyl) carbamate

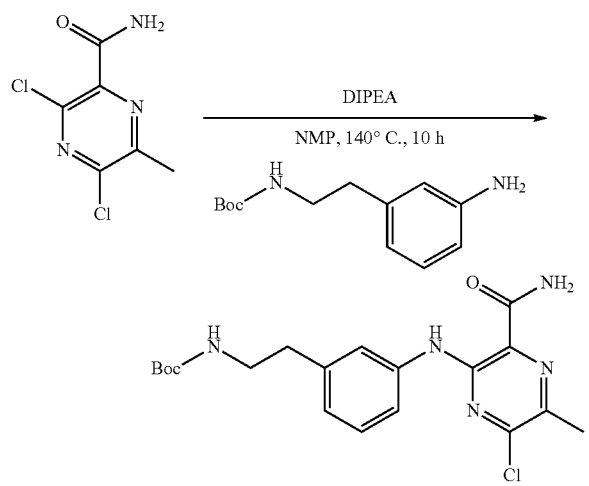

To a solution of 3,5-dichloro-6-methylpyrazine-2-carboxamide (5.3 g, 25.72 mmol, 1 eq), tert-butyl (3-aminophenethyl)carbamate (6.08 g, 25.72 mmol, 1 eq) in NMP (50 mL) at 16° C., DIPEA (66.49 g, 514.49 mmol, 89.61 mL, 20 eq) was added. The mixture was stirred at 140° C. for 10 hrs. LCMS indicated the reaction was complete. The mixture was poured into water (150 mL) and extracted with EtOAc (100 mL*2). The organic layers was washed with water (100 mL*2), saturated brine (100 mL*2), dried over $Na_2SO_4$, filtered, concentrated under reduced pressure to give a residue. The crude product was purified by chromatography on silica gel (petroleum ether/EtOAc=1:1) TLC (plate1) to give tert-butyl (3-((3-carbamoyl-6-chloro-5-methylpyrazin-2-yl) amino) phenethyl) carbamate (6 g, 14.78 mmol, 57.47% yield) as yellow solid. LC-MS (ES+, m/z): 406.2 [(M+H)+]. RT=0.880 min.

Intermediate 14

(S)-5-cyclopropyl-6-methyl-3-((3-(2-(2-(methylamino) propanamido) ethyl) phenyl) amino) pyrazine-2-carboxamide Step 1: tert-butyl (3-((3-carbamoyl-6-cyclopropyl-5-methylpyrazin-2-yl) amino) phenethyl) carbamate

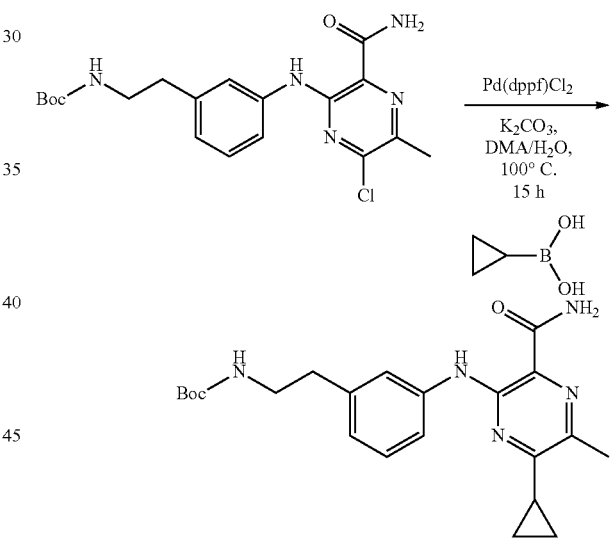

To a solution of tert-butyl (3-((3-carbamoyl-6-chloro-5-methylpyrazin-2-yl)amino)phenethyl)carbamate (3.47 g, 8.55 mmol, 1 eq), cyclopropylboronic acid (7.34 g, 85.49 mmol, 10 eq), $K_2CO_3$ (3.54 g, 25.65 mmol, 3 eq) in DMA (24 mL) and $H_2O$ (12 mL) at 16° C., Pd(dppf)Cl$_2$ (625.57 mg, 854.94 umol, 0.1 eq) was added. The mixture was stirred at 100° C. for 15 hrs under $N_2$. LCMS indicated the reaction was complete. The residue was dissolved in DCM (40 mL), scavenger (Pd) was added and then stirred at 25° C. for 1 h, and then filtered. The mixture was poured into water (120 mL) and extracted with EtOAc (80 mL*2). The organic layers was washed with water (80 mL*2), saturated brine (80 mL*2), dried over $Na_2SO_4$, filtered, concentrated under reduced pressure to give a residue. The crude product was purified by chromatography on silica gel (petroleum ether/EtOAc=1:1) give tert-butyl (3-((3-carbamoyl-6-cyclopropyl-5-methylpyrazin-2-yl) amino) phenethyl) carbamate (1.9 g, 4.62 mmol, 54.01% yield) as yellow solid. LC-MS (ES+, m/z): 412.2 [(M+H)+]. RT=0.893 min.

Step 2: 3-((3-(2-aminoethyl) phenyl) amino)-5-cyclopropyl-6-methylpyrazine-2-carboxamide

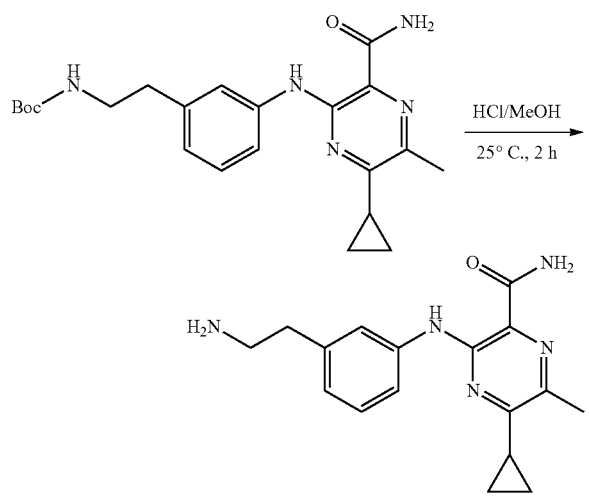

The mixture tert-butyl (3-((3-carbamoyl-6-cyclopropyl-5-methylpyrazin-2-yl) amino) phenethyl) carbamate (1.9 g, 4.62 mmol, 1 eq) and HCl/MeOH (4 M, 50 mL, 43.32 eq) was stirred at 25° C. for 2 hrs. LCMS indicated the reaction was complete. The mixture was concentrated under reduced pressure to give 3-((3-(2-aminoethyl) phenyl) amino)-5-cyclopropyl-6-methylpyrazine-2-carboxamide (1.8 g, crude) as yellow solid. LC-MS (ES+, m/z): 312.2 [(M+H)+]; RT=0.643 min.
Note: HCl/MeOH (4 M): HCl was bubbled into a solution MeOH at 0° C. for 0.5 h.

Step 3: tert-butyl (S)-(1-((3-((3-carbamoyl-6-cyclopropyl-5-methylpyrazin-2-yl) amino) phenethyl) amino)-1-oxopropan-2-yl) (methyl) carbamate

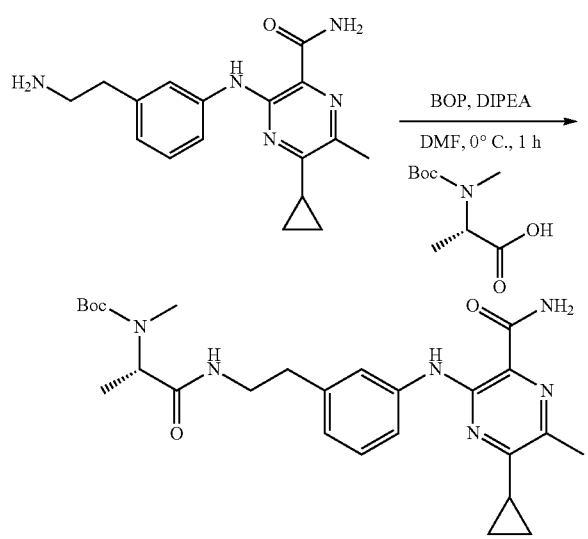

To a solution of, N-(tert-butoxycarbonyl)-N-methyl-L-alanine (1.16 g, 5.69 mmol, 1.1 eq) in DMF (15 mL), DIPEA (6.69 g, 51.75 mmol, 10 eq) 3-((3-(2-aminoethyl)phenyl) amino)-5-cyclopropyl-6-methylpyrazine-2-carboxamide (1.8 g, 5.17 mmol, 1 eq, HCl) was added at 0° C., and then BOP (3.43 g, 7.76 mmol, 1.5 eq) was added at 0° C. The mixture was stirred at 0° C. for 1 h. LCMS indicated the reaction was complete. The mixture was poured into water (80 mL) and extracted with EtOAc (50 mL*2). The organic layers was washed with water (50 mL*2), saturated brine (50 mL*2), dried over Na₂SO₄, filtered, concentrated under reduced pressure to give a residue. The crude product was purified by chromatography on silica gel (Petroleum ether: Ethyl acetate=2:1) to afford tert-butyl (S)-(1-((3-((3-carbamoyl-6-cyclopropyl-5-methylpyrazin-2-yl) amino) phenethyl) amino)-1-oxopropan-2-yl) (methyl) carbamate (2.42 g, 4.87 mmol, 94.17% yield) as yellow solid. LC-MS (ES+, m/z): 497.3 [(M+H)+]; RT=0.860 min.

Step 4: (S)-5-cyclopropyl-6-methyl-3-((3-(2-(2-(methylamino) propanamido) ethyl) phenyl) amino) pyrazine-2-carboxamide

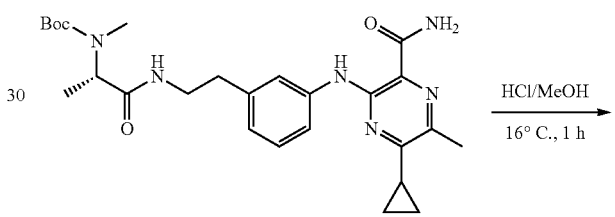

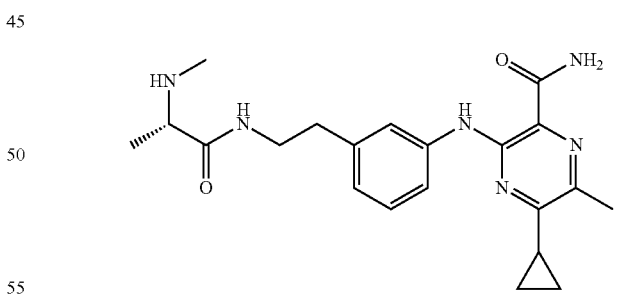

The mixture tert-butyl (S)-(1-((3-((3-carbamoyl-6-cyclopropyl-5-methylpyrazin-2-yl)amino)phenethyl)amino)-1-oxopropan-2-yl)(methyl)carbamate (1.5 g, 3.02 mmol, 1 eq) and HCl/MeOH (4 M, 50 mL, 66.21 eq) was stirred at 16° C. for 1 h. LCMS indicated the reaction was complete. The mixture was concentrated under reduced pressure to give (S)-5-cyclopropyl-6-methyl-3-((3-(2-(2-(methylamino) propanamido) ethyl) phenyl) amino) pyrazine-2-carboxamide (1.23 g, crude) as yellow solid. LC-MS (ES+, m/z): 397.3 [(M+H)+]; RT=0.680 min.

Intermediate 15

(S)-5-(isopropyl(methyl)amino)-6-methyl-3-((3-(2-(2-(methylamino)propanamido)ethyl)phenyl)amino)pyrazine-2-carboxamide

Step 1: 3,5-dichloro-6-methylpyrazine-2-carboxamide

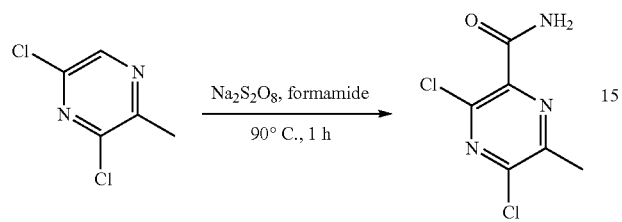

To a solution of 3,5-dichloro-2-methylpyrazine (8 g, 49.08 mmol, 1 eq) in formamide (53.05 g, 1.18 mol, 46.95 mL, 24 eq) at 25° C., Na₂S₂O₈ (18.70 g, 78.53 mmol, 17.00 mL, 1.6 eq) was added in batches at 90° C. The mixture was stirred at 90° C. for 1 h. LCMS indicated the reaction was complete. The mixture was poured into water (150 mL) and extracted with DCM (100 mL*2). The organic layers was washed with water (100 mL*2), saturated brine (100 mL*2), dried over Na₂SO₄, filtered, concentrated under reduced pressure to give a residue. The crude product was purified by chromatography on silica gel (petroleum ether/EtOAc=3:1) to give 3,5-dichloro-6-methylpyrazine-2-carboxamide (3 g, 14.56 mmol, 29.67% yield) as white solid. $^1$H NMR (400 MHz, DMSO-$d_6$) δ=8.27-8.13 (m, 1H), 8.02 (br s, 1H), 2.67 (s, 3H); LC-MS (ES+, m/z): 206.2 [(M+H)$^+$]. Rt=0.627 min.

Step 2: tert-butyl (3-((3-carbamoyl-6-chloro-5-methylpyrazin-2-yl)amino)phenethyl)carbamate

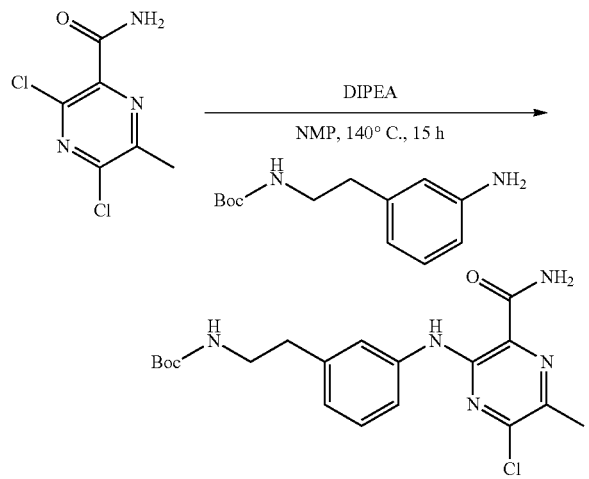

To a solution of 3,5-dichloro-6-methylpyrazine-2-carboxamide (1.7 g, 8.25 mmol, 1 eq) tert-butyl (3-aminophenethyl)carbamate (1.95 g, 8.25 mmol, 1 eq) in NMP (30 mL) at 25° C., DIPEA (31.99 g, 247.54 mmol, 43.12 mL, 30 eq) was added. The mixture was stirred at 140° C. for 15 hrs. LCMS indicated the reaction was complete. The mixture was poured into water (100 mL) and extracted with EtOAc (60 mL*2). The organic layers was washed with water (60 mL*2), saturated brine (60 mL*2), dried over Na₂SO₄, filtered, concentrated under reduced pressure to give a residue. The crude product was purified by chromatography on silica gel (petroleum ether/EtOAc=1:1) TLC to give tert-butyl (3-((3-carbamoyl-6-chloro-5-methylpyrazin-2-yl)amino)phenethyl)carbamate (2.52 g, 6.21 mmol, 75.25% yield) as yellow solid. LC-MS (ES+, m/z): 406.3 [(M+H)$^+$]. Rt=0.893 min.

Step 3: tert-butyl (3-((3-carbamoyl-6-(isopropyl(methyl) amino)-5-methylpyrazin-2-yl) amino) phenethyl) carbamate

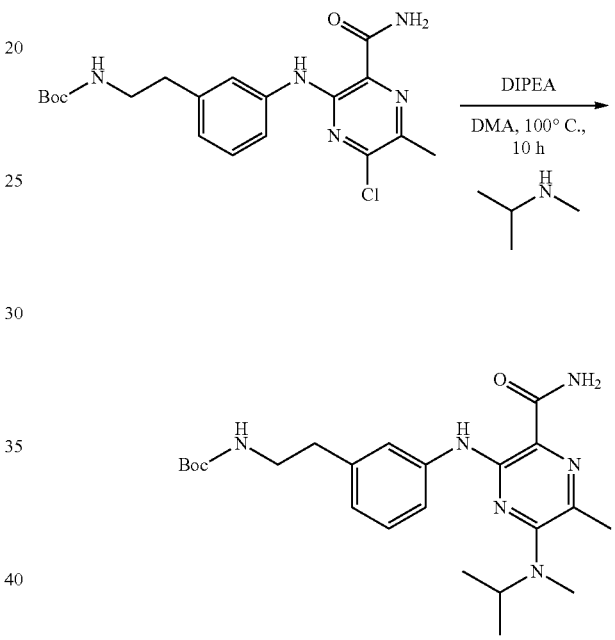

A solution of tert-butyl (3-((3-carbamoyl-6-chloro-5-methylpyrazin-2-yl) amino) phenethyl) carbamate (2.5 g, 6.16 mmol, 1 eq) in DMA (30 mL) saturated with N-methylpropan-2-amine (2.25 g, 30.80 mmol, 3.21 mL, 5 eq) DIEA (7.96 g, 61.59 mmol, 10.73 mL, 10 eq) was stirred at 100° C. for 10 hr in a 100 mL of autoclave. LCMS showed the reaction was completed. The reaction mixture was quenched by addition water (400 mL), and then extracted with EtOAc (300 mL*3). The combined organic layers were washed with saturated brine (350 mL*2), dried over Na₂SO₄, filtered and concentrated under reduced pressure to give a residue. The residue was purified by column chromatography (SiO₂, Petroleum ether/Ethyl acetate=10/1 to 1/1) to give tert-butyl (3-((3-carbamoyl-6-(isopropyl(methyl) amino)-5-methylpyrazin-2-yl) amino) phenethyl) carbamate as yellow solid (9 g, 18.30 mmol, 74.29% yield, 90% purity). $^1$H NMR (400 MHz, DMSO-$d_6$) δ=11.10 (s, 1H), 7.77 (br d, J=2.1 Hz, 1H), 7.61-7.53 (m, 1H), 7.45-7.35 (m, 2H), 7.23-7.15 (m, 1H), 6.95-6.82 (m, 1H), 6.81-6.75 (m, 1H), 4.40-4.30 (m, 1H), 3.16-3.09 (m, 2H), 2.94-2.85 (m, 3H), 2.69-2.63 (m, 2H), 2.44 (s, 3H), 1.39-1.32 (m, 9H), 1.21 (d, J=6.6 Hz, 6H) LC-MS (ES$^+$, m/z): 443.3 [(M+H)$^+$]; Rt=0.947 min;

Step 4: 3-((3-(2-aminoethyl) phenyl) amino)-5-(isopropyl (methyl) amino)-6-methylpyrazine-2-carboxamide

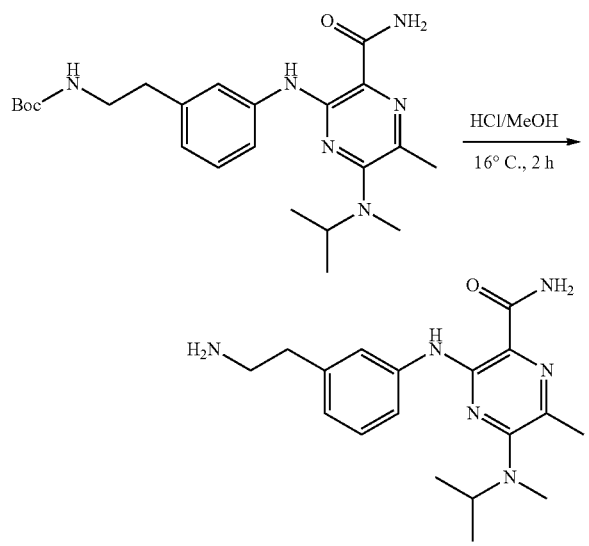

A mixture of tert-butyl (3-((3-(3-carbamoyl-6-(isopropyl (methyl) amino)-5-methylpyrazin-2-yl) amino) phenethyl) carbamate (9 g, 20.34 mmol, 1 eq) was added HCl/MeOH (4 M, 100 mL) was stirred at 16° C. for 2 hr. LCMS showed the reaction was completed. The reaction mixture was concentrated under reduced pressure to give a residue. The crude product was triturated with EtOAc at 25° C. for 10 min and then filtered to give 3-((3-(2-aminoethyl) phenyl) amino)-5-(isopropyl (methyl) amino)-6-methylpyrazine-2-carboxamide (7.7 g, 18.29 mmol, 89.94% yield) as yellow solid. $^1$H NMR (400 MHz, DMSO-$d_6$) δ=11.13 (s, 1H), 8.12-8.00 (m, 3H), 7.93-7.67 (m, 1H), 7.60-7.36 (m, 3H), 7.28-7.23 (m, 1H), 6.88-6.83 (m, 1H), 4.36-4.28 (m, 1H), 3.07-2.99 (m, 2H), 2.91-2.85 (m, 5H), 2.44 (s, 3H), 1.23-1.19 (m, 6H)(HCl salt). LC-MS (ES$^+$, m/z): 343.2 [(M+H)$^+$]; Rt=0.691 min.

Note: HCl/EtOAc (4 M): HCl was bubbled into a solution EtOAc at 0° C. for 0.5 h. Then, the solution was weighed to obtained the HCl/EtOAc (4 M).

Step 5: tert-butyl (S)-(1-((3-((3-carbamoyl-6-(isopropyl (methyl) amino)-5-methylpyrazin-2-yl) amino) phenethyl) amino)-1-oxopropan-2-yl) (methyl) carbamate

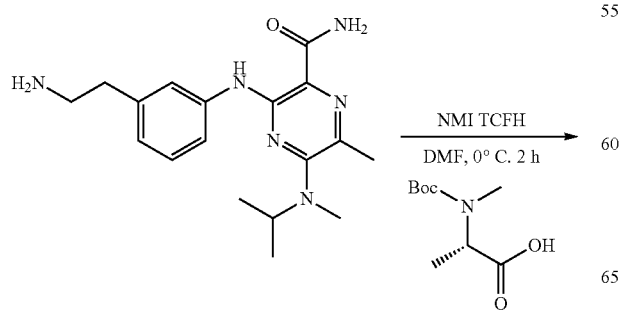

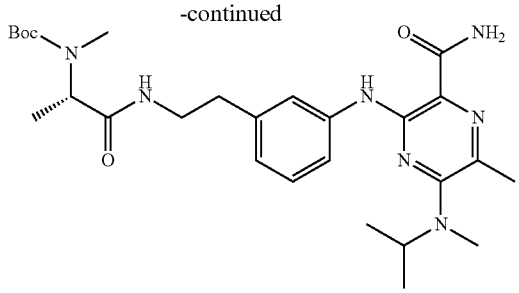

To a solution of N-(tert-butoxycarbonyl)-N-methyl-L-alanine (2.49 g, 12.27 mmol, 1.2 eq), 1-methylimidazole (8.39 g, 102.21 mmol, 8.15 mL, 10 eq) in DMF (35 mL) was added 3-((3-(2-aminoethyl) phenyl) amino)-5-(isopropyl (methyl) amino)-6-methylpyrazine-2-carboxamide (3.5 g, 10.22 mmol, 1 eq), and then added TCFH (3.44 g, 12.27 mmol, 1.2 eq) at 0° C. The mixture was stirred at 0° C. for 2 hr. LCMS showed the reaction was completed. The reaction mixture was quenched by addition water (120 mL) and then extracted with EtOAc (100 mL*3). The combined organic layers were washed with saturated brine (150 mL*2), dried over Na$_2$SO$_4$, filtered and concentrated under reduced pressure to give a residue. The residue was purified by column chromatography (SiO$_2$, Petroleum ether/Ethyl acetate=10/1 to 5/1) to give tert-butyl (S)-(1-((3-((3-carbamoyl-6-(isopropyl (methyl) amino)-5-methylpyrazin-2-yl) amino) phenethyl) amino)-1-oxopropan-2-yl) (methyl) carbamate (4.1 g, 7.38 mmol, 72.22% yield, 95% purity) as yellow solid. $^1$H NMR (400 MHz, DMSO-$d_6$) δ=11.11 (s, 1H), 7.84-7.73 (m, 2H), 7.56 (s, 1H), 7.44-7.37 (m, 2H), 7.24-7.14 (m, 1H), 6.83-6.75 (m, 1H), 4.41-4.31 (m, 1H), 4.04-4.01 (m, 1H), 3.31-3.22 (m, 2H), 2.93-2.86 (m, 3H), 2.72-2.65 (m, 5H), 2.46-2.41 (m, 3H), 1.42-1.32 (m, 9H), 1.17 (s, 9H). LC-MS (ES$^+$, m/z): 528.4 [(M+H)+]; Rt=0.902 min.

Step 6: (S)-5-(isopropyl (methyl) amino)-6-methyl-3-((3-(2-(2-(methylamino) propanamido) ethyl) phenyl) amino) pyrazine-2-carboxamide

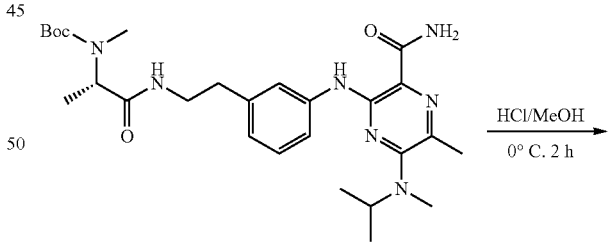

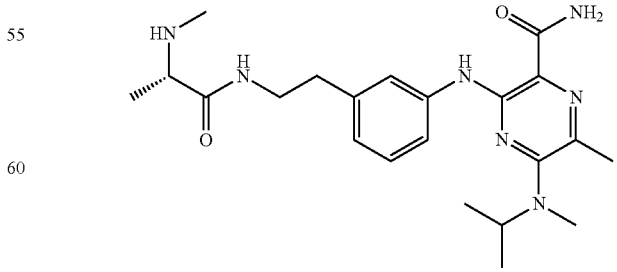

A mixture of tert-butyl (S)-(1-((3-((3-carbamoyl-6-(isopropyl (methyl) amino)-5-methylpyrazin-2-yl) amino)

phenethyl) amino)-1-oxopropan-2-yl) (methyl) carbamate (4.1 g, 7.77 mmol, 1 eq) HCl/MeOH (4 M, 21.67 mL, 11.15 eq) was stirred at 0° C. for 2 hr. LCMS showed the reaction was completed. The reaction mixture was concentrated under reduced pressure to give a residue. The crude product was concentrated to give (S)-5-(isopropyl (methyl) amino)-6-methyl-3-((3-(2-(2-(methylamino) propanamido) ethyl) phenyl) amino) pyrazine-2-carboxamide (4.1 g, crude, HCl). $^{1}$H NMR (400 MHz, DMSO-d$_6$) δ=11.14-11.05 (m, 1H), 9.49-9.38 (m, 1H), 8.90-8.78 (m, 1H), 8.76-8.70 (m, 1H), 7.52-7.47 (m, 2H), 7.23-7.18 (m, 1H), 6.82 (br d, J=7.5 Hz, 1H), 6.71-6.64 (m, 2H), 4.30 (s, 1H), 3.73-3.65 (m, 1H), 3.45-3.33 (m, 2H), 3.16-3.16 (m, 3H), 2.91-2.88 (m, 3H), 2.77-2.71 (m, 2H), 2.44 (s, 3H), 1.33-1.29 (m, 3H), 1.22-1.18 (m, 6H). LC-MS (ES$^+$, m/z): 428.3 [(M+H)$^+$]; Rt=0.693 min; 95.9% purity.

Note: HCl/EtOAc (4 M): HCl was bubbled into a solution EtOAc at 0° C. for 0.5 h. Then, the solution was weighed to obtained the HCl/EtOAc (4 M)

Example 1 (Compound 137)

(S,E)-5-(dimethylamino)-3-((3-(2-(2-(4-(dimethyl-amino)-N-methylbut-2-enamido)propanamido)ethyl) phenyl)amino)-6-ethylpyrazine-2-carboxamide Step 1: tert-butyl (S)-(1-((3-((3-carbamoyl-6-(dimethylamino)-5-ethylpyrazin-2-yl)amino)phenethyl) amino)-1-oxopropan-2-yl)(methyl)carbamate

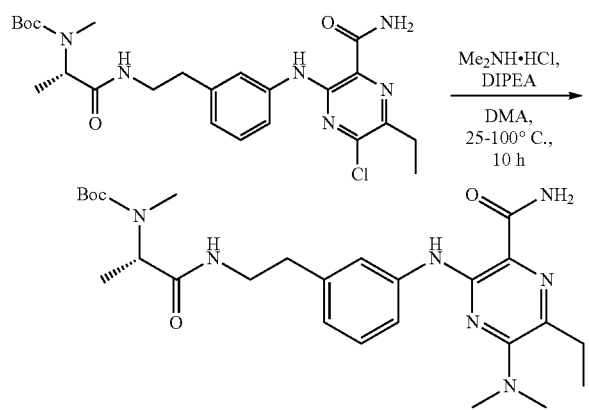

To a solution of tert-butyl (S)-(1-((3-((3-carbamoyl-6-chloro-5-ethylpyrazin-2-yl)amino)phenethyl)amino)-1-oxopropan-2-yl)(methyl)carbamate (600 mg, 1.19 mmol, 1 eq) Me$_2$NH (968.83 mg, 11.88 mmol, 10 eq, HCl) in DMA (6 mL) at 25° C., DIPEA (1.54 g, 11.88 mmol, 10 eq) was added. The mixture was stirred at 100° C. for 10 hrs. LCMS indicated the reaction was completed. The mixture was poured into water (20 mL) and extracted with EtOAc (15 mL*2). The organic layers was washed with water (15 mL*2), saturated brine (15 mL*2), dried over anhydrous Na$_2$SO$_4$, filtered, concentrated under reduced pressure to give a residue. The crude was purified by prep-HPLC column: C$_{18-1}$ 150*30 mm*5 um; mobile phase: [water (TFA)-ACN]; B %: 35%-80%, 8 min to afford tert-butyl N-[(1S)-2-[2-[3-[[3-carbamoyl-6-(dimethylamino)-5-ethyl-pyrazin-2-yl]amino]phenyl]ethylamino]-1-methyl-2-oxo-ethyl]-N-methyl-carbamate (251 mg, 449.58 µmol, 37.84% yield) as brown solid. $^{1}$H NMR (400 MHz, CDCl3-d) δ=10.67 (s, 1H), 7.65-7.39 (m, 4H), 7.17-7.12 (m, 2H), 6.74-6.71 (m, 1H), 4.17-3.94 (m, 1H), 3.51-3.39 (m, 2H), 3.03 (s, 6H), 2.72-2.68 (m, 4H), 2.60 (s, 3H), 1.34 (s, 9H), 1.24 (br d, J=7.1 Hz, 3H), 1.21-1.19 (m, 3H); LC-MS (ES$^+$, m/z): 514.3 [(M+H)$^+$]; Rt=0.872 min;

Step 2: (S)-5-(dimethylamino)-6-ethyl-3-((3-(2-(2-(methylamino)propanamido)ethyl)phenyl)amino) pyrazine-2-carboxamide

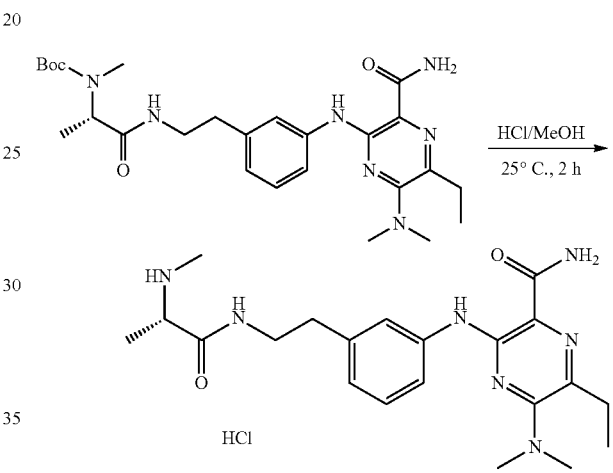

The mixture tert-butyl (S)-(1-((3-((3-carbamoyl-6-(dimethylamino)-5-ethylpyrazin-2-yl)amino)phenethyl)amino)-1-oxopropan-2-yl)(methyl)carbamate (251 mg, 488.68 µmol, 1 eq) and HCl/MeOH (4 M, 50 mL, 409.27 eq) was stirred at 25° C. for 2 h. LCMS indicated the reaction was completed. The mixture was concentrated under reduced pressure to afford (S)-5-(dimethylamino)-6-ethyl-3-((3-(2-(2-(methylamino)propanamido)ethyl)phenyl)amino)pyrazine-2-carboxamide (230 mg, crude) as brown solid. LC-MS (ES$^+$, m/z): 414.3 [(M+H)$^+$]; Rt=0.684 min.

Note: HCl/MeOH (4 M): HCl gas was bubbled into a solution MeOH at 0° C. for 0.5 h. Then, the solution was weighed to obtained the HCl/MeOH (4 M)

Step 3: (S,E)-5-(dimethylamino)-3-((3-(2-(2-(4-(dimethylamino)-N-methylbut-2-enamido)propanamido)ethyl)phenyl)amino)-6-ethylpyrazine-2-carboxamide

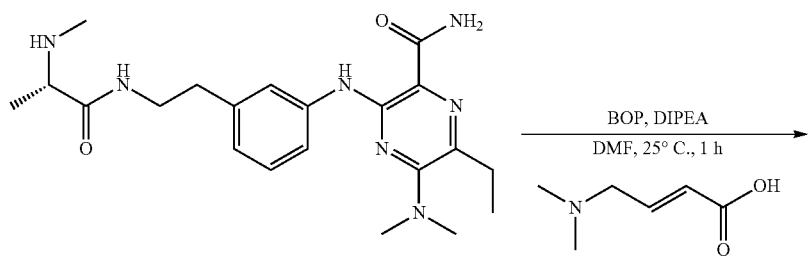

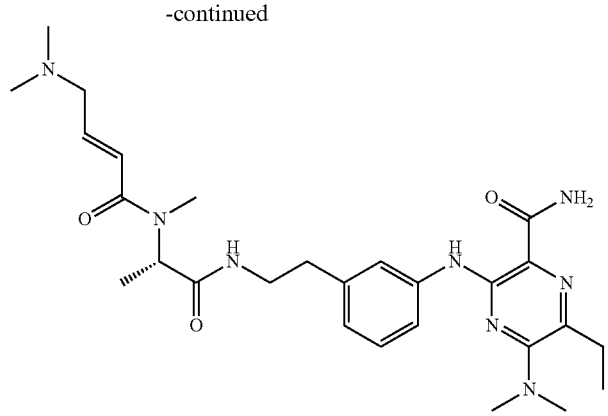

To a solution of (S)-5-(dimethylamino)-6-ethyl-3-((3-(2-(2-(methylamino)propanamido)ethyl)phenyl)amino)pyrazine-2-carboxamide (230 mg, 556.21 μmol, 1 eq) (E)-4-(dimethylamino)but-2-enoic acid (138.18 mg, 834.31 μmol, 1.5 eq), BOP (369.00 mg, 834.31 μmol, 1.5 eq) in DMF (4 mL) at 25° C., DIPEA (718.86 mg, 5.56 mmol, 10 eq) was added. The mixture was stirred at 25° C. for 1 h. LCMS indicated the reaction was completed. The mixture was filtered to give a residue. The crude was purified by prep-HPLC column: $C_{18-1}$ 150*30 mm*5 um; mobile phase: [water (TFA)-ACN]; B %: 5%-50%, 8 min to afford (S,E)-5-(dimethylamino)-3-((3-(2-(2-(4-(dimethylamino)-N-methylbut-2-enamido)propanamido)ethyl)phenyl)amino)-6-ethylpyrazine-2-carboxamide (155.89 mg, 293.50 μmol, 52.77% yield, 98.78% purity) as brown solid. $^1$H NMR (400 MHz, DMSO-$d_6$, TFA) δ=11.15-11.07 (m, 1H), 9.76-9.63 (m, 1H), 8.10-7.85 (m, 1H), 7.76 (br d, J=2.5 Hz, 1H), 7.58-7.40 (m, 3H), 7.25-7.17 (m, 1H), 6.86-6.76 (m, 2H), 6.64-6.46 (m, 1H), 5.01-4.51 (m, 1H), 3.95-3.78 (m, 2H), 3.32-3.26 (m, 2H), 3.07 (s, 6H), 2.90 (s, 2H), 2.80-2.67 (m, 11H), 1.30-1.21 (m, 6H); LC-MS (ES$^+$, m/z): 525.3 [(M+H)$^+$]; Rt=2.099 min; 98.777% purity; HRMS (EI): m/z [M+H]+ found: 525.3279.

Example 2 (Compound 138)

(S,E)-5-cyclopropyl-3-((3-(2-(2-(4-(dimethylamino)-N-methylbut-2-enamido)propanamido)ethyl)phenyl)amino)-6-ethylpyrazine-2-carboxamide Step 1: tert-butyl (S)-(1-((3-((3-carbamoyl-6-cyclopropyl-5-ethylpyrazin-2-yl)amino)phenethyl)amino)-1-oxopropan-2-yl)(methyl)carbamate

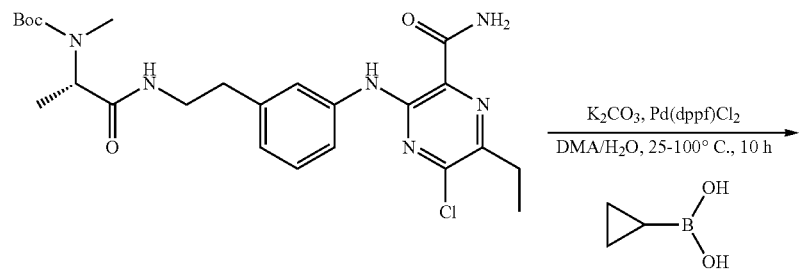

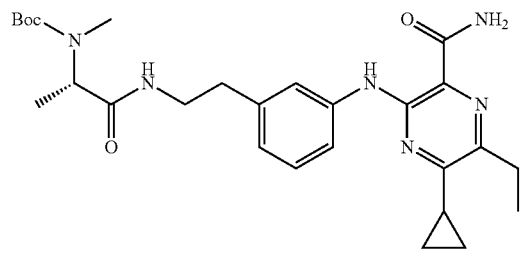

To a solution of tert-butyl (S)-(1-((3-((3-carbamoyl-6-chloro-5-ethylpyrazin-2-yl)amino)phenethyl)amino)-1-oxopropan-2-yl)(methyl)carbamate (600 mg, 1.19 mmol, 1 eq) cyclopropylboronic acid (1.02 g, 11.88 mmol, 10 eq) K$_2$CO$_3$ (492.61 mg, 3.56 mmol, 3 eq) in DMA (4 mL) and H$_2$O (2 mL) at 25° C., Pd(dppf)Cl$_2$ (86.93 mg, 118.81 μmol, 0.1 eq) was added. The mixture was stirred at 100° C. for 10 hrs. LCMS indicated the reaction was completed. The mixture was poured into saturated EDTA (10 mL), EA (5 mL) and extracted with EtOAc (5 mL*2). The organic layers was washed with water (10 mL*2), saturated brine (10 mL*2), dried over anhydrous Na$_2$SO$_4$, filtered, concentrated under reduced pressure to give a residue. The crude was purified by prep-HPLC column: C$_{18-1}$ 150*30 mm*5 um; mobile phase: [water (TFA)-ACN]; B %: 35%-80%, 8 min to afford tert-butyl(S)-(1-((3-((3-carbamoyl-6-cyclopropyl-5-ethylpyrazin-2-yl)amino) phenethyl)amino)-1-oxopropan-2-yl)(methyl)carbamate (338 mg, 661.93 μmol, 55.71% yield) as yellow solid. $^1$H NMR (400 MHz, CDCl$_3$-d) δ=10.61-10.54 (m, 1H), 7.86-7.75 (m, 1H), 7.48-7.40 (m, 2H), 7.19-7.13 (m, 1H), 6.76-6.73 (m, 1H), 6.18-5.88 (m, 1H), 5.58-5.41 (m, 1H), 4.10-4.00 (m, 1H), 3.58-3.41 (m, 2H), 2.84 (q, J=7.5 Hz, 2H), 2.77-2.69 (m, 2H), 2.65-2.57 (m, 3H), 2.12-2.06 (m, 1H), 1.36-1.32 (m, 9H), 1.25-1.17 (m, 6H), 1.17-1.11 (m, 2H), 1.06-1.00 (m, 2H); LC-MS (ES$^+$, m/z): 511.3 [(M+H)$^+$]; Rt=0.924 min.

Step 2: (S)-5-cyclopropyl-6-ethyl-3-((3-(2-(2-(methylamino)propanamido)ethyl)phenyl)amino)pyrazine-2-carboxamide

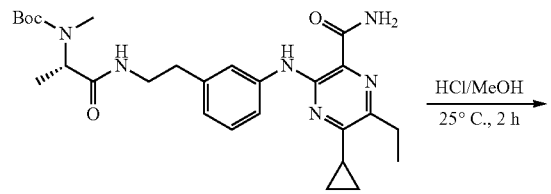

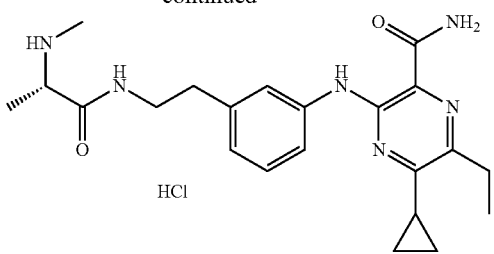

The mixture tert-butyl (S)-(1-((3-((3-carbamoyl-6-cyclopropyl-5-ethylpyrazin-2-yl)amino)phenethyl)amino)-1-oxopropan-2-yl)(methyl)carbamate (338 mg, 661.93 μmol, 1 eq) and HCl/MeOH (4 M, 50 mL, 302.15 eq) was stirred at 25° C. for 2 hrs. LCMS indicated the reaction was completed. The mixture was concentrated under reduced pressure to afford (S)-5-cyclopropyl-6-ethyl-3-((3-(2-(2-(methylamino)propanamido)ethyl)phenyl)amino)pyrazine-2-carboxamide (300 mg, crude) as yellow solid. LC-MS (ES$^+$, m/z): 411.3 [(M+H)$^+$]; Rt=0.707 min.

Note: HCl/MeOH (4 M): HCl gas was bubbled into a solution MeOH at 0° C. for 0.5 h. Then, the solution was weighed to obtained the HCl/MeOH (4 M)

Step 3: (S,E)-5-cyclopropyl-3-((3-(2-(2-(4-(dimethylamino)-N-methylbut-2-enamido)propanamido)ethyl)phenyl)amino)-6-ethylpyrazine-2-carboxamide

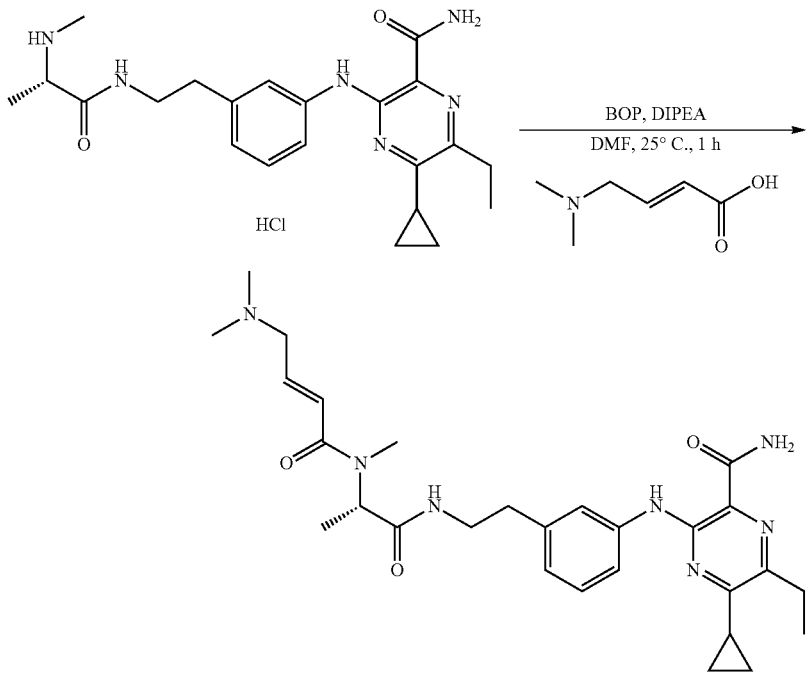

To a solution of (S)-5-cyclopropyl-6-ethyl-3-((3-(2-(2-(methylamino)propanamido)ethyl)phenyl)amino)pyrazine-2-carboxamide (300 mg, 730.80 μmol, 1 eq) (E)-4-(dimethylamino)but-2-enoic acid (181.55 mg, 1.10 mmol, 1.5 eq) BOP (484.83 mg, 1.10 mmol, 1.5 eq) in DMF (4 mL) at 25° C., DIPEA (944.50 mg, 7.31 mmol, 10 eq) was added. The mixture was stirred at 25° C. for 1 h. LCMS indicated the reaction was completed. The mixture was filtered to give a residue. The crude was purified by prep-HPLC column: $C_{18-1}$ 150*30 mm*5 um; mobile phase: [water (TFA)-ACN]; B %: 5%-50%, 8 min to afford (S,E)-5-cyclopropyl-3-((3-(2-(2-(4-(dimethylamino)-N-methylbut-2-enamido)propanamido)ethyl)phenyl)amino)-6-ethylpyrazine-2-carboxamide (207.25 mg, 395.71 μmol, 54.15% yield, 99.60% purity) as yellow solid. $^1$H NMR (400 MHz, D2O) δ=7.39-7.30 (m, 1H), 7.12-7.05 (m, 2H), 6.78-6.72 (m, 1H), 6.66-6.56 (m, 1H), 6.51-6.40 (m, 1H), 4.86-4.75 (m, 1H), 3.74-3.62 (m, 2H), 3.49-3.29 (m, 2H), 2.79-2.60 (m, 13H), 2.14-2.06 (m, 1H), 1.28-1.13 (m, 6H), 1.03-0.97 (m, 2H), 0.90 (br s, 2H); $^1$H NMR (400 MHz, DMSO-$d_6$) δ=11.10-11.00 (m, 1H), 9.74-9.59 (m, 1H), 8.21-8.12 (m, 1H), 8.07 (br s, 1H), 7.87-7.79 (m, 1H), 7.50-7.40 (m, 2H), 7.27-7.19 (m, 1H), 6.88-6.77 (m, 2H), 6.65-6.45 (m, 1H), 5.01-4.53 (m, 1H), 3.92-3.81 (m, 2H), 3.32-3.27 (m, 2H), 2.95-2.87 (m, 5H), 2.80-2.76 (m, 6H), 2.70 (br s, 2H), 2.35-2.31 (m, 1H), 1.31-1.20 (m, 6H), 1.14-1.05 (m, 4H); LC-MS (ES$^+$, m/z): 522.3 [(M+H)$^+$]; Rt=2.171 min; HRMS (EI): m/z [M+H]+ found: 522.3166.

Example 3 (Compound 142A)

(S,E)-3-((3-(2-(2-(4-(dimethylamino)-N-methylbut-2-enamido)propanamido)ethyl)phenyl)amino)-6-ethyl-5-methylpyrazine-2-carboxamide Step 1: tert-butyl (3-((3-carbamoyl-6-chloro-5-ethylpyrazin-2-yl)amino)phenethyl)carbamate

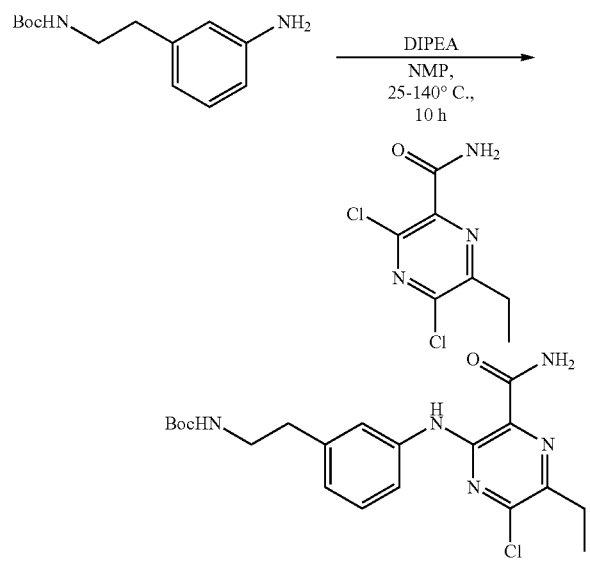

A mixture of tert-butyl (3-aminophenethyl)carbamate (2 g, 8.46 mmol, 1 eq), 3,5-dichloro-6-ethylpyrazine-2-carboxamide (1.86 g, 8.46 mmol, 1 eq) in NMP (5 mL), DIPEA (21.88 g, 169.27 mmol, 29.48 mL, 20 eq) was added at 25° C. The mixture was stirred at 140° C. for 10 hours. LCMS showed the reaction was completed. The reaction was poured into H$_2$O (50 mL). The aqueous phase was extracted with ethyl acetate (20 mL*3). The combined organic phase was washed with saturated brine (50 mL*1), dried with anhydrous Na$_2$SO$_4$. Filtered and concentrated in vacuum. The residue was purified by silica gel chromatography (column height: 250 mm, diameter: 100 mm, 100-200 mesh silica gel, Petroleum ether/Ethyl acetate=1/1, 10/1) to afford tert-butyl (3-((3-carbamoyl-6-chloro-5-ethylpyrazin-2-yl)amino)phenethyl)carbamate (3.5 g, 6.67 mmol, 78.79% yield) as a yellow solid. 1H NMR (400 MHz, DMSO-d6) δ=11.19 (s, 1H), 8.26 (s, 1H), 8.04 (br s, 1H), 7.59 (br d, J=7.9 Hz, 1H), 7.32-7.23 (m, 2H), 6.93-6.83 (m, 2H), 3.16 (q, J=6.5 Hz, 2H), 2.82 (q, J=7.5 Hz, 2H), 2.69 (t, J=7.3 Hz, 2H), 1.36 (s, 9H), 1.28-1.24 (m, 3H) LC-MS (ES+, m/z): 420.3 [(M+H)$^+$]; Rt=0.941 min.

Step 2: tert-butyl (3-((3-carbamoyl-5-ethyl-6-methylpyrazin-2-yl)amino)phenethyl)carbamate

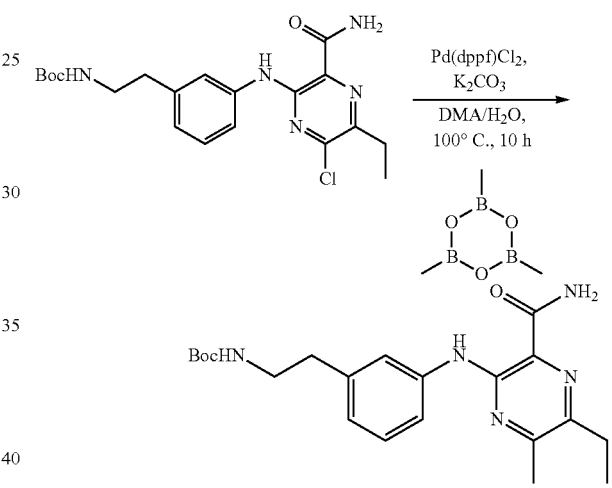

To a solution of tert-butyl (3-((3-carbamoyl-6-chloro-5-ethylpyrazin-2-yl)amino)phenethyl)carbamate (1 g, 2.38 mmol, 1 eq), 2,4,6-trimethyl-1,3,5,2,4,6-trioxatriborinane (1.49 g, 11.91 mmol, 5 eq) in DMA (12 mL) and H$_2$O (3 mL), K$_2$CO$_3$ (987.41 mg, 7.14 mmol, 3 eq) and Pd(dppf)Cl$_2$ (174.26 mg, 238.15 μmol, 0.1 eq) was added, the mixture was stirred at 100° C. for 10 hours. LCMS showed the reaction was completed. The residue was poured into saturated EDTA (100 mL) and EtOAc (30 mL) stirred for 60 min. The mixture was concentrated. The residue was diluted with NaHCO$_3$ (50 mL) and extracted with EtOAc (50 mL*4). The organic layers were combined, washed with water (50 ml*2), saturated brine (50 ml), dried with anhydrous Na$_2$SO$_4$, Filtered and concentrated to give crude product. The residue was purified by silica gel chromatography (column height: 250 mm, diameter: 100 mm, 100-200 mesh silica gel, Petroleum ether/Ethyl acetate=1/1, 10/1). To afford tert-butyl (3-((3-carbamoyl-5-ethyl-6-methylpyrazin-2-yl)amino)phenethyl)carbamate (650 mg, 1.63 mmol, 68.32% yield) as a yellow oil. 1H NMR (400 MHz, DMSO-d6) δ=11.05 (s, 1H), 8.14 (br d, J=1.6 Hz, 1H), 7.86 (br d, J=1.6 Hz, 1H), 7.65 (br d, J=8.1 Hz, 1H), 7.44-7.42 (m, 1H), 7.22 (t, J=7.8 Hz, 1H), 6.88-6.80 (m, 2H), 3.18-3.13 (m, 2H), 2.78-2.72 (m, 2H), 2.71-2.67 (m, 2H), 1.36 (s, 9H), 1.26-1.22 (m, 3H), 1.20-1.10 (m, 3H). LC-MS (ES+, m/z): 400.3 [(M+H)+]; Rt=0.912 min.

Step 3: 3-((3-(2-aminoethyl)phenyl)amino)-6-ethyl-5-methylpyrazine-2-carboxamide

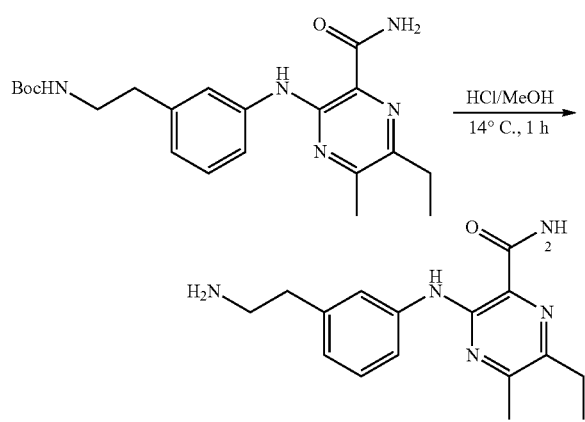

To a mixture of tert-butyl (3-((3-carbamoyl-5-ethyl-6-methylpyrazin-2-yl)amino)phenethyl)carbamate (650 mg, 1.63 mmol, 1 eq) in HCl/MeOH (4 M, 20 mL, 49.17 eq) at 14° C. for 1 hour. LCMS showed the reaction was completed. Filtered and concentrated in vacuum to afford 3-((3-(2-aminoethyl)phenyl)amino)-6-ethyl-5-methylpyrazine-2-carboxamide (450 mg, 1.50 mmol, 92.38% yield) as a yellow solid. 1H NMR (400 MHz, DMSO-d6) δ=11.08 (s, 1H), 8.15 (br s, 1H), 7.87 (br s, 1H), 7.71 (dd, J=1.3, 8.1 Hz, 1H), 7.49 (s, 1H), 7.31-7.19 (m, 2H), 7.18-7.12 (m, 1H), 6.88 (d, J=7.6 Hz, 1H), 3.07-3.01 (m, 2H), 2.91-2.86 (m, 2H), 2.74 (q, J=7.5 Hz, 2H), 1.33-1.11 (m, 5H), 1.10-0.76 (m, 1H) LC-MS (ES+, m/z): 300.3 [(M+H)+]; Rt=0.647 min. HCl/MeOH (4 M): HCl was bubbled into a solution MeOH at 0° C. for 0.5 h.

Step 4 tert-butyl (S)-(1-((3-((3-carbamoyl-5-ethyl-6-methylpyrazin-2-yl)amino)phenethyl)amino)-1-oxopropan-2-yl)(methyl)carbamate

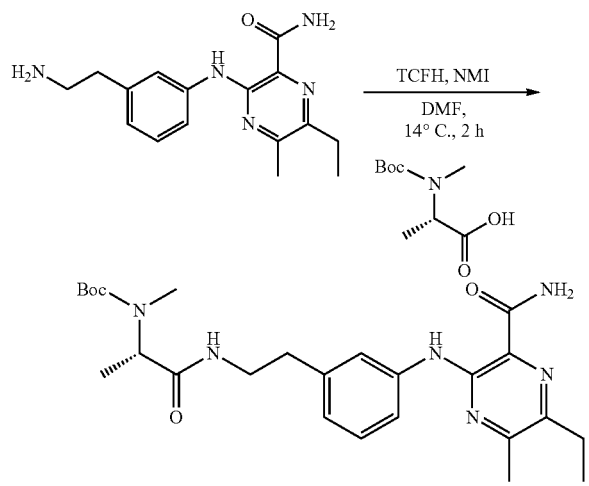

To a solution of 3-((3-(2-aminoethyl)phenyl)amino)-6-ethyl-5-methylpyrazine-2-carboxamide (450 mg, 1.50 mmol, 1 eq), N-(tert-butoxycarbonyl)-N-methyl-L-alanine (366.59 mg, 1.80 mmol, 1.2 eq) in DMF (8 mL), TCFH (632.63 mg, 2.25 mmol, 1.5 eq) and 1-methylimidazole (1.23 g, 15.03 mmol, 1.20 mL, 10 eq) was added, the mixture was stirred at 14° C. for 2 hours. LCMS showed the reaction was completed. The reaction was poured into H2O (30 mL). The aqueous phase was extracted with ethyl acetate (10 mL*6). The combined organic phase was washed with saturated brine (30 mL*1), dried with anhydrous Na2SO4. Filtered and concentrated in vacuum. The residue was purified by silica gel chromatography (column height: 250 mm, diameter: 100 mm, 100-200 mesh silica gel, Petroleum ether/Ethyl acetate=1/1, 10/1) to afford tert-butyl (S)-(1-((3-((3-carbamoyl-5-ethyl-6-methylpyrazin-2-yl)amino)phenethyl)amino)-1-oxopropan-2-yl)(methyl)carbamate (1 g, 1.28 mmol, 85.12% yield) as a yellow solid. 1H NMR (400 MHz, DMSO-d6) δ=11.06 (s, 1H), 8.14 (br d, J=2.0 Hz, 1H), 7.85 (br d, J=2.1 Hz, 1H), 7.83-7.76 (m, 1H), 7.67-7.60 (m, 1H), 7.45 (br s, 1H), 7.22 (t, J=7.8 Hz, 1H), 6.82 (d, J=7.7 Hz, 1H), 4.61-4.16 (d, 1H), 3.30 (br d, J=6.8 Hz, 2H), 2.94-2.89 (m, 2H), 2.78-2.73 (m, 2H), 2.69 (br d, J=8.3 Hz, 3H), 1.36 (br s, 9H), 1.25-1.21 (m, 3H), 1.19-1.15 (m, 3H). LC-MS (ES+, m/z): 485.4 [(M+H)+]; Rt=0.877 min.

Step 5: (S)-6-ethyl-5-methyl-3-((3-(2-(2-(methylamino)propanamido)ethyl)phenyl)amino)pyrazine-2-carboxamide

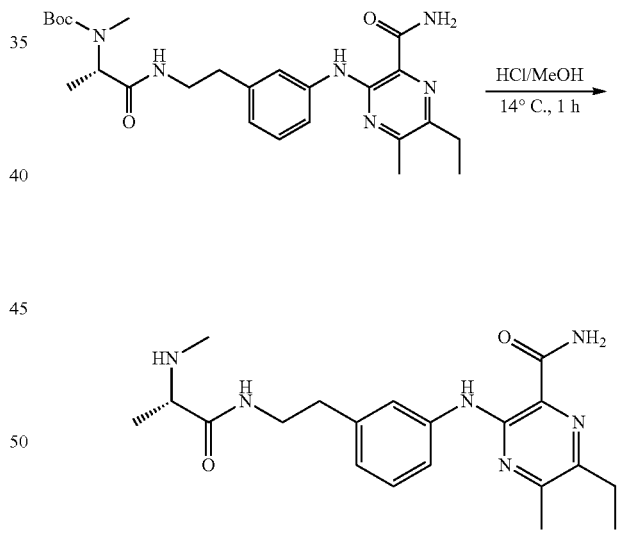

To a mixture of tert-butyl (S)-(1-((3-((3-carbamoyl-5-ethyl-6-methylpyrazin-2-yl)amino)phenethyl)amino)-1-oxopropan-2-yl)(methyl)carbamate (1 g, 1.28 mmol, 1 eq) in HCl/MeOH (4 M, 20 mL, 62.53 eq) at 14° C. for 1 hour. LCMS showed the reaction was completed. Filtered and concentrated in vacuum to afford (S)-6-ethyl-5-methyl-3-((3-(2-(2-(methylamino)propanamido)ethyl)phenyl)amino)pyrazine-2-carboxamide (430 mg, 1.12 mmol, 87.41% yield) as a yellow solid. LC-MS (ES+, m/z): 385.3 [(M+H)+]; Rt=0.671 min.

Note: HCl was bubbled into a solution MeOH at 0° C. for 0.5 h.

Step 6: (S,E)-3-((3-(2-(2-(4-(dimethylamino)-N-methylbut-2-enamido)propanamido)ethyl)phenyl)amino)-6-ethyl-5-methylpyrazine-2-carboxamide

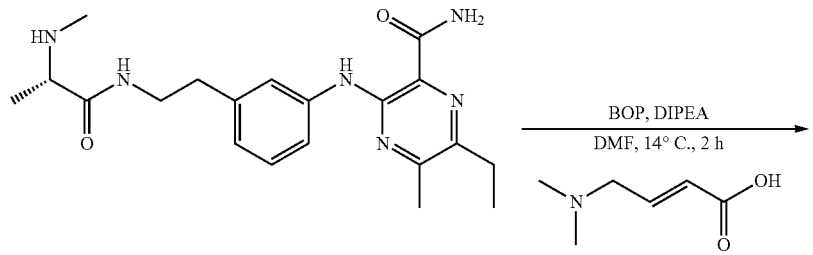

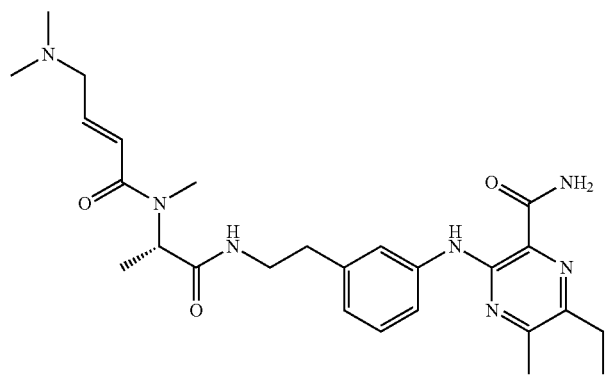

To a solution of (S)-6-ethyl-5-methyl-3-((3-(2-(2-(methylamino)propanamido)ethyl)phenyl)amino)pyrazine-2-carboxamide (400 mg, 1.04 mmol, 1 eq), (E)-4-(dimethylamino)but-2-enoic acid (161.25 mg, 1.25 mmol, 1.2 eq) in DMF (5 mL), BOP (690.21 mg, 1.56 mmol, 1.5 eq) and DIPEA (1.34 g, 10.40 mmol, 1.81 mL, 10 eq) was added at 14° C., the mixture was stirred at 14° C. for 2 hours. LCMS showed the reaction was completed. The residue was purified by prep-HPLC(column: Phenomenex luna C18 250*50 mm*10 μm; mobile phase: [water (TFA)-ACN]; B %: 20%-50%, 10 min) to afford (S,E)-3-((3-(2-(2-(4-(dimethylamino)-N-methylbut-2-enamido)propanamido)ethyl)phenyl)amino)-6-ethyl-5-methylpyrazine-2-carboxamide (100.3 mg, 202.37 μmol, 19.45% yield) as a yellow solid. 1H NMR (400 MHz, DMSO-d6) δ=11.09-11.03 (m, 1H), 9.75 (s, 1H) 8.16 (br s, 1H), 7.92 (br t, J=5.5 Hz, 1H), 7.86 (br s, 1H), 7.66 (br d, J=7.7 Hz, 1H), 7.43 (s, 1H), 7.28-7.17 (m, 1H), 6.88-6.73 (m, 2H), 6.66-6.44 (m, 1H), 5.03-4.51 (m, 1H), 3.94-3.78 (m, 2H), 3.34-3.26 (m, 2H), 2.90 (s, 2H), 2.78-2.70 (m, 11H), 2.50 (m, 3H), 1.29 (d, J=6.9 Hz, 1H), 1.27-1.19 (m, 5H). LC-MS (ES+, m/z): 496.4 [(M+H)+]; Rt=0.682 min; HRMS: 496.3003.

Example 4 (Compound 143)

(S,E)-5-(dimethylamino)-6-ethyl-3-((3-methoxy-5-(2-(2-(N-methyl-4-(methylamino)but-2-enamido)propanamido)ethyl)phenyl)amino)pyrazine-2-carboxamide Step 5: tert-butyl (S)-(1-((3-((3-carbamoyl-6-chloro-5-ethylpyrazin-2-yl)amino)-5-methoxyphenethyl)amino)-1-oxopropan-2-yl)(methyl)carbamate

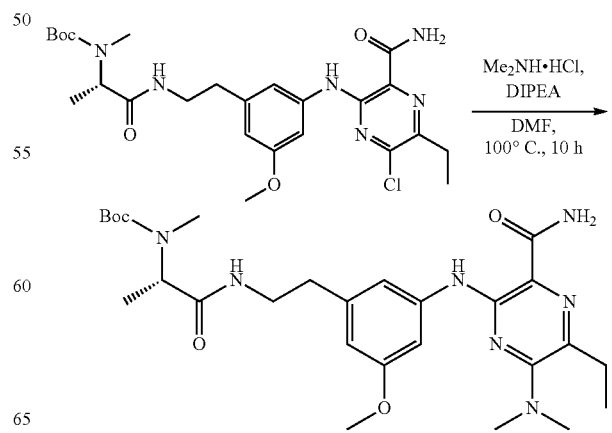

To a solution of tert-butyl (S)-(1-((3-((3-carbamoyl-6-chloro-5-ethylpyrazin-2-yl)amino)-5-methoxyphenethyl)amino)-1-oxopropan-2-yl)(methyl)carbamate (500 mg, 934.52 μmol, 1 eq), N-methylmethanamine; hydrochloride (762.05 mg, 9.35 mmol, 10 eq) in DMA (5 mL) was added DIEA (1.21 g, 9.35 mmol, 1.63 mL, 10 eq). The mixture was stirred at 100° C. for 10 hrs under N₂. LCMS indicated the reaction was completed. The reaction was poured into water (10 mL) and extracted with EtOAc (5 mL*2). The organic layers were combined, washed with water (20 mL*2), sat. brine (20 mL), dried with anhydrous Na₂SO₄, filtered and concentrated to give crude product. The crude product was purified by chromatography on silica thiol gel (petroleum ether/EtOAc=1/2). To afford tert-butyl (S)-(1-((3-((3-carbamoyl-6-(dimethylamino)-5-ethylpyrazin-2-yl)amino)-5-methoxyphenethyl)amino)-1-oxopropan-2-yl)(methyl)carbamate (300 mg, 551.82 μmol) as yellow solid. 1H NMR (400 MHz, CDCl3-d) δ=10.73 (s, 1H), 7.51 (br s, 1H), 7.22 (s, 1H), 7.06 (s, 1H), 6.31 (s, 1H), 5.27-5.22 (m, 1H), 4.70-4.42 (m, 1H), 3.72 (s, 3H), 3.52-3.41 (m, 3H), 3.04 (s, 6H), 2.72-2.66 (m, 4H), 2.62 (s, 3H), 1.33 (s, 9H), 1.27-1.19 (m, 6H). LC-MS (ES+, m/z): 544.4 [(M+H)⁺]; Rt=0.870 min.

Step 1: (S)-5-(dimethylamino)-6-ethyl-3-((3-methoxy-5-(2-(2-(methylamino) propanamido)ethyl)phenyl)amino)pyrazine-2-carboxamide

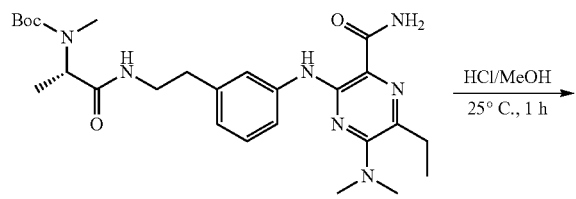

To a solution of tert-butyl (S)-(1-((3-((3-carbamoyl-6-(dimethylamino)-5-ethylpyrazin-2-yl)amino)-5-methoxyphenethyl)amino)-1-oxopropan-2-yl)(methyl) carbamate (300 mg, 551.82 μmol, 1 eq) in HCl/MeOH (50 mL). The mixture was stirred at 25° C. for 1 h. LCMS indicated the reaction was completed. The crude mixture was concentrated under reduced pressure. To afford the crude mixture of (S)-5-(dimethylamino)-6-ethyl-3-((3-methoxy-5-(2-(2-(methylamino)propanamido)ethyl) phenyl)amino)pyrazine-2-carboxamide (230 mg, 518.55 μmol, 93.97% yield) As yellow solid. LC-MS (ES+, m/z): 444.3 [(M+H)⁺]; Rt=0.734 min.

Note: HCl/MeOH (4 M): HCl was bubbled into a solution MeOH at 0° C. for 0.5 h. Then, the solution was weighed to obtained the HCl/MeOH (4 M)

Step 2: (S,E)-5-(dimethylamino)-6-ethyl-3-((3-methoxy-5-(2-(2-(N-methyl-4-(methylamino)but-2-enamido)propanamido)ethyl)phenyl)amino)pyrazine-2-carboxamide

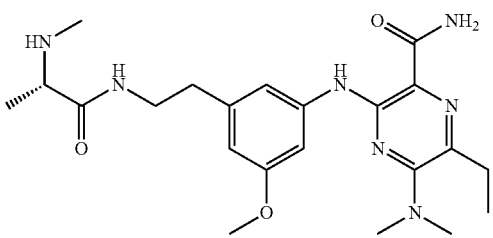

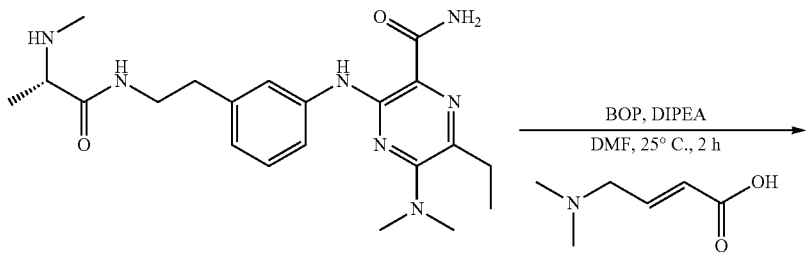

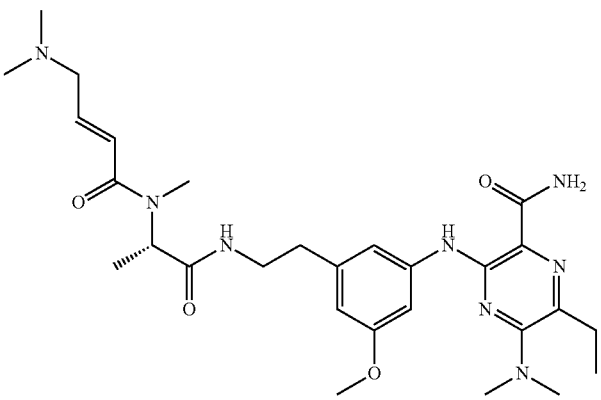

To a solution of (S)-5-(dimethylamino)-6-ethyl-3-((3-methoxy-5-(2-(2-(methylamino)propanamido)ethyl)phenyl)amino)pyrazine-2-carboxamide (230 mg, 518.55 µmol, 1 eq), (E)-4-(dimethylamino)but-2-enoic acid (171.76 mg, 1.04 mmol, 2 eq, HCl) in DMF (4 mL) was added DIEA (670.19 mg, 5.19 mmol, 903.23 µL, 10 eq), BOP (344.02 mg, 777.83 µmol, 1.5 eq). The mixture was stirred at 25° C. for 2 h under N₂ LCMS indicated the reaction has completed. The mixture was purified by prep-HPLC column: Phenomenex Luna 80*30 mm*3 um; mobile phase: [water (TFA)-ACN]; B %: 20%-50%, 8 min. to afford (S,E)-5-(dimethylamino)-6-ethyl-3-((3-methoxy-5-(2-(2-(N-methyl-4-(methylamino)but-2-enamido)propanamido)ethyl) phenyl)amino)pyrazine-2-carboxamide (60 mg, 108.17 µmol, 20.86% yield) as yellow solid. 1H NMR (400 MHz, DMSO-d6, TFA) δ=11.24-11.00 (m, 1H), 9.74 (br d, J=2.7 Hz, 1H), 8.12-7.86 (m, 1H), 7.77 (br s, 1H), 7.47 (br s, 1H), 7.41-7.35 (m, 1H), 6.90 (s, 1H), 6.85-6.77 (m, 1H), 6.64-6.48 (m, 1H), 6.38 (s, 1H), 5.05-4.53 (m, 1H), 3.90-3.80 (m, 2H), 3.75 (s, 3H), 3.34-3.24 (m, 2H), 3.08 (s, 6H), 2.91 (s, 2H), 2.81-2.63 (m, 11H), 1.32-1.20 (m, 6H). LC-MS (ES+, m/z): 555.3 [(M+H)⁺]; Rt=2.117 min; HRMS: 555.3435.

Example 5 (Compound 144)

(S,E)-5-cyclopropyl-3-((3-(2-(2-(4-(dimethylamino)-N-methylbut-2-enamido)propanamido)ethyl)-5-methoxyphenyl)amino)-6-ethylpyrazine-2-carboxamide Step 1: tert-butyl (S)-(1-((3-((3-carbamoyl-6-cyclopropyl-5-ethylpyrazin-2-yl)amino)-5-methoxyphenethyl)amino)-1-oxopropan-2-yl)(methyl)carbamate

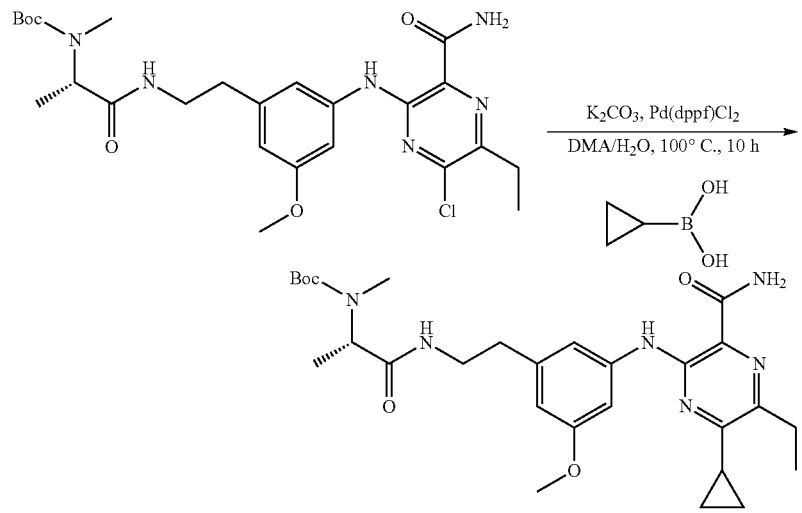

organic layers were combined, washed with water (20 mL*2), sat. brine (20 mL), dried with anhydrous Na₂SO₃, filtered and concentrated to give crude product. The crude product was purified by chromatography on silica thiol gel (petroleum ether/EtOAc=1/1). To afford tert-butyl (S)-(1-((3-((3-carbamoyl-6-cyclopropyl-5-ethylpyrazin-2-yl)amino)-5-methoxyphenethyl)amino)-1-oxopropan-2-yl)(methyl)carbamate (330 mg, 610.37 µmol, 65.31% yield) as white solid. LC-MS (ES+, m/z): 541.3 [(M+H)⁺]; Rt=0.890 min.

Step 2: (S)-5-cyclopropyl-6-ethyl-3-((3-methoxy-5-(2-(2-(methylamino)propanamido)ethyl)phenyl)amino)pyrazine-2-carboxamide

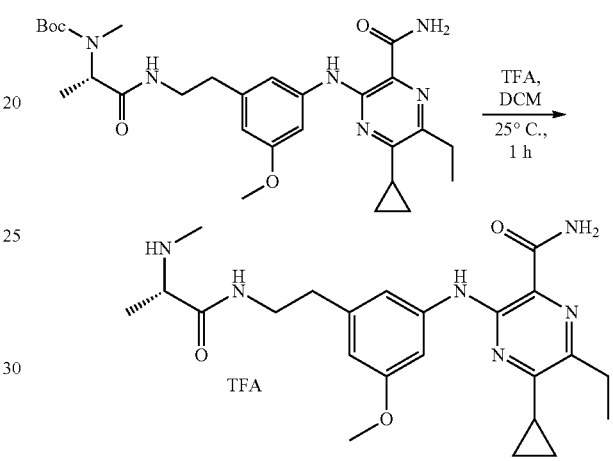

To a solution of tert-butyl (S)-(1-((3-((3-carbamoyl-6-chloro-5-ethylpyrazin-2-yl)amino)-5-methoxyphenethyl)amino)-1-oxopropan-2-yl)(methyl)carbamate (500 mg, 934.52 µmol, 1 eq), cyclopropylboronic acid (802.73 mg, 9.35 mmol, 10 eq) in DMA (4 mL), H₂O (2 mL). The mixture was stirred at 100° C. for 10 hrs under N₂ LCMS indicated the reaction has completed. The reaction was poured into saturated EDTA (10 mL), EtOAc (5 mL) and stirred 60 min, and extracted with EtOAc (5 mL*3). The To solution of tert-butyl (S)-(1-((3-((3-carbamoyl-6-cyclopropyl-5-ethylpyrazin-2-yl)amino)-5-methoxyphenethyl)amino)-1-oxopropan-2-yl)(methyl) carbamate (330 mg, 610.37 µmol, 1 eq) in DCM (40 mL) was added TFA (20 mL). The mixture was stirred at 25° C. for 1 h. LCMS indicated the reaction was completed. The crude mixture was concentrated under reduced pressure. Then, the mixture was put into next step directly. to afford crude mixture of (S)-5-cyclopropyl-6-ethyl-3-((3-methoxy-5-(2-(2-(methylamino)propanamido)ethyl)phenyl)amino)pyrazine-2-carboxamide (250 mg, 567.49 μmol, 92.97% yield) as yellow oil. LC-MS (ES+, m/z): 441.3 [(M+H)+]; Rt=0.753 min.

Step 3: (S,E)-5-cyclopropyl-3-((3-(2-(2-(4-(dimethylamino)-N-methylbut-2-enamido)propanamido)ethyl)-5-methoxyphenyl)amino)-6-ethylpyrazine-2-carboxamide

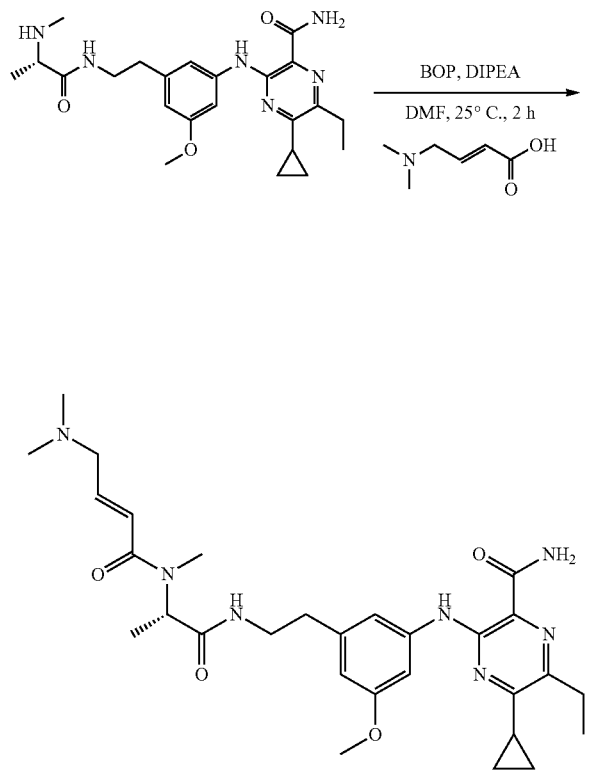

To a solution of (S)-5-cyclopropyl-6-ethyl-3-((3-methoxy-5-(2-(2-(methylamino)propanamido)ethyl)phenyl)amino)pyrazine-2-carboxamide (250 mg, 567.49 μmol, 1 eq), (E)-4-(dimethylamino)but-2-enoic acid (187.97 mg, 1.13 mmol, 2 eq, HCl) in DMF (4 mL) was added BOP (376.48 mg, 851.23 μmol, 1.5 eq), DIEA (733.44 mg, 5.67 mmol, 988.46 μL, 10 eq). The mixture was stirred at 25° C. for 2 hrs under N₂ LCMS indicated the reaction was completed. The crude mixture was purified by prep-HPLC column: Phenomenex Luna 80*30 mm*3 um; mobile phase: [water (TFA)-ACN]; B %: 20%-50%, 8 min. to afford (S,E)-5-cyclopropyl-3-((3-(2-(2-(4-(dimethylamino)-N-methylbut-2-enamido)propanamido)ethyl)-5-methoxyphenyl) amino)-6-ethylpyrazine-2-carboxamide (70 mg, 126.89 μmol, 22.36% yield) as yellow solid. 1H NMR (400 MHz, DMSO-d6, TFA) δ=11.18-11.02 (m, 1H), 9.75 (br s, 1H), 8.15 (s, 1H), 7.92 (t, J=5.6 Hz, 1H), 7.84 (br s, 1H), 7.38 (br d, J=1.9 Hz, 1H), 6.86-6.78 (m, 1H), 6.78-6.75 (m, 1H), 6.65-6.48 (m, 1H), 6.40 (s, 1H), 5.02-4.54 (m, 1H), 3.92-3.81 (m, 2H), 3.77 (s, 3H), 3.35-3.25 (m, 2H), 2.96-2.87 (m, 4H), 2.82-2.64 (m, 9H), 2.39-2.27 (m, 1H), 1.32-1.19 (m, 6H), 1.15-1.07 (m, 4H). LC-MS (ES+, m/z): 552.3 [(M+H)+]; Rt=2.188 min; HRMS: 552.3289

Example 6 (Compound 156)

Step 1: tert-butyl (E)-N-(4-bromobut-2-enoyl)-N-methyl-L-alaninate

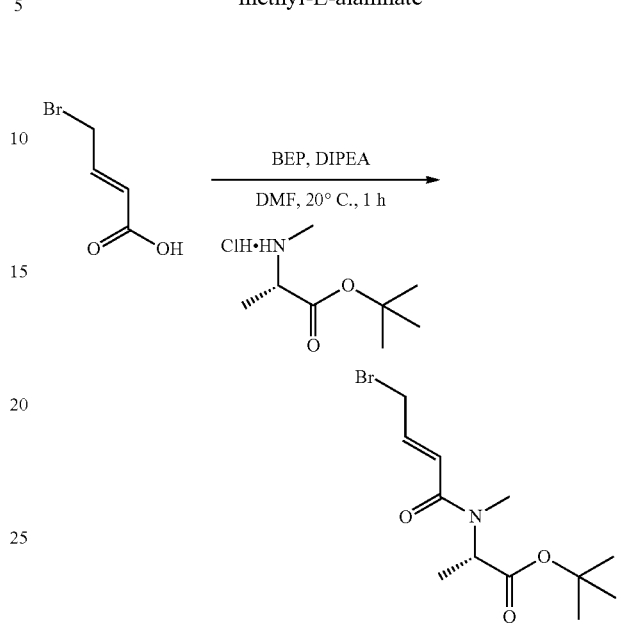

To a mixture of tert-butyl methyl-L-alaninate hydrochloride (9 g, 45.99 mmol, 1 eq) and (E)-4-bromobut-2-enoic acid (8.35 g, 50.59 mmol, 1.1 eq) in DMF (90 mL) was added 2-bromo-1-ethyl-pyridin-1-ium; tetrafluoroborate (18.89 g, 68.99 mmol, 1.5 eq) and DIEA (59.44 g, 459.92 mmol, 80.11 mL, 10 eq) in one portion at 20° C. under N₂. The mixture was stirred at 20° C. for 1 hr. LCMS indicated the reaction was completed. The residue was poured into water (200 mL). The aqueous phase was extracted with ethyl acetate (100 mL*3). The combined organic phase was washed with saturated brine (400 mL*1), dried with anhydrous Na₂SO₄, filtered and concentrated in vacuum. The residue was purified by column chromatography (SiO₂, Petroleum ether:Ethyl acetate=30/1 to 1/1). To afford the title compound tert-butyl (E)-N-(4-bromobut-2-enoyl)-N-methyl-L-alaninate (8 g, 26.13 mmol, 28.40% yield) as a yellow oil. LC-MS (ES+, m/z): 206.3 [(M+H)+]. Rt=1.837 min.

Step 2: tert-butyl (E)-N-(4-(azetidin-1-yl)but-2-enoyl)-N-methyl-L-alaninate

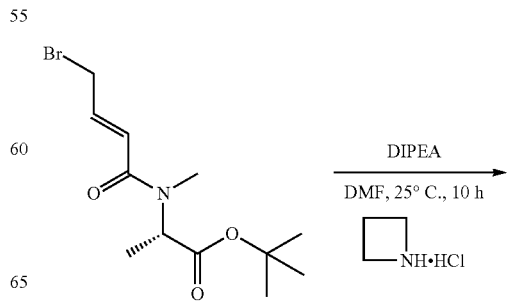

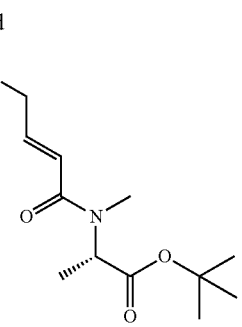

To a mixture of tert-butyl (E)-N-(4-bromobut-2-enoyl)-N-methyl-L-alaninate (8 g, 26.13 mmol, 1 eq) and azetidine hydrochloride (2.44 g, 26.13 mmol, 1 eq) in DMF (80 mL) was added DIPEA (10.13 g, 78.38 mmol, 3 eq) in one portion at 25° C. under $N_2$. The mixture was stirred at 25° C. for 10 hrs. LCMS indicated the reaction was completed. The reaction mixture was filtrated under reduced pressure to give a residue. The residue was purified by column chromatography ($SiO_2$, Petroleum ether:Ethyl acetate=1/1 to 1/1). To afford the title compound tert-butyl (E)-N-(4-(azetidin-1-yl)but-2-enoyl)-N-methyl-L-alaninate (550 mg, 1.95 mmol, 2.48% yield) as a yellow oil. LC-MS (ES+, m/z): 283.4 [(M+H)$^+$]. Rt=0.546 min Step 3: (E)-N-(4-(azetidin-1-yl)but-2-enoyl)-N-methyl-L-alanine

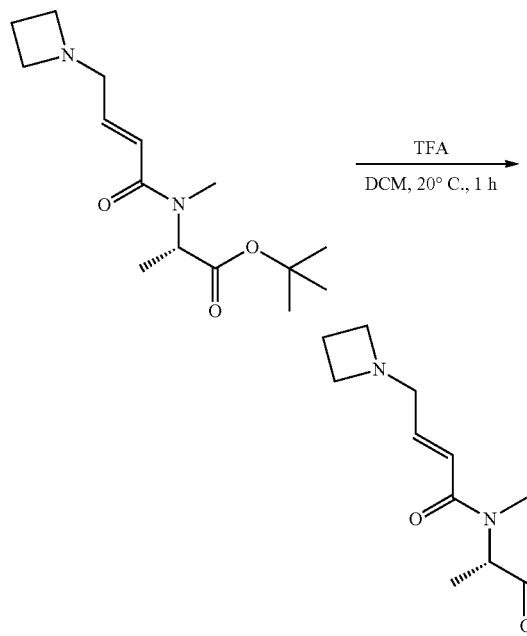

To a mixture of tert-butyl (E)-N-(4-(azetidin-1-yl)but-2-enoyl)-N-methyl-L-alaninate (500 mg, 1.77 mmol, 1 eq) in DCM (1.5 mL) was added TFA (77.00 g, 675.30 mmol, 50.00 mL, 381.38 eq) in one portion at 20° C. under $N_2$. The mixture was stirred at 20° C. for 1 hr. LCMS indicated the reaction was completed. The reaction mixture was concentrated under reduced pressure to give a residue. To afford the title compound (E)-N-(4-(azetidin-1-yl)but-2-enoyl)-N-methyl-L-alanine (480 mg, crude) as a yellow oil. LC-MS (ES+, m/z): 227.3 [(M+H)$^+$]. Rt=0.177 min.

Step 4: (S,E)-3-((3-(2-(2-(4-(azetidin-1-yl)-N-methylbut-2-enamido)propanamido)ethyl)phenyl)amino)-5-(dimethylamino)-6-ethylpyrazine-2-carboxamide

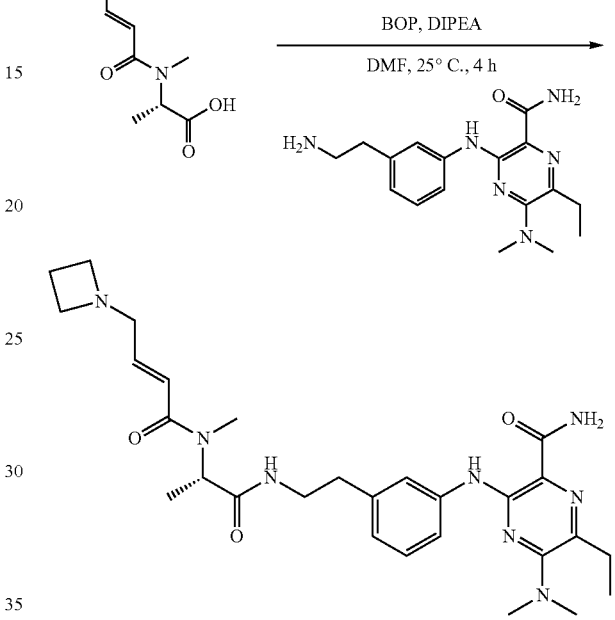

To a mixture of (E)-N-(4-(azetidin-1-yl)but-2-enoyl)-N-methyl-L-alanine propanoic acid (109.44 mg, 483.66 μmol, 2 eq) and 3-((3-(2-aminoethyl)phenyl)amino)-5-(dimethylamino)-6-ethylpyrazine-2-carboxamide (100 mg, 241.83 μmol, 1 eq) in DMF (2 mL) was added BOP (160.43 mg, 362.74 μmol, 1.5 eq) and DIPEA (312.55 mg, 2.42 mmol, 421.22 μL, 10 eq) in one portion at 25° C. under $N_2$. The mixture was stirred at 25° C. for 4 hrs LCMS indicated the reaction was completed. The reaction mixture was concentrated under reduced pressure to give a residue. The residue was purified by prep-HPLC (TFA condition). column: $C_{18-1}$ 150*30 mm*5 μm; mobile phase: [water (TFA)-ACN]; B %: 10%-55%, 8 min. To afford the title compound (S,E)-3-((3-(2-(2-(4-(azetidin-1-yl)-N-methylbut-2-enamido)propanamido)ethyl)phenyl)amino)-5-(dimethylamino)-6-ethylpyrazine-2-carboxamide (25.1 mg, 45.85 μmol, 18.96% yield) as a brown solid. $^1$H NMR (400 MHz, DMSO-d$_6$ TFA) δ=11.22-11.07 (m, 1H), 10.02-9.71 (m, 1H), 8.11-7.86 (m, 1H), 7.79-7.72 (m, 1H), 7.56-7.42 (m, 3H), 7.26-7.15 (m, 1H), 6.82-6.67 (m, 2H), 6.52-6.19 (m, 1H), 4.97-4.56 (m, 1H), 4.14 (br d, J=6.2 Hz, 2H), 4.00-3.98 (m, 4H), 3.35-3.24 (m, 2H), 3.09-3.04 (m, 6H), 2.92-2.86 (m, 2H), 2.80-2.67 (m, 6H), 2.44-2.35 (m, 2H), 1.28-1.19 (m, 6H). $^1$H NMR (400 MHz, D2O) δ=7.55-7.39 (m, 1H), 7.26-7.05 (m, 2H), 6.80 (br d, J=7.3 Hz, 1H), 6.58-6.40 (m, 1H), 6.38 (s, 1H), 4.85-4.41 (m, 1H), 4.31-4.07 (m, 2H), 4.05-3.86 (m, 2H), 3.84-3.59 (m, 2H), 3.53-3.27 (m, 2H), 3.05-2.93 (m, 6H), 2.79-2.62 (m, 7H), 2.58-2.29 (m, 2H), 1.32-1.12 (m, 6H) LC-MS (ES+, m/z): 537.3 [(M+H)$^+$]. Rt=2.117 min. HRMS (EI): m/z [M]$^+$ found: 537.3306.

Example 7 (Compound 158)

(S,E)-5-(dimethylamino)-3-((3-(2-(2-(4-(dimethylamino)-N-methylbut-2-enamido)propanamido)ethyl)-5-fluorophenyl)amino)-6-ethylpyrazine-2-carboxamide

Step 1: tert-butyl (S)-(1-((3-((3-carbamoyl-6-(dimethylamino)-5-ethylpyrazin-2-yl)amino)-5-fluorophenethyl)amino)-1-oxopropan-2-yl)(methyl)carbamate

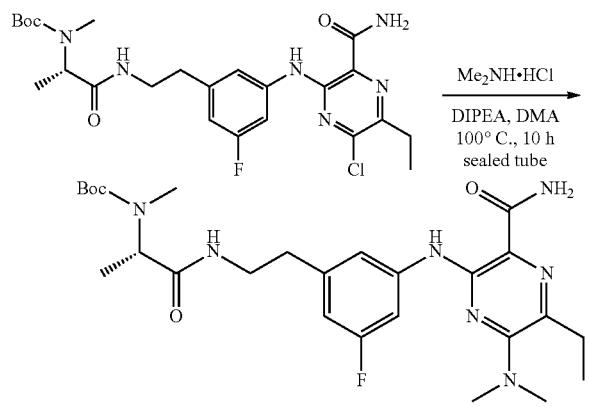

To a solution of tert-butyl (S)-(1-((3-((3-carbamoyl-6-chloro-5-ethylpyrazin-2-yl)amino)-5-fluorophenethyl)amino)-1-oxopropan-2-yl)(methyl)carbamate (500 mg, 956.03 μmol, 1 eq) in DMA (5 mL) was added DIPEA (1.24 g, 9.56 mmol, 1.67 mL, 10 eq) and dimethylamine (779.58 mg, 9.56 mmol, 875.94 μL, 10 eq, HCl). The mixture was stirred at 100° C. for 10 hrs in sealed tube. LC-MS showed the reaction was completed. The reaction mixture was poured into H$_2$O (5 mL) and extracted with EA (10 mL*3). The combined organic layers were washed with saturated brine (10 mL*3), dried over anhydrous Na$_2$SO$_4$, filtered and concentrated under reduced pressure to give a residue. The residue was purified by column chromatography (SiO$_2$, Petroleum ether/Ethyl acetate=5/1 to 1/5) to afford tert-butyl (S)-(1-((3-((3-carbamoyl-6-(dimethylamino)-5-ethylpyrazin-2-yl)amino)-5-fluorophenethyl)amino)-1-oxopropan-2-yl)(methyl)carbamate (300 mg, 564.31 μmol, 59.03% yield) as yellow oil. $^1$H NMR (400 MHz, DMSO-d$_6$) δ=11.38-11.23 (m, 1H), 7.87-7.73 (m, 2H), 7.72-7.60 (m, 1H), 7.58-7.47 (m, 1H), 7.17-7.05 (m, 1H), 6.68-6.55 (m, 1H), 4.57-4.22 (m, 1H), 3.17 (d, J=5.3 Hz, 2H), 3.07 (s, 5H), 2.79-2.74 (m, 4H), 2.71-2.68 (m, 4H), 1.40-1.20 (m, 15H). LC-MS (ES$^+$, m/z): 532.3 [(M+H)$^+$]; Rt=0.886 min.

Step 2: (S)-5-(dimethylamino)-6-ethyl-3-((3-fluoro-5-(2-(2-(methylamino) propanamido)ethyl)phenyl)amino)pyrazine-2-carboxamide

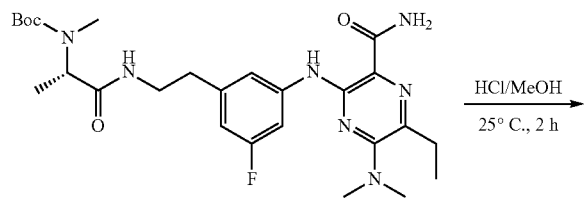

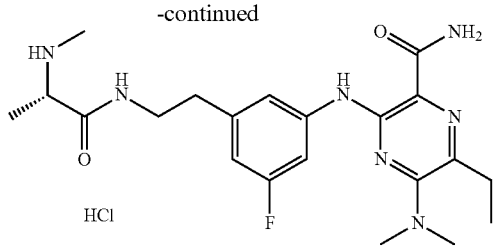

A mixture of tert-butyl (S)-(1-((3-((3-carbamoyl-6-(dimethylamino)-5-ethylpyrazin-2-yl)amino)-5-fluorophenethyl)amino)-1-oxopropan-2-yl)(methyl) carbamate (300 mg, 564.31 μmol, 1 eq), in HCl/MeOH (4 M, 48.70 mL, 345.21 eq) was stirred at 25° C. for 2 hrs. LC-MS showed the reaction was completed. The reaction mixture was filtered and concentrated under reduced pressure to afford (S)-5-(dimethylamino)-6-ethyl-3-((3-fluoro-5-(2-(2-(methylamino)propanamido)ethyl)phenyl)-amino)-pyrazine-2-carboxamide (287.4 mg, crude, HCl) was obtained as a yellow oil (150 mg, crude) as yellow oil. LC-MS (ES$^+$, m/z): 432.2 [(M+H)$^+$]; Rt=0.755 min.

Note: HCl/MeOH (4 M): HCl was bubbled into a solution MeOH at 0° C. for 0.5 h.

Step 3: (S,E)-5-(dimethylamino)-3-((3-(2-(2-(4-(dimethylamino)-N-methylbut-2-enamido)propanamido)ethyl)-5-fluorophenyl)amino)-6-ethylpyrazine-2-carboxamide

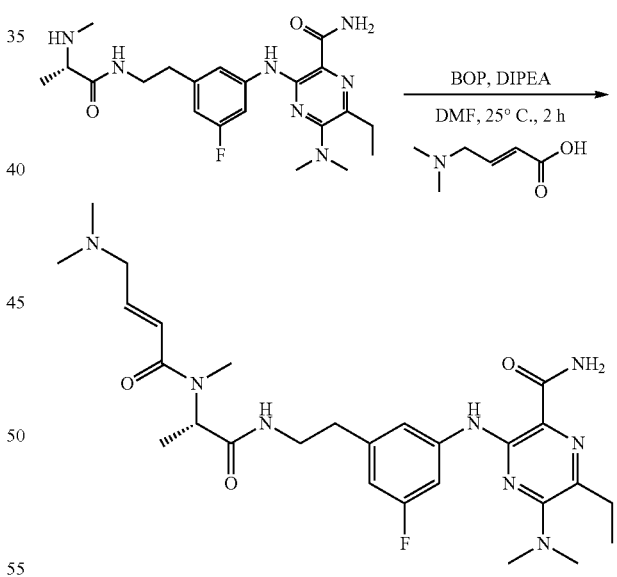

To a solution of (S)-5-(dimethylamino)-6-ethyl-3-((3-fluoro-5-(2-(2-(methylamino)propanamido)ethyl)phenyl)amino)pyrazine-2-carboxamide (287 mg, 665.11 μmol, 1 eq) in DMF (4 mL) was added BOP (441.25 mg, 997.67 μmol, 1.5 eq), DIPEA (1.60 g, 12.40 mmol, 2.16 mL, 18.64 eq) and (E)-4-(dimethylamino)but-2-enoic acid (352.36 mg, 2.73 mmol, 4.10 eq). The mixture was stirred at 25° C. for 2 hrs. LCMS showed the reaction was completed. The reaction mixture was filtered to give a residue. The residue was purified by prep-HPLC(column: Phenomenex Luna 80*30 mm*3 um; mobile phase: [water (TFA)-ACN]; B %: 20%-

50%, 8 min) to afford (S,E)-5-(dimethylamino)-3-((3-(2-(2-(4-(dimethylamino)-N-methylbut-2-enamido) propanamido)ethyl)-5-fluorophenyl)amino)-6-ethylpyrazine-2-carboxamide (246 mg, 449.25 μmol, 67.55% yield, 99.10% purity) as yellow solid. ¹H NMR (400 MHz, DMSO-d₆, TFA) δ=11.37-11.24 (m, 1H), 9.65 (br s, 1H), 8.14-7.86 (m, 1H), 7.79 (br s, 1H), 7.73-7.66 (m, 1H), 7.52 (br s, 1H), 7.08 (s, 1H), 6.86-6.75 (m, 1H), 6.65-6.46 (m, 2H), 4.96-4.55 (m, 1H), 3.91-3.86 (m, 2H), 3.33-3.24 (m, 2H), 3.10-3.06 (m, 6H), 2.89 (s, 2H), 2.77 (br d, J=7.3 Hz, 7H), 2.73-2.66 (m, 4H), 1.28-1.19 (m, 6H). LC-MS (ES⁺, m/z): 543.3 [(M+H)⁺]; Rt=2.200 min; 99.10% purity; HRMS: 543.3200.

Example 8 (Compound 159)

(S,E)-5-cyclopropyl-3-((3-(2-(2-(4-(dimethylamino)-N-methylbut-2-enamido) propanamido)ethyl)-5-fluorophenyl)amino)-6-ethylpyrazine-2-carboxamide Step 1: tert-butyl (S)-(1-((3-((3-carbamoyl-6-cyclopropyl-5-ethylpyrazin-2-yl) amino)-5-fluorophenethyl)amino)-1-oxopropan-2-yl)(methyl)carbamate

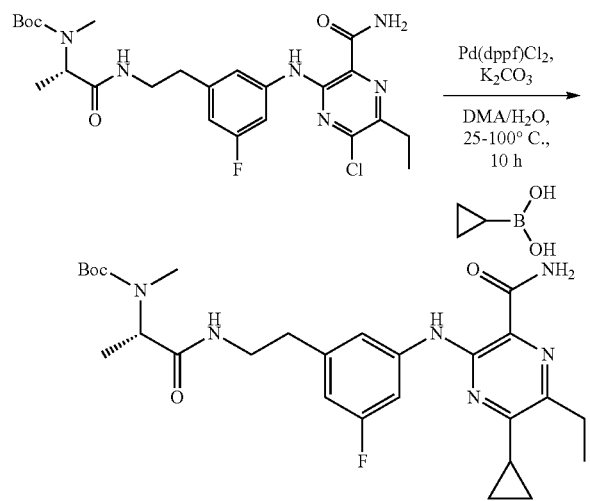

To a solution of tert-butyl (S)-(1-((3-((3-carbamoyl-6-chloro-5-ethylpyrazin-2-yl)amino)-5-fluorophenethyl)amino)-1-oxopropan-2-yl)(methyl) carbamate (500 mg, 956.03 μmol, 1 eq) in DMA (4 mL) and H₂O (2 mL) was added Pd(dppf)Cl₂ (69.95 mg, 95.60 μmol, 0.1 eq), cyclopropylboronic acid (821.20 mg, 9.56 mmol, 10 eq) and K₂CO₃ (396.39 mg, 2.87 mmol, 3 eq) at 25° C. The mixture was stirred at 100° C. for 10 hrs. LCMS showed the reaction was completed. The reaction mixture was poured into saturated EDTA (10 mL), EA (5 mL) and stirred 60 min, and then extracted with EA (5 mL*3). The combined organic layers were washed with saturated brine (10 mL*3), dried over anhydrous Na₂SO₄, filter and concentrated under reduced pressure to give a residue. The residue was purified by column chromatography (SiO₂, Petroleum ether/Ethyl acetate=5/1 to 1/1) to afford tert-butyl (S)-(1-((3-((3-carbamoyl-6-cyclopropyl-5-ethylpyrazin-2-yl)amino)-5-fluorophenethyl)amino)-1-oxopropan-2-yl)(methyl)carbamate (70 mg, 132.42 μmol, 13.85% yield) as yellow oil. LC-MS (ES⁺, m/z): 529.3 [(M+H)⁺]; Rt=0.904 min.

Step 2: (S)-5-cyclopropyl-6-ethyl-3-((3-fluoro-5-(2-(2-(methylamino)propanamido) ethyl)phenyl)amino) pyrazine-2-carboxamide

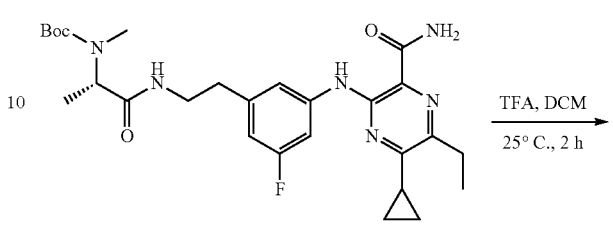

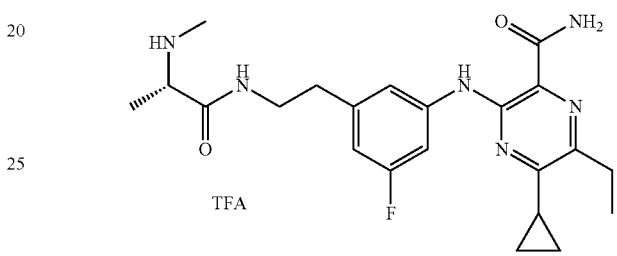

A mixture of tert-butyl (S)-(1-((3-((3-carbamoyl-6-cyclopropyl-5-ethylpyrazin-2-yl)amino)-5-fluorophenethyl)amino)-1-oxopropan-2-yl)(methyl) carbamate (310 mg, 586.44 μmol, 1 eq) and TFA (2.45 g, 21.47 mmol, 1.59 mL, 36.61 eq) in DCM (5 mL) was stirred at 25° C. for 2 hrs. LCMS showed the reaction was completed. The reaction mixture was filtered and concentrated under reduced pressure to afford (S)-5-cyclopropyl-6-ethyl-3-((3-fluoro-5-(2-(2-(methylamino)propanamido)ethyl)phenyl) amino)pyrazine-2-carboxamide (440 mg, crude, TFA) as yellow solid. ¹H NMR (400 MHz, DMSO-d₆) δ=11.28-11.19 (m, 1H), 8.79-8.67 (m, 2H), 8.54-8.47 (m, 1H), 8.18 (br s, 1H), 7.93-7.84 (m, 1H), 7.63 (br d, J=11.9 Hz, 1H), 7.07-7.00 (m, 1H), 6.68 (br d, J=8.8 Hz, 1H), 3.70-3.64 (m, 1H), 3.51-3.35 (m, 2H), 2.93-2.90 (m, 1H), 2.79-2.72 (m, 2H), 2.70-2.67 (m, 1H), 2.45-2.43 (m, 3H), 1.30-1.26 (m, 6H), 1.13 (br s, 2H), 1.09-1.05 (m, 2H). LC-MS (ES⁺, m/z): 429.3 [(M+H)⁺]; Rt=0.744 min; 91.31% purity.

Step 3: (S,E)-5-cyclopropyl-3-((3-(2-(2-(4-(dimethylamino)-N-methylbut-2-enamido)propanamido) ethyl)-5-fluorophenyl)amino)-6-ethylpyrazine-2-carboxamide

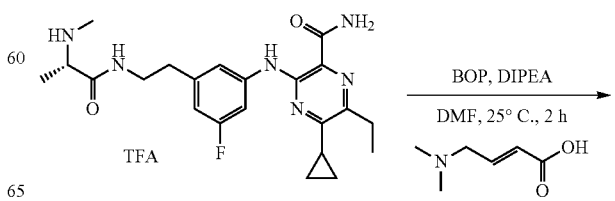

185

-continued

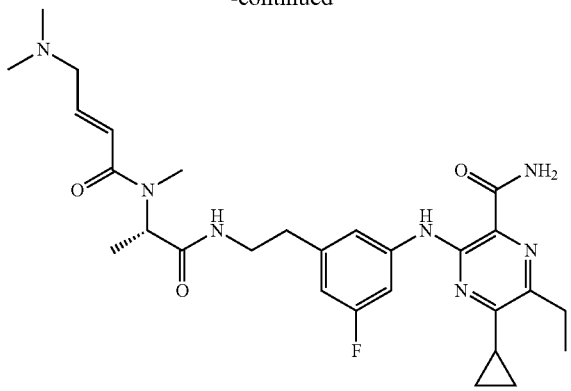

To a solution of (S)-5-cyclopropyl-6-ethyl-3-((3-fluoro-5-(2-(2-(methylamino)propanamido)ethyl)phenyl)amino)pyrazine-2-carboxamide (220 mg, 405.51 μmol, 1 eq, TFA) and (E)-4-(dimethylamino)but-2-enoic acid in DMF (2 mL) was added BOP (269.02 mg, 608.27 μmol, 1.5 eq), DIPEA (524.10 mg, 4.06 mmol, 706.33 μL, 10 eq). The mixture was stirred at 25° C. for 2 hrs. LCMS showed the reaction was completed The reaction mixture was filtered to give a residue. The residue was purified by prep-HPLC (column: Phenomenex Luna 80*30 mm*3 um; mobile phase: [water (TFA)-ACN]; B %: 20%-50%, 8 min) to afford (S,E)-5-cyclopropyl-3-((3-(2-(2-(4-(dimethylamino)-N-methylbut-2-enamido) propanamido)ethyl)-5-fluorophenyl) amino)-6-ethylpyrazine-2-carboxamide (60.81 mg, 106.44 μmol, 26.25% yield, 94.46% purity) as yellow solid. $^1$H NMR (400 MHz, DMSO-d$_6$) δ=11.23 (br s, 1H), 9.79-9.57 (m, 1H), 8.50-8.18 (m, 1H), 8.06-7.93 (m, 2H), 7.91-7.88 (m, 1H), 7.01-7.09 (m, 1H), 6.83-6.79 (m, 1H), 6.65-6.60 (m, 2H), 5.08-4.49 (m, 1H), 3.97-3.78 (m, 2H), 3.51-3.39 (m, 2H), 2.94-2.88 (m, 4H), 2.79-2.68 (m, 9H), 2.36-2.29 (m, 1H), 1.38-1.23 (m, 6H), 1.15-1.05 (m, 4H). LC-MS (ES$^+$, m/z): 540.2 [(M+H)$^+$]; Rt=2.261 min; 94.46 purity; HRMS: 540.3116.

Example 9 (Compound 162)

(S,Z)-5-(dimethylamino)-3-((3-(2-(2-(4-(dimethylamino)-2-fluoro-N-methylbut-2-enamido)propanamido)ethyl)phenyl)amino)-6-ethylpyrazine-2-carboxamide Step 1: ethyl (Z)-4-(dimethylamino)-2-fluorobut-2-enoate

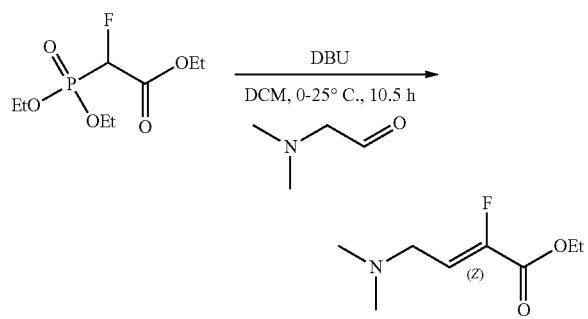

To a solution of ethyl 2-diethoxyphosphoryl-2-fluoroacetate (10 g, 41.29 mmol, 8.40 mL, 1 eq) in DCM (100 mL) was added DBU (31.43 g, 206.46 mmol, 31.12 mL, 5 eq) at 0° C. After addition, the mixture was stirred at this temperature for 30 min, and then 2-(dimethylamino)acetaldehyde (10.48 g, 61.94 mmol, 1.5 eq, H$_2$SO$_3$) was added at 0° C. The resulting mixture was stirred at 25° C. for 10 hrs. HPLC showed the reaction was completed. The reaction mixture was quenched by addition sat. NH$_4$Cl (200 mL) at 0° C., and then extracted with DCM (100 mL*3). The combined organic layers were washed with sat. brine (50 mL*2), dried over anhydrous Na2SO4, filtered and concentrated under reduced pressure to give ethyl (Z)-4-(dimethylamino)-2-fluoro-but-2-enoate (4 g, crude) as yellow oil. LC-MS (ES+, m/z): 176.4 [(M+H)$^+$]. Rt=0.247 min Step 2: (Z)-4-(dimethylamino)-2-fluorobut-2-enoic acid

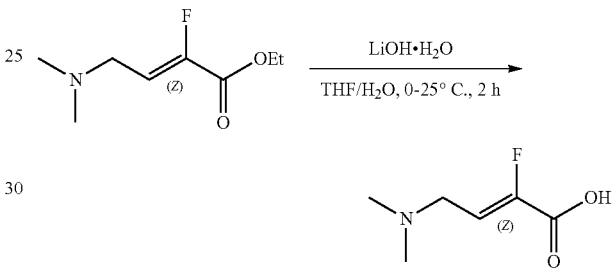

To a solution of ethyl (Z)-4-(dimethylamino)-2-fluorobut-2-enoate (1 g, 5.71 mmol, 1 eq) in THF (10 mL) and H$_2$O (1 mL) was added LiOH·H$_2$O (718.55 mg, 17.12 mmol, 3 eq) at 0° C. After addition, the mixture was stirred at 25° C. for 2 hrs. LC-MS showed the reaction was completed. The reaction mixture was neutralized with 1M HCl and concentrated under reduced pressure to give a residue. The residue was purified by prep-HPLC (column: Phenomenex Luna C18 100*30 mm*5 um; mobile phase: [water (TFA)-ACN]; B %: 95%-70%, 10 min) to give compound (Z)-4-(dimethylamino)-2-fluorobut-2-enoic acid (620 mg, 4.21 mmol, 73.82% yield) as a white solid. LC-MS (ES+, m/z): 148.3 [(M+H)$^+$]. Rt=0.183 min.

Step 3: (S,Z)-5-(dimethylamino)-3-((3-(2-(2-(4-(dimethylamino)-2-fluoro-N-methylbut-2-enamido) propanamido)ethyl)phenyl)amino)-6-ethylpyrazine-2-carboxamide

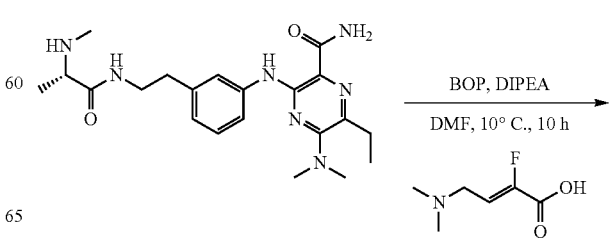

187

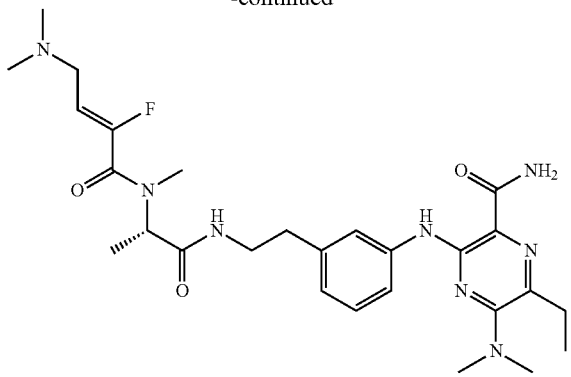

To a solution of (S)-5-(dimethylamino)-6-ethyl-3-((3-(2-(2-(methylamino)propanamido)ethyl)phenyl)amino)pyrazine-2-carboxamide (S,Z)-5-(dimethylamino)-3-((3-(2-(2-(methylamino)-propanamido)ethyl)phenyl)amino)-6-ethylpyrazine-2-carboxamide (100 mg, 241.83 µmol, 1.0 eq), (Z)-4-(dimethylamino)-2-fluorobut-2-enoic acid (284.68 mg, 1.93 mmol, 8.0 eq) in DMF (3 mL), BOP (160.43 mg, 362.74 µmol, 1.5 eq) and DIPEA (312.54 mg, 2.42 mmol, 10 eq) was added, the mixture was stirred at 10° C. for 10 hours. LCMS showed the reaction was completed. The residue was purified by prep-HPLC (column: Phenomenex C18 75*30 mm*3 um; mobile phase: [water (NH$_4$HCO$_3$)-ACN]; B %: 35%-65%, 8 min) to afford (S,Z)-5-(dimethylamino)-3-((3-(2-(2-(4-(dimethylamino)-2-fluoro-N-methylbut-2-enamido)propanamido)ethyl)phenyl)amino)-6-ethylpyrazine-2-carboxamide (13.41 mg, 24.61 µmol, 10.17% yield) as a brown solid. 1H NMR (400 MHz, DMSO-d6) δ=11.12-11.09 (m, 1H), 7.98 (br d, J=5.4 Hz, 1H), 7.74 (br d, J=2.5 Hz, 1H), 7.56 (s, 1H), 7.49-7.42 (m, 2H), 7.20 (t, J=7.8 Hz, 1H), 6.79 (d, J=7.6 Hz, 1H), 5.76-5.45 (m, 1H), 4.82-4.25 (m, 1H), 3.31-3.24 (m, 2H), 3.06 (s, 6H), 3.05-3.02 (m, 2H), 2.92-2.82 (m, 2H), 2.79-2.80 (m, 3H), 2.70 (br t, J=7.2 Hz, 2H), 2.16-2.13 (f, 6H), 1.22-1.17 (t, J=7.4 Hz, 6H). LC-MS (ES+, m/z): 543.4 [(M+H)$^+$]; Rt=2.894 min; HRMS: 543.3257.

Example 10 (Compound 202)

(S,E)-3-((3-(2-(2-(4-(azetidin-1-yl)-N-methylbut-2-enamido)propanamido)ethyl)phenyl)amino)-6-ethyl-5-methylpyrazine-2-carboxamide- Step 1: tert-butyl (E)-N-(4-bromobut-2-enoyl)-N-methyl-L-alaninate

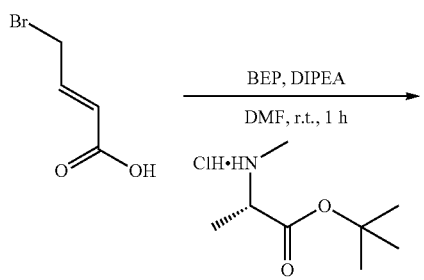

188

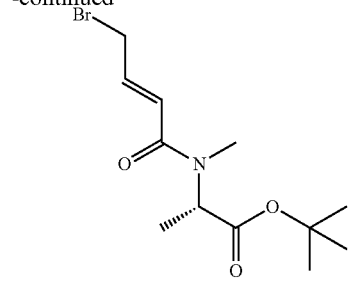

To a mixture of tert-butyl methyl-L-alaninate hydrochloride (9 g, 45.99 mmol, N/A purity, 1 eq) and (E)-4-bromobut-2-enoic acid (8.35 g, 50.59 mmol, 1.1 eq) in DMF (90 mL) was added BEP (18.89 g, 68.99 mmol, 1.5 eq) and DIEA (59.44 g, 459.92 mmol, 80.11 mL, 10 eq) in one portion at 20° C. under N$_2$. The mixture was stirred at 20° C. for 1 hr. LCMS indicated the reaction was complete. The residue was poured into ice-water (w/w=1/1) (120 mL). The aqueous phase was extracted with ethyl acetate (20 mL*3). The combined organic phase was washed with saturated brine (20 mL*2), dried with anhydrous Na$_2$SO$_4$, filtered and concentrated in vacuum. The residue was purified by column chromatography (SiO$_2$, Petroleum ether:Ethyl acetate=30/1 to 1/1) to afford tert-butyl (E)-N-(4-bromobut-2-enoyl)-N-methyl-L-alaninate (8 g, 26.13 mmol, 28.40% yield) as a yellow oil. LC-MS (ES+, m/z): 206.3 [(M+H-100)$^+$]. Rt=1.837 min.

Step 2: tert-butyl (E)-N-(4-(azetidin-1-yl)but-2-enoyl)-N-methyl-L-alaninate

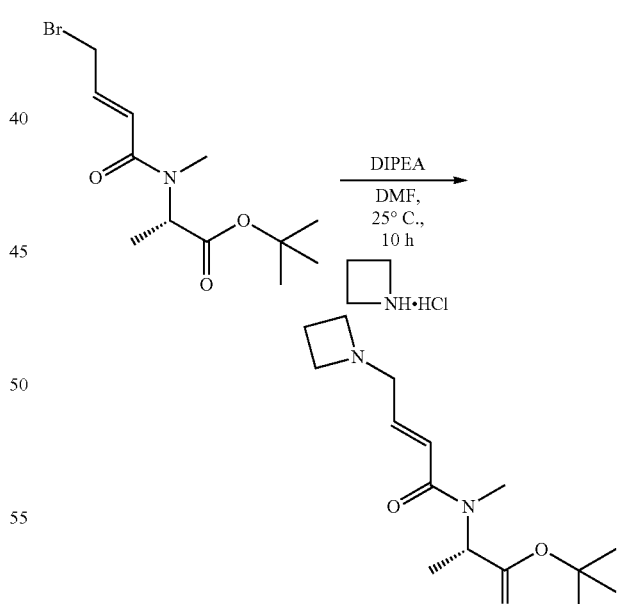

To a mixture of tert-butyl (E)-N-(4-bromobut-2-enoyl)-N-methyl-L-alaninate (8 g, 26.13 mmol, 1 eq) and azetidine hydrochloride (2.44 g, 26.13 mmol, 1 eq) in DMF (80 mL) was added DIPEA (10.13 g, 78.38 mmol, 13.65 mL, 3 eq) in one portion at 25° C. The mixture was stirred at 25° C. for 10 hrs. LCMS indicated the reaction was complete. The reaction mixture was filtrated under reduced pressure to give a residue. The residue was purified by column chromatography (SiO$_2$, Petroleum ether:Ethyl acetate=1/1 to 1/1). To afford the title compound tert-butyl (E)-N-(4-(azetidin-1-yl)but-2-enoyl)-N-methyl-L-alaninate (550 mg, 1.95 mmol, 2.48% yield) as a yellow oil. LC-MS (ES+, m/z): 283.4 [(M+H)$^+$]. Rt=0.546 min Step 3: (E)-N-(4-(azetidin-1-yl)but-2-enoyl)-N-methyl-L-alanine

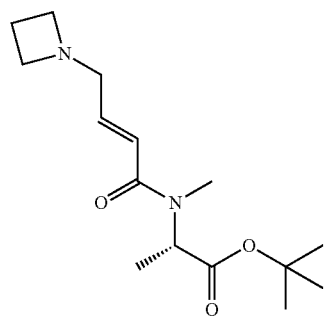

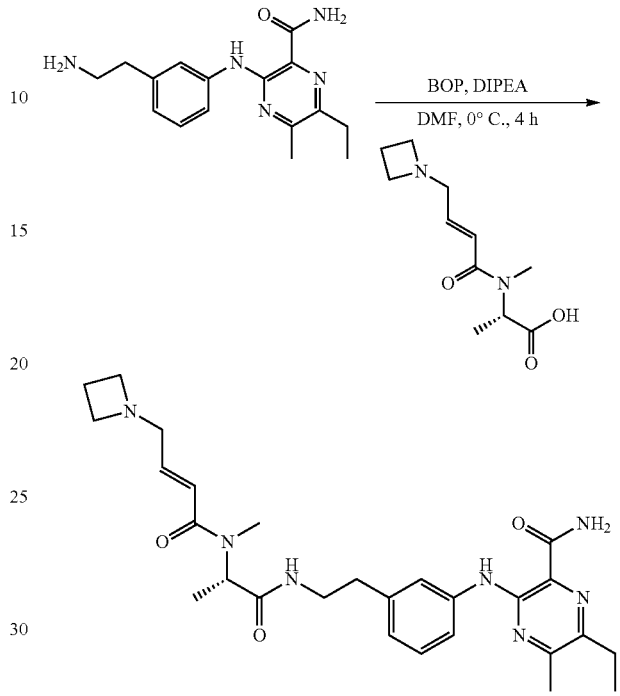

To a mixture of tert-butyl (E)-N-(4-(azetidin-1-yl)but-2-enoyl)-N-methyl-L-alaninate (500 mg, 1.77 mmol, 1 eq) in DCM (1.5 mL) was added TFA (77.00 g, 675.30 mmol, 381.38 eq) in one portion at 20° C. The mixture was stirred at 20° C. for 1 hr. LCMS indicated the reaction was complete. The reaction concentrated under reduced pressure to give a residue. To afford the title compound (E)-N-(4-(azetidin-1-yl)but-2-enoyl)-N-methyl-L-alanine (480 mg, crude) as a yellow oil. LC-MS (ES+, m/z): 227.3 [(M+H)$^+$]. Rt=0.177 min.

Step 4: (S,E)-3-((3-(2-(2-(4-(azetidin-1-yl)-N-methylbut-2-enamido)propanamido)ethyl)phenyl)amino)-6-ethyl-5-methylpyrazine-2-carboxamide To a mixture of 3-((3-(2-aminoethyl)phenyl)amino)-6-ethyl-5-methylpyrazine-2-carboxamide (250 mg, 835.09 μmol, 1 eq) and (E)-N-(4-(azetidin-1-yl)but-2-enoyl)-N-methyl-L-alanine (188.96 mg, 835.09 μmol, 1 eq) in DMF (2.5 mL), was added BOP (554.01 mg, 1.25 mmol, 1.5 eq) and DIPEA (1.08 g, 8.35 mmol, 1.45 mL, 10 eq) in one portion at 0° C. The mixture was stirred at 0° C. for 4 hr. LCMS indicated the reaction was complete. The reaction mixture was filtrated under reduced pressure to give a residue. The residue was purified by prep-HPLC (TFA condition). column: C$_{18-1}$ $_{150*30}$ mm*5 μm; mobile phase: [water (TFA)-ACN]; B %: 5%-50%, 8 min. To afford the title compound (S,E)-3-((3-(2-(2-(4-(azetidin-1-yl)-N-methylbut-2-enamido)propanamido)ethyl)phenyl)amino)-6-ethyl-5-methylpyrazine-2-carboxamide (60.43 mg, 117.29 μmol, 14.05% yield) as a yellow solid. $^1$H NMR (400 MHz, DMSO-d$_6$) δ=11.12-10.98 (m, 1H), 10.10-9.95 (m, 1H), 8.16 (br s, 1H), 8.07-7.74 (m, 2H), 7.66 (br d, J=8.0 Hz, 1H), 7.43 (s, 1H), 7.28-7.19 (m, 1H), 6.89-6.62 (m, 2H), 6.55-6.31 (m, 1H), 5.00-4.52 (m, 1H), 4.22-4.07 (m, 2H), 4.06-3.89 (m, 4H), 3.36-3.25 (m, 2H), 2.94-2.86 (m, 2H), 2.80-2.71 (m, 3H), 2.71-2.65 (m, 2H), 2.52-2.50 (m, 3H), 2.43-2.19 (m, 2H), 1.30-1.20 (m, 6H)(TFA, salt). $^1$H NMR (400 MHz, D$_2$O) δ=7.27-7.22 (m, 1H), 7.19-7.12 (m, 1H), 7.08-7.01 (m, 1H), 6.77-6.70 (m, 1H), 6.53 (br d, J=15.5 Hz, 1H), 6.47-6.29 (m, 1H), 4.85-4.80 (m, 1H), 4.53 (d, J=6.9 Hz, 1H), 4.28-4.17 (m, 2H), 4.05-3.93 (m, 2H), 3.91-3.80 (m, 2H), 3.44-3.29 (m, 2H), 2.83 (s, 2H), 2.70-2.65 (m, 2H), 2.57-2.43 (m, 3H), 2.19-2.18 (m, 1H), 2.19-2.13 (m, 3H), 1.33-1.25 (m, 1H), 1.24-1.19 (m, 2H), 1.08-1.03 (m, 3H). LC-MS (ES+, m/z): 508.3 [(M+H)+]; Rt=2.076 min. HRMS (EI): m/z [M]$^+$ found: 508.3055.

Example 11 (Compound 203)

(S)-5-(dimethylamino)-3-((3-(2-(2-(4-(dimethylamino)-N-methylbut-2-ynamido)propanamido)ethyl)phenyl)amino)-6-ethylpyrazine-2-carboxamide

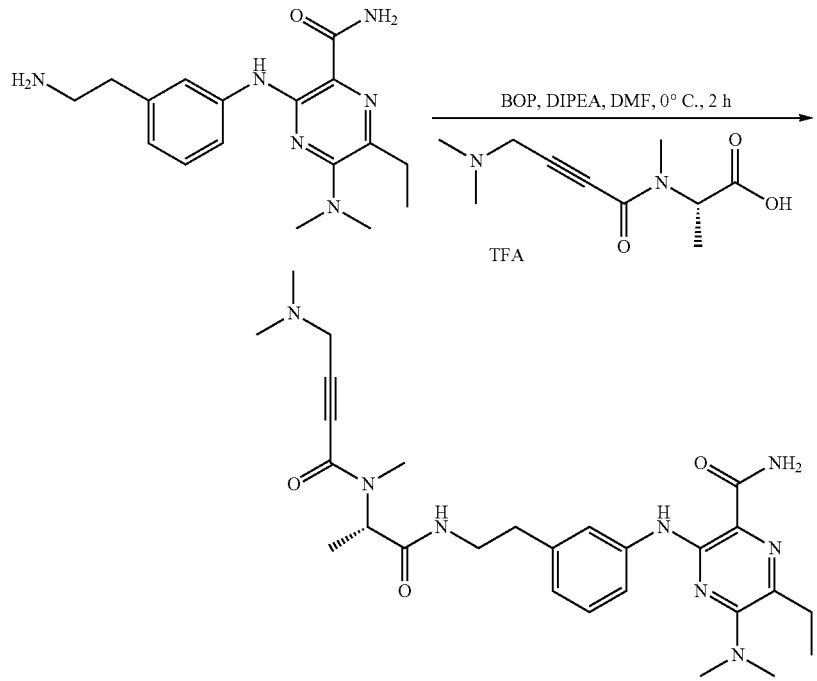

To a solution of N-(4-(dimethylamino)but-2-ynoyl)-N-methyl-L-alanine (198.69 mg, 608.99 μmol, 2 eq, TFA), BOP (202.01 mg, 456.74 μmol, 1.5 eq), DIEA (393.54 mg, 3.04 mmol, 530.38 μL, 10 eq) in DMF (2.5 mL) was added 3-((3-(2-aminoethyl)phenyl)amino)-5-(dimethylamino)-6-ethylpyrazine-2-carboxamide (100 mg, 304.50 μmol, 1 eq). The mixture was stirred at 0° C. for 2 hrs. LCMS indicated the reaction was complete. The reaction was concentrated. The crude was purified by prep-HPLC (column: $C_{18-1}$ 150*30 mm*5 um; mobile phase: [water (TFA)-ACN]; B %: 10%-55%, 8 min) then it was further purified by prep-HPLC column: Phenomenex Luna C18 100*30 mm*5 um; mobile phase: [water (TFA)-MeOH]; B %: 45%-75%, 10 min to give (S)-5-(dimethylamino)-3-((3-(2-(2-(4-(dimethylamino)-N-methylbut-2-ynamido) propanamido)ethyl)phenyl)amino)-6-ethylpyrazine-2-carboxamide (6.67 mg, 12.76 μmol, 4.19% yield) as yellow solid. 1H NMR (400 MHz, DMSO-$d_6$) δ=11.11 (d, J=3.9 Hz, 1H), 10.85-10.60 (m, 1H), 8.23-7.97 (m, 1H), 7.74 (br s, 1H), 7.55 (br d, J=6.1 Hz, 1H), 7.52-7.43 (m, 2H), 7.21 (dt, J=3.5, 7.8 Hz, 1H), 6.79 (td, J=1.4, 7.6 Hz, 1H), 4.93-4.79 (m, 1H), 4.24 (br d, J=16.0 Hz, 2H), 3.34-3.27 (m, 2H), 3.26-3.03 (m, 8H), 2.79-2.66 (m, 11H), 1.34-1.21 (m, 6H)(TFA salt). LC-MS (ES+, m/z): 523.3 [(M+H)+]; Rt=2.813 min; HRMS (EI): m/z [M]$^+$ found: 523.3130; SFC: 95.58%.

Example 12 (Compound 204)

(S,E)-3-((3-(2-(2-(4-(dimethylamino)-N-methylbut-2-enamido)propanamido)ethyl)phenyl)amino)-6-ethyl-5-(isopropyl(methyl)amino)pyrazine-2-carboxamide Step 1: (S,E)-3-((3-(2-(2-(4-(dimethylamino)-N-methylbut-2-enamido)propanamido)ethyl)phenyl)amino)-6-ethyl-5-(isopropyl(methyl)amino)pyrazine-2-carboxamide

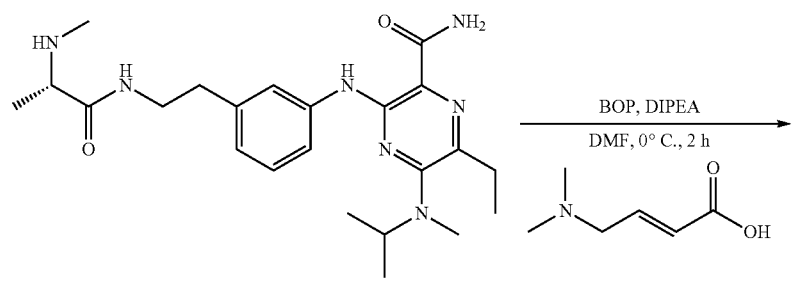

-continued

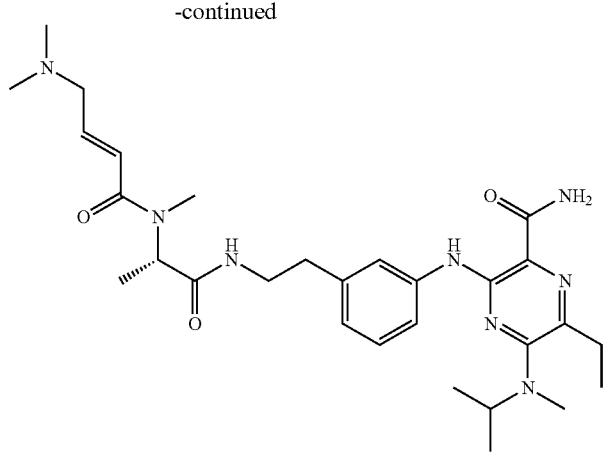

To a solution of (E)-4-(dimethylamino)but-2-enoic acid (118.46 mg, 917.19 μmol, 1.5 eq) in DMF (2.5 mL) was added DIEA (790.27 mg, 6.11 mmol, 1.07 mL, 10 eq) and (S)-6-ethyl-5-(isopropyl(methyl)amino)-3-((3-(2-(2-(methylamino) propanamido)ethyl)phenyl) amino)pyrazine-2-carboxamide (270 mg, 611.46 μmol, 1 eq), then BOP (405.65 mg, 917.19 μmol, 1.5 eq) was added. The mixture was stirred at 0° C. for 2 hrs. LCMS indicated the reaction was complete. The reaction was concentrated. The crude was purified by prep-HPLC (column: Phenomenex Luna C18 150*30 mm*5 um; mobile phase: [water (TFA)-ACN]; B %: 15%-45%, 8 min) to give (S,E)-3-((3-(2-(2-(4-(dimethylamino)-N-methylbut-2-enamido)propanamido)ethyl)phenyl)amino)-6-ethyl-5-(isopropyl(methyl)amino) pyrazine-2-carboxamide (64.81 mg, 116.25 μmol, 19.01% yield) as yellow solid. 1H NMR (400 MHz, DMSO-d$_6$) δ=11.15-11.06 (m, 1H), 9.67 (br s, 1H), 8.11-7.88 (m, 1H), 7.76 (br d, J=2.1 Hz, 1H), 7.55-7.50 (m, 1H), 7.49-7.42 (m, 2H), 7.24-7.16 (m, 1H), 6.86-6.75 (m, 2H), 6.65-6.46 (m, 1H), 4.99-4.54 (m, 1H), 4.25 (td, J=6.6, 13.2 Hz, 1H), 3.90-3.81 (m, 2H), 3.33-3.23 (m, 2H), 2.91-2.84 (m, 5H), 2.80-2.67 (m, 11H), 1.30-1.19 (m, 12H). LC-MS (ES+, m/z): 553.4 [(M+H)$^+$]; Rt=2.247 min; HRMS (EI): m/z [M]$^+$ found: 553.3696; SFC: 99.14%.

Example 13 (Compound 205)

(S,E)-3-((3-(2-(2-(4-(dimethylamino)-N-methylbut-2-enamido)propanamido)ethyl)phenyl)amino)-6-ethyl-5-(isopropylamino)pyrazine-2-carboxamide Step 1: tert-butyl (3-((3-carbamoyl-5-ethyl-6-(isopropylamino) pyrazin-2-yl) amino)phenethyl)carbamate

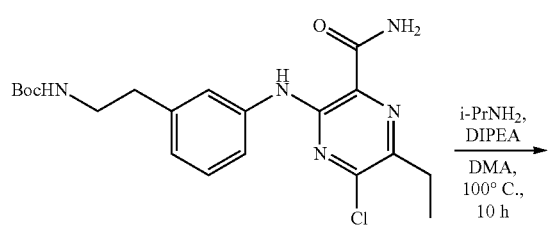

-continued

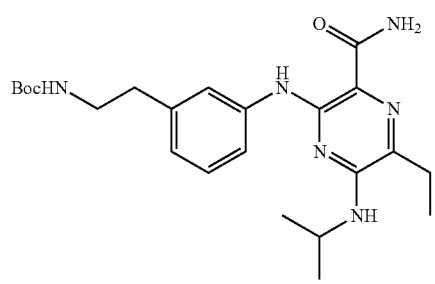

To a solution of tert-butyl (3-((3-carbamoyl-6-chloro-5-ethylpyrazin-2-yl)amino)phenethyl)carbamate (200 mg, 476.30 μmol, 1 eq) in DMA (2 mL) was added propan-2-amine (140.77 mg, 2.38 mmol, 5 eq) and DIPEA (615.58 mg, 4.76 mmol, 829.63 μL, 10 eq). The mixture was stirred at 100° C. for 10 hr. LCMS showed the reaction was completed. The reaction mixture was quenched by addition water (50 mL) at 25° C., and then extracted with EtOAc (30 mL*3). The combined organic layers were washed with saturated brine (20 mL*2), dried over Na$_2$SO$_4$, filtered and concentrated under reduced pressure to give a residue. The residue was purified by column chromatography (SiO$_2$, Petroleum ether/Ethyl acetate=10/1 to 1/1) to give tert-butyl (3-((3-carbamoyl-5-ethyl-6-(isopropylamino) pyrazin-2-yl) amino) phenethyl) carbamate (180 mg, 389.97 μmol, 81.88% yield) as yellow solid. $^1$H NMR (400 MHz, DMSO-d$_6$) δ=11.22 (s, 1H), 7.73-7.68 (m, 1H), 7.57-7.53 (m, 1H), 7.33-7.24 (m, 2H), 7.21-7.15 (m, 1H), 6.92 (t, J=5.3 Hz, 1H), 6.78-6.74 (m, 2H), 4.31-3.98 (m, 1H), 3.15-3.10 (m, 2H), 2.67-2.63 (m, 2H), 2.61-2.55 (m, 2H), 1.37 (s, 9H), 1.27 (d, J=6.6 Hz, 6H), 1.21-1.17 (m, 3H). LC-MS (ES$^+$, m/z): 443.3 [(M+H)+]; Rt=0.887 min.

Step 2: 3-((3-(2-aminoethyl) phenyl)amino)-6-ethyl-5-(isopropylamino)pyrazine-2-carboxamide

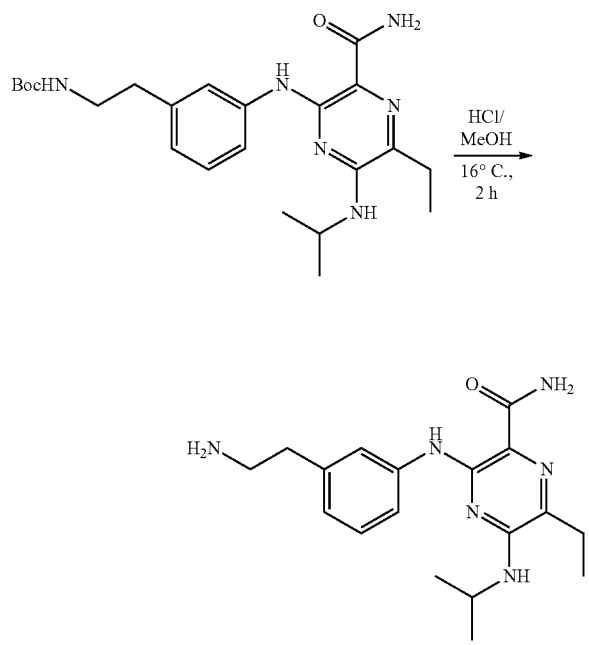 [SMILES: CCc1nc(C(N)=O)c(Nc2cccc(CCNC(=O)OC(C)(C)C)c2)nc1NC(C)C ; CCc1nc(C(N)=O)c(Nc2cccc(CCN)c2)nc1NC(C)C]

To tert-butyl (3-((3-carbamoyl-5-ethyl-6-(isopropylamino)pyrazin-2-yl)amino)phenethyl)carbamate (180 mg, 406.73 μmol, 1 eq) was added HCl/MeOH (4 M, 101.68 μL). The mixture was stirred at 16° C. for 2 hr. LCMS showed the reaction was completed. The reaction mixture was concentrated under reduced pressure to give a residue. to give a residue. The crude product was triturated with EtOAc at 25° C. for 10 min to give 3-((3-(2-aminoethyl) phenyl)amino)-6-ethyl-5-(isopropylamino)pyrazine-2-carboxamide (130 mg, 367.71 μmol, 90.41% yield) as yellow solid. 1H NMR (400 MHz, DMSO-$d_6$) δ=11.25 (br s, 1H), 8.08 (br s, 3H), 7.57 (s, 1H), 7.53 (br d, J=8.1 Hz, 1H), 7.24 (t, J=7.8 Hz, 2H), 6.86-6.82 (m, 1H), 6.82-6.74 (m, 1H), 4.29-4.18 (m, 1H), 3.05-2.96 (m, 2H), 2.90-2.83 (m, 2H), 2.61-2.55 (m, 2H), 1.28 (d, J=6.5 Hz, 6H), 1.19 (t, J=7.4 Hz, 3H); LC-MS (ES$^+$, m/z): 343.2 [(M+H)$^+$]; Rt=0.684 min

Step 3: tert-butyl (S)-(1-((3-((3-carbamoyl-5-ethyl-6-(isopropylamino) pyrazin-2-yl) amino) phenethyl) amino)-1-oxopropan-2-yl)(methyl)carbamate

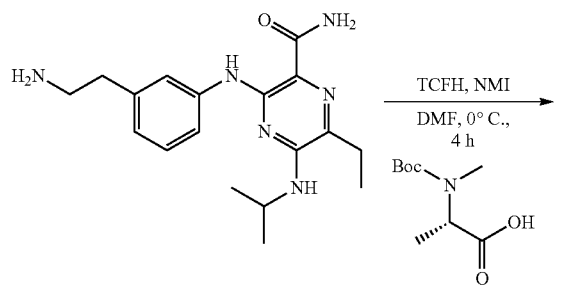

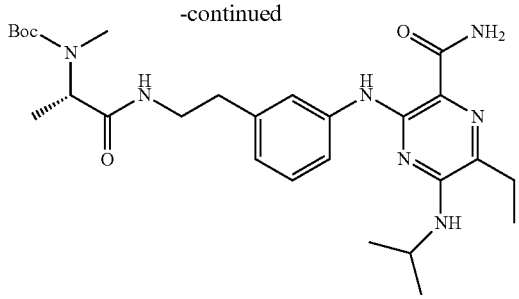

To a solution of 3-((3-(2-aminoethyl) phenyl)amino)-6-ethyl-5-(isopropylamino)pyrazine-2-carboxamide (130 mg, 379.63 μmol, 1 eq), 1-methylimidazole (311.68 mg, 3.80 mmol, 302.60 μL, 10 eq) and N-(tert-butoxycarbonyl)-N-methyl-L-alanine (115.73 mg, 569.45 μmol, 1.5 eq), 1-methylimidazole (311.68 mg, 3.80 mmol, 302.60 μL, 10 eq) in DMF (1.5 mL) was added TCFH (159.78 mg, 569.45 μmol, 1.5 eq) at 0° C. The mixture was stirred at 0° C. for 4 hrs. LCMS showed the reaction was completed. The reaction mixture was quenched by addition water (50 mL) at 25° C., and then extracted with EtOAc (30 mL*3). The combined organic layers were washed with saturated brine (20 mL*2), dried over Na$_2$SO$_4$, filtered and concentrated under reduced pressure to give a residue. The residue was purified by column chromatography (SiO$_2$, Petroleum ether/Ethyl acetate=10/1 to 5/1) to give tert-butyl (S)-(1-((3-((3-carbamoyl-5-ethyl-6-(isopropylamino) pyrazin-2-yl) amino) phenethyl) amino)-1-oxopropan-2-yl)(methyl)carbamate (130 mg, 204.32 μmol, 53.82% yield) as yellow solid. $^1$H NMR (400 MHz, DMSO-$d_6$) δ=11.21 (s, 1H), 7.84-7.77 (m, 1H), 7.67 (s, 1H), 7.57-7.51 (m, 1H), 7.35 (br d, J=8.1 Hz, 1H), 7.24 (br d, J=2.4 Hz, 1H), 7.18 (t, J=7.8 Hz, 1H), 6.76 (t, J=8.3 Hz, 2H), 4.29-4.23 (m, 1H), 3.32-3.26 (m, 3H), 2.69 (s, 5H), 2.58 (q, J=7.4 Hz, 2H), 1.37 (br s, 9H), 1.28-1.17 (m, 12H), LC-MS (ES$^+$, m/z): 528.4 [(M+H)$^+$]; Rt=0.929 min.

Step 4: (S)-6-ethyl-5-(isopropylamino)-3-((3-(2-(2-(methylamino) propanamido) ethyl) phenyl) amino) pyrazine-2-carboxamide

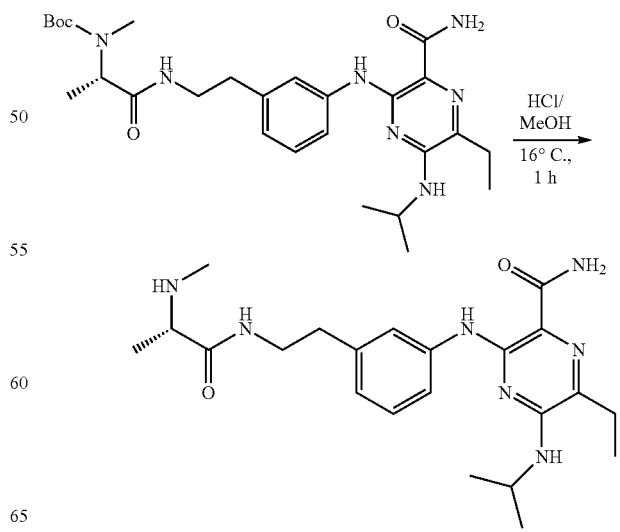

A mixture of tert-butyl (S)-(1-((3-((3-carbamoyl-5-ethyl-6-(isopropylamino) pyrazin-2-yl) amino) phenethyl) amino)-1-oxopropan-2-yl)(methyl)carbamate (130 mg, 246.37 μmol, 1 eq) HCl/MeOH (4 M, 61.59 μL, 1 eq) was stirred at 16° C. for 1 hr. LCMS showed the reaction was completed. The reaction mixture was concentrated under reduced pressure to give a residue. The crude product was triturated with EtOAc at 25° C. for 10 min to give (S)-6-ethyl-5-(isopropylamino)-3-((3-(2-(2-(methylamino) propanamido) ethyl) phenyl) amino) pyrazine-2-carboxamide as yellow solid (100 mg, 215.39 μmol, 87.43% yield). ¹H NMR (400 MHz, DMSO-d₆) δ=11.21 (br s, 1H), 9.24-9.15 (m, 1H), 8.85-8.76 (m, 1H), 8.64 (br t, J=5.4 Hz, 1H), 7.58 (s, 1H), 7.45 (br d, J=8.0 Hz, 1H), 7.20 (t, J=7.8 Hz, 1H), 6.80 (br d, J=7.4 Hz, 2H), 4.27 (br s, 1H), 3.74-3.64 (m, 1H), 3.43-3.37 (m, 1H), 2.85-2.67 (m, 4H), 2.59 (q, J=7.4 Hz, 3H), 2.42-2.40 (m, 2H), 1.32-1.17 (m, 12H); LC-MS (ES⁺, m/z): 428.3 [(M+H)⁺]; Rt=0.731 min.; LC-MS (ES⁺, m/z): 428.3 [(M+H)⁺]; Rt=0.731 min.

Note: HCl/EtOAc (4 M): HCl was bubbled into a solution EtOAc at 0° C. for 0.5 h. Then, the solution was weighed to obtained the HCl/EtOAc (4 M)

Step 5: (S,E)-3-((3-(2-(2-(4-(dimethylamino)-N-methylbut-2-enamido) propanamido) ethyl) phenyl) amino)-6-ethyl-5-(isopropylamino) pyrazine-2-carboxamide To a solution of (S)-6-ethyl-5-(isopropylamino)-3-((3-(2-(2-(methylamino) propanamido) ethyl) phenyl) amino) pyrazine-2-carboxamide (100 mg, 233.90 μmol, 1 eq) in DMF (3 mL) was added BOP (124.14 mg, 280.67 μmol, 1.2 eq) and DIPEA (302.29 mg, 2.34 mmol, 407.40 μL, 10 eq), (E)-4-(dimethylamino)but-2-enoic acid (36.25 mg, 280.67 μmol, 1.2 eq). The mixture was stirred at 0° C. for 4 hrs. LC-MS indicated the mixture was complete. The reaction mixture was quenched by addition water (50 mL) at 25° C., and then extracted with EtOAc (30 mL*3). The combined organic layers were washed with saturated brine (20 mL*2), dried over Na₂SO₄, filtered and concentrated under reduced pressure to give a residue. The residue was purified by prep-HPLC (column: Phenomenex Luna C18 150*30 mm*5 um; mobile phase: [water (TFA)-ACN]; B %: 15%-45%, 8 min) to give desired compound to give (S,E)-3-((3-(2-(2-(4-(dimethylamino)-N-methylbut-2-enamido) propanamido) ethyl) phenyl) amino)-6-ethyl-5-(isopropylamino) pyrazine-2-carboxamide (13.13 mg, 23.96 μmol, 10.24% yield) as yellow solid. ¹H NMR (400 MHz, DMSO-d₆) δ=11.25-11.18 (m, 1H), 9.90 (br s, 1H), 7.92 (br t, J=5.5 Hz, 1H), 7.64-7.52 (m, 2H), 7.44-7.37 (m, 1H), 7.25 (br s, 1H), 7.21-7.15 (m, 1H), 6.85-6.73 (m, 3H), 6.66-6.47 (m, 1H), 4.57 (q, J=6.7 Hz, 1H), 4.26 (qd, J=6.7, 13.6 Hz, 1H), 3.93-3.81 (m, 2H), 3.34-3.23 (m, 2H), 2.90 (s, 2H), 2.80-2.74 (m, 6H), 2.73-2.66 (m, 3H), 2.62-2.56 (m, 2H), 1.29-1.16 (m, 12H)(TFA, salt); LC-MS (ES⁺, m/z): 539.3 [(M+H)⁺]; Rt=2.117 min; 98.31% purity; HRMS: 539.3476.

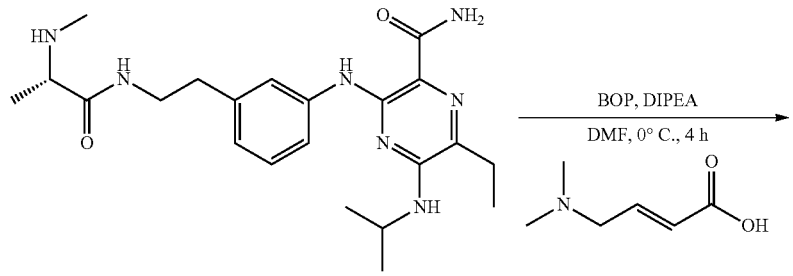

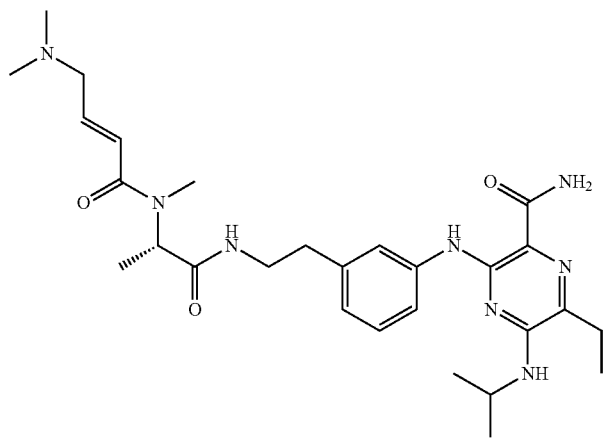

Example 14 (Compound 213)

(S)-5-(dimethylamino)-6-ethyl-3-((3-(2-(2-(N-methylacrylamido)propanamido)ethyl)phenyl)amino)pyrazine-2-carboxamide

Step 1: 3-((3-(2-aminoethyl)phenyl)amino)-5-(dimethylamino)-6-ethylpyrazine-2-carboxamide

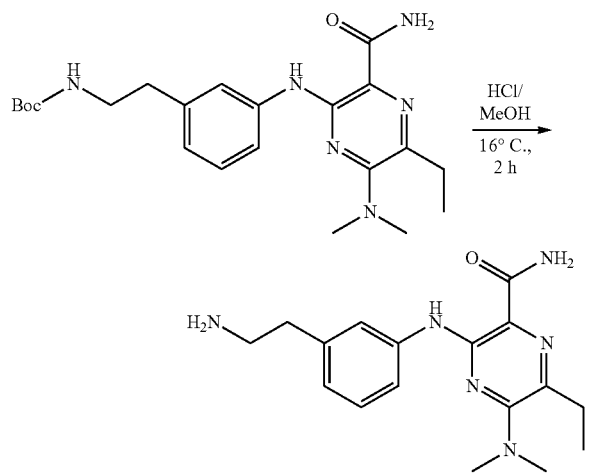

To a mixture of tert-butyl (3-((3-(3-carbamoyl-6-(dimethylamino)-5-ethylpyrazin-2-yl)amino)phenethyl)carbamate (400 mg, 933.43 μmol, 1 eq) in MeOH (7 mL) was added MeOH/HCl (933.43 μmol, 30 mL, 1 eq). The mixture was stirred at 16° C. for 2 hrs. The crude was concentrated under reduced pressure to afford 3-((3-(2-aminoethyl)phenyl)amino)-5-(dimethylamino)-6-ethylpyrazine-2-carboxamide as yellow solid. LC-MS (ES+, m/z): 329.3 [(M+H)$^+$]; Rt=0.646 min.

Note: HCl/MeOH (4 M): HCl was bubbled into a solution MeOH at 0° C. for 0.5 h. Then, the solution was weighed to obtained the HCl/MeOH (4 M).

Step 2: tert-butyl (S)-(1-((3-((3-carbamoyl-6-(dimethylamino)-5-ethylpyrazin-2-yl)amino)phenethyl)amino)-1-oxopropan-2-yl)(methyl)carbamate

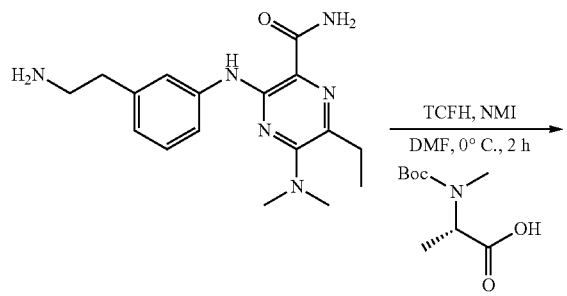

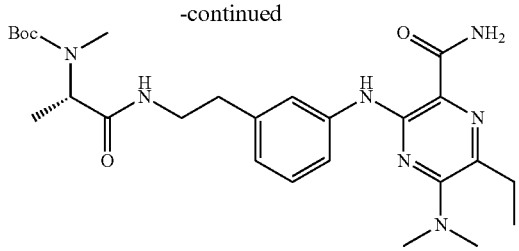

To a mixture of N-(tert-butoxycarbonyl)-N-methyl-L-alanine (631.22 mg, 3.11 mmol, 1.2 eq), 1-methylimidazole (2.12 g, 25.88 mmol, 2.06 mL, 10 eq), 3-((3-(2-aminoethyl)phenyl)amino)-5-(dimethylamino)-6-ethylpyrazine-2-carboxamide (850 mg, 2.59 mmol, 1 eq) and in DMF (6 mL) was added TCFH (1.09 g, 3.88 mmol, 1.5 eq) at 0° C. The mixture was stirred at 0° C. for 2 hrs. LCMS indicated the reaction was completed. The residue was poured into ice-water (w/w=1/1) (200 mL). The aqueous phase was extracted with ethyl acetate (100 mL*3). The combined organic phase was washed with saturated brine (100 mL*2), dried with anhydrous Na$_2$SO$_4$, filtered and concentrated in vacuum. The residue was purified by column chromatography (SiO$_2$, Petroleum ether:Ethyl acetate=1/1). to afford the title compound tert-butyl (S)-(1-((3-((3-carbamoyl-6-(dimethylamino)-5-ethylpyrazin-2-yl)amino)phenethyl)amino)-1-oxopropan-2-yl)(methyl)carbamate (1 g, 1.95 mmol, 91.34% yield) as a yellow oil. LC-MS (ES+, m/z): 514.4 [(M+H)$^+$]; Rt=0.892 min.

Step 3: (S)-5-(dimethylamino)-6-ethyl-3-((3-(2-(2-(methylamino)propanamido)ethyl)phenyl)amino)pyrazine-2-carboxamide

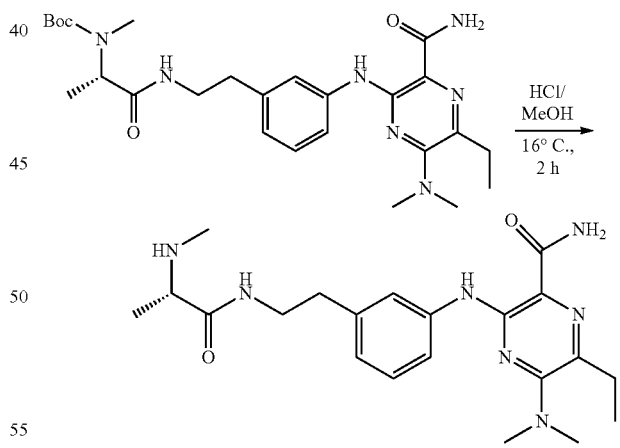

To a solution of tert-butyl (S)-(1-((3-((3-carbamoyl-6-(dimethylamino)-5-ethylpyrazin-2-yl)amino)phenethyl)amino)-1-oxopropan-2-yl)(methyl)carbamate (700 mg, 1.36 mmol, 1 eq) in HCl/MeOH (60 mL). The mixture was stirred at 16° C. for 2 hrs. LCMS indicated the reaction was completed. The crude was concentrated under reduced pressure to afford (S)-5-(dimethylamino)-6-ethyl-3-((3-(2-(2-(methylamino)propanamido)ethyl)phenyl)amino)pyrazine-2-carboxamide (700 mg, crude) as yellow solid. LC-MS (ES+, m/z): 414.3 [(M+H)$^+$]; Rt=0.690 min.

Note: HCl/MeOH (4 M): HCl was bubbled into a solution MeOH at 0° C. for 0.5 h. Then, the solution was weighed to obtained the HCl/MeOH (4 M).

Step 4: (S)-5-(dimethylamino)-6-ethyl-3-((3-(2-(2-(N-methylacrylamido)propanamido)ethyl)phenyl)amino)pyrazine-2-carboxamide

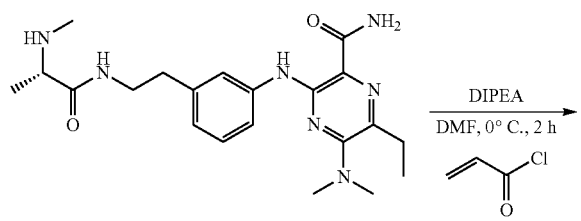

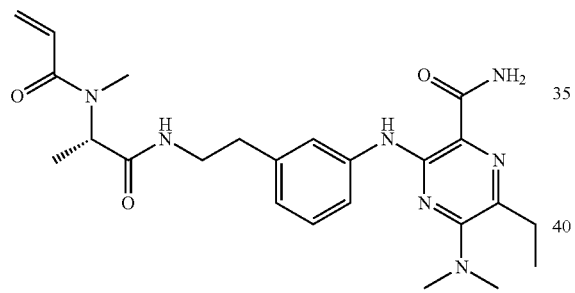

To a solution of (S)-5-(dimethylamino)-6-ethyl-3-((3-(2-(2-(methylamino)propanamido)ethyl)phenyl)amino)pyrazine-2-carboxamide (700 mg, 1.69 mmol, 1 eq) in DMF (2 mL) at ice bath. The resulting mixture was stirred at 0° C., DIEA (1.09 g, 8.46 mmol, 1.47 mL, 5 eq), and then acryloyl chloride (183.86 mg, 2.03 mmol, 165.64 µL, 1.2 eq) were added. The mixture was stirred at 0° C. for 2 hrs. LCMS indicated the reaction was completed. The crude mixture was purified by prep-HPLC column: Waters Xbridge BEH C18 100*30 mm*10 um; mobile phase: [water (NH₄HCO₃)-ACN]; B %: 30%-60%, 8 min to afford (S)-5-(dimethylamino)-6-ethyl-3-((3-(2-(2-(N-methylacrylamido)propanamido)ethyl)phenyl)amino)pyrazine-2-carboxamide (150 mg, 320.81 µmol, 18.95% yield) as yellow solid. ¹H NMR (400 MHz, DMSO-d₆) δ=11.11 (s, 1H), 8.10-7.82 (m, 1H), 7.75 (br d, J=2.4 Hz, 1H), 7.56 (s, 1H), 7.46 (br s, 2H), 7.20 (t, J=7.8 Hz, 1H), 6.79 (d, J=7.6 Hz, 1H), 6.71 (dd, J=10.3, 16.5 Hz, 1H), 6.15-6.01 (m, 1H), 5.70-5.58 (m, 1H), 4.56 (br s, 1H), 3.30-3.22 (m, 2H), 3.07 (s, 6H), 2.86 (s, 2H), 2.79-2.67 (m, 5H), 1.27-1.15 (m, 6H). LC-MS (ES+, m/z): 468.3 [(M+H)⁺]; Rt=2.535 min; HRMS: 468.2704.

Example 15 (Compound 219)

(E)-5-cyclopropyl-3-((3-(2-(2-(4-(dimethylamino)-N-methylbut-2-enamido) acetamido) ethyl) phenyl) amino)-6-ethylpyrazine-2-carboxamide Step 1: tert-butyl (3-((3-carbamoyl-6-cyclopropyl-5-ethylpyrazin-2-yl) amino) phenethyl) carbamate

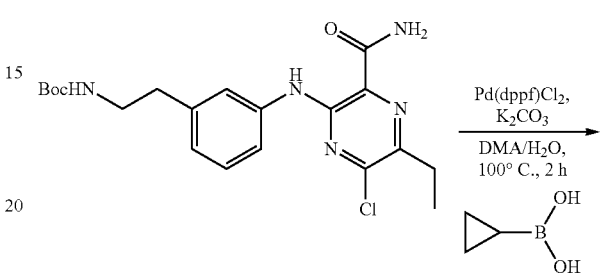

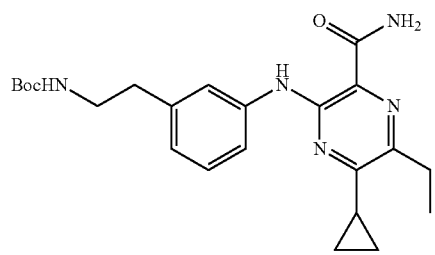

To a solution of tert-butyl (3-((3-carbamoyl-6-chloro-5-ethylpyrazin-2-yl) amino) phenethyl) carbamate (1 g, 2.38 mmol, 1 eq) in DMA (10 mL) was added K₂CO₃ (1.15 g, 8.34 mmol, 3.5 eq) and Pd(dppf)Cl₂ (1.74 g, 2.38 mmol, 1 eq), cyclopropylboronic acid (245.48 mg, 2.86 mmol, 1.2 eq). The mixture was stirred at 100° C. for 2 hours under N₂. LCMS showed the reaction was completed. The reaction mixture was quenched by addition water (50 mL) at 25° C., The reaction mixture was poured into saturated EDTA (50 mL) and stirred 60 min, then extracted with EtOAc (30 mL*3). The combined organic layers were washed with saturated brine (20 mL*2), dried over Na₂SO₄, filtered and concentrated under reduced pressure to give a residue. The residue was purified by column chromatography (SiO₂, Petroleum ether/Ethyl acetate=10/1 to 5/1) to give tert-butyl (3-((3-carbamoyl-6-cyclopropyl-5-ethylpyrazin-2-yl) amino) phenethyl) carbamate as yellow solid (1 g, 2.04 mmol, 85.85% yield, 87% purity). ¹H NMR (400 MHz, DMSO-d₆) δ=11.06-11.00 (m, 1H), 8.13-8.09 (m, 1H), 7.81 (br d, J=1.5 Hz, 1H), 7.41 (s, 1H), 7.26 (s, 1H), 7.21 (t, J=7.8 Hz, 1H), 6.81 (br d, J=7.5 Hz, 1H), 4.07-3.97 (m, 1H), 3.19-3.12 (m, 2H), 2.92-2.85 (m, 2H), 2.67 (br t, J=7.3 Hz, 2H), 2.31-2.23 (m, 1H), 1.35-1.15 (m, 12H), 1.13-1.06 (m, 4H). LC-MS (ES⁺, m/z): 426.2 [(M+H)⁺]; Rt=0.928 min.

Step 2: 3-((3-(2-aminoethyl)phenyl)amino)-5-cyclopropyl-6-ethylpyrazine-2-carboxamide hydrochloride

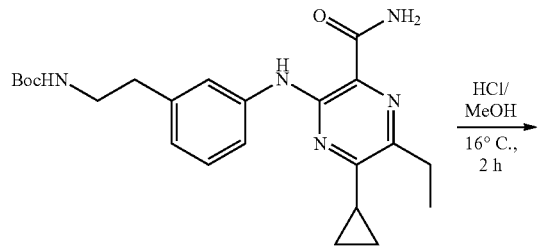

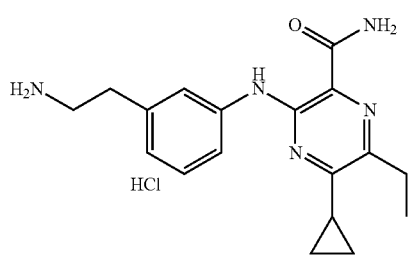

To tert-butyl (3-((3-carbamoyl-6-cyclopropyl-5-ethylpyrazin-2-yl) amino) phenethyl) carbamate (1 g, 2.35 mmol, 1 eq) was added HCl/MeOH (4 M, 25.00 mL, 42.55 eq). The mixture was stirred at 16° C. for 2 hours. LCMS showed the reaction was completed, the reaction mixture was concentrated under reduced pressure to give 3-((3-(2-aminoethyl)phenyl)amino)-5-cyclopropyl-6-ethylpyrazine-2-carboxamide hydrochloride as yellow solid (0.9 g, crude, HCl). $^1$H NMR (400 MHz, DMSO-d$_6$) δ=11.07 (s, 1H), 8.13 (br s, 4H), 7.88-7.78 (m, 1H), 7.59-7.48 (m, 1H), 7.46-7.40 (m, 1H), 7.33-7.22 (m, 1H), 6.95-6.81 (m, 1H), 3.10-2.99 (m, 2H), 2.96-2.83 (m, 4H), 2.37-2.21 (m, 1H), 1.27 (t, J=7.5 Hz, 3H), 1.14-1.03 (m, 4H)(HCl salt); LC-MS (ES$^+$, m/z): 362.2 [(M+H)$^+$]. Rt=0.711 min.

Note: HCl/MeOH (4 M): HCl gas was bubbled into a solution MeOH at 0° C. for 0.5 h.

Step 3: (E)-5-cyclopropyl-3-((3-(2-(2-(4-(dimethylamino)-N-methylbut-2-enamido) acetamido) ethyl) phenyl) amino)-6-ethylpyrazine-2-carboxamide

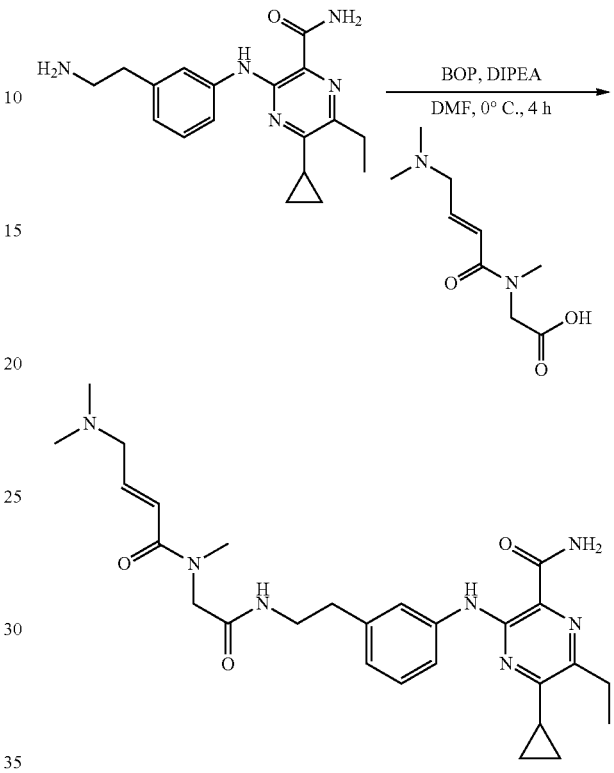

To a solution of 3-((3-(2-aminoethyl) phenyl) amino)-5-cyclopropyl-6-ethylpyrazine-2-carboxamide (80 mg, 245.85 μmol, 1 eq) in DMF (0.5 mL) was added DIEA (317.73 mg, 2.46 mmol, 428.21 μL, 10 eq) (E)-N-(4-(dimethylamino) but-2-enoyl)-N-methylglycine (172.29 mg, 344.18 μmol, 40% purity, 1.4 eq) and then BOP (152.23 mg, 344.18 μmol, 1.4 eq). The mixture was stirred at 0° C. for 4 hours. LCMS indicated the reaction was completed. The reaction mixture was quenched by addition water (50 mL), and then extracted with EtOAc (30 mL*3). The combined organic layers were washed with saturated brine (20 mL*2), dried over Na$_2$SO$_4$, filtered and concentrated under reduced pressure to give a residue. The residue was purified by prep-HPLC (column: Phenomenex Luna C18 150*30 mm*5 um; mobile phase: [water (TFA)-ACN]; B %: 15%-35%, 8 min) to give desired compound (E)-5-cyclopropyl-3-((3-(2-(2-(4-(dimethylamino)-N-methylbut-2-enamido) acetamido) ethyl) phenyl) amino)-6-ethylpyrazine-2-carboxamide (10.37 mg, 20.43 μmol, 8.31% yield, 100% purity) as yellow solid. $^1$H NMR (400 MHz, DMSO-d$_6$) δ=11.05 (d, J=2.3 Hz, 1H), 9.69 (br d, J=1.5 Hz, 1H), 8.23-7.99 (m, 2H), 7.84-7.78 (m, 1H), 7.50-7.38 (m, 2H), 7.27-7.20 (m, 1H), 6.91-6.67 (m, 2H), 6.63-6.49 (m, 1H), 4.04-3.94 (m, 2H), 3.92-3.79 (m, 2H), 3.31-3.27 (m, 2H), 3.06-3.02 (m, 2H), 2.94-2.87 (m, 2H), 2.80-2.66 (m, 9H), 2.32-2.24 (m, 1H), 1.27 (t, J=7.5 Hz, 3H), 1.13-1.04 (m, 4H), LC-MS (ES$^+$, m/z): 508.3 [(M+H)$^+$]. Rt=2.182 min. HRMS (EI): m/z [M]$^+$ found: 508.3000.

Example 16 (Compound 221)

(S,E)-3-((3-(2-(2-(4-(dimethylamino)-N-methylbut-2-enamido)propanamido) ethyl)phenyl)amino)-6-ethyl-5-(ethyl(methyl)amino)pyrazine-2-carboxamide

Step 1: tert-butyl (3-((3-carbamoyl-5-ethyl-6-(ethyl(methyl)amino)pyrazin-2-yl) amino)phenethyl)carbamate

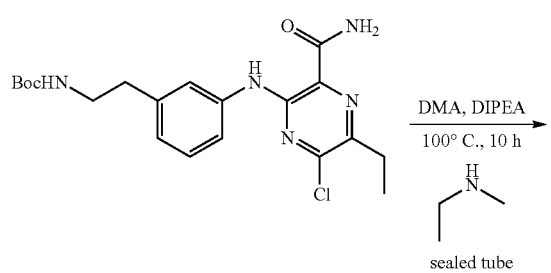

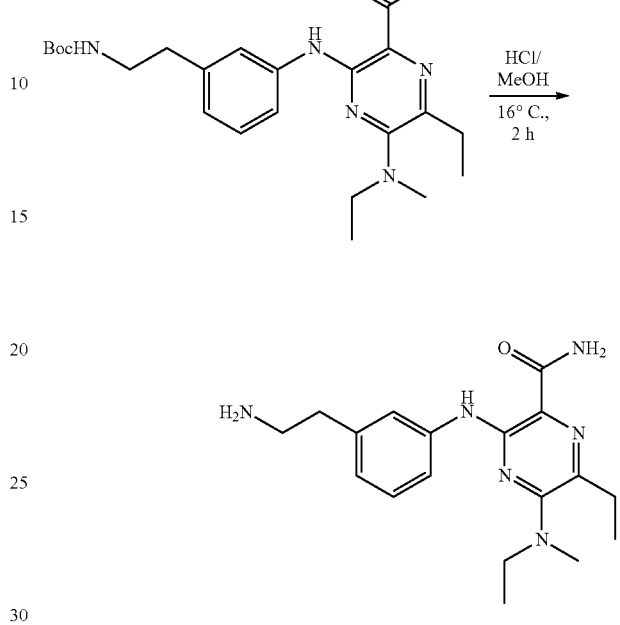

To a solution of tert-butyl (3-((3-carbamoyl-6-chloro-5-ethylpyrazin-2-yl)amino)phenethyl)carbamate in DMA (10 mL) was added DIPEA (1.54 g, 11.91 mmol, 2.07 mL, 10 eq) and N-methylethanamine (703.85 mg, 11.91 mmol, 1.02 mL, 10 eq) at 20° C. The mixture was stirred at 100° C. for 10 hr at sealed tube. LCMS showed the reaction was completed. The reaction was poured into water (15 mL) and extracted with EtOAc (20 mL*3). The organic layers were combined, washed with water (10 mL*3), saturated brine (10 mL*3), dried ($Na_2SO_4$), filtered and concentrated to give crude product. The residue was purified by column chromatography ($SiO_2$, Petroleum ether/Ethyl acetate=5/1 to 1/1) to afford tert-butyl (3-((3-carbamoyl-5-ethyl-6-(ethyl(methyl)amino)pyrazin-2-yl)amino)phenethyl)carbamate (430 mg, 971.63 μmol, 81.60% yield) as a yellow solid. $^1$H NMR (400 MHz, DMSO-$d_6$) δ=11.12-11.06 (m, 1H), 7.81-7.65 (m, 1H), 7.61-7.52 (m, 1H), 7.49-7.36 (m, 2H), 7.23-7.16 (m, 1H), 6.92-6.83 (m, 1H), 6.78 (d, J=7.4 Hz, 1H), 3.52-3.40 (m, 2H), 3.17-3.14 (m, 2H), 3.04 (s, 3H), 2.76-2.64 (m, 4H), 1.38-1.33 (m, 9H), 1.24-1.18 (m, 6H). LC-MS (ES+, m/z): 443.3 [(M+H)$^+$]; Rt=0.908 min.

Step 2: 3-((3-(2-aminoethyl)phenyl)amino)-6-ethyl-5-(ethyl(methyl)amino) pyrazine-2-carboxamide A mixture of tert-butyl (3-((3-carbamoyl-5-ethyl-6-(ethyl(methyl)amino) pyrazin-2-yl)amino)phenethyl)carbamate (400 mg, 903.85 μmol, 1 eq) in HCl/MeOH (40 mL) was stirred at 16° C. for 2 hrs. LCMS showed the reaction was completed. The reaction mixture was filtered and concentrated under reduced pressure to afford 3-((3-(2-aminoethyl)phenyl)amino)-6-ethyl-5-(ethyl(methyl)amino)pyrazine-2-carboxamide (410 mg, crude) as yellow solid. $^1$H NMR (400 MHz, DMSO-$d_6$) δ=11.14 (s, 1H), 7.75 (br s, 4H), 7.61-7.55 (m, 1H), 7.52 (s, 1H), 7.50-7.41 (m, 1H), 7.26 (t, J=7.8 Hz, 1H), 6.89-6.83 (m, 1H), 4.11 (br s, 2H), 3.46 (q, J=7.0 Hz, 2H), 3.04 (s, 3H), 2.88-2.81 (m, 2H), 2.74 (q, J=7.4 Hz, 2H), 1.25-1.18 (m, 6H). LC-MS (ES+, m/z): 343.1 [(M+H)$^+$]; Rt=0.703 min. HCl/MeOH (4 M): HCl was bubbled into a solution MeOH at 0° C. for 0.5 h.

Step 3 tert-butyl (S)-(1-((3-((3-carbamoyl-5-ethyl-6-(ethyl(methyl)amino)pyrazin-2-yl)amino)phenethyl) amino)-1-oxopropan-2-yl)(methyl)carbamate

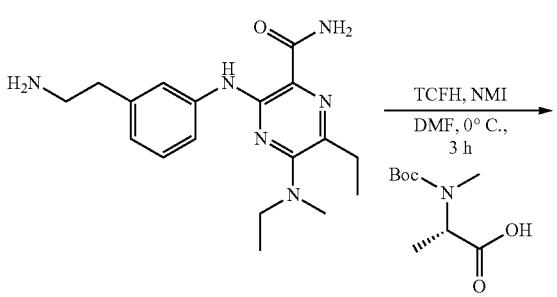

-continued

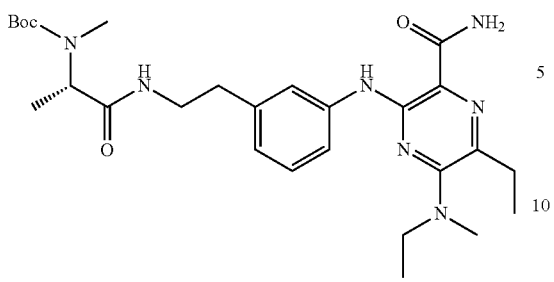

To a solution of 3-((3-(2-aminoethyl)phenyl)amino)-6-ethyl-5-(ethyl (methyl)amino)pyrazine-2-carboxamide (390 mg, 1.14 mmol, 1 eq) and N-(tert-butoxycarbonyl)-N-methyl-L-alanine (347.19 mg, 1.71 mmol, 1.5 eq) in DMF (4 mL) was added 1-methylimidazole (935.07 mg, 11.39 mmol, 907.84 μL, 10 eq), and then TCFH (479.32 mg, 1.71 mmol, 1.5 eq) at 0° C. The mixture was stirred at 0° C. for 3 hrs. LCMS showed the reaction was completed. The reaction was poured into water (10 mL) and extracted with EtOAc (15 mL*3). The organic layers were combined, washed with water (10 mL*3), saturated brine (10 mL*3), dried (Na$_2$SO$_4$), filtered and concentrated to give crude product. The residue was purified by column chromatography (SiO$_2$, Petroleum ether/Ethyl acetate=5/1 to 1/1) to afford tert-butyl (S)-(1-((3-((3-carbamoyl-5-ethyl-6-(ethyl (methyl)amino)pyrazin-2-yl)amino)phenethyl)amino)-1-oxopropan-2-yl)(methyl) carbamate (506 mg, 958.96 μmol, 84.20% yield) as yellow solid. $^1$H NMR (400 MHz, DMSO-d$_6$) δ=10.95-10.87 (m, 1H), 7.68-7.50 (m, 2H), 7.42-7.34 (m, 1H), 7.31-7.19 (m, 2H), 7.05-6.97 (m, 1H), 6.60 (d, J=7.5 Hz, 1H), 4.43-3.99 (m, 1H), 3.27 (q, J=7.0 Hz, 2H), 3.12-3.05 (m, 2H), 2.88-2.82 (m, 3H), 2.57-2.53 (m, 2H), 2.32-2.31 (m, 5H), 1.21-1.13 (m, 9H), 1.06-0.98 (m, 9H). LC-MS (ES+, m/z): 528.2 [(M+H)$^+$]; Rt=0.890 min.

Step 4: (S)-6-ethyl-5-(ethyl(methyl)amino)-3-((3-(2-(2-(methylamino) propanamido)ethyl)phenyl)amino) pyrazine-2-carboxamide

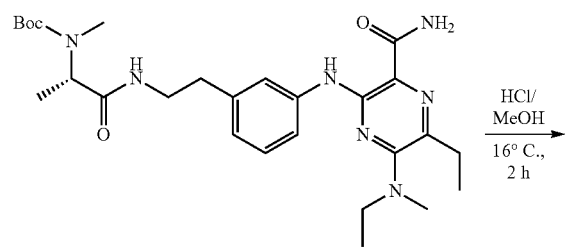

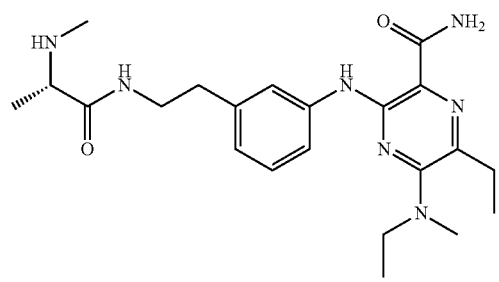

A mixture of tert-butyl (S)-(1-((3-((3-carbamoyl-5-ethyl-6-(ethyl(methyl) amino)pyrazin-2-yl)amino)phenethyl) amino)-1-oxopropan-2-yl)(methyl)carbamate (300 mg, 568.55 μmol, 1 eq) in HCl/MeOH (30 mL) was stirred at 16° C. for 2 hr. LCMS showed the reaction was completed. The reaction mixture was filtered and concentrated under reduced pressure to afford (S)-6-ethyl-5-(ethyl(methyl) amino)-3-((3-(2-(2-(methylamino)propanamido)ethyl)phenyl)amino)pyrazine-2-carboxamide (298 mg, crude) as yellow oil. LC-MS (ES+, m/z): 428.2 [(M+H)$^+$]; Rt=0.721 min. Note: HCl was bubbled into a solution MeOH at 0° C. for 0.5 h.

Step 5: (S,E)-3-((3-(2-(2-(4-(dimethylamino)-N-methylbut-2-enamido) propanamido)ethyl)phenyl) amino)-6-ethyl-5-(ethyl(methyl)amino)pyrazine-2-carboxamide

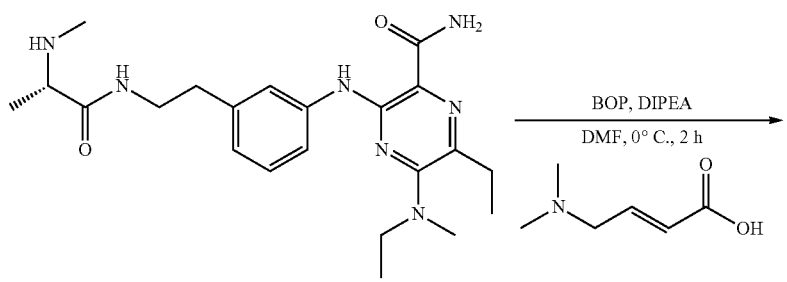

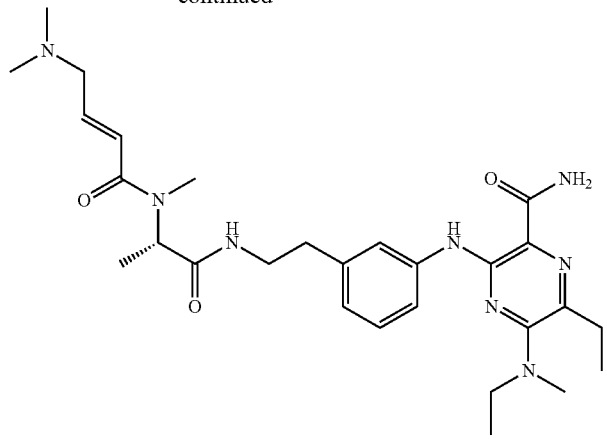

To a solution of (E)-4-(dimethylamino)but-2-enoic acid (131.41 mg, 1.02 mmol, 1.5 eq) in DMF (2.5 mL) was added DIPEA (876.63 mg, 6.78 mmol, 1.18 mL, 10 eq), (S)-6-ethyl-5-(ethyl(methyl)amino)-3-((3-(2-(2-(methylamino) propanamido) ethyl)phenyl)amino)pyrazine-2-carboxamide (290 mg, 678.30 μmol, 1 eq) and then BOP (450.00 mg, 1.02 mmol, 1.5 eq) at 0° C. The mixture was stirred at 0° C. for 2 hours. LCMS indicated the reaction was completed. The reaction mixture was filtered to give a residue. The residue was purified by prep-HPLC column: Phenomenex Luna C18 75*30 mm*3 um; mobile phase: [water (TFA)-ACN]; B %: 20%-50%, 7 min. to afford (S,E)-3-((3-(2-(2-(4-(dimethylamino)-N-methylbut-2-enamido)propanamido)ethyl) phenyl)amino)-6-ethyl-5-(ethyl(methyl)amino)pyrazine-2-carboxamide (89.46 mg, 165.14 μmol, 24.35% yield) as yellow solid. $^1$H NMR (400 MHz, DMSO-$d_6$) δ=11.16-11.05 (m, 1H), 10.10-9.61 (m, 1H), 8.15-7.85 (m, 1H), 7.74 (br d, J=1.9 Hz, 1H), 7.59-7.50 (m, 1H), 7.50-7.40 (m, 2H), 7.26-7.16 (m, 1H), 6.87-6.75 (m, 2H), 6.65-6.46 (m, 1H), 5.00-4.54 (m, 1H), 3.91-3.82 (m, 2H), 3.50-3.41 (m, 2H), 3.35-3.24 (m, 2H), 3.04 (s, 3H), 2.89 (s, 2H), 2.80-2.66 (m, 11H), 1.30-1.17 (m, 9H)(TFA salt). LC-MS (ES+, m/z): 539.3 [(M+H)$^+$]; Rt=2.205 min; HRMS (EI): m/z [M]$^+$ found: 539.3488

Example 17 (Compound 224)

(S,E)-5-cyclopropyl-6-ethyl-3-((3-(2-(2-(N-methyl-4-(methylamino)but-2-enamido)propanamido)ethyl) phenyl)amino)pyrazine-2-carboxamide Step 1: tert-butyl (S)-(1-((3-((3-carbamoyl-6-cyclopropyl-5-ethylpyrazin-2-yl) amino) phenethyl) amino)-1-oxopropan-2-yl) (methyl) carbamate

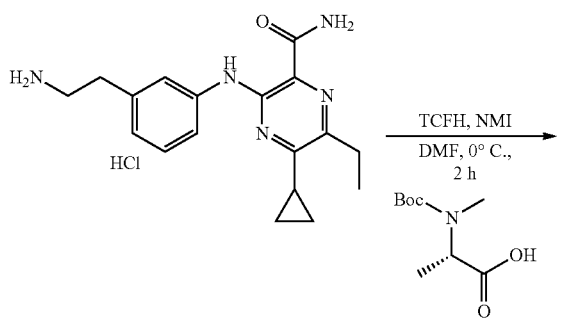

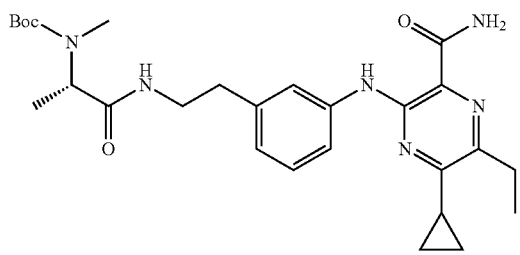

To a solution of 1-methylimidazole (1.51 g, 18.44 mmol, 1.47 mL, 10 eq), N-(tert-butoxycarbonyl)-N-methyl-L-alanine (449.68 mg, 2.21 mmol, 1.20 eq), 3-((3-(2-aminoethyl) phenyl)amino)-5-cyclopropyl-6-ethylpyrazine-2-carboxamide hydrochloride (600 mg, 1.84 mmol, 1 eq) in DMF (5 mL), TCFH (620.81 mg, 2.21 mmol, 1.2 eq) was added at 0° C. The mixture was stirred at 0° C. for 2 hrs. LCMS showed the reaction was completed. The reaction mixture was quenched by addition water (50 mL) at 25° C., and then extracted with EtOAc (30 mL*3). The combined organic layers were washed with saturated brine (20 mL*2), dried over Na$_2$SO$_4$, filtered and concentrated under reduced pressure to give a residue. The residue was purified by column chromatography (SiO$_2$, Petroleum ether/Ethyl acetate=10/1 to 5/1) to give tert-butyl (S)-(1-((3-((3-carbamoyl-6-cyclopropyl-5-ethylpyrazin-2-yl) amino) phenethyl) amino)-1-oxopropan-2-yl) (methyl) carbamate as yellow solid (400 mg, 721.86 μmol, 39.15% yield, 92.15% purity). $^1$H NMR (400 MHz, DMSO-d6) δ=11.05 (s, 1H), 8.14-8.09 (m, 1H), 7.98-7.93 (m, 1H), 7.82-7.80 (m, 1H), 7.42 (br s, 2H), 7.21 (t, J=7.9 Hz, 1H), 6.81 (d, J=7.5 Hz, 1H), 4.27 (br s, 1H), 4.02 (q, J=7.1 Hz, 2H), 2.93-2.88 (m, 4H), 2.71 (br s, 3H), 2.31-2.24 (m, 1H), 1.36-1.16 (m, 15H), 1.10-1.05 (m, 4H); LC-MS (ES$^+$, m/z): 511.4 [(M+H)$^+$]; Rt=0.889 min

211

Step 2: tert-butyl (S,E)-(4-((1-((3-((3-carbamoyl-6-cyclopropyl-5-ethylpyrazin-2-yl)amino) phenethyl)amino)-1-oxopropan-2-yl)(methyl)amino)-4-oxobut-2-en-1-yl)(methyl)carbamate

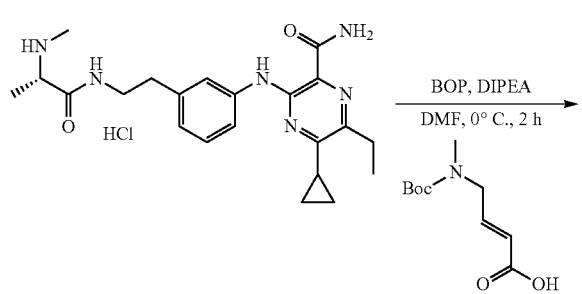

To a solution of (S)-5-cyclopropyl-6-ethyl-3-((3-(2-(2-(methylamino)propanamido)ethyl)phenyl)amino)pyrazine-2-carboxamide hydrochloride (300 mg, 671.18 μmol, 1 eq, HCl) and (E)-4-((tert-butoxycarbonyl)(methyl)amino)but-2-enoic acid (175.36 mg, 814.70 μmol, 1.21 eq) in DMF (3 mL) was added DIEA (433.73 mg, 3.36 mmol, 584.54 μL, 5 eq) and then BOP (296.85 mg, 671.18 μmol, 1 eq) at 0° C. The mixture was stirred at 0° C. for 2 hour. LC-MS showed the reaction was completed. The reaction mixture was quenched by addition water (100 mL) and then extracted with EtOAc (50 mL*3). The combined organic layers were washed with saturated brine (30 mL*2), dried over Na$_2$SO$_4$, filtered and concentrated under reduced pressure to give a residue. The residue was purified by prep-TLC (SiO$_2$, PE:EtOAc=0:1) to give tert-butyl (S,E)-(4-((1-((3-((3-carbamoyl-6-cyclopropyl-5-ethylpyrazin-2-yl)amino)phenethyl)amino)-1-oxopropan-2-yl)(methyl)amino)-4-oxobut-2-en-1-yl)(methyl)carbamate as yellow gum (200 mg, 329.09 μmol, 49.03% yield). LC-MS (ES+, m/z): 608.5 [(M+H)$^+$]. Rt=0.894 min.

212

Step 2: (S,E)-5-cyclopropyl-6-ethyl-3-((3-(2-(2-(N-methyl-4-(methylamino)but-2-enamido)propanamido)ethyl)phenyl)amino)pyrazine-2-carboxamide

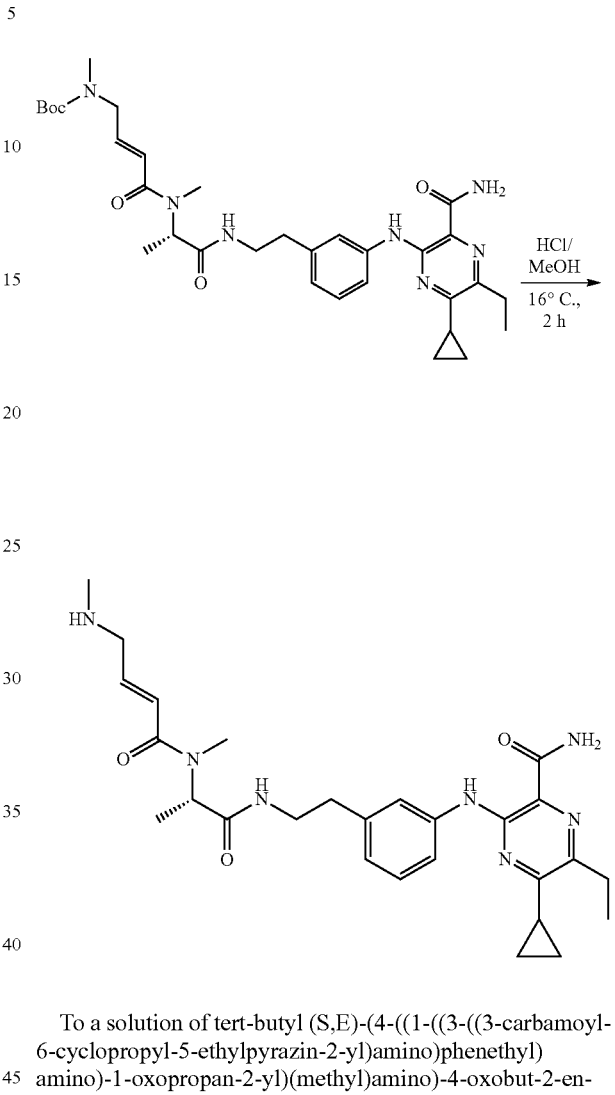

To a solution of tert-butyl (S,E)-(4-((1-((3-((3-carbamoyl-6-cyclopropyl-5-ethylpyrazin-2-yl)amino)phenethyl)amino)-1-oxopropan-2-yl)(methyl)amino)-4-oxobut-2-en-1-yl)(methyl)carbamate (200 mg, 329.09 μmol, 1 eq) was added HCl/MeOH (4 M, 82.27 μL, 1 eq). The mixture was stirred at 16° C. for 2 hours. LC-MS showed the reaction was completed. The reaction mixture was concentrated under reduced pressure to give a residue. The residue was purified by prep-HPLC (column: Phenomenex Luna C18 150*30 mm*5 um; mobile phase: [water (TFA)-ACN]; B %: 15%-45%, 8 min) to give compound (S,E)-5-cyclopropyl-6-ethyl-3-((3-(2-(2-(N-methyl-4-(methylamino)but-2-enamido)propanamido)ethyl)phenyl)amino)pyrazine-2-carboxamide as a yellow solid (60.74 mg, 97.33 μmol, 29.57% yield, 99.61% purity, TFA). $^1$H NMR (400 MHz, DMSO-d$_6$) δ=11.04 (s, 1H), 8.81 (br s, 2H), 8.22-7.87 (m, 2H), 7.86-7.77 (m, 1H), 7.49-7.37 (m, 2H), 7.21 (br t, J=7.7 Hz, 1H), 6.85-6.70 (m, 2H), 6.64-6.46 (m, 1H), 5.01-4.55 (m, 1H), 3.80-3.66 (m, 2H), 3.37 (br s, 2H), 2.96-2.84 (m, 4H), 2.77-2.65 (m, 3H), 2.63-2.53 (m, 3H), 2.34-2.23 (m, 1H), 1.31-1.19 (m, 6H), 1.14-1.03 (m, 4H)(TFA salt). LC-MS (ES+, m/z): 508.3 [(M+H)$^+$]. Rt=2.202 min;

Note: HCl/MeOH (4 M): HCl gas was bubbled into a solution MeOH at 0° C. for 0.5 h.

Example 18 (Compound 226)

(E)-3-((3-(2-(2-(4-(dimethylamino)-N-methylbut-2-enamido)acetamido)ethyl) phenyl)amino)-6-ethyl-5-methylpyrazine-2-carboxamide

Step 1: tert-butyl (E)-N-(4-(dimethylamino)but-2-enoyl)-N-methylglycinate

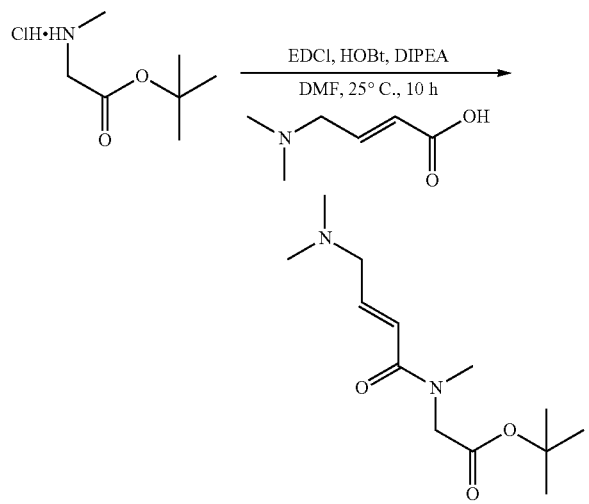

To a solution of (E)-4-(dimethylamino)but-2-enoic acid (1.52 g, 9.17 mmol, 2 eq, HCl) in DMF (5 mL) was added DIPEA (5.93 g, 45.85 mmol, 7.99 mL, 10 eq), tert-butyl methylglycinate (1.00 g, 4.58 mmol, 1 eq, HCl), HOBt (619.49 mg, 4.58 mmol, 1 eq) and EDCI (1.32 g, 6.88 mmol, 1.5 eq). The mixture was stirred at 25° C. for 10 hours. LCMS showed the reaction was completed. The reaction mixture was filtered and concentrated under reduced pressure to give a residue. The residue was purified by prep-HPLC column: C18 (250*50 mm*10 um); mobile phase: [water (NH₄HCO₃)-ACN]; B %: 15%-40%, 10 min. to afford tert-butyl (E)-N-(4-(dimethylamino)but-2-enoyl)-N-methylglycinate (540 mg, 2.11 mmol, 45.95% yield) as a brown oil. ¹H NMR (400 MHz, DMSO-d₆) δ=6.68-6.34 (m, 2H), 4.23-3.95 (m, 2H), 3.11-2.84 (m, 5H), 2.18-2.07 (m, 6H), 1.45-1.37 (m, 9H) LC-MS (ES+, m/z): 257.1 [(M+H)⁺]; Rt=1.329 min.

Step 2: (E)-N-(4-(dimethylamino)but-2-enoyl)-N-methylglycine

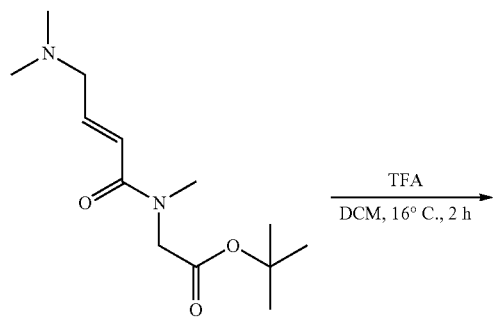

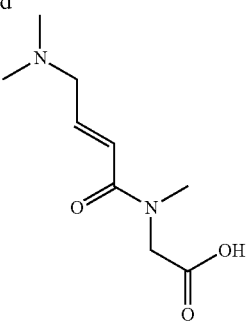

To a solution of tert-butyl (E)-N-(4-(dimethylamino)but-2-enoyl)-N-methylglycinate (270 mg, 1.05 mmol, 1 eq) in DCM (2 mL) was added TFA (3.08 g, 27.01 mmol, 2 mL, 25.65 eq). The mixture was stirred at 16° C. for 2 hours. LCMS showed the reaction was completed. The reaction mixture was concentrated under reduced pressure to afford (E)-N-(4-(dimethylamino)but-2-enoyl)-N-methylglycine (466 mg, crude) as a yellow oil. ¹H NMR (400 MHz, DMSO-d₆) δ=9.97 (br d, J=17.4 Hz, 1H), 6.97-6.48 (m, 2H), 4.28-4.02 (m, 2H), 3.95-3.82 (m, 2H), 3.10 (s, 3H), 2.76 (br d, J=13.4 Hz, 6H). LC-MS (ES+, m/z): 201.1 [(M+H)⁺]; Rt=0.089 min.

Step 3: (E)-3-((3-(2-(2-(4-(dimethylamino)-N-methylbut-2-enamido)acetamido) ethyl)phenyl)amino)-6-ethyl-5-methylpyrazine-2-carboxamide

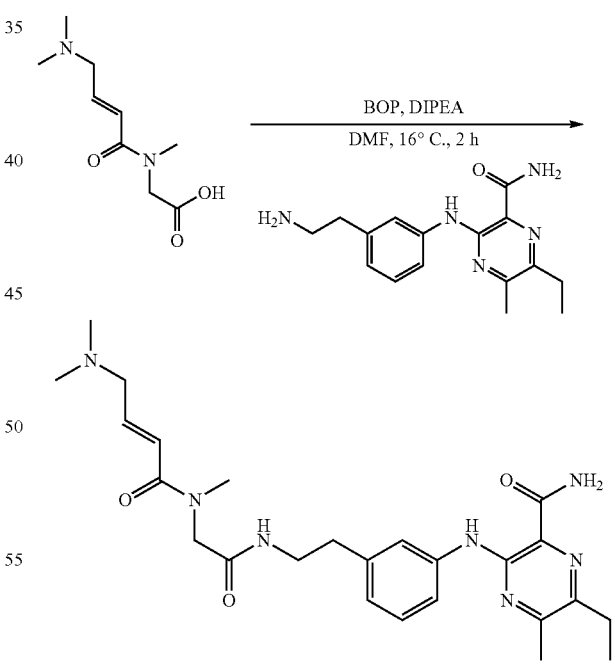

To a solution of (E)-N-(4-(dimethylamino)but-2-enoyl)-N-methylglycine (200.66 mg, 400.84 μmol, 40% purity, 1.5 eq) in DMF (1 mL) was added DIPEA (345.37 mg, 2.67 mmol, 465.46 μL, 10 eq), 3-((3-(2-aminoethyl)phenyl)amino)-6-ethyl-5-methylpyrazine-2-carboxamide (80 mg, 267.23 μmol, 1 eq) and then BOP (177.28 mg, 400.84 μmol, 1.5 eq). The mixture was stirred at 16° C. for 2 hours. LCMS indicated the reaction was completed. The reaction mixture was filtered to give a residue. The residue was purified by prep-HPLC column: C$_{18-11}$50*30 mm*5 um; mobile phase: [water (TFA)-ACN]; B %: 5%-50%, 8 min to afford (E)-3-((3-(2-(2-(4-(dimethylamino)-N-methylbut-2-enamido)acetamido)ethyl)phenyl)amino)-6-ethyl-5-methylpyrazine-2-carboxamide (84.28 mg, 174.48 μmol, 65.29% yield) as a yellow solid. $^1$H NMR (400 MHz, DMSO-d$_6$) δ=11.09-11.04 (m, 1H), 9.84-9.67 (m, 1H), 8.21 (br s, 2H), 7.89-7.83 (m, 1H), 7.72-7.63 (m, 1H), 7.47-7.41 (m, 1H), 7.27-7.21 (m, 1H), 6.91-6.68 (m, 2H), 6.63-6.48 (m, 1H), 4.03-3.95 (m, 2H), 3.91-3.81 (m, 2H), 3.36-3.29 (m, 2H), 3.04 (s, 2H), 2.80-2.70 (m, 11H), 2.50-2.47 (m, 3H), 1.26-1.21 (m, 3H) (TFA salt). LC-MS (ES+, m/z): 482.3 [(M+H)$^+$]; Rt=2.056 min. HRMS (EI): m/z [M+H]+: 482.2882.

Example 19 (Compound 227)

(S,E)-3-((3-(2-(2-(4-(azetidin-1-yl)-N-methylbut-2-enamido)propanamido)ethyl) phenyl)amino)-6-ethyl-5-methylpyrazine-2-carboxamide Step 1 tert-butyl (S,E)-(4-((1-((3-((3-carbamoyl-5-ethyl-6-methylpyrazin-2-yl)amino)phenethyl) amino)-1-oxopropan-2-yl)(methyl)amino)-4-oxobut-2-en-1-yl) (methyl)carbamate

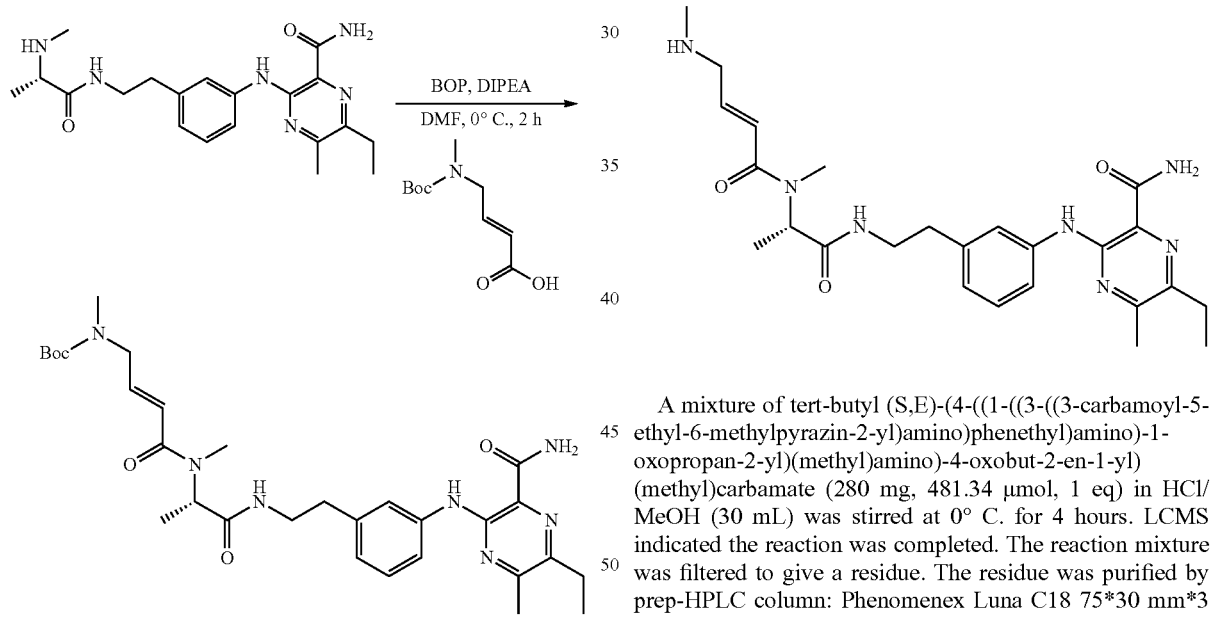

To a solution of (E)-4-((tert-butoxycarbonyl)(methyl) amino)but-2-enoic acid (279.92 mg, 1.30 mmol, 2 eq) in DMF (3 mL) was added DIPEA (840.39 mg, 6.50 mmol, 1.13 mL, 10 eq), (S)-6-ethyl-5-methyl-3-((3-(2-(2-(methylamino)propanamido) ethyl)phenyl)amino)pyrazine-2-carboxamide (250 mg, 650.24 μmol, 1 eq) and then BOP (431.38 mg, 975.36 μmol, 1.5 eq) at 0° C. The mixture was stirred at 0° C. for 2 hours. LCMS indicated the reaction was completed. The reaction was poured into water (5 mL) and extracted with EtOAc (10 mL*3). The organic layers were combined, washed with water (10 mL*3), saturated brine (10 mL*3), dried (Na$_2$SO$_4$), filtered and concentrated to give crude product. The residue was purified by column chromatography (SiO$_2$, Petroleum ether/Ethyl acetate=5/1 to 1/1) to afford tert-butyl (S,E)-(4-((1-((3-((3-carbamoyl-5-ethyl-6-methylpyrazin-2-yl)amino)phenethyl)amino)-1-oxopropan-2-yl)(methyl) amino)-4-oxobut-2-en-1-yl)(methyl)carbamate (300 mg, 515.73 μmol, 79.31% yield) as yellow solid. LC-MS (ES+, m/z): 582.3 [(M+H)$^+$]; Rt=0.782 min.

Step 2: (S,E)-6-ethyl-5-methyl-3-((3-(2-(2-(N-methyl-4-(methylamino)but-2-enamido)propanamido)ethyl)phenyl)amino)pyrazine-2-carboxamide

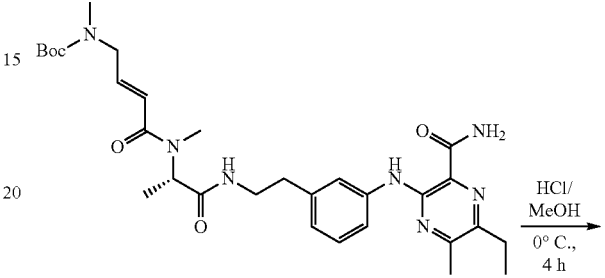

A mixture of tert-butyl (S,E)-(4-((1-((3-((3-carbamoyl-5-ethyl-6-methylpyrazin-2-yl)amino)phenethyl)amino)-1-oxopropan-2-yl)(methyl)amino)-4-oxobut-2-en-1-yl) (methyl)carbamate (280 mg, 481.34 μmol, 1 eq) in HCl/MeOH (30 mL) was stirred at 0° C. for 4 hours. LCMS indicated the reaction was completed. The reaction mixture was filtered to give a residue. The residue was purified by prep-HPLC column: Phenomenex Luna C18 75*30 mm*3 um; mobile phase: [water (TFA)-ACN]; B %: 15%-45%, 7 min to afford (S,E)-6-ethyl-5-methyl-3-((3-(2-(2-(N-methyl-4-(methylamino)but-2-enamido)propanamido)ethyl)phenyl)amino)pyrazine-2-carboxamide (96.08 mg, 196.89 μmol, 40.90% yield) as yellow solid. $^1$H NMR (400 MHz, DMSO-d$_6$) δ=11.08-11.04 (m, 1H), 8.73-8.52 (m, 2H), 8.19-8.12 (m, 1H), 8.10-7.90 (m, 1H), 7.89-7.83 (m, 1H), 7.69-7.64 (m, 1H), 7.46-7.41 (m, 1H), 7.28-7.19 (m, 1H), 6.85-6.79 (m, 1H), 6.79-6.69 (m, 1H), 6.63-6.45 (m, 1H), 5.01-4.53 (m, 1H), 3.77-3.67 (m, 2H), 3.32-3.26 (m, 2H), 2.93-2.87 (m, 2H), 2.77-2.67 (m, 5H), 2.59-2.54 (m, 3H), 2.49-2.47 (m, 3H), 1.30-1.18 (m, 6H). LC-MS (ES+, m/z): 482.3 [(M+H)$^+$]; Rt=2.084 min; HRMS (EI): m/z [M]$^+$ found: 482.2899. Note: HCl was bubbled into a solution MeOH at 0° C. for 0.5 h.

Example 20 (Compound 228)

(S,E)-5-cyclopropyl-3-((3-(2-(2-(4-(dimethylamino)-N-methylbut-2-enamido)propanamido)ethyl)phenyl)amino)-6-methylpyrazine-2-carboxamide Step 1: (S,E)-5-cyclopropyl-3-((3-(2-(2-(4-(dimethylamino)-N-methylbut-2-enamido)propanamido)ethyl)phenyl)amino)-6-methylpyrazine-2-carboxamide

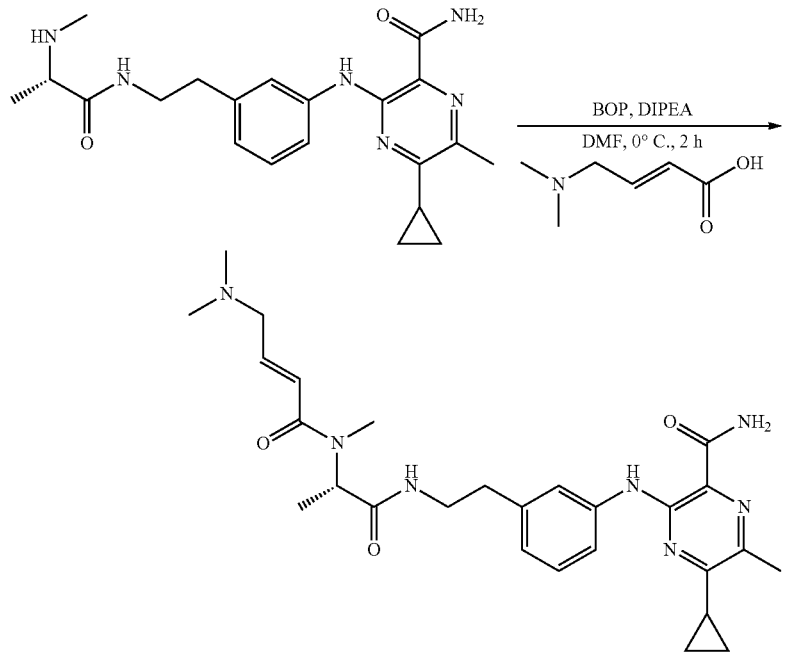

A mixture of (E)-4-(dimethylamino)but-2-enoic acid (573.80 mg, 3.46 mmol, 1.5 eq, HCl) in DMF (8 mL), DIPEA (2.99 g, 23.10 mmol, 10 eq), (S)-5-cyclopropyl-6-methyl-3-((3-(2-(2-(methylamino)propanamido)ethyl)phenyl)amino) pyrazine-2-carboxamide (1 g, 2.31 mmol, 1 eq, HCl) was added at 0° C., and then BOP (1.53 g, 3.46 mmol, 1.5 eq) was added. The mixture was stirred at 0° C. for 2 h. LCMS indicated the reaction was complete. The mixture was concentrated to dryness. The mixture was purified by prep-HPLC (column: Phenomenex luna C18 250*50 mm*10 μm; mobile phase: [water (TFA)-ACN]; B %: 20%-50%, 10 min) to give (S,E)-5-cyclopropyl-3-((3-(2-(2-(4-(dimethylamino)-N-methylbut-2-enamido) propanamido) ethyl)phenyl)amino)-6-methylpyrazine-2-carboxamide (320 mg, 622.44 μmol, 26.95% yield) as yellow solid. $^1$H NMR (400 MHz, DMSO-d$_6$) δ=11.05 (s, 1H), 9.70 (br s, 1H), 8.20 (br s, 1H), 8.11-7.88 (m, 1H), 7.80 (br s, 1H), 7.54-7.36 (m, 2H), 7.22 (brt, J=7.8 Hz, 1H), 6.81 (q, J=8.0 Hz, 2H), 6.66-6.45 (m, 1H), 5.05-4.51 (m, 1H), 3.98-3.80 (m, 2H), 3.45-3.28 (m, 2H), 2.90 (s, 2H), 2.81-2.66 (m, 9H), 2.56 (s, 3H), 2.30-2.20 (m, 1H), 1.33-1.18 (m, 3H), 1.14-1.01 (m, 4H)(TFA, salt); LCMS (ES+, m/z): 508.2 [(M+H)$^+$]; Rt=2.117 min; HRMS (EI): m/z [M]$^+$ found: 508.3014

Example 21 (Compound 230)

(S,E)-3-((3-(2-(2-(4-(azetidin-1-yl)-N-methylbut-2-enamido)propanamido)ethyl)phenyl)amino)-5-(dimethylamino)-6-methylpyrazine-2-carboxamide Step 1: (S,E)-3-((3-(2-(2-(4-bromo-N-methylbut-2-enamido)propanamido)ethyl) phenyl)amino)-5-(dimethylamino)-6-methylpyrazine-2-carboxamide

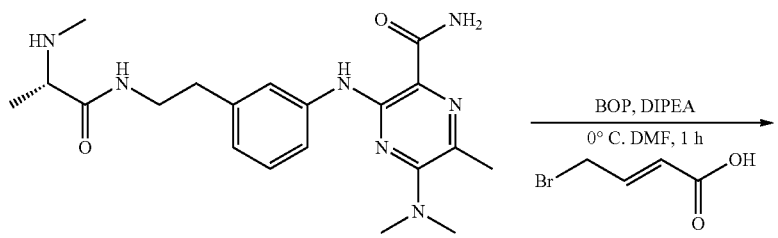

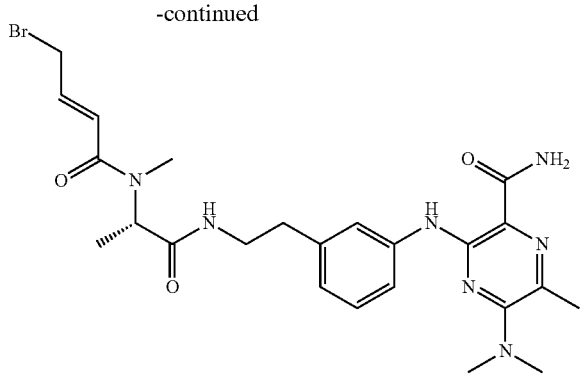

To a mixture of (E)-4-bromobut-2-enoic acid (45.43 mg, 275.35 µmol, 1.1 eq) in DMF (1 mL) was added DIPEA (323.52 mg, 2.50 mmol, 10 eq) and (S)-5-(dimethylamino)-6-methyl-3-((3-(2-(2-(methylamino)propanamido)ethyl)phenyl) amino)pyrazine-2-carboxamide (100 mg, 250.32 µmol, 1 eq), finally added BOP (166.07 mg, 375.48 µmol, 1.5 eq) in one portion at 0° C. under $N_2$. The mixture was stirred at 0° C. for 1 hour. LCMS showed the reaction was completed. The residue was poured into water (20 mL). The aqueous phase was extracted with ethyl acetate (20 mL*3). The combined organic phase was washed with saturated brine (20 mL), dried with anhydrous $Na_2SO_4$, filtered and concentrated in vacuum. The residue was purified by column chromatography ($SiO_2$, Petroleum ether:Ethyl acetate=0:1). Compound (S,E)-3-((3-(2-(2-(4-bromo-N-methylbut-2-enamido)propanamido)ethyl)phenyl) amino)-5-(dimethylamino)-6-methylpyrazine-2-carboxamide (100 mg, 183.00 µmol, 73.11% yield) was obtained as a yellow solid. LC-MS (ES+, m/z): 546.3 [(M+H)$^+$]. Rt=0.804 min.

Step 2: (S,E)-3-((3-(2-(2-(4-(azetidin-1-yl)-N-methylbut-2-enamido)propanamido) ethyl)phenyl) amino)-5-(dimethylamino)-6-methylpyrazine-2-carboxamide

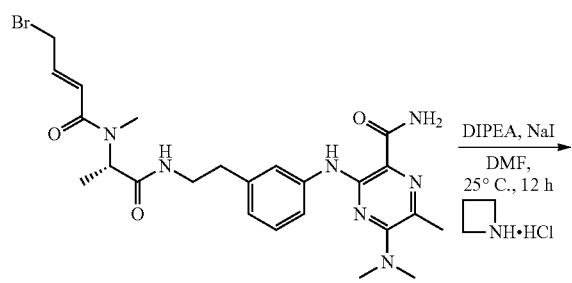

DIPEA, NaI
DMF,
25° C., 12 h

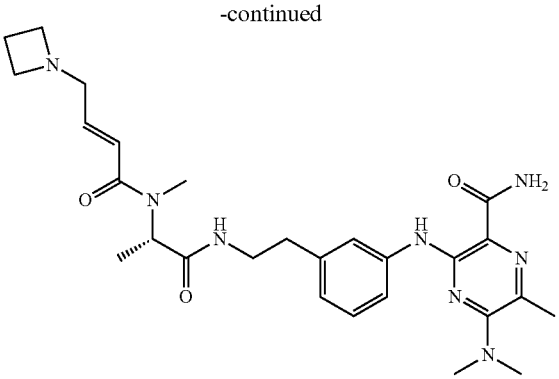

To a mixture of azetidine hydrochloride (18.83 mg, 201.30 µmol, 1.1 eq) in DMA (2 mL) was added NaI (82.29 mg, 548.99 µmol, 3 eq) and DIPEA (236.51 mg, 1.83 mmol, 10 eq), finally added (S,E)-3-((3-(2-(2-(4-bromo-N-methylbut-2-enamido)propanamido)ethyl)phenyl) amino)-5-(dimethylamino)-6-methylpyrazine-2-carboxamide (100 mg, 183.00 µmol, 1 eq) in one portion at 25° C. under $N_2$. The mixture was stirred at 25° C. for 12 hrs. LCMS showed the reaction was completed. The residue was purified by prep-HPLC (column: Phenomenex C18 80*30 mm*3 um; mobile phase: [water (TFA)-ACN]; B %: 15%-45%, 7 min). Compound (S,E)-3-((3-(2-(2-(4-(azetidin-1-yl)-N-methylbut-2-enamido)propanamido)ethyl)phenyl)amino)-5-(dimethylamino)-6-methylpyrazine-2-carboxamide (10.27 mg, 19.65 µmol, 10.74% yield) was obtained as a yellow solid. $^1$H NMR (400 MHz, DMSO-$d_6$) δ=11.15-11.09 (m, 1H), 10.03-9.91 (m, 1H), 8.11-7.90 (m, 1H), 7.83-7.77 (m, 1H), 7.54 (s, 1H), 7.51-7.41 (m, 2H), 7.24-7.17 (m, 1H), 6.81-6.76 (m, 1H), 6.75-6.68 (m, 1H), 6.51-6.33 (m, 1H), 4.95-4.57 (m, 1H), 4.18-4.10 (m, 2H), 4.03-3.89 (m, 4H), 3.28 (td, J=6.6, 13.3 Hz, 2H), 3.10 (s, 6H), 2.89 (s, 2H), 2.74-2.64 (m, 3H), 2.47 (s, 3H), 2.42-2.30 (m, 2H), 1.29-1.19 (m, 3H)(TFA salt) LC-MS (ES+, m/z): 523.3 [(M+H)$^+$]. Rt=2.046 min; HRMS (EI): m/z [M]$^+$ found: 523.3141.

Example 22 (Compound 232)

(S,E)-3-((3-(2-(2-(4-(dimethylamino)-N-methylbut-2-enamido) propanamido) ethyl) phenyl) amino)-5-(isopropyl (methyl) amino)-6-methylpyrazine-2-carboxamide Step 1: (S,E)-3-((3-(2-(2-(4-(dimethylamino)-N-methylbut-2-enamido) propanamido) ethyl) phenyl) amino)-5-(isopropyl (methyl) amino)-6-methylpyrazine-2-carboxamide

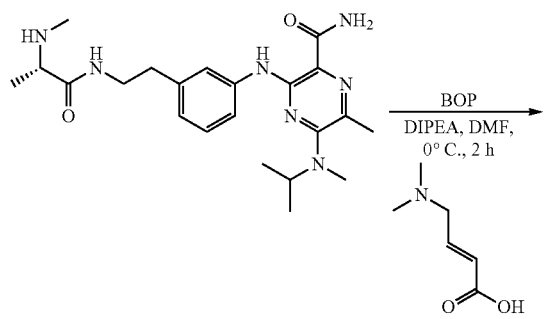

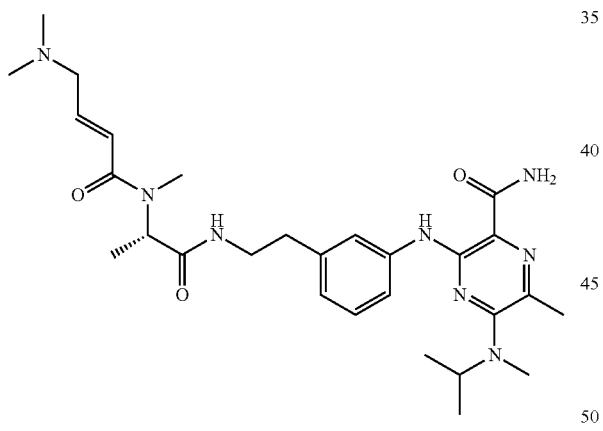

To a solution of (E)-4-(dimethylamino)but-2-enoic acid (1.49 g, 11.51 mmol, 1.2 eq) in DMF (40 mL) was added DIEA (12.39 g, 95.90 mmol, 16.70 mL, 10 eq), (S)-5-(isopropyl (methyl) amino)-6-methyl-3-((3-(2-(2-(methylamino) propanamido) ethyl) phenyl) amino) pyrazine-2-carboxamide (4.1 g, 9.59 mmol, 1 eq), and then added BOP (5.09 g, 11.51 mmol, 1.2 eq). The mixture was stirred at 0° C. for 2 hr. LCMS showed the reaction was completed. The reaction mixture was quenched by addition water (120 mL), and then extracted with EtOAc (90 mL*3). The combined organic layers were washed with saturated brine (100 mL*2), dried over $Na_2SO_4$, filtered and concentrated under reduced pressure to give a residue. The residue was purified by column chromatography ($SiO_2$, DCM/MeOH=30/1 to 5/1) to give (S,E)-3-((3-(2-(2-(4-(dimethylamino)-N-methylbut-2-enamido) propanamido) ethyl) phenyl) amino)-5-(isopropyl (methyl) amino)-6-methylpyrazine-2-carboxamide as yellow solid (96.13 mg, 198.40 µmol, 32.58% yield). $^1$H NMR (400 MHz, DMSO-$d_6$) δ=11.11 (s, 1H), 8.07 (br s, 1H), 7.81-7.77 (m, 1H), 7.55-7.51 (m, 1H), 7.46-7.41 (m, 2H), 7.22-7.16 (m, 1H), 6.80-6.75 (m, 1H), 6.62-6.49 (m, 2H), 5.02-4.94 (m, 1H), 4.34 (quin, J=6.6 Hz, 1H), 3.32-3.24 (m, 2H), 3.16-3.08 (m, 2H), 2.91-2.88 (m, 3H), 2.86-2.83 (m, 2H), 2.67 (br s, 3H), 2.44 (s, 3H), 2.24-2.20 (m, 6H), 1.24-1.16 (m, 9H). LC-MS (ES$^+$, m/z): 539.4 [(M+H)+]; Rt=2.178 min; HRMS (EI): m/z [M]$^+$ found: 539.3435.

Example 23 (Compound 233)

(S,E)-5-(dimethylamino)-3-((3-(2-(2-(4-(dimethylamino)-N-methylbut-2-enamido)propanamido)ethyl) phenyl)amino)-6-methylpyrazine-2-carboxamide Step 1: (E)-1-(4-(dimethylamino)-N-methylbut-2-enamido)cyclobutane-1-carboxylic acid

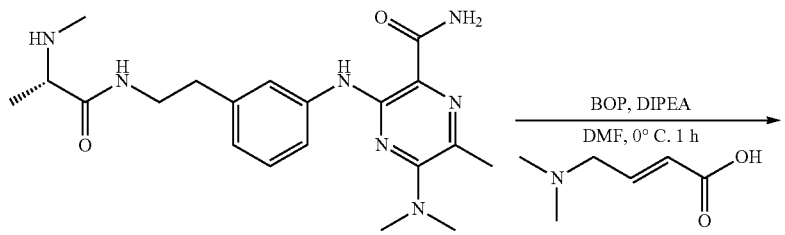

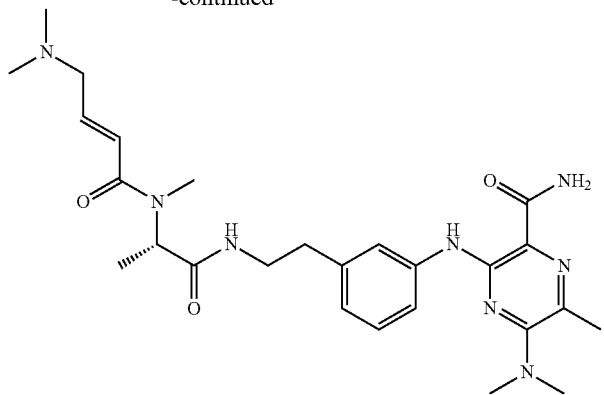

To a mixture of (E)-4-(dimethylamino)but-2-enoic acid (41.46 mg, 250.32 μmol, 1 eq) in DMF (1 mL) was added DIPEA (323.51 mg, 2.50 mmol, 10 eq) and (S)-5-(dimethylamino)-6-methyl-3-((3-(2-(2-(methylamino)propanamido)ethyl)phenyl) amino)pyrazine-2-carboxamide (100 mg, 250.32 μmol, 1 eq) finally added BOP (166.07 mg, 375.48 μmol, 1.5 eq) in one portion at 0° C. under $N_2$. The mixture was stirred at 0° C. for 1 h. LCMS showed the reaction was completed. The residue was purified by prep-HPLC (column: Phenomenex C18 80*30 mm*3 um; mobile phase: [water (TFA)-ACN]; B %: 10%-40%, 7 min). Compound (S,E)-5-(dimethylamino)-3-((3-(2-(2-(4-(dimethylamino)-N-methylbut-2-enamido)propanamido)ethyl)phenyl)amino)-6-methylpyrazine-2-carboxamide (10.43 mg, 20.43 μmol, 8.16% yield) was obtained as a white solid. $^1$H NMR (400 MHz, DMSO-$d_6$) δ=11.15-11.10 (m, 1H), 9.81-9.69 (m, 1H), 8.12-7.90 (m, 1H), 7.83-7.79 (m, 1H), 7.55-7.53 (m, 1H), 7.51-7.41 (m, 2H), 7.20 (br t, J=7.7 Hz, 1H), 6.86-6.75 (m, 2H), 6.63-6.45 (m, 1H), 5.02-4.50 (m, 1H), 3.91-3.80 (m, 2H), 3.35-3.24 (m, 2H), 3.12-3.09 (m, 6H), 2.89 (s, 2H), 2.80-2.75 (m, 6H), 2.72-2.65 (m, 3H), 2.47 (s, 3H), 1.31-1.18 (m, 3H)(TFA salt). LC-MS (ES+, m/z): 511.3 [(M+H)$^+$]. Rt=2.031 min; HRMS (EI): m/z [M]$^+$ found: 511.3134.

Example 24 (Compound 241)

(E)-5-cyclopropyl-3-((3-(2-(2-(4-(dimethylamino)-N-methylbut-2-enamido) acetamido)ethyl)phenyl) amino)-6-methylpyrazine-2-carboxamide Step 1: (E)-5-cyclopropyl-3-((3-(2-(2-(4-(dimethylamino)-N-methylbut-2-enamido) acetamido)ethyl) phenyl)amino)-6-methylpyrazine-2-carboxamide

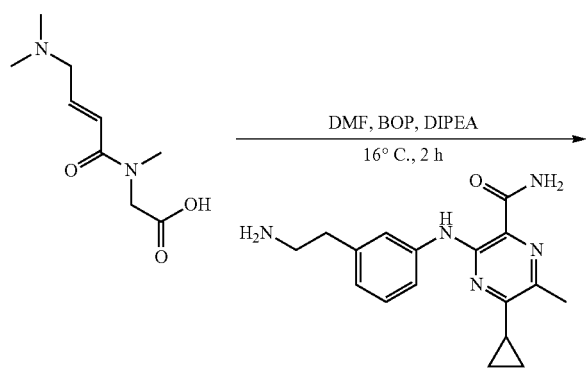

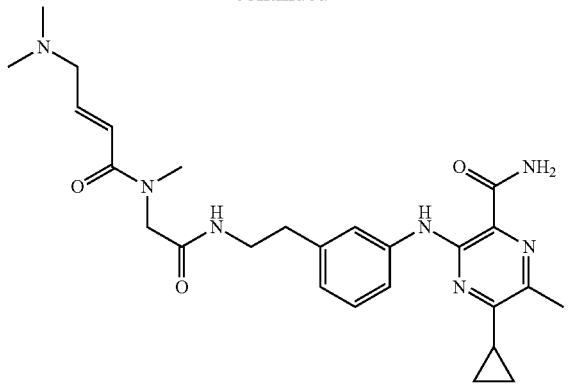

To a solution of (E)-N-(4-(dimethylamino)but-2-enoyl)-N-methylglycine (500.00 mg, 636.42 μmol, 40% purity, 9.91e-1 eq, TFA) in DMF (3 mL) was added DIPEA (830.13 mg, 6.42 mmol, 1.12 mL, 10 eq), 3-((3-(2-aminoethyl) phenyl)amino)-5-cyclopropyl-6-methylpyrazine-2-carboxamide (200 mg, 642.30 μmol, 1 eq) and BOP (426.12 mg, 963.45 μmol, 1.5 eq) at 16° C. The mixture was stirred at 16° C. for 2 hrs. LCMS showed the reaction was completed. The reaction mixture was filtered to give a residue. The residue was purified by prep-HPLC (column: Phenomenex C18 80*30 mm*3 um; mobile phase: [water (TFA)-ACN]; B %: 10%-40%, 8 min) to afford (E)-5-cyclopropyl-3-((3-(2-(2-(4-(dimethylamino)-N-methylbut-2-enamido)acetamido) ethyl)phenyl)amino)-6-methylpyrazine-2-carboxamide (121.59 mg, 185.02 μmol, 28.81% yield) as yellow solid. $^1$H NMR (400 MHz, DMSO-$d_6$) δ=11.13-10.99 (m, 1H), 9.80-9.61 (m, 1H), 8.03 (brt, J=5.6 Hz, 2H), 7.83-7.76 (m, 1H), 7.49-7.39 (m, 2H), 7.27-7.18 (m, 1H), 6.91-6.68 (m, 2H), 6.63-6.49 (m, 1H), 4.03-3.81 (m, 4H), 3.37-3.33 (m, 2H), 3.05-3.03 (m, 1.5H), 2.81-2.70 (m, 9.5H), 2.57-2.55 (m, 3H), 2.28-2.21 (m, 1H), 1.13-1.05 (m, 4H)(TFA salt). LC-MS (ES+, m/z): 494.3 [(M+H)$^+$]; Rt=2.088 min; HRMS (EI): m/z [M]$^+$ found: 494.2855.

Example 25 (Compound 242)

(S,E)-3-((3-(2-(2-(4-(azetidin-1-yl)-N-methylbut-2-enamido)propanamido)ethyl)phenyl)amino)-5-cyclopropyl-6-methylpyrazine-2-carboxamide Step 1: (S,E)-3-((3-(2-(2-(4-(azetidin-1-yl)-N-methylbut-2-enamido)propanamido)ethyl)phenyl)amino)-5-cyclopropyl-6-methylpyrazine-2-carboxamide

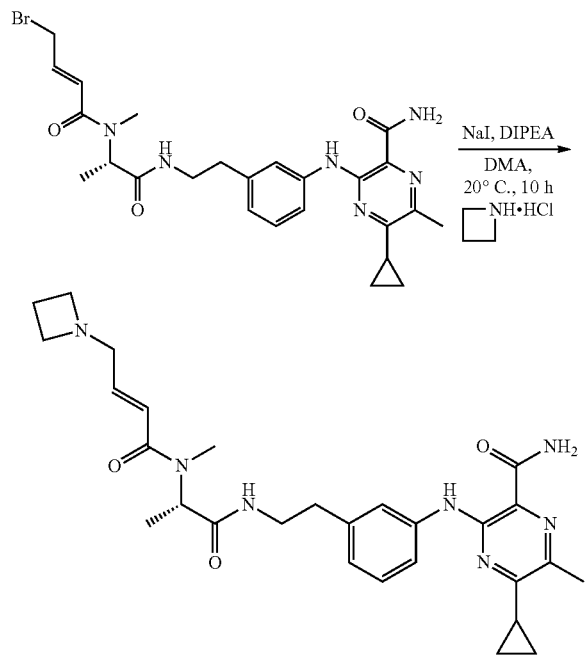

To a solution of azetidine hydrochloride (28.40 mg, 303.61 μmol, 1.1 eq), NaI (124.12 mg, 828.04 μmol, 3 eq), DIPEA (356.73 mg, 2.76 mmol, 480.76 μL, 10 eq) in DMA (1 mL) at 20° C., (S,E)-3-((3-(2-(2-(4-bromo-N-methylbut-2-enamido) propanamido)ethyl)phenyl)amino)-5-cyclopropyl-6-methylpyrazine-2-carboxamide (150 mg, 276.01 μmol, 1 eq) was added. The mixture was stirred at 20° C. for 12 h. LCMS indicated the reaction was complete. The mixture was filtered to give a residue. The crude was purified by prep-HPLC column: Waters Xbridge BEH C18 100*30 mm*10 um; mobile phase: [water (NH$_4$HCO$_3$)-ACN]; B %: 30%) to give (S,E)-3-((3-(2-(2-(4-(azetidin-1-yl)-N-methylbut-2-enamido)propanamido)ethyl) phenyl)amino)-5-cyclopropyl-6-methylpyrazine-2-carboxamide (5.85 mg, 11.26 μmol, 4.08% yield) as yellow solid. $^1$H NMR (400 MHz, DMSO-d$_6$) δ=11.13-10.98 (m, 1H), 8.24-8.12 (m, 1H), 8.10-7.72 (m, 2H), 7.49-7.35 (m, 2H), 7.26-7.17 (m, 1H), 6.84-6.78 (m, 1H), 6.60-6.28 (m, 2H), 5.02-4.46 (m, 1H), 3.32-3.03 (m, 8H), 2.85-2.64 (m, 5H), 2.56 (s, 3H), 2.28-2.21 (m, 1H), 2.05-1.77 (m, 2H), 1.17 (br d, J=7.2 Hz, 3H), 1.14-1.04 (m, 4H); LC-MS (ES+, m/z): 520.3 [(M+H)$^+$]. Rt=2.132 min; HRMS (EI): m/z [M]+ found: 520.3032.

Example 26 (Compound 243)

(S,E)-3-((3-(2-(2-(4-(dimethylamino)-N-methylbut-2-enamido)propanamido)ethyl)phenyl)amino)-5,6-diethylpyrazine-2-carboxamide Step 1: (S,E)-3-((3-(2-(2-(4-(dimethylamino)-N-methylbut-2-enamido) propanamido)ethyl)phenyl)amino)-5,6-diethylpyrazine-2-carboxamide

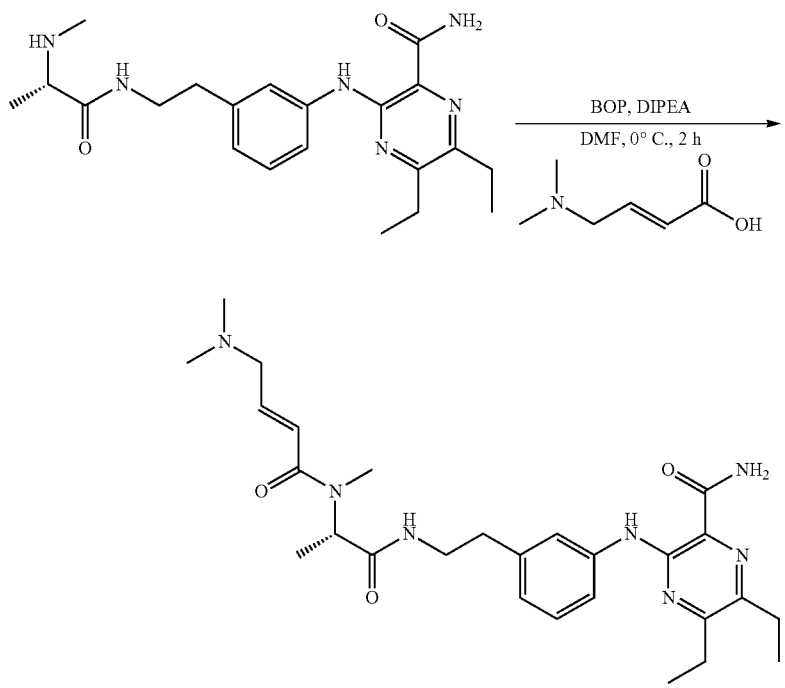

To a mixture of (E)-4-(dimethylamino)but-2-enoic acid (91.43 mg, 552.07 µmol, 1.1 eq, HCl) in DMF (0.5 mL) was added DIEA (648.65 mg, 5.02 mmol, 874.19 µL, 10 eq) and (S)-5,6-diethyl-3-((3-(2-(2-(methylamino)propanamido) ethyl phenylamino) pyrazine-2-carboxamide (200 mg, 501.88 µmol, 1 eq), and then BOP (332.96 mg, 752.82 µmol, 1.5 eq) in one portion at 0° C. under $N_2$. The mixture was stirred at 0° C. for 2 hr. LCMS showed the reaction was completed. The residue was poured into water (10 mL) and then extracted with ethyl acetate (20 mL*3). The combined organic phase was washed with saturated brine (20 mL*2), dried with anhydrous $Na_2SO_4$, filtered and concentrated in vacuum. The residue was purified by prep-HPLC (TFA condition) (column: Phenomenex Luna C18 150*30 mm*5 um; mobile phase: [water (TFA)-ACN]; B %: 20%-50%, 8 min) to afford the title compound (S,E)-3-((3-(2-(2-(4-(dimethylamino)-N-methylbut-2-enamido propanamido)ethyl) phenyl)amino)-5,6-diethylpyrazine-2-carboxamide (26.08 mg, 51.02 µmol, 10.16% yield) as a yellow solid. $^1$H NMR (400 MHz, DMSO-$d_6$) δ=11.22-10.90 (m, 1H), 9.76-9.52 (m, 1H), 8.22-8.10 (m, 1H), 7.92 (br t, J=5.6 Hz, 1H), 7.90-7.80 (m, 1H), 7.66-7.59 (m, 1H), 7.52 (s, 1H), 7.28-7.18 (m, 1H), 6.90-6.73 (m, 2H), 6.66-6.42 (m, 1H), 5.07-4.44 (m, 1H), 3.93-3.77 (m, 2H), 3.32-3.27 (m, 2H), 2.90 (s, 2H), 2.88-2.82 (m, 2H), 2.81-2.69 (m, 11H), 1.33-1.21 (m, 9H)(TFA salt). $^1$H NMR (400 MHz, $D_2O$) δ=7.56-7.44 (m, 1H), 7.32-7.24 (m, 1H), 7.24-7.08 (m, 1H), 6.86 (br d, J=7.2 Hz, 1H), 6.80-6.55 (m, 1H), 6.54 (br s, 1H), 4.84 (br d, J=7.3 Hz, 1H), 3.86-3.67 (m, 2H), 3.54-3.33 (m, 2H), 2.84-2.63 (m, 15H), 1.35-1.16 (m, 9H). LC-MS (ES+, m/z): 510.4 [(M+H)$^+$]; Rt=2.199 min. HRMS (EI): m/z [M]$^+$ found: 510.3169.

Example 271 (Compound 244)

(S)-3-((3-(2-(2-(4-(dimethylamino)-N-methylbut-2-ynamido) propanamido) ethyl) phenyl) amino)-6-ethyl-5-methylpyrazine-2-carboxamide Step 1: (S)-3-((3-(2-(2-(4-(dimethylamino)-N-methylbut-2-ynamido) propanamido) ethyl) phenyl) amino)-6-ethyl-5-methylpyrazine-2-carboxamide

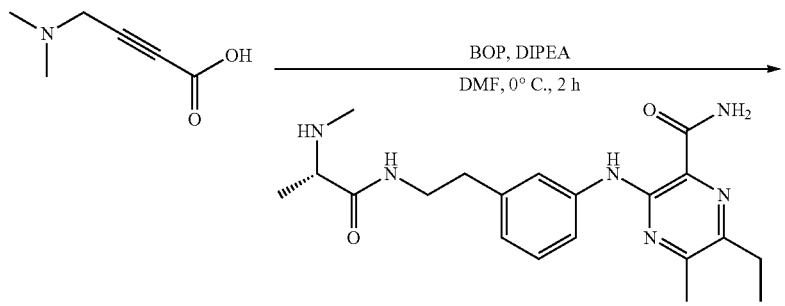

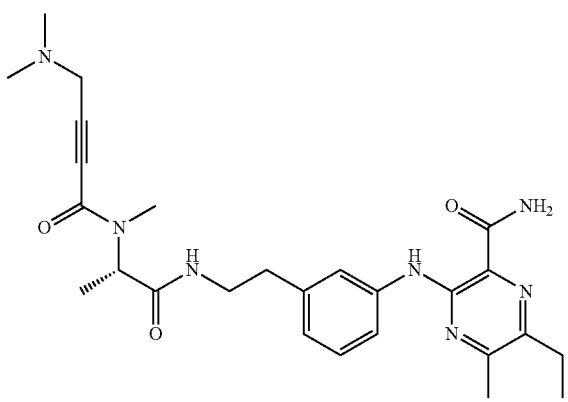

To a solution of 4-(dimethylamino)but-2-ynoic acid (148.81 mg, 1.17 mmol, 3 eq) (150 mg, 390.14 µmol, 1 eq) in DMF (3 mL) was added DIEA (504.23 mg, 3.90 mmol, 679.56 µL, 10 eq) (S)-6-ethyl-5-methyl-3-((3-(2-(2-(methylamino) propanamido) ethyl) phenyl) amino) pyrazine-2-carboxamide at 0° C., and then BOP (517.66 mg, 1.17 mmol, 3 eq) at 0° C. The mixture was stirred at 0° C. for 2 hr. LCMS showed the reaction was completed. The reaction mixture was quenched by addition water (50 mL), and then extracted with EtOAc (30 mL*3). The combined organic layers were washed with saturated brine (20 mL*2), dried over $Na_2SO_4$, filtered and concentrated under reduced pressure to give a residue. The residue was purified by prep-HPLC (column: Phenomenex Luna C18 150*30 mm*5 um; mobile phase: [water (TFA)-ACN]; B %: 15%-45%, 8 min) to give (S)-3-((3-(2-(2-(4-(dimethylamino)-N-methylbut-2-ynamido) propanamido) ethyl) phenyl) amino)-6-ethyl-5-methylpyrazine-2-carboxamide as yellow solid (96.13 mg, 198.40 µmol, 32.58% yield, 98.36% purity). $^1$H NMR (400 MHz, DMSO-$d_6$) δ=11.11-11.01 (m, 1H), 8.05 (br t, J=5.6 Hz, 2H), 7.90-7.81 (m, 1H), 7.71-7.63 (m, 1H), 7.47-7.41 (m, 1H), 7.26-7.19 (m, 1H), 6.85-6.80 (m, 1H), 4.89-4.78 (m, 1H), 4.44-4.24 (m, 2H), 3.40-3.24 (m, 2H), 3.08-3.06 (m, 2H), 2.87-2.68 (m, 10H), 2.77-2.66 (m, 1H), 2.50 (br s, 3H), 1.36-1.20 (m, 6H) LC-MS (ES$^+$, m/z): 494.3 [(M+H)+]; Rt=2.122 min; HRMS (EI): m/z [M+H]+: 494.2875.

Example 28 (Compound 246)

(S,E)-3-((3-(2-(2-(4-(bis(methyl-d3)amino)-N-methylbut-2-enamido)propanamido)ethyl)phenyl)amino)-6-ethyl-5-(ethyl(methyl)amino)pyrazine-2-carboxamide Step 1: (S,E)-3-((3-(2-(2-(4-(bis(methyl-d3)amino)-N-methylbut-2-enamido)propanamido)ethyl)phenyl)amino)-6-ethyl-5-(ethyl(methyl)amino)pyrazine-2-carboxamide

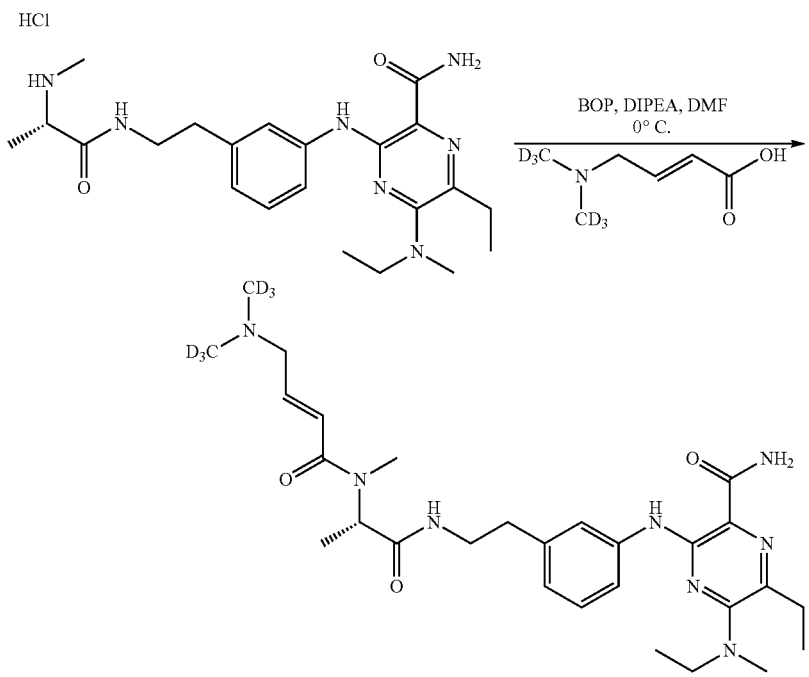

A solution of benzotriazol-1-yloxytris(dimethylamino)-phosphonium hexafluorophosphate (429 mg, 0.970 mmol, 3 eq) in N,N-dimethylformamide (1 mL) was added to a mixture of (E)-4-[bis(trideuteriomethyl)amino]but-2-enoic acid hydrochloride (290 mg, 0.970 mmol, 3 eq) with lithium chloride as an impurity, (S)-6-ethyl-5-(ethyl(methyl)amino)-3-((3-(2-(2-(methylamino)propanamido)ethyl)phenyl) amino)pyrazine-2-carboxamide hydrochloride (150 mg, 0.323 mmol, 1 eq) and N,N-diisopropylethylamine (0.45 mL, 2.59 mmol, 8 eq) in N,N-dimethylformamide (0.5 mL) at 0° C. After 1 h the reaction was diluted with ethyl acetate (20 mL) and quenched with saturated sodium bicarbonate (10 mL) at 0° C. The organic phase was washed with 5% lithium chloride (3×10 mL) and brine (10 mL). The organic phase was dried over sodium sulfate and the solvent was removed under reduced pressure. The residue was subjected to flash chromatography (0-40% methanol/dichloromethane). The clean fractions containing product were combined and the solvent was removed under reduced pressure. The residue was co-evaporated with acetonitrile (10 mL). The residue was taken up in acetonitrile (10 mL) and water (10 mL), and subjected to lyophilization, providing (S,E)-3-((3-(2-(2-(4-(bis(methyl-d3)amino)-N-methylbut-2-enamido)propanamido)ethyl)phenyl)amino)-6-ethyl-5-(ethyl(methyl)amino)pyrazine-2-carboxamide (61 mg, 0.112 mmol, 34.53% yield). $^1$H NMR (400 MHz, DMSO-d6) δ 11.12 (s, 1H), 7.85 (s, 1H), 7.75 (s, 1H), 7.55 (s, 1H), 7.51-7.42 (m, 2H), 7.21 (t, J=7.9 Hz, 1H), 6.80 (d, J=7.5 Hz, 1H), 6.65-6.57 (m, 1H), 6.56-6.41 (m, 1H), 4.99 (m, 1H), 3.47 (q, J=7.2 Hz, 2H), 3.33-3.20 (m, 2H), 3.05 (s, 3H), 3.03-2.93 (m, 2H), 2.85 (s, 2H), 2.80-2.65 (m, 5H), 1.31-1.14 (m, 9H). LC-MS (ES+, m/z): 545.3 [(M+H)$^+$]; Rt=3.818 min.

Example 29 (Compound 247)

(S,E)-3-((3-(2-(2-(4-(bis(methyl-d3)amino)-N-methylbut-2-enamido)propanamido)ethyl)phenyl)amino)-5-(isopropyl(methyl)amino)-6-methylpyrazine-2-carboxamide Step 1: (S,E)-3-((3-(2-(2-(4-(bis(methyl-d3)amino)-N-methylbut-2-enamido)propanamido)ethyl)phenyl)amino)-5-(isopropyl(methyl)amino)-6-methylpyrazine-2-carboxamide A solution of 5-[isopropyl(methyl)amino]-6-methyl-3-[3-[2-[[(2S)-2-(methylamino)propanoyl]amino]ethyl]anilino]pyrazine-2-carboxamide; methane; hydrochloride (120 mg, 0.25 mmol, 1 eq) and (E)-4-[bis(trideuteriomethyl)amino]but-2-enoic acid (135 mg, 1.002, 4.0 eq) in DMF (0.25 mL) was added DIPEA (194 mg, 1.5 mmol, 0.26 mL, 5 eq) stirred at 0° C. followed by addition of HOBt (444 mg, 1.002 mmol, 4.0 eq). The suspension was clear and then turned to dark brown. The reaction was stirred at same temperature for 3 hrs. LCMS indicated the reaction was not complete. Ethyl acetate (10 mL) was added at 0° C. The combined organic layers were washed with sodium bicarbonate (sat.) 2× and then brine 2×. The combined organic layers were dried over sodium sulfate. The solvent was concentrated to give as yellow solid. (170 mg). The mixture was purified using silica gel normal phase column 24 g eluting dcm to 10% methanol in dcm in 30 minutes. The product was collected and were concentrated and lyophilized to give (S,E)-3-((3-(2-(2-(4-(bis(methyl-d3)amino)-N-methylbut-2-enamido)propanamido)ethyl)phenyl)amino)-5-(isopropyl(methyl)amino)-6-methylpyrazine-2-carboxamide (29 mg, 0.0532 mmol, 21.2% yield) as off white solid. 1H NMR (400 MHz, DMSO) δ 11.12 (s, 1H), 7.92 (s, 1H), 7.81 (s, 1H), 7.61-7.35 (m, 3H), 7.22 (t, J=7.7 Hz, 1H), 6.88-6.70 (m, 2H), 6.70-6.40 (m, 1H), 4.99 (d, J=7.5 Hz, 1H), 4.48-4.23 (m, 1H), 3.66 (s, 1H), 2.90 (d, J=6.1 Hz, 6H), 2.71 (s, 4H), 2.45 (d, J=2.2 Hz, 4H), 1.43-0.99 (m, 11H). LC-MS (ES$^+$, m/z): 545.3 [(M+H)$^+$]; Rt=3.906 min.

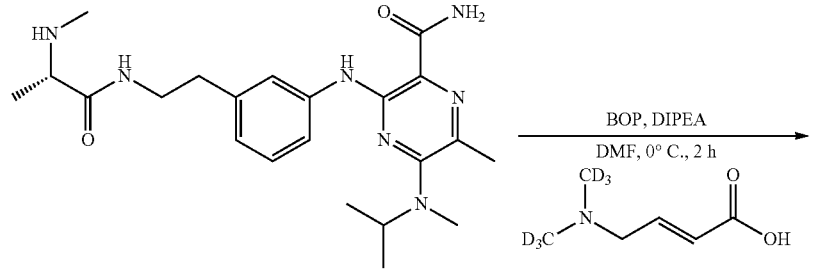

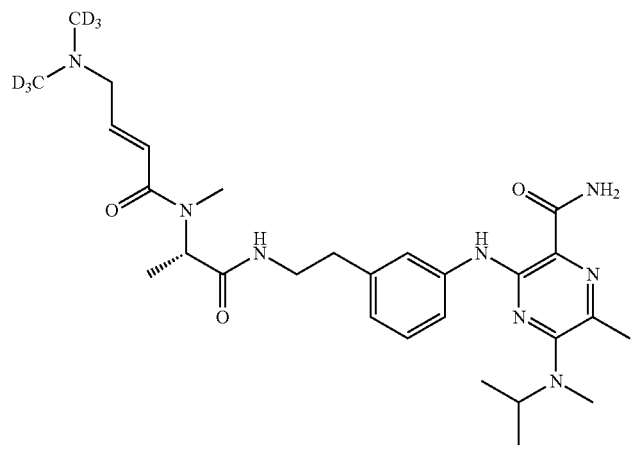

Example 30 (Compound 248)

(S,E)-3-((3-(2-(2-(4-(bis(methyl-d3)amino)-N-methylbut-2-enamido)propanamido)ethyl)phenyl)amino)-5-cyclopropyl-6-methylpyrazine-2-carboxamide Step 1. (S,E)-3-((3-(2-(2-(4-(bis(methyl-d3)amino)-N-methylbut-2-enamido)propanamido)ethyl)phenyl)amino)-5-cyclopropyl-6-methylpyrazine-2-carboxamide

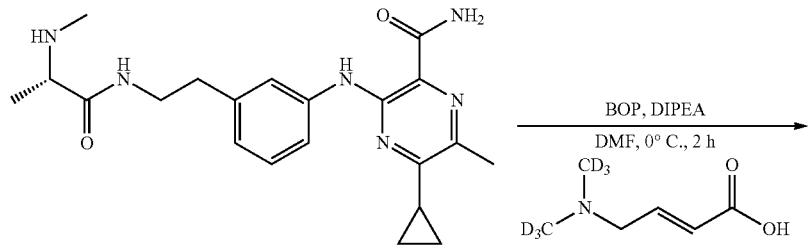

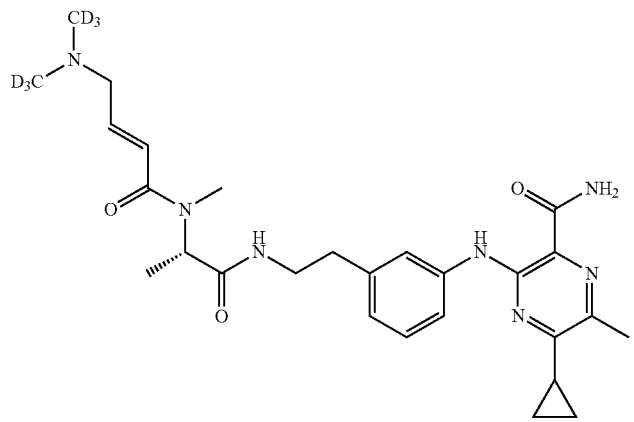

To a slurry of (E)-4-[bis(trideuteriomethyl)amino]but-2-enoic acid; chlorolithium; hydrochloride (248.49 mg, 831.5 μmol, 3.0 eq) in DMF (0.7 mL) was added DIEA (358.21 mg, 2.77 mmol, 0.48 mL, 10 eq) and (S)-5-cyclopropyl-6-methyl-3-((3-(2-(2-(methylamino)propanamido)ethyl)phenyl)amino)pyrazine-2-carboxamide (120 mg, 277.17 μmol, 1 eq), then BOP (367.76 mg, 831.5 μmol, 3 eq) in 0.8 ml DMF was added. The mixture was stirred at 0° C. for 2 hrs. LCMS indicated the reaction was complete. The reaction was concentrated and purified by silica gel column to give (S,E)-3-((3-(2-(2-(4-(bis(methyl-d3)amino)-N-methylbut-2-enamido)propanamido)ethyl)phenyl)amino)-5-cyclopropyl-6-methylpyrazine-2-carboxamide (35 mg, 66.8 μmol, 24.09% yield) as yellow solid. 1H NMR (400 MHz, CDCl3) δ 10.71 (s, 1H), 7.85 (s, 1H), 7.49 (m, 2H), 7.20 (m, 1H), 6.87-6.80 (m, 2H), 6.41 m, 2H), 5.94 (s, 1H), 5.18 (m, 1H), 3.63 (m, 1H), 3.45 (m, 1H), 3.20-3.09 (m, 2H), 2.87 (s, 3H), 2.79 (m, 2H), 2.56 (m, 3H), 2.11 (m, 1H), 1.35-01.32 (m, 3H), 1.20 (m, 2H), 1.11 (m, 2H). LC-MS (ES+, m/z): 514.3 [(M+H)$^+$]; Rt=3.790 min

Example 31 (Compound 249)

(S,E)-3-((3-(2-(2-(4-(bis(methyl-d3)amino)-N-methylbut-2-enamido)propanamido)ethyl)phenyl)amino)-6-ethyl-5-(isopropyl(methyl)amino)pyrazine-2-carboxamide Step 1: (S,E)-3-((3-(2-(2-(4-(bis(methyl-d3)amino)-N-methylbut-2-enamido)propanamido)ethyl)phenyl)amino)-6-ethyl-5-(isopropyl(methyl)amino)pyrazine-2-carboxamide

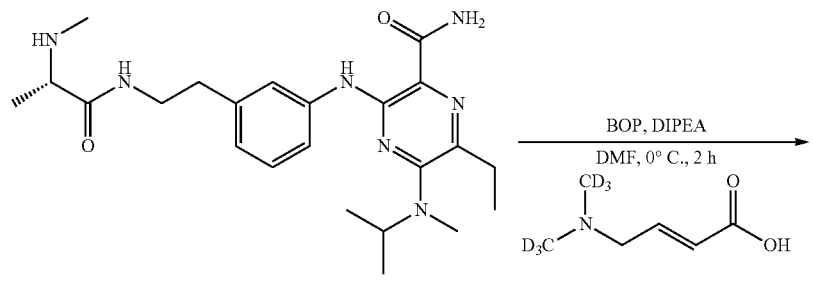

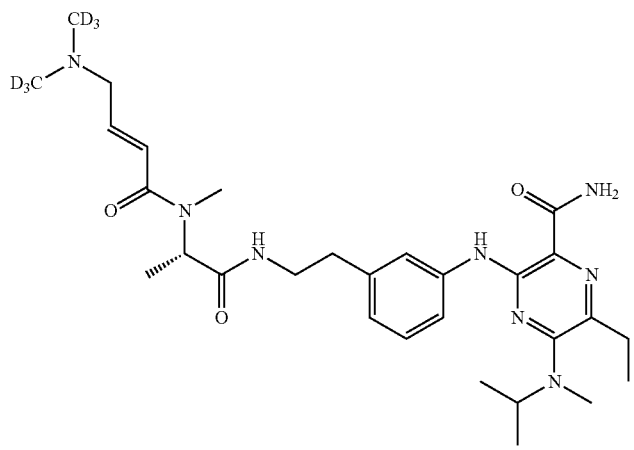

To a mixture of (E)-4-[bis(trideuteriomethyl)amino]but-2-enoic acid (1.50 eq, 164 mg, 0.631 mmol) and N,N-Diisopropylethylamine (10.0 eq, 0.73 mL, 4.20 mmol) in DMF (0.75 mL), was added 6-ethyl-5-[isopropyl(methyl)amino]-3-[3-[2-[[(2S)-2-(methylamino)propanoyl]amino]ethyl]anilino]pyrazine-2-carboxamide; hydrochloride (1.00 eq, 201 mg, 0.420 mmol). The mixture was cooled to 0° C. under nitrogen, a solution of BOP (1.50 eq, 279 mg, 0.631 mmol) in DMF (0.75 mL) was injected dropwise. The reaction was stirred at 0° C. for 2 hours. The reaction mixture was diluted with EtOAc (30 mL) and NaHCO$_3$ (aq) (10 mL), washed with NaHCO$_3$ (aq) (1×), water (2×) and brine (1×). The organic layer was separated, dried over Na$_2$SO$_4$, filtered and concentrated. The crude was purified on silica gel column, 0-10% MeOH/DCM to provide (S,E)-3-((3-(2-(2-(4-(bis(methyl-d3)amino)-N-methylbut-2-enamido)propanamido)ethyl)phenyl)amino)-6-ethyl-5-(isopropyl(methyl)amino)pyrazine-2-carboxamide (61 mg, 0.109 mmol, 25.96% yield) as off-white solid. $^1$H NMR (400 MHz, CD$_3$OD) δ 10.66 (s, 1H), 7.49 (d, J=10.9 Hz, 1H), 7.40 (d, J=8.2 Hz, 1H), 7.10 (t, J=7.9 Hz, 1H), 6.74 (d, J=7.6 Hz, 1H), 6.70-6.52 (m, 1H), 6.40 (dd, J=25.3, 15.1 Hz, 1H), 4.96 (q, J=7.0 Hz, 1H), 4.24 (p, J=6.8 Hz, 1H), 3.35 (ddd, J=42.2, 13.3, 6.3 Hz, 2H), 3.08-2.95 (m, 2H), 2.88-2.76 (m, 5H), 2.68 (dt, J=14.8, 6.4 Hz, 5H), 1.39-1.07 (m, 12H). LC-MS (ES$^+$, m/z): 559.4 [(M+H)$^+$]; Rt=3.992 min.

Example 32 (Compound 250)

(E)-3-((3-(2-(2-(4-(dimethylamino)-N-methylbut-2-enamido)acetamido)ethyl) phenyl)amino)-5-(isopropyl(methyl)amino)-6-methylpyrazine-2-carboxamide

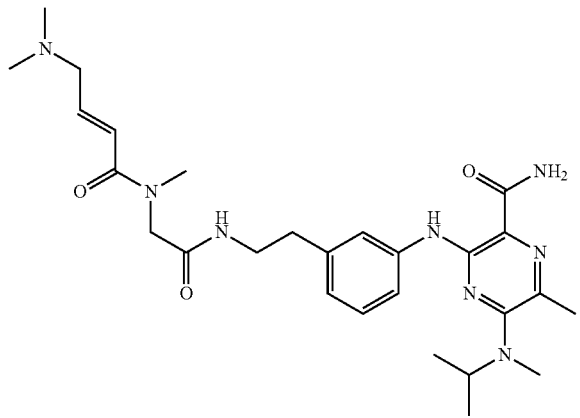

Step 1: (E)-3-((3-(2-(2-(4-(dimethylamino)-N-methylbut-2-enamido)acetamido)ethyl)phenyl)amino)-5-(isopropyl(methyl)amino)-6-methylpyrazine-2-carboxamide

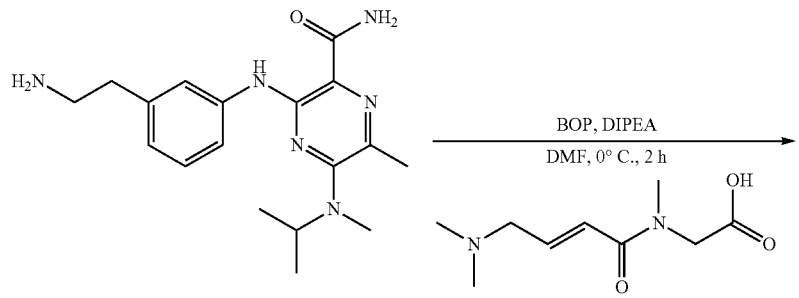

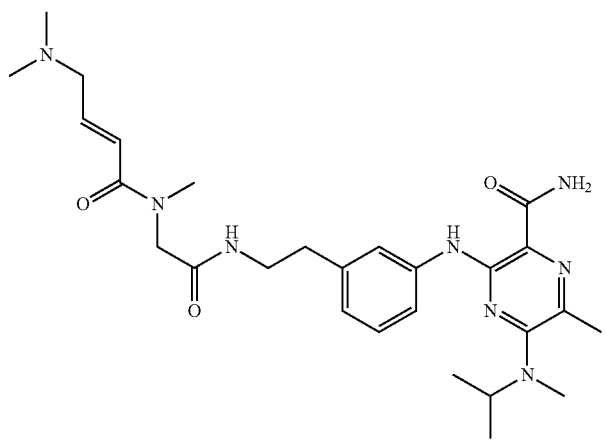

To a solution of (E)-N-(4-(dimethylamino)but-2-enoyl)-N-methylglycine (248.82 mg, 395.88 μmol, 1.5 eq, TFA), BOP (175.09 mg, 395.88 μmol, 1.5 eq) in DMF (0.5 mL), then 3-((3-(2-aminoethyl)phenyl)amino)-5-(isopropyl(methyl)amino)-6-methylpyrazine-2-carboxamide (100 mg, 263.92 μmol, 1 eq, HCl) in DMF (0.5 mL), DIPEA (341.09 mg, 2.64 mmol, 10 eq) was added, the mixture was stirred at 0° C. for 2 hrs. LCMS showed the reaction was completed. The residue was purified by prep-HPLC(column: Phenomenex Luna C18 150*30 mm*5 um; mobile phase: [water (TFA)-ACN]; B %: 10%-40%, 8 min) to afford (E)-3-((3-(2-(2-(4-(dimethylamino)-N-methylbut-2-enamido)acetamido)ethyl)phenyl) amino)-5-(isopropyl(methyl)amino)-6-methylpyrazine-2-carboxamide (10.95 mg, 20.87 μmol, 7.91% yield, 100% purity) as a yellow solid. H NMR (400 MHz, DMSO-$d_6$) δ=11.11 (d, J=1.5 Hz, 1H), 8.24-7.99 (m, 1H), 7.79 (br s, 1H), 7.56-7.37 (m, 3H), 7.21 (dt, J=3.2, 7.7 Hz, 1H), 6.92-6.67 (m, 2H), 6.64-6.48 (m, 1H), 4.34 (td, J=6.6, 13.2 Hz, 1H), 4.03-3.94 (m, 2H), 3.93-3.82 (m, 2H), 3.37-3.25 (m, 2H), 3.04 (s, 1.5H), 2.89 (s, 3H), 2.82-2.77 (m, 4.5H), 2.76-2.66 (m, 5H), 2.44 (s, 3H), 1.20 (d, J=6.6 Hz, 6H). LC-MS (ES+, m/z): 525.3 [(M+H)$^+$]; Rt=2.170 min. HRMS: 525.3257. SFC: 100%.

Intermediate 4D (S)-5-(ethyl(methyl)amino)-6-methyl-3-((3-(2-(2-(methylamino)propanamido)ethyl)phenyl)amino)pyrazine-2-carboxamide Step 1: tert-butyl (3-((3-carbamoyl-6-(ethyl(methyl)amino)-5-methylpyrazin-2-yl)amino)phenethyl)carbamate

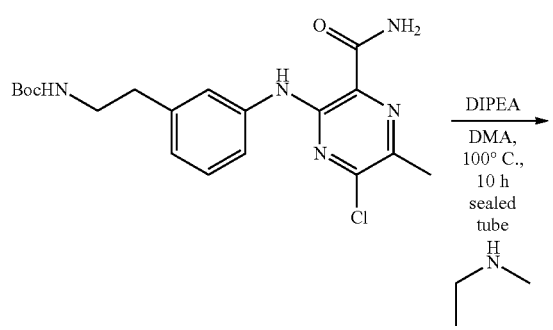

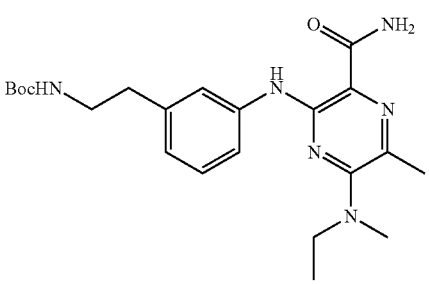

To a solution of tert-butyl (3-((3-carbamoyl-6-chloro-5-ethylpyrazin-2-yl)amino)phenethyl)carbamate, N-methylethanamine (1.17 g, 19.71 mmol, 1.69 mL, 8 eq) in DMA (10 mL) was added DIPEA (3.18 g, 24.64 mmol, 4.29 mL 10 eq) at 20° C. The mixture was stirred at 100° C. for 10 hrs. LC-MS showed the desired compound was detected. The reaction mixture was poured into water (50 mL), then extracted with EtOAc (30 mL*3). The combined organic layers were washed with saturated brine (30 mL*1) dried over anhydrous Na₂SO₄, filtered and concentrated under reduced pressure to give a residue. The residue was purified by column chromatography (SiO₂, Petroleum ether/Ethyl acetate=1/1 to 0/1) To afford the title compound tert-butyl (3-((3-carbamoyl-6-(ethyl(methyl)amino)-5-methylpyrazin-2-yl)amino)phenethyl)carbamate (900 mg, 2.10 mmol, 85.24% yield) as a yellow solid. LC-MS (ES+, m/z): 429.3 [(M+H)+]; Rt=0.906 min.

Step 2: 3-((3-(2-aminoethyl)phenyl)amino)-5-(ethyl(methyl)amino)-6-methylpyrazine-2-carboxamide

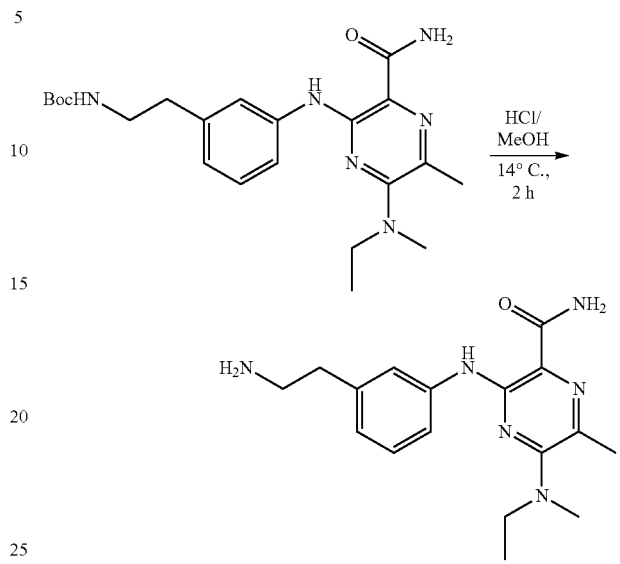

To a solution of tert-butyl (3-((3-carbamoyl-6-(ethyl(methyl)amino)-5-methylpyrazin-2-yl)amino)phenethyl)carbamate (900 mg, 1.94 mmol, 1 eq, HCl) in HCl/MeOH (4 M, 4.8 mL, 10 eq). The mixture was stirred at 14° C. for 2 hrs. TLC showed the reaction was completed. The reaction mixture was concentrated under reduced pressure to give a residue. To afford the title compound 3-((3-(2-aminoethyl)phenyl)amino)-5-(ethyl(methyl)amino)-6-methylpyrazine-2-carboxamide (750 mg, 2.06 mmol, crude) as a yellow solid.

Step 3: tert-butyl (S)-(1-((3-((3-carbamoyl-6-(ethyl(methyl)amino)-5-methylpyrazin-2-yl)amino)phenethyl)amino)-1-oxopropan-2-yl)(methyl)carbamate

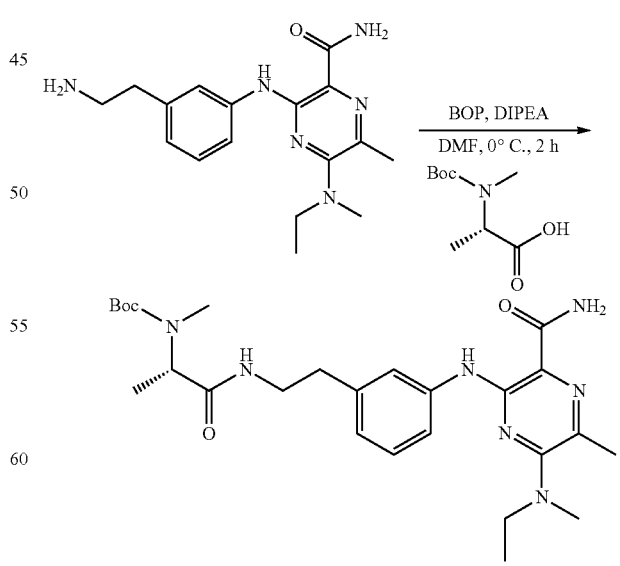

To a solution of 3-((3-(2-aminoethyl)phenyl)amino)-5-(ethyl(methyl)amino)-6-methylpyrazine-2-carboxamide (750 mg, 2.06 mmol, 1 eq, HCl), N-(tert-butoxycarbonyl)-N-methyl-L-alanine (459.53 mg, 2.26 mmol, 1.1 eq) in DMF (3 mL) was added BOP (1.36 g, 3.08 mmol, 1.5 eq) and DIPEA (2.66 g, 20.56 mmol, 3.58 mL, 10 eq). The mixture was stirred at 0° C. for 2 hrs. LC-MS showed desired compound was detected. The reaction mixture was poured into water (30 mL), then extracted with EA (3*30 mL). The combined organic layers were washed with saturated brine (1*30 mL) dried over anhydrous Na$_2$SO$_4$ filtered and concentrated under reduced pressure to give a residue. The residue was purified by column chromatography (SiO2, Petroleum ether/Ethyl acetate=1/1 to 0/1). To afford the little compound tert-butyl (S)-(1-((3-((3-carbamoyl-6-(ethyl (methyl)amino)-5-methylpyrazin-2-yl)amino)phenethyl) amino)-1-oxopropan-2-yl)(methyl)carbamate (800 mg, 1.56 mmol, 75.77% yield) as a yellow solid. LC-MS (ES+, m/z): 514.3 [(M+H)$^+$]; Rt=0.881 min.

Step 4: (S)-5-(ethyl(methyl)amino)-6-methyl-3-((3-(2-(2-(methylamino)propanamido)ethyl)phenyl) amino)pyrazine-2-carboxamide

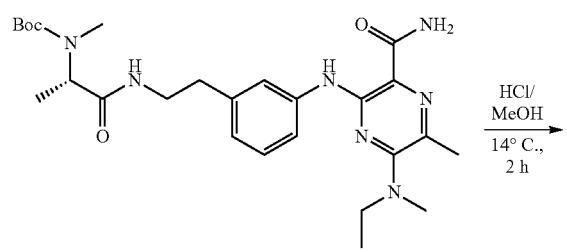

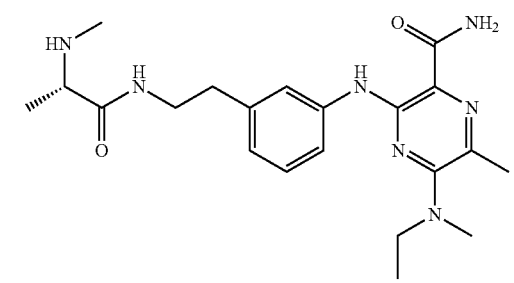

To a solution of tert-butyl (S)-(1-((3-((3-carbamoyl-6-(ethyl(methyl)amino)-5-methylpyrazin-2-yl)amino)phenethyl)amino)-1-oxopropan-2-yl)(methyl)carbamate (800 mg, 1.56 mmol, 1 eq) was added HCl/MeOH (4 M, 389.38 µL, 1 eq). The mixture was stirred at 14° C. for 1 hr. TLC showed the reaction was completed. The reaction mixture was concentrated under reduced pressure to give a residue. To afford the title compound (S)-5-(ethyl(methyl)amino)-6-methyl-3-((3-(2-(2-(methylamino)propanamido)ethyl)phenyl)amino)pyrazine-2-carboxamide (700 mg, crude) as a yellow solid.

Example 33 (Compound 252)

(E)-3-((3-(2-(2-(4-(dimethylamino)-N-methylbut-2-enamido) acetamido) ethyl) phenyl) amino)-6-ethyl-5-(ethyl (methyl) amino) pyrazine-2-carboxamide Step 1: (E)-3-((3-(2-(2-(4-(dimethylamino)-N-methylbut-2-enamido) acetamido) ethyl) phenyl) amino)-6-ethyl-5-(ethyl (methyl) amino) pyrazine-2-carboxamide

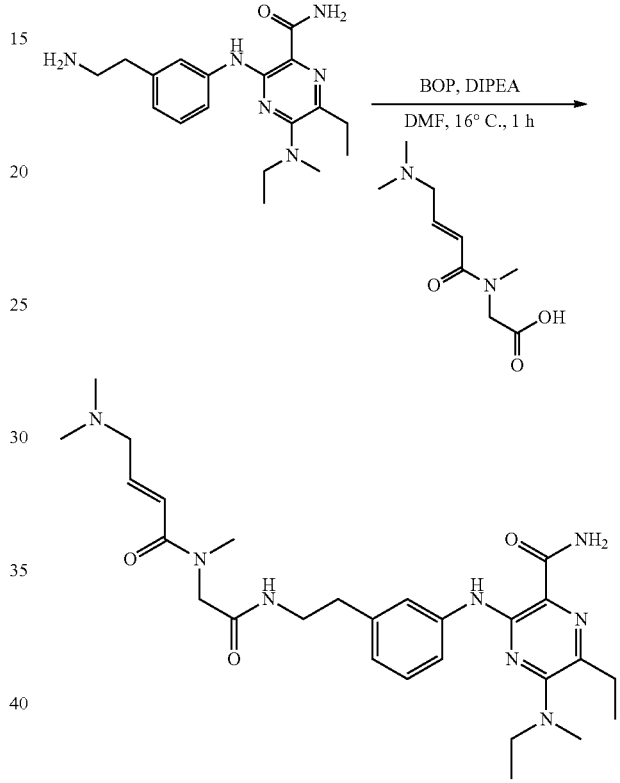

To a solution of 3-((3-(2-aminoethyl)phenyl)amino)-6-ethyl-5-(ethyl(methyl)amino)pyrazine-2-carboxamide (100 mg, 292.02 µmol, 1 eq) (E)-N-(4-(dimethylamino)but-2-enoyl)-N-methylglycine (175.42 mg, 438.04 µmol, 50% purity, 1.5 eq) BOP (193.74 mg, 438.04 µmol, 1.5 eq) in DMF (1 mL) at 16° C., DIPEA (377.42 mg, 2.92 mmol, 508.65 µL, 10 eq) was added. The mixture was stirred at 16° C. for 1 h. LCMS showed the reaction was completed. The mixture was filtered to give a residue. The crude was purified by prep-HPLC column: Phenomenex Luna 80*30 mm*3 um; mobile phase: [water (TFA)-ACN]; B %: 15%-45%, 8 min) to give (E)-3-((3-(2-(2-(4-(dimethylamino)-N-methylbut-2-enamido) acetamido) ethyl) phenyl) amino)-6-ethyl-5-(ethyl(methyl)amino)pyrazine-2-carboxamide (11.6 mg, 22.10 µmol, 7.57% yield, 99.94% purity) as yellow solid. $^1$H NMR (400 MHz, DMSO-d$_6$) δ=11.17-11.06 (m, 1H), 9.90-9.63 (m, 1H), 8.23-8.00 (m, 1H), 7.75 (br s, 1H), 7.59-7.42 (m, 3H), 7.26-7.18 (m, 1H), 6.92-6.68 (m, 2H), 6.65-6.49 (m, 1H), 4.04-3.95 (m, 2H), 3.93-3.81 (m, 2H), 3.46 (q, J=7.0 Hz, 2H), 3.36-3.26 (m, 2H), 3.04 (s, 4H), 2.82-2.67 (m, 12H), 1.26-1.17 (m, 6H); LC-MS (ES+, m/z): 525.3 [(M+H)$^+$]. RT=2.177 min; HRMS (EI): m/z [M]$^+$ found: 525.3267.

Example 34 (Compound 253)

(S,E)-3-((3-(2-(2-(4-(dimethylamino)-N-methylbut-2-enamido)propanamido)ethyl)phenyl)amino)-5-(ethyl(methyl)amino)-6-methylpyrazine-2-carboxamide

Step 1: (S,E)-3-((3-(2-(2-(4-(dimethylamino)-N-methylbut-2-enamido)propanamido)ethyl)phenyl)amino)-5-(ethyl(methyl)amino)-6-methylpyrazine-2-carboxamide

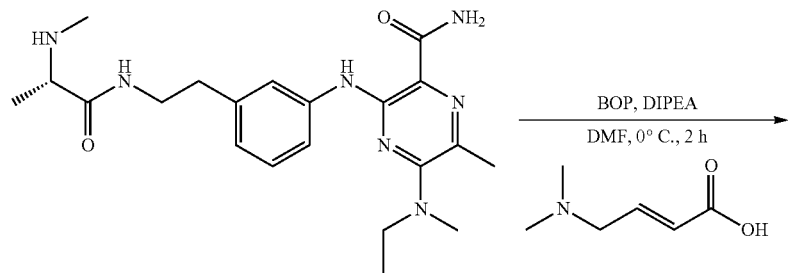

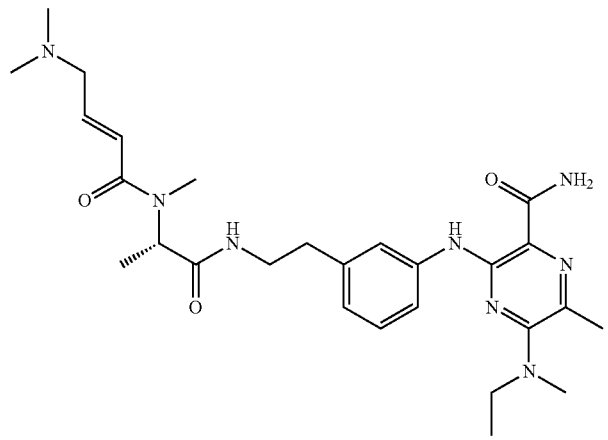

To a solution of (S)-5-(ethyl(methyl)amino)-6-methyl-3-((3-(2-(2-(methylamino)propanamido)ethyl)phenyl)amino)pyrazine-2-carboxamide (130 mg, 314.38 μmol, 1 eq), (E)-4-(dimethylamino)but-2-enoic acid (57.27 mg, 345.82 μmol, 1.1 eq, HCl) in DMF (1 mL) was added BOP (208.56 mg, 471.57 μmol, 1.5 eq) and DIEA (406.30 mg, 3.14 mmol, 547.58 μL, 10 eq). The mixture was stirred at 0° C. for 2 hrs. LC-MS, HPLC showed desired compound was detected the reaction mixture was poured into water (30 mL), then extracted with EtOAc (30 mL*3). The combined organic layers were washed with saturated brine (30 mL*1), dried over anhydrous $Na_2SO_4$, filtered and concentrated under reduced pressure to give a residue. The residue was purified by prep-HPLC (TFA condition; column: Phenomenex Luna C18 150*30 mm*5 um; mobile phase: [water (TFA)-ACN]; B %: 10%-40%, 8 min). To afford the title compound (S,E)-3-((3-(2-(2-(4-(dimethylamino)-N-methylbut-2-enamido)propanamido)ethyl)phenyl)amino)-5-(ethyl(methyl)amino)-6-methylpyrazine-2-carboxamide (10.3 mg, 19.59 μmol, 6.23% yield) as a yellow solid. $^1$H NMR (400 MHz, DMSO-$d_6$) δ=11.13-11.09 (m, 1H), 8.11-7.89 (m, 1H), 7.79 (br d, J=2.0 Hz, 1H), 7.52 (br s, 1H), 7.49-7.43 (m, 1H), 7.40 (br s, 1H), 7.23-7.17 (m, 1H), 6.85-6.76 (m, 2H), 6.64-6.47 (m, 1H), 4.59 (br s, 1H), 5.00-4.52 (m, 1H), 3.92-3.80 (m, 2H), 3.50 (q, J=7.0 Hz, 2H), 3.36-3.24 (m, 2H), 3.08 (s, 3H), 2.89 (s, 2H), 2.80-2.74 (m, 6H), 2.73-2.66 (m, 3H), 2.47 (s, 3H), 1.29 (s, 1H), 1.28 (s, 1H), 1.31-1.17 (m, 4H). LC-MS (ES+, m/z): 525.33 [(M+H)+]; Rt=2.131 min. HRMS (EI): m/z [M+H]$^+$ found: 525.3257. SFC: 97.58%.

Example 35 (Compound 254)

(S,E)-5-cyclopropyl-3-((3-(2-(2-(4-(dimethylamino)-N-methylbut-2-enamido)propanamido)ethyl)-5-fluorophenyl)amino)-6-methylpyrazine-2-carboxamide Step 1: (S,E)-5-cyclopropyl-3-((3-(2-(2-(4-(dimethylamino)-N-methylbut-2-enamido)propanamido) ethyl)-5-fluorophenyl)amino)-6-methylpyrazine-2-carboxamide

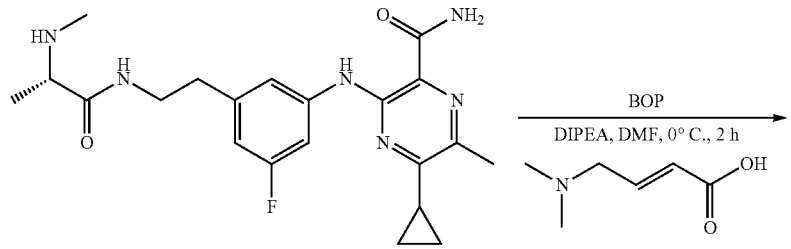

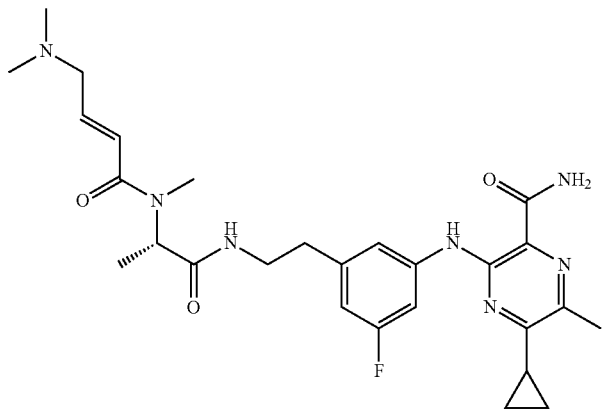

To a mixture of (E)-4-(dimethylamino)but-2-enoic acid (35.16 mg, 212.32 µmol, 1.1 eq, HCl) in DMF (1 mL) was added DIPEA (249.46 mg, 1.93 mmol, 336.20 µL, 10 eq) and (S)-5-cyclopropyl-3-((3-fluoro-5-(2-(2-(methylamino)propanamido) ethyl)phenyl)amino)-6-methylpyrazine-2-carboxamide (80 mg, 193.02 µmol, 1 eq) and BOP (128.05 mg, 289.52 µmol, 1.5 eq) in one portion at 0° C. under $N_2$. The mixture was stirred at 0° C. for 2 hrs. LCMS showed the reaction was completed. The residue was poured into water (20 mL). The aqueous phase was extracted with ethyl acetate (100 mL*3). The combined organic phase was washed with brine (10 mL*3), dried with anhydrous $Na_2SO_4$, filtered and concentrated in vacuum. The residue was purified by prep-HPLC (TFA condition) column: Phenomenex Luna C18 150*30 mm*5 um; mobile phase: [water (TFA)-ACN]; B %: 30%-50%, 8 min To afford the title compound (S,E)-5-cyclopropyl-3-((3-(2-(2-(4-(dimethylamino)-N-methylbut-2-enamido)propanamido) ethyl)-5-fluorophenyl) amino)-6-methylpyrazine-2-carboxamide (11.17 mg, 21.09 µmol, 10.93% yield) as a yellow solid. 1H NMR (400 MHz, DMSO-$d_6$) δ=11.27-11.19 (m, 1H), 9.73-9.64 (m, 1H), 8.26-8.21 (m, 1H), 8.09-7.89 (m, 1H), 7.84 (br s, 1H), 7.63-7.55 (m, 1H), 7.01-6.97 (m, 1H), 6.84-6.76 (m, 1H), 6.64-6.47 (m, 2H), 5.01-4.52 (m, 1H), 3.95-3.81 (m, 2H), 3.32-3.26 (m, 2H), 2.88 (s, 2H), 2.78-2.74 (m, 6H), 2.72-2.66 (m, 3H), 2.56 (s, 3H), 2.30-2.24 (m, 1H), 1.28-1.19 (m, 3H), 1.15 (br s, 2H), 1.07-1.03 (m, 2H). $^1$H NMR (400 MHz, $D_2O$) δ=7.00 (br d, J=11.9 Hz, 1H), 6.79-6.60 (m, 2H), 6.59-6.44 (m, 1H), 6.35 (br d, J=8.9 Hz, 1H), 4.90-4.54 (m, 1H), 3.86-3.73 (m, 2H), 3.46-3.28 (m, 2H), 2.85-2.79 (m, 8H), 2.72-2.53 (m, 3H), 2.29 (br s, 3H), 2.00-1.87 (m, 1H), 1.34-1.20 (m, 3H), 0.97 (br s, 2H), 0.79 (br s, 2H). LC-MS (ES+, m/z): 526.3 [(M+H)$^+$]; Rt=2.202 min. HRMS (EI): m/z [M]+ found: 526.2921.

Example 36 (Compound 302)

(R,E)-3-((3-(2-(2-(4-(dimethylamino)-N-methylbut-2-enamido) propanamido) ethyl) phenyl) amino)-6-ethyl-5-(isopropyl (methyl) amino) pyrazine-2-carboxamide Step 3: (R,E)-3-((3-(2-(2-(4-(dimethylamino)-N-methylbut-2-enamido)propanamido)ethyl)phenyl)amino)-6-ethyl-5-(isopropyl(methyl)amino)pyrazine-2-carboxamide

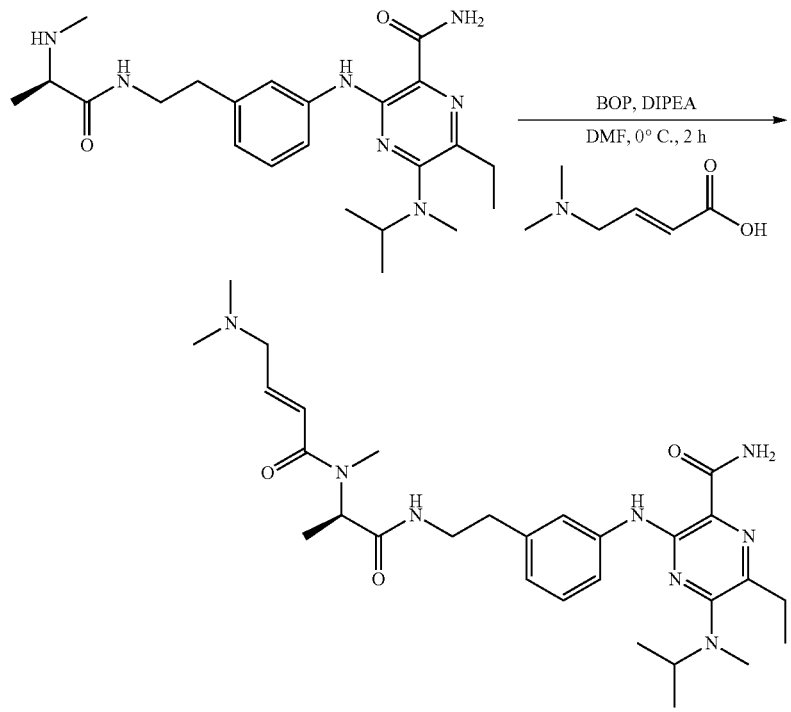

To a solution of (E)-4-(dimethylamino)but-2-enoic acid (260.85 mg, 1.58 mmol, 1.5 eq, HCl), DIPEA (1.36 g, 10.50 mmol, 1.83 mL, 10 eq) in DMF (3 mL), then added a solution of (R)-6-ethyl-5-(isopropyl(methyl)amino)-3-((3-(2-(2-(methylamino)propanamido)ethyl) phenyl)amino) pyrazine-2-carboxamide (500.00 mg, 1.05 mmol, 1 eq, HCl) in DMF (3 mL) at 0° C., then BOP (696.59 mg, 1.58 mmol, 1.5 eq) was added at 0° C., the mixture was stirred at 0° C. for 2 hours. LCMS showed the reaction was completed. The residue was purified by prep-HPLC(column: Phenomenex luna C18 250*50 mm*10 µm; mobile phase: [water (TFA)-ACN]; B %: 25%-55%, 10 min) to afford (R,E)-3-((3-(2-(2-(4-(dimethylamino)-N-methylbut-2-enamido)propanamido) ethyl) phenyl)amino)-6-ethyl-5-(isopropyl(methyl) amino) pyrazine-2-carboxamide (109.07 mg, 193.18 µmol, 18.75% yield, 99.75% purity)) as a yellow solid. $^1$H NMR (400 MHz, DMSO-$d_6$) δ=11.10 (s, 1H), 8.12-7.88 (m, 1H), 7.76 (br d, J=2.0 Hz, 1H), 7.56-7.42 (m, 3H), 7.21 (br t, J=7.8 Hz, 1H), 6.87-6.74 (m, 2H), 6.67-6.45 (m, 1H), 5.02-4.53 (m, 1H), 4.25 (quind, J=6.7, 13.2 Hz, 1H), 3.94-3.81 (m, 2H), 3.36-3.23 (m, 2H), 2.94-2.84 (m, 5H), 2.82-2.65 (m, 11H), 1.31-1.14 (m, 12H). LC-MS (ES+, m/z): 553.3 [(M+H)$^+$]; Rt=2.293 min; HRMS: 553.3621. SFC: 100%

Example 37 (Compound 303)

(S,E)-6-ethyl-5-(isopropylamino)-3-((3-(2-(2-(N-methyl-4-(methylamino) but-2-enamido) propanamido) ethyl) phenyl) amino) pyrazine-2-carboxamide Step 1: tert-butyl (S,E)-(4-((1-((3-((3-carbamoyl-5-ethyl-6-(isopropylamino) pyrazin-2-yl) amino) phenethyl) amino)-1-oxopropan-2-yl) (methyl) amino)-4-oxobut-2-en-1-yl) (methyl) carbamate

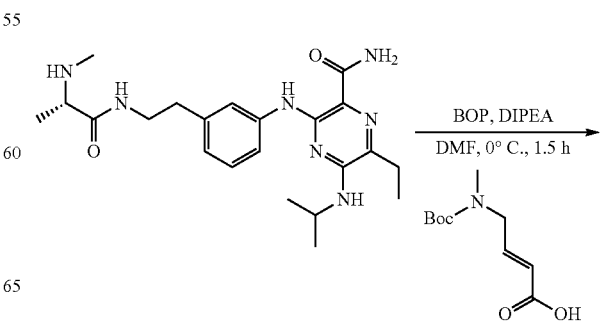

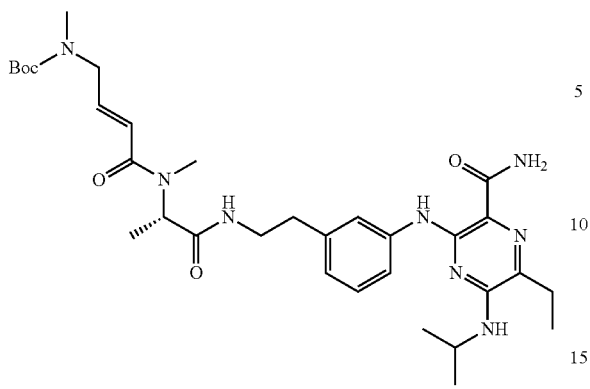

To a solution of (E)-4-((tert-butoxycarbonyl)(methyl)amino)but-2-enoic acid (194.83 mg, 905.17 μmol, 1.2 eq) in DMF (3 mL) at 0° C. was added DIPEA (974.89 mg, 7.54 mmol, 10 eq) and (S)-6-ethyl-5-(isopropylamino)-3-((3-(2-(2-(methylamino)propanamido)ethyl)phenyl)amino)pyrazine-2-carboxamide (350 mg, 754.31 μmol, 1 eq, HCl), and then BOP (500.42 mg, 1.13 mmol, 1.5 eq) was added. The mixture was stirred at 0° C. for 1.5 h. LCMS indicated the reaction was complete. The mixture was poured into water (20 mL) and extracted with EtOAc (10 mL*2). The organic layers was washed with water (10 mL*2), saturated brine (10 mL*2), dried over Na$_2$SO$_4$, filtered, concentrated under reduced pressure to give a residue. The crude product was purified by chromatography on silica gel (DCM/MeOH=10:1) to afford tert-butyl (S,E)-(4-((1-((3-((3-carbamoyl-5-ethyl-6-(isopropylamino)pyrazin-2-yl)amino)phenethyl)amino)-1-oxopropan-2-yl)(methyl)amino)-4-oxobut-2-en-1-yl)(methyl)carbamate (437.5 mg, 700.26 μmol, 92.83% yield) as yellow solid. $^1$H NMR (400 MHz, DMSO-d$_6$) δ=11.30-11.25 (m, 1H), 8.16-7.88 (m, 1H), 7.73 (br s, 1H), 7.65-7.56 (m, 1H), 7.47-7.40 (m, 1H), 7.35-7.19 (m, 2H), 6.87-6.76 (m, 2H), 6.65-6.36 (m, 2H), 5.09-4.54 (m, 1H), 4.37-4.26 (m, 1H), 4.03-3.88 (m, 2H), 3.32 (br d, J=7.5 Hz, 2H), 2.91-2.79 (m, 5H), 2.76 (s, 3H), 2.65 (q, J=7.4 Hz, 2H), 1.48-1.42 (m, 9H), 1.35-1.24 (m, 12H); LC-MS (ES+, m/z): 625.5 [(M+H)$^+$]. RT=0.855 min.

Step 2: (S,E)-6-ethyl-5-(isopropylamino)-3-((3-(2-(2-(N-methyl-4-(methylamino) but-2-enamido) propanamido) ethyl) phenyl) amino) pyrazine-2-carboxamide

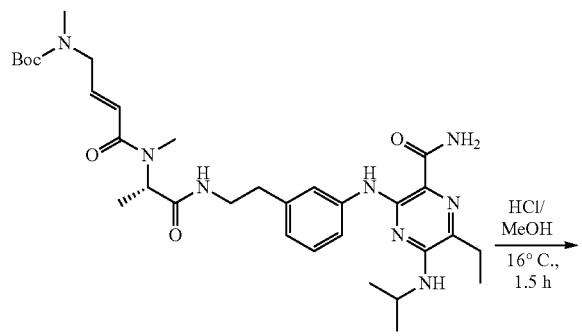

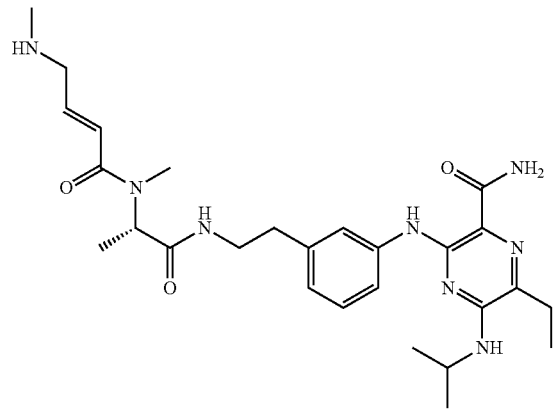

The mixture tert-butyl (S,E)-(4-((1-((3-((3-carbamoyl-5-ethyl-6-(isopropylamino)pyrazin-2-yl)amino)phenethyl)amino)-1-oxopropan-2-yl)(methyl)amino)-4-oxobut-2-en-1-yl)(methyl)carbamate (500 mg, 800.29 μmol, 1 eq) and HCl/MeOH (4 M, 30 mL, 149.95 eq) was stirred at 16° C. for 1.5 h. LCMS indicated the reaction was complete. The reaction mixture was concentrated under reduced pressure to give a residue. The resulting product was dissolved in DMF and filtered to give a crude. The crude was purified by prep-HPLC column: Phenomenex luna C18 100*40 mm*3 μm; mobile phase: [water (TFA)-ACN]; B %: 5%-50%, 8 min) to afford (S,E)-6-ethyl-5-(isopropylamino)-3-((3-(2-(2-(N-methyl-4-(methylamino)but-2-enamido)propanamido)ethyl)phenyl)amino)pyrazine-2-carboxamide (90.4 mg, 167.67 μmol, 20.95% yield, 97.31% purity) as yellow solid. $^1$H NMR (400 MHz, DMSO-d$_6$) δ=11.25-11.19 (m, 1H), 8.79-8.51 (m, 2H), 8.10-7.88 (m, 1H), 7.64-7.54 (m, 2H), 7.46-7.37 (m, 1H), 7.28-7.15 (m, 2H), 6.81-6.69 (m, 3H), 6.63-6.44 (m, 1H), 4.70 (s, 1H), 4.33-4.19 (m, 1H), 3.79-3.67 (m, 2H), 3.31-3.24 (m, 2H), 2.93-2.88 (m, 2H), 2.73 (br s, 3H), 2.58 (br t, J=7.3 Hz, 5H), 1.29-1.17 (m, 12H); $^1$H NMR (400 MHz, DMSO-d$_6$) δ=8.08-7.86 (m, 1H), 7.66-7.57 (m, 1H), 7.44-7.36 (m, 1H), 7.19 (t, J=7.8 Hz, 1H), 6.82-6.66 (m, 2H), 6.60-6.43 (m, 1H), 4.98-4.51 (m, 1H), 4.28-4.20 (m, 1H), 3.72 (br d, J=6.5 Hz, 2H), 3.36-3.23 (m, 2H), 2.88 (s, 2H), 2.72-2.64 (m, 3H), 2.58-2.53 (m, 5H), 1.27-1.15 (m, 12H); LC-MS (ES+, m/z): 525.3 [(M+H)$^+$]. RT=2.143 min; HRMS (EI): m/z [M+H]$^+$ found: 525.3275.

Example 38 (Compound 305)

(S,E)-3-((3-(2-(2-(4-(dimethylamino)-N-methylbut-2-enamido)propanamido) ethyl)phenyl)amino)-5-isopropyl-6-methylpyrazine-2-carboxamide Step 1: (S,E)-3-((3-(2-(2-(4-(dimethylamino)-N-methylbut-2-enamido) propanamido)ethyl)phenyl)amino)-5-isopropyl-6-methylpyrazine-2-carboxamide

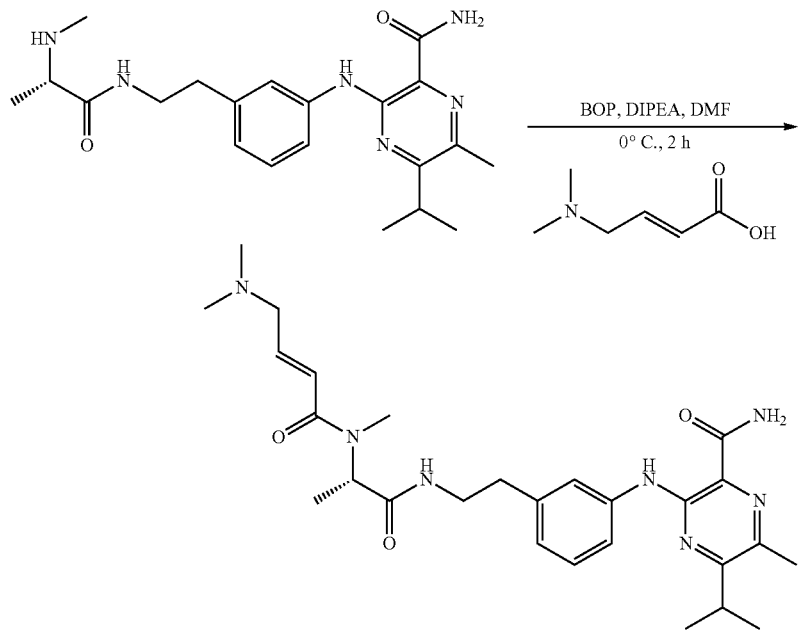

To a solution of (E)-4-(dimethylamino)but-2-enoic acid (68.54 mg, 413.83 µmol, 1.5 eq, HCl) in DMF (1 mL) was added DIPEA (356.56 mg, 2.76 mmol, 480.54 µL, 10 eq), (S)-5-isopropyl-6-methyl-3-((3-(2-(2-(methylamino)propanamido)ethyl) phenyl)amino)pyrazine-2-carboxamide (120 mg, 275.89 µmol, 1 eq, HCl) and BOP (183.03 mg, 413.83 µmol, 1.5 eq). The mixture was stirred at 0° C. for 2 hrs. LCMS indicated the reaction was completed. The reaction mixture was filtered to give a residue. The residue was purified by prep-HPLC column: Phenomenex Luna 80*30 mm*3 um; mobile phase: [water (TFA)-ACN]; B %: 10%-50%, 8 min to afford (S,E)-3-((3-(2-(2-(4-(dimethylamino)-N-methylbut-2-enamido)propanamido)ethyl) phenyl) amino)-5-isopropyl-6-methylpyrazine-2-carboxamide (27 mg, 52.95 µmol, 19.19% yield) as yellow solid. $^1$H NMR (400 MHz, DMSO-$d_6$) δ=11.12-11.01 (m, 1H), 9.82-9.58 (m, 1H), 8.32-8.14 (m, 1H), 8.12-7.87 (m, 1H), 7.83 (br s, 1H), 7.67-7.56 (m, 1H), 7.56-7.49 (m, 1H), 7.28-7.19 (m, 1H), 6.87-6.75 (m, 2H), 6.65-6.45 (m, 1H), 5.04-4.51 (m, 1H), 3.94-3.79 (m, 2H), 3.34-3.23 (m, 3H), 2.92-2.87 (m, 2H), 2.80-2.68 (m, 9H), 2.49-2.47 (m, 3H), 1.30-1.21 (m, 9H). (TFA salt) LC-MS (ES+, m/z): 510.3 [(M+H)$^+$]; Rt=2.162 min; HRMS (EI): m/z [M+H]$^+$ found: 510.3194.

Example 39 (Compound 306) (S,E)-5-cyclopropyl-3-((5-(2-(2-(4-(dimethylamino)-N-methylbut-2-enamido) propanamido) ethyl) pyridin-3-yl) amino)-6-ethylpyrazine-2-carboxamide Step 1: (S,E)-5-cyclopropyl-3-((5-(2-(2-(4-(dimethylamino)-N-methylbut-2-enamido) propanamido) ethyl) pyridin-3-yl) amino)-6-ethylpyrazine-2-carboxamide

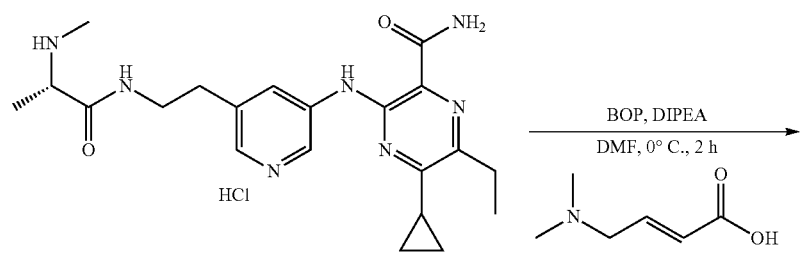

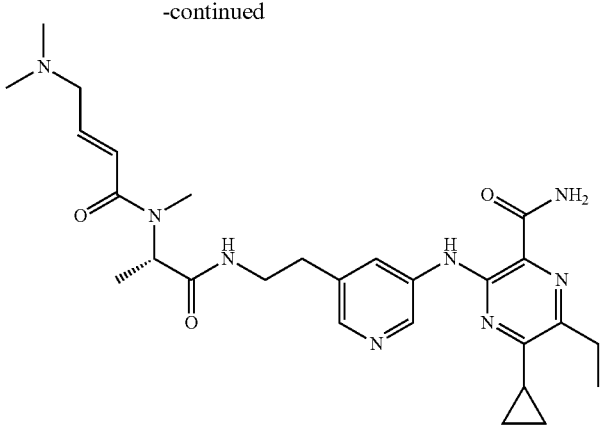

To a solution of (S)-5-cyclopropyl-6-ethyl-3-((5-(2-(2-(methylamino)propanamido)ethyl)pyridin-3-yl)amino)pyrazine-2-carboxamide hydrochloride (50 mg, 111.62 µmol, 1 eq, HCl) in DMF (1 mL) was added (E)-4-(dimethylamino)but-2-enoic acid (17.30 mg, 104.45 µmol, 9.36e-1 eq, HCl), BOP (59.24 mg, 133.94 µmol, 1.2 eq) and DIEA (72.13 mg, 558.08 µmol, 97.21 µL, 5 eq) at 0° C. The mixture was stirred at 0° C. for 2 hr. LC-MS showed the reaction was consumed completely. The reaction mixture was quenched by addition water (50 mL) at 15° C., and then extracted with EtOAc (20 mL*3). The combined organic layers were washed with sat. brine (20 mL*2), dried over Na$_2$SO$_4$, filtered and concentrated under reduced pressure to give a residue. The residue was purified by prep-HPLC (column: Phenomenex Luna C18 75*30 mm*3 um; mobile phase: [water (TFA)-ACN]; B %: 5%-35%, 8 min) to afford (S,E)-5-cyclopropyl-3-((5-(2-(2-(4-(dimethylamino)-N-methyl-but-2-enamido)propanamido)ethyl)pyridin-3-yl)amino)-6-ethylpyrazine-2-carboxamide as a light yellow solid (44.03 mg, 84.40 µmol, 75.62% yield, 100% purity). $^1$H NMR (400 MHz, DMSO-d$_6$) δ=11.19 (s, 1H), 10.70-10.05 (m, 1H), 8.78 (br s, 1H), 8.19 (br s, 1H), 8.17-7.94 (m, 3H), 7.91 (br s, 1H), 6.86-6.76 (m, 1H), 6.66-6.46 (m, 1H), 4.97-4.52 (m, 1H), 3.92-3.84 (m, 2H), 3.36 (br d, J=6.0 Hz, 2H), 2.95-2.89 (m, 2H), 2.87 (s, 2H), 2.77 (br s, 8H), 2.66 (s, 1H), 2.34-2.26 (m, 1H), 1.30-1.18 (m, 6H), 1.14-1.04 (m, 4H). LC-MS (ES+, m/z): 523.3 [(M+H)$^+$]; Rt=1.753 min. HRMS (EI): m/z [M]$^+$ found: 523.3149.

Example 40 (Compound 307)
(S,E)-6-ethyl-5-(isopropyl(methyl)amino)-3-((3-(2-(2-(N-methyl-4-(methylamino)but-2-enamido)propanamido)ethyl)phenyl)amino)pyrazine-2-carboxamide Step 1: tert-butyl (S,E)-(4-((1-((3-((3-carbamoyl-5-ethyl-6-(isopropyl(methyl)amino)pyrazin-2-yl)amino)phenethyl)amino)-1-oxopropan-2-yl)(methyl)amino)-4-oxobut-2-en-1-yl)(methyl)carbamate

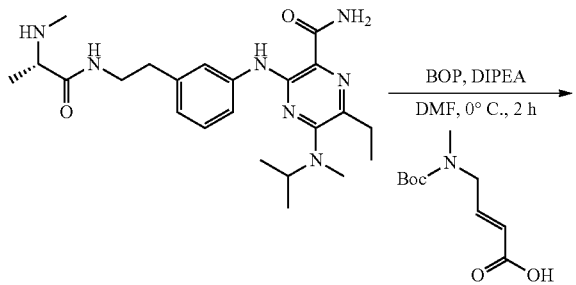

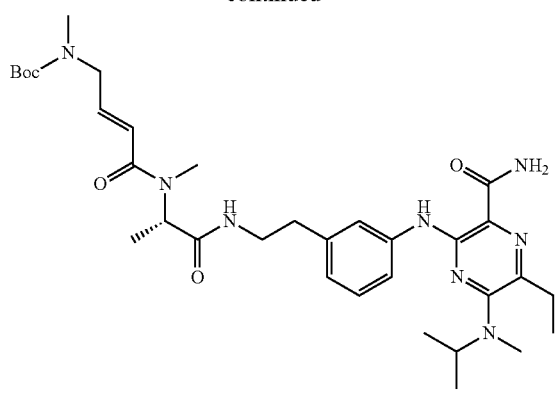

To a solution of (E)-4-((tert-butoxycarbonyl)(methyl)amino)but-2-enoic acid (189.12 mg, 878.61 µmol, 1.2 eq) and DIEA (946.26 mg, 7.32 mmol, 1.28 mL, 10 eq) in DMF (2 mL) was added (S)-6-ethyl-5-(isopropyl(methyl)amino)-3-((3-(2-(2-(methylamino)propanamido)ethyl)phenyl)amino)pyrazine-2-carboxamide (350 mg, 732.17 µmol, 1 eq, HCl), and then BOP (485.74 mg, 1.10 mmol, 1.5 eq) was added. The mixture was stirred at 0° C. for 2 hrs. LCMS showed the reaction was completed. The reaction was poured into water (15 mL) and extracted with EtOAc (10 mL*2). The organic layers were combined, washed with water (10 mL*2), saturated brine (10 ml), dried (Na$_2$SO$_4$), filtered and concentrated to give crude product. The crude product was purified by chromatography on silica thiol gel (petroleum ether/EtOAc=1/1) TLC (plate 1 Rf=0.69) to afford tert-butyl (S,E)-(4-((1-((3-((3-carbamoyl-5-ethyl-6-(isopropyl(methyl)amino)pyrazin-2-yl)amino)phenethyl)amino)-1-oxopropan-2-yl)(methyl)amino)-4-oxobut-2-en-1-yl)(methyl)carbamate (400 mg, 626.18 µmol, 85.52% yield) as yellow solid. LC-MS (ES+, m/z): 639.5 [(M+H)$^+$]; Rt=0.827 min.

Step 2: (S,E)-6-ethyl-5-(isopropyl(methyl)amino)-3-((3-(2-(2-(N-methyl-4-(methylamino)but-2-enamido)propanamido)ethyl)phenyl)amino)pyrazine-2-carboxamide

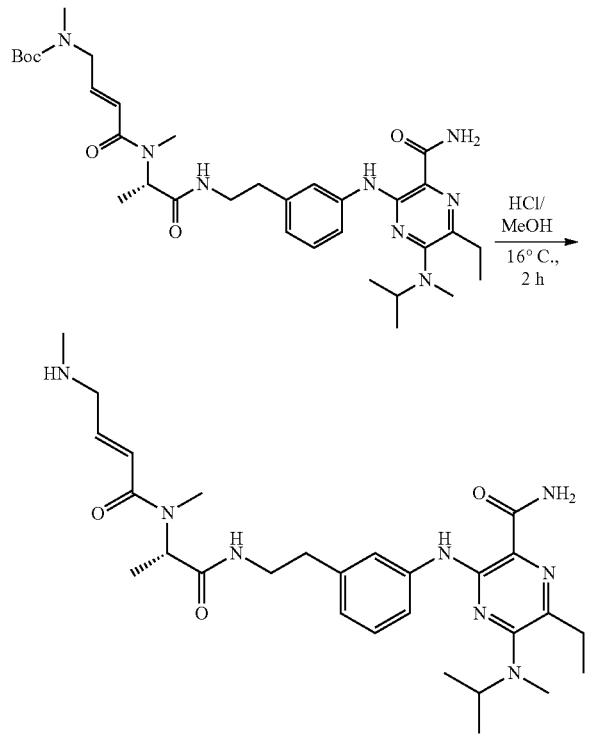

A mixture of tert-butyl (S,E)-(4-((1-((3-((3-carbamoyl-5-ethyl-6-(isopropyl(methyl)amino)pyrazin-2-yl)amino)phenethyl)amino)-1-oxopropan-2-yl)(methyl)amino)-4-oxobut-2-en-1-yl)(methyl)carbamate (400 mg, 626.18 μmol, 1 eq) and HCl/MeOH (4 M, 15 mL, 95.82 eq) was stirred at 16° C. for 2 hrs. LCMS showed the reaction was completed. Filtered to give filtrate. The crude was purified by prep-HPLC column: Phenomenex Luna C18 75*30 mm*3 um; mobile phase: [water (TFA)-ACN]; B %: 10%-40%, 8 min to afford (S,E)-6-ethyl-5-(isopropyl(methyl)amino)-3-((3-(2-(2-(N-methyl-4-(methylamino)but-2-enamido)propanamido)ethyl)phenyl)amino) pyrazine-2-carboxamide (101.00 mg, 175.61 μmol, 28.04% yield, HCl) as yellow solid. $^1$H NMR (400 MHz, DMSO-$d_6$) δ=11.14-11.07 (m, 1H), 8.74-8.46 (m, 2H), 8.13-7.83 (m, 1H), 7.76 (br s, 1H), 7.56-7.50 (m, 1H), 7.50-7.39 (m, 2H), 7.25-7.14 (m, 1H), 6.79 (d, J=7.3 Hz, 1H), 6.77-6.66 (m, 1H), 6.63-6.43 (m, 1H), 5.02-4.51 (m, 1H), 4.25 (quin, J=6.6 Hz, 1H), 3.90-3.55 (m, 2H), 3.30-3.24 (m, 2H), 2.93-2.84 (m, 5H), 2.78-2.63 (m, 6H), 2.57 (br s, 2H), 1.29-1.19 (m, 12H)(TFA, salt). $^1$H NMR (400 MHz, D$_2$O) δ=8.09-7.63 (m, 1H), 7.54-7.49 (m, 1H), 7.46-7.40 (m, 1H), 7.20 (br t, J=7.7 Hz, 1H), 6.82-6.65 (m, 2H), 6.63-6.38 (m, 1H), 5.00-4.50 (m, 1H), 4.24 (quin, J=6.6 Hz, 1H), 3.82-3.59 (m, 2H), 3.33-3.20 (m, 2H), 2.93-2.84 (m, 5H), 2.76-2.64 (m, 6H), 2.56 (s, 2H), 1.22-1.16 (m, 12H)(TFA, salt). LC-MS (ES+, m/z): 539.3 [(M+H)+]; Rt=2.276 min. HRMS (EI): m/z [M]$^+$ found: 539.3473. SFC: 95.15%.

Example 41 (Compound 308)

6-ethyl-5-(isopropyl(methyl)amino)-3-((3-(2-(2-(N-methylacrylamido) acetamido) ethyl)phenyl)amino) pyrazine-2-carboxamide Step 3: 6-ethyl-5-(isopropyl(methyl)amino)-3-((3-(2-(2-(N-methylacrylamido)acetamido)ethyl)phenyl) amino)pyrazine-2-carboxamide

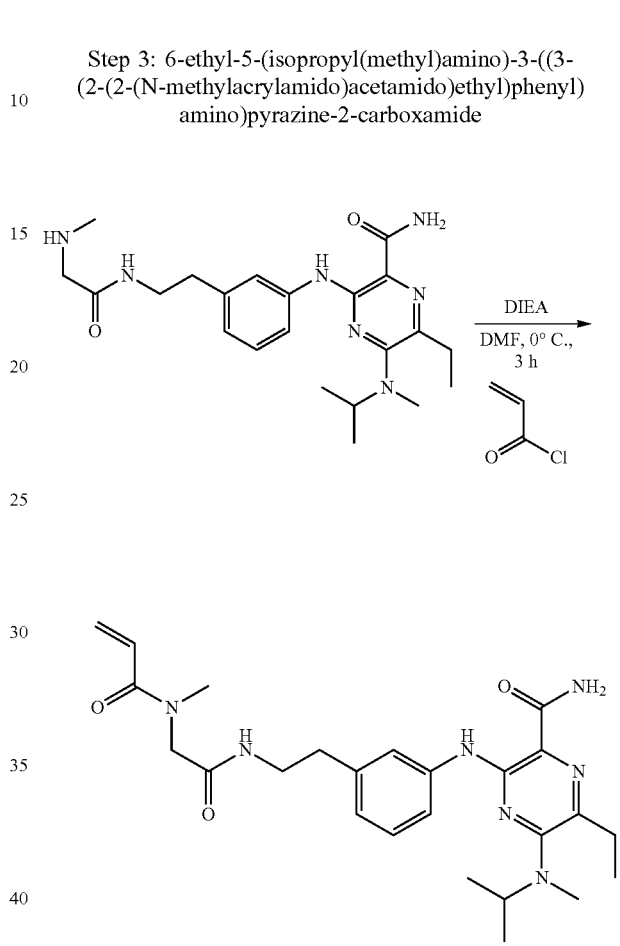

To a mixture of 6-ethyl-5-(isopropyl(methyl)amino)-3-((3-(2-(2-(methylamino) acetamido)ethyl)phenyl)amino) pyrazine-2-carboxamide (160 mg, 280.67 μmol, 1 eq) in DMF (3 mL) was added DIEA (362.75 mg, 2.81 mmol, 10 eq), and then added acryloyl chloride (25.40 mg, 280.67 μmol, 1 eq) in one portion at 0° C. under N$_2$. The mixture was stirred for 3 hours. LCMS showed the reaction was completed. The reaction mixture was filtered to give a residue. The residue was purified by prep-HPLC column: Phenomenex Luna C18 75*30 mm*3 um; mobile phase: [water (TFA)-ACN]; B %: 35%-65%, 8 min to afford 6-ethyl-5-(isopropyl(methyl)amino)-3-((3-(2-(2-(N-methylacrylamido)acetamido)ethyl)phenyl)amino)pyrazine-2-carboxamide (10.22 mg, 21.06 μmol, 7.50% yield) as yellow solid. $^1$H NMR (400 MHz, DMSO-$d_6$) δ=11.10 (d, J=1.5 Hz, 1H), 8.13-7.96 (m, 1H), 7.75 (br s, 1H), 7.56 (br d, J=6.5 Hz, 1H), 7.47-7.42 (m, 2H), 7.21 (t, J=7.8 Hz, 1H), 6.81-6.78 (m, 1H), 6.78-6.47 (m, 1H), 6.13-6.02 (m, 1H), 5.70-5.56 (m, 1H), 4.28-4.21 (m, 1H), 3.96 (d, J=18.4 Hz, 2H), 3.31 (br dd, J=7.5, 14.1 Hz, 2H), 3.02 (s, 2H), 2.86 (s, 3H), 2.81 (s, 1H), 2.73-2.68 (m, 4H), 1.22-1.19 (m, 9H). LC-MS (ES+, m/z): 482.3 [(M+H)$^+$]; Rt=2.637 min; HRMS (EI): m/z [M+H]+: 482.2864.

Example 42 (Compound 310)

(S,E)-5-cyclopropyl-3-((2-(2-(2-(4-(dimethylamino)-N-methylbut-2-enamido) propanamido)ethyl)pyridin-4-yl)amino)-6-ethylpyrazine-2-carboxamide

Step 1: tert-butyl (S)-(1-((2-(4-((3-carbamoyl-6-cyclopropyl-5-ethylpyrazin-2-yl)amino)pyridin-2-yl)ethyl)amino)-1-oxopropan-2-yl)(methyl)carbamate

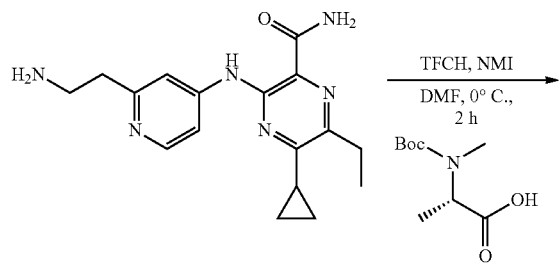

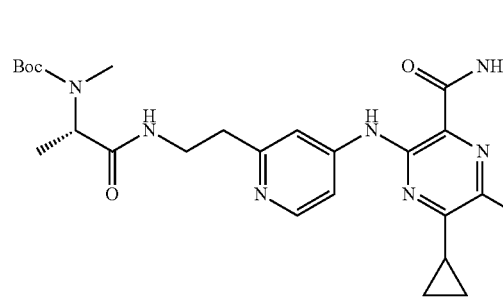

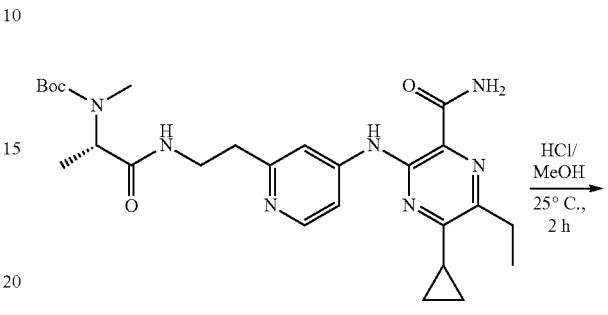

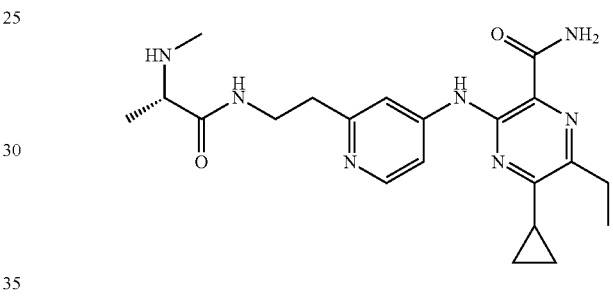

To a mixture of N-(tert-butoxycarbonyl)-N-methyl-L-alanine (74.72 mg, 367.65 μmol, 1.5 eq), NMI (201.23 mg, 2.45 mmol, 195.37 μL, 10.0 eq) in DMF (2 mL) was added 3-((2-(2-aminoethyl)pyridin-4-yl)amino)-5-cyclopropyl-6-ethylpyrazine-2-carboxamide (80 mg, 245.10 μmol, 1 eq, HCl), then TCFH (82.52 mg, 294.12 μmol, 1.2 eq) was added at 0° C. and the reaction mixture was stirred at 0° C. for 2 hrs. LC-MS showed the reaction was completed. The reaction mixture was quenched by addition H₂O (50 mL), then extracted with DCM (20 mL*3). The combined organic layers were washed with saturated brine (30 mL), dried over anhydrous Na₂SO₄ filtered and concentrated under reduced pressure to give a residue. The residue was purified by prep-TLC (SiO₂, DCM:MeOH=10:1) to give tert-butyl (S)-(1-((2-(4-((3-carbamoyl-6-cyclopropyl-5-ethylpyrazin-2-yl)amino)pyridin-2-yl)ethyl)amino)-1-oxopropan-2-yl)(methyl)carbamate (85 mg, 166.14 μmol, 67.78% yield) as a yellow solid. LC-MS (ES⁺, m/z): 512.3 [(M+H)⁺]. Rt=0.720 min.

Step 2: (S)-5-cyclopropyl-6-ethyl-3-((2-(2-(2-(methylamino)propanamido)ethyl)pyridin-4-yl)amino)pyrazine-2-carboxamide A solution of (S)-tert-butyl (1-((2-(4-((3-carbamoyl-6-cyclopropyl-5-ethylpyrazin-2-yl)amino)pyridin-2-yl)ethyl)amino)-1-oxopropan-2-yl)(methyl)carbamate (85 mg, 166.14 μmol, 1.0 eq) in HCl/MeOH (4 M, 3 mL, 72.23 eq) was stirred at 25° C. for 2 hrs. LC-MS showed reaction was completed. The reaction mixture was concentrated under reduced pressure to give (S)-5-cyclopropyl-6-ethyl-3-((2-(2-(2-(methylamino)propanamido)ethyl)pyridin-4-yl)amino)pyrazine-2-carboxamide (90 mg, crude, HCl) as a yellow solid. LC-MS (ES⁺, m/z): 412.3 [(M+H)⁺]. Rt=0.568 min.

Step 3: (S,E)-5-cyclopropyl-3-((2-(2-(2-(4-(dimethylamino)-N-methylbut-2-enamido)propanamido)ethyl)pyridin-4-yl)amino)-6-ethylpyrazine-2-carboxamide

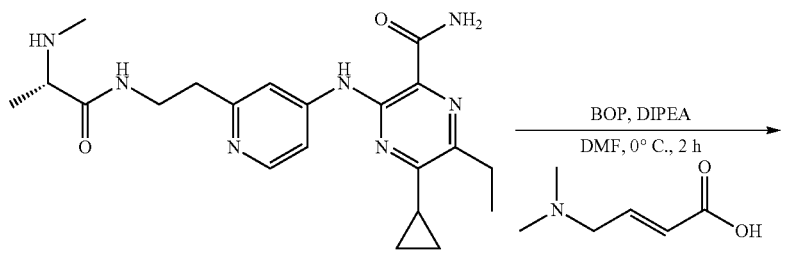

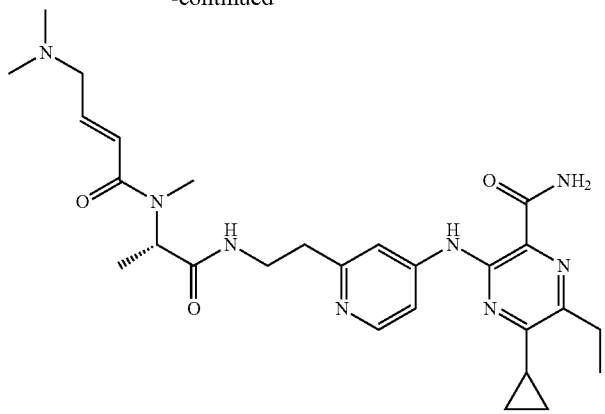

To a solution of (S)-5-cyclopropyl-6-ethyl-3-((2-(2-(2-(methylamino)propanamido)ethyl)pyridin-4-yl)amino)pyrazine-2-carboxamide (70 mg, 156.26 µmol, 1.0 eq, HCl) and (E)-4-(dimethylamino)but-2-enoic acid (38.82 mg, 234.40 µmol, 1.5 eq, HCl), DIEA (201.96 mg, 1.56 mmol, 272.18 µL, 10 eq) in DMF (2 mL) was added BOP (103.67 mg, 234.40 µmol, 1.5 eq) at 0° C., then the reaction mixture was stirred at 0° C. for 2 hrs. LC-MS showed reaction was completed. The reaction mixture was quenched by addition $H_2O$ (20 mL), extracted with DCM (10 mL*3). The combined organic layers were washed with saturated brine (10 mL), dried over anhydrous $Na_2SO_4$, filtered and concentrated under reduced pressure to give a residue. The residue was purified by prep-HPLC (basic condition column: Phenomenex C18 75*30 mm*3 um; mobile phase: [water ($NH_3H_2O+NH_4HCO_3$)-ACN]; B %: 10%-50%, 8 min) to give (S,E)-5-cyclopropyl-3-((2-(2-(2-(4-(dimethylamino)-N-methylbut-2-enamido)propanamido)ethyl)pyridin-4-yl)amino)-6-ethylpyrazine-2-carboxamide (13.3 mg, 25.45 µmol, 16.29% yield, 100% purity) as a white solid. $^1H$ NMR (400 MHz, DMSO-$d_6$) δ=11.43-11.34 (m, 1H), 8.32-8.17 (m, 2H), 8.12-7.75 (m, 2H), 7.49-7.32 (m, 2H), 6.69-6.29 (m, 2H), 5.06-4.44 (m, 1H), 3.52-3.25 (m, 2H), 3.01-2.89 (m, 4H), 2.87-2.68 (m, 4H), 2.75-2.64 (m, 1H), 2.38-2.28 (m, 1H), 2.16-2.03 (m, 6H), 1.33-1.23 (m, 4H), 1.21-1.09 (m, 6H). LC-MS (ES$^+$, m/z): 523.2 [(M+H)$^+$]. Rt=1.773 min. HRMS (EI): m/z [M+H]$^+$ found: 523.3130.

Example 43 (Compound 315)

(S)-6-ethyl-5-(isopropyl(methyl)amino)-3-((3-(2-(2-(N-methylacrylamido)propanamido)ethyl)phenyl)amino)pyrazine-2-carboxamide Step 1: (S)-6-ethyl-5-(isopropyl(methyl)amino)-3-((3-(2-(2-(N-methylacrylamido)propanamido)ethyl)phenyl)amino)pyrazine-2-carboxamide

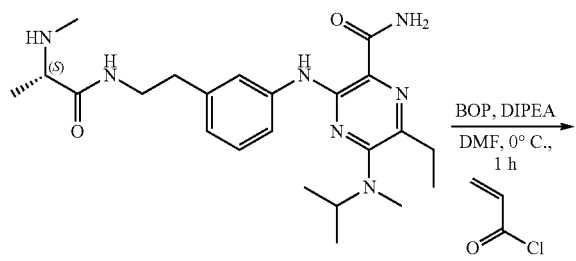

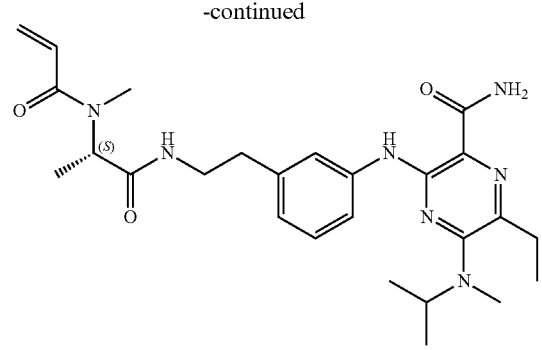

To a solution of (S)-6-ethyl-5-(isopropyl(methyl)amino)-3-((3-(2-(2-(methylamino)propanamido)ethyl)phenyl)amino)pyrazine-2-carboxamide (200 mg, 418.38 µmol, 1 eq, HCl) and DIEA (270.36 mg, 2.09 mmol, 364.37 µL, 5 eq) in DMF (3 mL) was added prop-2-enoyl chloride (45.44 mg, 502.06 µmol, 40.94 µL, 1.2 eq) at 0° C., then the mixture was stirred at 0° C. for 1 hr. LCMS showed the reaction was completed. The reaction mixture was concentrated in vacuum to give a residue. The residue was purified by prep-HPLC(column: Phenomenex luna C18 250*50 mm*10 µm; mobile phase: [water (TFA)-ACN]; B %: 25%-55%, 10 min) to afford (S)-6-ethyl-5-(isopropyl(methyl)amino)-3-((3-(2-(2-(N-methylacrylamido) propanamido)ethyl)phenyl)amino)pyrazine-2-carboxamide (10.92 mg, 22.03 µmol, 5.27% yield, 100% purity) as a yellow solid. $^1H$ NMR (400 MHz, DMSO-$d_6$) δ=11.10 (br s, 1H), 8.10-7.84 (m, 1H), 7.77-7.51 (m, 2H), 7.50-7.39 (m, 2H), 7.20 (t, J=7.8 Hz, 1H), 6.79 (d, J=7.6 Hz, 1H), 6.71 (br dd, J=10.4, 16.8 Hz, 1H), 6.15-6.01 (m, 1H), 5.70-5.57 (m, 1H), 4.99 (br d, J=7.2 Hz, 1H), 4.25 (quin, J=6.6 Hz, 1H), 3.35-3.19 (m, 2H), 2.92-2.80 (m, 5H), 2.77-2.65 (m, 5H), 1.28-1.14 (m, 12H). LC-MS (ES+, m/z): 496.3 [(M+H)$^+$]; Rt=2.752 min; HRMS (EI): m/z [M]$^+$ found: 496.3052.

Example 44 (Compound 321)

(R,E)-3-((3-(1-(2-(4-(dimethylamino)-N-methylbut-2-enamido)acetamido)propan-2-yl)phenyl)amino)-6-ethyl-5-methylpyrazine-2-carboxamide Step 4: (R,E)-3-((3-(1-(2-(4-(dimethylamino)-N-methylbut-2-enamido)acetamido) propan-2-yl)phenyl)amino)-6-ethyl-5-methylpyrazine-2-carboxamide

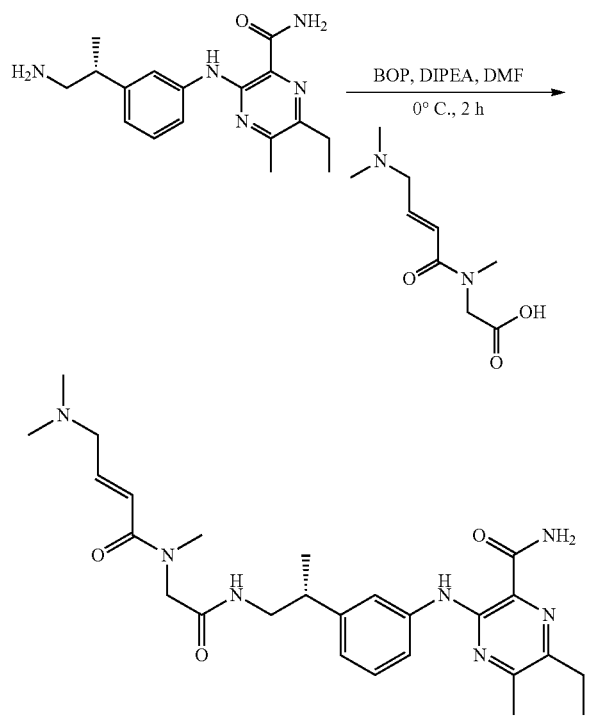

To a solution of (E)-N-(4-(dimethylamino)but-2-enoyl)-N-methylglycine (162.37 mg, 343.00 μmol, 50% purity, 1.5 eq, HCl) in DMF (0.5 mL) was added DIPEA (329.92 mg, 2.55 mmol, 444.63 μL, 10 eq), (R)-3-((3-(1-aminopropan-2-yl)phenyl) amino)-6-ethyl-5-methylpyrazine-2-carboxamide (80 mg, 228.66 μmol, 1 eq, HCl) and BOP (151.70 mg, 343.00 μmol, 1.5 eq). The mixture was stirred at 0° C. for 2 hrs. LCMS indicated the reaction was complete. The reaction mixture was filtered to give a residue. The residue was purified by prep-HPLC column: Waters Xbridge Prep OBD C18 150*40 mm*10 um; mobile phase: [water (NH$_4$HCO$_3$)-ACN]; B %: 30%-70%, 8 min) to afford (R,E)-3-((3-(1-(2-(4-(dimethylamino)-N-methylbut-2-enamido) acetamido) propan-2-yl)phenyl)amino)-6-ethyl-5-methylpyrazine-2-carboxamide (11.16 mg, 22.33 μmol, 9.77% yield) as a yellow solid $^1$H NMR (400 MHz, DMSO-d$_6$) δ=11.11-10.98 (m, 1H), 8.20-8.09 (m, 1H), 8.09-7.81 (m, 2H), 7.64-7.56 (m, 1H), 7.54-7.48 (m, 1H), 7.28-7.20 (m, 1H), 6.89-6.81 (m, 1H), 6.64-6.24 (m, 2H), 3.99-3.88 (m, 2H), 3.28-3.18 (m, 2H), 3.04-3.00 (m, 1H), 2.99-2.96 (m, 1H), 2.94-2.84 (m, 2H), 2.81-2.70 (m, 4H), 2.53-2.51 (m, 3H), 2.17-2.06 (m, 6H), 1.26-1.17 (m, 6H). LC-MS (ES+, m/z): 496.3 [(M+H)$^+$]; Rt=0.967 min; HRMS (EI): m/z [M]$^+$ found: 496.2995.

Example 45 (Compound 322)

(S,E)-6-(dimethylamino)-2-((3-(2-(2-(4-(dimethylamino)-N-methylbut-2-enamido)propanamido)ethyl)phenyl)amino)-5-ethylnicotinamide Step 1: (S,E)-6-(dimethylamino)-2-((3-(2-(2-(4-(dimethylamino)-N-methylbut-2-enamido)propanamido)ethyl)phenyl)amino)-5-ethylnicotinamide

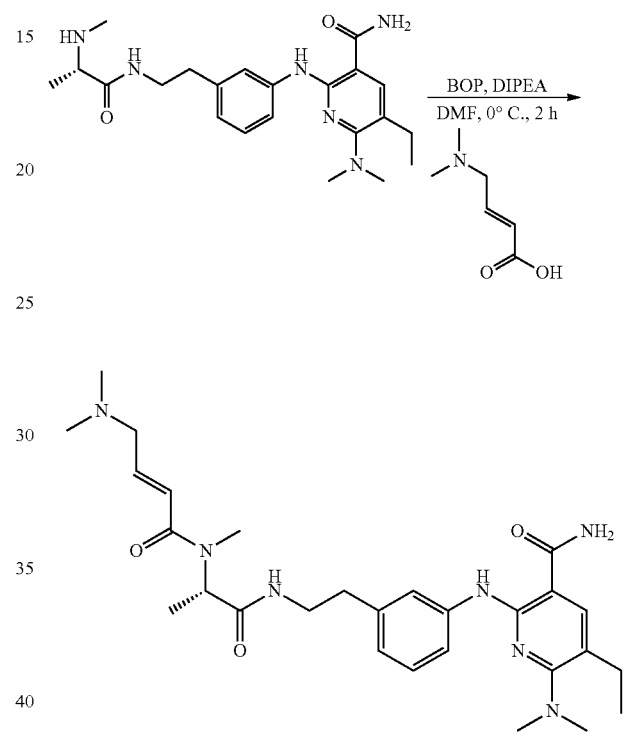

To a mixture of (E)-4-(dimethylamino)but-2-enoic acid (110.66 mg, 668.17 μmol, 1.5 eq, HCl) in DMF (4 mL) was added DIPEA (4.45 mmol, 775.87 μL, 10 eq) and (S)-6-(dimethylamino)-5-ethyl-2-((3-(2-(2-(methylamino)propanamido) ethyl) phenyl)amino)nicotinamide (200 mg, 445.45 μmol, 1 eq, HCl), finally was added BOP (295.52 mg, 668.17 μmol, N/A purity, 1.5 eq) in one portion at 0° C. The mixture was stirred at 0° C. for 2 hrs under N$_2$. LCMS showed the reaction was completed. The reaction mixture was filtered to give a residue. The residue was purified by prep-HPLC (TFA): column: Phenomenex Luna 80*30 mm*3 um; mobile phase: [water (TFA)-ACN]; B %: 5%-40%, 8 min to afford (S,E)-6-(dimethylamino)-2-((3-(2-(2-(4-(dimethylamino)-N-methylbut-2-enamido)propanamido)ethyl)phenyl)amino)-5-ethylnicotinamide (13.15 mg, 25.07 μmol, 5.63% yield) as yellow solid. $^1$H NMR (400 MHz, DMSO-d$_6$) δ=11.40 (br s, 1H), 9.86 (br dd, J=1.4, 3.4 Hz, 1H), 8.14-7.80 (m, 3H), 7.59 (s, 1H), 7.52-7.46 (m, 1H), 7.30-7.13 (m, 2H), 6.86-6.77 (m, 1H), 6.73 (d, J=7.5 Hz, 1H), 6.63-6.46 (m, 1H), 5.03-4.51 (m, 1H), 3.91-3.79 (m, 2H), 3.33-3.24 (m, 2H), 2.96-2.94 (m, 6H), 2.91-2.88 (m, 2H), 2.79-2.66 (m, 9H), 2.58-2.54 (m, 2H), 1.30-1.17 (m, 6H)(TFA, salt). LC-MS (ES+, m/z): 524.3 [(M+H)$^+$]; Rt=1.951 min; HRMS (EI): m/z [M+H]$^+$ found: 524.3328.

Example 46 (Compound 323)

(S,E)-6-cyclopropyl-2-((5-(2-(2-(4-(dimethylamino)-N-methylbut-2 enamido) propanamido)ethyl)pyridin-3-yl)amino)-5-methylnicotinamide Step 1: (S,E)-6-cyclopropyl-2-((5-(2-(2-(4-(dimethylamino)-N-methylbut-2-enamido)propanamido)ethyl)pyridin-3-yl)amino)-5-methylnicotinamide

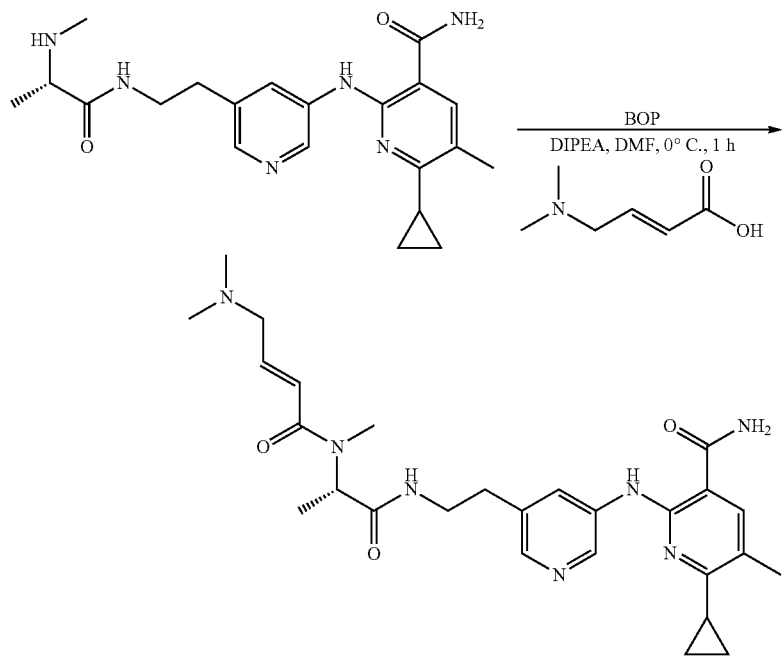

To a solution of (S)-6-cyclopropyl-5-methyl-2-((5-(2-(2-(methylamino)propanamido)ethyl)pyridin-3-yl)amino)nicotinamide (122 mg, 281.79 µmol, 1 eq), (E)-4-(dimethylamino)but-2-enoic acid (70.00 mg, 422.69 µmol, 1.5 eq, HCl) in DMF (2 mL) was added DIPEA (364.19 mg, 2.82 mmol, 10 eq), and then BOP (186.95 mg, 422.69 µmol, 1.5 eq) was added at 0° C. The mixture was stirred at 0° C. for 1 hr. LC-MS showed desired compound was detected. The reaction mixture was quenched with (H$_2$O) 10 mL, and then extracted with EtOAc (10 mL*3). The combined organic layers were washed with saturated brine (10 mL*3), dried over anhydrous Na$_2$SO$_4$, filtered and concentrated under reduced pressure to give a residue. The residue was purified by prep-HPLC (neutral condition; column: Waters Xbridge BEH C18 100*30 mm*10 um; mobile phase: [water (NH$_4$HCO$_3$)-ACN]; B %: 20%-50%, 8 min). To afford the little compound (S,E)-6-cyclopropyl-2-((5-(2-(2-(4-(dimethylamino)-N-methylbut-2-enamido)propanamido)ethyl) pyridin-3-yl)amino)-5-methylnicotinamide (11.08 mg, 21.83 µmol, 7.75% yield) as a black brown solid. 1H NMR (400 MHz, MeOD-d$_4$) δ=8.81-8.75 (m, 1H), 8.04-7.94 (m, 2H), 7.87-7.84 (m, 1H), 6.81-6.67 (m, 1H), 6.56-6.43 (m, 1H), 5.09-5.01 (m, 1H), 3.58-3.45 (m, 2H), 3.32 (s, 2H), 3.14-3.06 (m, 2H), 2.90-2.80 (m, 3H), 2.39 (s, 3H), 2.27-2.21 (m, 7H), 1.40-1.29 (m, 3H), 1.17-1.13 (m, 2H), 1.10-1.05 (m, 2H). 1H NMR (400 MHz, DMSO-d$_6$) δ=11.14 (s, 1H), 8.62 (d, J=1.9 Hz, 1H), 8.15-7.88 (m, 5H), 7.90-7.86 (m, 1H), 6.65-6.37 (m, 2H), 5.01-4.93 (m, 1H), 3.40-3.32 (m, 2H), 3.32 (s, 2H), 3.04-2.92 (m, 2H), 2.76-2.63 (m, 3H), 2.32 (s, 3H), 2.19 (br s, 7H), 1.24 (br d, J=6.4 Hz, 3H), 1.08-0.98 (m, 4H). LC-MS (ES+, m/z): 508.3 [(M+H)$^+$]; Rt=1.750 min. HRMS (EI): m/z [M]+ found: 508.3040.

Example 47 (Compound 324)

(S,E)-3-((3-(1-(2-(4-(dimethylamino)-N-methylbut-2-enamido)acetamido)propan-2-yl)phenyl)amino)-6-ethyl-5-methylpyrazine-2-carboxamide Step 1: (S,E)-3-((3-(1-(2-(4-(dimethylamino)-N-methylbut-2-enamido)acetamido)propan-2-yl)phenyl)amino)-6-ethyl-5-methylpyrazine-2-carboxamide

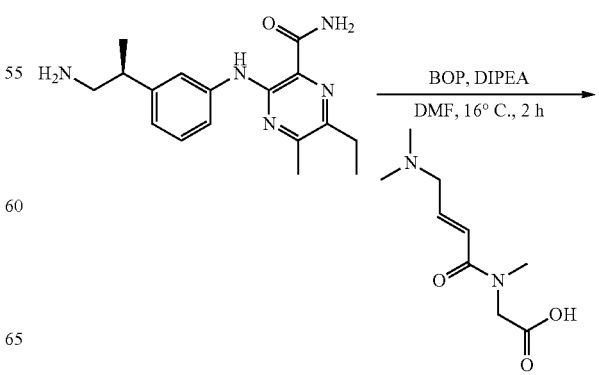

-continued

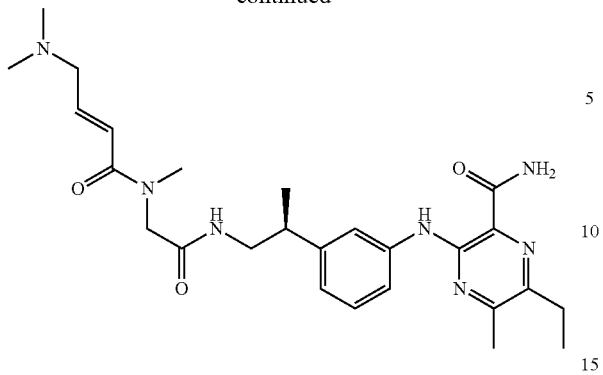

To a mixture of (E)-N-(4-(dimethylamino)but-2-enoyl)-N-methylglycine (51.51 mg, 257.25 μmol, 1.5 eq) in DMF (1 mL) was added DIPEA (221.64 mg, 1.71 mmol, 298.71 μL, 10 eq) and (S)-3-((3-(1-aminopropan-2-yl)phenyl)amino)-6-ethyl-5-methylpyrazine-2-carboxamide (60 mg, 171.50 μmol, 1 eq, HCl), finally added BOP (113.78 mg, 257.25 μmol, 1.5 eq) in one portion at 16° C. The mixture was stirred at 16° C. for 2 hrs under $N_2$. LCMS showed the reaction was completed. The residue was concentrated. The residue was purified by prep-HPLC (column: Waters Xbridge BEH C18 100*30 mm*10 um; mobile phase: [water ($NH_4HCO_3$)-ACN]; B %: 25%-55%, 8 min) to give (S,E)-3-((3-(1-(2-(4-(dimethylamino)-N-methylbut-2-enamido)acetamido)propan-2-yl)phenyl)amino)-6-ethyl-5-methylpyrazine-2-carboxamide (10.42 mg, 20.91 μmol, 12.19% yield) as yellow solid. $^1$H NMR (400 MHz, DMSO-$d_6$) δ=11.05 (d, J=5.0 Hz, 1H), 8.15 (br d, J=1.9 Hz, 1H), 8.09-7.82 (m, 2H), 7.60 (br t, J=8.3 Hz, 1H), 7.55-7.51 (m, 1H), 7.24 (t, J=7.8 Hz, 1H), 6.85 (d, J=7.6 Hz, 1H), 6.62-6.24 (m, 2H), 3.94 (d, J=17.9 Hz, 2H), 3.28-3.18 (m, 2H), 3.02 (s, 1H), 2.99-2.95 (m, 1.5H), 2.94-2.84 (m, 2H), 2.81-2.70 (m, 3.5H), 2.51 (br s, 3H), 2.15-2.12 (m, 3H), 2.11-2.04 (m, 3H), 1.27-1.17 (m, 6H). 1H NMR (400 MHz, MeOD-$d_4$) δ=7.64-7.56 (m, 2H), 7.28-7.19 (m, 1H), 6.88 (br d, J=7.5 Hz, 1H), 6.80-6.64 (m, 1H), 6.61-6.26 (m, 1H), 4.09-3.95 (m, 2H), 3.48-3.33 (m, 2H), 3.14-2.94 (m, 5H), 2.88 (s, 1H), 2.79 (q, J=7.5 Hz, 2H), 2.53 (s, 3H), 2.28-2.18 (m, 6H), 1.32-1.26 (m, 6H). LC-MS (ES+, m/z): 496.1 [(M+H)$^+$]; Rt=2.710 min; HRMS (EI): m/z [M+H]$^+$ found: 496.3041.

Example 48 (Compound 326)

3-((3-((R)-1-((S)-2-((E)-4-(dimethylamino)-N-methylbut-2-enamido)propanamido)propan-2-yl)phenyl)amino)-6-ethyl-5-methylpyrazine-2-carboxamide Step 1: 3-((3-((R)-1-((S)-2-((E)-4-(dimethylamino)-N-methylbut-2-enamido) propanamido)propan-2-yl)phenyl)amino)-6-ethyl-5-methylpyrazine-2-carboxamide

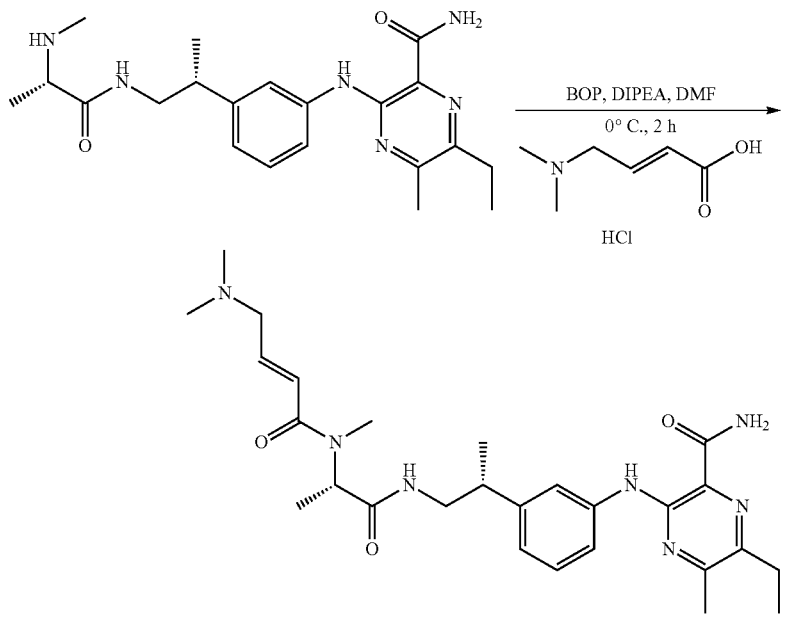

To a solution of (E)-4-(dimethylamino)but-2-enoic acid (57.11 mg, 344.86 μmol, 1.5 eq, HCl) in DMF (1 mL) was added DIPEA (297.14 mg, 2.30 mmol, 400.45 μL, 10 eq), 6-ethyl-5-methyl-3-((3-((R)-1-((S)-2-(methylamino)propanamido)propan-2-yl)phenyl)amino)pyrazine-2-carboxamide (100 mg, 229.91 μmol, 1 eq, HCl), and then BOP (152.52 mg, 344.86 μmol, 1.5 eq) at 0° C. The mixture was stirred at 0° C. for 2 hrs. LCMS indicated the reaction was complete. The reaction mixture was filtered to give a residue. The residue was purified by prep-HPLC column: Phenomenex luna C18 100*40 mm*3 μm; mobile phase: [water (TFA)-ACN]; B %: 5%-50%, 8 min to afford 3-((3-((R)-1-((S)-2-((E)-4-(dimethylamino)-N-methylbut-2-enamido)propanamido)propan-2-yl)phenyl) amino)-6-ethyl-5-methylpyrazine-2-carboxamide (11.02 mg, 21.62 μmol, 9.41% yield) as a yellow solid. $^1$H NMR (400 MHz, DMSO-$d_6$) δ=11.11-10.95 (m, 1H), 9.83-9.59 (m, 1H), 8.24-8.07 (m, 1H), 8.02-7.81 (m, 2H), 7.65-7.56 (m, 1H), 7.51 (s, 1H), 7.27-7.18 (m, 1H), 6.85-6.74 (m, 2H), 6.62-6.43 (m, 1H), 5.00-4.50 (m, 1H), 3.91-3.77 (m, 2H), 3.28-3.15 (m, 2H), 2.98-2.86 (m, 3H), 2.78-2.72 (m, 8H), 2.66-2.61 (m, 1H), 2.53-2.51 (m, 3H), 1.26-1.17 (m, 9H). (TFA salt) LC-MS (ES+, m/z): 510.3 [(M+H)+]; Rt=2.168 min; HRMS (EI): m/z [M]+ found: 510.3176.

Example 49 (Compound 327)

(E)-3-((3-(2-(2-(4-(dimethylamino)-N-methylbut-2-enamido) acetamido) ethyl) phenyl) amino)-6-ethynyl-5-(isopropyl (methyl) amino) pyrazine-2-carboxamide Step 1: tert-butyl (2-((3-((5-bromo-3-carbamoyl-6-(isopropyl (methyl) amino) pyrazin-2-yl) amino) phenethyl) amino)-2-oxoethyl) (methyl) carbamate

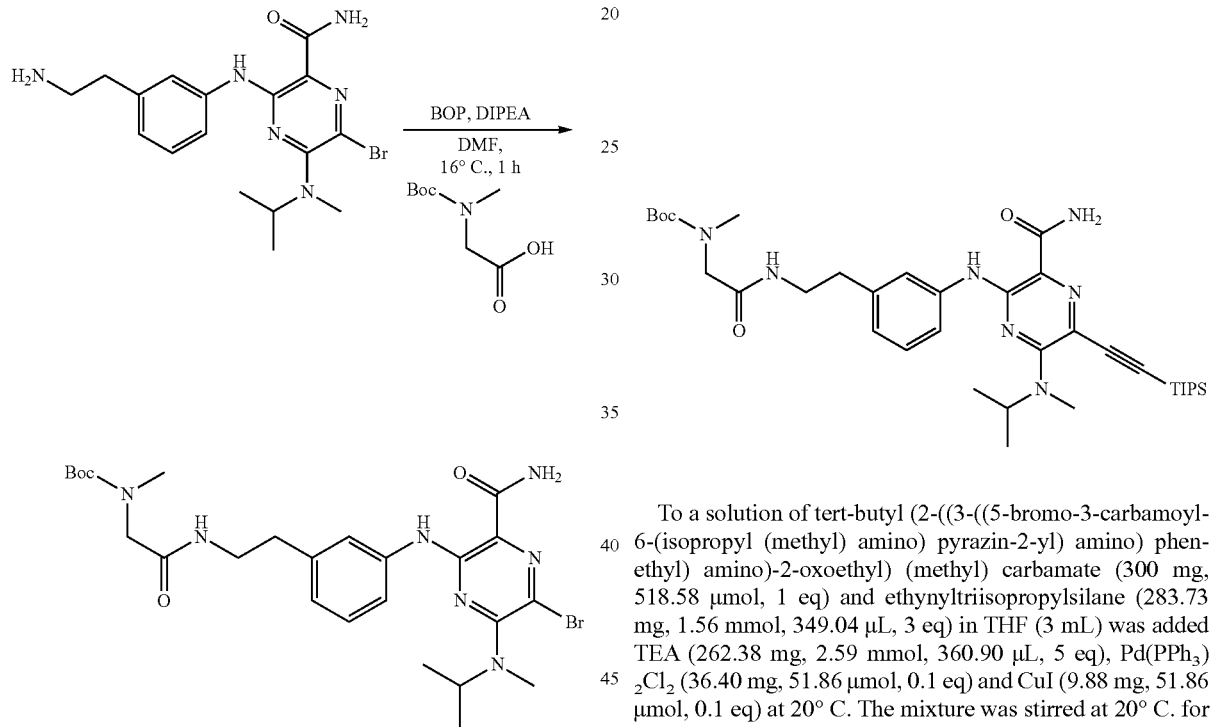

To a solution of 3-((3-(2-aminoethyl) phenyl) amino)-6-bromo-5-(isopropyl (methyl) amino) pyrazine-2-carboxamide (1.1 g, 2.70 mmol, 1 eq), N-(tert-butoxycarbonyl)-N-methylglycine (1.02 g, 5.40 mmol, 2 eq), BOP (1.79 g, 4.05 mmol, 1.5 eq) in DMF (10 mL) was added DIPEA (5.24 g, 40.51 mmol, 7.06 mL, 15 eq). The mixture was stirred at 16° C. for 1 h. LCMS showed the reaction was completed. The mixture was poured into water (30 mL) and extracted with EtOAc (30 mL*2). The organic layers was washed with water (60 mL*2), saturated brine (60 mL*2), dried over Na$_2$SO$_4$, filtered, concentrated under reduced pressure to give a residue. The crude product was purified by chromatography on silica gel (Petroleum ether:Ethyl acetate=1:1) to give tert-butyl (2-((3-((5-bromo-3-carbamoyl-6-(isopropyl (methyl) amino) pyrazin-2-yl) amino) phenethyl) amino)-2-oxoethyl) (methyl) carbamate (370 mg, 639.58 µmol, 65.13% yield) as yellow oil. LC-MS (ES+, m/z): 578.4 [(M+H)+]; Rt=0.813 min.

Step 2: tert-butyl (2-((3-((3-carbamoyl-6-(isopropyl (methyl) amino)-5-((triisopropylsilyl) ethynyl) pyrazin-2-yl) amino) phenethyl) amino)-2-oxoethyl) (methyl) carbamate

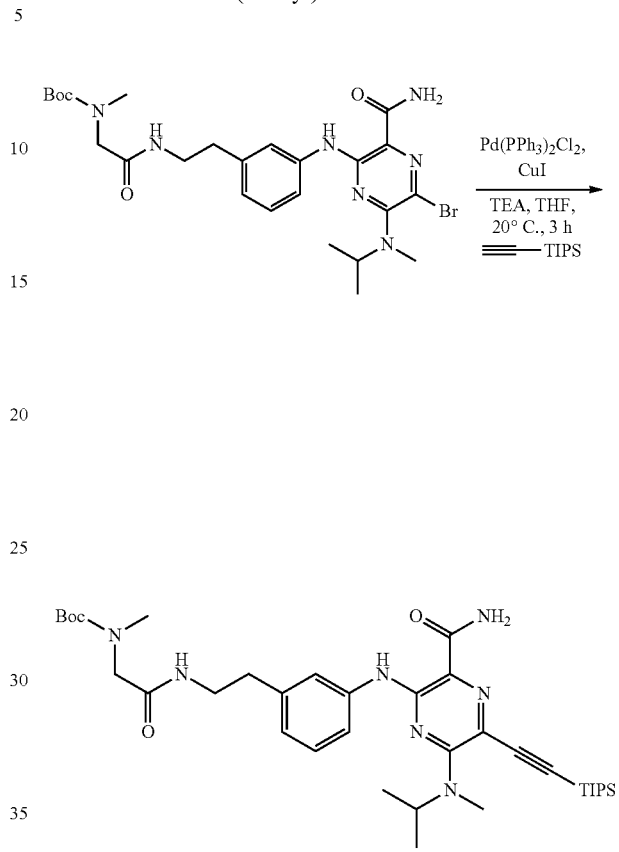

To a solution of tert-butyl (2-((3-((5-bromo-3-carbamoyl-6-(isopropyl (methyl) amino) pyrazin-2-yl) amino) phenethyl) amino)-2-oxoethyl) (methyl) carbamate (300 mg, 518.58 µmol, 1 eq) and ethynyltriisopropylsilane (283.73 mg, 1.56 mmol, 349.04 µL, 3 eq) in THF (3 mL) was added TEA (262.38 mg, 2.59 mmol, 360.90 µL, 5 eq), Pd(PPh$_3$)$_2$Cl$_2$ (36.40 mg, 51.86 µmol, 0.1 eq) and CuI (9.88 mg, 51.86 µmol, 0.1 eq) at 20° C. The mixture was stirred at 20° C. for 3 h under N$_2$. LCMS showed the reaction was completed. The residue was dissolved in DCM (10 mL), scavenger (Pd) was added and then stirred at 20° C. for 1 h, and then filtered. The mixture was poured into water (10 mL) and extracted with DCM (10 mL*2). The organic layers was washed with water (20 mL*2), saturated brine (20 mL*2), dried over Na$_2$SO$_4$, filtered, concentrated under reduced pressure to give a residue. The crude product was purified by chromatography on silica gel (Petroleum ether:Ethyl acetate=1:3) to give tert-butyl (2-((3-((3-carbamoyl-6-(isopropyl (methyl) amino)-5-((triisopropylsilyl) ethynyl) pyrazin-2-yl) amino) phenethyl) amino)-2-oxoethyl) (methyl) carbamate (206 mg, 302.96 µmol, 58.42% yield) as yellow solid. $^1$H NMR (400 MHz, DMSO-d$_6$) δ=11.45-11.40 (m, 1H), 7.91 (br s, 1H), 7.62-7.53 (m, 3H), 7.45-7.38 (m, 1H), 7.30-7.22 (m, 1H), 6.92-6.86 (m, 1H), 5.28-5.15 (m, 1H), 3.76-3.66 (m, 2H), 3.31-3.26 (m, 2H), 3.13-3.08 (m, 3H), 2.79-2.69 (m, 5H), 1.41-1.31 (m, 9H), 1.22 (d, J=6.6 Hz, 6H), 1.15-1.09 (m, 21H); LC-MS (ES+, m/z): 680.4 [(M+H)+]; Rt=1.250 min.

Step 3: 5-(isopropyl (methyl) amino)-3-((3-(2-(2-(methylamino) acetamido) ethyl) phenyl) amino)-6-((triisopropylsilyl) ethynyl) pyrazine-2-carboxamide

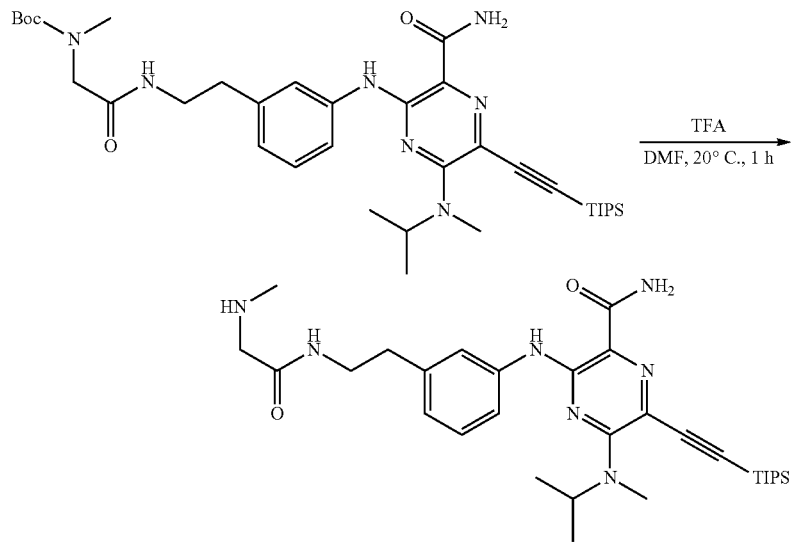

To a solution of tert-butyl (2-((3-((3-carbamoyl-6-(isopropyl (methyl) amino)-5-((triisopropylsilyl) ethynyl) pyrazin-2-yl) amino) phenethyl) amino)-2-oxoethyl) (methyl) carbamate (200 mg, 294.13 μmol, 1 eq) in DCM (2 mL) was added TFA (1.54 g, 13.51 mmol, 1 mL, 45.92 eq), the mixture was stirred at 20° C. for 1 h. LCMS indicated the reaction was complete. The reaction mixture was concentrated under reduced pressure to give 5-(isopropyl (methyl) amino)-3-((3-(2-(2-(methylamino) acetamido) ethyl) phe-nyl) amino)-6-((triisopropylsilyl) ethynyl) pyrazine-2-carboxamide (200 mg, crude) as black brown oil. LC-MS (ES+, m/z): 580.6 [(M+H)]$^+$; RT=0.913 min.

Step 4: (E)-3-((3-(2-(2-(4-(dimethylamino)-N-methylbut-2-enamido) acetamido) ethyl) phenyl) amino)-5-(isopropyl (methyl) amino)-6-((triisopropylsilyl) ethynyl) pyrazine-2-carboxamide

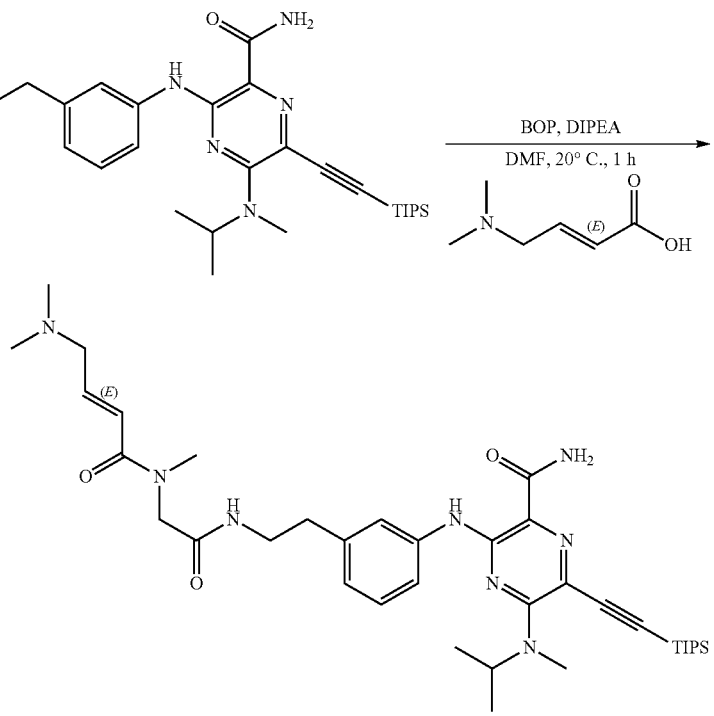

To a solution of (E)-4-(dimethylamino) but-2-enoic acid (85.93 mg, 518.83 μmol, 1.5 eq, HCl) in DMF (3 mL) was added DIPEA (670.55 mg, 5.19 mmol, 903.70 μL, 15 eq) and 5-(isopropyl (methyl) amino)-3-((3-(2-(2-(methylamino) acetamido) ethyl) phenyl) amino)-6-((triisopropylsilyl) ethynyl) pyrazine-2-carboxamide (240 mg, 345.88 μmol, 1 eq, TFA), and then BOP (229.47 mg, 518.83 μmol, 1.5 eq) was added. The mixture was stirred at 20° C. for 1 hr. LCMS indicated the reaction was completed. The mixture was poured into water (10 mL) and extracted with EtOAc (10 mL*2). The organic layers was washed with water (20 mL*2), saturated brine (20 mL*2), dried over Na₂SO₄, filtered, concentrated under reduced pressure to give a residue. The crude product was purified by chromatography on silica gel (DCM:MeOH=10:1) to give (E)-3-((3-(2-(2-(4-(dimethylamino)-N-methylbut-2-enamido) acetamido) ethyl) phenyl) amino)-5-(isopropyl (methyl) amino)-6-((triisopropylsilyl) ethynyl) pyrazine-2-carboxamide (76 mg, 109.99 μmol, 31.80% yield) as yellow solid. ¹H NMR (400 MHz, DMSO-d₆) δ=11.46-11.40 (m, 1H), 8.17-7.89 (m, 1H), 7.73-7.53 (m, 3H), 7.49-7.40 (m, 1H), 7.30-7.21 (m, 1H), 6.94-6.84 (m, 1H), 6.67-6.47 (m, 2H), 5.29-5.14 (m, 1H), 4.02-3.90 (m, 2H), 3.12-3.00 (m, 6H), 2.86-2.69 (m, 6H), 2.24-2.10 (m, 6H), 1.25-1.08 (m, 27H); LC-MS (ES+, m/z): 691.4 [(M+H)+]; RT=0.947 min.

Step 5: (E)-3-((3-(2-(2-(4-(dimethylamino)-N-methylbut-2-enamido) acetamido) ethyl) phenyl) amino)-6-ethynyl-5-(isopropyl (methyl) amino) pyrazine-2-carboxamide To a solution of (E)-3-((3-(2-(2-(4-(dimethylamino)-N-methylbut-2-enamido) acetamido) ethyl) phenyl) amino)-5-(isopropyl (methyl) amino)-6-((triisopropylsilyl) ethynyl) pyrazine-2-carboxamide (76 mg, 109.99 μmol, 1 eq) in DMF (1.5 mL) was added CsF (66.83 mg, 439.95 μmol, 16.22 μL, 4 eq) at 16° C., the mixture was stirred at 16° C. for 2 hrs. LCMS indicated the reaction was complete. The mixture was filtered to give a residue. The crude was purified by prep-HPLC column: Waters Xbridge Prep OBD C18 150*40 mm*10 um; mobile phase: [water (NH₄HCO₃)-ACN]; B %: 30%-70%, 8 min) to afford (E)-3-((3-(2-(2-(4-(dimethylamino)-N-methylbut-2-enamido) acetamido) ethyl) phenyl) amino)-6-ethynyl-5-(isopropyl (methyl) amino) pyrazine-2-carboxamide (10.36 mg, 19.18 μmol, 17.44% yield, 98.97% purity) as yellow solid. ¹H NMR (400 MHz, DMSO-d₆) δ=11.50-11.42 (m, 1H), 8.16-7.89 (m, 1H), 7.79-7.68 (m, 1H), 7.64-7.38 (m, 3H), 7.25 (t, J=7.8 Hz, 1H), 6.93-6.83 (m, 1H), 6.67-6.48 (m, 2H), 5.08-4.94 (m, 1H), 4.46 (s, 1H), 4.01-3.91 (m, 2H), 3.31-3.26 (m, 2H), 3.09-2.93 (m, 7H), 2.81 (s, 1H), 2.75-2.68 (m, 2H), 2.18-2.07 (m, 6H), 1.23 (d, J=6.6 Hz, 6H); ¹H NMR (400 MHz, DMSO-d₆) δ=11.42-11.31 (m, 1H), 8.18-7.90 (m, 1H), 7.62-7.53 (m, 1H), 7.46-7.37 (m, 1H), 7.29-7.20 (m, 1H), 6.93-6.83 (m, 1H), 6.68-6.44 (m, 2H), 5.08-4.90 (m, 1H), 4.40 (s, 1H), 4.00-3.90 (m, 2H), 3.36-3.24 (m, 2H), 3.08-2.90 (m, 7H), 2.76 (br s, 1H), 2.74-2.67 (m, 2H), 2.17-2.03 (m, 6H), 1.21 (d, J=6.6 Hz, 6H); LCMS (ES+, m/z): 535.3 [(M+H)+]; Rt=2.167 min; HRMS (EI): m/z [M+H]⁺ found: 535.3162.

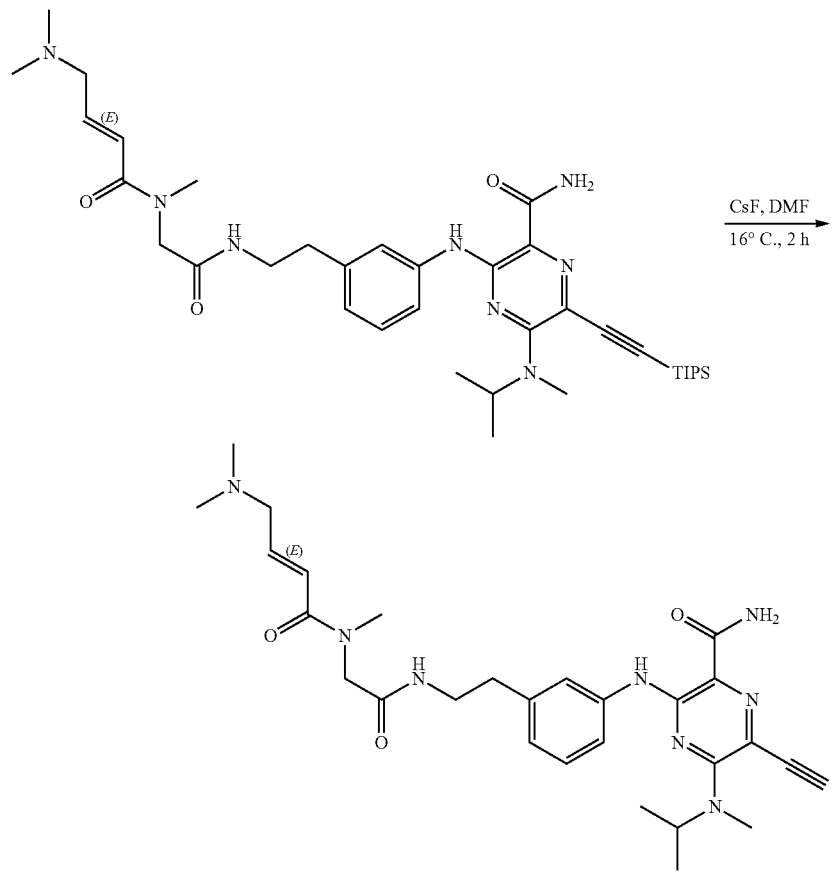

Example 50 (Compound 328)

(E)-3-((3-(2-(2-(4-(dimethylamino)-N-methylbut-2-enamido)acetamido)ethyl)phenyl)amino)-5-(isopropyl(methyl)amino)-6-vinylpyrazine-2-carboxamide Step 2: tert-butyl (2-((3-((3-carbamoyl-6-(isopropyl(methyl)amino)-5-vinylpyrazin-2-yl)amino)phenethyl)amino)-2-oxoethyl)(methyl)carbamate

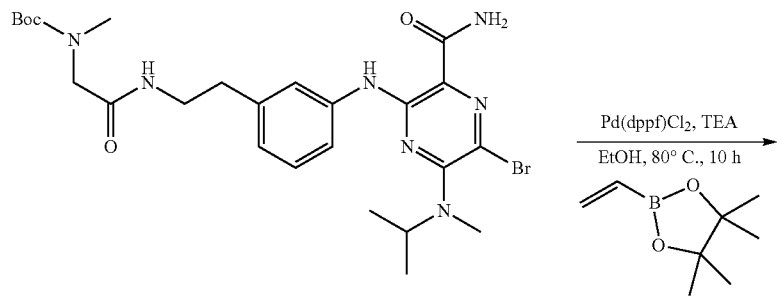

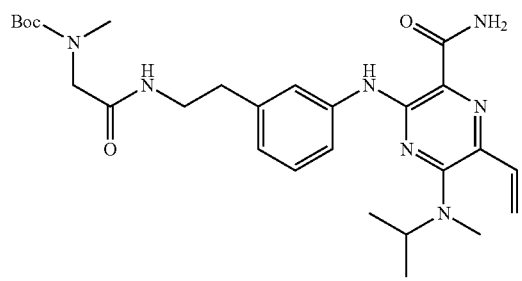

To a solution of tert-butyl (2-((3-((5-bromo-3-carbamoyl-6-(isopropyl(methyl)amino)pyrazin-2-yl)amino)phenethyl)amino)-2-oxoethyl)(methyl)carbamate (300 mg, 518.58 µmol, 1 eq) and TEA (157.43 mg, 1.56 mmol, 216.54 µL, 3 eq) in DMF (5 mL) was added 4,4,5,5-tetramethyl-2-vinyl-1,3,2-dioxaborolane (239.61 mg, 1.56 mmol, 263.88 µL, 3 eq), and then Pd(dppf)Cl$_2$ (37.95 mg, 51.86 µmol, 0.1 eq) was added. The mixture was degassed and purged with N$_2$ for 3 times, and then stirred at 80° C. for 10 hrs under N$_2$ atmosphere. LCMS showed the reaction was completed. The residue was dissolved in EtOAc (10 mL), scavenger (Pd) was added and then stirred at 20° C. for 1 h, and then filtered. The mixture was poured into water (30 mL) and extracted with EtOAc (20 mL*2). The organic layers were combined, washed with water (10 mL*2), saturated brine (10 mL), dried (Na$_2$SO$_4$), filtered and concentrated to give crude product. The crude product was purified by prep-TLC (PE/EA=1/2) to give tert-butyl (2-((3-((3-carbamoyl-6-(isopropyl(methyl) amino)-5-vinylpyrazin-2-yl)amino)phenethyl)amino)-2-oxoethyl)(methyl)carbamate (150 mg, 285.37 µmol, 55.03% yield) as yellow solid. LC-MS (ES+, m/z): 526.5 [(M+H)$^+$]; Rt=0.821 min.

Step 3: 5-(isopropyl(methyl)amino)-3-((3-(2-(2-(methylamino)acetamido)ethyl)phenyl)amino)-6-vinylpyrazine-2-carboxamide

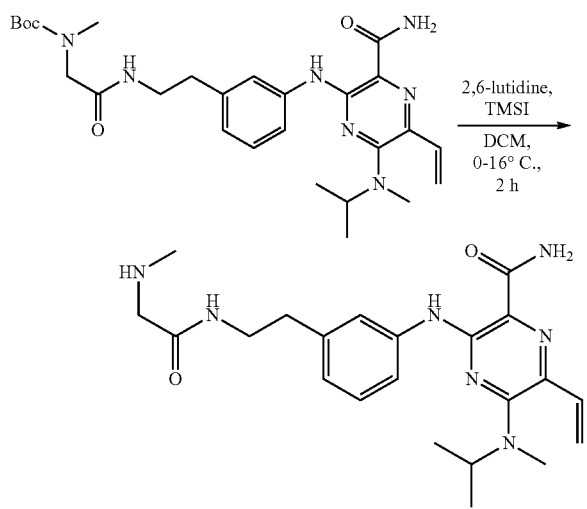

To a solution of tert-butyl (2-((3-((3-carbamoyl-6-(isopropyl(methyl)amino)-5-vinylpyrazin-2-yl)amino)phenethyl)amino)-2-oxoethyl)(methyl)carbamate (70 mg, 133.17 µmol, 1 eq) and 2,6-lutidine (230.00 mg, 2.15 mmol, 250.00 µL, 16.12 eq) in DCM (1 mL) was added dropwise TMSI (257.25 mg, 1.29 mmol, 175.00 µL, 9.65 eq) at 0° C. After addition, the resulting mixture was stirred at 16° C. for 2 hrs. LCMS showed the reaction was completed. The mixture was concentrated under reduced pressure to give 5-(isopropyl(methyl)amino)-3-((3-(2-(2-(methylamino)acetamido)ethyl)phenyl)amino)-6-vinylpyrazine-2-carboxamide (80 mg, crude) as yellow solid. LC-MS (ES+, m/z): 426.5 [(M+H)$^+$]; Rt=0.605 min.

Step 4: (E)-3-((3-(2-(2-(4-(dimethylamino)-N-methylbut-2-enamido)acetamido)ethyl)phenyl)amino)-5-(isopropyl(methyl)amino)-6-vinylpyrazine-2-carboxamide

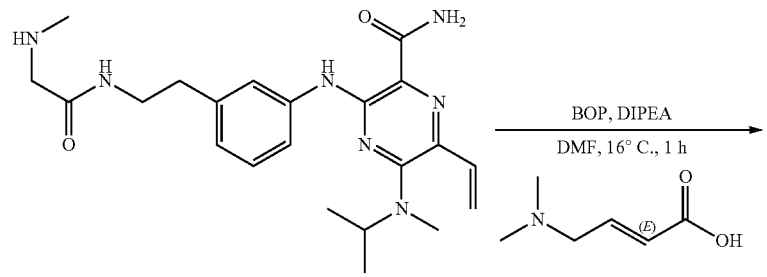

282.00 µmol, 1.5 eq) was added. The mixture was stirred at 16° C. for 1 hr. LCMS showed the reaction was completed. After filter, the filtrate was purified by prep-HPLC (column: Waters Xbridge BEH C18 100*30 mm*10 um; mobile phase: [water (NH$_4$HCO$_3$)-ACN]; B %: 30%-60%, 8 min) and further purified by SFC separation (column: ChiralPak IH, 250*30 mm, 10 um; mobile phase: [MeOH (0.1% IPAm)]; B %: 18%-18%, 12 min) to give (E)-3-((3-(2-(2-(4-(dimethylamino)-N-methylbut-2-enamido)acetamido)ethyl)phenyl)amino)-5-(isopropyl(methyl)amino)-6-vinylpyrazine-2-carboxamide (6.37 mg, 11.77 µmol, 6.26% yield) as yellow solid. $^1$H NMR (400 MHz, DMSO-d$_6$) δ=11.34 (d, J=5.1 Hz, 1H), 8.18-7.89 (m, 2H), 7.57 (br d, J=15.8 Hz, 2H), 7.51-7.43 (m, 1H), 7.23 (t, J=7.8 Hz, 1H), 6.84 (d, J=7.4 Hz, 1H), 6.68 (dd, J=10.8, 17.1 Hz, 1H), 6.61-6.55 (m, 1H), 6.55-6.29 (m, 1H), 6.23 (dd, J=2.1, 17.1 Hz, 1H), 5.32-5.25 (m, 1H), 4.31-4.19 (m, 1H), 3.95 (d, J=19.4 Hz, 2H), 3.37-3.31 (m, 2H), 3.07 (br d, J=3.8 Hz, 1H), 3.03-2.96 (m, 2H), 2.87 (s, 3H), 2.81 (s, 2H), 2.76-2.68

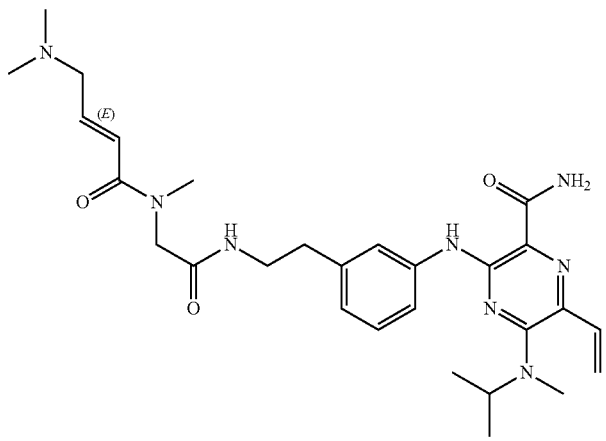

To a solution of (E)-4-(dimethylamino)but-2-enoic acid (46.70 mg, 282.00 µmol, 1.5 eq, HCl) in DMF (1 mL) was added DIEA (242.98 mg, 1.88 mmol, 327.47 µL, 10 eq) and 5-(isopropyl(methyl)amino)-3-((3-(2-(2-(methylamino)acetamido) ethyl)phenyl) amino)-6-vinylpyrazine-2-carboxamide (80 mg, 188.00 µmol, 1 eq), then BOP (124.72 mg, (m, 2H), 2.21-2.11 (m, 6H), 1.20 (d, J=6.6 Hz, 6H); $^1$H NMR (400 MHz, DMSO-d$_6$+D$_2$O) δ=11.14 (d, J=8.1 Hz, 1H), 7.58 (s, 1H), 7.44-7.39 (m, 1H), 7.22 (t, J=7.8 Hz, 1H), 6.83 (d, J=7.2 Hz, 1H), 6.65 (dd, J=10.8, 17.1 Hz, 1H), 6.59-6.22 (m, 2H), 6.13 (dd, J=1.6, 17.1 Hz, 1H), 5.32-5.26 (m, 1H), 4.28-4.20 (m, 1H), 3.96-3.90 (m, 2H), 3.32-3.25 (m, 2H), 3.07 (br d, J=4.6 Hz, 1H), 2.98-2.94 (m, 3H), 2.84 (s, 3H), 2.78 (s, 1H), 2.72-2.67 (m, 2H), 2.17-2.06 (m, 6H), 1.16 (d, J=6.6 Hz, 6H). LCMS (ES+, m/z): 537.3 [(M+H)$^+$]; Rt=2.259 min; HRMS (EI): m/z [M+H]$^+$ found: 537.3313.

Example 51

Compound 501

(S,E)-3-((3-(2-(2-(4-(dimethylamino) but-2-enamido) propanamido) ethyl) phenyl) amino)-6-ethyl-5-(isopropylamino) pyrazine-2-carboxamide Step 1: tert-butyl (S)-(1-((3-((3-carbamoyl-5-ethyl-6-(isopropylamino) pyrazin-2-yl) amino) phenethyl) amino)-1-oxopropan-2-yl) carbamate

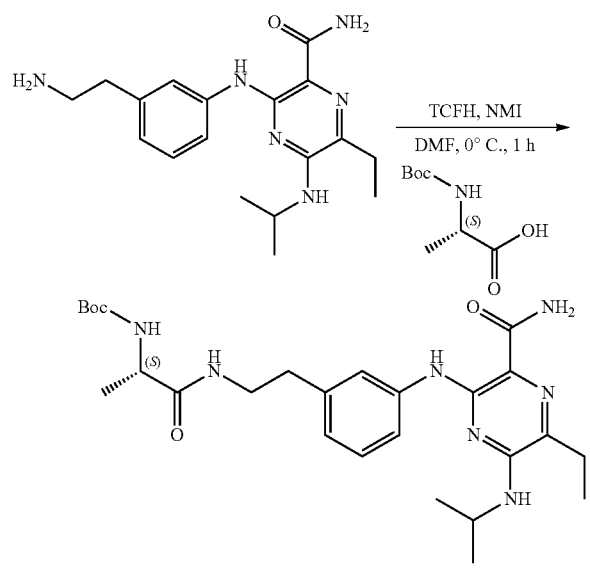

To a solution of (tert-butoxycarbonyl)-L-alanine (397.82 mg, 2.10 mmol, 1.2 eq), 3-((3-(2-aminoethyl) phenyl) amino)-6-ethyl-5-(isopropylamino) pyrazine-2-carboxamide (600 mg, 1.75 mmol, 1 eq) and NMI (1.44 g, 17.52 mmol, 1.40 mL, 10 eq) in DMF (6 mL) at 0° C., TCFH (737.42 mg, 2.63 mmol, 1.5 eq) was added. The mixture was stirred at 0° C. for 1 hour. The mixture was poured into water (5 mL) and extracted with EtOAc (5 mL*2). The organic layers were combined, washed with water (10 mL*2), saturated brine (10 mL*2), dried over Na$_2$SO$_4$, filtered, concentrated under reduced pressure to give a residue. The crude product was purified by chromatography on silica gel (Petroleum ether:Ethyl acetate=1:1) to afford tert-butyl (S)-(1-((3-((3-carbamoyl-5-ethyl-6-(isopropylamino) pyrazin-2-yl) amino) phenethyl) amino)-1-oxopropan-2-yl) carbamate (710 mg, 1.38 mmol, 78.89% yield) as yellow oil. $^1$H NMR (400 MHz, DMSO-d$_6$) δ=11.27-11.15 (m, 1H), 7.88-7.76 (m, 1H), 7.69 (s, 1H), 7.55 (br d, J=2.6 Hz, 1H), 7.35 (br d, J=8.4 Hz, 1H), 7.28-7.14 (m, 2H), 6.89-6.65 (m, 3H), 4.35-4.20 (m, 1H), 4.06-3.89 (m, 1H), 3.31 (br s, 2H), 2.69-2.64 (m, 2H), 2.63-2.55 (m, 2H), 1.44-1.07 (m, 21H). LCMS (ES+, m/z): 514.3 [(M+H)$^+$]; Rt=0.762 min.

Step 2: (S)-3-((3-(2-(2-aminopropanamido) ethyl) phenyl) amino)-6-ethyl-5-(isopropylamino) pyrazine-2-carboxamide

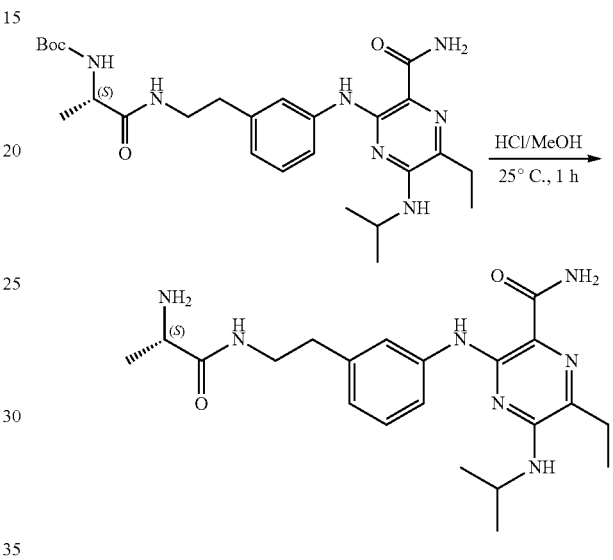

The mixture tert-butyl (S)-(1-((3-((3-carbamoyl-5-ethyl-6-(isopropylamino) pyrazin-2-yl) amino) phenethyl) amino)-1-oxopropan-2-yl) carbamate (710 mg, 1.38 mmol, 1 eq) and HCl/MeOH (4 M, 40 mL, 115.75 eq) was stirred at 25° C. for 1 hour. The reaction mixture was concentrated under reduced pressure to give (S)-3-((3-(2-(2-aminopropanamido) ethyl) phenyl) amino)-6-ethyl-5-(isopropylamino) pyrazine-2-carboxamide (650 mg, crude) as yellow solid. $^1$H NMR (400 MHz, DMSO-d$_6$) δ=11.31-11.12 (m, 1H), 8.55 (t, J=5.6 Hz, 1H), 8.18 (br d, J=3.9 Hz, 3H), 7.62-7.58 (m, 1H), 7.47-7.43 (m, 1H), 7.29-7.12 (m, 2H), 6.88-6.73 (m, 2H), 4.33-4.21 (m, 1H), 3.45 (dt, J=7.0, 13.4 Hz, 2H), 3.33-3.25 (m, 1H), 2.80-2.70 (m, 2H), 2.59 (q, J=7.4 Hz, 2H), 1.35-1.14 (m, 12H). LCMS (ES$^+$, m/z): 414.3 [(M+H)$^+$]; Rt=0.565 min.

Step 3: (S,E)-3-((3-(2-(2-(4-(dimethylamino) but-2-enamido) propanamido) ethyl) phenyl) amino)-6-ethyl-5-(isopropylamino) pyrazine-2-carboxamide

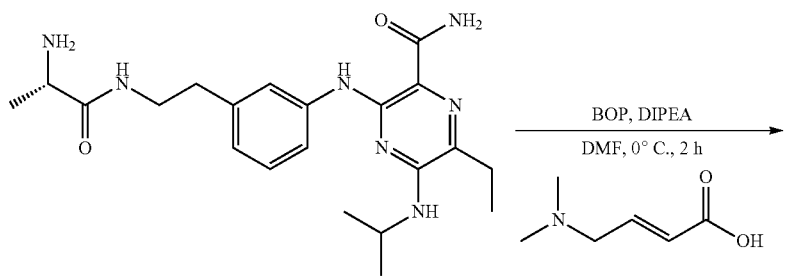

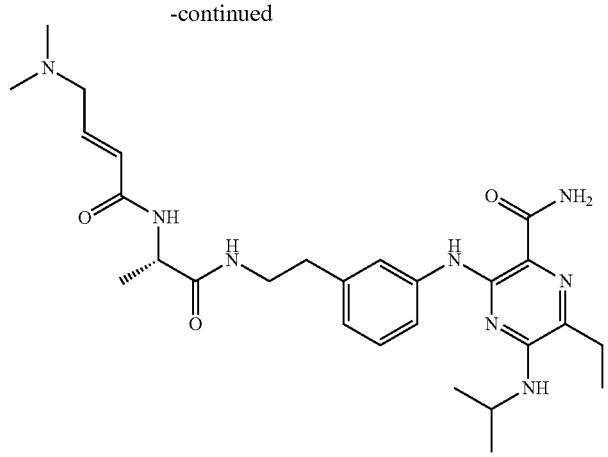

To a solution of (E)-4-(dimethylamino) but-2-enoic acid (520.66 mg, 3.14 mmol, 2 eq, HCl), (S)-3-((3-(2-(2-amino-propanamido) ethyl) phenyl) amino)-6-ethyl-5-(isopropylamino) pyrazine-2-carboxamide (650 mg, 1.57 mmol, 1 eq) and DIPEA (2.03 g, 15.72 mmol, 2.74 mL, 10 eq) in DMF (4 mL) at 0° C., BOP (1.04 g, 2.36 mmol, 1.5 eq) was added. The mixture was stirred at 0° C. for 2 hours. The mixture was filtered to give a residue. The crude was purified by prep-HPLC (column: Waters Xbridge Prep OBD C18 150*40 mm*10 um; mobile phase: [water (NH$_4$HCO$_3$)-ACN]; B %: 25%-65%, 8 min) to afford (S,E)-3-((3-(2-(2-(4-(dimethylamino) but-2-enamido) propanamido) ethyl) phenyl) amino)-6-ethyl-5-(isopropylamino) pyrazine-2-carboxamide (165.87 mg, 308.53 μmol, 19.63% yield, 97.59% purity) as white solid. $^1$H NMR (400 MHz, DMSO-d$_6$) δ=11.21 (s, 1H), 8.17-8.09 (m, 1H), 8.01-7.93 (m, 1H), 7.70-7.62 (m, 1H), 7.55 (br d, J=2.6 Hz, 1H), 7.41-7.34 (m, 1H), 7.29-7.21 (m, 1H), 7.21-7.15 (m, 1H), 6.77 (t, J=8.1 Hz, 2H), 6.60-6.50 (m, 1H), 6.17-6.07 (m, 1H), 4.37-4.20 (m, 2H), 3.31-3.18 (m, 2H), 3.02-2.91 (m, 2H), 2.71-2.65 (m, 2H), 2.62-2.56 (m, 2H), 2.17-2.10 (m, 6H), 1.28-1.16 (m, 12H). $^1$H NMR (400 MHz, DMSO-d$_6$) δ=11.15-11.00 (m, 1H), 8.00-7.91 (m, 1H), 7.71-7.51 (m, 2H), 7.40-7.29 (m, 1H), 7.24-7.07 (m, 2H), 6.83-6.70 (m, 2H), 6.61 (br d, J=1.8 Hz, 1H), 6.04 (s, 1H), 4.32-4.17 (m, 2H), 3.34-3.18 (m, 2H), 2.98-2.93 (m, 2H), 2.69-2.63 (m, 2H), 2.59-2.53 (m, 2H), 2.16-2.06 (m, 6H), 1.26-1.15 (m, 12H). LC-MS (ES+, m/z): 525.3 [(M+H)$^+$]; Rt=2.068 min. HRMS (EI): m/z (M+H)$^+$ found: 525.3270.

Example 52

Compound 502

(S,E)-3-((3-(2-(2-(4-(dimethylamino)but-2-enamido) propanamido) ethyl) phenyl) amino)-6-ethyl-5-(isopropyl(methyl)amino) pyrazine-2-carboxamide Step 1: tert-butyl (S)-(1-((3-((3-carbamoyl-5-ethyl-6-(isopropyl(methyl)amino) pyrazin-2-yl) amino) phenethyl) amino)-1-oxopropan-2-yl) carbamate

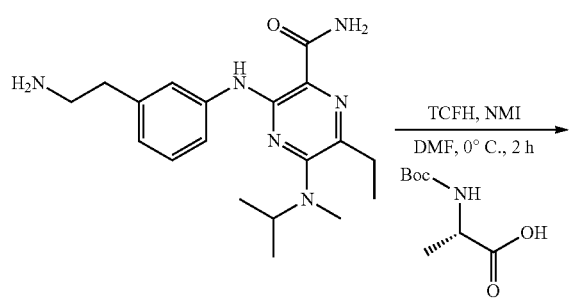

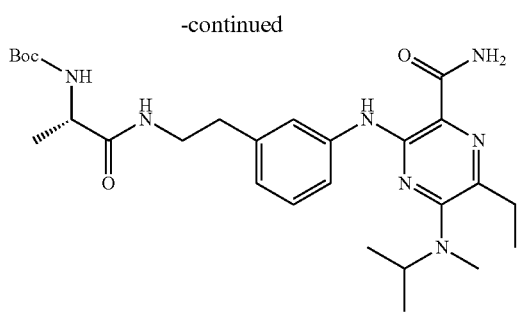

To a solution of (tert-butoxycarbonyl)-L-alanine (361.15 mg, 1.91 mmol, 1.5 eq) in DMF (5 mL) was added NMI (1.04 g, 12.73 mmol, 1.01 mL, 10 eq), 3-((3-(2-aminoethyl) phenyl)amino)-6-ethyl-5-(isopropyl(methyl)amino)pyrazine-2-carboxamide (500 mg, 1.27 mmol, 1 eq, HCl) at 0° C., and then TCFH (535.56 mg, 1.91 mmol, 1.5 eq) at 0° C. The mixture was stirred at 0° C. for 2 hours. The reaction was poured into H$_2$O (10 mL). The aqueous phase was extracted with ethyl acetate (15 mL*3). The combined organic phase was washed with saturated brine (10 mL*3), dried with anhydrous Na$_2$SO$_4$, filtered, and concentrated under reduced pressure. The residue was purified by prep-HPLC (column: Phenomenex luna C18 100*40 mm*3 um; mobile phase: [water (TFA)-ACN]; B %: 40%-75%, 8 min) to afford tert-butyl (S)-(1-((3-((3-carbamoyl-5-ethyl-6-(isopropyl(methyl) amino)pyrazin-2-yl)amino)phenethyl) amino)-1-oxopropan-2-yl)carbamate (350 mg, 663.31 μmol, 52.13% yield) as yellow oil. $^1$H NMR (400 MHz, DMSO-d$_6$) δ=11.16-11.04 (m, 1H), 7.92-7.68 (m, 2H), 7.63-7.52 (m, 1H), 7.50-7.34 (m, 2H), 7.26-7.13 (m, 1H), 6.88-6.72 (m, 2H), 4.32-4.17 (m, 1H), 3.97-3.74 (m, 1H), 3.40-3.33 (m, 1H), 3.28-3.17 (m, 1H), 2.92-2.82 (m, 3H), 2.75-2.63 (m, 4H), 1.37 (s, 9H), 1.25-1.19 (m, 9H), 1.12 (d, J=7.1 Hz, 3H). LC-MS (ES+, m/z): 528.4 [(M+H)+]; Rt=0.989 min.

Step 2: (S)-3-((3-(2-(2-aminopropanamido) ethyl) phenyl) amino)-6-ethyl-5-(isopropyl(methyl)amino) pyrazine-2-carboxamide

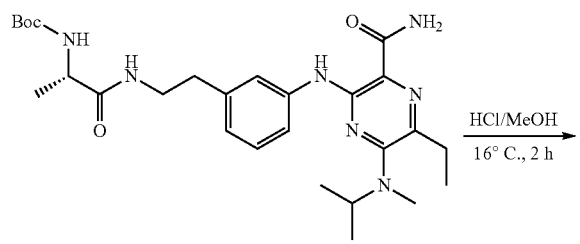

A mixture of tert-butyl (S)-(1-((3-((3-carbamoyl-5-ethyl-6-(isopropyl(methyl)amino) yrazin-2-yl) amino) phenethyl) amino)-1-oxopropan-2-yl) carbamate (350 mg, 663.31 µmol, 1 eq) in HCl/MeOH (20 mL) was stirred at 16° C. for 2 hours. The reaction mixture was concentrated under reduced pressure to afford (S)-3-((3-(2-(2-aminopropanamido) ethyl) phenyl) amino)-6-ethyl-5-(isopropyl(methyl) amino) pyrazine-2-carboxamide (307 mg, crude) as yellow solid. $^1$H NMR (400 MHz, DMSO-d$_6$) δ=11.19-10.99 (m, 1H), 8.60-8.38 (m, 1H), 8.15 (br d, J=3.4 Hz, 3H), 7.88-7.60 (m, 1H), 7.58-7.38 (m, 3H), 7.25-7.19 (m, 1H), 6.82 (d, J=7.5 Hz, 1H), 4.28-4.19 (m, 1H), 3.75-3.71 (m, 1H), 3.48-3.41 (m, 1H), 3.32-3.24 (m, 1H), 2.89-2.83 (m, 3H), 2.76-2.67 (m, 4H), 1.29 (d, J=6.9 Hz, 3H), 1.24-1.19 (m, 9H) (HCl salt). LC-MS (ES+, m/z): 428.3 [(M+H)$^+$]; Rt=0.815 min.

Step 3: (S,E)-3-((3-(2-(2-(4-(dimethylamino)but-2-enamido)propanamido)ethyl) phenyl) amino)-6-ethyl-5-(isopropyl(methyl)amino) pyrazine-2-carboxamide

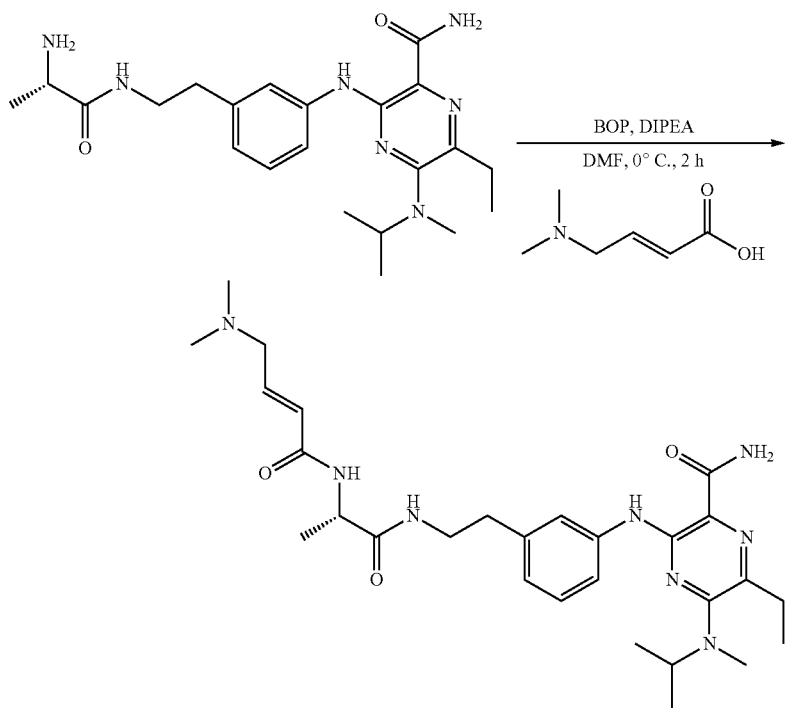

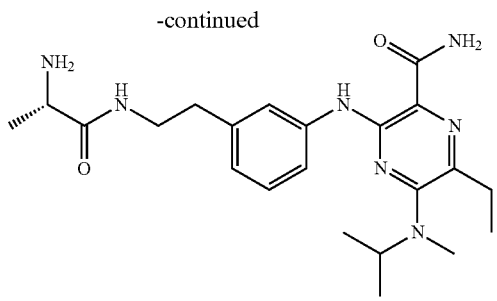

To a solution of (E)-4-(dimethylamino)but-2-enoic acid (123.14 mg, 743.53 µmol, 1.5 eq, HCl) in DMF (3 mL) was added DIPEA (640.64 mg, 4.96 mmol, 863.40 µL, 10 eq), (S)-3-((3-(2-(2-aminopropanamido) ethyl) phenyl) amino)-6-ethyl-5-(isopropyl(methyl) amino) pyrazine-2-carboxamide (230 mg, 495.69 µmol, 1 eq, HCl) at 0° C., and then BOP (328.85 mg, 743.53 µmol, 1.5 eq) at 0° C. The mixture was stirred at 0° C. for 2 hours. The reaction was poured into H$_2$O (5 mL). The aqueous phase was extracted with ethyl acetate (10 mL*3). The combined organic phase was washed with saturated brine (10 mL*3), dried with anhydrous Na$_2$SO$_4$, filtered, and concentrated under reduced pressure. residue was purified by prep-HPLC (column: Waters Xbridge Prep OBD C18 150*40 mm*10 um; mobile phase: [water (NH$_4$HCO$_3$)-ACN]; B %: 35%-75%, 8 min) to afford (S,E)-3-((3-(2-(2-(4-(dimethylamino)but-2-enamido)propanamido)ethyl) phenyl)amino)-6-ethyl-5-(isopropyl (methyl)amino)pyrazine-2-carboxamide (55.27 mg, 102.05 µmol, 20.59% yield) as yellow solid. $^1$H NMR (400 MHz, DMSO-d$_6$) δ=11.17-11.03 (m, 1H), 8.16-8.08 (m, 1H), 8.01-7.90 (m, 1H), 7.78-7.69 (m, 1H), 7.59-7.51 (m, 1H), 7.49-7.38 (m, 2H), 7.24-7.14 (m, 1H), 6.82-6.76 (m, 1H), 6.59-6.48 (m, 1H), 6.14-6.07 (m, 1H), 4.32 (s, 2H), 3.31-3.20 (m, 2H), 2.98-2.92 (m, 2H), 2.88-2.82 (m, 3H), 2.73-2.65 (m, 4H), 2.14-2.11 (m, 6H), 1.23-1.14 (m, 12H). LC-MS (ES+, m/z): 539.3 [(M+H)$^+$]; Rt=2.309 min. HRMS (EI): m/z [M]$^+$ found: 539.3442.

Intermediate 1 tert-butyl (R)-(2-(3-((3-carbamoyl-6-chloro-5-ethylpyrazin-2-yl) amino) phenyl) propyl) carbamate Step 1: 2-(3-bromophenyl) propanenitrile

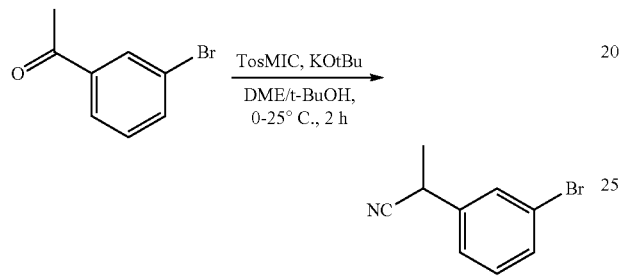

To a solution of 1-(3-bromophenyl) ethan-1-one (10 g, 50.24 mmol, 6.62 mL, 1 eq) and 1-((isocyanomethyl)sulfonyl)-4-methylbenzene (11.77 g, 60.29 mmol, 1.2 eq) in 1,2-DME (100 mL) was added KOtBu (1 M in THF, 100.70 mL, 2.00 eq) and t-BuOH (50 mL). The mixture was stirred at 0° C., then warm to 25° C. for 2 hours. The reaction was poured into water (150 mL) and extracted with ethyl acetate (200 mL*3). The organic layers were combined, washed with water (100 mL*2), saturated brine (100 mL*2), dried with Na$_2$SO$_4$, filtered, and concentrated to give crude product. The residue was purified by column chromatography (SiO$_2$, Petroleum ether/Ethyl acetate=30/1 to 3/1). The residue was purified by prep-HPLC (column: Phenomenex luna C18 250 mm*100 mm*10 um; mobile phase: [water (TFA)-ACN]; B %: 35%-65%, 20 min) to afford 2-(3-bromophenyl) propanenitrile (4.7 g, 22.37 mmol, 44.53% yield) as a yellow oil. $^1$H NMR (400 MHz, DMSO-d$_6$) δ=7.65-7.61 (m, 1H), 7.59-7.52 (m, 1H), 7.46-7.42 (m, 1H), 7.41-7.35 (m, 1H), 4.38-4.30 (m, 1H), 1.55 (d, J=7.3 Hz, 3H).

Step 2: 2-(3-bromophenyl) propan-1-amine

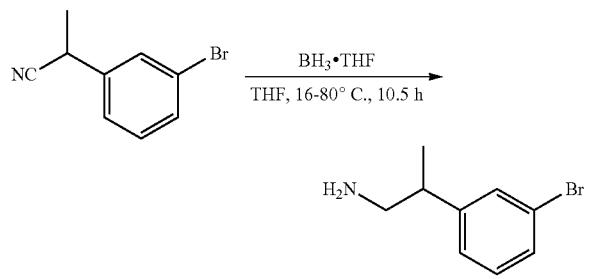

To a solution of 2-(3-bromophenyl) propanenitrile (11.3 g, 53.79 mmol, 1 eq) in THF (30 mL) was added BH$_3$·THF (1 M, 268.96 mL, 5 eq) at 16° C. for 0.5 hr. The mixture was heated to 80° C. for 10 hours. The mixture was added slowly dropwise to MeOH, then heated to 80° C. for 1 hour. The reaction mixture was concentrated under reduced pressure to afford 2-(3-bromophenyl) propan-1-amine (13.11 g, crude) as a white oil. LC-MS (ES+, m/z): 214.1 [(M+H)$^+$]; Rt=0.508 min.

Step 3: tert-butyl (2-(3-bromophenyl) propyl) carbamate

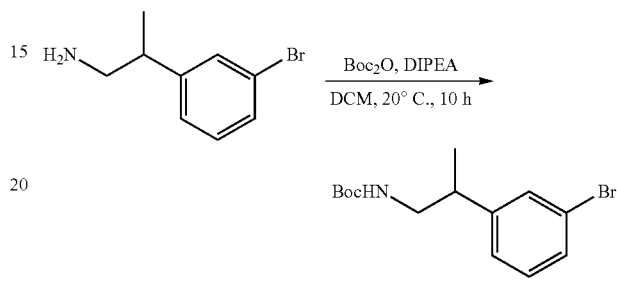

To a solution of 2-(3-bromophenyl) propan-1-amine (25.6 g, 119.57 mmol, 1 eq) in DCM (256 mL) was added Boc$_2$O (52.19 g, 239.14 mmol, 54.94 mL, 2 eq) and DIPEA (46.36 g, 358.71 mmol, 62.48 mL, 3 eq). The mixture was stirred at 20° C. for 10 hours. The reaction was poured into water (300 mL) and extracted with DCM (300 mL*3). The organic layers were combined, washed with water (200 mL*2), saturated brine (200 mL*2), dried with Na$_2$SO$_4$, filtered, and concentrated to give crude product. The residue was purified by column chromatography (SiO$_2$, Petroleum ether/Ethyl acetate=20/1 to 3/1) to afford tert-butyl (2-(3-bromophenyl) propyl) carbamate (28 g, 89.11 mmol, 74.53% yield) as a colorless oil. $^1$H NMR (400 MHz, DMSO-d$_6$) δ=7.44-7.34 (m, 2H), 7.30-7.18 (m, 2H), 6.90-6.81 (m, 1H), 3.15-2.98 (m, 2H), 2.94-2.81 (m, 1H), 1.34 (s, 9H), 1.15 (d, J=7.0 Hz, 3H). LC-MS (ES+, m/z): 258.0[(M-56)$^+$]; Rt=1.005 min.

Step 4: tert-butyl (2-(3-((diphenylmethylene) amino) phenyl) propyl) carbamate

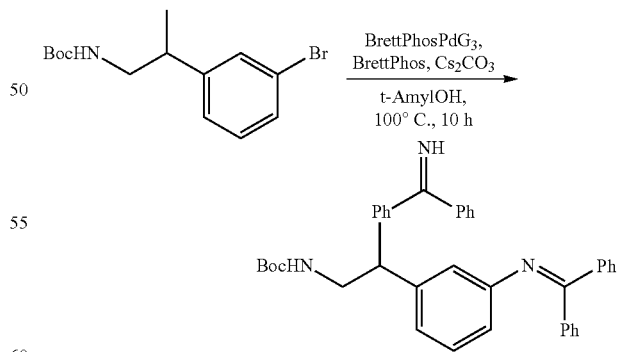

To a solution of tert-butyl (2-(3-bromophenyl) propyl) carbamate (6.00 g, 19.10 mmol, 1 eq) and diphenylmethanimine (6.92 g, 38.19 mmol, 6.41 mL, 2 eq) in t-AmylOH (60 mL) was added Cs$_2$CO$_3$ (18.66 g, 57.29 mmol, 3 eq), BrettPhos (1.02 g, 1.91 mmol, 0.1 eq) and BrettPhos Pd G3 (1.73 g, 1.91 mmol, 0.1 eq). The mixture was degassed and purged with N₂ for 3 times, then stirred at 100° C. for 10 hours under N₂ atmosphere. The reaction was poured into water (40 mL) and extracted with ethyl acetate (60 mL*3). The organic layers were combined, washed with water (50 mL*2), saturated brine (50 mL*2), dried with Na₂SO₄, filtered, and concentrated to give crude product. The residue was dissolved in DCM (50 mL), scavenger (Pd) was added and then stirred at 25° C. for 1 hr, and then filtered. The residue was purified by column chromatography (SiO₂, Petroleum ether/Ethyl acetate=100/1 to 1/1) to afford tert-butyl (2-(3-((diphenylmethylene)amino) phenyl) propyl) carbamate (7.40 g, crude) as a yellow oil. LC-MS (ES+, m/z): 415.3 [(M+H)⁺]; Rt=1.086 min.

Step 5: tert-butyl (2-(3-aminophenyl) propyl) carbamate

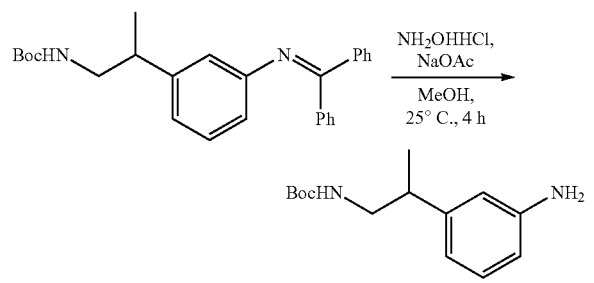 [SMILES: CC(CNC(=O)OC(C)(C)C)c1cccc(N=C(c2ccccc2)c2ccccc2)c1 ; CC(CNC(=O)OC(C)(C)C)c1cccc(N)c1]

To a solution of tert-butyl (2-(3-((diphenylmethylene) amino) phenyl) propyl) carbamate (11.00 g, 26.54 mmol, 1 eq) in MeOH (110 mL) was added NH₂OH·HCl (3.32 g, 47.76 mmol, 1.8 eq) and NaOAc (5.22 g, 63.69 mmol, 2.4 eq). The mixture was stirred at 25° C. for 4 hours. The reaction mixture was concentrated under reduced pressure to remove MeOH. The residue was diluted with H₂O (100 mL) and extracted with ethyl acetate 300 mL (100 mL*3). The combined organic layers were washed with water (100 mL*2), saturated brine (100 mL*2), dried with Na₂SO₄, filtered, and concentrated under reduced pressure to give a residue. The residue was purified by prep-HPLC (column: Phenomenex luna C18 (250*70 mm, 15 um); mobile phase: [water (TFA)-ACN]; B %: 10%-40%, 20 min) to afford tert-butyl (2-(3-aminophenyl) propyl) carbamate (5.40 g, 21.57 mmol, 81.29% yield) as a yellow oil. ¹H NMR (400 MHz, DMSO-d₆) δ=6.95-6.87 (m, 1H), 6.81-6.70 (m, 1H), 6.44-6.29 (m, 3H), 3.07-2.88 (m, 2H), 2.72-2.59 (m, 1H), 1.37 (s, 9H), 1.08 (d, J=6.9 Hz, 3H) (the active N—H was not detected). LC-MS (ES+, m/z): 251.3 [(M+H)⁺]; Rt=0.695 min.

Step 6: tert-butyl (R)-(2-(3-aminophenyl) propyl) carbamate

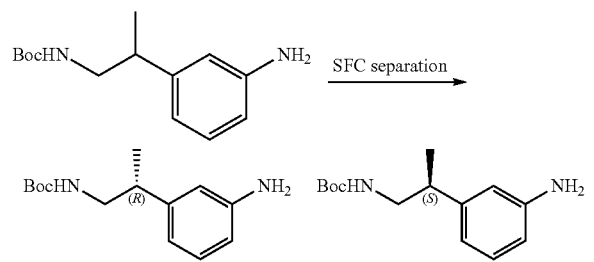

The tert-butyl (2-(3-aminophenyl)propyl)carbamate (10.80 g, 43.14 mmol, 1 eq) was separated by SFC (column: DAICEL CHIRALCEL OJ (250 mm*50 mm, 10 um); mobile phase: [0.1% NH₃H₂O IPA]; B %: 20%-20%, 4.4 min) to afford tert-butyl (R)-(2-(3-aminophenyl)propyl)carbamate (5 g, 19.97 mmol, 46.30% yield) and tert-butyl (S)-(2-(3-aminophenyl)propyl)carbamate (4.90 g, 19.57 mmol, 45.37% yield) were obtained as a colorless oil. ¹H NMR (400 MHz, DMSO-d₆) δ=6.91 (t, J=7.7 Hz, 1H), 6.82-6.68 (m, 1H), 6.49-6.27 (m, 3H), 3.10-2.82 (m, 2H), 2.73-2.58 (m, 1H), 1.36 (s, 9H), 1.14-1.02 (m, 3H) (the active N—H was not detected). LC-MS (ES+, m/z): 251.2 [(M+H)⁺]; Rt=0.695 min.

Step 7: tert-butyl (R)-(2-(3-((3-carbamoyl-6-chloro-5-ethylpyrazin-2-yl) amino) phenyl) propyl) carbamate

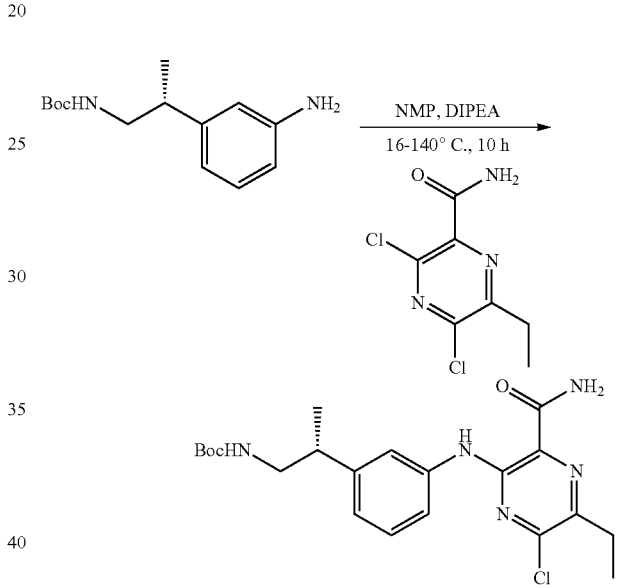

To a solution of tert-butyl (R)-(2-(3-aminophenyl) propyl) carbamate (2.50 g, 9.99 mmol, 1 eq) and 3,5-dichloro-6-ethylpyrazine-2-carboxamide (2.20 g, 9.99 mmol, 1 eq) in NMP (25 mL) was added DIPEA (12.91 g, 99.87 mmol, 17.39 mL, 10 eq) at 16° C. The mixture was heated to 140° C. for 10 hours under N₂ atmosphere. The reaction was poured into water (100 mL) and extracted with ethyl acetate (200 mL*3). The organic layers were combined, washed with water (150 mL*2), saturated brine (150 mL*2), dried with Na₂SO₄, filtered, and concentrated to give crude product. The residue was purified by prep-TLC (column: Welch Xtimate C18 250*70 mm #10 um; mobile phase: [water (NH₄HCO₃)-ACN]; B %: 60%-95%, 20 min) to afford tert-butyl (R)-(2-(3-((3-carbamoyl-6-chloro-5-ethylpyrazin-2-yl) amino) phenyl) propyl) carbamate (2.05 g, 4.60 mmol, 46.04% yield) as a yellow solid. ¹H NMR (400 MHz, DMSO-d₆) δ=11.23-11.11 (m, 1H), 8.35-8.18 (m, 1H), 8.11-7.96 (m, 1H), 7.60-7.46 (m, 1H), 7.34 (s, 1H), 7.31-7.23 (m, 1H), 6.91 (d, J=7.5 Hz, 1H), 6.87-6.78 (m, 1H), 3.15-2.98 (m, 2H), 2.89-2.76 (m, 3H), 1.36-1.32 (m, 9H), 1.26 (t, J=7.5 Hz, 3H), 1.17 (d, J=6.9 Hz, 3H). LC-MS (ES+, m/z): 378.1 [(M+H-56)⁺]; Rt=3.120 min. HRMS (EI): m/z found: 434.1916.

Intermediate 2

Step 1: tert-butyl (E)-N-(4-(dimethylamino) but-2-enoyl)-N-methylglycinate

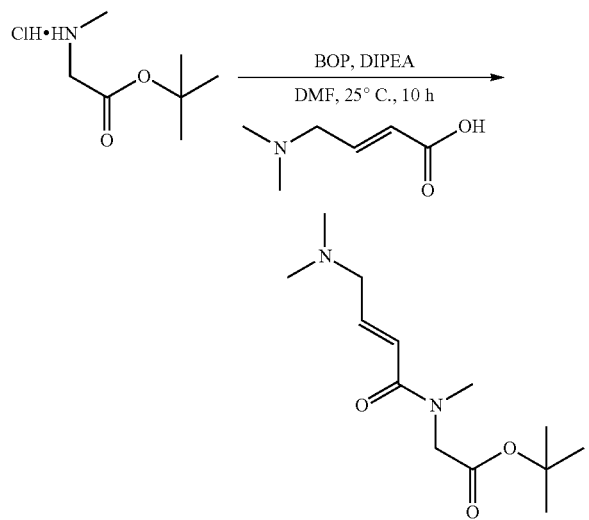

To a solution of (E)-4-(dimethylamino)but-2-enoic acid (1.52 g, 9.17 mmol, 2 eq, HCl) in DMF (5 mL) was added DIPEA (5.93 g, 45.85 mmol, 7.99 mL, 10 eq), tert-butyl 2-(imino(methyl)-λ$^5$-chloraneyl)acetate (1.00 g, 4.58 mmol, 1 eq, HCl), HOBt (619.49 mg, 4.58 mmol, 1 eq) and EDCI (1.32 g, 6.88 mmol, 1.5 eq). The mixture was stirred at 25° C. for 10 hours. The reaction mixture was filtered and concentrated under reduced pressure to give a residue. The residue was purified by prep-HPLC (column: C18 (250*50 mm*10 um); mobile phase: [water (NH$_4$HCO$_3$)-ACN]; B %: 15%-40%, 10 min) to afford tert-butyl (E)-N-(4-(dimethylamino) but-2-enoyl)-N-methylglycinate (540 mg, 2.11 mmol, 45.95% yield) as a brown oil. $^1$H NMR (400 MHz, DMSO-d$_6$) δ=6.68-6.34 (m, 2H), 4.23-3.95 (m, 2H), 3.11-2.84 (m, 5H), 2.18-2.07 (m, 6H), 1.45-1.37 (m, 9H) LC-MS (ES+, m/z): 257.1 [(M+H)$^+$]; Rt=1.329 min.

Step 2: (E)-N-(4-(dimethylamino) but-2-enoyl)-N-methylglycine

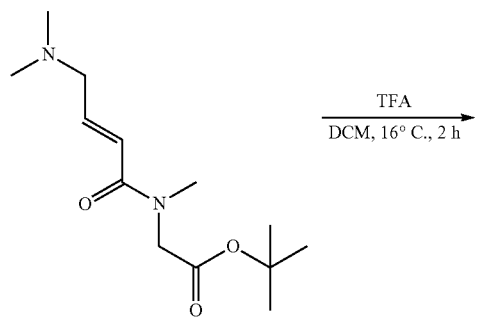

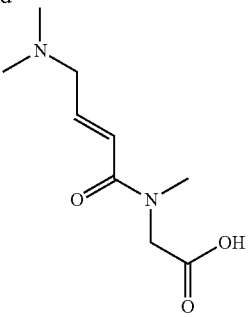

To a solution of tert-butyl (E)-N-(4-(dimethylamino) but-2-enoyl)-N-methylglycinate (270 mg, 1.05 mmol, 1 eq) in DCM (2 mL) was added TFA (3.08 g, 27.01 mmol, 2 mL, 25.65 eq). The mixture was stirred at 16° C. for 2 hours. The reaction mixture was filtered and concentrated under reduced pressure to afford (E)-N-(4-(dimethylamino) but-2-enoyl)-N-methylglycine (466 mg, crude) as a yellow oil. $^1$H NMR (400 MHz, DMSO-d$_6$) δ=9.97 (br d, J=17.4 Hz, 1H), 6.97-6.48 (m, 2H), 4.28-4.02 (m, 2H), 3.95-3.82 (m, 2H), 3.10 (s, 3H), 2.76 (br d, J=13.4 Hz, 6H). LC-MS (ES+, m/z): 201.1 [(M+H)$^+$]; Rt=0.089 min.

Example 53

Compound 503

(R,E)-3-((3-(1-(2-(4-(dimethylamino)-N-methylbut-2-enamido) acetamido) propan-2-yl) phenyl) amino)-5,6-diethylpyrazine-2-carboxamide Step 1: tert-butyl (R)-(2-(3-((3-carbamoyl-5,6-diethylpyrazin-2-yl) amino) phenyl) propyl) carbamate

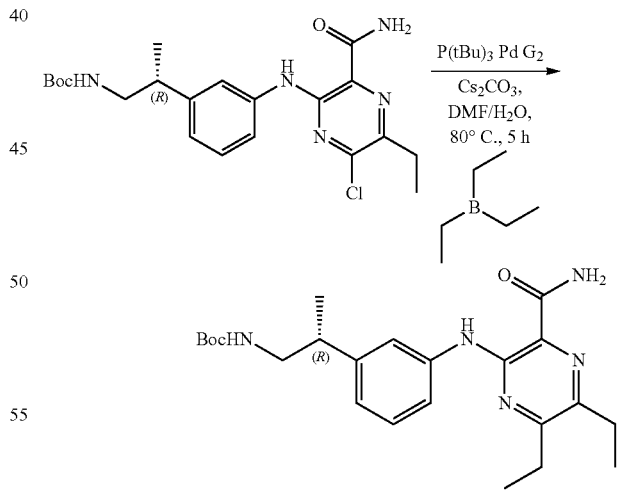

To a solution of tert-butyl (R)-(2-(3-((3-carbamoyl-6-chloro-5-ethylpyrazin-2-yl) amino) phenyl) propyl) carbamate (400 mg, 921.81 µmol, 1 eq), triethylborane (903.31 mg, 9.22 mmol, 1.33 mL, 10 eq), Cs$_2$CO$_3$ (901.03 mg, 2.77 mmol, 3 eq) in DMF (5 mL) and H$_2$O (2 mL), P(tBu)$_3$ Pd G2 (47.23 mg, 92.18 µmol, 0.1 eq) was added. The mixture was stirred at 80° C. for 5 hours under N$_2$. The residue was dissolved in DCM (10 mL), scavenger (Pd) was added and then stirred at 25° C. for 1 hour, and then filtered. The mixture was poured into water (10 mL) and extracted with DCM (10 mL*2). The organic layers were combined, washed with water (20 mL*2), saturated brine (20 mL*2), dried over Na₂SO₄, filtered, concentrated under reduced pressure. The crude product was purified by chromatography on silica gel (Petroleum ether:Ethyl acetate=3:1) to afford tert-butyl (R)-(2-(3-((3-carbamoyl-5,6-diethylpyrazin-2-yl) amino) phenyl) propyl) carbamate (350 mg, 818.64 μmol, 88.81% yield) as yellow oil. ¹H NMR (400 MHz, DMSO-d₆) δ=11.08 (s, 1H), 8.20-8.10 (m, 1H), 7.86 (br d, J=1.8 Hz, 1H), 7.66-7.48 (m, 2H), 7.28-7.19 (m, 1H), 6.89-6.78 (m, 2H), 3.15-2.99 (m, 2H), 2.92-2.80 (m, 3H), 2.80-2.71 (m, 2H), 1.36-1.16 (m, 18H). LCMS (ES+, m/z): 428.2 [(M+H)⁺]; Rt=0.947 min.

Step 2: (R)-3-((3-(1-aminopropan-2-yl) phenyl) amino)-5,6-diethylpyrazine-2-carboxamide Step 3: (R,E)-3-((3-(1-(2-(4-(dimethylamino)-N-methylbut-2-enamido) acetamido) propan-2-yl) phenyl) amino)-5,6-diethylpyrazine-2-carboxamide

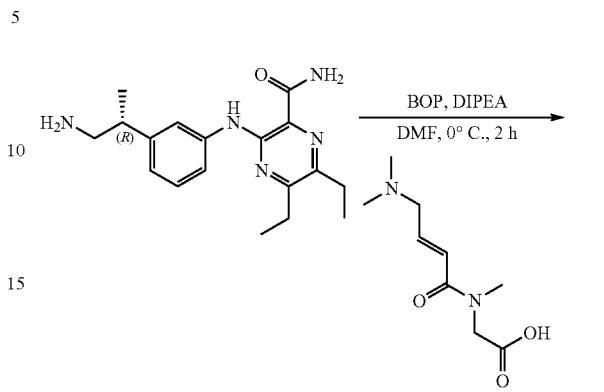

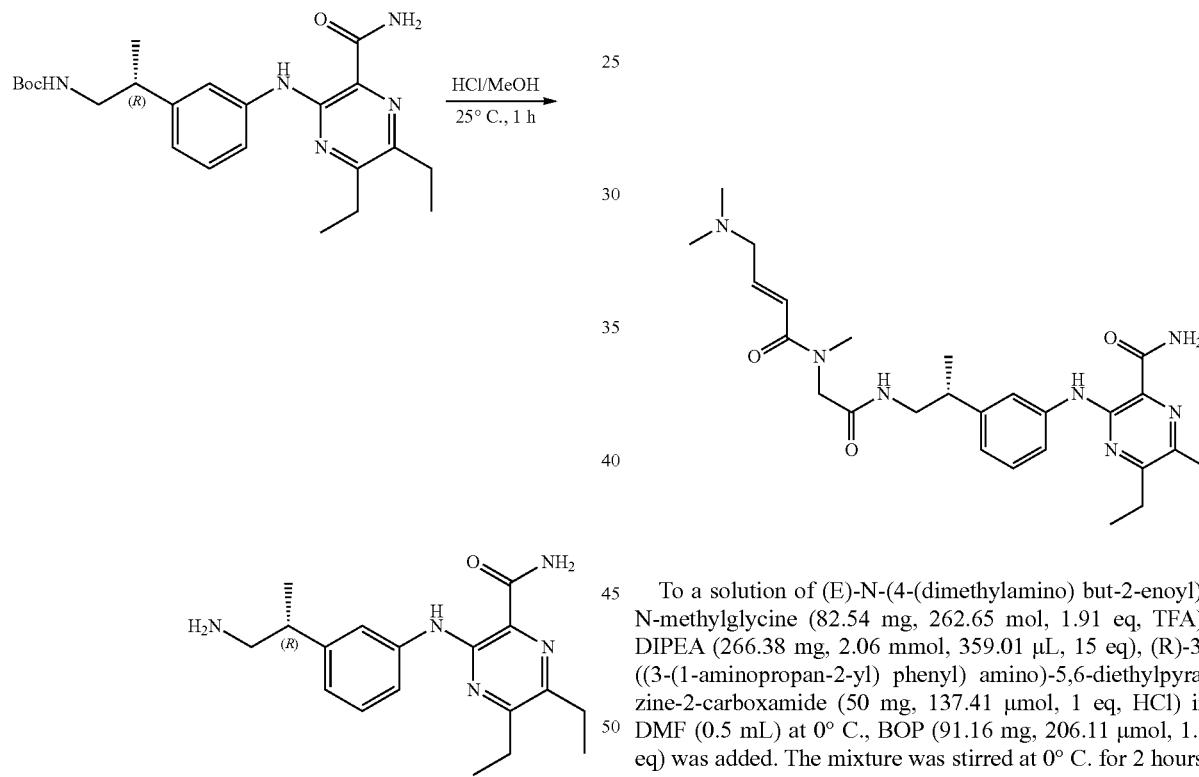

The mixture tert-butyl (R)-(2-(3-((3-carbamoyl-5,6-diethylpyrazin-2-yl) amino) phenyl) propyl) carbamate (440 mg, 1.03 mmol, 1 eq) and HCl/MeOH (4 M, 40 mL, 155.47 eq) was stirred at 25° C. for 1 hour. The reaction mixture was concentrated under reduced pressure to give (R)-3-((3-(1-aminopropan-2-yl) phenyl) amino)-5,6-diethylpyrazine-2-carboxamide (350 mg, crude, HCl) as yellow solid. ¹H NMR (400 MHz, DMSO-d₆) δ=11.12 (s, 1H), 8.22-8.12 (m, 1H), 7.90 (br d, J=13.0 Hz, 4H), 7.74-7.66 (m, 1H), 7.63-7.57 (m, 1H), 7.34-7.26 (m, 1H), 6.96-6.89 (m, 1H), 3.07-2.97 (m, 3H), 2.85 (q, J=7.4 Hz, 2H), 2.76 (q, J=7.5 Hz, 2H), 1.33-1.22 (m, 9H)(HCl salt). LCMS (ES⁺, m/z): 328.2 [(M+H)⁺]; Rt=0.568 min.

To a solution of (E)-N-(4-(dimethylamino) but-2-enoyl)-N-methylglycine (82.54 mg, 262.65 mol, 1.91 eq, TFA), DIPEA (266.38 mg, 2.06 mmol, 359.01 μL, 15 eq), (R)-3-((3-(1-aminopropan-2-yl) phenyl) amino)-5,6-diethylpyrazine-2-carboxamide (50 mg, 137.41 μmol, 1 eq, HCl) in DMF (0.5 mL) at 0° C., BOP (91.16 mg, 206.11 μmol, 1.5 eq) was added. The mixture was stirred at 0° C. for 2 hours. The mixture was filtered to give a residue. The crude was purified by prep-HPLC (column: Waters Xbridge BEH C18 100*30 mm*10 um; mobile phase: [water (NH₄HCO₃)-ACN]; B %: 15%-55%, 8 min) to afford (R,E)-3-((3-(1-(2-(4-(dimethylamino)-N-methylbut-2-enamido) acetamido) propan-2-yl) phenyl) amino)-5,6-diethylpyrazine-2-carboxamide (20.15 mg, 38.51 μmol, 28.02% yield, 97.39% purity) as yellow solid. ¹H NMR (400 MHz, DMSO-d₆) δ=11.13-11.07 (m, 1H), 8.19-8.12 (m, 1H), 8.10-7.83 (m, 2H), 7.66-7.61 (m, 1H), 7.59-7.51 (m, 1H), 7.28-7.21 (m, 1H), 6.87-6.82 (m, 1H), 6.28 (d, J=15.0 Hz, 2H), 3.94 (d, J=17.3 Hz, 2H), 3.29-3.21 (m, 2H), 3.03-2.73 (m, 10H), 2.19-2.05 (m, 6H), 1.34-1.18 (m, 9H). LC-MS (ES+, m/z): 510.3 [(M+H)⁺]; Rt=2.149 min. HRMS (EI): m/z [M]⁺ found: 510.3174.

Example 54

Compound 504

(R,E)-5-cyclopropyl-3-((3-(1-(2-(4-(dimethyl-amino)-N-methylbut-2-enamido)acetamido)propan-2-yl)phenyl)amino)-6-ethylpyrazine-2-carboxamide Step 1: tert-butyl (R)-(2-(3-((3-carbamoyl-6-cyclopropyl-5-ethylpyrazin-2-yl) amino) phenyl) propyl) carbamate

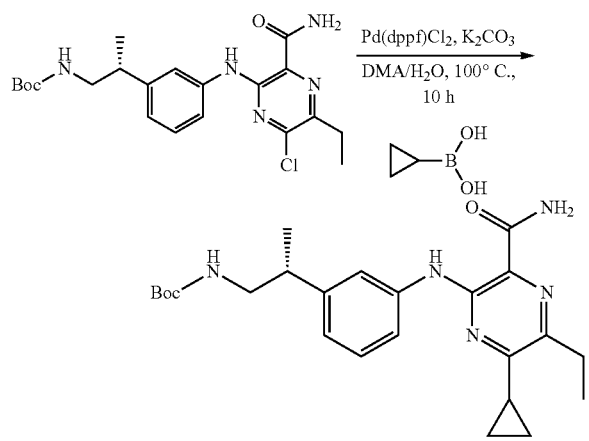

To a solution of tert-butyl (R)-(2-(3-((3-carbamoyl-6-chloro-5-ethylpyrazin-2-yl) amino) phenyl) propyl) carbamate (400 mg, 921.81 umol, 1 eq), cyclopropylboronic acid (791.81 mg, 9.22 mmol, 10 eq) and $K_2CO_3$ (382.20 mg, 2.77 mmol, 3 eq) in DMA (10 mL) and $H_2O$ (5 mL), Pd(dppf)$Cl_2$ (67.45 mg, 92.18 μmol, 0.1 eq) was added. The mixture was stirred at 100° C. for 10 hours under $N_2$. The residue was dissolved in EtOAc (40 mL), scavenger (Pd) was added and then stirred at 20° C. for 1 hour, and then filtered. The mixture was poured into water (30 mL) and extracted with EtOAc (20 mL*2). The organic layers were combined, washed with water (10 mL*2), saturated brine (10 mL), dried ($Na_2SO_4$), filtered and concentrated. The crude product was purified by chromatography on silica thiol gel (petroleum ether/EtOAc=1/1) to afford tert-butyl (R)-(2-(3-((3-carbamoyl-6-cyclopropyl-5-ethylpyrazin-2-yl) amino) phenyl)propyl)carbamate (320 mg, 728.02 μmol, 78.98% yield) as yellow solid. LC-MS (ES+, m/z): 440.3 [(M+H)$^+$]; Rt=1.047 min.

Step 2: (R)-3-((3-(1-aminopropan-2-yl) phenyl) amino)-5-cyclopropyl-6-ethylpyrazine-2-carboxamide

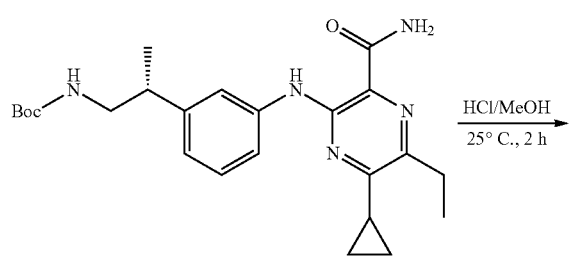

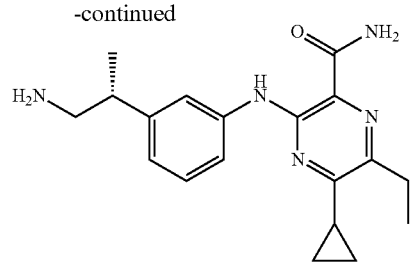

A mixture of tert-butyl (R)-(2-(3-((3-carbamoyl-6-cyclopropyl-5-ethylpyrazin-2-yl) amino) phenyl) propyl) carbamate (400 mg, 910.02 umol, 1 eq) and HCl/MeOH (10 mL) was stirred at 25° C. for 2 hours. The mixture was concentrated under reduced pressure to afford (R)-3-((3-(1-aminopropan-2-yl) phenyl) amino)-5-cyclopropyl-6-ethylpyrazine-2-carboxamide (270 mg, crude, HCl) as yellow solid. LC-MS (ES+, m/z): 340.3 [(M+H)$^+$]; Rt=0.543 min.

Step 3: (R,E)-5-cyclopropyl-3-((3-(1-(2-(4-(dimethylamino)-N-methylbut-2-enamido) acetamido) propan-2-yl) phenyl)amino)-6-ethylpyrazine-2-carboxamide

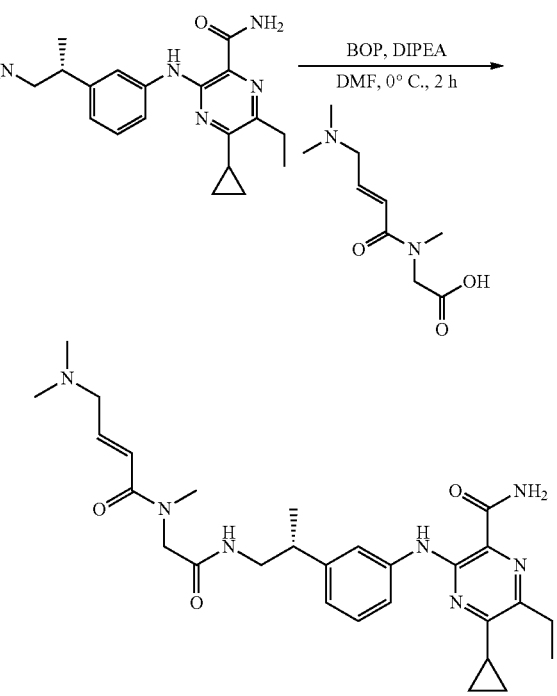

To a solution of (E)-N-(4-(dimethylamino)but-2-enoyl)-N-methylglycine (125.40 mg, 399.05 umol, 3 eq, TFA) in DMF (1 mL) was added DIEA (171.91 mg, 1.33 mmol, 231.69 μL, 10 eq) and (R)-3-((3-(1-aminopropan-2-yl)phenyl)amino)-5-cyclopropyl-6-ethylpyrazine-2-carboxamide (50 mg, 133.02 μmol, 1 eq, HCl), then BOP (88.25 mg, 199.52 μmol, 1.5 eq) was added. The mixture was stirred at 0° C. for 2 hours. Filtered to give filtrate. The crude was purified by prep-HPLC (column: Waters Xbridge Prep OBD C18 150*40 mm*10 um; mobile phase: [water ($NH_4HCO_3$)-ACN]; B %: 30%-70%, 8 min) to afford (R,E)-5-cyclopropyl-3-((3-(1-(2-(4-(dimethylamino)-N-methylbut-2-enamido)acetamido)propan-2-yl)phenyl) amino)-6-ethylpyrazine-2-carboxamide (20.08 mg, 37.71 mol, 28.35% yield) as yellow solid. $^1$H NMR (400 MHz, DMSO-d$_6$) δ=11.08 (d, J=5.0 Hz, 1H), 8.12 (br d, J=1.9 Hz, 1H), 8.08-7.84 (m, 1H), 7.82 (br d, J=1.9 Hz, 1H), 7.54 (br s, 1H), 7.34 (br d, J=8.0 Hz, 1H), 7.22 (t, J=7.8 Hz, 1H), 6.83 (d, J=7.5 Hz, 1H), 6.63-6.23 (m, 2H), 3.93 (d, J=16.4 Hz, 2H), 3.28-3.21 (m, 2H), 3.01 (d, J=5.1 Hz, 1H), 2.98-2.86 (m, 6H), 2.77 (s, 1H), 2.29 (brt, J=6.2 Hz, 1H), 2.16-2.06 (m, 6H), 1.29-1.08 (m, 10H). LC-MS (ES+, m/z): 522.4 [(M+H)$^+$]; Rt=2.170 min. HRMS (EI): m/z [M]$^+$ found: 522.3186.

Example 55

Compound 505

(S,E)-3-((3-(2-(2-(4-(bis(methyl-d3)amino)-N-methylbut-2-enamido)propanamido)ethyl)phenyl)amino)-6-ethyl-5-(isopropylamino)pyrazine-2-carboxamide Step 1: (S,E)-3-((3-(2-(2-(4-(bis(methyl-d3)amino)-N-methylbut-2-enamido) propanamido) ethyl) phenyl) amino)-6-ethyl-5-(isopropylamino) pyrazine-2-carboxamide To a mixture of (E)-4-[bis(trideuteriomethyl)amino]but-2-enoic acid (155.8 mg, 0.5994 mmol, 1.5 eq) and N,N-Diisopropylethylamine (0.6961 mL, 3.996 mmol, 10 eq) in DMF (1 mL), was added 6-ethyl-5-(isopropylamino)-3-[3-[2-[[(2S)-2-(methylamino) propanoyl] amino] ethyl] anilino]pyrazine-2-carboxamide dihydrochloride (200.0 mg, 0.3996 mmol, 1 eq). The mixture was cooled to 0° C. under nitrogen. A solution of benzotriazole-1-yloxytris(dimethylamino)-phosphonium hexafluorophosphate (265.1 mg, 0.5994 mmol, 1.5 eq) in DMF (1 mL) was injected dropwise. The reaction was stirred at 0° C. for 2 hours. The reaction mixture was diluted with EtOAc (30 mL) and NaHCO$_3$ (aq) (10 mL), washed with NaHCO$_3$ (aq) (1×), water (2×) and brine (1×). Dried over Na$_2$SO$_4$, filtered and concentrated. The crude material was purified on silica gel column, 0-30% MeOH/EtOAc to provide 149 mg desired product as a gum. The compound was dissolved in ACN (2 mL), filtered, rinsed with ACN (2×1 mL), added water (6 mL), lyophilized to provide 3-[3-[2-[[(2S)-2-[[(E)-4-[bis(trideuteriomethyl) amino] but-2-enoyl]-methyl-amino] propanoyl] amino] ethyl] anilino]-6-ethyl-5-(isopropylamino) pyrazine-2-carboxamide (134.0 mg, 0.2460 mmol, 61.56% yield) as white solid. $^1$H NMR (400 MHz, DMSO-d$_6$) δ=11.14 (s, 1H), 7.74 (s, 1H), 7.57 (d, J=12.0 Hz, 1H), 7.7 (d, J=3.3 Hz, 1H), 7.1 (d, J=8.2 HZ, 1H), 7.22-7.06 (m, 2H), 6.76-6.62 (m, 2H), 6.59-6.34 (m, 2H), 4.92 (q, J=7.2 Hz, 1H), 4.20 (dq, J=13.4, 6.6 Hz, 1H), 3.15-3.35 (m, 2H), 2.97-2.85 (m, 2H), 2.77 (s, 2H) 2.70-2.57 (m, 3H) 2.52 (q, J=7.3 Hz, 2H), 1.30-1.00 (m, 12H). LC-MS (ES+, m/z): 545.4 [(M+H)$^+$]:

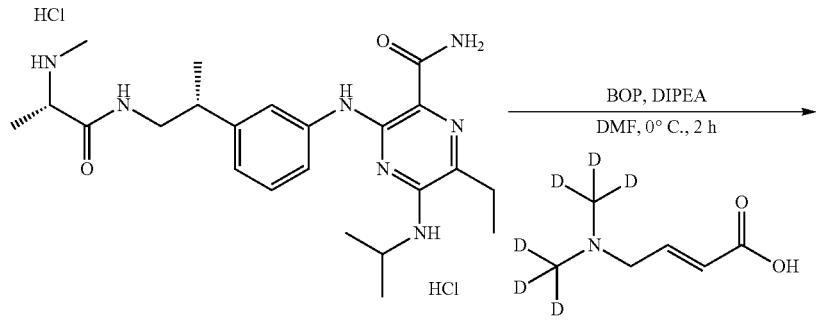

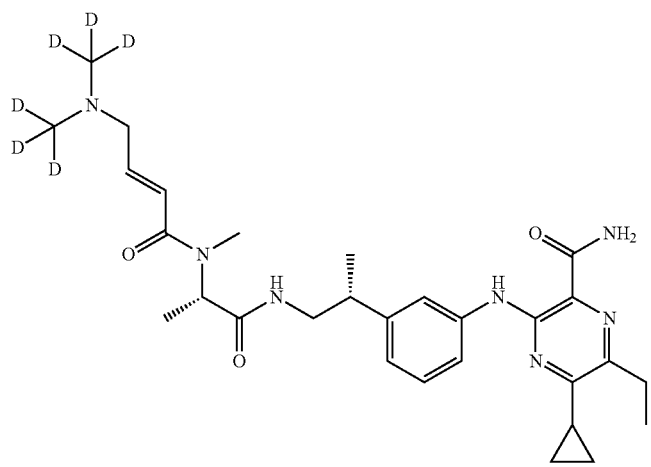

Intermediate 3

(E)-N-(4-(azetidin-1-yl) but-2-enoyl)-N-methylglycine

Step 1: ethyl (E)-4-(azetidin-1-yl) but-2-enoate

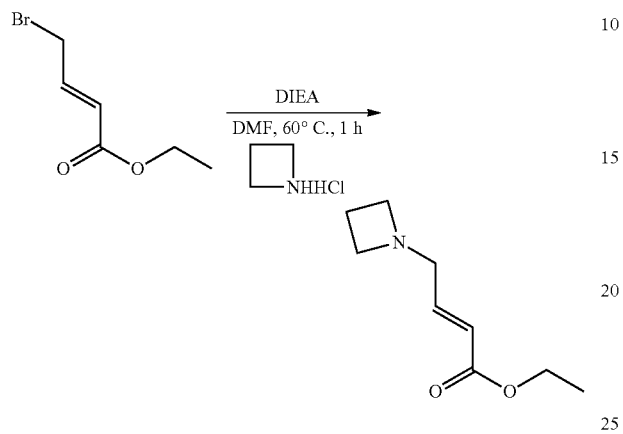

To a solution of ethyl (E)-4-bromobut-2-enoate (5.00 g, 25.90 mmol, 3.57 mL, 1 eq) and DIEA (10.04 g, 77.70 mmol, 13.53 mL, 3 eq) in DMF (100 mL) was added azetidine hydrochloride (2.42 g, 25.90 mmol, 1 eq). The mixture was stirred at 60° C. for 1 hour. The 5 parallel reactions were concentrated under reduced pressure. The crude was purified by prep-HPLC (column: Waters Xbridge BEH C18 250*70 mm*10 um; mobile phase: [water (NH$_4$HCO$_3$)-ACN]; B %: 0%-35%, 20 min). The mixture was adjusted to pH=2 with TFA and concentrated to afford ethyl (E)-4-(azetidin-1-yl) but-2-enoate (16.00 g, 56.49 mmol, 43.62% yield, TFA) as yellow oil. $^1$H NMR (400 MHz, DMSO-d$_6$) δ=6.71 (td, J=5.2, 15.7 Hz, 1H), 5.89 (td, J=1.9, 15.8 Hz, 1H), 4.13-4.07 (m, 2H), 3.14-3.07 (m, 6H), 2.02-1.93 (m, 2H), 1.20 (t, J=7.1 Hz, 3H). LC-MS (ES+, m/z): 170.1 [(M+H)$^+$]; Rt=1.879 min.

Step 2: (E)-4-(azetidin-1-yl) but-2-enoic acid

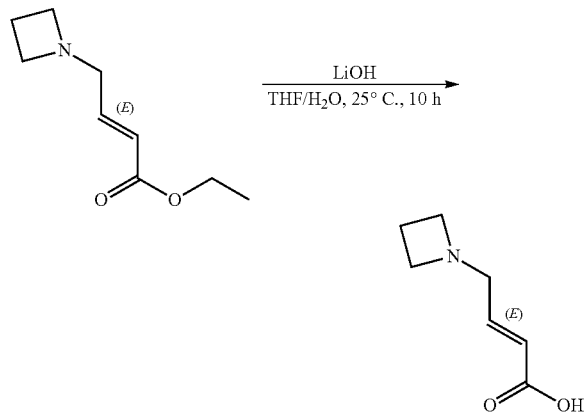

To a solution of ethyl (E)-4-(azetidin-1-yl) but-2-enoate (12.00 g, 46.08 mmol, 1 eq, 0.8 TFA) in THF (40 mL) and H$_2$O (20 mL) was added LiOH·H$_2$O (3.87 g, 92.15 mmol, 2 eq). The mixture was stirred at 25° C. for 10 hours. The mixture was concentrated under reduced pressure to afford (E)-4-(azetidin-1-yl) but-2-enoic acid (5.50 g, crude) as yellow oil. $^1$H NMR (400 MHz, DMSO-d$_6$) δ=6.20 (br d, J=15.5 Hz, 1H), 5.73 (d, J=15.5 Hz, 1H), 3.04 (d, J=7.0 Hz, 4H), 2.96 (dd, J=1.1, 5.9 Hz, 2H), 1.93 (br d, J=6.9 Hz, 2H) (the active COO—H was not detected). LC-MS (ES+, m/z): 142.1 [(M+H)$^+$]; Rt=0.210 min.

Step 3: tert-butyl (E)-N-(4-(azetidin-1-yl) but-2-enoyl)-N-methylglycinate

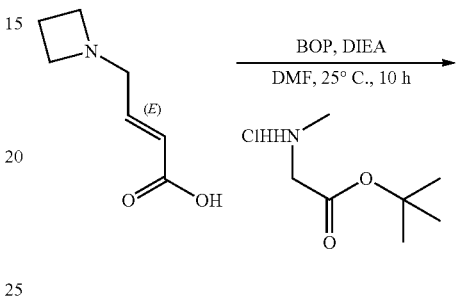

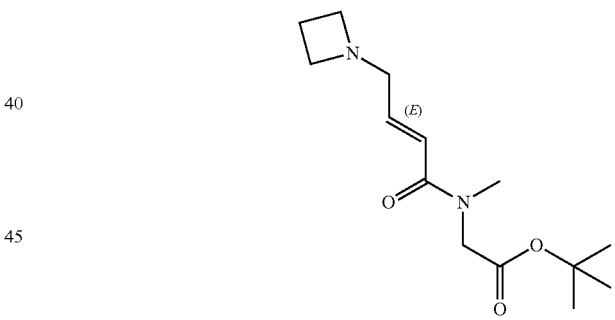

To a solution of (E)-4-(azetidin-1-yl) but-2-enoic acid (5.50 g, 38.96 mmol, 2 eq) and DIEA (25.18 g, 194.80 mmol, 33.93 mL, 10 eq) in DMF (85 mL) was added tert-butyl methylglycinate hydrochloride (3.54 g, 19.48 mmol, 1 eq), then BOP (12.92 g, 29.22 mmol, 1.5 eq) was added. The mixture was stirred at 25° C. for 10 hours. The mixture was concentrated under reduced pressure. The crude was purified by prep-HPLC (column: Phenomenex luna c18 250 mm*100 mm*10 um; mobile phase: [water (TFA)-ACN]; B %: 10%-40%, 20 min), and then adjusted to pH=7 with saturated NaHCO$_3$ (20 mL), extracted with EtOAc (200 mL*2). The organic layers were combined, washed with water (200 mL*2), saturated brine (150 mL*1), dried with Na$_2$SO$_4$, filtered and concentrated to afford tert-butyl (E)-N-(4-(azetidin-1-yl) but-2-enoyl)-N-methylglycinate (1.00 g, 3.73 mmol, 19.13% yield) as yellow oil. LC-MS (ES+, m/z): 269.2 [(M+H)$^+$]; Rt=3.385 min.

Step 4: (E)-N-(4-(azetidin-1-yl) but-2-enoyl)-N-methylglycine

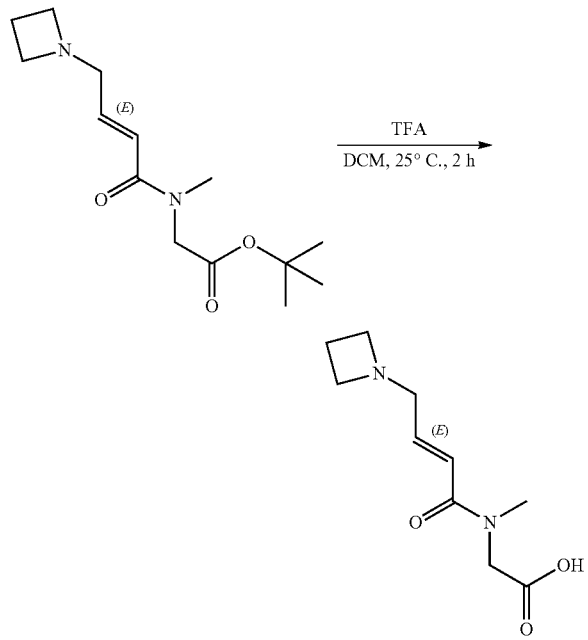

A mixture of tert-butyl (E)-N-(4-(azetidin-1-yl) but-2-enoyl)-N-methylglycinate (800 mg, 2.98 mmol, 1 eq), TFA (12.32 g, 108.05 mmol, 8.00 mL, 36.24 eq) and DCM (16 mL), the mixture was stirred at 25° C. for 2 hours. The mixture was concentrated under reduced pressure to afford (E)-N-(4-(azetidin-1-yl)but-2-enoyl)-N-methylglycine (800 mg, crude, TFA) as yellow oil. LC-MS (ES+, m/z): 213.2 [(M+H)+]; Rt=0.122 min.

Example 56

Compound 506

(R,E)-3-((3-(1-(2-(4-(azetidin-1-yl)-N-methylbut-2-enamido)acetamido)propan-2-yl)phenyl)amino)-5-cyclopropyl-6-ethylpyrazine-2-carboxamide Step 1: tert-butyl (R)-(2-(3-((3-carbamoyl-6-cyclopropyl-5-ethylpyrazin-2-yl) amino) phenyl) propyl) carbamate

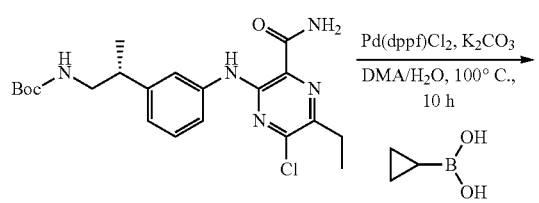

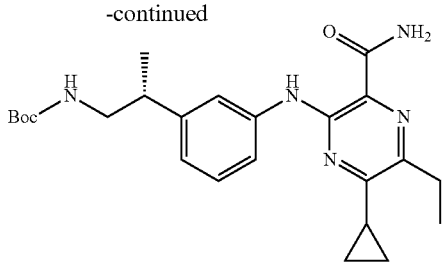

To a solution of tert-butyl (R)-(2-(3-((3-carbamoyl-6-chloro-5-ethylpyrazin-2-yl)amino)phenyl) propyl) carbamate (400 mg, 921.81 μmol, 1 eq), cyclopropylboronic acid (791.81 mg, 9.22 mmol, 10 eq) and K$_2$CO$_3$ (382.20 mg, 2.77 mmol, 3 eq) in DMA (10 mL) and H$_2$O (5 mL), Pd(dppf)Cl$_2$ (67.45 mg, 92.18 μmol, 0.1 eq) was added. The mixture was stirred at 100° C. for 10 hours under N$_2$. The residue was dissolved in EtOAc (40 mL), scavenger (Pd) was added and then stirred at 25° C. for 1 hour, and then filtered. The mixture was poured into water (30 mL) and extracted with EtOAc (20 mL*2). The organic layers were combined, washed with water (10 mL*2), saturated brine (10 mL*1), dried with Na$_2$SO$_4$, filtered, and concentrated to give crude product. The crude product was purified by chromatography on silica thiol gel (petroleum ether/EtOAc=1/1) to afford tert-butyl (R)-(2-(3-((3-carbamoyl-6-cyclopropyl-5-ethylpyrazin-2-yl) amino) phenyl) propyl) carbamate (320 mg, 728.02 μmol, 78.98% yield) as yellow solid. LC-MS (ES+, m/z): 440.3 [(M+H)+]; Rt=1.047 min.

Step 2: (R)-3-((3-(1-aminopropan-2-yl) phenyl) amino)-5-cyclopropyl-6-ethylpyrazine-2-carboxamide

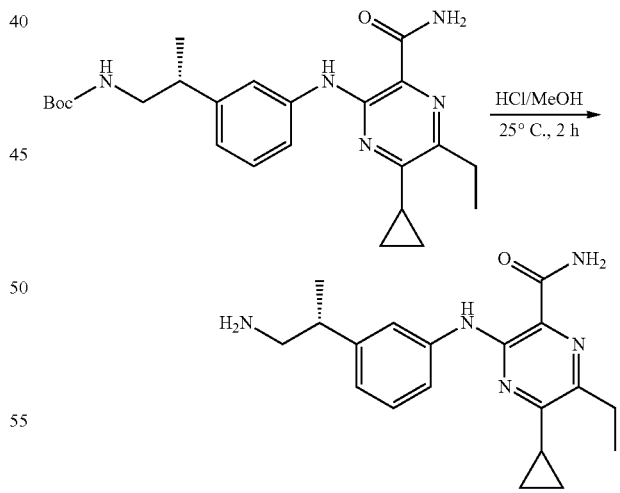

A mixture of tert-butyl (R)-(2-(3-((3-carbamoyl-6-cyclopropyl-5-ethylpyrazin-2-yl) amino) phenyl) propyl) carbamate (400 mg, 910.02 μmol, 1 eq) and HCl/MeOH (10 mL, 4 M) was stirred at 25° C. for 2 hours. The mixture was concentrated under reduced pressure to afford (R)-3-((3-(1-aminopropan-2-yl) phenyl) amino)-5-cyclopropyl-6-ethylpyrazine-2-carboxamide (270 mg, crude, HCl) as yellow solid. LC-MS (ES+, m/z): 340.3 [(M+H)+]; Rt=0.543 min.

Step 3: (R,E)-3-((3-(1-(2-(4-(azetidin-1-yl)-N-methylbut-2-enamido) acetamido) propan-2-yl) phenyl) amino)-5-cyclopropyl-6-ethylpyrazine-2-carboxamide

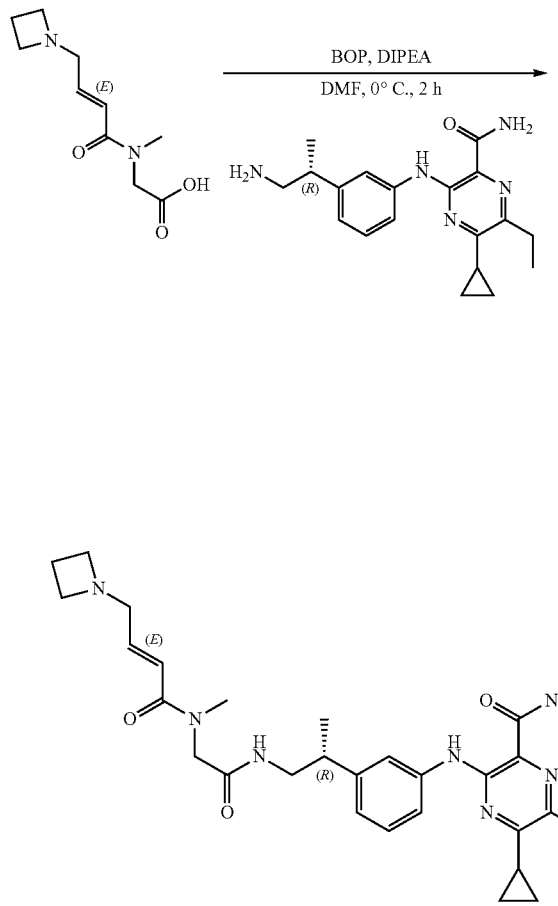

To a solution of (E)-N-(4-(azetidin-1-yl)but-2-enoyl)-N-methylglycine (347.19 mg, 1.06 mmol, 2 eq, TFA) in DMF (1 mL) was added DIEA (687.66 mg, 5.32 mmol, 926.76 µL, 10 eq) and (R)-3-((3-(1-aminopropan-2-yl)phenyl)amino)-5-cyclopropyl-6-ethylpyrazine-2-carboxamide (200 mg, 532.06 µmol, 1 eq, HCl), then BOP (352.98 mg, 798.10 µmol, 1.5 eq) was added. The mixture was stirred at 0° C. for 2 hours. Filtered to give filtrate. The crude was purified by prep-HPLC (column: Phenomenex C18 75*30 mm*3 um; mobile phase: [water (NH$_4$HCO$_3$)-ACN]; B %: 25%-75%, 8 min) to afford (R,E)-3-((3-(1-(2-(4-(azetidin-1-yl)-N-methylbut-2-enamido) acetamido) propan-2-yl) phenyl) amino)-5-cyclopropyl-6-ethylpyrazine-2-carboxamide (89.9 mg, 160.04 µmol, 30.08% yield) as yellow solid. $^1$H NMR (400 MHz, DMSO-d$_6$) δ=11.08 (d, J=6.8 Hz, 1H), 8.12 (br s, 1H), 8.08-7.79 (m, 2H), 7.54 (br d, J=7.9 Hz, 1H), 7.35 (br d, J=8.0 Hz, 1H), 7.23 (dt, J=4.3, 7.8 Hz, 1H), 6.83 (br dd, J=3.7, 7.3 Hz, 1H), 6.50-6.14 (m, 2H), 3.92 (d, J=16.4 Hz, 2H), 3.28-3.20 (m, 2H), 3.14-3.08 (m, 3H), 3.07-3.00 (m, 3H), 2.96-2.77 (m, 6H), 2.33-2.26 (m, 1H), 1.95 (td, J=7.0, 19.8 Hz, 2H), 1.27 (t, J=7.5 Hz, 3H), 1.21 (t, J=7.1 Hz, 3H), 1.13-1.08 (m, 4H). LC-MS (ES+, m/z): 534.3 [(M+H)$^+$]; Rt=2.265 min. HRMS (EI): m/z [M]+ found: 534.3185.

Example 57

Compound 507

(R,E)-3-((3-(1-(2-(4-(azetidin-1-yl)-N-methylbut-2-enamido)acetamido)propan-2-yl)phenyl)amino)-6-ethyl-5-propylpyrazine-2-carboxamide

Step 1: tert-butyl (R)-(2-(3-((6-allyl-3-carbamoyl-5-ethylpyrazin-2-yl) amino) phenyl) propyl) carbamate

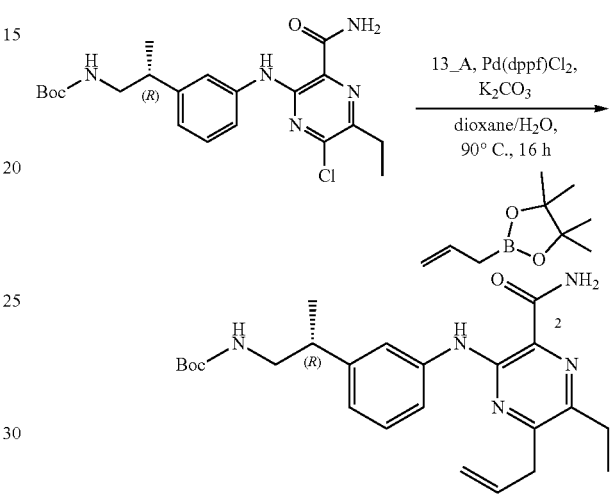

A mixture of tert-butyl (R)-(2-(3-((3-carbamoyl-6-chloro-5-ethylpyrazin-2 yl) amino) phenyl) propyl) carbamate (400 mg, 921.81 µmol, 1 eq), 2-allyl-4,4,5,5-tetramethyl-1,3,2-dioxaborolane (1.55 g, 9.22 mmol, 10 eq), Pd(dppf)Cl$_2$ (67.45 mg, 92.18 µmol, 0.1 eq), Cs$_2$CO$_3$ (901.03 mg, 2.77 mmol, 3 eq) in dioxane (20 mL) and H$_2$O (5 mL) was stirred at 90° C. for 16 hours under N$_2$. The residue was poured into saturated EDTA (20 mL) and stirred for 60 min. The aqueous phase was extracted with ethyl acetate (20 mL*3). The combined organic phase was washed with saturated brine (20 mL), dried with anhydrous Na$_2$SO$_4$, filtered, and concentrated in vacuum. The crude product was purified by chromatography on silica thiol gel (petroleum ether/EtOAc=20/1 to 2/1) to give tert-butyl (R)-(2-(3-((6-allyl-3-carbamoyl-5-ethylpyrazin-2-yl) amino) phenyl) propyl) carbamate (300 mg, 682.52 mol, 74.04% yield) as yellow solid. LC-MS (ES+, m/z): 440.2 [(M+H)$^+$]; Rt=0.865 min.

Step 2: tert-butyl (R)-(2-(3-((3-carbamoyl-5-ethyl-6-propylpyrazin-2-yl) amino) phenyl) propyl) carbamate

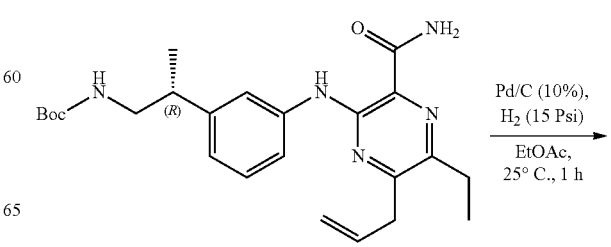

-continued

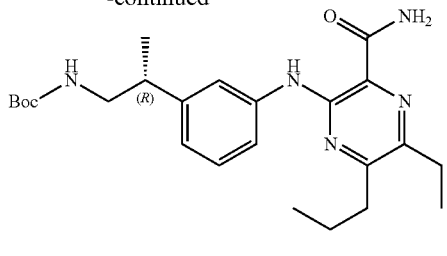

To a suspension of Pd/C (10.0 mg, 682.52 μmol, 50% purity, 1 eq) in EtOAc (80 mL) at 25° C., tert-butyl (R)-(2-(3-((6-allyl-3-carbamoyl-5-ethylpyrazin-2-yl) amino) phenyl) propyl) carbamate (300 mg, 682.52 μmol, 1 eq) was added and stirred at 25° C. for 1 hour under 15 psi of $H_2$ atmosphere. The mixture was filtered and concentrated to dryness to give tert-butyl (R)-(2-(3-((3-carbamoyl-5-ethyl-6-propylpyrazin-2-yl) amino) phenyl) propyl) carbamate (150 mg, crude) as yellow solid. $^1$H NMR (400 MHz, $CDCl_3$) δ=10.69 (s, 1H), 7.87 (br d, J=2.6 Hz, 1H), 7.66-7.52 (m, 2H), 7.28-7.21 (m, 1H), 6.84 (br d, J=7.7 Hz, 1H), 5.48-5.37 (m, 1H), 4.50-4.36 (m, 1H), 3.53-3.40 (m, 1H), 3.22-3.10 (m, 1H), 2.95-2.84 (m, 1H), 2.79-2.71 (m, 4H), 1.90-1.81 (m, 2H), 1.47-1.33 (m, 9H), 1.31-1.19 (m, 6H), 1.03 (t, J=7.3 Hz, 3H). LC-MS (ES+, m/z): 442.2 [(M+H)$^+$]; Rt=2.406 min.

Step 3: (R)-3-((3-(1-aminopropan-2-yl) phenyl) amino)-6-ethyl-5-propylpyrazine-2-carboxamide

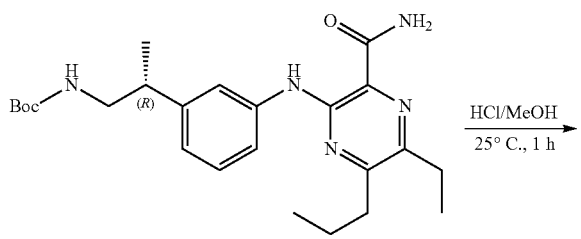

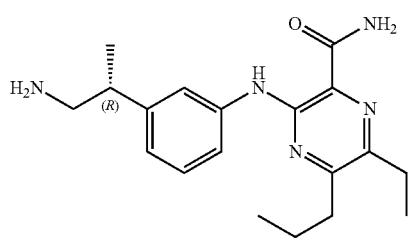

A mixture of tert-butyl (R)-(2-(3-((3-carbamoyl-5-ethyl-6-propylpyrazin-2-yl) amino) phenyl) propyl) carbamate (150 mg, 339.70 μmol, 1 eq) and HCl/MeOH (4 M, 20 mL, 235.50 eq) was stirred at 25° C. for 1 hour. The mixture was concentrated to dryness to give (R)-3-((3-(1-aminopropan-2-yl) phenyl) amino)-6-ethyl-5-propylpyrazine-2-carboxamide (140 mg, crude, HCl) as yellow solid. LC-MS (ES+, m/z): 342.2 [(M+H)$^+$]; Rt=0.585 min.

Step 4: (R,E)-3-((3-(1-(2-(4-(azetidin-1-yl)-N-methylbut-2-enamido) acetamido) propan-2-yl) phenyl) amino)-6-ethyl-5-propylpyrazine-2-carboxamide

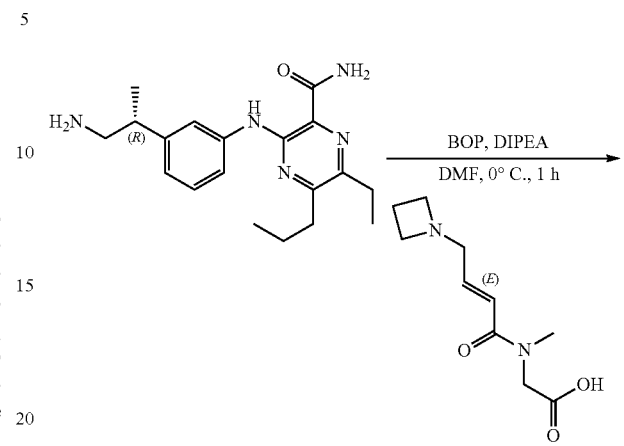

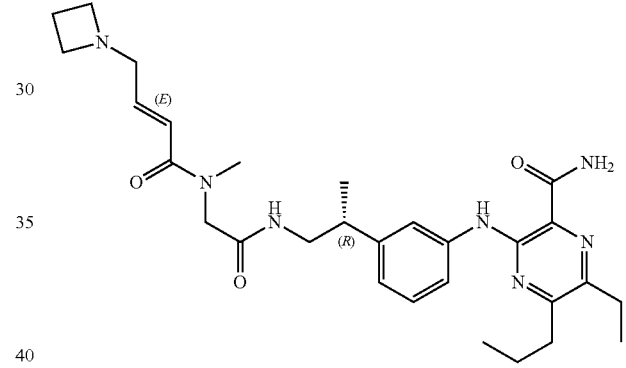

To a solution of (E)-N-(4-(azetidin-1-yl)but-2-enoyl)-N-methylglycine (193.39 mg, 592.73 mol, 1.6 eq, TFA) in DMF (1.5 mL) at ° C., DIPEA (478.79 mg, 3.70 mmol, 645.27 μL, 10 eq) and (R)-3-((3-(1-aminopropan-2-yl)phenyl)amino)-6-ethyl-5-propylpyrazine-2-carboxamide (140 mg, 370.46 μmol, 1 eq, HCl) was added. Then BOP (245.77 mg, 555.69 μmol, 1.5 eq) was added at 0° C. The mixture was stirred at 0° C. for 1 hour. The mixture was filtered. The residue was purified by prep-HPLC (column: Waters Xbridge BEH C18 100*30 mm*10 um; mobile phase: [water ($NH_4HCO_3$)-ACN]; B %: 30%-60%, 8 min) to give (R,E)-3-((3-(1-(2-(4-(azetidin-1-yl)-N-methylbut-2-enamido)acetamido)propan-2-yl)phenyl)amino)-6-ethyl-5-propylpyrazine-2-carboxamide (70.0 mg, 127.03 μmol, 34.29% yield, 97.21% purity) as yellow oil. $^1$H NMR (400 MHz, DMSO-$d_6$) δ=11.16-11.02 (m, 1H), 8.22-8.13 (m, 1H), 8.11-7.82 (m, 2H), 7.64 (br d, J=7.4 Hz, 1H), 7.52 (br d, J=7.9 Hz, 1H), 7.30-7.19 (m, 1H), 6.88-6.80 (m, 1H), 6.51-6.21 (m, 2H), 3.93 (d, J=17.3 Hz, 2H), 3.26-3.19 (m, 2H), 3.16-3.08 (m, 3H), 3.07-2.96 (m, 4H), 2.94-2.87 (m, 1H), 2.83-2.69 (m, 6H), 2.04-1.88 (m, 2H), 1.82 (sxt, J=7.4 Hz, 2H), 1.27-1.17 (m, 6H), 1.00 (t, J=7.4 Hz, 3H). LC-MS (ES+, m/z): 536.3 [(M+H)$^+$]; Rt=2.328 min. HRMS (EI): m/z [M]$^+$ found: 536.3325.

Example 58

Compound 508

(R,E)-3-((3-(1-(2-(4-(azetidin-1-yl)-N-methylbut-2-enamido) acetamido) propan-2-yl) phenyl) amino)-5,6-diethylpyrazine-2-carboxamide Step 1: tert-butyl (R)-(2-(3-((3-carbamoyl-5,6-diethylpyrazin-2-yl) amino) phenyl) propyl) carbamate

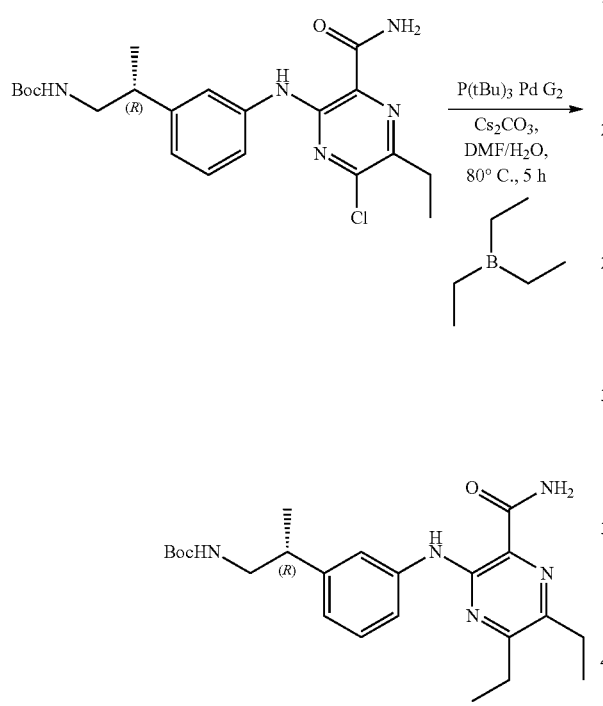

To a solution of tert-butyl (R)-(2-(3-((3-carbamoyl-6-chloro-5-ethylpyrazin-2-yl) amino) phenyl) propyl) carbamate (400 mg, 921.81 µmol, 1 eq), triethylborane (903.31 mg, 9.22 mmol, 1.33 mL, 10 eq), $Cs_2CO_3$ (901.03 mg, 2.77 mmol, 3 eq) in DMF (5 mL) and $H_2O$ (2 mL) at 25° C., $P(tBu)_3$ Pd G2 (47.23 mg, 92.18 µmol, 0.1 eq) was added. The mixture was stirred at 80° C. for 5 hours under $N_2$. The residue was dissolved in DCM (10 mL), scavenger (Pd) was added and then stirred at 25° C. for 1 hour, and then filtered. The mixture was poured into water (10 mL) and extracted with DCM (10 mL*2). The organic layers were combined, washed with water (20 mL*2), saturated brine (20 mL*2), dried over $Na_2SO_4$, filtered, concentrated under reduced pressure. The crude product was purified by chromatography on silica gel (Petroleum ether:Ethyl acetate=3:1) to afford tert-butyl (R)-(2-(3-((3-carbamoyl-5,6-diethylpyrazin-2-yl) amino) phenyl) propyl) carbamate (350 mg, 818.64 µmol, 88.81% yield) as yellow oil. $^1$H NMR (400 MHz, DMSO-$d_6$) δ=11.08 (s, 1H), 8.20-8.10 (m, 1H), 7.86 (br d, J=1.8 Hz, 1H), 7.66-7.48 (m, 2H), 7.28-7.19 (m, 1H), 6.89-6.78 (m, 2H), 3.15-2.99 (m, 2H), 2.92-2.80 (m, 3H), 2.80-2.71 (m, 2H), 1.36-1.16 (m, 18H). LCMS (ES+, m/z): 428.2 [(M+H)$^+$]; Rt=0.947 min.

Step 2: (R)-3-((3-(1-aminopropan-2-yl) phenyl) amino)-5,6-diethylpyrazine-2-carboxamide

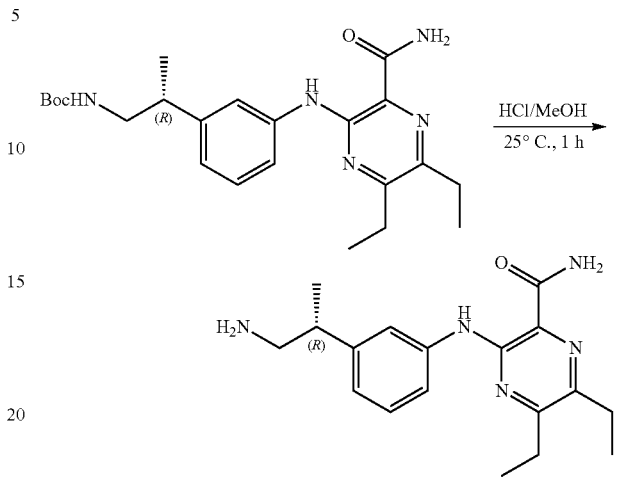

The mixture tert-butyl (R)-(2-(3-((3-carbamoyl-5,6-diethylpyrazin-2-yl) amino) phenyl) propyl) carbamate (440 mg, 1.03 mmol, 1 eq) and HCl/MeOH (4 M, 40 mL, 155.47 eq) was stirred at 25° C. for 1 hour. The reaction mixture was concentrated under reduced pressure to give (R)-3-((3-(1-aminopropan-2-yl) phenyl) amino)-5,6-diethylpyrazine-2-carboxamide (350 mg, crude, HCl) as yellow solid. $^1$H NMR (400 MHz, DMSO-$d_6$) δ=11.12 (s, 1H), 8.22-8.12 (m, 1H), 7.90 (br d, J=13.0 Hz, 4H), 7.74-7.66 (m, 1H), 7.63-7.57 (m, 1H), 7.34-7.26 (m, 1H), 6.96-6.89 (m, 1H), 3.07-2.97 (m, 3H), 2.85 (q, J=7.4 Hz, 2H), 2.76 (q, J=7.5 Hz, 2H), 1.33-1.22 (m, 9H)(HCl salt). LCMS (ES+, m/z): 328.2 [(M+H)$^+$]; Rt=0.568 min.

Step 3: tert-butyl (R)-(2-((2-(3-((3-carbamoyl-5,6-diethylpyrazin-2-yl) amino) phenyl) propyl) amino)-2-oxoethyl) (methyl) carbamate

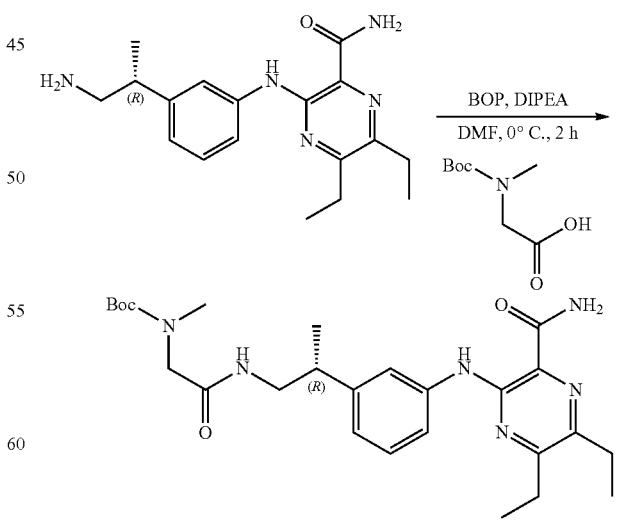

To a solution of (R)-3-((3-(1-aminopropan-2-yl) phenyl) amino)-5,6-diethylpyrazine-2-carboxamide (230 mg, 632.07 µmol, 1 eq, HCl), N-(tert-butoxycarbonyl)-N-methylglycine (179.39 mg, 948.10 µmol, 1.5 eq), DIPEA (816.91 mg, 6.32 mmol, 1.10 mL, 10 eq) in DMF (3 mL) at 0° C., BOP (419.33 mg, 948.10 µmol, 1.5 eq) was added. The mixture was stirred at 0° C. for 2 hours. The mixture was poured into water (5 mL) and extracted with EtOAc (5 mL*2). The organic layers were combined, washed with water (10 mL*2), saturated brine (10 mL*2), dried over Na₂SO₄, filtered, concentrated under reduced pressure to give a residue. The crude product was purified by chromatography on silica gel (Petroleum ether:Ethyl acetate=1:3) to afford tert-butyl (R)-(2-((2-(3-((3-carbamoyl-5,6-diethylpyrazin-2-yl) amino) phenyl) propyl) amino)-2-oxoethyl) (methyl) carbamate (240 mg, 481.33 mol, 76.15% yield) as yellow oil. ¹H NMR (400 MHz, DMSO-d₆) δ=11.13-11.06 (m, 1H), 8.22-8.11 (m, 1H), 7.93-7.77 (m, 2H), 7.69-7.60 (m, 1H), 7.59-7.48 (m, 1H), 7.29-7.20 (m, 1H), 6.89-6.80 (m, 1H), 3.78-3.62 (m, 2H), 3.29-3.19 (m, 2H), 2.95-2.66 (m, 8H), 1.41-1.18 (m, 18H). LCMS (ES+, m/z): 499.4 [(M+H)⁺]; Rt=0.836 min.

Step 4: (R)-5,6-diethyl-3-((3-(1-(2-(methylamino) acetamido) propan-2-yl) phenyl) amino) pyrazine-2-carboxamide

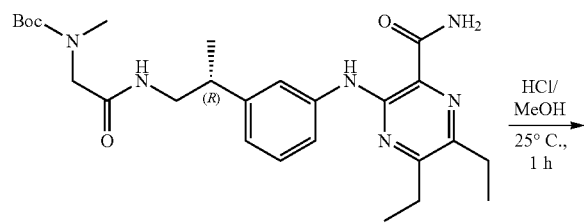

The mixture tert-butyl (R)-(2-((2-(3-((3-carbamoyl-5,6-diethylpyrazin-2-yl) amino) phenyl) propyl) amino)-2-oxoethyl) (methyl) carbamate (240 mg, 481.33 µmol, 1 eq) and HCl/MeOH (4 M, 27.69 mL, 230.13 eq) was stirred at 25° C. for 1 hour. The reaction mixture was concentrated under reduced pressure to give (R)-5,6-diethyl-3-((3-(1-(2-(methylamino) acetamido) propan-2-yl) phenyl) amino) pyrazine-2-carboxamide (230 mg, crude) as yellow solid. LCMS (ES+, m/z): 399.4 [(M+H)⁺]; Rt=0.579 min.

Step 5: (R,E)-3-((3-(1-(2-(4-(azetidin-1-yl)-N-methylbut-2-enamido) acetamido) propan-2-yl) phenyl) amino)-5,6-diethylpyrazine-2-carboxamide

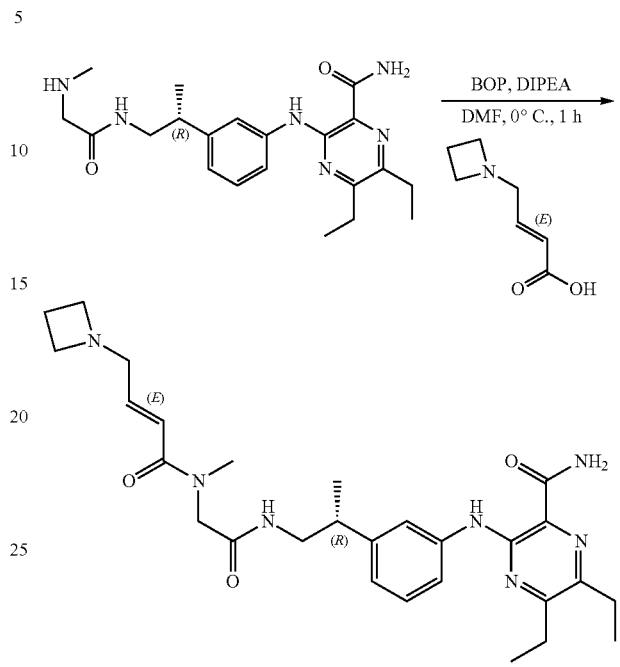

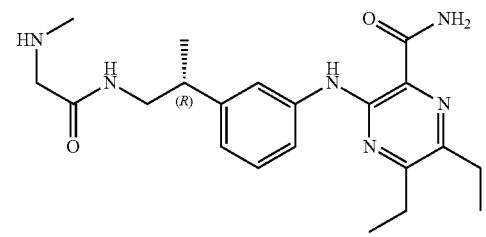

To a solution of (R)-5,6-diethyl-3-((3-(1-(2-(methylamino) acetamido) propan-2-yl) phenyl) amino) pyrazine-2-carboxamide (200 mg, 459.81 µmol, 1 eq, HCl), (E)-4-(azetidin-1-yl) but-2-enoic acid (293.35 mg, 1.15 mmol, 2.5 eq, TFA salt), DIPEA (594.27 mg, 4.60 mmol, 800.91 µL, 10 eq) in DMF (2 mL) at 0° C., BOP (305.05 mg, 689.72 µmol, 1.5 eq) was added. The mixture was stirred at 0° C. for 1 hour. The mixture was filtered to give a residue. The crude was purified by prep-HPLC (column: Waters Xbridge BEH C18 100*30 mm*10 um; mobile phase: [water (NH₄HCO₃)-ACN]; B %: 30%-65%, 8 µmin) to afford (R,E)-3-((3-(1-(2-(4-(azetidin-1-yl)-N-methylbut-2-enamido)acetamido) propan-2-yl)phenyl)amino)-5,6-diethylpyrazine-2-carboxamide (30.10 mg, 24.75 mol, 12.28% yield, 97.89% purity) as yellow solid. ¹H NMR (400 MHz, DMSO-d₆) δ=11.11 (d, J=6.5 Hz, 1H), 8.20-8.04 (m, 1H), 7.93-7.81 (m, 2H), 7.68-7.52 (m, 2H), 7.32-7.18 (m, 1H), 6.92-6.80 (m, 1H), 6.61-6.37 (m, 2H), 6.29-6.14 (m, 1H), 3.99-3.90 (m, 2H), 3.29-3.22 (m, 2H), 3.17-3.02 (m, 6H), 2.98 (s, 2H), 2.92-2.82 (m, 3H), 2.81-2.73 (m, 3H), 2.06-1.87 (m, 2H), 1.35-1.19 (m, 9H)(TFA salt). ¹H NMR (400 MHz, DMSO-d₆+D₂O) δ=11.01-10.92 (m, 1H), 7.68-7.60 (m, 1H), 7.51 (br d, J=7.8 Hz, 1H), 7.30-7.20 (m, 1H), 6.90-6.80 (m, 1H), 6.58-6.36 (m, 2H), 3.92 (br d, J=19.6 Hz, 2H), 3.29-3.19 (m, 2H), 3.16-3.09 (m, 3H), 3.08-2.98 (m, 3H), 2.95 (s, 2H), 2.90-2.80 (m, 3H), 2.78-2.71 (m, 3H), 2.02-1.87 (m, 2H), 1.32-1.16 (m, 9H). ¹H NMR (400 MHz, DMSO-d₆ T=273+ 80 K) δ=11.02-10.90 (m, 1H), 8.06-7.90 (m, 1H), 7.74-7.41 (m, 4H), 7.30-7.20 (m, 1H), 6.91-6.81 (m, 1H), 6.66-6.10 (m, 2H), 3.97-3.89 (m, 2H), 3.29 (br t, J=6.4 Hz, 2H), 3.20-3.10 (m, 5H), 3.00-2.71 (m, 9H), 2.06-1.91 (m, 2H), 1.35-1.22 (m, 9H). LC-MS (ES+, m/z): 522.2 [(M+H)⁺]; Rt=2.267 min. HRMS (EI): m/z (M+H)⁺ found: 522.3195.

Example 59

Compound 509

(R,E)-3-((3-(1-(2-(4-(azetidin-1-yl)-N-methylbut-2-enamido)acetamido)propan-2-yl)phenyl)amino)-6-ethyl-5-isopropylpyrazine-2-carboxamide Step 1: tert-butyl (R)-(2-(3-((3-carbamoyl-5-ethyl-6-(prop-1-en-2-yl) pyrazin-2-yl) amino) phenyl) propyl) carbamate

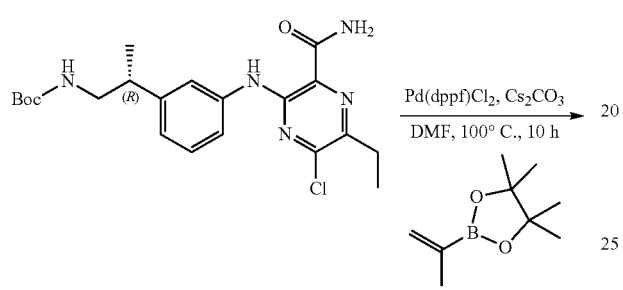

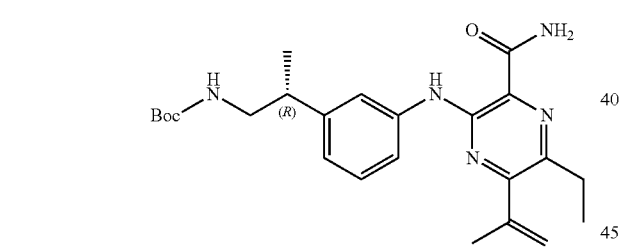

To a solution of tert-butyl (R)-(2-(3-((3-carbamoyl-6-chloro-5-ethylpyrazin-2-yl) amino) phenyl) propyl) carbamate (400.00 mg, 921.81 μmol, 1 eq) and 4,4,5,5-tetramethyl-2-(prop-1-en-2-yl)-1,3,2-dioxaborolane (774.50 mg, 4.61 mmol, 5 eq) in DMF (4 mL) was added Pd(dppf)Cl$_2$ (67.45 mg, 92.18 μmol, 0.1 eq) and Cs$_2$CO$_3$ (901.03 mg, 2.77 mmol, 3 eq). The mixture was stirred at 100° C. for 10 hours under N$_2$ atmosphere. The reaction was poured into water (10 mL) and extracted with EtOAc (20 mL*3). The organic layers were combined, washed with water (15 mL*2), saturated brine (15 mL*2), dried with Na$_2$SO$_4$, filtered, and concentrated to give crude product. The residue was dissolved in DCM (20 mL). scavenger (Pd) was added and then stirred at 25° C. for 1 hour, and then filtered. The residue was purified by column chromatography (SiO$_2$, Petroleum ether/Ethyl acetate=20/1 to 1/1) to afford tert-butyl (R)-(2-(3-((3-carbamoyl-5-ethyl-6-(prop-1-en-2-yl) pyrazin-2-yl)amino) phenyl)propyl)carbamate (300 mg, 682.52 μmol, 74.04% yield) as a yellow solid. LC-MS (ES+, m/z): 440.3 [(M+H)$^+$]; Rt=1.053 min.

Step 2: tert-butyl (R)-(2-(3-((3-carbamoyl-5-ethyl-6-isopropylpyrazin-2-yl) amino) phenyl) propyl) carbamate

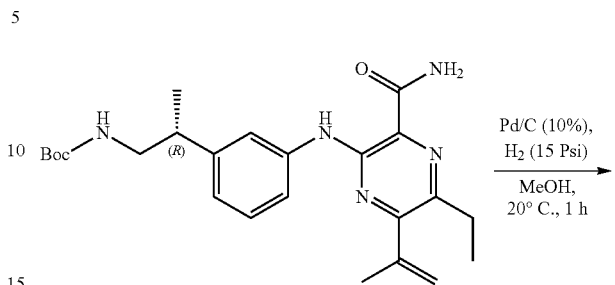

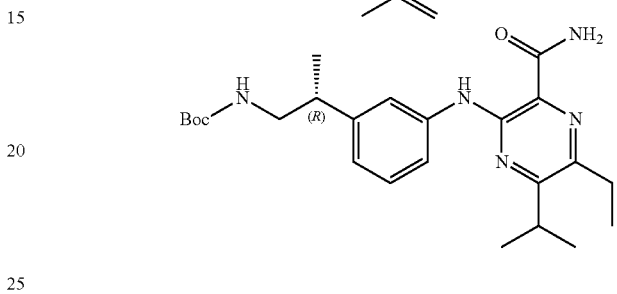

To a solution of tert-butyl (R)-(2-(3-((3-carbamoyl-5-ethyl-6-(prop-1-en-2-yl) pyrazin-2-yl) amino) phenyl) propyl) carbamate (190 mg, 432.26 μmol, 1 eq) in MeOH (30 mL) was added Pd/C (200 mg, 432.26 μmol, 50% purity, 1 eq) under H$_2$ atmosphere. The suspension was degassed and purged with H$_2$ for 3 times. The mixture was stirred under 15 Psi of H$_2$ at 20° C. for 1 hour. The reaction mixture was filtered and concentrated under reduced pressure to afford tert-butyl (R)-(2-(3-((3-carbamoyl-5-ethyl-6-isopropylpyrazin-2-yl) amino) phenyl)propyl) carbamate (160 mg, 362.35 μmol, 83.83% yield) as a yellow oil. LC-MS (ES$^+$, m/z): 442.3 [(M+H)$^+$]; Rt=1.067 min.

Step 3: (R)-3-((3-(1-aminopropan-2-yl) phenyl) amino)-6-ethyl-5-isopropylpyrazine-2-carboxamide

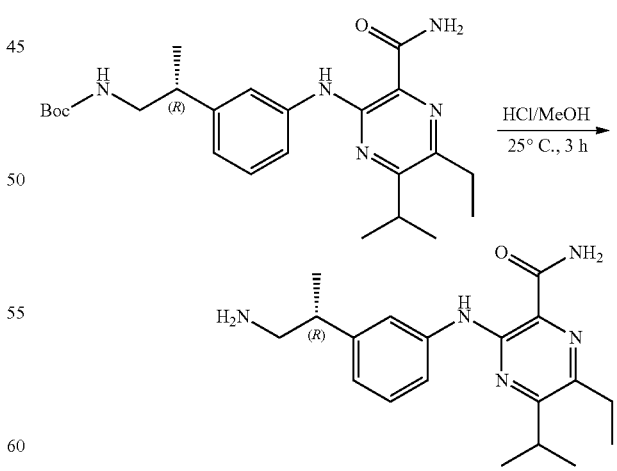

A mixture of tert-butyl (R)-(2-(3-((3-carbamoyl-5-ethyl-6-isopropylpyrazin-2-yl) amino) phenyl) propyl) carbamate (100 mg, 226.47 μmol, 1 eq) in HCl/MeOH (30 mL) was stirred at 25° C. for 1 hour. The reaction mixture was filtered and concentrated under reduced pressure to afford (R)-3-

((3-(1-aminopropan-2-yl) phenyl) amino)-6-ethyl-5-isopropylpyrazine-2-carboxamide (100 mg, crude) as a yellow oil. LC-MS (ES+, m/z): 342.3 [(M+H)$^+$]; Rt=0.134 min.

Step 4: (R,E)-3-((3-(1-(2-(4-(azetidin-1-yl)-N-methylbut-2-enamido) acetamido) propan-2-yl) phenyl) amino)-6-ethyl-5-isopropylpyrazine-2-carboxamide

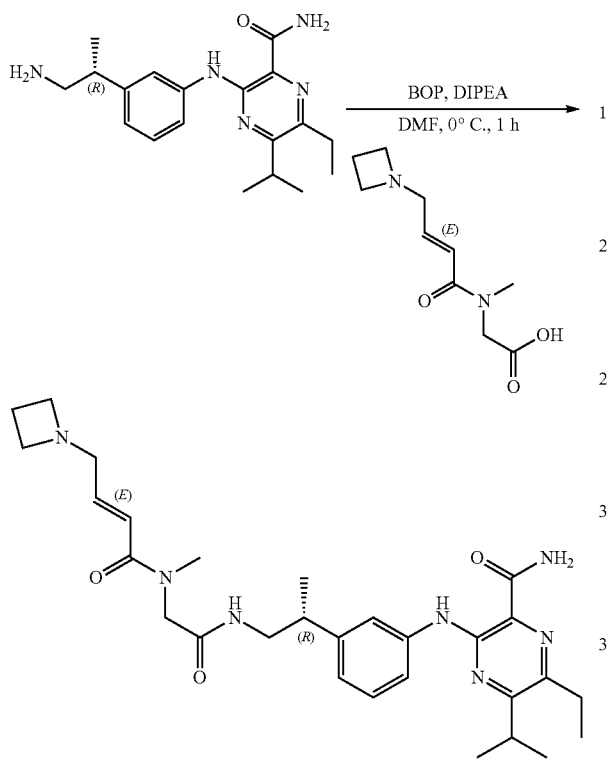

To a solution of (E)-N-(4-(azetidin-1-yl)but-2-enoyl)-N-methylglycine (64.75 mg, 198.46 mol, 1.5 eq, TFA) in DMF (0.5 mL) was added DIPEA (171.00 mg, 1.32 mmol, 230.45 μL, 10 eq), (R)-3-((3-(1-aminopropan-2-yl)phenyl)amino)-6-ethyl-5-isopropylpyrazine-2-carboxamide (50 mg, 132.31 μmol, 1 eq, HCl) and BOP (87.77 mg, 198.46 μmol, 1.5 eq). The mixture was stirred at 0° C. for 1 hour. The reaction mixture was filtered and concentrated under reduced pressure to give a residue. The residue was purified by prep-HPLC (column: Waters Xbridge BEH C18 100*30 mm*10 um; mobile phase: [water (NH$_4$HCO$_3$)-ACN]; B %: 30%-60%, 8 min) to afford (R,E)-3-((3-(1-(2-(4-(azetidin-1-yl)-N-methylbut-2-enamido)acetamido)propan-2-yl)phenyl)amino)-6-ethyl-5-isopropylpyrazine-2-carboxamide (14.02 mg, 25.67 μmol, 19.40% yield) as a yellow solid. $^1$H NMR (400 MHz, DMSO-d$_6$) δ=11.14-11.02 (m, 1H), 8.22-8.11 (m, 1H), 8.10-7.83 (m, 2H), 7.71-7.63 (m, 1H), 7.54-7.44 (m, 1H), 7.30-7.18 (m, 1H), 6.89-6.77 (m, 1H), 6.53-6.13 (m, 2H), 3.96-3.89 (m, 2H), 3.28-3.20 (m, 3H), 3.14-3.08 (m, 3H), 3.07-3.00 (m, 3H), 2.97-2.84 (m, 3H), 2.81-2.77 (m, 3H), 2.01 (s, 2H), 1.27-1.18 (m, 12H). LC-MS (ES+, m/z): 536.3 [(M+H)$^+$]; Rt=2.323 min. HRMS (EI): m/z [M+H]$_+$ found: 536.3359.

Example 60

Compound 510

6-ethyl-5-isobutyl-3-((3-(2-(2-(N-methylacrylamido) acetamido) ethyl) phenyl) amino) pyrazine-2-carboxamide Step 1: 6-ethyl-5-isobutyl-3-((3-(2-(2-(N-methylacrylamido) acetamido) ethyl) phenyl) amino) pyrazine-2-carboxamide

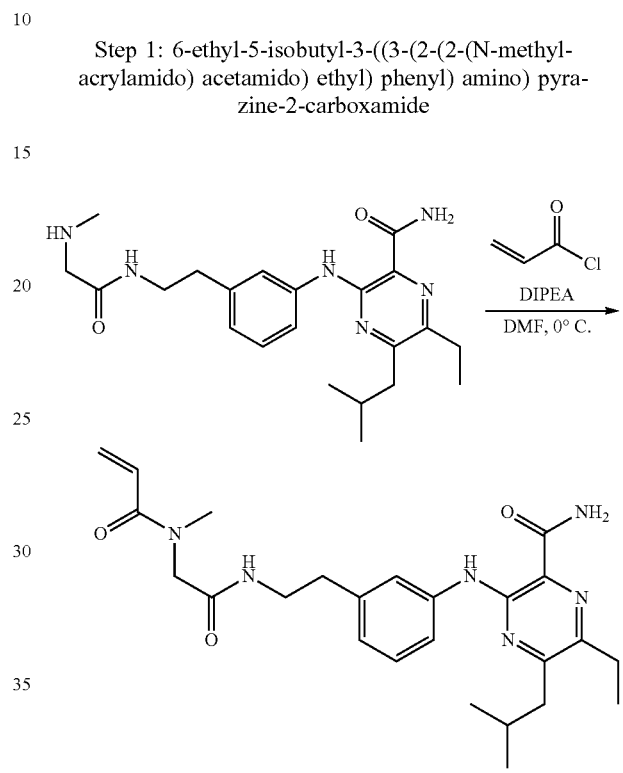

To a suspension of 6-ethyl-5-isobutyl-3-[3-[2-[[2-(methylamino) acetyl] amino] ethyl]anilino] pyrazine-2-carboxamide hydrochloride (97.60 mg, 0.2174 mmol, 1 eq) in DMF (1 mL), was added N,N-Diisopropylethylamine (0.3786 mL, 2.174 mmol, 10 eq). The mixture was cooled down to 0° C. Acryloyl chloride (0.02650 mL, 0.3261 mmol, 1.5 eq) in DMF (0.1 mL) was injected dropwise. The reaction was continued to stir from 0° C. to room temperature for 2 hours. The mixture was diluted with EtOAc (20 mL), washed with NaHCO$_3$ (aq) (1×), water (2×), brine (1×). Dried over MgSO4, filtered and concentrated. The crude was dissolved in MeOH/DCM (1:1), loaded on silica gel, purified by 12 g silica gel column (0-5% MeOH/EtOAc) to provide 6-ethyl-5-isobutyl-3-[3-[2-[[2-[methyl(prop-2-enoyl) amino] acetyl] amino] ethyl] anilino] pyrazine-2-carboxamide (76.00 mg, 0.1621 mmol, 74.56% yield) as yellow solid. $^1$H NMR (400 MHz, DMSO) δ 10.99 (d, J=2.5 Hz, 1H), 8.10 (s, 1H), 7.98 (dt, J=56.4, 5.6 Hz, 1H), 7.82 (d, J=2.6 Hz, 1H), 7.49 (d, J=4.4 Hz, 2H), 7.16 (t, J=7.9 Hz, 1H), 6.80-6.73 (m, 1H), 6.73-6.39 (m, 1H), 6.01 (ddd, J=26.5, 16.7, 2.5 Hz, 1H), 5.56 (ddd, J=47.1, 10.4, 2.5 Hz, 1H), 3.90 (d, J=19.0 Hz, 2H), 3.31-3.19 (m, 2H), 2.85 (d, J=83.1 Hz, 3H), 2.73-2.54 (m, 6H), 2.18 (hept, J=6.8 Hz, 1H), 1.17 (t, J=7.4 Hz, 3H), 0.91 (d, J=6.6 Hz, 6H). LCMS (ES+, m/z): 467.400 [(M+H)$^+$].

Example 61

Compound 511

6-ethyl-5-(ethyl(methyl)amino)-3-((3-(2-(2-(N-methylacrylamido) acetamido) ethyl) phenyl) amino) pyrazine-2-carboxamide

Step 1: tert-butyl (3-((3-carbamoyl-5-ethyl-6-(ethyl(methyl) amino) pyrazin-2-yl) amino) phenethyl) carbamate

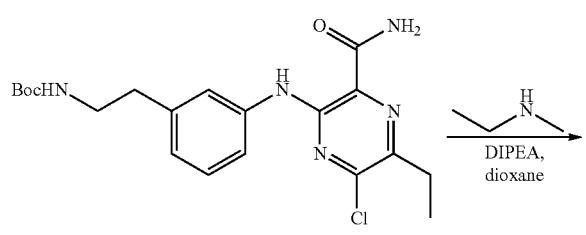

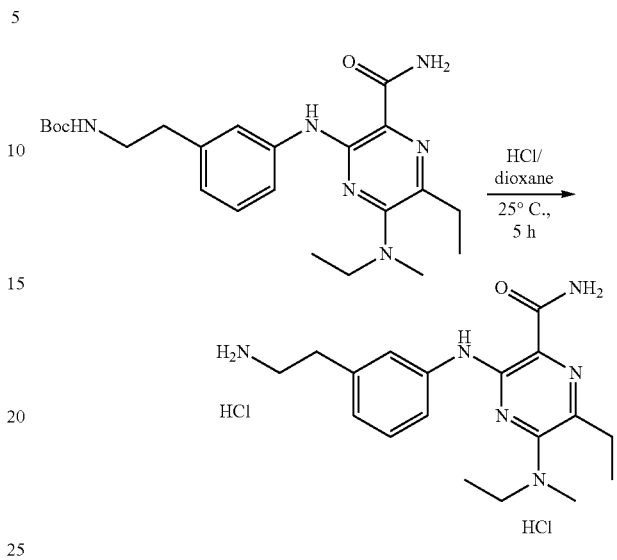

To the solution of tert-butyl N-[2-[3-[(3-carbamoyl-6-chloro-5-ethyl-pyrazin-2-yl) amino]phenyl] ethyl] carbamate (3.465 g, 8.252 mmol, 1 eq) in 1,4-Dioxane (10 mL), was added N-ethylmethylamine (7.173 mL, 82.52 mmol, 10 eq) followed by N,N-Diisopropylethylamine (1.437 mL, 8.252 mmol, 1 eq). The reaction mixture was heated under reflux for 70 hours. The reaction mixture was concentrated on rota-vapor. The residue was partitioned between EtOAc (100 mL) and NaHCO₃ (50 mL)/water (50 mL), and then the layers were separated. The aqueous was extracted with EtOAc (50 mL). The combined organics were washed with water (2×) and brined (1×). Dried over MgSO₄, filtered and concentrated. The crude was purified on 80 g silica gel column (0-40% EtOAc/hexanes) to provide tert-butyl N-[2-[3-[[3-carbamoyl-5-ethyl-6-[ethyl(methyl)amino] pyrazin-2-yl] amino]phenyl] ethyl] carbamate (2.650 g, 5.988 mmol, 72.57% yield) as yellow solid. ¹H NMR (400 MHz, DMSO) δ 11.10 (s, 1H), 7.74 (d, J=3.0 Hz, 1H), 7.58 (s, 1H), 7.46 (d, J=3.0 Hz, 1H), 7.44-7.38 (m, 1H), 7.21 (t, J=7.8 Hz, 1H), 6.89 (t, J=5.7 Hz, 1H), 6.83-6.73 (m, 1H), 3.47 (q, J=7.1 Hz, 2H), 3.14 (dt, J=8.2, 6.1 Hz, 2H), 3.05 (s, 3H), 2.74 (q, J=7.4 Hz, 2H), 2.67 (dd, J=8.5, 6.4 Hz, 2H), 1.37 (s, 9H), 1.22 (dt, J=12.2, 7.2 Hz, 6H). LCMS (ES+, m/z): 443.304 [(M+H)⁺].

Step 2: 3-((3-(2-aminoethyl) phenyl) amino)-6-ethyl-5-(ethyl(methyl) amino) pyrazine-2-carboxamide To a solution of tert-butyl N-[2-[3-[[3-carbamoyl-5-ethyl-6-[ethyl(methyl) amino] pyrazin-2-yl] amino] phenyl] ethyl] carbamate (2.650 g, 5.988 mmol, 1 eq) in 1,4-Dioxane (15 mL) was added 4N HCl in dioxane (15 mL, 10 eq) at ambient temperature. The reaction mixture was stirred for 5 hours. The reaction mixture was diluted with EtOAc (30 mL), filtered, rinsed with EtOAc (3×), dried in vacuo to provide 3-[3-(2-aminoethyl) anilino]-6-ethyl-5-[ethyl (methyl) amino] pyrazine-2-carboxamide dihydrochloride (2.440 g, 5.874 mmol, 98.10% yield) as a yellow solid. ¹H NMR (400 MHz, DMSO) δ 11.13 (s, 1H), 8.07 (s, 3H), 7.74 (s, 1H), 7.63-7.38 (m, 3H), 7.30-7.21 (m, 1H), 6.90-6.83 (m, 1H), 3.45 (q, J=7.1 Hz, 2H), 3.11-2.95 (m, 5H), 2.87 (dd, J=9.7, 6.2 Hz, 2H), 2.73 (q, J=7.3 Hz, 2H), 1.21 (dt, J=11.9, 7.2 Hz, 6H). LCMS (ES+, m/z): 343.230 [(M+H)⁺].

Step 3: tert-butyl (2-((3-((3-carbamoyl-5-ethyl-6-(ethyl(methyl) amino) pyrazin-2-yl) amino) phenethyl) amino)-2-oxoethyl) (methyl) carbamate

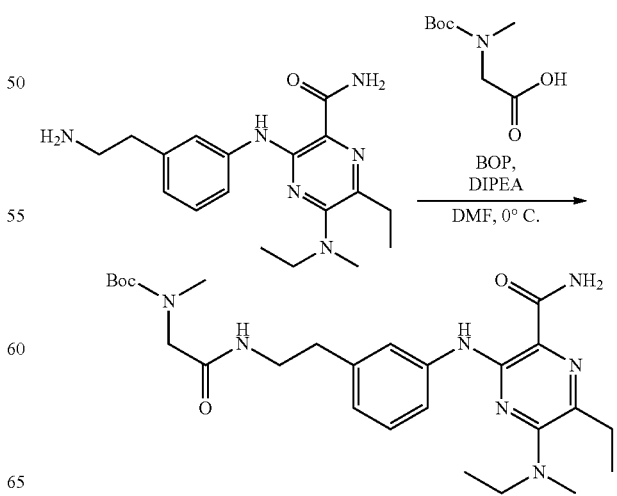

To a solution of 2-[tert-butoxycarbonyl(methyl) amino] acetic acid (273.3 mg, 1.445 mmol, 1.2 eq) and 3-[3-(2-aminoethyl) anilino]-6-ethyl-5-[ethyl(methyl)amino] pyrazine-2-carboxamide dihydrochloride (500.0 mg, 1.204 mmol, 10 eq) in DMF (1 mL) at 0° C., was injected dropwise N,N-Diisopropylethylamine (2.097 mL, 12.04 mmol, 10 eq) followed by a solution of benzotriazole-1-yloxytris(dimethylamino)-phosphonium hexafluorophosphate (638.9 mg, 1.445 mmol, 1.2 eq) in DMF (2 mL). The reaction was stirred for 1 hour from 0° C. to room temperature. The reaction mixture was diluted with EtOAc (60 mL), washed with NaHCO$_3$ (aq) (1×), water (2×), brines (1×). Dried over MgSO$_4$, filtered and concentrated. The crude material was purified on 40 g silica gel column (0-100% EtOAc/hexanes) to provide tert-butyl N-[2-[2-[3-[[3-carbamoyl-5-ethyl-6-[ethyl(methyl)amino]pyrazin-2-yl] amino] phenyl] ethylamino]-2-oxo-ethyl]-N-methylcarbamate (537.0 mg, 1.046 mmol, 86.85% yield) as yellow solid. $^1$H NMR (400 MHz, DMSO) δ 11.11 (s, 1H), 7.91 (s, 1H), 7.73 (d, J=3.0 Hz, 1H), 7.60 (s, 1H), 7.44 (dd, J=11.2, 5.6 Hz, 2H), 7.22 (t, J=7.8 Hz, 1H), 6.81 (d, J=7.5 Hz, 1H), 3.72 (d, J=14.5 Hz, 2H), 3.46 (q, J=7.0 Hz, 2H), 3.32 (s, 2H), 3.05 (s, 3H), 2.77 (s, 3H), 2.73 (dd, J=12.6, 5.2 Hz, 4H), 1.37 (d, J=27.3 Hz, 9H), 1.22 (dt, J=12.7, 7.2 Hz, 6H). LCMS (ES+, m/z): 514.400 [(M+H)$^+$].

Step 4: 6-ethyl-5-(ethyl(methyl)amino)-3-((3-(2-(2-(methylamino) acetamido) ethyl) phenyl) amino) pyrazine-2-carboxamide

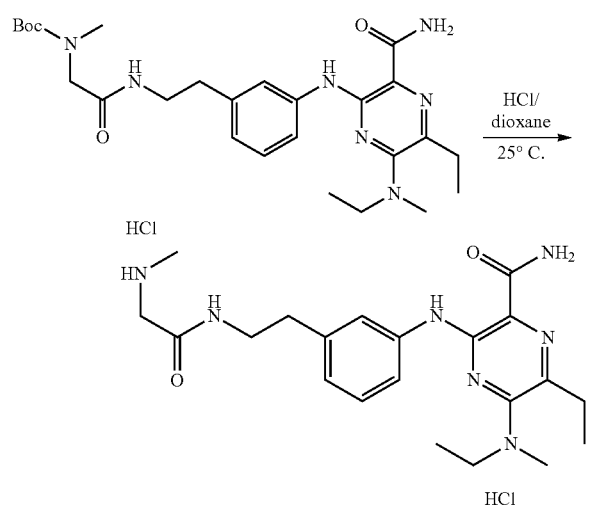

To a solution of tert-butyl N-[2-[2-[3-[[3-carbamoyl-5-ethyl-6-[ethyl(methyl)amino] pyrazin-2-yl] amino] phenyl] ethylamino]-2-oxo-ethyl]-N-methyl-carbamate (520.0 mg, 1.012 mmol, 1 eq) in dioxane (3 mL) at room temperature, was added 4N HCl in dioxane (3.0 mL, 12 eq) was dropwise. The reaction was stirred for 2 hours. The solvent was decanted. The residue was triturated with MTBE/EtOAc/MeOH (1:2:2), filtered, rinsed with EtOAc (5×), dried in vacuo to provide 6-ethyl-5-[ethyl(methyl)amino]-3-[3-[2-[[2-(methylamino) acetyl] amino] ethyl] anilino] pyrazine-2-carboxamide dihydrochloride (442.0 mg, 0.9086 mmol, 89.75% yield) as yellow solid. $^1$H NMR (400 MHz, DMSO) δ 11.04 (s, 1H), 8.85 (s, 2H), 8.55 (t, J=5.6 Hz, 1H), 7.67 (s, 1H), 7.51 (t, J=2.0 Hz, 1H), 7.40 (dd, J=8.0, 2.2 Hz, 2H), 7.16 (t, J=7.8 Hz, 1H), 6.77 (d, J=7.5 Hz, 1H), 3.57 (t, J=5.8 Hz, 2H), 3.39 (q, J=7.0 Hz, 2H), 3.31 (q, J=6.8 Hz, 2H), 3.10 (s, 1H), 2.98 (s, 3H), 2.66 (dd, J=8.6, 6.6 Hz, 4H), 1.14 (dt, J=11.4, 7.2 Hz, 6H). LCMS (ES+, m/z): 414.300 [(M+H)$^+$].

Step 5: 6-ethyl-5-(ethyl(methyl)amino)-3-((3-(2-(2-(N-methylacrylamido) acetamido) ethyl) phenyl) amino) pyrazine-2-carboxamide

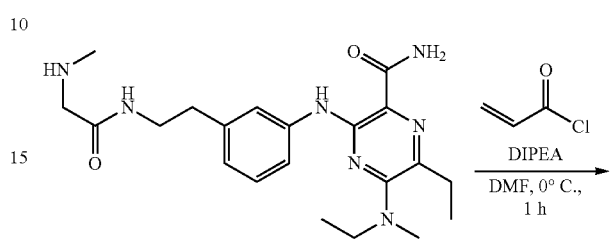

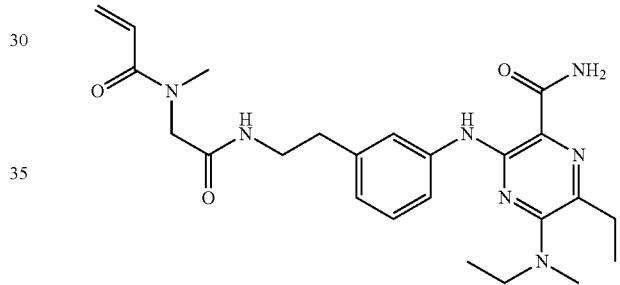

To a suspension of 6-ethyl-5-[ethyl(methyl)amino]-3-[3-[2-[[2-(methylamino) acetyl] amino]ethyl] anilino] pyrazine-2-carboxamide dihydrochloride (100.0 mg, 0.2056 mmol, 1 eq) in DMF at 0° C., was added N,N-diisopropylethylamine (0.3581 mL, 2.056 mmol, 10 eq). Acryloyl chloride (0.01840 mL, 0.2261 mmol, 1.1 eq) was then added. The reaction mixture was stirred at 0° C. for 45 minutes. More acryloyl chloride (10.0 µL) was added, continued for additional 30 minutes. The reaction mixture was diluted with EtOAc (20 mL), washed with NaHCO$_3$ (aq) (1×), water (2×), brine (1×). Dried over MgSO$_4$, filtered and concentrated. The crude was dissolved in MeOH/DCM (1:1), loaded on silica gel, purified by 12 g silica gel column (0-5% MeOH/EtOAc) to provide 6-ethyl-5-[ethyl(methyl) amino]-3-[3-[2-[[2-[methyl(prop-2-enoyl) amino] acetyl] amino] ethyl] anilino] pyrazine-2-carboxamide (69.00 mg, 0.1468 mmol, 71.43% yield) as off-white solid. $^1$H NMR (400 MHz, DMSO) δ 11.04 (d, J=2.0 Hz, 1H), 7.98 (dt, J=55.5, 5.6 Hz, 1H), 7.67 (d, J=3.0 Hz, 1H), 7.50 (dt, J=8.8, 2.0 Hz, 1H), 7.43-7.31 (m, 2H), 7.14 (t, J=7.8 Hz, 1H), 6.76-6.71 (m, 1H), 6.71-6.39 (m, 1H), 6.01 (ddd, J=26.2, 16.7, 2.5 Hz, 1H), 5.57 (ddd, J=46.5, 10.4, 2.5 Hz, 1H), 3.90 (d, J=18.7 Hz, 2H), 3.39 (q, J=7.0 Hz, 2H), 3.22 (d, J=7.8 Hz, 2H), 2.97 (s, 3H), 2.85 (d, J=83.8 Hz, 3H), 2.70-2.57 (m, 4H), 1.14 (dt, J=12.9, 7.2 Hz, 6H). LCMS (ES+, m/z): 468.300 [(M+H)$^+$].

Example 62

Compound 512

(R)-6-ethyl-5-isobutyl-3-((3-(1-(2-(N-methylacrylamido) acetamido) propan-2-yl) phenyl) amino) pyrazine-2-carboxamide Step 1: tert-butyl (R)-(2-(3-((3-carbamoyl-5-ethyl-6-isobutylpyrazin-2-yl) amino) phenyl) propyl) carbamate

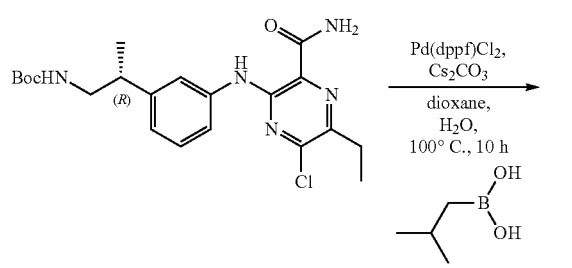

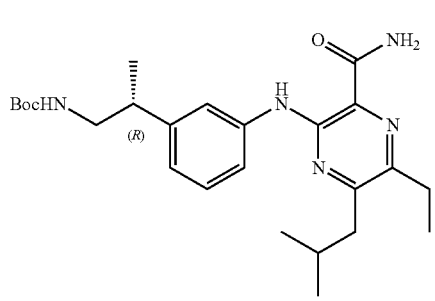

To a solution of tert-butyl (R)-(2-(3-((3-carbamoyl-6-chloro-5-ethylpyrazin-2-yl) amino) phenyl) propyl) carbamate (250 mg, 576.13 μmol, 1 eq), isobutylboronic acid (587.30 mg, 5.76 mmol, 10 eq) and $Cs_2CO_3$ (563.14 mg, 1.73 mmol, 3 eq) in dioxane (2.5 mL) and $H_2O$ (0.5 mL) was added Pd(dppf)$Cl_2$ (42.16 mg, 57.61 μmol, 0.1 eq). The mixture was stirred at 100° C. for 10 hours under $N_2$. The mixture was poured into water (5 mL) and extracted with EtOAc (5 mL*2). The organic layers were combined, washed with water (10 mL*2), saturated brine (10 mL*2), dried over $Na_2SO_4$, filtered, concentrated under reduced pressure to give a residue. The crude product was purified by chromatography on silica gel (Petroleum ether:Ethyl acetate=2:1) to afford tert-butyl (R)-(2-(3-((3-carbamoyl-5-ethyl-6-isobutylpyrazin-2-yl) amino) phenyl) propyl) carbamate (160 mg, 351.19 umol, 60.96% yield) as a yellow oil. $^1$H NMR (400 MHz, DMSO-$d_6$) δ=11.08-11.02 (m, 1H), 8.16 (br s, 1H), 7.92-7.82 (m, 1H), 7.70-7.62 (m, 1H), 7.49-7.41 (m, 1H), 7.27-7.18 (m, 1H), 6.83 (br d, J=7.0 Hz, 2H), 3.16-2.99 (m, 2H), 2.91-2.81 (m, 1H), 2.76 (q, J=7.5 Hz, 2H), 2.68 (d, J=7.1 Hz, 2H), 2.32-2.21 (m, 1H), 1.39-1.31 (m, 9H), 1.24 (t, J=7.4 Hz, 3H), 1.18 (br d, J=6.9 Hz, 3H), 1.03-0.94 (m, 6H). LCMS (ES+, m/z): 456.2 [(M+H)$^+$]; Rt=1.002 min Step 2: (R)-3-((3-(1-aminopropan-2-yl) phenyl) amino)-6-ethyl-5-isobutylpyrazine-2-carboxamide

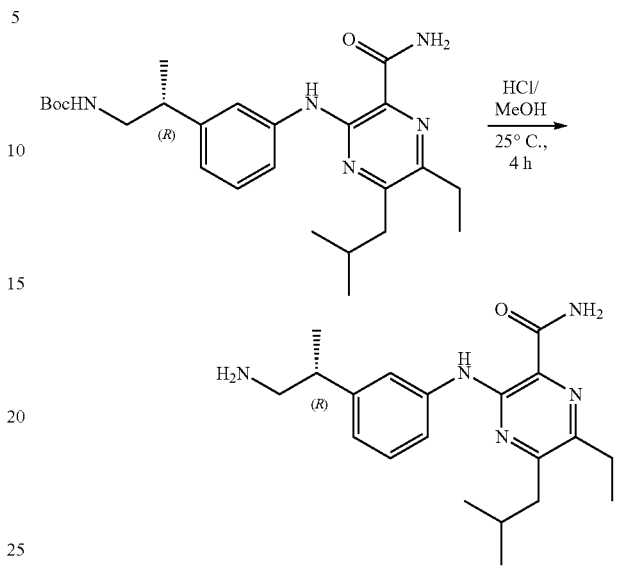

The mixture tert-butyl (R)-(2-(3-((3-carbamoyl-6-ethyl-6-isobutylpyrazin-2-yl) amino) phenyl) propyl) carbamate (180 mg, 395.09 μmol, 1 eq) and HCl/MeOH (4 M, 25 mL, 253.11 eq) was stirred at 25° C. for 4 hours. The reaction mixture was concentrated under reduced pressure to give (R)-3-((3-(1-aminopropan-2-yl) phenyl) amino)-6-ethyl-5-isobutylpyrazine-2-carboxamide (160 mg, crude) as yellow solid. LCMS (ES+, m/z): 356.3 [(M+H)$^+$]; Rt=0.635 min.

Step 3: tert-butyl (R)-(2-((2-(3-((3-carbamoyl-5-ethyl-6-isobutylpyrazin-2-yl) amino) phenyl) propyl) amino)-2-oxoethyl) (methyl) carbamate

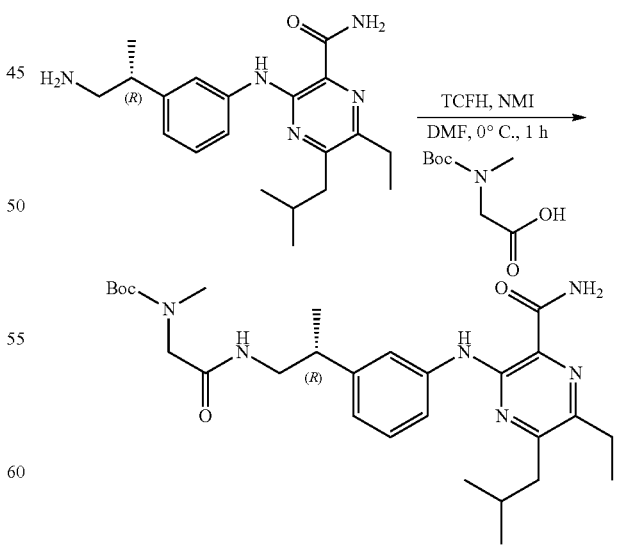

To a solution of (R)-3-((3-(1-aminopropan-2-yl) phenyl) amino)-6-ethyl-5-isobutylpyrazine-2-carboxamide (270 mg, 688.89 μmol, 1 eq, HCl), N-(tert-butoxycarbonyl)-N-methylglycine (260.69 mg, 1.38 mmol, 2 eq) in DMF (2.5 mL) was added NMI (565.60 mg, 6.89 mmol, 549.13 uL, 10 eq) at 0° C., then TCFH (289.93 mg, 1.03 mmol, 1.5 eq) was added. The mixture was stirred at 0° C. for 1 hour. The mixture was poured into water (5 mL) and extracted with EtOAc (5 mL*2). The organic layers were combined, washed with water (10 mL*2), saturated brine (10 mL*2), dried over $Na_2SO_4$, filtered, concentrated under reduced pressure. The crude product was purified by chromatography on silica gel (Petroleum ether:Ethyl acetate=1:1) to afford tert-butyl (R)-(2-((2-(3-((3-carbamoyl-5-ethyl-6-isobutylpyrazin-2-yl) amino) phenyl) propyl) amino)-2-oxoethyl) (methyl) carbamate (300 mg, 569.62 μmol, 82.69% yield) as yellow oil. $^1$H NMR (400 MHz, DMSO-$d_6$) δ=11.15-11.09 (m, 1H), 8.28-8.16 (m, 1H), 7.98-7.82 (m, 2H), 7.73 (br s, 1H), 7.57-7.47 (m, 1H), 7.34-7.25 (m, 1H), 6.94-6.87 (m, 1H), 3.83-3.69 (m, 2H), 3.30 (br s, 2H), 3.01-2.89 (m, 1H), 2.86-2.78 (m, 5H), 2.75-2.71 (m, 2H), 2.38-2.26 (m, 1H), 1.46-1.24 (m, 15H), 1.08-0.99 (m, 6H). LC-MS (ES+, m/z): 527.3 [(M+H)$^+$]; Rt=0.916 min.

Step 4: (R)-6-ethyl-5-isobutyl-3-((3-(1-(2-(methylamino) acetamido) propan-2-yl) phenyl) amino) pyrazine-2-carboxamide

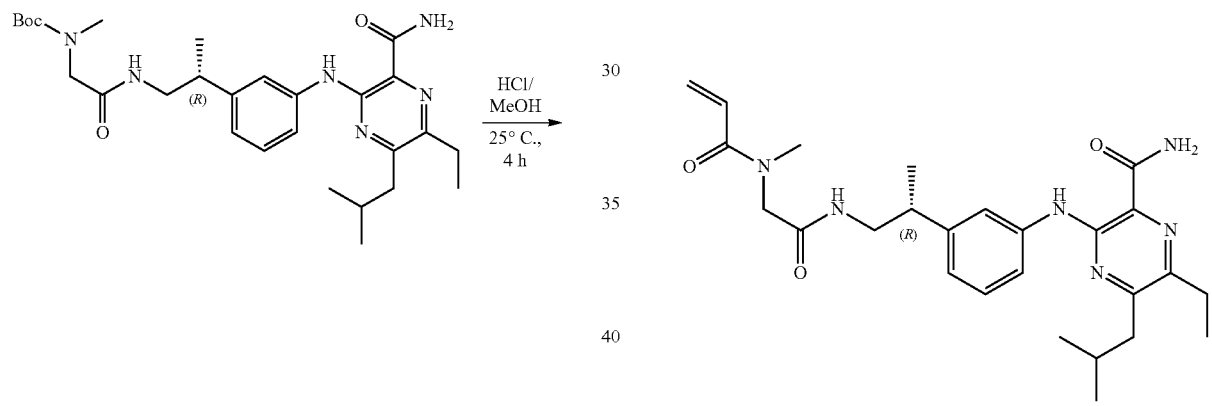

The mixture tert-butyl (R)-(2-((2-(3-((3-carbamoyl-5-ethyl-6-isobutylpyrazin-2-yl) amino) phenyl) propyl) amino)-2-oxoethyl) (methyl) carbamate (180 mg, 341.77 μmol, 1 eq) and HCl/MeOH (4 M, 25 mL, 292.59 eq) was stirred at 25° C. for 4 hours. The reaction mixture was concentrated under reduced pressure to give (R)-6-ethyl-5-isobutyl-3-((3-(1-(2-(methylamino) acetamido) propan-2-yl) phenyl) amino) pyrazine-2-carboxamide (185 mg, crude) as yellow solid. LCMS (ES+, m/z): 427.3 [(M+H)$^+$]; Rt=0.709 min.

Step 5: (R)-6-ethyl-5-isobutyl-3-((3-(1-(2-(N-methylacrylamido) acetamido) propan-2-yl) phenyl) amino) pyrazine-2-carboxamide

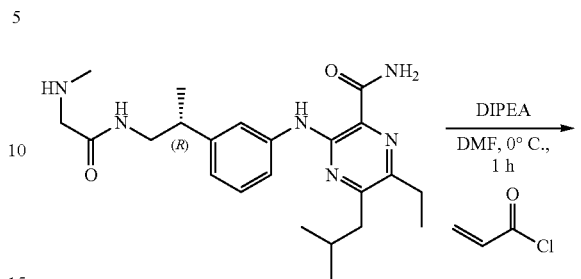

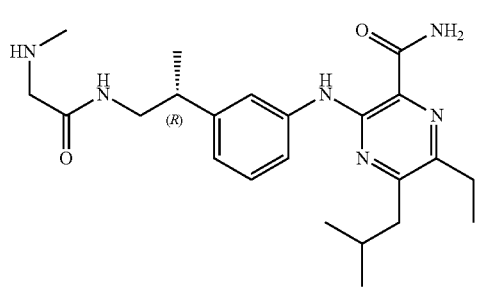

To a solution of (R)-6-ethyl-5-isobutyl-3-((3-(1-(2-(methylamino) acetamido) propan-2-yl) phenyl) amino) pyrazine-2-carboxamide (370 mg, 799.11 μmol, 1 eq, HCl) and DIPEA (619.68 mg, 4.79 mmol, 835.14 μL, 6 eq) in DMF (4 mL) at 0° C., acryloyl chloride (86.79 mg, 958.93 μmol, 78.19 L, 1.2 eq) was added. The mixture was stirred at 0° C. for 1 hour. The mixture was filtered to give a residue. The crude was purified by prep-HPLC (column: Phenomenex Luna C18 75*30 mm*3 um; mobile phase: [water (TFA)-ACN]; B %: 35%-65%, 8 min) to give (R)-6-ethyl-5-isobutyl-3-((3-(1-(2-(N-methylacrylamido) acetamido) propan-2-yl) phenyl) amino) pyrazine-2-carboxamide (72.26 mg, 149.53 μmol, 18.71% yield, 99.45% purity) as yellow solid. $^1$H NMR (400 MHz, DMSO-$d_6$) δ=11.11-11.03 (m, 1H), 8.23-8.12 (m, 1H), 8.10-7.81 (m, 2H), 7.71-7.59 (m, 1H), 7.55-7.43 (m, 1H), 7.29-7.19 (m, 1H), 6.89-6.40 (m, 2H), 6.16-5.97 (m, 1H), 5.74-5.51 (m, 1H), 4.01-3.90 (m, 2H), 3.29-3.20 (m, 2H), 3.04-2.96 (m, 1H), 2.94-2.85 (m, 1H), 2.82 (br s, 4H), 2.70-2.64 (m, 2H), 2.32-2.20 (m, 1H), 1.29-1.16 (m, 6H), 1.02-0.93 (m, 6H). LC-MS (ES+, m/z): 481.3 [(M+H)$^+$]; Rt=2.757 min. HRMS (EI): m/z [M+H]$^+$ found: 481.2929.

Example 63

Compound 513

(R)-6-ethyl-5-(ethyl (methyl) amino)-3-((3-(1-(2-(N-methylacrylamido) acetamido) propan-2-yl) phenyl) amino) pyrazine-2-carboxamide Step 1: tert-butyl (R)-(2-(3-((3-carbamoyl-5-ethyl-6-(ethyl (methyl) amino) pyrazin-2-yl) amino) phenyl) propyl) carbamate

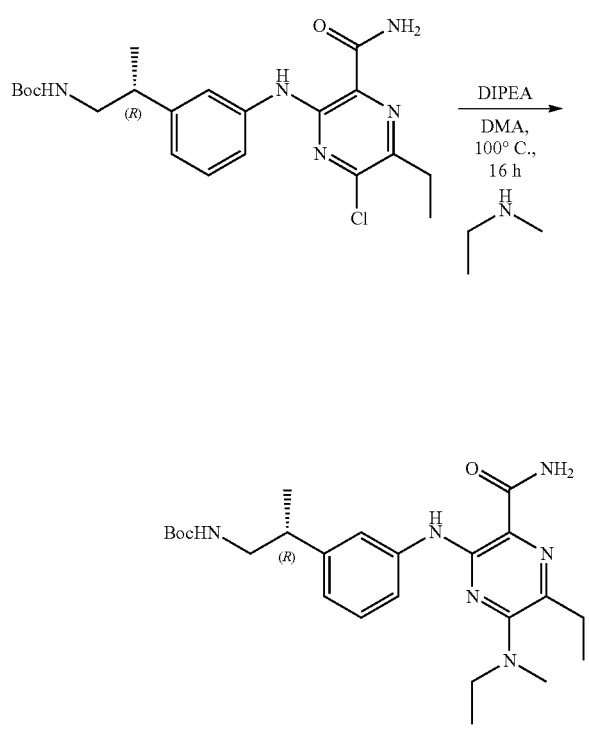

A mixture of tert-butyl (R)-(2-(3-((3-carbamoyl-6-chloro-5-ethylpyrazin-2-yl) amino) phenyl) propyl) carbamate (500 mg, 1.15 mmol, 1 eq) DIPEA (743.15 mg, 5.75 mmol, 1.00 mL, 5 eq) N-methylethanamine (1.36 g, 23.00 mmol, 1.98 mL, 20 eq) and DMA (5 mL) was stirred at 100° C. for 16 hours in sealed tube. The reaction was poured into water (50 mL) and extracted with EtOAc (30 mL*2). The organic layers were combined, washed with water (10 mL*2), saturated brine (10 mL), dried with Na₂SO₄, filtered, and concentrated to give crude product. The crude product was purified by chromatography on silica gel (petroleum ether/EtOAc=3/1) to afford tert-butyl (R)-(2-(3-((3-carbamoyl-5-ethyl-6-(ethyl (methyl) amino) pyrazin-2-yl) amino) phenyl) propyl) carbamate (450 mg, 969.82 μmol, 84.33% yield, 98.4% purity) as yellow solid. ¹H NMR (400 MHz, DMSO-d₆) δ=11.11 (s, 1H), 7.74 (br d, J=2.5 Hz, 1H), 7.57 (s, 1H), 7.46 (br d, J=2.4 Hz, 1H), 7.39 (br d, J=7.8 Hz, 1H), 7.21 (t, J=7.8 Hz, 1H), 6.87-6.76 (m, 2H), 3.46 (q, J=7.0 Hz, 2H), 3.14-2.94 (m, 5H), 2.87-2.79 (m, 1H), 2.73 (q, J=7.3 Hz, 2H), 1.39-1.29 (m, 9H), 1.27-1.14 (m, 10H). LCMS (ES+, m/z): 457.2 [(M+H)⁺]; Rt=0.944 min.

Step 2: (R)-3-((3-(1-aminopropan-2-yl) phenyl) amino)-6-ethyl-5-(ethyl (methyl) amino) pyrazine-2-carboxamide

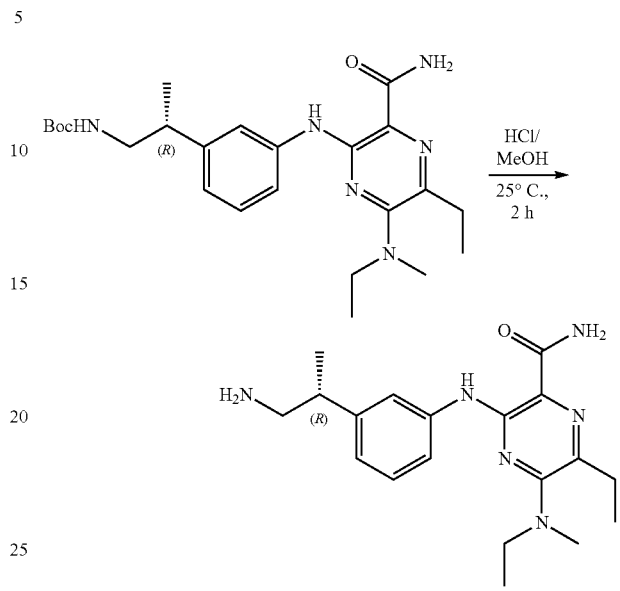

A mixture of tert-butyl (R)-(2-(3-((3-carbamoyl-5-ethyl-6-(ethyl (methyl) amino) pyrazin-2-yl) amino) phenyl) propyl) carbamate (450 mg, 985.59 μmol, 1 eq) HCl/MeOH (4 M, 30 mL, 121.75 eq) was stirred at 25° C. for 2 hours. The mixture was concentrated to give 3(R)-3-((3-(1-aminopropan-2-yl) phenyl) amino)-6-ethyl-5-(ethyl (methyl) amino) pyrazine-2-carboxamide (400 mg, crude, HCl) as yellow solid. LCMS (ES⁺, m/z): 357.1 [(M+H)⁺]; Rt=0.598 min.

Step 3: tert-butyl (R)-(2-((2-(3-((3-carbamoyl-5-ethyl-6-(ethyl (methyl) amino) pyrazin-2-yl) amino) phenyl) propyl) amino)-2-oxoethyl) (methyl) carbamate

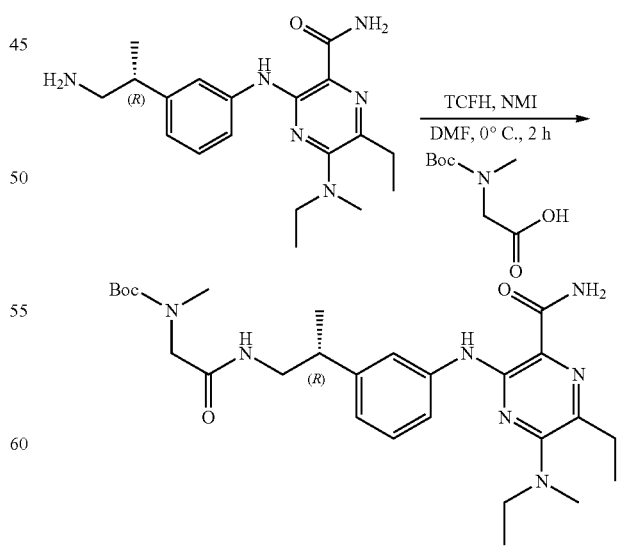

To a solution of N-(tert-butoxycarbonyl)-N-methylglycine (288.92 mg, 1.53 mmol, 1.5 eq), NMI (835.82 mg, 10.18 mmol, 811.48 µL, 10 eq) in DMF (10 mL) at 0° C., (R)-3-((3-(1-aminopropan-2-yl) phenyl) amino)-6-ethyl-5-(ethyl (methyl) amino) pyrazine-2-carboxamide (400 mg, 1.02 mmol, 1 eq, HCl) was added and then TCFH (428.45 mg, 1.53 mmol, 1.5 eq) was added. The mixture was stirred at 0° C. for 2 hours. The reaction was poured into water (30 mL) and extracted with EtOAc (25 mL*2). The organic layers were combined, washed with water (10 mL*2), saturated brine (10 mL), dried with Na$_2$SO$_4$, filtered, and concentrated to give crude product. The crude product was purified by chromatography on silica gel (petroleum ether/EtOAc=2/1) to afford tert-butyl (R)-(2-((2-(3-((3-carbamoyl-5-ethyl-6-(ethyl (methyl) amino) pyrazin-2-yl) amino) phenyl) propyl) amino)-2-oxoethyl) (methyl) carbamate (450 mg, 782.21 µmol, 76.84% yield, 91.72% purity) as yellow oil. LC-MS (ES+, m/z): 528.4 [(M+H)$^+$]; Rt=0.852 min.

Step 4: (R)-6-ethyl-5-(ethyl (methyl) amino)-3-((3-(1-(2-(methylamino) acetamido) propan-2-yl) phenyl) amino) pyrazine-2-carboxamide

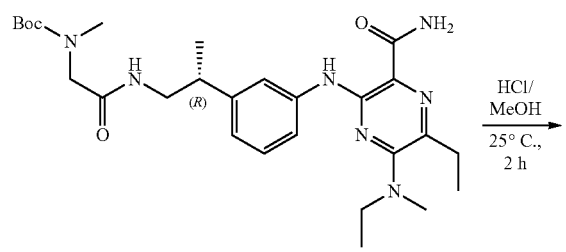

A mixture of tert-butyl (R)-(2-((2-(3-((3-carbamoyl-5-ethyl-6-(ethyl (methyl) amino) pyrazin-2-yl) amino) phenyl) propyl) amino)-2-oxoethyl) (methyl) carbamate (450 mg, 852.83 µmol, 1 eq) HCl/MeOH (4 M, 27.00 mL, 126.64 eq) was stirred at 25° C. for 2 hours. The mixture was concentrated to give (R)-6-ethyl-5-(ethyl (methyl) amino)-3-((3-(1-(2-(methylamino) acetamido) propan-2-yl) phenyl) amino) pyrazine-2-carboxamide (400 mg, crude, HCl) as yellow oil. LCMS (ES+, m/z): 428.4 [(M+H)$^+$]; Rt=0.582 min.

Step 5: (R)-6-ethyl-5-(ethyl (methyl) amino)-3-((3-(1-(2-(N-methylacrylamido) acetamido) propan-2-yl) phenyl) amino) pyrazine-2-carboxamide

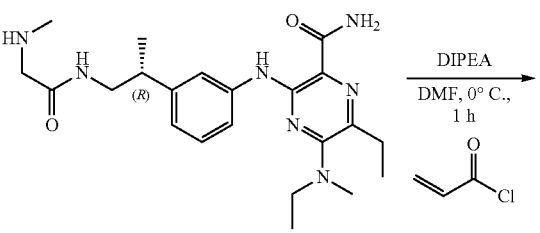

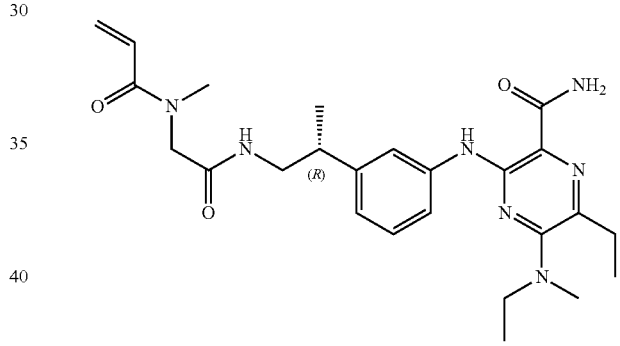

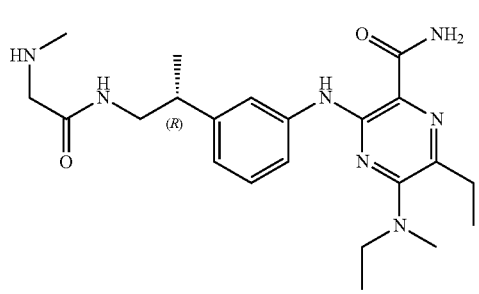

To a solution of (R)-6-ethyl-5-(ethyl (methyl) amino)-3-((3-(1-(2-(methylamino) acetamido) propan-2-yl) phenyl) amino) pyrazine-2-carboxamide (350 mg, 754.31 µmol, 1 eq, HCl), DIPEA (487.44 mg, 3.77 mmol, 656.93 µL, 5 eq) in DMF (3 mL) at 0° C., acryloyl chloride (75.10 mg, 829.74 mol, 67.66 µL, 1.1 eq) was added. The mixture was stirred at 0° C. for 1 hour. The mixture was filtered to give a residue. The crude was purified by prep-HPLC (column: Phenomenex Luna C18 75*30 mm*3 um; mobile phase: [water (TFA)-ACN]; B %: 30%-60%, 8 min) to give (R)-6-ethyl-5-(ethyl (methyl) amino)-3-((3-(1-(2-(N-methylacrylamido) acetamido) propan-2-yl) phenyl) amino) pyrazine-2-carboxamide (76.04 mg, 157.89 umol, 20.93% yield, 100% purity) as yellow solid. $^1$H NMR (400 MHz, DMSO-d$_6$) δ=11.13 (s, 1H), 8.09-7.85 (m, 1H), 7.74 (br s, 1H), 7.58 (br d, J=6.9 Hz, 1H), 7.51-7.37 (m, 2H), 7.22 (t, J=7.8 Hz, 1H), 6.88-6.80 (m, 1H), 6.79-6.39 (m, 1H), 6.16-5.97 (m, 1H), 5.73-5.48 (m, 1H), 3.95 (d, J=14.6 Hz, 2H), 3.31 (br s, 2H), 3.27-3.20 (m, 2H), 3.09-2.97 (m, 5H), 2.89 (td, J=7.6, 15.5 Hz, 1H), 2.81-2.70 (m, 3H), 1.25-1.16 (m, 9H); HRMS (EI): m/z [M+H]$^+$ found: 482.2856. LC-MS (ES+, m/z): 482.3 [(M+H)$^+$]; Rt=2.605 min.

Example 64

Compound 515

6-ethyl-5-(ethyl(methyl)amino)-3-((2-(2-(2-(N-methylacrylamido) acetamido) ethyl) pyridin-4-yl) amino) pyrazine-2-carboxamide Step 1: tert-butyl (2-(4-((3-carbamoyl-5-ethyl-6-(ethyl(methyl)amino) pyrazin-2-yl) amino) pyridin-2-yl) ethyl) carbamate

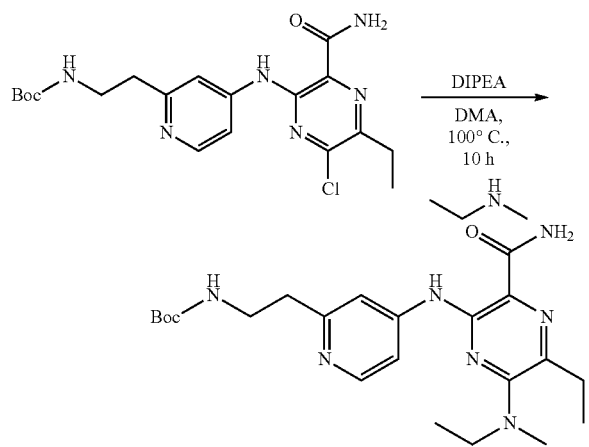

A mixture of tert-butyl (2-(4-((3-carbamoyl-6-chloro-5-ethylpyrazin-2-yl) amino) pyridin-2-yl) ethyl) carbamate (500 mg, 1.19 mmol, 1 eq), N-methylethanamine (1.40 g, 23.76 mmol, 2.04 mL, 20 eq), DIPEA (767.65 mg, 5.94 mmol, 1.03 mL, 5 eq) in DMA (3 mL) was heated to 100° C. for 10 hours. The mixture was poured into water (60 mL) and extracted with EtOAc (60 mL*2). The organic layers was washed with water (40 mL*2), saturated brine (40 mL*2), dried over Na₂SO₄, filtered, concentrated under reduced pressure the crude product was purified by chromatography on silica gel (Petroleum ether:Ethylacetate=1:1) to tert-butyl (2-(4-((3-carbamoyl-5-ethyl-6-(ethyl(methyl)amino)pyrazin-2-yl)amino)pyridin-2-yl)ethyl)carbamate (400 mg, 901.83 μmol, 75.91% yield) as yellow solid. $^1$H NMR (400 MHz, CDCl$_3$) δ=11.06 (br s, 1H), 8.25 (d, J=5.8 Hz, 1H), 7.62-7.49 (m, 2H), 7.39 (br d, J=3.3 Hz, 1H), 5.29-5.24 (m, 1H), 5.20-5.12 (m, 1H), 3.46 (q, J=7.0 Hz, 4H), 3.05 (s, 3H), 2.86 (br t, J=5.9 Hz, 2H), 2.70 (q, J=7.3 Hz, 2H), 1.35 (s, 9H), 1.22 (dt, J=4.3, 7.2 Hz, 6H). LC-MS (ES+, m/z): 444.4 [(M+H)$^+$]; Rt=0.390 min.

Step 2: 3-((2-(2-aminoethyl) pyridin-4-yl) amino)-6-ethyl-5-(ethyl(methyl)amino) pyrazine-2-carboxamide

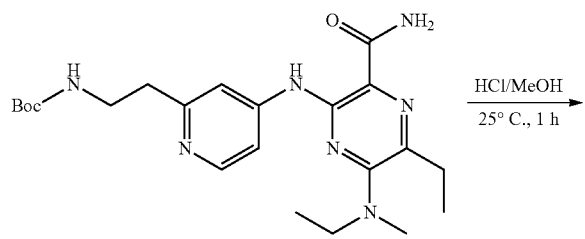

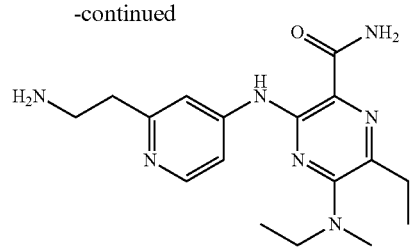

A mixture of tert-butyl (2-(4-((3-carbamoyl-5-ethyl-6-(ethyl(methyl)amino) pyrazin-2-yl) amino) pyridin-2-yl) ethyl) carbamate (400 mg, 901.83 μmol, 1 eq), HCl/MeOH (4 M, 26.67 mL, 118.28 eq) was stirred at 25° C. for 1 hour. The mixture was concentrated to dryness to give 3-((2-(2-aminoethyl) pyridin-4-yl) amino)-6-ethyl-5-(ethyl(methyl) amino) pyrazine-2 carboxamide (400 mg, crude, HCl) as yellow solid. LC-MS (ES+, m/z): 344.3 [(M+H)$^+$]; Rt=0.320 min.

Step 3: tert-butyl (2-((2-(4-((3-carbamoyl-5-ethyl-6-(ethyl(methyl)amino) pyrazin-2-yl) amino) pyridin-2-yl) ethyl) amino)-2-oxoethyl) (methyl)carbamate

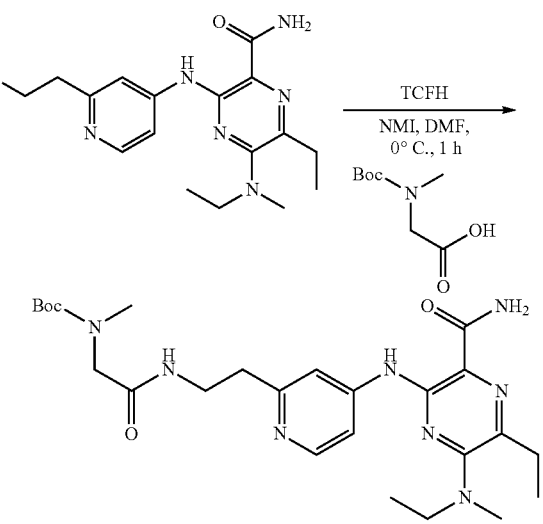

To a solution of N-(tert-butoxycarbonyl)-N-methylglycine (398.45 mg, 2.11 mmol, 2 eq), NMI (864.51 mg, 10.53 mmol, 839.33 μL, 10 eq) in DMF (5 mL) at 0° C., 3-((2-(2-aminoethyl)pyridin-4-yl)amino)-6-ethyl-5-(ethyl (methyl)amino)pyrazine-2-carboxamide (400 mg, 1.05 mmol, 1 eq, HCl) was added, then TCFH (443.15 mg, 1.58 mmol, 1.5 eq) was added at 0° C. The mixture was stirred at 0° C. for 1 hour. The mixture was poured into water (60 mL) and extracted with EtOAc (60 mL*2). The organic layers were combined, washed with water (40 mL*2), saturated brine (40 mL*2), dried over Na₂SO₄, filtered, concentrated under reduced pressure. The crude product was purified by chromatography on silica gel (Petroleum ether: Ethyl acetate=1:1) to give tert-butyl (2-((2-(4-((3-carbamoyl-5-ethyl-6-(ethyl(methyl)amino) pyrazin-2-yl) amino) pyridin-2-yl) ethyl) amino)-2-oxoethyl) (methyl)carbamate (400 mg, 777.27 μmol, 73.82% yield) as yellow oil. LC-MS (ES+, m/z): 515.3 [(M+H)$^+$]; Rt=0.399 min.

Step 4: 6-ethyl-5-(ethyl(methyl)amino)-3-((2-(2-(2-(methylamino) acetamido) ethyl) pyridin-4-yl) amino) pyrazine-2-carboxamide

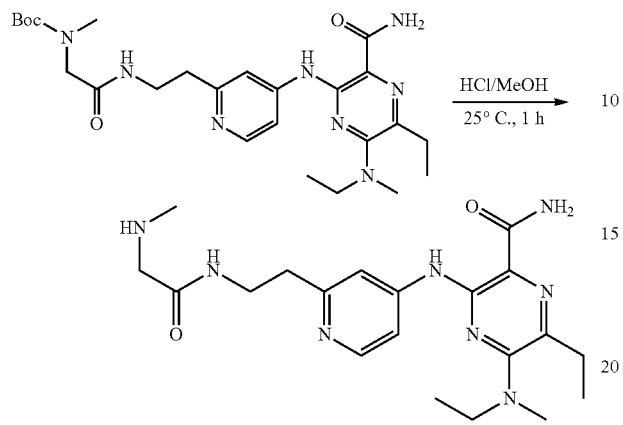

A mixture of tert-butyl (2-((2-(4-((3-carbamoyl-5-ethyl-6-(ethyl(methyl) amino) pyrazin-2-yl) amino) pyridin-2-yl) ethyl) amino)-2-oxoethyl) (methyl)carbamate (400 mg, 777.27 µmol, 1 eq), HCl/MeOH (4 M, 30.00 mL, 154.39 eq) was stirred at 25° C. for 1 hour. The mixture was concentrated to dryness to give 6-ethyl-5-(ethyl(methyl)amino)-3-((2-(2-(2-(methylamino) acetamido) ethyl) pyridin-4-yl) amino) pyrazine-2-carboxamide (400 mg, crude, HCl) as yellow oil. LC-MS (ES+, m/z): 415.3 [(M+H)+]; Rt=0.319 min.

Step 5: 6-ethyl-5-(ethyl(methyl)amino)-3-((2-(2-(2-(N-methylacrylamido) acetamido) ethyl) pyridin-4-yl) amino) pyrazine-2-carboxamide

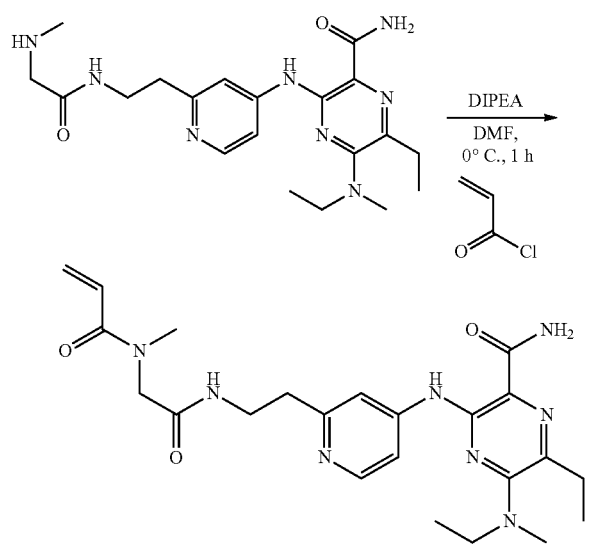

To a solution of 6-ethyl-5-(ethyl(methyl)amino)-3-((2-(2-(2-(methylamino) acetamido) ethyl) pyridin-4-yl)) pyrazine-2-carboxamide (200 mg, 410.32 µmol, 1 eq, 2HCl), DIPEA (549.20 mg, 4.25 mmol, 740.16 µL, 10.36 eq) in DCM (10 mL) at 0° C., acryloyl chloride (37.14 mg, 410.32 µmol, 33.34 µL, 1 eq) was added. The mixture was stirred at 0° C. for 1 hour. The mixture was filtered and then purified by prep-HPLC (column: Waters Xbridge Prep OBD C18 150*40 mm*10 um; mobile phase: [A: H$_2$O (10 mM NH$_4$HCO$_3$); B: ACN]; B %: 5.00%-35.00%, 8.00 min) to give 6-ethyl-5-(ethyl(methyl)amino)-3-((2-(2-(2-(N-methylacrylamido) acetamido)ethyl)pyridin-4-yl)amino)pyrazine-2-carboxamide (37.25 mg, 79.50 µmol, 19.38% yield, 100% purity) as white solid. $^1$H NMR (400 MHz, DMSO-d$_6$) δ=11.42 (s, 1H), 8.24 (d, J=5.5 Hz, 1H), 8.17-7.88 (m, 1H), 7.80 (br d, J=0.7 Hz, 1H), 7.63-7.48 (m, 2H), 7.47-7.34 (m, 1H), 6.81-6.42 (m, 1H), 6.14-5.95 (m, 1H), 5.71-5.48 (m, 1H), 3.92 (d, J=19.1 Hz, 2H), 3.51-3.35 (m, 4H), 3.05 (s, 3H), 2.99 (s, 1.5H), 2.80-2.69 (m, 5.5H), 1.23-1.16 (m, 6H). LC-MS (ES+, m/z): 469.2 [(M+H)+]; Rt=2.006 min. HRMS (EI): m/z (M+H)+ found: 469.2668.

Example 65

Compound 516

(E)-3-((3-(2-(2-(4-(azetidin-1-yl)-N-methylbut-2-enamido) acetamido) ethyl)-5-fluorophenyl) amino)-5-cyclopropyl-6-ethylpyrazine-2-carboxamide Step 1: tert-butyl (3-((3-carbamoyl-6-chloro-5-ethylpyrazin-2-yl) amino)-5-fluorophenethyl) carbamate

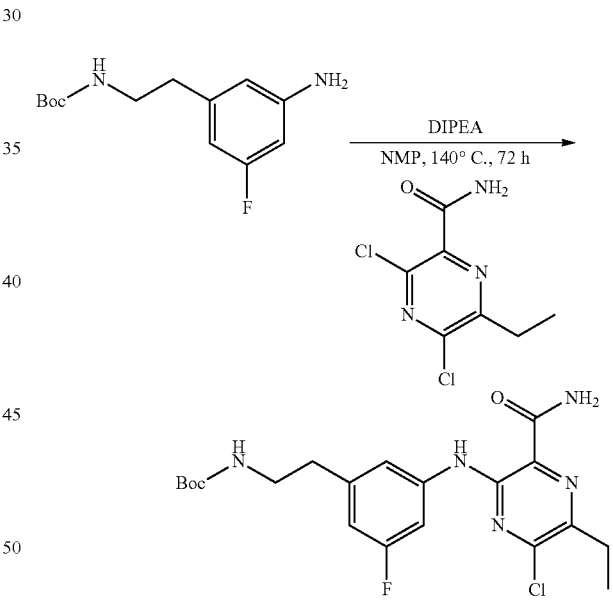

To a solution of tert-butyl (3-amino-5-fluorophenethyl) carbamate (2.00 g, 7.86 mmol, 1 eq) and 3,5-dichloro-6-ethylpyrazine-2-carboxamide (1.73 g, 7.86 mmol, 1 eq) in NMP (20 mL) was added DIPEA (40.66 g, 314.59 mmol, 54.80 mL, 40 eq). The mixture was stirred at 140° C. for 72 hours under N$_2$ atmosphere. The reaction mixture was poured into H$_2$O (100 mL) and extracted with EtOAc (150 mL*3). The organic phase was separated, washed with water (200 mL*2), saturated brine (100 mL*3), dried over anhydrous Na$_2$SO$_4$, filtered, and concentrated under reduced pressure to give a residue. The residue was purified by column chromatography (SiO$_2$, Petroleum ether/Ethyl acetate=20/1 to 1/5) to afford tert-butyl (3-((3-carbamoyl-6-chloro-5-ethylpyrazin-2-yl) amino)-5-fluorophenethyl)

carbamate (1.40 g, 3.20 mmol, 40.65% yield) as a yellow solid. $^1$H NMR (400 MHz, DMSO-$d_6$) δ=11.42-11.30 (m, 1H), 8.37-8.26 (m, 1H), 8.18-8.04 (m, 1H), 7.71-7.60 (m, 1H), 7.04-6.95 (m, 1H), 6.93-6.85 (m, 1H), 6.75-6.69 (m, 1H), 3.18-3.14 (m, 2H), 2.86-2.80 (m, 2H), 2.72-2.67 (m, 2H), 1.36-1.33 (m, 9H), 1.26 (t, J=7.6 Hz, 3H). LC-MS (ES+, m/z): 382.2 [(M+H-56)$^+$]; Rt=0.897 min.

Step 2: tert-butyl (3-((3-carbamoyl-6-cyclopropyl-5-ethylpyrazin-2-yl) amino)-5-fluorophenethyl) carbamate

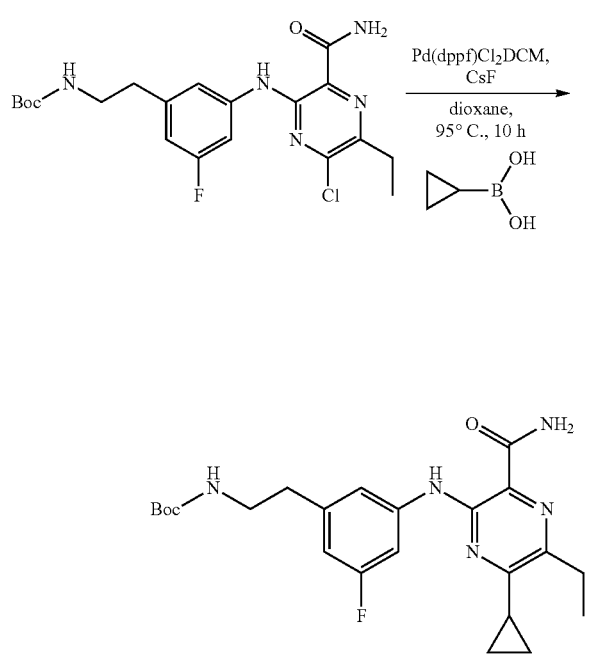

To a solution of tert-butyl (3-((3-carbamoyl-6-chloro-5-ethylpyrazin-2-yl) amino)-5-fluorophenethyl) carbamate (500.00 mg, 1.14 mmol, 1 eq) and cyclopropylboronic acid (490.40 mg, 5.71 mmol, 5 eq) in dioxane (10 mL) was added CsF (607.07 mg, 4.00 mmol, 147.53 μL, 3.5 eq) and Pd(dppf)Cl$_2$·CH$_2$Cl$_2$ (93.25 mg, 114.18 μmol, 0.1 eq). The mixture was stirred at 95° C. for 10 hours under N$_2$ atmosphere. The reaction was poured into water (50 mL) and extracted with EtOAc (80 mL*3). The organic layers were combined, washed with water (80 mL*2), saturated brine (60 mL*2), dried with Na$_2$SO$_4$, filtered, and concentrated to give crude product. The residue was dissolved in DCM (30 mL). scavenger (Pd) was added and then stirred at 25° C. for 1 hr, and then filtered. The residue was purified by column chromatography (SiO$_2$, Petroleum ether/Ethyl acetate=20/1 to 1/5) to afford tert-butyl (3-((3-carbamoyl-6-cyclopropyl-5-ethylpyrazin-2-yl) amino)-5-fluorophenethyl) carbamate (310 mg, 698.96 mol, 61.21% yield) as a yellow solid. $^1$H NMR (400 MHz, DMSO-$d_6$) δ=11.28-11.18 (m, 1H), 8.27-8.09 (m, 1H), 7.97-7.83 (m, 1H), 7.65-7.52 (m, 1H), 7.07-6.95 (m, 1H), 6.94-6.82 (m, 1H), 6.69-6.58 (m, 1H), 3.20-3.10 (m, 2H), 2.97-2.86 (m, 2H), 2.70-2.65 (m, 2H), 2.34-2.28 (m, 1H), 1.37-1.31 (m, 9H), 1.27 (t, J=7.5 Hz, 3H), 1.16-1.10 (m, 2H), 1.09-1.02 (m, 2H). LC-MS (ES+, m/z): 444.3 [(M+H)$^+$]; Rt=0.623 min.

Step 3: 3-((3-(2-aminoethyl)-5-fluorophenyl) amino)-5-cyclopropyl-6-ethylpyrazine-2-carboxamide

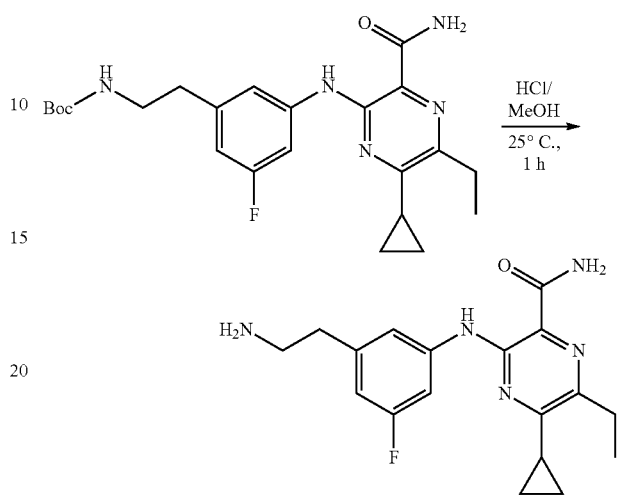

A mixture of tert-butyl (3-((3-carbamoyl-6-cyclopropyl-5-ethylpyrazin-2-yl) amino)-5-fluorophenethyl) carbamate (300.00 mg, 676.42 μmol, 1 eq) in HCl/MeOH (40 mL) was degassed and purged with N$_2$ for 3 times, and then the mixture was stirred at 25° C. for 1 hour under N$_2$ atmosphere. The reaction mixture was concentrated under reduced pressure to afford 3-((3-(2-aminoethyl)-5-fluorophenyl) amino)-5-cyclopropyl-6-ethylpyrazine-2-carboxamide (249 mg, crude, HCl) as a yellow solid. LC-MS (ES+, m/z): 344.2 [(M+H-56)$^+$]; Rt=0.407 min.

Step 4: tert-butyl (2-((3-((3-carbamoyl-6-cyclopropyl-5-ethylpyrazin-2-yl) amino)-5-fluorophenethyl) amino)-2-oxoethyl) (methyl)carbamate

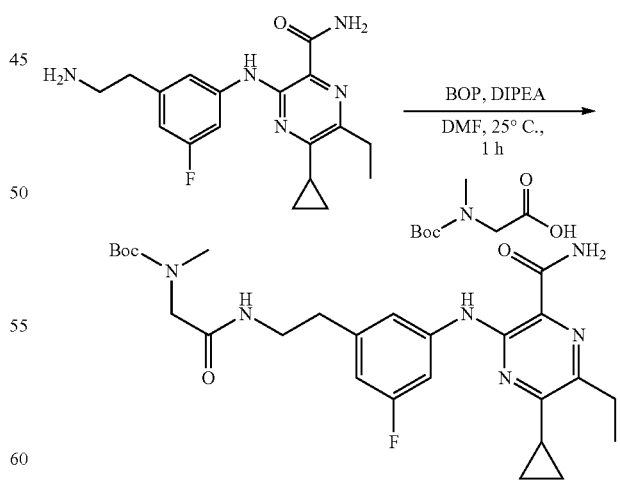

To a solution of N-(tert-butoxycarbonyl)-N-methylglycine (248.05 mg, 1.31 mmol, 2 eq) in DMF (3 mL) was added DIPEA (847.20 mg, 6.56 mmol, 1.14 mL, 10 eq), 3-((3-(2-aminoethyl)-5-fluorophenyl)amino)-5-cyclopropyl-6-ethylpyrazine-2-carboxamide (249 mg, 655.51 μmol, 1 eq, HCl) and BOP (434.88 mg, 983.26 μmol, 1.5 eq). The mixture was stirred at 25° C. for 1 hour. LCMS showed the reaction was completed. The reaction was poured into H₂O (20 mL) and extracted with EtOAc (30 mL*3). The organic layers were combined, washed with water (35 mL*2), saturated brine (30 mL*2), dried with Na₂SO₄, filtered, and concentrated to give crude product. The residue was purified by column chromatography (SiO₂, Petroleum ether/Ethyl acetate=20/1 to 1/1) to afford tert-butyl (2-((3-((3-carbamoyl-6-cyclopropyl-5-ethylpyrazin-2-yl) amino)-5-fluorophenethyl) amino)-2-oxoethyl) (methyl)carbamate (320 mg, 621.85 μmol, 94.87% yield) as a yellow solid. ¹H NMR (400 MHz, DMSO-d₆) δ=11.26-11.20 (m, 1H), 8.21-8.12 (m, 1H), 7.95-7.85 (m, 2H), 7.64-7.53 (m, 1H), 7.07-6.98 (m, 1H), 6.71-6.59 (m, 1H), 3.74-3.65 (m, 2H), 2.96-2.85 (m, 3H), 2.78-2.66 (m, 6H), 2.34-2.29 (m, 1H), 1.38 (s, 3H), 1.33-1.23 (m, 9H), 1.15-1.10 (m, 2H), 1.09-1.03 (m, 2H). LC-MS (ES+, m/z): 515.3 [(M+H)⁺]; Rt=0.571 min.

Step 5: 5-cyclopropyl-6-ethyl-3-((3-fluoro-5-(2-(2-(methylamino) acetamido) ethyl) phenyl) amino) pyrazine-2-carboxamide Step 6: (E)-3-((3-(2-(2-(4-(azetidin-1-yl)-N-methyl-but-2-enamido) acetamido) ethyl)-5-fluorophenyl) amino)-5-cyclopropyl-6-ethylpyrazine-2-carboxamide

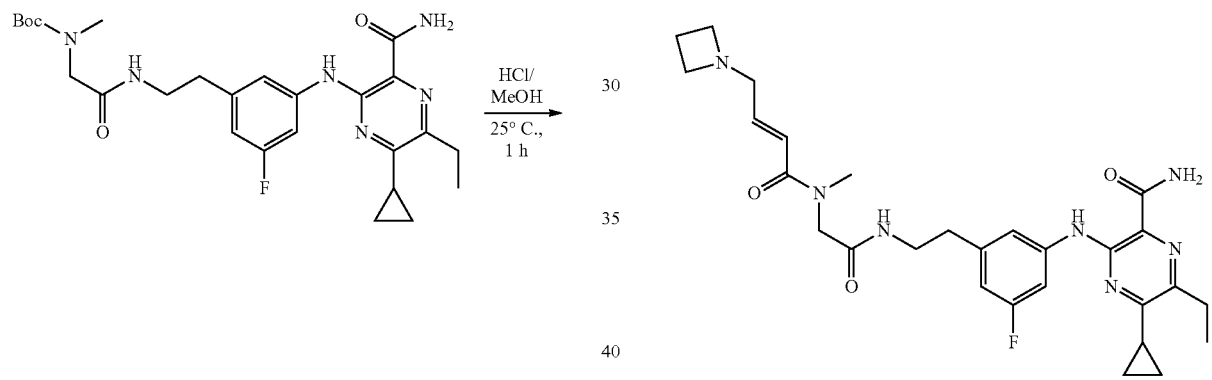

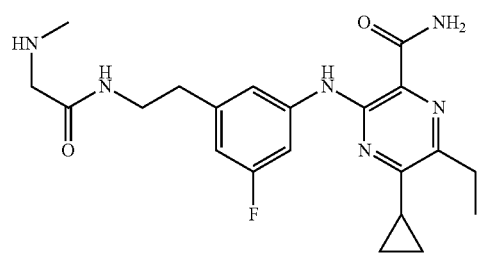

A mixture of tert-butyl (2-((3-((3-carbamoyl-6-cyclopropyl-5-ethylpyrazin-2-yl) amino)-5-fluorophenethyl) amino)-2-oxoethyl) (methyl)carbamate (320 mg, 621.85 μmol, 1 eq) in HCl/MeOH (40 mL, 4 M) was stirred at 25° C. for 1 hour. The reaction mixture was concentrated under reduced pressure to afford 5-cyclopropyl-6-ethyl-3-((3-fluoro-5-(2-(2-(methylamino) acetamido) ethyl) phenyl) amino) pyrazine-2-carboxamide (300 mg, crude, HCl) as a yellow solid. LC-MS (ES+, m/z): 415.3 [(M+H)+]; Rt=0.408 min.

To a solution of (E)-4-(azetidin-1-yl)but-2-enoic acid (254.66 mg, 997.92 μmol, 3 eq, TFA) in DMF (1.5 mL) was added DIPEA (429.92 mg, 3.33 mmol, 579.40 μL, 10 eq), 5-cyclopropyl-6-ethyl-3-((3-fluoro-5-(2-(2-(methylamino) acetamido) ethyl) phenyl) amino) pyrazine-2-carboxamide (150 mg, 332.64 μmol, 1 eq, HCl) and BOP (220.68 mg, 498.96 μmol, 1.5 eq). The mixture was stirred at 25° C. for 1 hour. The reaction mixture was filtered to give a residue. The residue was purified by prep-HPLC (column: 2_Phenomenex Gemini C18 75*40 μmm*3 um; mobile phase: [H₂O (0.05% NH₃H₂O+10 mM NH4HCO₃)-ACN]; gradient: 30%-55% B over 8.0 min) to afford (E)-3-((3-(2-(2-(4-(azetidin-1-yl)-N-methylbut-2-enamido)acetamido)ethyl)-5-fluorophenyl)amino)-5-cyclopropyl-6-ethylpyrazine-2-carboxamide (37.32 mg, 69.42 μmol, 20.87% yield) as a white solid. ¹H NMR (400 MHz, DMSO-d₆) δ=11.25-11.18 (m, 1H), 8.17-8.12 (m, 1H), 8.11-7.88 (m, 1H), 7.87-7.84 (m, 1H), 7.65-7.51 (m, 1H), 7.03-6.95 (m, 1H), 6.68-6.57 (m, 1H), 6.48-6.13 (m, 2H), 3.95-3.83 (m, 2H), 3.36-3.30 (m, 2H), 3.11-3.05 (m, 3H), 3.03-2.94 (m, 5H), 2.92-2.84 (m, 2H), 2.80-2.74 (m, 1H), 2.72-2.63 (m, 2H), 2.32-2.24 (m, 1H), 1.98-1.83 (m, 2H), 1.24 (t, J=7.5 Hz, 3H), 1.13-1.00 (m, 4H). LC-MS (ES+, m/z): 538.3 [(M+H)⁺]; Rt=2.892 min. HRMS (EI): m/z [M+H]⁺ found: 548.2975.

Example 66

Compound 516A (E)-3-((3-(2-(2-(4-(azetidin-1-yl)-N-methylbut-2-enamido) acetamido) ethyl) phenyl) amino)-6-ethyl-5-(ethyl(methyl) amino) pyrazine-2-carboxamide Step 1: (E)-3-((3-(2-(2-(4-(azetidin-1-yl)-N-methyl-but-2-enamido) acetamido) ethyl) phenyl) amino)-6-ethyl-5-(ethyl(methyl) amino) pyrazine-2-carboxamide

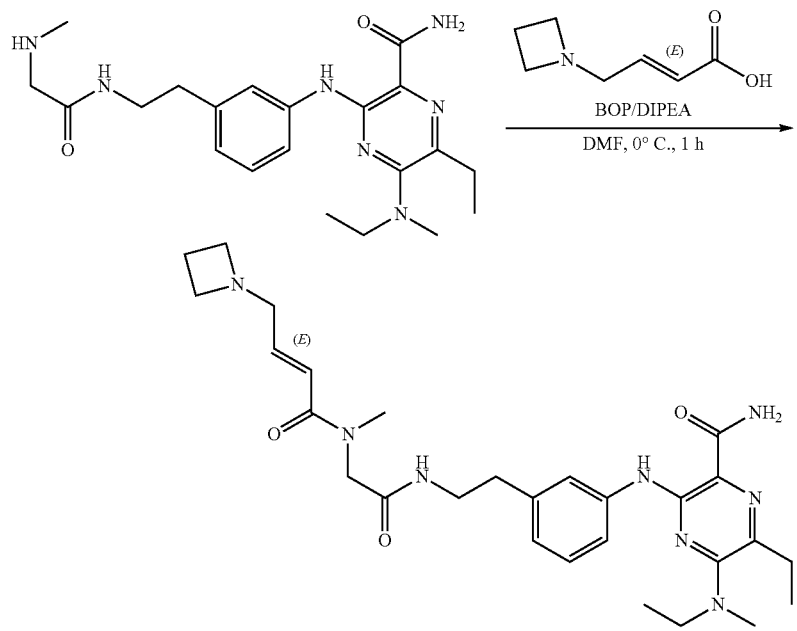

Benzotriazol-1-yloxytris(dimethylamino)-phosphonium hexafluorophosphate (181.84 mg, 0.4112 mmol, 2 eq) was added into a solution of (E)-4-(azetidin-1-yl)but-2-enoic acid; 2,2,2-trifluoroacetic acid (104.92 mg, 0.4112 mmol, 2 eq), 6-ethyl-5-[ethyl(methyl)amino]-3-[3-[2-[[2-(methylamino)acetyl]amino]ethyl]anilino]pyrazine-2-carboxamide dihydrochloride (100.0 mg, 0.2056 mmol, 1 eq) and N,N-Diisopropylethylamine (318.82 mg, 2.4669 mmol, 0.4297 mL 12 eq) in DMF (0.60 mL) at 0° C. The reaction was stirred for 1 hour. The reaction was diluted with EtOAc (20 mL), washed with saturated NaHCO₃ (aq) (1×), water (2×), brine. Dried over MgSO4, filtered and concentrated. Purified by preparative HPLC (Gilson) on Gemini 10 uM NX-C18 110A 150×30 mm, eluted with (B/A)=5-95% ACN with 0.1% TFA/water with 0.1% TFA. The pure fractions were combined, adjusted pH=10 by NaHCO₃ (aq), extracted with EtOAc (3×), dried over MgSO₄, filtered and concentrated. Dissolved in 1:1 ACN/water (1 mL), lyophilized to provide (E)-3-((3-(2-(2-(4-(azetidin-1-yl)-N-methylbut-2-enamido) ethyl) phenyl) amino)-6-ethyl-5-(ethyl(methyl) amino) pyrazine-2-carboxamide (30.0 mg, 0.05230 mmol, 25.43% yield) as white solid. ¹H NMR (400 MHz, DMSO-d₆) δ 11.12 (d, J=6.9 Hz, 1H), 8.13 (t, J=5.5 Hz, 0.5H), 7.94 (t, J=5.7 Hz, 0.5H), 7.73 (d, J=3.1 Hz, 1H), 7.57 (s, 1H), 7.51-7.39 (m, 2H), 7.21 (td, J=7.9, 4.0 Hz, 1H), 6.80 (d, J=7.6 Hz, 1H), 6.50-6.19 (m, 2H), 3.94 (d, J=19.1 Hz, 2H), 3.45 (q, J=7.0 Hz, 2H), 3.27 (t, J=7.1 Hz, 2H), 3.17-3.09 (m, 3H), 3.09-2.97 (m, 7H), 2.84-2.64 (m, 6H), 1.95 (dp, J=21.0, 7.0 Hz, 2H), 1.21 (dt, J=12.5, 7.2 Hz, 6H). LC-MS (ES+, m/z): 537.400 [(M+H)⁺].

Example 67

Compound 517

(R,E)-3-((3-(1-(2-(4-(azetidin-1-yl)-N-methylbut-2-enamido) acetamido) propan-2-yl) phenyl) amino)-6-ethyl-5-isobutylpyrazine-2-carboxamide Step 1: (R,E)-3-((3-(1-(2-(4-(azetidin-1-yl)-N-methylbut-2-enamido) acetamido) propan-2-yl) phenyl) amino)-6-ethyl-5-isobutylpyrazine-2-carboxamide

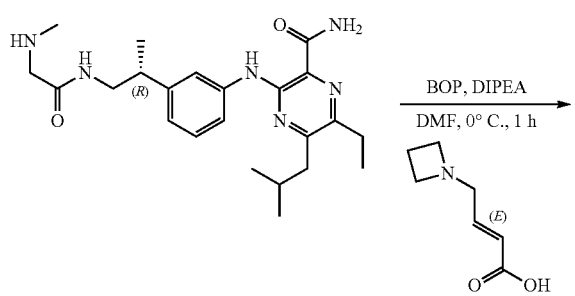

333
-continued

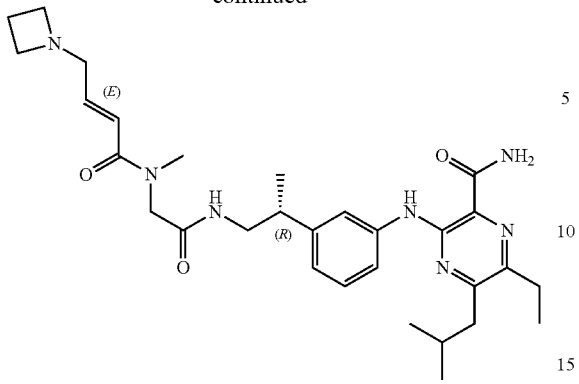

334
-continued

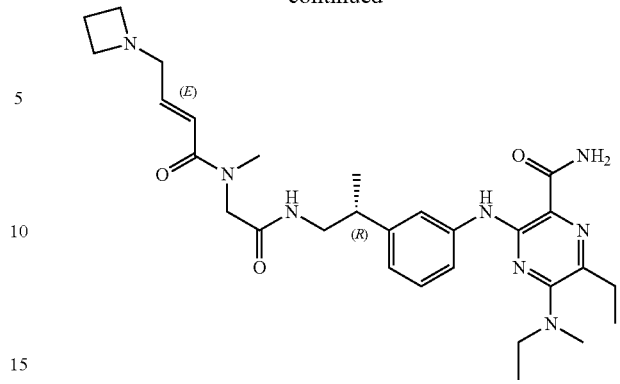

To a solution of (R)-6-ethyl-5-isobutyl-3-((3-(1-(2-(methylamino) acetamido) propan-2-yl) phenyl) amino) pyrazine-2-carboxamide (230 mg, 496.74 μmol, 1 eq, HCl), (E)-4-(azetidin-1-yl) but-2-enoic acid (316.91 mg, 1.24 mmol, 2.5 eq, TFA), DIPEA (642.01 mg, 4.97 mmol, 865.24 μL, 10 eq) in DMF (2.5 mL) at 0° C., BOP (329.55 mg, 745.12 μmol, 1.5 eq) was added. The mixture was stirred at 0° C. for 1 hour. The mixture was filtered to give a residue. The crude was purified by prep-HPLC (column: Phenomenex Luna C18 75*30 mm*3 um; mobile phase: [water (TFA)-ACN]; B %: 20%-50%, 8 min) to give (R,E)-3-((3-(1-(2-(4-(azetidin-1-yl)-N-methylbut-2-enamido) acetamido) propan-2-yl) phenyl) amino)-6-ethyl-5-isobutylpyrazine-2-carboxamide (66.07 mg, 114.96 μmol, 23.14% yield, 95.65% purity) as yellow solid. $^1$H NMR (400 MHz, DMSO-$d_6$) δ=11.08 (d, J=2.4 Hz, 1H), 9.99-9.78 (m, 1H), 8.19 (br s, 1H), 8.17-7.95 (m, 1H), 7.93-7.84 (m, 1H), 7.69-7.60 (m, 1H), 7.57-7.44 (m, 1H), 7.30-7.19 (m, 1H), 6.91-6.74 (m, 1H), 6.69-6.57 (m, 1H), 6.52-6.35 (m, 1H), 4.22-3.86 (m, 8H), 3.28-3.21 (m, 2H), 3.04-3.00 (m, 1H), 2.94-2.84 (m, 1H), 2.81-2.72 (m, 4H), 2.69-2.66 (m, 2H), 2.38-2.21 (m, 3H), 1.27-1.19 (m, 6H), 0.98 (d, J=6.5 Hz, 6H). $^1$H NMR (400 MHz, DMSO-$d_6$) δ=7.67 (br d, J=8.9 Hz, 1H), 7.46-7.37 (m, 1H), 7.28-7.19 (m, 1H), 6.89-6.71 (m, 2H), 6.47-6.31 (m, 1H), 4.16-4.02 (m, 2H), 3.94-3.82 (m, 6H), 3.28-3.17 (m, 2H), 3.00-2.95 (m, 2H), 2.91-2.81 (m, 1H), 2.76-2.69 (m, 3H), 2.64 (d, J=7.0 Hz, 2H), 2.31 (br s, 2H), 2.22 (td, J=6.7, 13.5 Hz, 1H), 1.23-1.14 (m, 6H), 0.97-0.90 (m, 6H)(TFA salt). LC-MS (ES+, m/z): 550.3 [(M+H)$^+$]; Rt=1.979 min. HRMS (EI): m/z [M+H]$^+$ found: 550.3502.

Example 68
Compound 518
(R,E)-3-((3-(1-(2-(4-(azetidin-1-yl)-N-methylbut-2-enamido)acetamido)propan-2-yl)phenyl)amino)-6-ethyl-5-(ethyl(methyl)amino)pyrazine-2-carboxamide Step 1: (R,E)-3-((3-(1-(2-(4-(azetidin-1-yl)-N-methylbut-2-enamido)acetamido) propan-2-yl)phenyl) amino)-6-ethyl-5-(ethyl(methyl)amino)pyrazine-2-carboxamide To a solution of (E)-4-(azetidin-1-yl)but-2-enoic acid (481.23 mg, 1.89 mmol, 2.5 eq, TFA) in DMF (3 mL) at 0° C. was added DIPEA (974.89 mg, 7.54 mmol, 1.31 mL, 10 eq), (R)-6-ethyl-5-(ethyl(methyl)amino)-3-((3-(1-(2-(methylamino)acetamido)propan-2-yl) phenyl)amino)pyrazine-2-carboxamide (350 mg, 754.31 μmol, 1 eq, HCl) and then BOP (500.42 mg, 1.13 mmol, 1.5 eq) at 0° C. The mixture was stirred at 0° C. for 1 hour. The reaction mixture was filtered and concentrated under reduced pressure. The residue was purified by prep-HPLC (column: Waters Xbridge Prep OBD C18 150*40 mm*10 um; mobile phase: [water (NH$_4$HCO$_3$)-ACN]; B %: 30%-60%, 8 min) to afford (R,E)-3-((3-(1-(2-(4-(azetidin-1-yl)-N-methylbut-2-enamido) acetamido) propan-2-yl) phenyl) amino)-6-ethyl-5-(ethyl (methyl)amino) pyrazine-2-carboxamide (140 mg, 244.56 μmol, 32.42% yield, 96.2% purity) as a yellow solid. $^1$H NMR (400 MHz, DMSO-$d_6$) δ=11.21-11.05 (m, 1H), 8.12-7.80 (m, 1H), 7.79-7.66 (m, 1H), 7.63-7.52 (m, 1H), 7.51-7.32 (m, 2H), 7.27-7.16 (m, 1H), 6.86-6.77 (m, 1H), 6.58-6.14 (m, 2H), 3.99-3.86 (m, 2H), 3.49-3.40 (m, 2H), 3.27-3.19 (m, 2H), 3.15-3.08 (m, 3H), 3.07-2.97 (m, 6H), 2.96 (s, 1.5H), 2.88 (dt, J=4.0, 7.1 Hz, 1H), 2.79-2.69 (m, 3.5H), 2.02-1.89 (m, 2H), 1.24-1.16 (m, 9H). LC-MS (ES+, m/z): 551.3 [(M+H)$^+$]; Rt=2.274 min. HRMS (EI): m/z [M+H]$^+$ found: 551.3468.

Example 69

Compound 519

(S,E)-3-((3-(1-(2-(4-(azetidin-1-yl)-N-methylbut-2-enamido)acetamido)propan-2-yl)phenyl)amino)-5,6-diethylpyrazine-2-carboxamide Step 1: tert-butyl (S)-(2-(3-((3-carbamoyl-6-chloro-5-ethylpyrazin-2-yl) amino) phenyl) propyl) carbamate

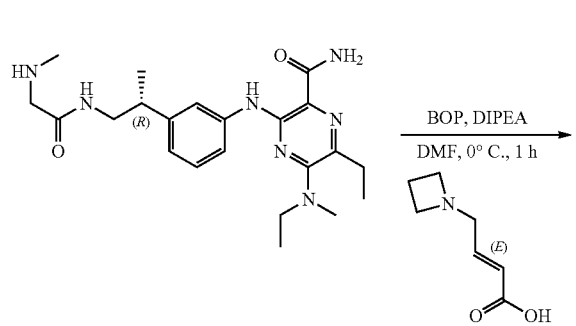

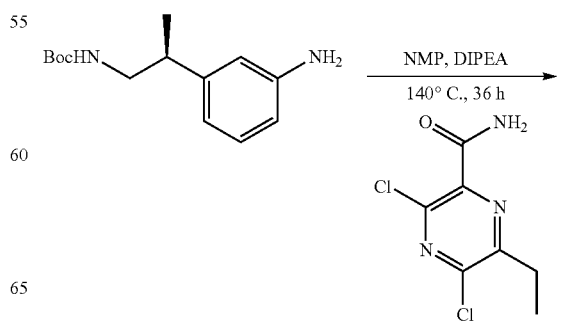

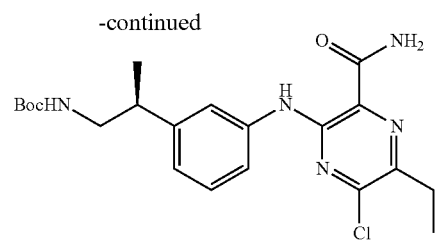

To a solution of tert-butyl (S)-(2-(3-aminophenyl) propyl) carbamate (2.00 g, 7.99 mmol, 1 eq) and 3,5-dichloro-6-ethylpyrazine-2-carboxamide (1.76 g, 7.99 mmol, 1 eq) in NMP (20 mL) was added DIPEA (10.33 g, 79.89 mmol, 13.92 mL, 10 eq). The mixture was heated to 140° C. and stirred for 36 hours under N₂ atmosphere. The reaction was poured into water (40 mL) and extracted with ethyl acetate (60 mL*3). The organic layers were combined, washed with water (80 mL*2), saturated brine (80 mL*2), dried with Na₂SO₄, filtered, and concentrated to give crude product. The residue was purified by column chromatography (SiO₂, Petroleum ether/Ethyl acetate=20/1 to 1/1) to afford tert-butyl (S)-(2-(3-((3-carbamoyl-6-chloro-5-ethylpyrazin-2-yl) amino) phenyl) propyl) carbamate (2.3 g, 5.30 mmol, 66.34% yield) as a yellow solid. ¹H NMR (400 MHz, DMSO-d₆) δ=11.21-11.11 (m, 1H), 8.32-8.19 (m, 1H), 8.09-7.98 (m, 1H), 7.59-7.47 (m, 1H), 7.41-7.22 (m, 2H), 6.95-6.78 (m, 2H), 3.15-2.99 (m, 2H), 2.89-2.78 (m, 3H), 1.34 (s, 9H), 1.26 (t, J=7.5 Hz, 3H), 1.17 (d, J=6.9 Hz, 3H). LC-MS (ES+, m/z): 378.2 [(M+H-56)⁺]; Rt=0.909 min.

Step 2: tert-butyl (S)-(2-(3-((3-carbamoyl-5,6-diethylpyrazin-2-yl) amino) phenyl) propyl) carbamate

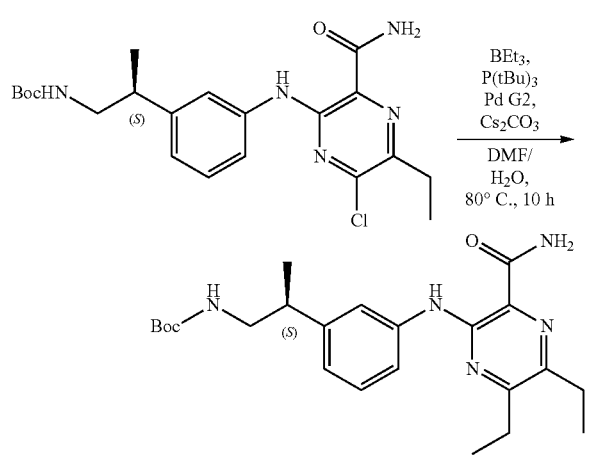

To a solution of 3,5-dichloro-6-ethylpyrazine-2-carboxamide (500 mg, 1.06 mmol, 1 eq, HCl) and triethylborane (1 M, 10.63 mL, 10 eq) in DMF (5 mL) and H₂O (2 mL) was added P(tBu)₃ Pd G₂ (54.47 mg, 106.29 μmol, 0.1 eq) and Cs₂CO₃ (1.04 g, 3.19 mmol, 3 eq). The mixture was heated to 80° C. for 10 hours under N₂ atmosphere. The reaction was poured into water (10 mL) and extracted with EtOAc (20 mL*3). The organic layers were combined, washed with water (15 mL*2), saturated brine (15 mL*2), dried with Na₂SO₄, filtered, and concentrated to give crude product. The residue was dissolved in DCM (20 mL), scavenger (Pd) was added and then stirred at 25° C. for 1 hour, and then filtered. The residue was purified by column chromatography (SiO₂, Petroleum ether/Ethyl acetate=20/1 to 1/1) to afford tert-butyl (S)-(2-(3-((3-carbamoyl-5,6-diethylpyrazin-2-yl) amino) phenyl) propyl) carbamate (350 mg, 818.64 μmol, 77.02% yield) as a yellow solid. ¹H NMR (400 MHz, DMSO-d₆) δ=11.15-11.00 (m, 1H), 8.21-8.05 (m, 1H), 7.90-7.51 (m, 4H), 7.32-7.19 (m, 1H), 6.82 (br d, J=7.3 Hz, 1H), 3.08-2.99 (m, 2H), 2.88-2.71 (m, 5H), 1.39-1.07 (m, 18H). LC-MS (ES+, m/z): 428.4 [(M+H)⁺]; Rt=0.919 min.

Step 3: (S)-3-((3-(1-aminopropan-2-yl) phenyl) amino)-5,6-diethylpyrazine-2-carboxamide

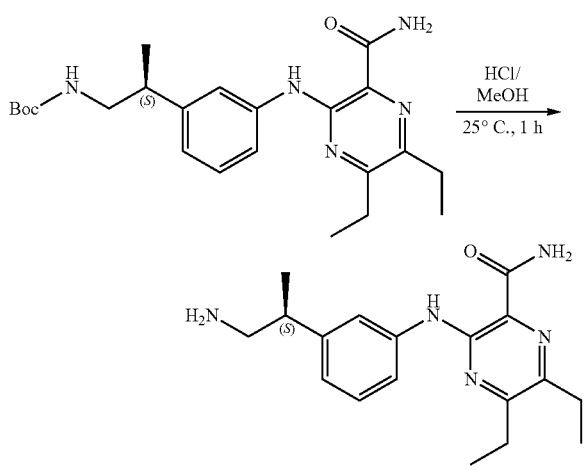

A mixture of tert-butyl (S)-(2-(3-((3-carbamoyl-5,6-diethylpyrazin-2-yl) amino) phenyl) propyl) carbamate (330 mg, 771.86 μmol, 1 eq) in HCl/MeOH (20 mL, 4 M) was stirred at 25° C. for 1 hour under N₂ atmosphere. The reaction mixture was concentrated under reduced pressure to afford (S)-3-((3-(1-aminopropan-2-yl) phenyl) amino)-5,6-diethylpyrazine-2-carboxamide (320 mg, crude) as a yellow solid. ¹H NMR (400 MHz, DMSO-d₆) δ=11.22-11.00 (m, 1H), 8.21-8.11 (m, 1H), 7.97 (br s, 2H), 7.87 (br s, 1H), 7.73-7.65 (m, 1H), 7.60 (s, 1H), 7.29 (br t, J=7.8 Hz, 1H), 6.92 (br d, J=7.5 Hz, 1H), 3.08-2.95 (m, 3H), 2.84 (q, J=7.3 Hz, 2H), 2.75 (q, J=7.5 Hz, 2H), 1.34-1.20 (m, 9H). LC-MS (ES+, m/z): 328.3 [(M+H)⁺]; Rt=0.598 min.

Step 4: tert-butyl (S)-(2-((2-(3-((3-carbamoyl-5,6-diethylpyrazin-2-yl) amino) phenyl) propyl) amino)-2-oxoethyl) (methyl)carbamate

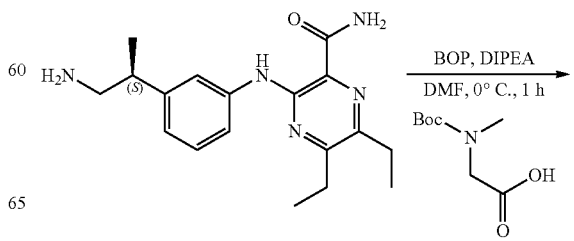

-continued

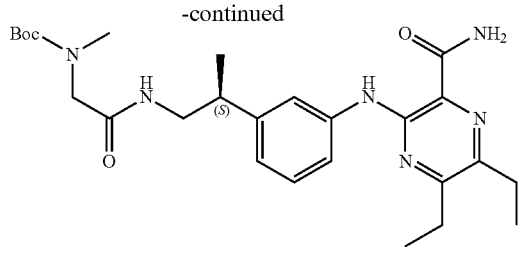

To a solution of N-(tert-butoxycarbonyl)-N-methylglycine (243.35 mg, 1.29 mmol, 1.5 eq) in DMF (3 mL) was added DIPEA (1.11 g, 8.57 mmol, 1.49 mL, 10 eq), (S)-3-((3-(1-aminopropan-2-yl)phenyl)amino)-5,6-diethylpyrazine-2-carboxamide (312 mg, 857.42 μmol, 1 eq, HCl) at 0° C., and then BOP (568.83 mg, 1.29 mmol, 1.5 eq) was added at 0° C. The mixture was stirred at 0° C. for 1 hour. The reaction was poured into water (5 mL) and extracted with EtOAc (10 mL*3). The organic layers were combined, washed with water (10 mL*2), saturated brine (10 mL*2), dried with $Na_2SO_4$, filtered, and concentrated to give crude product. The residue was purified by column chromatography ($SiO_2$, Petroleum ether/Ethyl acetate=20/1 to 1/1) to afford tert-butyl (S)-(2-((2-(3-((3-carbamoyl-5,6-diethylpyrazin-2-yl) amino) phenyl) propyl) amino)-2-oxoethyl) (methyl)carbamate (320 mg, 641.78 umol, 74.85% yield) as a yellow solid. LC-MS (ES+, m/z): 499.4 [(M+H)$^+$]; Rt=0.827 min.

Step 5: (S)-5,6-diethyl-3-((3-(1-(2-(methylamino) acetamido) propan-2-yl) phenyl) amino) pyrazine-2-carboxamide

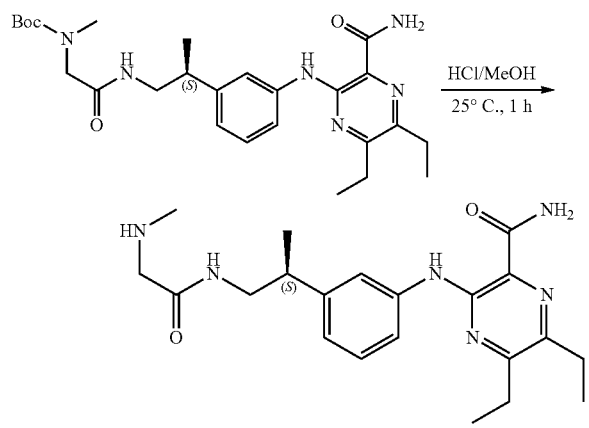

A mixture of tert-butyl (S)-(2-((2-(3-((3-carbamoyl-5,6-diethylpyrazin-2-yl) amino) phenyl) propyl) amino)-2-oxoethyl) (methyl)carbamate (310 mg, 621.72 μmol, 1 eq) in HCl/MeOH (20 mL, 4 M) was stirred at 25° C. for 1 hour. LCMS showed the reaction was completed. The reaction mixture was concentrated under reduced pressure to afford (S)-5,6-diethyl-3-((3-(1-(2-(methylamino) acetamido) propan-2-yl) phenyl) amino) pyrazine-2-carboxamide (320 mg, crude) as a yellow solid. $^1$H NMR (400 MHz, DMSO-$d_6$) δ=11.13-11.04 (m, 1H), 8.89-8.72 (m, 2H), 8.54-8.45 (m, 1H), 8.21-8.11 (m, 1H), 7.92-7.82 (m, 1H), 7.68-7.61 (m, 1H), 7.60-7.53 (m, 1H), 7.25 (s, 1H), 7.19-7.13 (m, 1H), 6.90-6.83 (m, 1H), 3.67-3.55 (m, 1H), 3.43-3.22 (m, 3H), 2.91-2.80 (m, 3H), 2.78-2.71 (m, 2H), 1.31 (t, J=7.4 Hz, 3H), 1.27-1.21 (m, 6H). LC-MS (ES+, m/z): 399.3 [(M+H)$^+$]; Rt=0.572 min.

Step 6: (S,E)-3-((3-(1-(2-(4-(azetidin-1-yl)-N-methylbut-2-enamido)acetamido) propan-2-yl)phenyl) amino)-5,6-diethylpyrazine-2-carboxamide

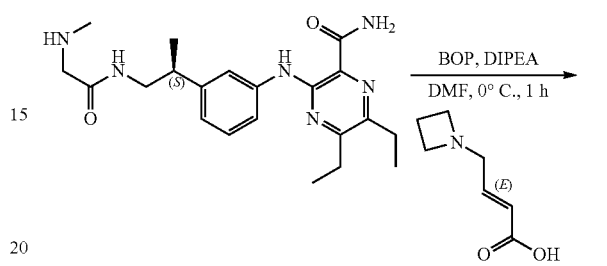

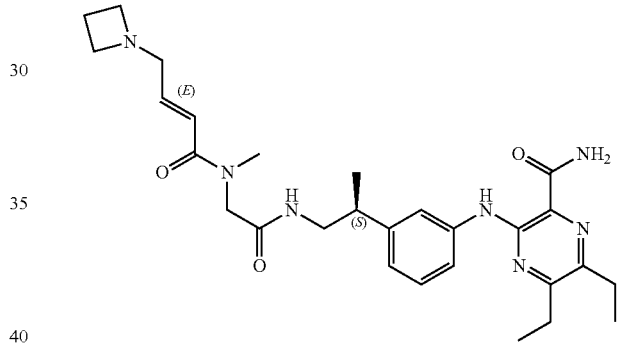

To a solution of (E)-4-(azetidin-1-yl)but-2-enoic acid (396.02 mg, 1.55 mmol, 2.5 eq, TFA) in DMF (3 mL) was added DIPEA (802.27 mg, 6.21 mmol, 1.08 mL, 10 eq), (S)-5,6-diethyl-3-((3-(1-(2-(methylamino)acetamido)propan-2-yl)phenyl)amino)pyrazine-2-carboxamide (270 mg, 620.74 μmol, 1 eq, HCl) at 0° C., and BOP (411.82 mg, 931.12 μmol, 1.5 eq) was added at 0° C. The mixture was stirred at 0° C. for 1 hour. The reaction mixture was filtered and concentrated under reduced pressure to give a residue. The residue was purified by prep-HPLC (column: Waters Xbridge Prep OBD C18 150*40 mm*10 um; mobile phase: [water ($NH_4HCO_3$)-ACN]; B %: 30%-70%, 8 min) to afford (S,E)-3-((3-(1-(2-(4-(azetidin-1-yl)-N-methylbut-2-enamido) acetamido)propan-2-yl)phenyl)amino)-5,6-diethylpyrazine-2-carboxamide (159.54 mg, 302.10 μmol, 48.67% yield) as a yellow solid. $^1$H NMR (400 MHz, DMSO-$d_6$) δ=11.14-11.05 (m, 1H), 8.21-8.10 (m, 1H), 8.09-7.81 (m, 2H), 7.67-7.59 (m, 1H), 7.58-7.50 (m, 1H), 7.28-7.19 (m, 1H), 6.88-6.80 (m, 1H), 6.52-6.15 (m, 2H), 4.00-3.85 (m, 2H), 3.27-3.20 (m, 2H), 3.15-3.08 (m, 3H), 3.07-2.98 (m, 3H), 2.96 (s, 1.5H), 2.92-2.81 (m, 3H), 2.79-2.71 (m, 3.5H), 2.01-1.88 (m, 2H), 1.31 (t, J=7.4 Hz, 3H), 1.26-1.17 (m, 6H). LC-MS (ES+, m/z): 522.3 [(M+H)$^+$]; Rt=2.248 min. HRMS (EI): m/z [M+H]$^+$ found: 522.3185.

Example 70

Compound 520

(E)-3-((2-(2-(2-(4-(azetidin-1-yl)-N-methylbut-2-enamido) acetamido) ethyl) pyridin-4-yl) amino)-5-cyclopropyl-6-ethylpyrazine-2-carboxamide Step 1: tert-butyl (2-((2-(4-((3-carbamoyl-6-cyclopropyl-5-ethylpyrazin-2-yl) amino) pyridin-2-yl) ethyl) amino)-2-oxoethyl) (methyl)carbamate

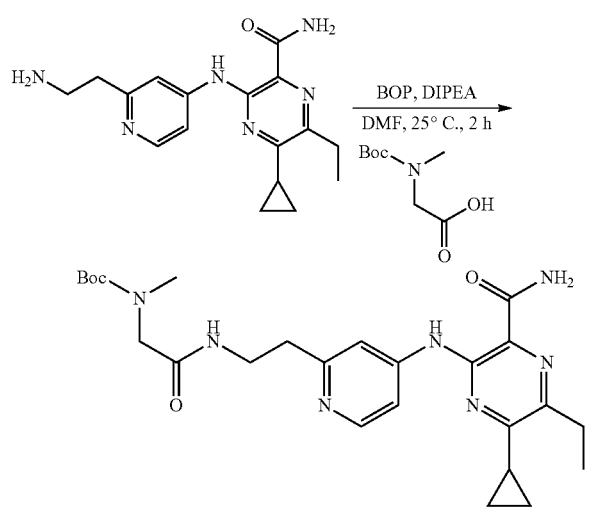

To a solution of N-(tert-butoxycarbonyl)-N-methylglycine (521.72 mg, 2.76 mmol, 1.5 eq) in DMF (12 mL) was added DIPEA (2.38 g, 18.38 mmol, 3.20 mL, 10 eq), tert-butyl (2-((2-(4-((3-carbamoyl-6-cyclopropyl-5-ethylpyrazin-2-yl)amino)pyridin-2-yl)ethyl)amino)-2-oxoethyl)(methyl)carbamate (600 mg, 1.84 mmol, 1 eq) and BOP (1.22 g, 2.76 mmol, 1.5 eq) at 25° C. The mixture was stirred at 25° C. for 2 hours. The reaction mixture was quenched by addition H$_2$O (20 mL), then extracted with DCM (20 mL*3). The combined organic layers were washed with saturated brine (20 mL), dried over anhydrous Na$_2$SO$_4$ filtered and concentrated under reduced pressure. The residue was purified by column chromatography (SiO$_2$, DCM:MeOH=20:1) to give tert-butyl (2-((2-(4-((3-carbamoyl-6-cyclopropyl-5-ethylpyrazin-2-yl)amino)pyridin-2-yl)ethyl)amino)-2-oxoethyl)(methyl)carbamate (722 mg, 1.45 mmol, 78.93% yield) as a yellow solid. LC-MS (ES+, m/z): 498.3 [(M+H)$^+$]. Rt=0.627 min.

Step 2: 5-cyclopropyl-6-ethyl-3-((2-(2-(2-(methylamino) acetamido) ethyl) pyridin-4-yl) amino) pyrazine-2-carboxamide

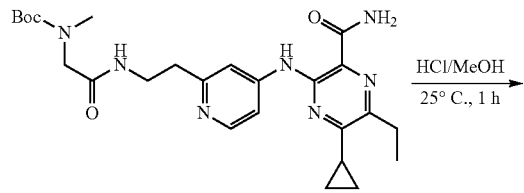

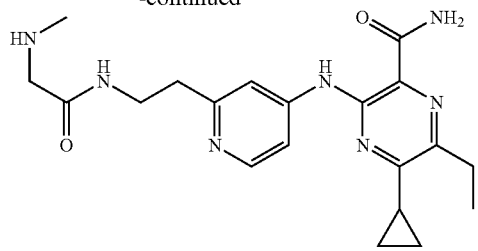

A solution of tert-butyl (2-((2-(4-((3-carbamoyl-6-cyclopropyl-5-ethylpyrazin-2-yl)amino)pyridin-2-yl)ethyl) amino)-2-oxoethyl)(methyl)carbamate (722 mg, 1.45 mmol, 1.0 eq) in HCl/MeOH (4 M, 20 mL, 722.3 eq) was stirred at 25° C. for 1 hour. The reaction mixture was concentrated under reduced pressure to give 5-cyclopropyl-6-ethyl-3-((2-(2-(2-(methylamino)acetamido)ethyl)pyridin-4-yl)amino) pyrazine-2-carboxamide (600 mg, crude, HCl) as a yellow solid. LC-MS (ES+, m/z): 398.2 [(M+H)$^+$]. Rt=0.953 min.

Step 3: (E)-3-((2-(2-(2-(4-(azetidin-1-yl)-N-methylbut-2-enamido) acetamido) ethyl) pyridin-4-yl) amino)-5-cyclopropyl-6-ethylpyrazine-2-carboxamide

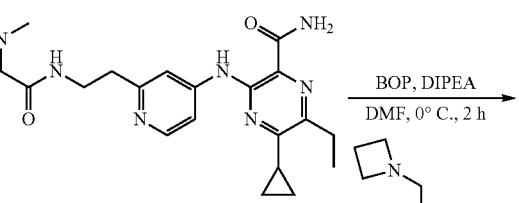

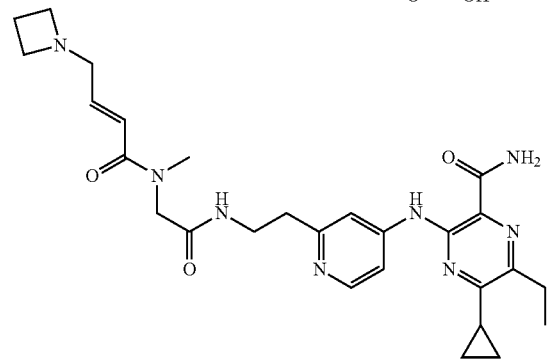

To a solution of (E)-4-(azetidin-1-yl)but-2-enoic acid (882.13 mg, 3.46 mmol, 2.5 eq, TFA) in DMF (8 mL) at 0° C. was added and DIPEA (1.79 g, 13.83 mmol, 2.41 mL, 10 eq) and 5-cyclopropyl-6-ethyl-3-((2-(2-(2-(methylamino) acetamido)ethyl)pyridin-4-yl)amino)pyrazine-2-carboxamide (600 mg, 1.38 mmol, 1 eq, HCl) and then BOP (917.31 mg, 2.07 mmol, 1.5 eq) as added at 0° C. The mixture was stirred at 0° C. for 2 hours. The mixture was purified by prep-HPLC (column: Waters Xbridge BEH C18 250*70 mm*10 um; mobile phase: [water (NH$_4$HCO$_3$)-ACN]; B %: 25%-55%, 20 min) to give (E)-3-((2-(2-(2-(4-(azetidin-1-yl)-N-methylbut-2-enamido)acetamido)ethyl)pyridin-4-yl) amino)-5-cyclopropyl-6-ethylpyrazine-2-carboxamide (44.11 mg, 84.72 umol, 6.13% yield, 98.94% purity) as a yellow solid, ¹H NMR (400 MHz, DMSO-d₆) δ=11.39 (br d, J=6.88 Hz, 1H), 8.33-8.19 (m, 2H), 8.17-7.92 (m, 2H), 7.45 (br dd, J=10.57, 6.07 Hz, 2H), 6.59-6.17 (m, 2H), 4.01-3.83 (m, 2H), 3.51-3.41 (m, 2H), 3.15-2.99 (m, 7H), 2.98-2.78 (m, 6H), 2.38-2.30 (m, 1H), 2.02-1.86 (m, 2H), 1.29 (t, J=7.50 Hz, 3H), 1.20-1.08 (m, 4H). LC-MS (ES+, m/z): 521.3 [(M+H)⁺]. Rt=2.471 min.

HRMS (EI): m/z [M+H]+ found: 521.3025.

Example 71

Compound 601

(E)-3-((3-(2-(2-(4-(azetidin-1-yl)-N-methylbut-2-enamido) acetamido) ethyl) phenyl) amino)-6-ethyl-5-isobutylpyrazine-2-carboxamide Step 1: tert-butyl (3-((3-carbamoyl-5-ethyl-6-isobutylpyrazin-2-yl) amino) phenethyl) carbamate

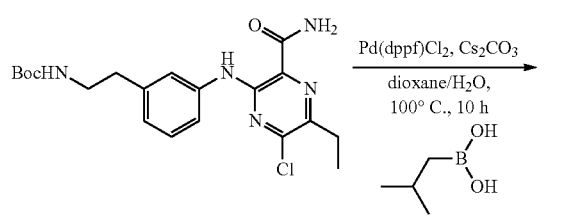

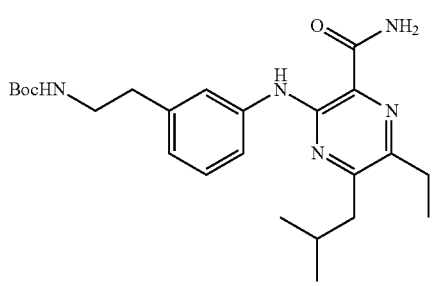

To a solution of tert-butyl (3-((3-carbamoyl-6-chloro-5-ethylpyrazin-2-yl) amino) phenethyl) carbamate (500 mg, 1.19 mmol, 1 eq), isobutylboronic acid (1.21 g, 11.91 mmol, 10 eq), Cs₂CO₃ (1.16 g, 3.57 mmol, 3 eq) in dioxane (5 mL) and H₂O (1 mL), Pd(dppf)Cl₂ (87.13 mg, 119.07 μmol, 0.1 eq) was added. The mixture was stirred at 100° C. for 10 hours under N₂. The residue was dissolved in DCM (20 mL), scavenger (Pd) was added and then stirred at 25° C. for 1 hour, and then filtered. The mixture was poured into water (60 mL) and extracted with DCM (60 mL*2). The organic layers were combined, washed with water (40 mL*2), saturated brine (40 mL*2), dried over Na₂SO₄, filtered, concentrated under reduced pressure. The crude product was purified by chromatography on silica gel (Petroleum ether: Ethyl acetate=1:1) to give tert-butyl (3-((3-carbamoyl-5-ethyl-6-isobutylpyrazin-2-yl) amino) phenethyl) carbamate (300 mg, 679.40 μmol, 57.06% yield) as yellow solid. LCMS (ES+, m/z): 442.3 [(M+H)⁺]; Rt=0.949 min.

Step 2: 3-((3-(2-aminoethyl) phenyl) amino)-6-ethyl-5-isobutylpyrazine-2-carboxamide

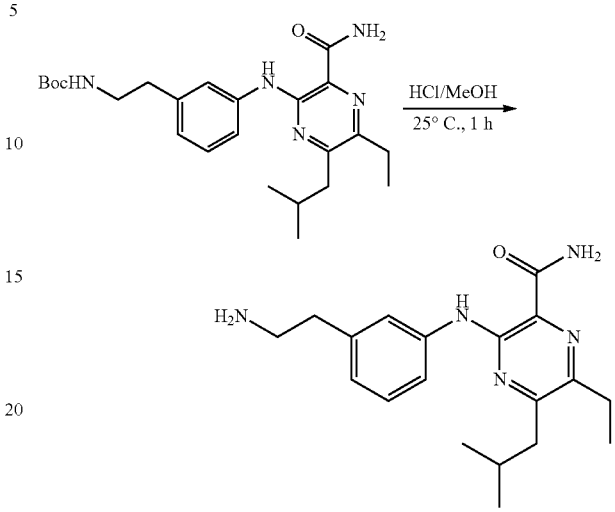

The mixture tert-butyl (3-((3-carbamoyl-5-ethyl-6-isobutylpyrazin-2-yl) amino) phenethyl) carbamate (300 mg, 679.40 μmol, 1 eq) and HCl/MeOH (4 M, 16.9 mL, 100 eq) was stirred at 25° C. for 1 hour. The reaction mixture was concentrated under reduced pressure to give 3-((3-(2-aminoethyl) phenyl) amino)-6-ethyl-5-isobutylpyrazine-2-carboxamide (170 mg, crude) as yellow oil. LCMS (ES+, m/z): 342.3 [(M+H)⁺]; Rt=0.618 min.

Step 3: tert-butyl (2-((3-((3-carbamoyl-5-ethyl-6-isobutylpyrazin-2-yl) amino) phenethyl) amino)-2-oxoethyl) (methyl) carbamate

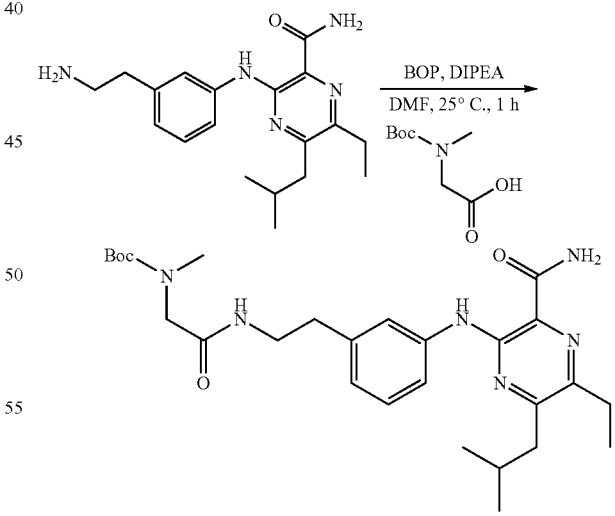

To a solution of 3-((3-(2-aminoethyl) phenyl) amino)-6-ethyl-5-isobutylpyrazine-2-carboxamide (170 mg, 449.84 μmol, 1 eq, HCl), N-(tert-butoxycarbonyl)-N-methylglycine (170.23 mg, 899.68 μmol, 2 eq), DIPEA (581.39 mg, 4.50 mmol, 783.54 μL, 10 eq) in DMF (2 mL) at 25° C., BOP (298.43 mg, 674.76 μmol, 1.5 eq) was added. The mixture was stirred at 25° C. for 1 hour. The mixture was poured into water (20 mL) and extracted with EtOAc (30 mL*2). The organic layers were combined, washed with water (10 mL*2), saturated brine (10 mL*2), dried over Na$_2$SO$_4$, filtered, concentrated under reduced pressure to give a residue. The crude product was purified by chromatography on silica gel (Ethyl acetate:Petroleum ether=3:1) to give tert-butyl (2-((3-((3-carbamoyl-5-ethyl-6-isobutylpyrazin-2-yl) amino) phenethyl) amino)-2-oxoethyl) (methyl) carbamate (200 mg, 390.14 μmol, 86.73% yield) as yellow oil. $^1$H NMR (400 MHz, DMSO-d$_6$) δ=11.14-10.99 (m, 1H), 8.23-8.12 (m, 1H), 8.00-7.84 (m, 2H), 7.66-7.45 (m, 2H), 7.28-7.19 (m, 1H), 6.89-6.78 (m, 1H), 3.80-3.64 (m, 2H), 3.22-3.12 (m, 1H), 2.83-2.64 (m, 10H), 2.30-2.20 (m, 1H), 1.24 (br t, J=7.5 Hz, 12H), 1.06-0.92 (m, 6H). LC-MS (ES+, m/z): 513.5 [(M+H)$^+$]; Rt=0.870 min.

Step 4: 6-ethyl-5-isobutyl-3-((3-(2-(2-(methyl-amino) acetamido) ethyl) phenyl) amino) pyrazine-2-carboxamide

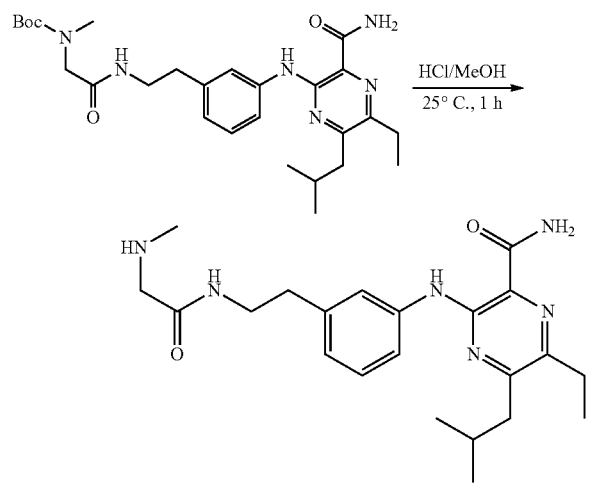

The mixture tert-butyl (2-((3-((3-carbamoyl-5-ethyl-6-isobutylpyrazin-2-yl) amino) phenethyl) amino)-2-oxoethyl) (methyl) carbamate (200 mg, 390.14 μmol, 1 eq) and HCl/MeOH (4 M, 20 mL, 205.06 eq) was stirred at 25° C. for 1 hour. The reaction mixture was concentrated under reduced pressure to give 6-ethyl-5-isobutyl-3-((3-(2-(2-(methylamino) acetamido) ethyl) phenyl) amino) pyrazine-2-carboxamide (180 mg, crude) as yellow solid. LCMS (ES+, m/z): 413.3 [(M+H)$^+$]; Rt=0.654 min.

Step 5: (E)-3-((3-(2-(2-(4-(azetidin-1-yl)-N-methyl-but-2-enamido) acetamido) ethyl) phenyl) amino)-6-ethyl-5-isobutylpyrazine-2-carboxamide

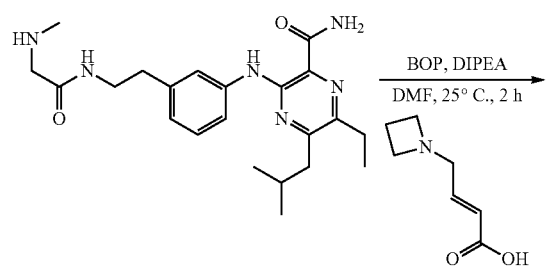

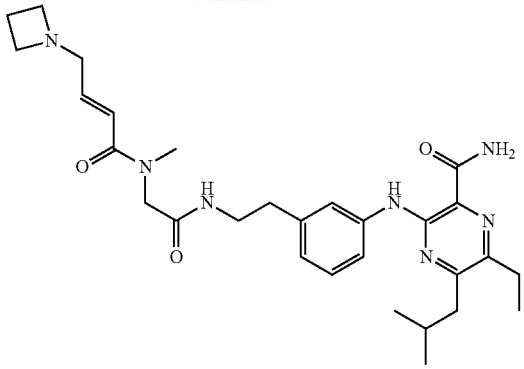

To a solution of 6-ethyl-5-isobutyl-3-((3-(2-(2-(methylamino) acetamido) ethyl) phenyl) amino) pyrazine-2-carboxamide (110 mg, 245.00 μmol, 1 eq, HCl), (E)-4-(azetidin-1-yl) but-2-enoic acid (218.82 mg, 857.48 μmol, 3.5 eq, TFA), DIPEA (316.64 mg, 2.45 mmol, 426.74 μL, 10 eq) in DMF (1 mL) at 25° C., BOP (162.54 mg, 367.49 μmol, 1.5 eq) was added. The mixture was stirred at 25° C. for 2 hrs. LCMS showed the reaction was completed. The mixture was filtered to give a residue. The crude was purified by prep-HPLC (column: Waters Xbridge Prep OBD C18 150*40 mm*10 um; mobile phase: [water (NH$_4$HCO$_3$)-ACN]; B %: 35%-65%, 8 min) to give (E)-3-((3-(2-(2-(4-(azetidin-1-yl)-N-methylbut-2-enamido) acetamido) ethyl) phenyl) amino)-6-ethyl-5-isobutylpyrazine-2-carboxamide (60.70 mg, 111.12 μmol, 45.35% yield, 98.06% purity) as yellow solid. $^1$H NMR (400 MHz, DMSO-d$_6$) δ=11.07 (d, J=6.9 Hz, 1H), 8.23-7.82 (m, 3H), 7.57 (br d, J=6.9 Hz, 2H), 7.24 (dt, J=4.2, 7.9 Hz, 1H), 6.84 (br d, J=7.4 Hz, 1H), 6.61-6.12 (m, 2H), 3.95 (d, J=18.8 Hz, 2H), 3.32-3.26 (m, 2H), 3.17-3.02 (m, 6H), 3.02-2.98 (m, 2H), 2.85-2.80 (m, 1H), 2.78-2.66 (m, 6H), 2.25 (td, J=6.9, 13.7 Hz, 1H), 2.03-1.90 (m, 2H), 1.24 (t, J=7.5 Hz, 3H), 0.98 (d, J=6.6 Hz, 6H); $^1$H NMR (400 MHz, DMSO-d$_6$) δ=10.86-10.78 (m, 1H), 7.60-7.53 (m, 1H), 7.48 (br d, J=8.3 Hz, 1H), 7.22 (dt, J=3.3, 7.8 Hz, 1H), 6.83 (br d, J=7.3 Hz, 1H), 6.13 (br d, J=15.3 Hz, 2H), 3.96-3.88 (m, 2H), 3.31 (td, J=7.4, 17.8 Hz, 2H), 3.16-2.98 (m, 6H), 2.98-2.94 (m, 2H), 2.80 (br s, 1H), 2.74-2.62 (m, 6H), 2.23-2.14 (m, 1H), 2.02-1.85 (m, 2H), 1.19 (t, J=7.4 Hz, 3H), 0.95-0.91 (m, 6H). LC-MS (ES+, m/z): 536.4 [(M+H)$^+$]; Rt=2.336 min. HRMS (EI): m/z (M+H)$^+$ found: 536.3323.

Example 72

Compound 602

(E)-3-((3-(2-(2-(4-(azetidin-1-yl)-N-methylbut-2-enamido) acetamido) ethyl) phenyl) amino)-5-ethoxy-6-ethylpyrazine-2-carboxamide Step 1: tert-butyl (3-((3-carbamoyl-6-ethoxy-5-ethylpyrazin-2-yl) amino) phenethyl) carbamate

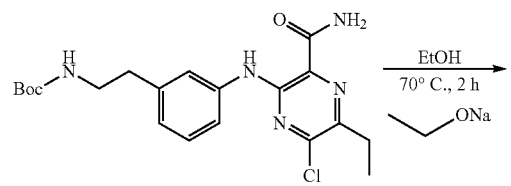

-continued

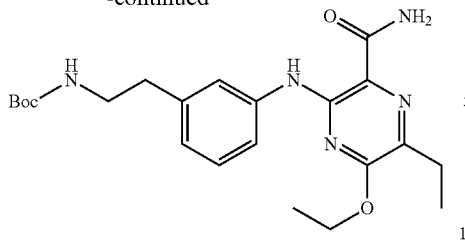

To a solution of tert-butyl (3-((3-carbamoyl-6-chloro-5-ethylpyrazin-2-yl) amino) phenethyl) carbamate (600 mg, 1.43 mmol, 1 eq) in EtOH (6 mL), EtONa (486.18 mg, 7.14 mmol, 5 eq) was added. The mixture was stirred at 70° C. for 2 hours. The mixture was poured into water (60 mL) and extracted with EtOAc (60 mL*2). The organic layers were combined, washed with water (40 mL*2), saturated brine (40 mL*2), dried over $Na_2SO_4$, filtered, concentrated under reduced pressure to give a residue. The crude product was purified by chromatography on silica gel (Petroleum ether: Ethyl acetate=1:1) to give tert-butyl (3-((3-carbamoyl-6-ethoxy-5-ethylpyrazin-2-yl) amino) phenethyl) carbamate (440 mg, 1.02 mmol, 71.69% yield) as white solid. $^1H$ NMR (400 MHz, DMSO-$d_6$) δ=11.27 (s, 1H), 7.88 (br s, 1H), 7.68-7.56 (m, 2H), 7.43-7.33 (m, 1H), 7.24 (t, J=7.8 Hz, 1H), 6.93-6.80 (m, 2H), 4.46 (q, J=7.0 Hz, 2H), 3.20-3.10 (m, 2H), 2.74-2.62 (m, 4H), 1.45-1.36 (m, 12H), 1.22 (t, J=7.5 Hz, 3H). LCMS (ES+, m/z): 430.3 [(M+H)$^+$]; Rt=0.911 min.

Step 2: 3-((3-(2-aminoethyl) phenyl) amino)-5-ethoxy-6-ethylpyrazine-2-carboxamide

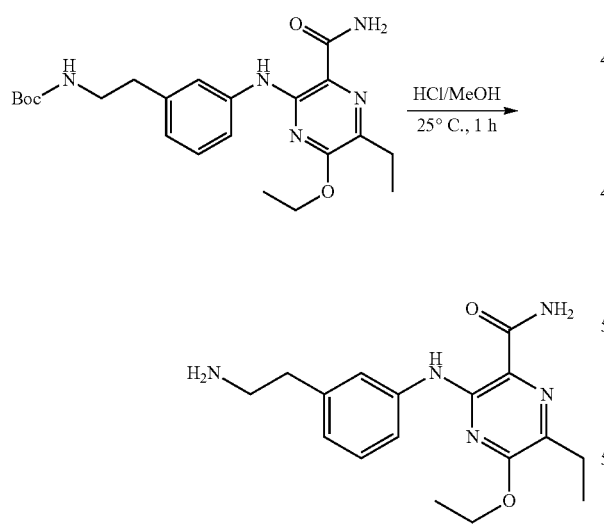

The mixture tert-butyl (3-((3-carbamoyl-6-ethoxy-5-ethylpyrazin-2-yl) amino) phenethyl) carbamate (340 mg, 791.60 μmol, 1 eq) and HCl/MeOH (4 M, 20 mL, 101.06 eq) was stirred at 25° C. for 1 hour. The reaction mixture was concentrated under reduced pressure to give 3-((3-(2-aminoethyl) phenyl) amino)-5-ethoxy-6-ethylpyrazine-2-carboxamide (310 mg, crude) as yellow solid. LCMS (ES+, m/z): 330.2 [(M+H)$^+$]; Rt=0.598 min.

Step 3: tert-butyl (2-((3-((3-carbamoyl-6-ethoxy-5-ethylpyrazin-2-yl) amino) phenethyl) amino)-2-oxoethyl) (methyl) carbamate

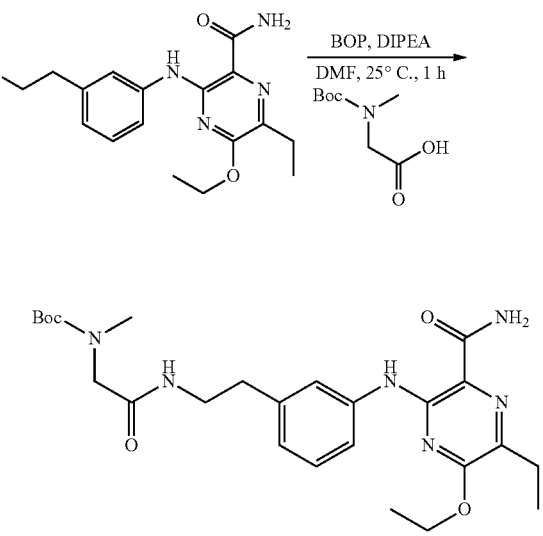

To a solution of 3-((3-(2-aminoethyl) phenyl) amino)-5-ethoxy-6-ethylpyrazine-2-carboxamide (350 mg, 956.66 μmol, 1 eq, HCl), N-(tert-butoxycarbonyl)-N-methylglycine (362.02 mg, 1.91 mmol, 2 eq), DIPEA (1.24 g, 9.57 mmol, 1.67 mL, 10 eq) in DMF (4 mL) at 25° C., BOP (634.67 mg, 1.43 mmol, 1.5 eq) was added. The mixture was stirred at 25° C. for 1 hour. The mixture was poured into water (50 mL) and extracted with EtOAc (50 mL*2). The organic layers were combined, washed with water (50 mL*2), saturated brine (50 mL*2), dried over $Na_2SO_4$, filtered, concentrated under reduced pressure to give a residue. The crude product was purified by chromatography on silica gel (Ethyl acetate:Petroleum ether=2:1) to give tert-butyl (2-((3-((3-carbamoyl-6-ethoxy-5-ethylpyrazin-2-yl) amino) phenethyl) amino)-2-oxoethyl) (methyl) carbamate (350 mg, 699.18 μmol, 73.09% yield) as yellow solid. LC-MS (ES+, m/z): 501.4 [(M+H)$^+$]; Rt=0.819 min; $^1H$ NMR (400 MHz, DMSO-$d_6$) δ=11.38-11.28 (m, 1H), 8.04-7.89 (m, 2H), 7.73-7.61 (m, 2H), 7.46 (br d, J=8.1 Hz, 1H), 7.30 (t, J=7.8 Hz, 1H), 6.95-6.86 (m, 1H), 4.56-4.46 (m, 2H), 3.82-3.72 (m, 2H), 3.38-3.33 (m, 2H), 2.85-2.68 (m, 7H), 1.50-1.34 (m, 12H), 1.27 (t, J=7.5 Hz, 3H).

Step 4: 5-ethoxy-6-ethyl-3-((3-(2-(2-(methylamino) acetamido) ethyl) phenyl) amino) pyrazine-2-carboxamide

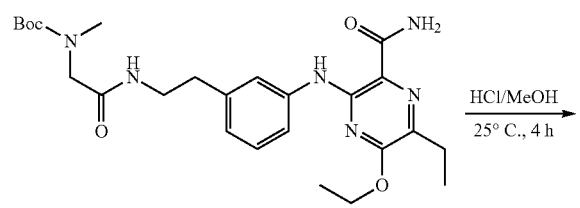

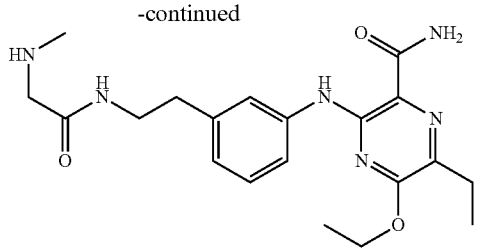

The mixture tert-butyl (2-((3-((3-carbamoyl-6-ethoxy-5-ethylpyrazin-2-yl) amino) phenethyl) amino)-2-oxoethyl) (methyl) carbamate (350 mg, 699.18 μmol, 1 eq) and HCl/MeOH (4 M, 20 mL, 114.42 eq) was stirred at 25° C. for 4 hours. The reaction mixture was concentrated under reduced pressure to give 5-ethoxy-6-ethyl-3-((3-(2-(2-(methylamino) acetamido) ethyl) phenyl) amino) pyrazine-2-carboxamide (280 mg, crude) as yellow solid. LCMS (ES+, m/z): 401.3 [(M+H)+]; Rt=0.609 min.

Step 5: (E)-3-((3-(2-(2-(4-(azetidin-1-yl)-N-methylbut-2-enamido) acetamido) ethyl) phenyl) amino)-5-ethoxy-6-ethylpyrazine-2-carboxamide

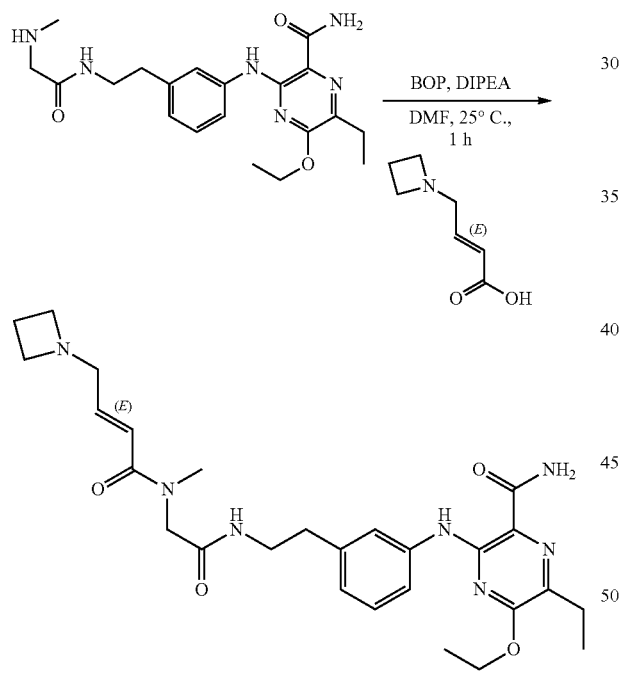

To a solution of 5-ethoxy-6-ethyl-3-((3-(2-(2-(methylamino) acetamido) ethyl) phenyl)amino) pyrazine-2-carboxamide (280 mg, 640.83 μmol, 1 eq, HCl), (E)-4-(azetidin-1-yl) but-2-enoic acid (490.60 mg, 1.92 mmol, 3 eq, TFA), DIPEA (1.24 g, 9.61 mmol, 1.67 mL, 15 eq) in DMF (2.5 mL) at 25° C., BOP (566.85 mg, 1.28 mmol, 2 eq) was added. The mixture was stirred at 25° C. for 1 hour. The mixture was filtered to give a residue. The crude was purified by prep-HPLC (column: Waters Xbridge Prep OBD C18 150*40 mm*10 um; mobile phase: [water (NH4HCO3)-ACN]; B %: 30%-60%, 8 min) to give (E)-3-((3-(2-(2-(4-(azetidin-1-yl)-N-methylbut-2-enamido) acetamido) ethyl) phenyl) amino)-5-ethoxy-6-ethylpyrazine-2-carboxamide (69.94 mg, 131.75 μmol, 20.56% yield, 98.64% purity) as white solid. 1H NMR (400 MHz, DMSO-d6) δ=11.32-11.25 (m, 1H), 8.21-7.83 (m, 2H), 7.69-7.54 (m, 2H), 7.50-7.37 (m, 1H), 7.31-7.19 (m, 1H), 6.91-6.81 (m, 1H), 6.23 (br d, J=15.1 Hz, 2H), 4.51-4.41 (m, 2H), 3.95 (d, J=19.6 Hz, 2H), 3.32-3.25 (m, 2H), 3.17-3.03 (m, 6H), 3.02-2.99 (m, 2H), 2.84-2.78 (m, 1H), 2.74-2.64 (m, 4H), 2.04-1.87 (m, 2H), 1.45-1.37 (m, 3H), 1.26-1.18 (m, 3H); 1H NMR (400 MHz, DMSO-d6) δ=11.15-10.98 (m, 1H), 7.55 (s, 1H), 7.44-7.35 (m, 1H), 7.29-7.19 (m, 1H), 6.90-6.80 (m, 1H), 6.55-6.08 (m, 2H), 4.42 (q, J=7.0 Hz, 2H), 3.98-3.91 (m, 2H), 3.36-3.23 (m, 2H), 3.18-2.99 (m, 6H), 2.99-2.94 (m, 2H), 2.82-2.75 (m, 1H), 2.73-2.61 (m, 4H), 2.03-1.86 (m, 2H), 1.40-1.32 (m, 3H), 1.17 (t, J=7.5 Hz, 3H). LC-MS (ES+, m/z): 524.3 [(M+H)+]; Rt=2.226 min. HRMS (EI): m/z (M+H)+ found: 524.2995.

Example 73

Compound 603

(E)-3-((3-(2-(2-(4-(azetidin-1-yl)-N-methylbut-2-enamido) acetamido) ethyl) phenyl) amino)-6-ethyl-5-isopropoxypyrazine-2-carboxamide Step 1: tert-butyl (3-((3-carbamoyl-5-ethyl-6-isopropoxypyrazin-2-yl) amino) phenethyl) carbamate

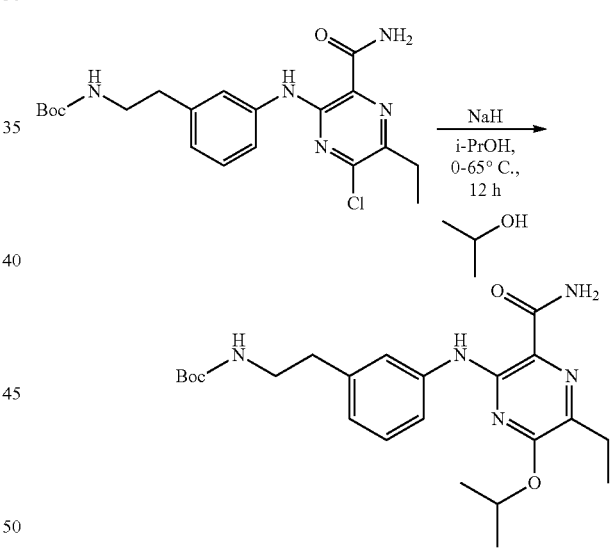

To a solution of 2-methylpropan-1-ol (8.02 g, 108.20 mmol, 10 mL, 45.46 eq) was added NaH (2 g, 50.00 mmol, 60% purity, 21 eq). The mixture was stirred at 0° C. for 0.5 hr. And tert-butyl (3-((3-carbamoyl-6-chloro-5-ethylpyrazin-2-yl) amino) phenethyl) carbamate (1 g, 2.38 mmol, 1 eq) in 2-methylpropan-1-ol (50 mL) was added at 0° C. The mixture was stirred at 65° C. for 12 hours. The residue was diluted with H2O (20 mL). The reaction mixture was concentrated under reduced pressure to remove 2-methylpropan-1-ol (50 mL). The residue was diluted with EtOAc 20 mL and extracted with EtOAc 30 mL (10 mL*3). The combined organic layers were washed with saturated brine (15 mL), dried over Na2SO4, filtered, and concentrated under reduced pressure to give a residue. The residue was purified by column chromatography (SiO2, Petroleum ether/

Ethyl acetate=4/1) to give tert-butyl (3-((3-carbamoyl-5-ethyl-6-isopropoxypyrazin-2-yl) amino) phenethyl) carbamate (0.53 g, 1.19 mmol, 50.18% yield) as a light-yellow solid. $^1$H NMR (400 MHz, DMSO-d$_6$) δ=11.31-11.26 (m, 1H), 7.91-7.86 (m, 1H), 7.66-7.61 (m, 2H), 7.33-7.20 (m, 2H), 6.96-6.90 (m, 1H), 6.86-6.81 (m, 1H), 5.33-5.24 (m, 1H), 3.17-3.09 (m, 2H), 2.70-2.60 (m, 4H), 1.40 (d, J=6.14 Hz, 6H), 1.36 (s, 9H), 1.20 (t, J=7.45 Hz, 3H). LC-MS (ES+, m/z): 466.2 [(M+Na)$^+$]; Rt=2.273 min.

Step 2: 3-((3-(2-aminoethyl) phenyl) amino)-6-ethyl-5-isopropoxypyrazine-2-carboxamide

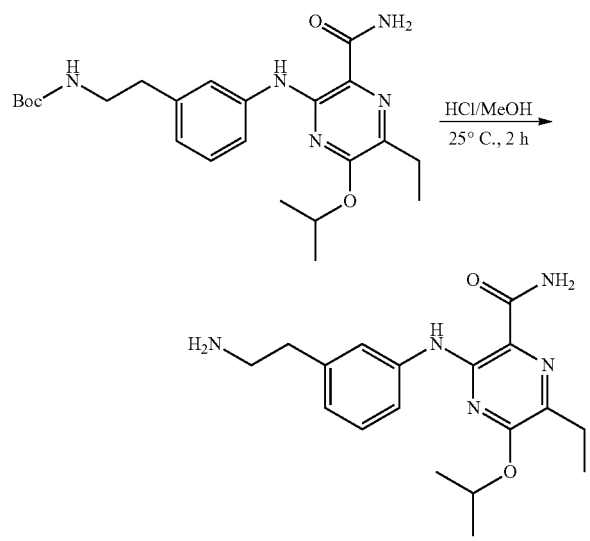

To a solution of tert-butyl (3-((3-carbamoyl-5-ethyl-6-isopropoxypyrazin-2-yl) amino) phenethyl) carbamate (430 mg, 969.48 mol, 1 eq) was added HCl/MeOH (4 M, 40 mL, 165.04 eq). The mixture was stirred at 25° C. for 2 hours. The reaction mixture was concentrated under reduced pressure to remove solvent to give 3-((3-(2-aminoethyl) phenyl) amino)-6-ethyl-5-isopropoxypyrazine-2-carboxamide (410 mg, crude) as a light-yellow solid. LC-MS (ES+, m/z): 344.2 [(M+H)$^+$]; Rt=1.560 min.

Step 3: tert-butyl (2-((3-((3-carbamoyl-5-ethyl-6-isopropoxypyrazin-2-yl) amino) phenethyl) amino)-2-oxoethyl) (methyl)carbamate

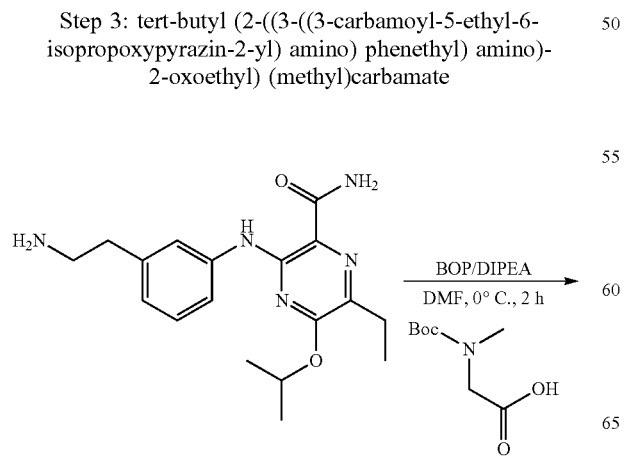

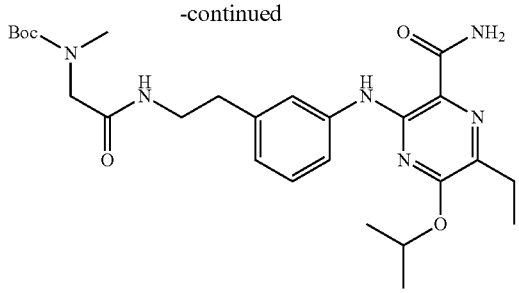

To a solution of N-(tert-butoxycarbonyl)-N-methylglycine (272.72 mg, 1.44 mmol, 1.5 eq) in DMF (6 mL) was added DIPEA (1.24 g, 9.61 mmol, 1.67 mL, 10 eq) and 3-((3-(2-aminoethyl) phenyl) amino)-6-ethyl-5-isopropoxypyrazine-2-carboxamide (330 mg, 960.92 μmol, 1 eq) and BOP (637.49 mg, 1.44 mmol, 1.5 eq). The mixture was stirred at 0° C. for 2 hours. The reaction mixture was diluted with EtOAc (50 mL) and water (50 mL), and extracted with EtOAc (50 mL*3). The combined organic layers were washed with saturated brine 30 mL, dried over Na$_2$SO$_4$, filtered, and concentrated under reduced pressure to give a residue. The residue was purified by column chromatography (SiO$_2$, DCM:MeOH=15:1) to give tert-butyl (2-((3-((3-carbamoyl-5-ethyl-6-isopropoxypyrazin-2-yl) amino) phenethyl) amino)-2-oxoethyl) (methyl) carbamate (500 mg, crude) as a light-yellow solid. $^1$H NMR (400 MHz, DMSO-d$_6$) δ=11.31-11.25 (m, 1H), 7.96-7.93 (m, 1H), 7.90-7.85 (m, 1H), 7.66-7.59 (m, 2H), 7.38-7.20 (m, 2H), 6.88-6.82 (m, 1H), 5.34-5.23 (m, 1H), 2.89 (s, 3H), 2.78-2.72 (m, 6H), 2.68-2.61 (m, 2H), 1.39 (d, J=6.14 Hz, 9H), 1.32 (s, 4H), 1.22-1.15 (m, 5H). LC-MS (ES+, m/z): 515.3 [(M+H)$^+$]; Rt=2.225 min.

Step 4: 6-ethyl-5-isopropoxy-3-((3-(2-(2-(methylamino) acetamido) ethyl) phenyl) amino) pyrazine-2-carboxamide

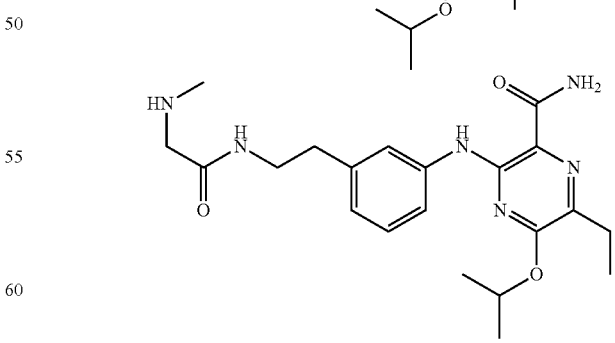

To a solution of tert-butyl (2-((3-((3-carbamoyl-5-ethyl-6-isopropoxypyrazin-2-yl) amino) phenethyl) amino)-2-oxoethyl) (methyl)carbamate (500 mg, 621.84 μmol, 1 eq) was added HCl/MeOH (4 M, 40 mL, 115.32 eq). The mixture was stirred at 25° C. for 1 hour. The reaction mixture was concentrated under reduced pressure to remove solvent to give 6-ethyl-5-isopropoxy-3-((3-(2-(2-(methylamino) acetamido) ethyl) phenyl) amino) pyrazine-2-carboxamide (500 mg, crude) as a light-yellow solid. LC-MS (ES+, m/z): 415.3 [(M+H)+]; Rt=0.688 min.

Step 5: (E)-3-((3-(2-(2-(4-(azetidin-1-yl)-N-methyl-but-2-enamido) acetamido) ethyl) phenyl) amino)-6-ethyl-5-isopropoxypyrazine-2-carboxamide

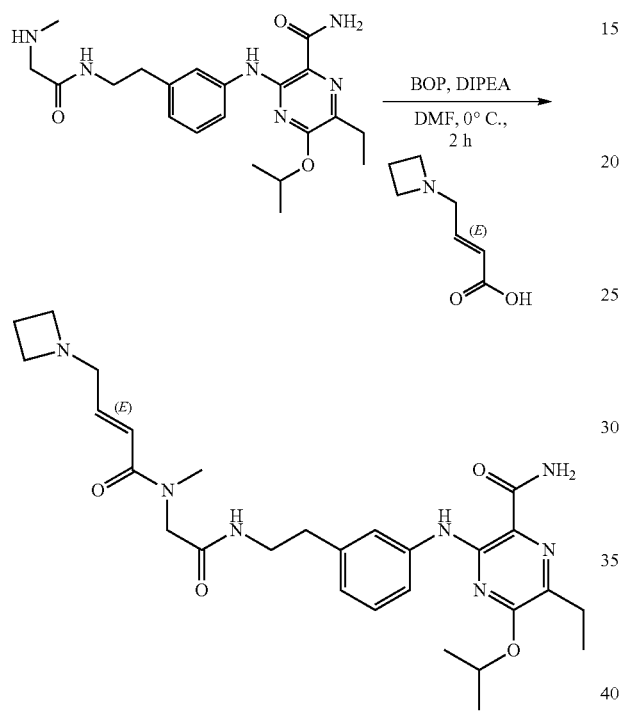

To a solution of (E)-4-(azetidin-1-yl)but-2-enoic acid (636.62 mg, 2.49 mmol, 2.5 eq, TFA) in DMF (4 mL) was added DIPEA (1.29 g, 9.98 mmol, 1.74 mL, 10 eq), 6-ethyl-5-isopropoxy-3-((3-(2-(2-(methylamino)acetamido)ethyl) phenyl)amino)pyrazine-2-carboxamide (450 mg, 997.87 μmol, 1 eq, HCl) and BOP (662.01 mg, 1.50 mmol, 1.5 eq). The mixture was stirred at 0° C. for 2 hours. The residue was purified by prep-HPLC (column: Waters Xbridge BEH C18 100*30 mm*10 um; mobile phase: [water (NH4HCO3)-ACN]; B %: 30%-70%, 8 min) to give (E)-3-((3-(2-(2-(4-(azetidin-1-yl)-N-methylbut-2-enamido)acetamido) ethyl) phenyl)amino)-6-ethyl-5-isopropoxypyrazine-2-carboxamide (61.55 mg, 114.48 μmol, 11.47% yield, 100% purity) as a white solid. $^1$H NMR (400 MHz, CDCl3) δ=10.97-10.87 (m, 1H), 7.70-7.60 (m, 1H), 7.58-7.47 (m, 2H), 7.26-7.21 (m, 1H), 6.89-6.75 (m, 2H), 6.42-6.34 (m, 1H), 5.39-5.26 (m, 2H), 4.04-3.94 (m, 2H), 3.62-3.49 (m, 2H), 3.28-3.15 (m, 5H), 3.11 (s, 2H), 3.03-2.92 (m, 1H), 2.85-2.77 (m, 2H), 2.72 (q, J=7.42 Hz, 2H), 2.17-2.06 (m, 2H), 1.60 (br s, 2H), 1.45 (d, J=6.25 Hz, 6H), 1.25 (t, J=7.44 Hz, 3H). LC-MS (ES+, m/z): 538.3 [(M+H)+]; Rt=2.956 min. HRMS (EI): m/z [M+H]+ found: 538.3119.

Example 74

Compound 604

(E)-3-((2-(2-(2-(4-(azetidin-1-yl)-N-methylbut-2-enamido) acetamido) ethyl) pyridin-4-yl) amino)-6-ethyl-5-isobutylpyrazine-2-carboxamide Step 1: tert-butyl (2-(4-((3-cyano-5-ethyl-6-isobutylpyrazin-2-yl) amino) pyridin-2-yl)ethyl) carbamate

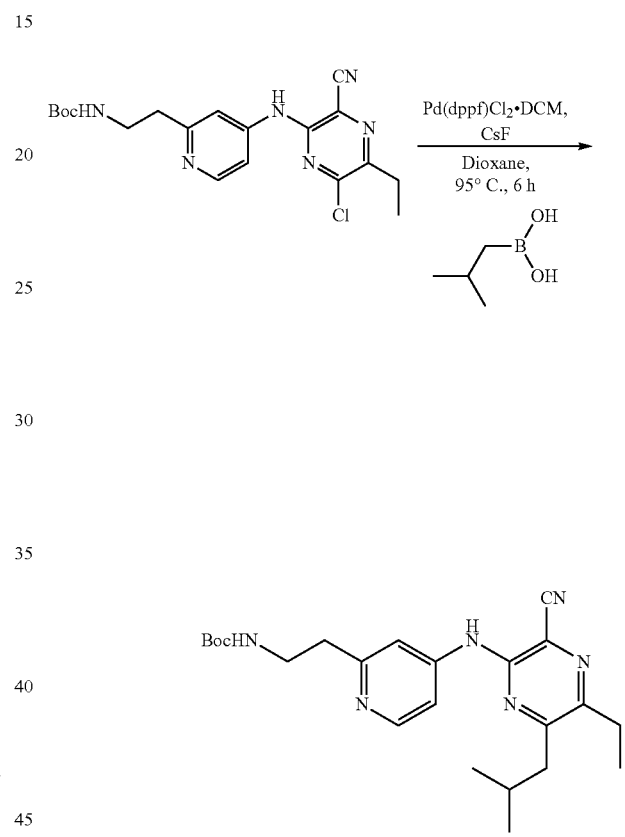

A mixture of tert-butyl (2-(4-((6-chloro-3-cyano-5-ethylpyrazin-2-yl)amino)pyridin-2-yl)ethyl)carbamate (1.00 g, 1.74 mmol, 1 eq), isobutylboronic acid (885.60 mg, 8.69 mmol, 5 eq), CsF (923.74 mg, 6.08 mmol, 224.48 μL, 3.5 eq), Pd(dppf)Cl2 (141.89 mg, 173.75 μmol, 0.1 eq) in dioxane (18 mL) was degassed and purged with N2 for 3 times, and then the mixture was stirred at 95° C. for 6 hours under N2 atmosphere. The residue was dissolved in DCM (20 mL), scavenger (Pd) was added and then stirred at 25° C. for 1 hour, and then filtered. The residue was partitioned between EtOAc (80 mL) and water (40 mL) and then separated. The aqueous was extracted with EtOAc (40 mL*3). The combined organics were washed with saturated brined (40 mL), dried over MgSO4, filtered and concentrated. The residue was purified by column chromatography (SiO2, Ethyl acetate) to give tert-butyl (2-(4-((3-cyano-5-ethyl-6-isobutylpyrazin-2-yl) amino) pyridin-2-yl) ethyl) carbamate (500 mg, 1.18 mmol, 67.78% yield) was obtained as a yellow solid. LCMS (ES+, m/z): 425.2 [(M+H)+]; Rt=1.443 min.

Step 2: tert-butyl (2-(4-((3-carbamoyl-5-ethyl-6-isobutylpyrazin-2-yl) amino) pyridin-2-yl) ethyl) carbamate

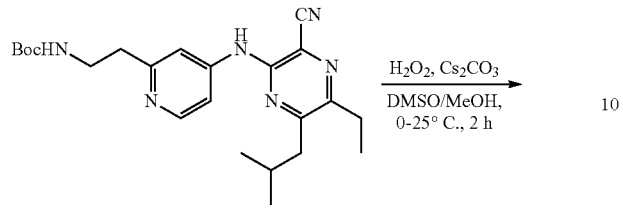

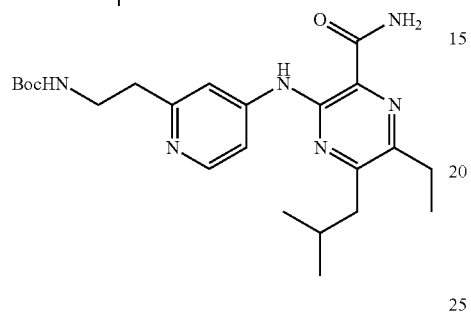

To a solution of tert-butyl (2-(4-((3-cyano-5-ethyl-6-isobutylpyrazin-2-yl) amino) pyridin-2-yl) ethyl) carbamate (500 mg, 1.18 mmol, 1 eq) in MeOH (4 mL) and DMSO (0.4 mL) was added $Cs_2CO_3$ (767.47 mg, 2.36 mmol, 2 eq) and $H_2O_2$ (620 mg, 5.47 mmol, 525.42 μL, 30% purity, 4.64 eq) at 0° C. The mixture was stirred at 25° C. for 2 hours. The reaction mixture was quenched by addition $H_2O$ (15 mL) and extracted with ethyl acetate (15 mL*3). The combined organic layers were washed with saturated $Na_2S_2O_3$ (15 mL), dried over anhydrous $Na_2SO_4$, filtered and concentrated under reduced pressure to give tert-butyl (2-(4-((3-carbamoyl-5-ethyl-6-isobutylpyrazin-2-yl) amino) pyridin-2-yl) ethyl) carbamate (500 mg, crude) as a yellow solid. LCMS (ES+, m/z): 443.3 [(M+H)$^+$]; Rt=0.709 min.

Step 3: 3-((2-(2-aminoethyl) pyridin-4-yl) amino)-6-ethyl-5-isobutylpyrazine-2-carboxamide

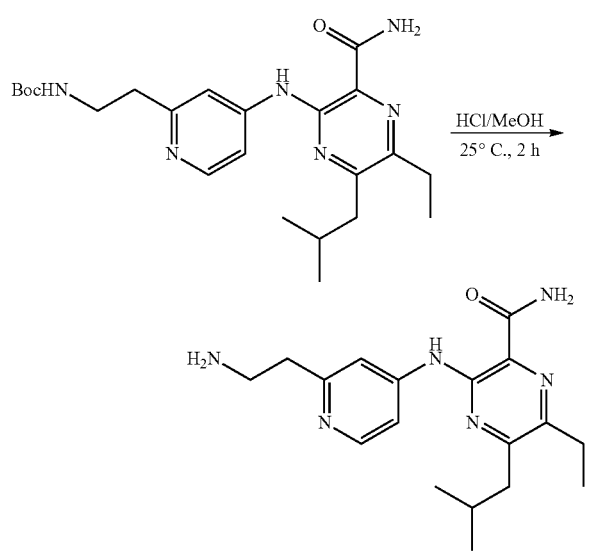

To a solution of tert-butyl (2-(4-((3-carbamoyl-5-ethyl-6-isobutylpyrazin-2-yl) amino) pyridin-2-yl) ethyl) carbamate (500 mg, 1.13 mmol, 1 eq) was added HCl/MeOH (4 M, 40 mL, 141.62 eq). The mixture was stirred at 25° C. for 2 hours. The reaction mixture was concentrated under reduced pressure to remove solvent to give 3-((2-(2-aminoethyl) pyridin-4-yl) amino)-6-ethyl-5-isobutylpyrazine-2-carboxamide (400 mg, crude, HCl) as a yellow solid. LC-MS (ES+, m/z): 343.2 [(M+H)$^+$]; Rt=0.554 min.

Step 4: tert-butyl (2-((2-(4-((3-carbamoyl-5-ethyl-6-isobutylpyrazin-2-yl) amino) pyridin-2-yl) ethyl) amino)-2-oxoethyl) (methyl)carbamate

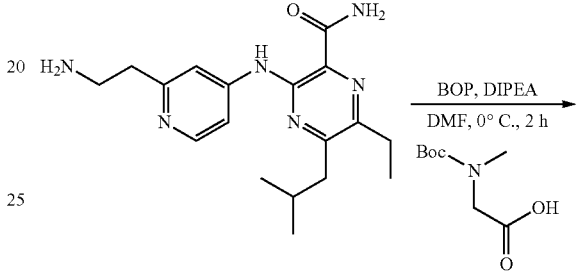

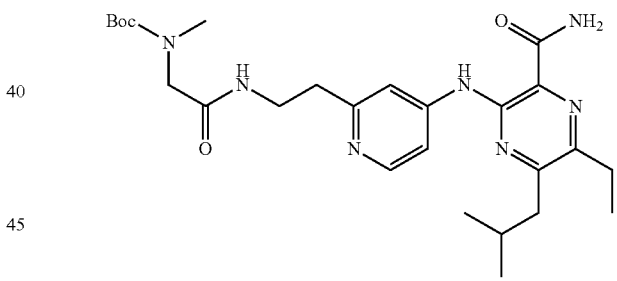

To a solution of N-(tert-butoxycarbonyl)-N-methylglycine (331.52 mg, 1.75 mmol, 1.5 eq) in DMF (3 mL) was added DIPEA (1.51 g, 11.68 mmol, 2.03 mL, 10 eq), 3-((2-(2-aminoethyl)pyridin-4-yl)amino)-6-ethyl-5-isobutylpyrazine-2-carboxamide (400 mg, 1.17 mmol, 1 eq, HCl) and BOP (774.94 mg, 1.75 mmol, 1.5 eq) at 0° C. The mixture was stirred at 0° C. for 2 hrs. LCMS showed the reaction was completed. The reaction mixture was diluted with EtOAc (50 mL) and water (50 mL) and extracted with EtOAc (50 mL*3). The combined organic layers were washed with saturated brine (50 mL), dried over $Na_2SO_4$, filtered, and concentrated under reduced pressure to give a residue. The residue was purified by prep-TLC ($SiO_2$, DCM: MeOH=10:1, 0.5% $Et_3N$) to give tert-butyl (2-((2-(4-((3-carbamoyl-5-ethyl-6-isobutylpyrazin-2-yl) amino) pyridin-2-yl) ethyl) amino)-2-oxoethyl) (methyl) carbamate (450 mg, 876.12 mol, 75.00% yield) as a light-yellow solid. LCMS (ES+, m/z): 514.3 [(M+H)$^+$]; Rt=0.686 min.

Step 5: 6-ethyl-5-isobutyl-3-((2-(2-(2-(methyl-amino) acetamido) ethyl) pyridin-4-yl) amino) pyrazine-2-carboxamide

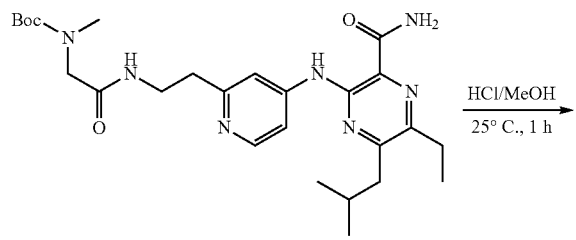

To a solution of tert-butyl (2-((2-(4-((3-carbamoyl-5-ethyl-6-isobutylpyrazin-2-yl) amino) pyridin-2-yl) ethyl) amino)-2-oxoethyl) (methyl)carbamate (450 mg, 876.12 µmol, 1 eq) was added HCl/MeOH (4 M, 40 mL, 182.62 eq). The mixture was stirred at 25° C. for 1 hr. LCMS showed the reaction was completed. The reaction mixture was concentrated under reduced pressure to remove solvent to give 6-ethyl-5-isobutyl-3-((2-(2-(2-(methylamino) acetamido) ethyl) pyridin-4-yl) amino) pyrazine-2-carboxamide (400 mg, crude, HCl) as a yellow solid. LC-MS (ES+, m/z): 414.3 [(M+H)+]; Rt=0.549 min.

Step 6: (E)-3-((2-(2-(2-(4-(azetidin-1-yl)-N-methyl-but-2-enamido) acetamido) ethyl) pyridin-4-yl) amino)-6-ethyl-5-isobutylpyrazine-2-carboxamide

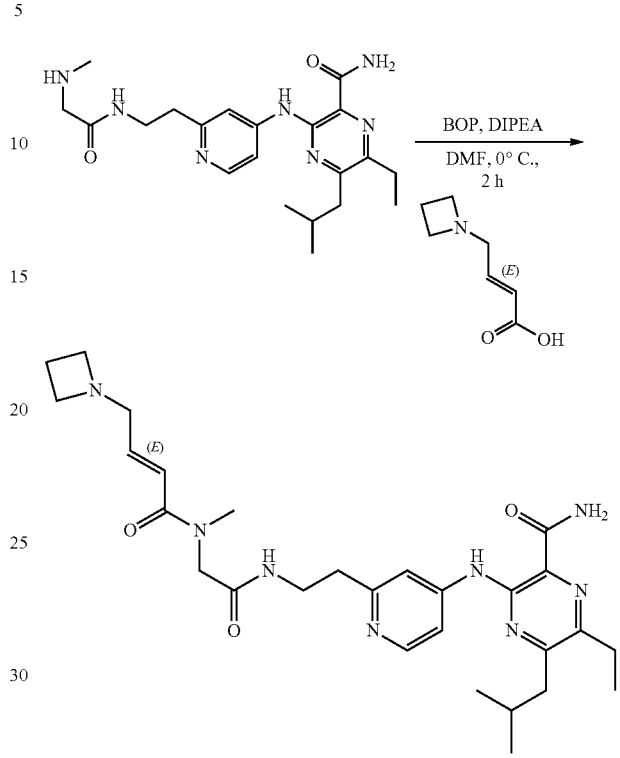

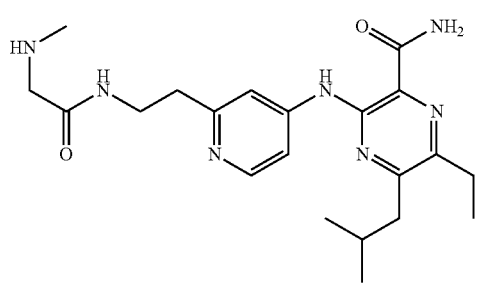

To a solution of (E)-4-(azetidin-1-yl)but-2-enoic acid (567.12 mg, 2.22 mmol, 2.5 eq, TFA) in DMF (5 mL) was added DIEA (1.15 g, 8.89 mmol, 1.55 mL, 10 eq) and 6-ethyl-5-isobutyl-3-((2-(2-(2-(methylamino)acetamido) ethyl)pyridin-4-yl)amino)pyrazine-2-carboxamide (400 mg, 888.94 µmol, 1 eq, HCl) and BOP (589.74 mg, 1.33 mmol, 1.5 eq). The mixture was stirred at 0° C. for 2 hrs. LCMS showed the reaction was completed. The residue was purified by prep-HPLC (column: Phenomenex Luna C18 75*30 mm*3 um; mobile phase: [water (TFA)-ACN]; B %: 5%-35%, 8 min). The residue was diluted with DCM 15 mL and saturated Na$_2$CO$_3$ aqueous solution 15 mL and extracted with DCM 30 mL (10 mL*3). The combined organic layers were washed with saturated brine (15 mL), dried over Na$_2$SO$_4$, filtered and concentrated under reduced pressure to give (E)-3-((2-(2-(2-(4-(azetidin-1-yl)-N-methylbut-2-enamido)acetamido)ethyl)pyridin-4-yl)amino)-6-ethyl-5-isobutylpyrazine-2-carboxamide (103.16 mg, 190.19 µmol, 21.39% yield, 98.94% purity) as a yellow solid. $^1$H NMR (400 MHz, CDCl$_3$) δ=11.05 (br s, 1H), 8.33-8.26 (m, 1H), 7.96-7.89 (m, 1H), 7.67-7.49 (m, 2H), 7.41-7.34 (m, 1H), 6.87-6.72 (m, 1H), 6.47-6.16 (m, 1H), 5.71 (s, 1H), 4.11-4.00 (m, 2H), 3.74-3.62 (m, 2H), 3.29-3.23 (m, 2H), 3.23-3.16 (m, 2H), 3.16-3.11 (m, 3H), 3.11-2.97 (m, 2H), 2.94-2.88 (m, 2H), 2.80 (q, J=7.42 Hz, 2H), 2.73 (d, J=7.00 Hz, 2H), 2.36-2.26 (m, 1H), 2.14-2.01 (m, 2H), 1.29 (d, J=7.44 Hz, 3H), 1.05 (d, J=6.63 Hz, 6H); HRMS (EI): m/z [M+H]+ found: 537.3302. LCMS (ES+, m/z): 537.3 [(M+H)+]; Rt=1.894 min;

Example 75

Compound 605

(S,E)-3-((2-(2-(2-(4-(dimethylamino)-N-methylbut-2-enamido) propanamido) ethyl) pyridin-4-yl) amino)-6-ethyl-5-(isopropyl (methyl) amino) pyrazine-2-carboxamide

Step 1: tert-butyl (2-(4-((3-carbamoyl-6-chloro-5-ethylpyrazin-2-yl) amino) pyridin-2-yl) ethyl) carbamate

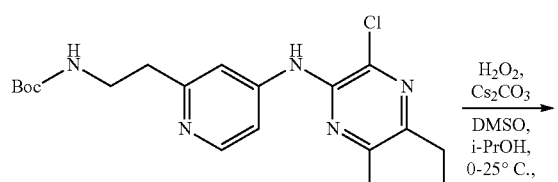

To a solution of tert-butyl (2-(4-((6-chloro-3-cyano-5-ethylpyrazin-2-yl) amino) pyridin-2-yl) ethyl) carbamate (1.8 g, 4.47 mmol, 1 eq) in DMSO (5 mL) and i-PrOH (20 mL) at 0° C., Cs$_2$CO$_3$ (5.82 g, 17.87 mmol, 4 eq) and H$_2$O$_2$ (8.11 g, 71.49 mmol, 6.87 mL, 30% purity, 16 eq) was added. The mixture was allowed to warm to 25° C. and stirred for 17 hours. The reaction mixture was quenched by addition H$_2$O (100 mL) and extracted with ethyl acetate (100 mL*2). The combined organic layers were washed with saturated Na$_2$S$_2$O$_3$ (100 mL), dried over anhydrous Na$_2$SO$_4$, filtered, and concentrated under reduced pressure to give a residue. The crude product was purified by chromatography on silica gel (Ethyl acetate:Petroleum ether=5:1) to give tert-butyl (2-(4-((3-carbamoyl-6-chloro-5-ethylpyrazin-2-yl) amino) pyridin-2-yl) ethyl) carbamate (750 mg, 1.78 mmol, 19.94% yield) as yellow solid. $^1$H NMR (400 MHz, DMSO-d$_6$) δ=11.56-11.46 (m, 1H), 8.42-8.31 (m, 2H), 8.20-8.13 (m, 1H), 7.66-7.58 (m, 1H), 7.37-7.30 (m, 1H), 6.93-6.80 (m, 1H), 3.31-3.25 (m, 2H), 2.90-2.79 (m, 4H), 1.38-1.35 (m, 9H), 1.31-1.25 (m, 3H). LCMS (ES+, m/z): 421.3 [(M+H)$^+$]; Rt=0.543 min.

Step 2: tert-butyl (2-(4-((3-carbamoyl-5-ethyl-6-(isopropyl (methyl) amino) pyrazin-2-yl) amino) pyridin-2-yl) ethyl) carbamate

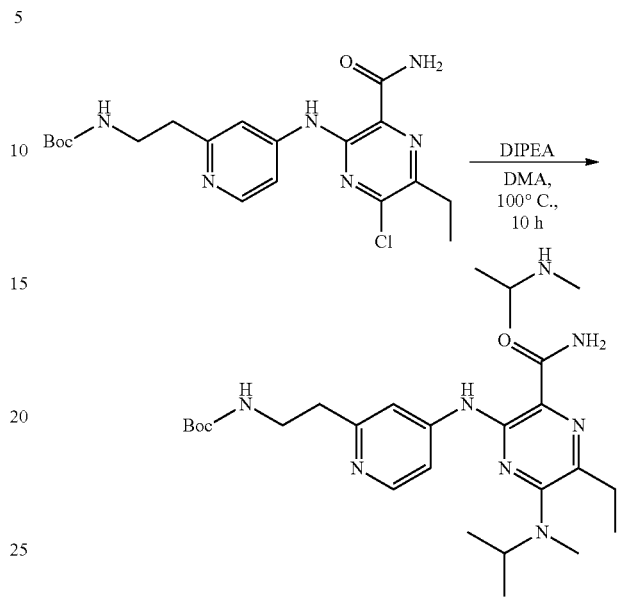

To a solution of tert-butyl (2-(4-((3-carbamoyl-6-chloro-5-ethylpyrazin-2-yl) amino) pyridin-2-yl) ethyl) carbamate (300 mg, 712.77 mol, 1 eq), N-methylpropan-2-amine (521.30 mg, 7.13 mmol, 742.59 µL, 10 eq) in DMA (3 mL), DIPEA (1.84 g, 14.26 mmol, 2.48 mL, 20 eq) was added. The mixture was stirred at 100° C. for 10 hrs. LCMS showed the reaction was completed. The mixture was poured into water (50 mL) and extracted with EtOAc (530 mL*2). The organic layers were combined, washed with water (50 mL*2), saturated brine (50 mL*2), dried over Na$_2$SO$_4$, filtered, concentrated under reduced pressure to give a residue. The crude product was purified by chromatography on silica gel (Ethyl acetate:Petroleum ether=5:1) to give tert-butyl (2-(4-((3-carbamoyl-5-ethyl-6-(isopropyl (methyl) amino) pyrazin-2-yl) amino) pyridin-2-yl) ethyl) carbamate (210 mg, 458.95 µmol, 64.39% yield) as yellow solid. $^1$H NMR (400 MHz, DMSO-d$_6$) δ=11.52-11.47 (m, 1H), 8.37-8.28 (m, 1H), 7.94-7.85 (m, 1H), 7.70-7.56 (m, 2H), 7.51-7.41 (m, 1H), 6.96-6.85 (m, 1H), 4.41-4.29 (m, 1H), 3.34-3.28 (m, 2H), 2.97 (s, 3H), 2.86-2.77 (m, 4H), 1.41 (s, 9H), 1.34-1.25 (m, 9H). LCMS (ES+, m/z): 458.3 [(M+H)$^+$]; Rt=0.635 min.

Step 3: tert-butyl (2-(4-((3-carbamoyl-5-ethyl-6-(isopropyl (methyl) amino) pyrazin-2-yl) amino) pyridin-2-yl) ethyl) carbamate

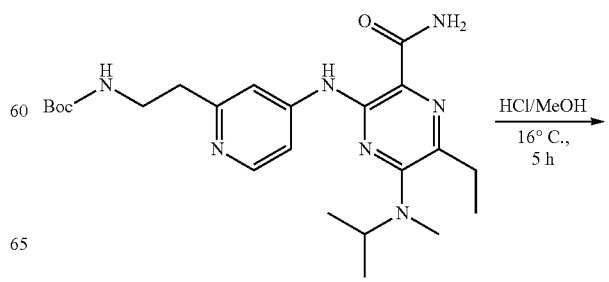

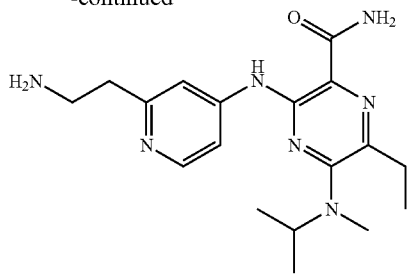

The mixture tert-butyl (2-(4-((3-carbamoyl-5-ethyl-6-(isopropyl (methyl) amino) pyrazin-2-yl) amino) pyridin-2-yl) ethyl) carbamate (210 mg, 458.95 μmol, 1 eq) and HCl/MeOH (4 M, 25 mL, 217.89 eq) was stirred at 16° C. for 5 hours. The reaction mixture was concentrated under reduced pressure to give 3-((2-(2-aminoethyl) pyridin-4-yl) amino)-6-ethyl-5-(isopropyl (methyl) amino) pyrazine-2-carboxamide (200 mg, crude) as yellow solid. LCMS (ES+, m/z): 358.3 [(M+H)+]; Rt=0.331 min.

Step 4: tert-butyl (S)-(1-((2-(4-((3-carbamoyl-5-ethyl-6-(isopropyl (methyl) amino) pyrazin-2-yl) amino) pyridin-2-yl) ethyl) amino)-1-oxopropan-2-yl) (methyl) carbamate

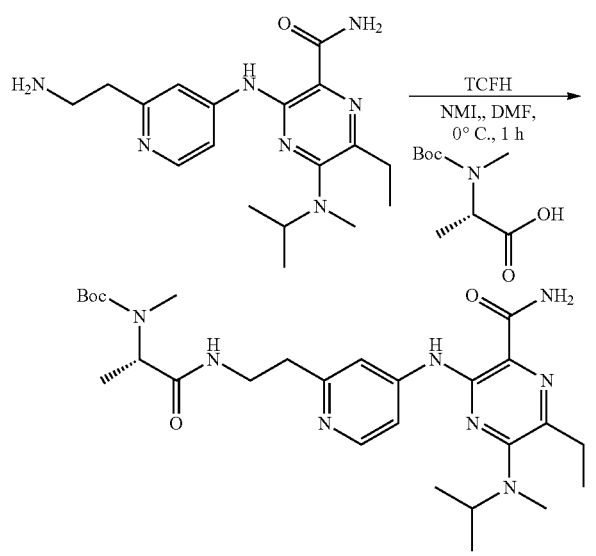

To a solution of 3-((2-(2-aminoethyl) pyridin-4-yl) amino)-6-ethyl-5-(isopropyl (methyl) amino) pyrazine-2-carboxamide (200 mg, 559.52 μmol, 1 eq), N-(tert-butoxycarbonyl)-N-methyl-L-alanine (170.57 mg, 839.27 μmol, 1.5 eq), NMI (459.38 mg, 5.60 mmol, 446.00 μL, 10 eq) in DMF (2 mL) at 0° C., TCFH (235.48 mg, 839.27 mol, 1.5 eq) was added. The mixture was stirred at 0° C. for 1 hr. LCMS showed the reaction was completed. The mixture was poured into water (40 mL) and extracted with EtOAc (50 mL*2). The organic layers were combined, washed with water (40 mL*2), saturated brine (40 mL*2), dried over Na₂SO₄, filtered, concentrated under reduced pressure to give a residue. The crude product was purified by chromatography on silica gel (Dichloromethane:Methanol=10:1) to give tert-butyl (S)-(1-((2-(4-((3-carbamoyl-5-ethyl-6-(isopropyl (methyl) amino) pyrazin-2-yl) amino) pyridin-2-yl) ethyl) amino)-1-oxopropan-2-yl) (methyl) carbamate (200 mg, 368.55 μmol, 65.87% yield) as yellow solid. ¹H NMR (400 MHz, DMSO-d₆) δ=11.60-11.44 (m, 1H), 8.37-8.30 (m, 1H), 7.92 (br d, J=2.1 Hz, 2H), 7.69 (br d, J=2.3 Hz, 1H), 7.63 (s, 1H), 7.54-7.44 (m, 1H), 4.37-4.31 (m, 1H), 3.44 (br s, 2H), 2.96-2.94 (m, 2H), 2.90-2.74 (m, 9H), 1.41 (br s, 9H), 1.34-1.20 (m, 12H). LC-MS (ES+, m/z): 543.3 [(M+H)+]; Rt=0.422 min.

Step 5: (S)-6-ethyl-5-(isopropyl (methyl) amino)-3-((2-(2-(2-(methylamino) propanamido) ethyl) pyridin-4-yl) amino) pyrazine-2-carboxamide

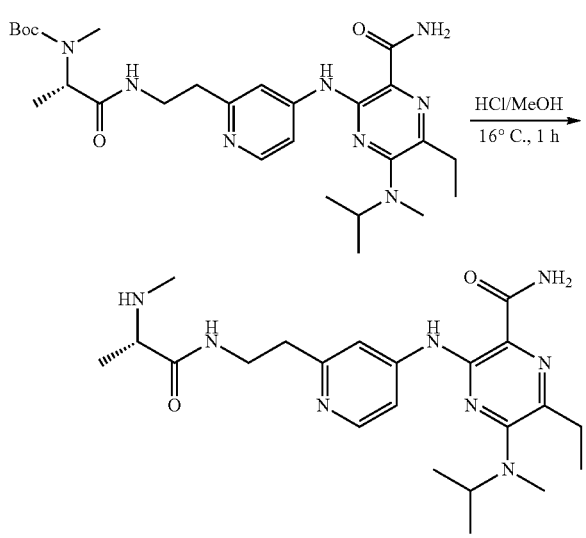

The mixture tert-butyl (S)-(1-((2-(4-((3-carbamoyl-5-ethyl-6-(isopropyl (methyl) amino) pyrazin-2-yl) amino) pyridin-2-yl) ethyl) amino)-1-oxopropan-2-yl) (methyl) carbamate (200 mg, 368.55 μmol, 1 eq) and HCl/MeOH (4 M, 20 mL, 217.07 eq) was stirred at 16° C. for 1 hour. The reaction mixture was concentrated under reduced pressure to give (S)-6-ethyl-5-(isopropyl (methyl) amino)-3-((2-(2-(2-(methylamino) propanamido) ethyl) pyridin-4-yl) amino) pyrazine-2-carboxamide (210 mg, crude) as yellow solid. LCMS (ES+, m/z): 443.4 [(M+H)+]; Rt=0.331 min.

Step 6: (S,E)-3-((2-(2-(2-(4-(dimethylamino)-N-methylbut-2-enamido) propanamido) ethyl) pyridin-4-yl) amino)-6-ethyl-5-(isopropyl (methyl) amino) pyrazine-2-carboxamide

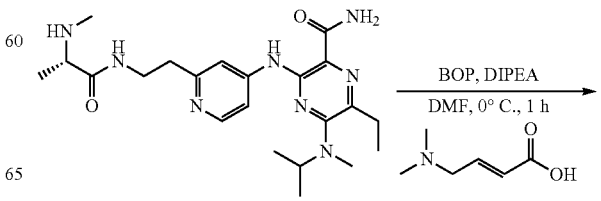

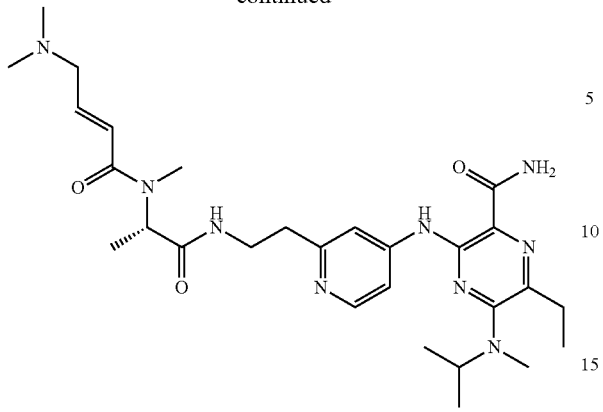

To a solution of (S)-6-ethyl-5-(isopropyl (methyl) amino)-3-((2-(2-(2-(methylamino) propanamido) ethyl) pyridin-4-yl) amino) pyrazine-2-carboxamide (210 mg, 438.40 mol, 1 eq, HCl), (E)-4-(dimethylamino) but-2-enoic acid (108.91 mg, 657.60 μmol, 1.5 eq, HCl), DIPEA (566.60 mg, 4.38 mmol, 763.61 μL, 10 eq) in DMF (2 mL) at 0° C., BOP (290.84 mg, 657.60 μmol, 1.5 eq) was added. The mixture was stirred at 0° C. for 1 hour. The mixture was filtered to give a residue. The crude was purified by prep-HPLC (column: Waters Xbridge BEH C18 100*30 mm*10 um; mobile phase: [water (NH₄HCO₃)-ACN]; B %: 25%-55%, 8 min) to give (S,E)-3-((2-(2-(2-(4-(dimethylamino)-N-methylbut-2-enamido) propanamido) ethyl) pyridin-4-yl) amino)-6-ethyl-5-(isopropyl (methyl) amino) pyrazine-2-carboxamide (51.85 mg, 87.50 μmol, 19.96% yield, 93.44% purity) as yellow solid. ¹H NMR (400 MHz, DMSO-d₆) δ=11.50-11.42 (m, 1H), 8.20 (s, 1H), 7.85 (br d, J=2.1 Hz, 2H), 7.66-7.58 (m, 1H), 7.57-7.50 (m, 1H), 7.48-7.42 (m, 1H), 6.67-6.35 (m, 2H), 5.06-4.49 (m, 1H), 4.37-4.20 (m, 1H), 3.53-3.36 (m, 2H), 3.06-2.69 (m, 12H), 2.23-1.99 (m, 6H), 1.30-1.15 (m, 12H); HRMS (EI): m/z (M+H)⁺ found: 554.3552. LC-MS (ES+, m/z): 554.3 [(M+H)⁺]; Rt=1.919 min.

Example 76

Compound 606

(E)-3-((2-(2-(2-(4-(dimethylamino)-N-methylbut-2-enamido) acetamido) ethyl) pyridin-4-yl) amino)-6-ethyl-5-(ethyl(methyl)amino)pyrazine-2-carboxamide Step 1: (E)-3-((2-(2-(2-(4-(dimethylamino)-N-methylbut-2-enamido) acetamido) ethyl) pyridin-4-yl) amino)-6-ethyl-5-(ethyl(methyl)amino)pyrazine-2-carboxamide

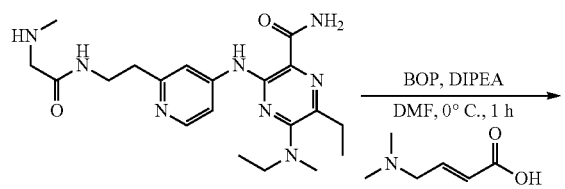

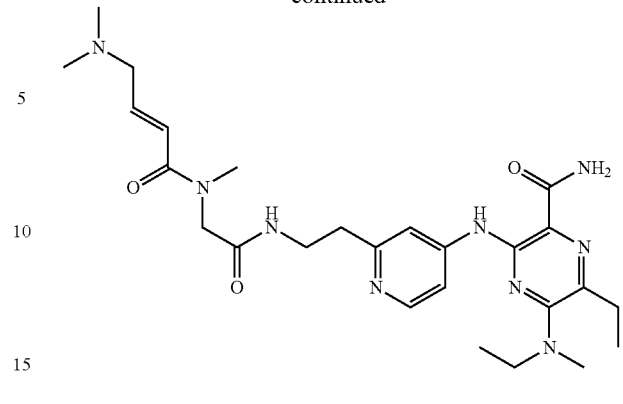

To a solution of (E)-4-(dimethylamino)but-2-enoic acid (101.93 mg, 615.48 μmol, 1.5 eq, HCl) in DMF (2 mL) was added DIPEA (530.31 mg, 4.10 mmol, 10 eq), 6-ethyl-5-(ethyl(methyl)amino)-3-((2-(2-(2-(methylamino)acetamido) ethyl)pyridin-4-yl)amino)pyrazine-2-carboxamide (200 mg, 410.32 μmol, 1 eq, 2HCl) at 0° C., and then BOP (272.21 mg, 615.48 mol, 1.5 eq). The mixture was stirred at 0° C. for 1 hour. The reaction mixture was filtered to give a residue. The residue was purified by prep-HPLC (column: Waters Xbridge Prep OBD C18 150*40 mm*10 um; mobile phase: [water (NH₄HCO₃)-ACN]; B %: 25%-55%, 8 min) to afford (E)-3-((2-(2-(2-(4-(dimethylamino)-N-methylbut-2-enamido)acetamido)ethyl) pyridin-4-yl)amino)-6-ethyl-5-(ethyl(methyl)amino)pyrazine-2-carboxamide (40.68 mg, 76.74 μmol, 18.7% yield) as a yellow solid. ¹H NMR (400 MHz, DMSO-d₆) δ=11.47-11.41 (m, 1H), 8.30-8.23 (m, 1H), 7.95 (t, J=5.4 Hz, 1H), 7.85-7.79 (m, 1H), 7.60-7.51 (m, 2H), 7.48-7.40 (m, 1H), 6.62-6.25 (m, 2H), 3.98-3.90 (m, 2H), 3.51-3.38 (m, 4H), 3.09-3.05 (m, 3H), 3.03-3.00 (m, 3H), 2.92-2.88 (m, 1H), 2.82-2.73 (m, 5H), 2.14-2.05 (m, 6H), 1.22 (dt, J=4.6, 7.1 Hz, 6H). LC-MS (ES+, m/z): 526.3 [(M+H)⁺]; Rt=1.795 min. HRMS (EI): m/z [M+H]⁺ found: 526.3239.

Example 77

Compound 607

(E)-3-((3-(2-(2-(4-(azetidin-1-yl)-N-methylbut-2-enamido) acetamido) ethyl)-4-fluorophenyl) amino)-5-cyclopropyl-6-ethylpyrazine-2-carboxamide Step 1: 2-(2-fluoro-5-nitrophenyl) acetonitrile

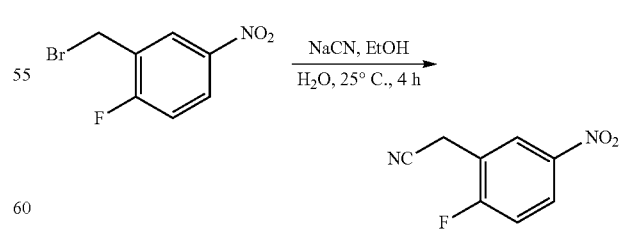

To a solution of NaCN (2.450 g, 49.99 mmol, 1.95 eq) in H₂O (20 mL) at 25° C., a mixture of 2-(bromomethyl)-1-fluoro-4-nitrobenzene (6 g, 25.64 mmol, 1 eq) in EtOH (90 mL) was added dropwise. The mixture was stirred at 25° C. for 4 hrs. LCMS indicated the reaction was completed. The

Step 2: 2-(2-fluoro-5-nitrophenyl) ethan-1-amine

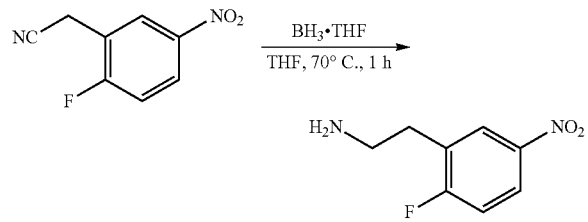

To a solution of 2-(2-fluoro-5-nitro-phenyl) acetonitrile (3 g, 16.65 mmol, 1 eq) in THF (50 mL), BH$_3$·THF (1 M, 69.00 mL, 4.14 eq) was added dropwise. The mixture was refluxed at 70° C. for 2 hrs. TLC indicated the reaction was completed. The mixture was added dropwise to MeOH (100 mL) and then refluxed at 70° C. for 1 hr, and then concentrated to dryness to give 2-(2-fluoro-5-nitrophenyl) ethan-1-amine (3 g, crude) as yellow oil.

Step 3: tert-butyl (2-fluoro-5-nitrophenethyl) carbamate

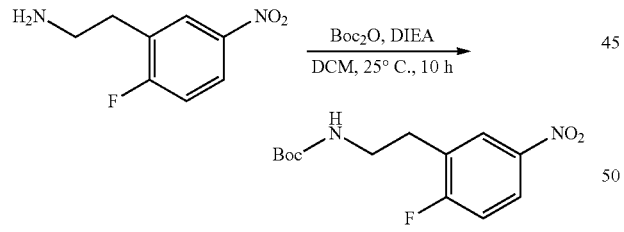

A mixture of 2-(2-fluoro-5-nitrophenyl) ethan-1-amine (3 g, 16.29 mmol, 1 eq), Boc$_2$O (7.11 g, 32.58 mmol, 7.48 mL, 2 eq), DIPEA (10.53 g, 81.45 mmol, 14.19 mL, 5 eq) and DCM (60 mL) was stirred at 25° C. for 10 hrs. LCMS indicated the reaction was completed. The mixture was concentrated to dryness and then purified by chromatography on silica gel (Petroleum ether:Ethylacetate=5:1) to give tert-butyl (2-fluoro-5-nitrophenethyl) carbamate (2 g, 7.04 mmol, 43.19% yield) as yellow oil. $^1$H NMR (400 MHz, CDCl$_3$) δ=8.15-8.00 (m, 2H), 7.11 (t, J=9.1 Hz, 1H), 4.54 (br s, 1H), 3.34 (q, J=6.2 Hz, 2H), 2.87 (brt, J=6.7 Hz, 2H), 1.34 (s, 9H). LC-MS (ES+, m/z): 485.2 [(M+H-100)$^+$]; Rt=0.527 min.

Step 4: tert-butyl (5-amino-2-fluorophenethyl) carbamate

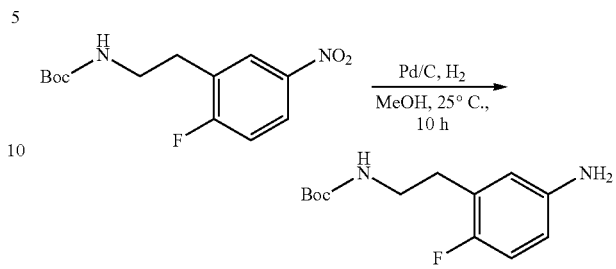

To a solution of tert-butyl (2-fluoro-5-nitrophenethyl) carbamate (2 g, 7.04 mmol, 1 eq), Pd/C (200 mg, 7.04 mmol, 50% purity, 1 eq) in MeOH (100 mL) was stirred at 25° C. for 10 hrs under 50 psi of H$_2$. LCMS indicated the reaction was completed. The mixture was filtered and concentrated to dryness to give tert-butyl (5-amino-2-fluorophenethyl) carbamate (1.5 g, crude) as yellow oil. LCMS (ES+, m/z): 155.3 [(M+H-100)$^+$]; Rt=0.319 min;

Step 5: tert-butyl (5-((3-carbamoyl-6-chloro-5-ethylpyrazin-2-yl) amino)-2-fluorophenethyl) carbamate

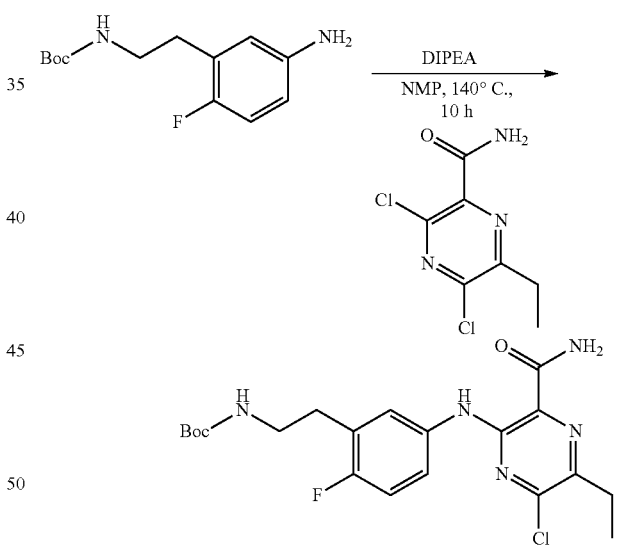

A mixture of tert-butyl (5-amino-2-fluorophenethyl) carbamate (500 mg, 1.97 mmol, 1 eq), 3,5-dichloro-6-ethylpyrazine-2-carboxamide (519.20 mg, 2.36 mmol, 1.2 eq), DIPEA (7.42 g, 57.41 mmol, 10.00 mL, 29.20 eq) and NMP (40 mL) was stirred at 140° C. for 10 hrs. LCMS indicated the reaction was completed. The mixture was poured into water (150 mL) and extracted with EtOAc (150 mL*2). The organic layers were combined and washed with water (80 mL*2), saturated brine (80 mL*2), dried over Na$_2$SO$_4$, filtered, concentrated under reduced pressure. The crude product was purified by chromatography on silica gel (Petroleum ether:Ethyl acetate=5:1) to give tert-butyl (5-((3-carbamoyl-6-chloro-5-ethylpyrazin-2-yl) amino)-2-fluorophenethyl) carbamate (500 mg, 1.14 mmol, 58.07% yield) as yellow solid. LCMS (ES+, m/z): 460.2 [(M+Na)+]; Rt=0.619 min;

Step 6: tert-butyl (5-((3-carbamoyl-6-cyclopropyl-5-ethylpyrazin-2-yl) amino)-2-fluorophenethyl) carbamate

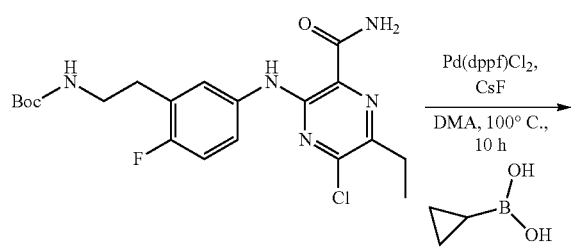

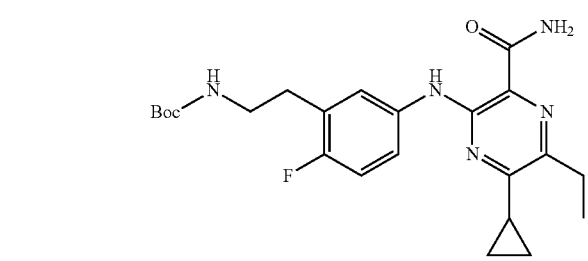

A mixture of tert-butyl (5-((3-carbamoyl-6-chloro-5-ethylpyrazin-2-yl)amino)-2-fluorophenethyl)carbamate (500 mg, 1.14 mmol, 1 eq), cyclopropylboronic acid (980.80 mg, 11.42 mmol, 10 eq), Pd(dppf)Cl$_2$ (83.55 mg, 114.18 mol, 0.1 eq), CsF (867.24 mg, 5.71 mmol, 210.75 μL, 5 eq), DMA (2 mL) was stirred at 100° C. for 10 hrs under N$_2$. LCMS indicated the reaction was completed. The mixture was poured into water (40 mL) and extracted with EtOAc (40 mL*2). The organic layers was washed with water (80 mL*2), saturated brine (80 mL*2), dried over Na$_2$SO$_4$, filtered, concentrated under reduced pressure. The residue was dissolved in DCM (30 mL), scavenger (Pd) was added and then stirred at 25° C. for 1 hr, and then filtered and concentrated. The crude was purified by prep-HPLC (column: PhenomenexLuna C18 75*30 mm*3 um; mobile phase: [H$_2$O (0.1% TFA)-ACN]; gradient: 60%-97% B over 8.0 min) to give tert-butyl (5-((3-carbamoyl-6-cyclopropyl-5-ethylpyrazin-2-yl) amino)-2-fluorophenethyl) carbamate (58 mg, 130.77 μmol, 11.45% yield) as yellow solid. $^1$H NMR (400 MHz, CDCl$_3$) δ=10.48 (br s, 1H), 7.79 (br s, 1H), 7.44-7.31 (m, 2H), 6.90 (br t, J=9.3 Hz, 1H), 5.42 (br dd, J=1.8, 2.9 Hz, 1H), 4.61-4.43 (m, 1H), 3.34 (br d, J=4.1 Hz, 2H), 2.96-2.65 (m, 4H), 2.12-2.02 (m, 1H), 1.34 (br s, 9H), 1.24 (br t, J=7.5 Hz, 3H), 0.84-0.75 (m, 4H). LC-MS (ES+, m/z): 444.3 [(M+H)+]; Rt=2.216 min;

Step 7: 3-((3-(2-aminoethyl)-4-fluorophenyl) amino)-5-cyclopropyl-6-ethylpyrazine-2-carboxamide

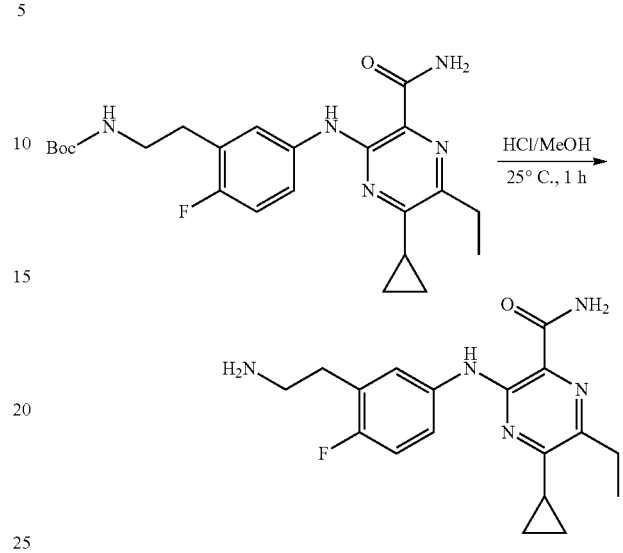

A mixture of tert-butyl (5-((3-carbamoyl-6-cyclopropyl-5-ethylpyrazin-2-yl) amino)-2-fluorophenethyl) carbamate (95 mg, 214.20 μmol, 1 eq), HCl/MeOH (4 M, 47.50 mL, 887.03 eq) was stirred at 25° C. for 1 hr. LCMS indicated the reaction was completed. The mixture was concentrated to give 3-((3-(2-aminoethyl)-4-fluorophenyl) amino)-5-cyclopropyl-6-ethylpyrazine-2-carboxamide (85 mg, crude, HCl) as yellow oil. LC-MS (ES+, m/z): 344.3 [(M+H)+]; Rt=0.400 min;

Step 8: tert-butyl (5-((3-carbamoyl-6-cyclopropyl-5-ethylpyrazin-2-yl) amino)-2-fluorophenethyl) carbamate

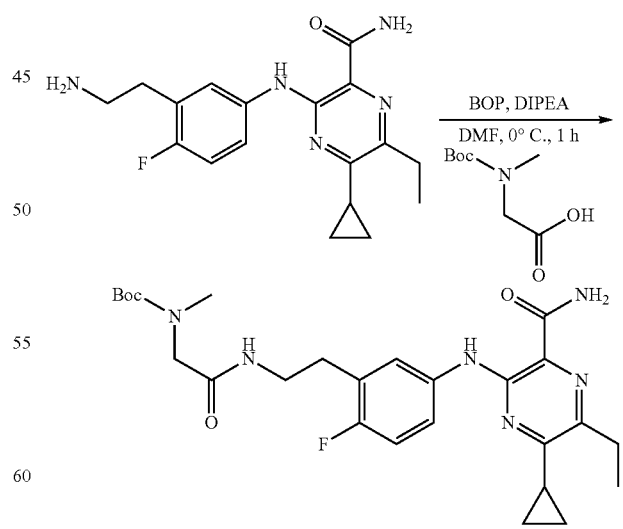

To a mixture of 3-((3-(2-aminoethyl)-4-fluorophenyl) amino)-5-cyclopropyl-6-ethylpyrazine-2-carboxamide (85 mg, 223.77 mol, 1 eq, HCl), N-(tert-butoxycarbonyl)-N-methylglycine (63.51 mg, 335.65 μmol, 1.5 eq), DIPEA (289.20 mg, 2.24 mmol, 389.76 µL, 10 eq) in DMF (2 mL) at 0° C., BOP (148.45 mg, 335.65 µmol, 1.5 eq) was added. The mixture was stirred at 0° C. for 1 hr. LCMS indicated the reaction was completed. The mixture was poured into water (40 mL) and extracted with EtOAc (40 mL*2). The organic layers were combined and washed with water (40 mL*2), saturated brine (40 mL*2), dried over Na$_2$SO$_4$, filtered, concentrated under reduced pressure. The crude product was purified by prep-TLC (Petroleum ether:Ethyl acetate=1:2) to give tert-butyl (2-((5-((3-carbamoyl-6-cyclopropyl-5-ethylpyrazin-2-yl) amino)-2-fluorophenethyl) amino)-2-oxoethyl) (methyl)carbamat (85 mg, 165.18 µmol, 73.82% yield)) as yellow oil. $^1$H NMR (400 MHz, CDCl$_3$) δ=10.54 (s, 1H), 7.76 (br d, J=1.0 Hz, 1H), 7.53-7.43 (m, 1H), 7.39-7.30 (m, 1H), 6.90 (br t, J=9.1 Hz, 1H), 6.21-5.85 (m, 1H), 5.32 (br s, 1H), 3.76 (s, 2H), 3.50 (q, J=6.0 Hz, 2H), 2.91-2.73 (m, 7H), 2.13-2.02 (m, 1H), 1.34 (s, 9H), 1.24 (t, J=7.5 Hz, 3H), 1.09 (br dd, J=2.6, 4.5 Hz, 2H), 1.05-0.99 (m, 2H); LC-MS (ES+, m/z): 515.2 [(M+H)$^+$]; Rt=0.584 min;

Step 9: 5-cyclopropyl-6-ethyl-3-((4-fluoro-3-(2-(2-(methylamino) acetamido) ethyl) phenyl)amino) pyrazine-2-carboxamide

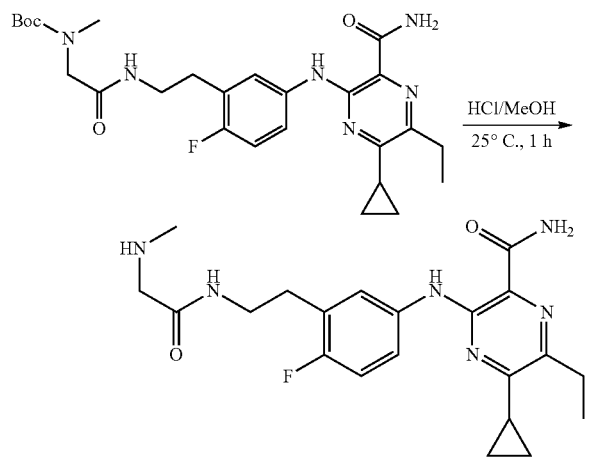

A mixture of tert-butyl (2-((5-((3-carbamoyl-6-cyclopropyl-5-ethylpyrazin-2-yl) amino)-2-fluorophenethyl) amino)-2-oxoethyl) (methyl)carbamate (85 mg, 165.18 µmol, 1 eq), HCl/MeOH (4 M, 28.33 mL, 686.12 eq) was stirred at 25° C. for 1 hr. LCMS indicated the reaction was completed. The mixture was concentrated to give 5-cyclopropyl-6-ethyl-3-((4-fluoro-3-(2-(2 (methylamino)acetamido) ethyl) phenyl) amino)pyrazine-2-carboxamide (80 mg, crude, HCl) as yellow oil. LC-MS (ES+, m/z): 415.2 [(M+H)$^+$]; Rt=0.422 min;

Step 10: (E)-3-((3-(2-(2-(4-(azetidin-1-yl)-N-methylbut-2-enamido) acetamido) ethyl)-4-fluorophenyl) amino)-5-cyclopropyl-6-ethylpyrazine-2-carboxamide

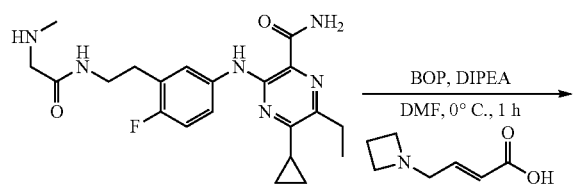

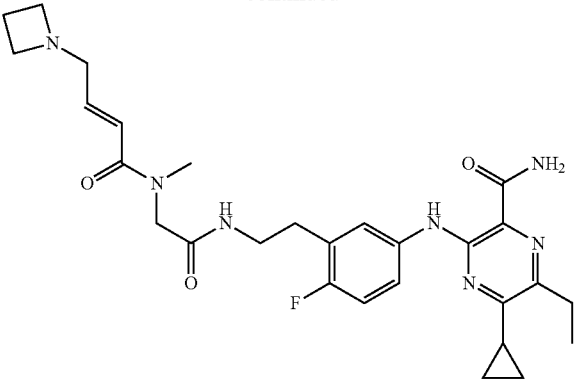

To a solution of 5-cyclopropyl-6-ethyl-3-((4-fluoro-3-(2-(2-(methylamino) acetamido) ethyl)phenyl)amino)pyrazine-2-carboxamide (80 mg, 177.41 µmol, 1 eq, HCl), (E)-4-(azetidin-1-yl)but-2-enoic acid (362.18 mg, 1.42 mmol, 8 eq, TFA), DIPEA (356.16 mg, 2.76 mmol, 480.00 µL, 15.53 eq) in DMF (0.8 mL) at 0° C., BOP (117.70 mg, 266.11 µmol, 1.5 eq) was added. The mixture was stirred at 0° C. for 1 hr. LCMS indicated the reaction was completed. The mixture was filtered. The crude was purified by prep-HPLC (column: Waters Xbridge Prep OBD C18 150*40 mm*10 um; mobile phase: [H$_2$O (10 mM NH$_4$HCO$_3$)-ACN]; gradient: 20%-500% B over 8.0 min) to give (E)-3-((3-(2-(2-(4-(azetidin-1-yl)-N-methylbut-2-enamido)acetamido) ethyl)-4-fluorophenyl)amino)-5-cyclopropyl-6-ethylpyrazine-2-carboxamide (26.84 mg, 49.92 µmol, 28.14% yield) as yellow solid. $^1$H NMR (400 MHz, DMSO-d$_6$) δ=11.03-10.92 (m, 1H), 8.22-7.92 (m, 2H), 7.87-7.77 (m, 1H), 7.54-7.36 (m, 2H), 7.17-7.04 (m, 1H), 6.52 (s, 2H), 4.00-3.83 (m, 2H), 3.28 (br s, 2H), 3.17-2.94 (m, 7H), 2.90 (q, J=7.5 Hz, 2H), 2.81-2.68 (m, 4H), 2.31-2.23 (m, 1H), 2.01-1.87 (m, 2H), 1.27 (t, J=7.5 Hz, 3H), 1.12-1.01 (m, 4H). LC-MS (ES+, m/z): 538.2 [(M+H)$^+$]; Rt=2.284 min, HRMS (EI): m/z [M+H]$^+$ found: 538.2981.

Additional Exemplary Compounds

Comparator compounds C-1, C-2, and C-3 are or can be prepared by using methods and procedures consistent with the general methods and procedures described in published literature (For example AR 110273, WO 2012/053606, WO2010/128659, U.S. Pat. Nos. 8,969,336, and 9,487,491), the content of each of which is hereby incorporated by reference.

The representative compounds prepared or can be prepared from readily available starting materials using the general methods and procedures described herein are depicted in Table 2A and 2B.

Example B1

FLT3 In Vitro Inhibitory Activity

The proliferation inhibitory effect was investigated in human AML cell lines MOLM-13 (AddexBio: C0003003) and MV-4-11 (ATCC: CRL-9591), and CML cell line K-652 (ATCC: CRL-3343). Molm-13 is heterozygous for FLT3-ITD mutation, while MV4-11 is homozygous for FLT3-ITD (Quentmeier H, et al., Leukemia. 17(1):120-4). K562 does not harbor any FLT3 mutations. Cells were maintained in RPMI-1640 medium (ThermoFisher catalog no. 61870036)

supplemented with 10% of Heat Inactivated FBS (ThermoFisher catalog no. A31605) and 1% Pen-Strep (ThermoFisher catalog no. 10378016) and cultured at 37° C. in a humidified incubator with 5% $CO_2$. Cell lines were grown by adhering to culture flasks, and the cells were maintained in a range 70%-80% confluency.

ATP is present in all metabolically active cells and is considered as a marker for cell viability and proliferation. Metabolic cell activity was determined using the CellTiter-Glo kit (Promega catalog no. G7572), an ATP monitoring system based on the production of luminescence by the reaction of ATP with added UltraGlo® recombinant luciferase (Kawano et al., 2016, PLOS One, 8; 11(7):e0158888), according to the supplier's experimental recommendations. The assay was based on a 96 well plate format.

Test compounds were dissolved at 10 mM in DMSO (Sigma catalog no. D8418; purity >99.9%) and stored at −20° C. Eight concentrations of test compound were assessed in duplicate in an individual test occasion in parallel in the selected cell lines. Gilteratinib and FF-10101 were used as reference compounds and tested in duplicate at eight concentrations. 100% of proliferation is represented by the untreated cells (0.2% DMSO).

On the day of the experiment, cells were quantified with the cell viability analyzer NucleoCounter (Chemometec NC-200) and diluted with fresh medium to obtain the cell density of about 10,000 cells per 200 µL medium. 200 µL of cell suspension were added into wells in the 96 well plate.

After 2 hours from seeding cells, compounds at desired concentrations were added using a D300e compound dispenser (Life Sciences Tecan D300) with shaking between each compound dispensed. Assay plates were incubated at 37° C. in a humidified incubator with 5% $CO_2$ On day 4 (~96 hrs after compound addition) assay plates were equilibrated at room temperature for approximately 15 min, and then 40 µL/well of the Promega CellTiterGlo® reagent was added. Contents were mixed for 5 min on an orbital shaker to promote cell lysis, and then incubated at room temperature for an additional 10 min in the dark to stabilize the luminescent signal. Luminescence was read by using a GloMax GM300 plate reader (Promega) using the luminescence for 96 well plate standard protocol.

Data was expressed as % of inhibition compared to the 0.2% DMSO (vehicle) negative control, and is calculated as follows: % inhibition=100−[(RLU sample)×100/(RLU average controls*)], where * indicates the average for 0.2% DMSO.

Results were analyzed by GraphPad (Prism) and $IC_{50}$ values were calculated by non-linear regression using four parameter-logistic equation. $IC_{50}$ values measured on day T4 (4 days) are reported in the Table 2A below: *** ≤1 nM,  1-10 nM, * 10-100 nM, ** 100-500 nM, * >500 nM.

Figure 3A:
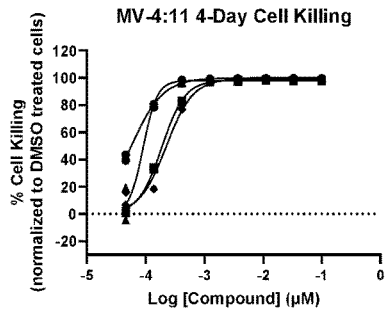
FIG. 3A depicts cell-based and biochemical activity of compounds 204, 205, 307, and 232 in MOLM-13 cells.
Figure 3B:
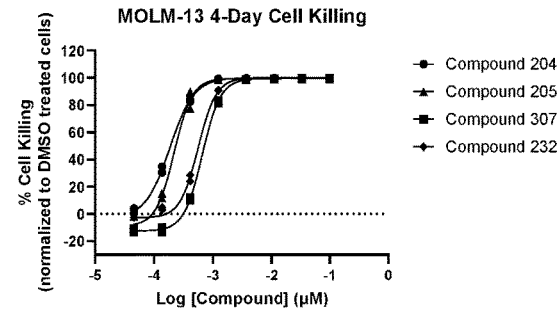
FIG. 3B depicts cell-based and biochemical activity of compounds 204, 205, 307, and 232 in K-562 cells.
Figure 4A:
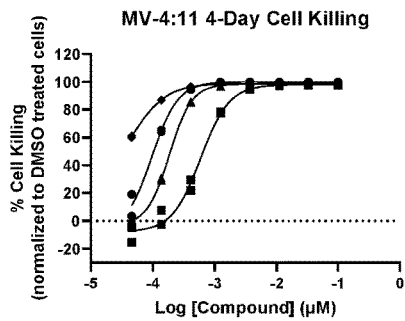
FIG. 4A depicts cell-based and biochemical activity of compounds 250, 252, 507, and 516 in MOLM-13 cells.
Figure 4B:
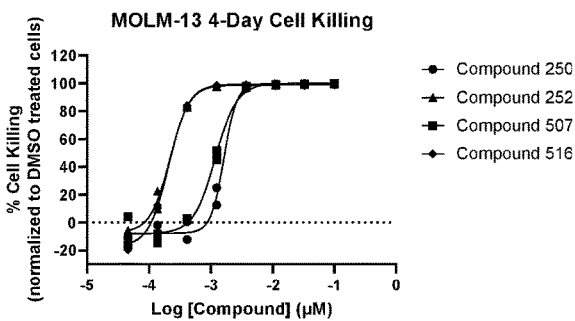
FIG. 4B depicts cell-based and biochemical activity of compounds 250, 252, 507, and 516 in K-562 cells.
Figure 5A:
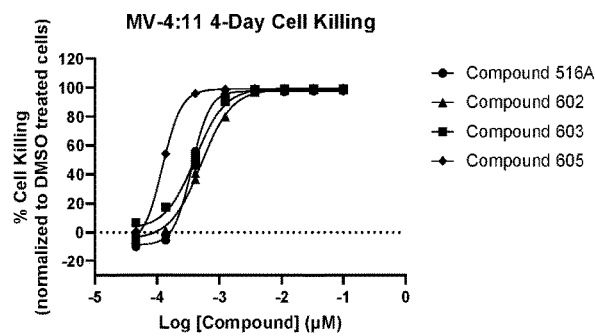
FIG. 5A depicts cell-based and biochemical activity of compounds 516A, 602, 603, and 605 in MOLM-13 cells.
Figure 5B:
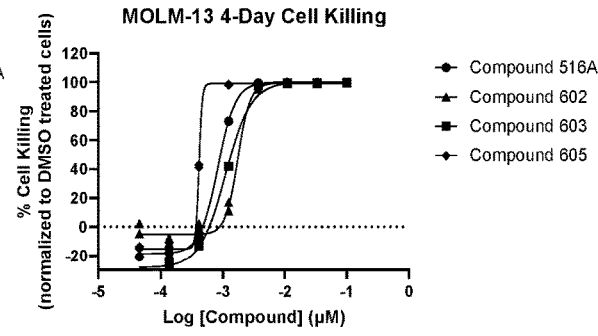
FIG. 5B depicts cell-based and biochemical activity of compounds 516A, 602, 603, and 605 in K-562 cells.

FIGS. 1, 2a, 2b, 3a, 3b, 4a, 4b, 5a, and 5b depict cell-based activity of representative compounds in various cell lines.

Compounds of the disclosure provided the following $IC_{50}$ (4 days) values:

TABLE 2A

Representative compounds and their $IC_{50}$ values

| Compd ID | Structure | MW | MOLM-13 | MV-4:11 | K-562 |
|---|---|---|---|---|---|
| 137 | 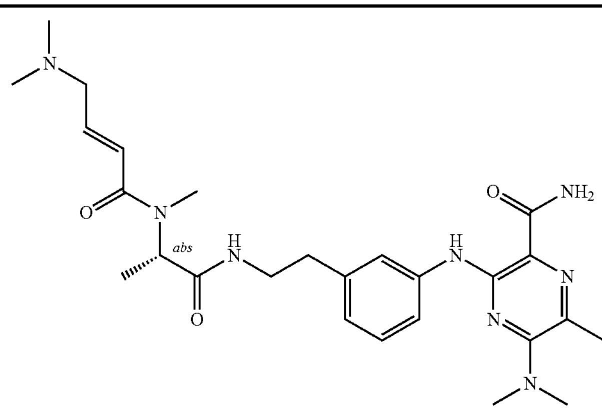 | 524.66 | *** | *** | * |
| 138 | 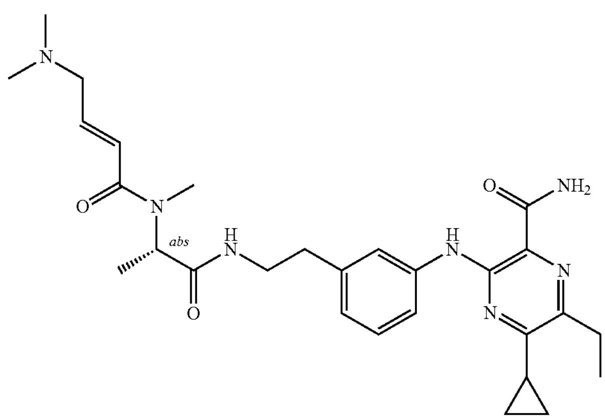 [SMILES: CCc1nc(C(N)=O)c(Nc2cccc(CCNC(=O)[C@H](C)N(C)C(=O)/C=C/CN(C)C)c2)nc1C1CC1] | 521.65 | ** | *** | * |

TABLE 2A-continued

Representative compounds and their IC$_{50}$ values

| Compd ID | Structure | MW | MOLM-13 | MV-4:11 | K-562 |
|---|---|---|---|---|---|
| 142A | 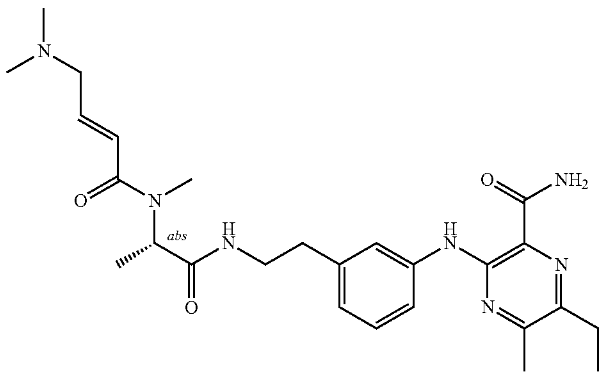 [SMILES: CCc1nc(C(N)=O)c(Nc2cccc(CCNC(=O)[C@H](C)N(C)C(=O)/C=C/CN(C)C)c2)nc1C] | 495.63 | ** | ** | * |
| 143 | 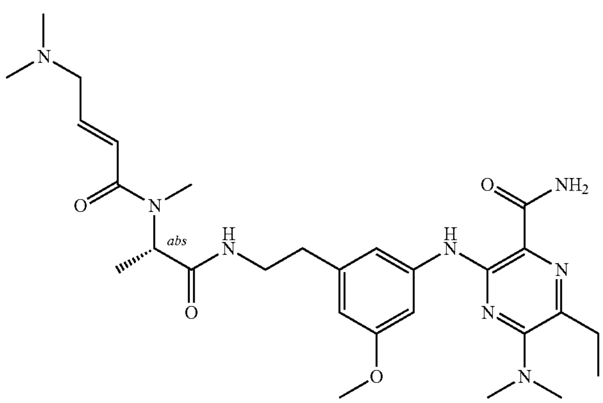 [SMILES: CCc1nc(C(N)=O)c(Nc2cc(CCNC(=O)[C@H](C)N(C)C(=O)/C=C/CN(C)C)cc(OC)c2)nc1N(C)C] | 554.68 | *** | *** | * |
| 144 | 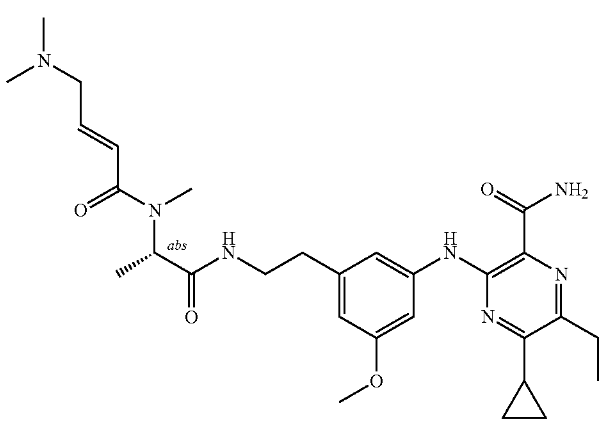 [SMILES: CCc1nc(C(N)=O)c(Nc2cc(CCNC(=O)[C@H](C)N(C)C(=O)/C=C/CN(C)C)cc(OC)c2)nc1C1CC1] | 551.68 | *** | *** | * |

TABLE 2A-continued
Representative compounds and their IC$_{50}$ values
| Compd ID | Structure | MW | MOLM-13 | MV-4:11 | K-562 |
|---|---|---|---|---|---|
| 156 | 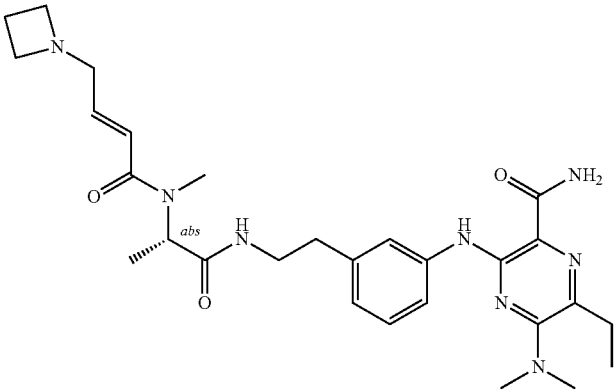 [SMILES: CCc1nc(C(N)=O)c(Nc2cccc(CCNC(=O)[C@H](C)N(C)C(=O)/C=C/CN3CCC3)c2)nc1N(C)C] | 536.67 | *** | *** | * |
| 158 | 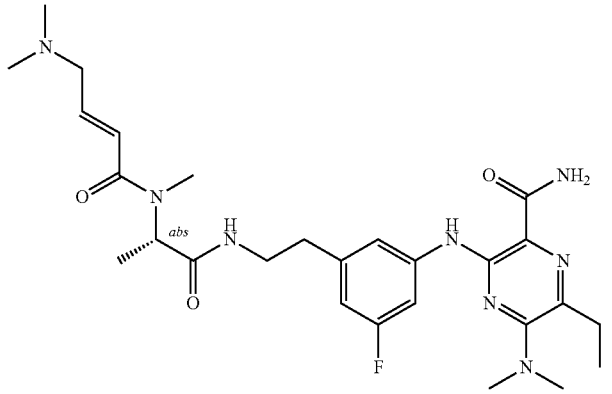 [SMILES: CCc1nc(C(N)=O)c(Nc2cc(F)cc(CCNC(=O)[C@H](C)N(C)C(=O)/C=C/CN(C)C)c2)nc1N(C)C] | 542.65 | *** | *** | * |
| 159 | 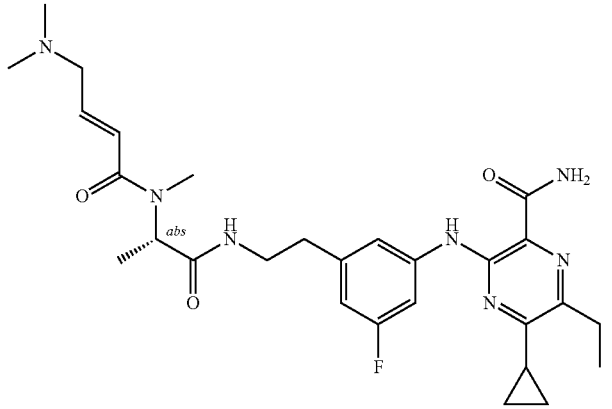 [SMILES: CCc1nc(C(N)=O)c(Nc2cc(F)cc(CCNC(=O)[C@H](C)N(C)C(=O)/C=C/CN(C)C)c2)nc1C1CC1] | 539.64 | ** | *** | * |

TABLE 2A-continued

Representative compounds and their IC$_{50}$ values

| Compd ID | Structure | MW | MOLM-13 | MV-4:11 | K-562 |
| --- | --- | --- | --- | --- | --- |
| 160 | 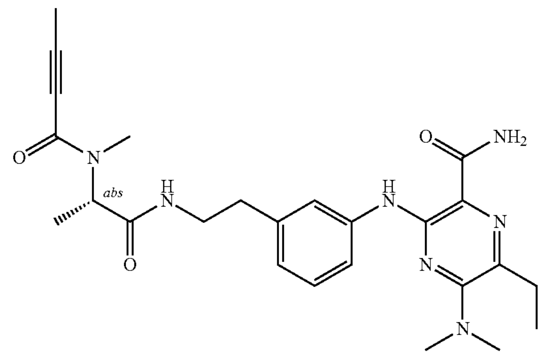 [SMILES: CC#CC(=O)N(C)[C@@H](C)C(=O)NCCc1cccc(Nc2nc(N(C)C)c(CC)nc2C(N)=O)c1] | 479.57 | * | ** | * |
| 162 | 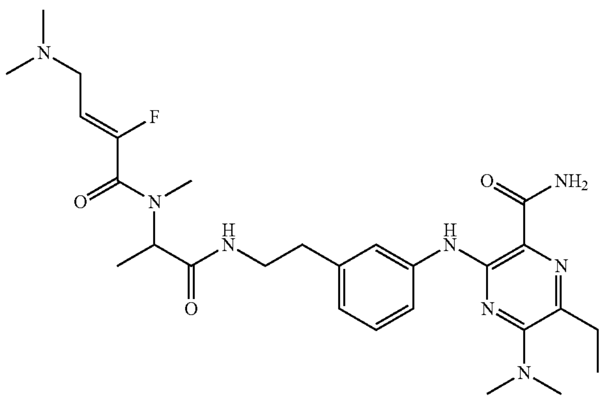 [SMILES: CCc1nc(C(N)=O)c(Nc2cccc(CCNC(=O)C(C)N(C)C(=O)/C(F)=C/CN(C)C)c2)nc1N(C)C] | 542.65 |  | * | * |
| 163 | 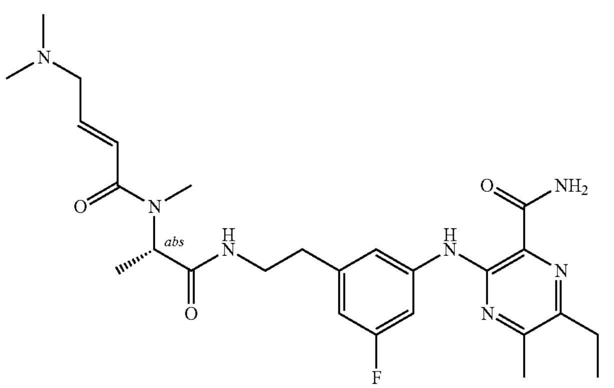 [SMILES: CCc1nc(C(N)=O)c(Nc2cc(F)cc(CCNC(=O)[C@H](C)N(C)C(=O)/C=C/CN(C)C)c2)nc1C] | 513.61 | ** | ** | * |
| 164 | 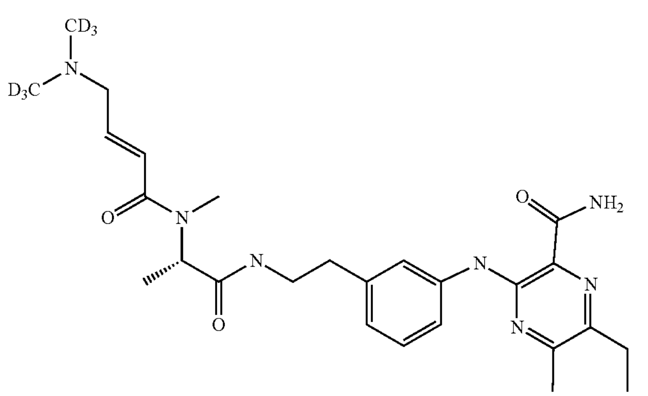 | 501.65 | * | ** | * |

TABLE 2A-continued

Representative compounds and their IC$_{50}$ values

| Compd ID | Structure | MW | MOLM-13 | MV-4:11 | K-562 |
|---|---|---|---|---|---|
| 202 | 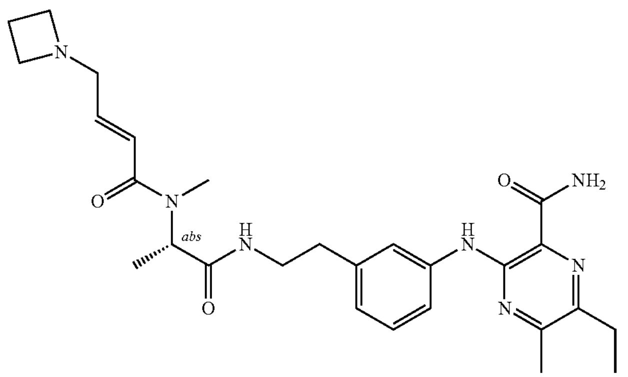 [SMILES: CCc1nc(C(N)=O)c(Nc2cccc(CCNC(=O)[C@H](C)N(C)C(=O)/C=C/CN3CCC3)c2)nc1C] | 507.63 | ** | ** | * |
| 203 | 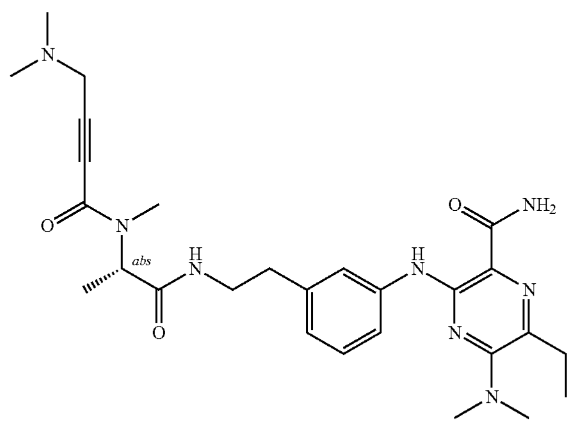 [SMILES: CCc1nc(C(N)=O)c(Nc2cccc(CCNC(=O)[C@H](C)N(C)C(=O)C#CCN(C)C)c2)nc1N(C)C] | 522.64 | ** | *** | * |
| 204 | 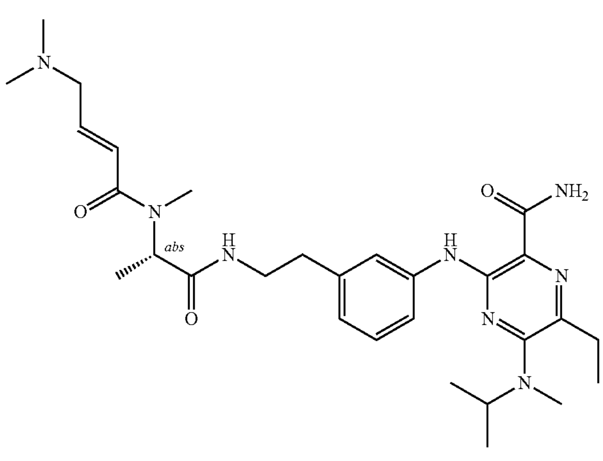 | 552.71 | *** | *** | * |

TABLE 2A-continued

Representative compounds and their IC$_{50}$ values

| Compd ID | Structure | MW | MOLM-13 | MV-4:11 | K-562 |
|---|---|---|---|---|---|
| 205 | 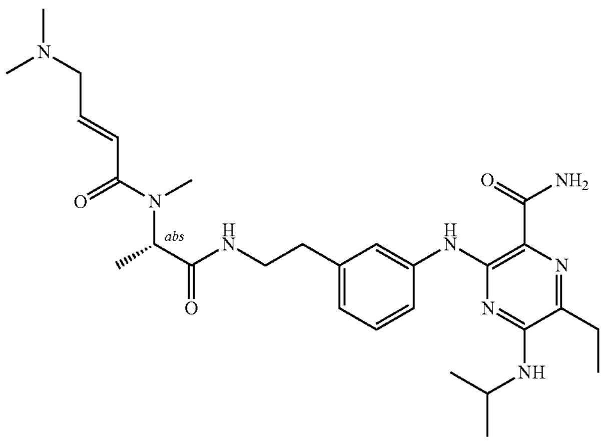 [SMILES: CCc1nc(C(N)=O)c(Nc2cccc(CCNC(=O)[C@H](C)N(C)C(=O)/C=C/CN(C)C)c2)nc1NC(C)C] | 538.68 | *** | *** | * |
| 207 | 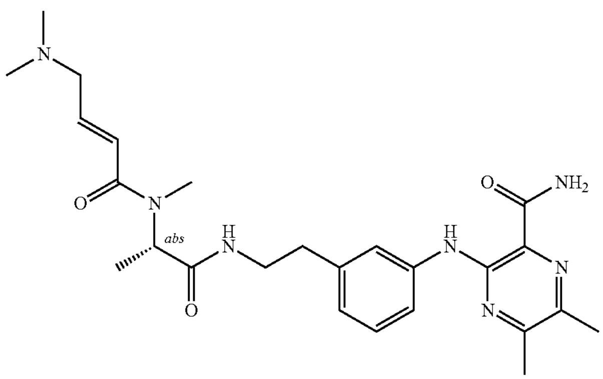 | 481.59 | * | * | * |
| 208 | 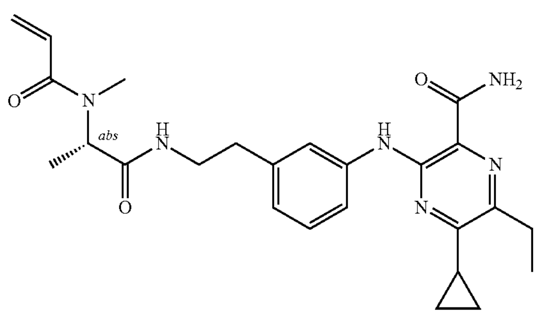 [SMILES: C=CC(=O)N(C)[C@@H](C)C(=O)NCCc1cccc(Nc2nc(C3CC3)c(CC)nc2C(N)=O)c1] | 464.56 | * | ** | * |
| 209 | 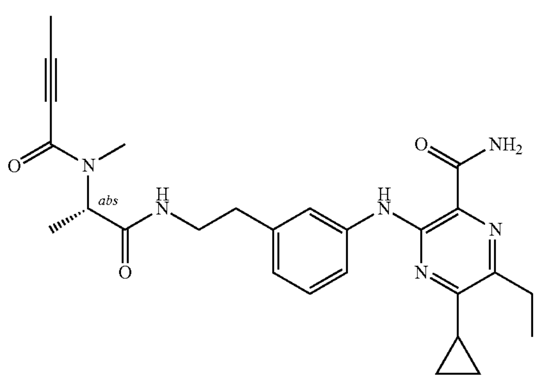 [SMILES: CC#CC(=O)N(C)[C@@H](C)C(=O)NCCc1cccc(Nc2nc(C3CC3)c(CC)nc2C(N)=O)c1] | 476.57 | * | ** | * |

TABLE 2A-continued
Representative compounds and their IC$_{50}$ values
| Compd ID | Structure | MW | MOLM-13 | MV-4:11 | K-562 |
|---|---|---|---|---|---|
| 211 | 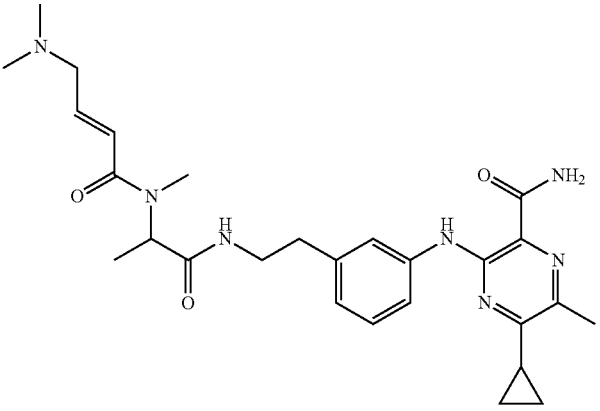 | 507.63 | * | ** | * |
| 213 | 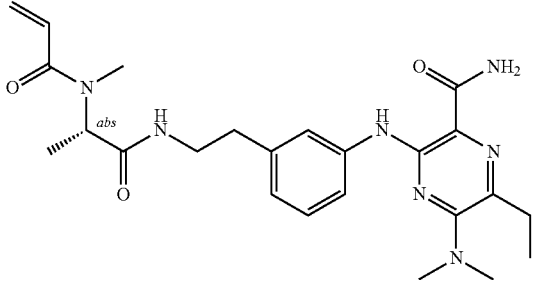 [SMILES: C=CC(=O)N(C)[C@@H](C)C(=O)NCCc1cccc(Nc2nc(N(C)C)c(CC)nc2C(N)=O)c1] | 467.56 | ** | *** | * |
| 214 | 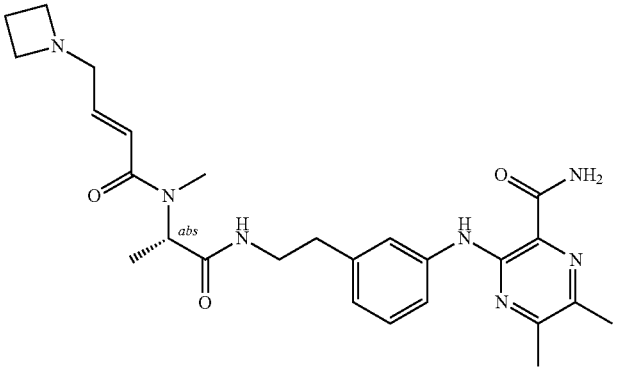 [SMILES: Cc1nc(Nc2cccc(CCNC(=O)[C@H](C)N(C)C(=O)/C=C/CN3CCC3)c2)c(C(N)=O)nc1C] | 493.6 | * | * | * |
| 215 | 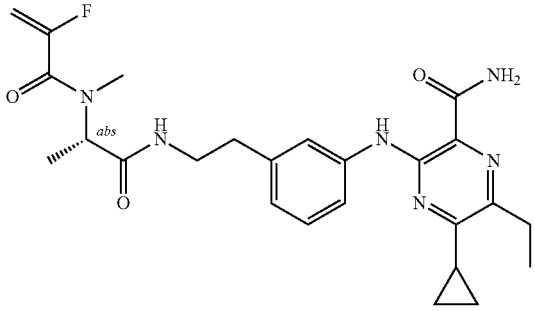 [SMILES: C=C(F)C(=O)N(C)[C@@H](C)C(=O)NCCc1cccc(Nc2nc(C3CC3)c(CC)nc2C(N)=O)c1] | 482.55 | * | * | * |

TABLE 2A-continued
Representative compounds and their IC$_{50}$ values
| Compd ID | Structure | MW | MOLM-13 | MV-4:11 | K-562 |
|---|---|---|---|---|---|
| 216 | 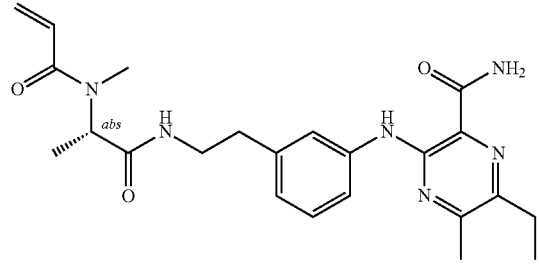 [SMILES: C=CC(=O)N(C)[C@@H](C)C(=O)NCCc1cccc(Nc2nc(C)c(CC)nc2C(N)=O)c1] | 438.52 | * | * | * |
| 217 | 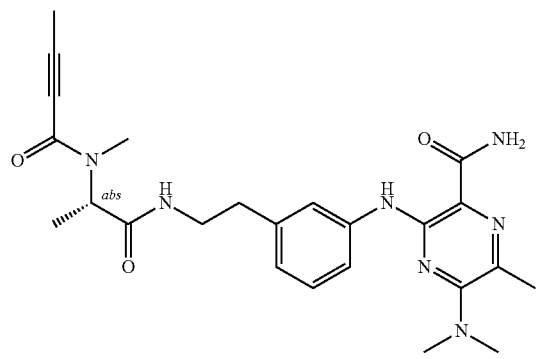 [SMILES: CC#CC(=O)N(C)[C@@H](C)C(=O)NCCc1cccc(Nc2nc(N(C)C)c(C)nc2C(N)=O)c1] | 465.55 | * | * | * |
| 218 | 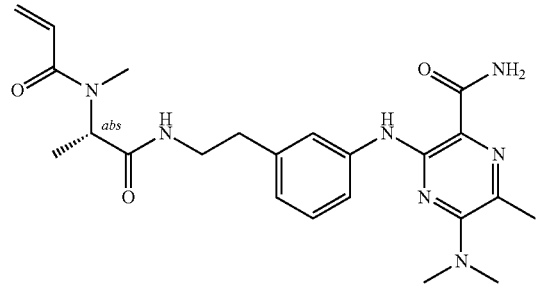 [SMILES: C=CC(=O)N(C)[C@@H](C)C(=O)NCCc1cccc(Nc2nc(N(C)C)c(C)nc2C(N)=O)c1] | 453.54 | * | ** | * |
| 219 | 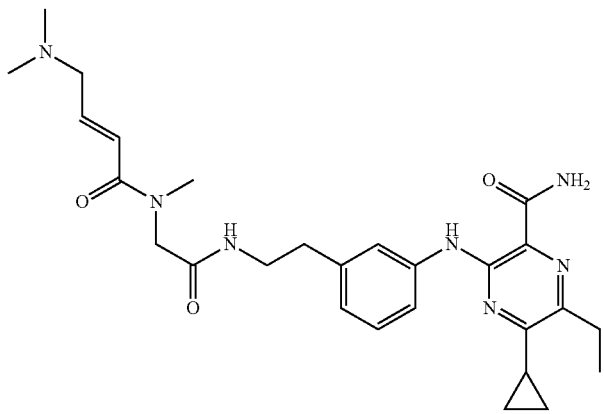 [SMILES: CCc1nc(C(N)=O)c(Nc2cccc(CCNC(=O)CN(C)C(=O)/C=C/CN(C)C)c2)nc1C1CC1] | 507.63 | *** | *** | * |

TABLE 2A-continued

Representative compounds and their IC$_{50}$ values

| Compd ID | Structure | MW | MOLM-13 | MV-4:11 | K-562 |
|---|---|---|---|---|---|
| 220 | 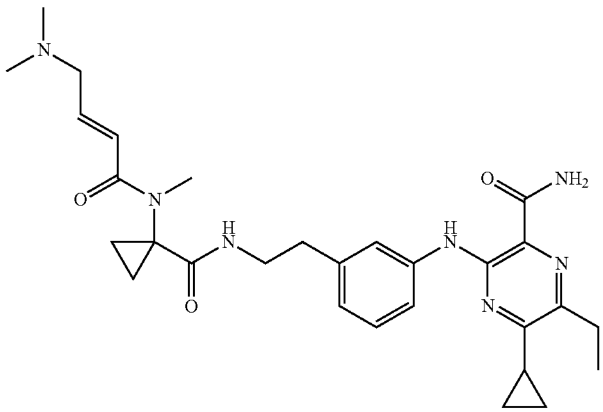 [SMILES: CCc1nc(C(N)=O)c(Nc2cccc(CCNC(=O)C3(N(C)C(=O)/C=C/CN(C)C)CC3)c2)nc1C1CC1] | 533.67 | * | ** | * |
| 221 | 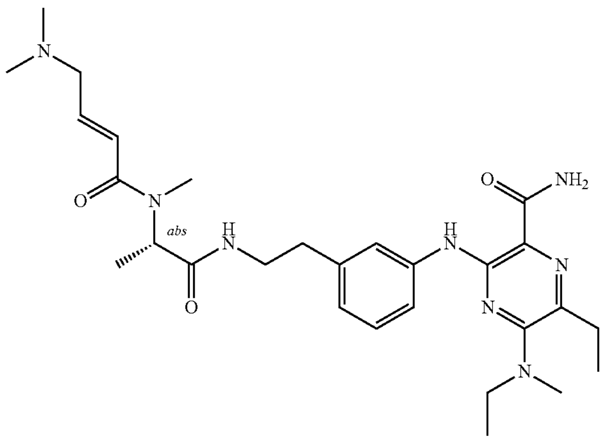 [SMILES: CCc1nc(C(N)=O)c(Nc2cccc(CCNC(=O)[C@H](C)N(C)C(=O)/C=C/CN(C)C)c2)nc1N(C)CC] | 538.68 | *** | *** | * |
| 222 | 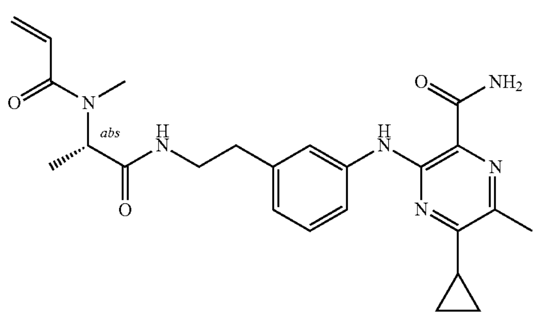 [SMILES: C=CC(=O)N(C)[C@@H](C)C(=O)NCCc1cccc(Nc2nc(C3CC3)c(C)nc2C(N)=O)c1] | 450.53 | * | * | * |
| 223 | 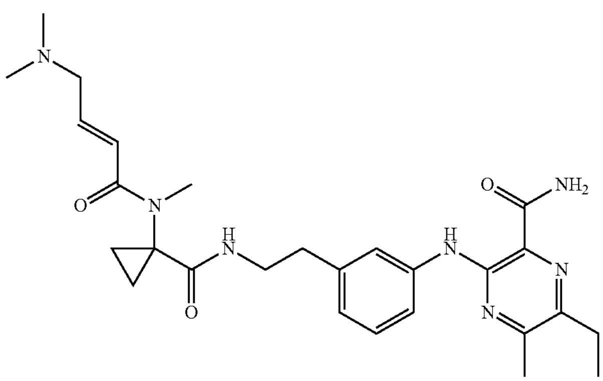 [SMILES: CCc1nc(C(N)=O)c(Nc2cccc(CCNC(=O)C3(N(C)C(=O)/C=C/CN(C)C)CC3)c2)nc1C] | 507.63 | * | ** | * |

TABLE 2A-continued
Representative compounds and their IC$_{50}$ values
| Compd ID | Structure | MW | MOLM-13 | MV-4:11 | K-562 |
|---|---|---|---|---|---|
| 224 | 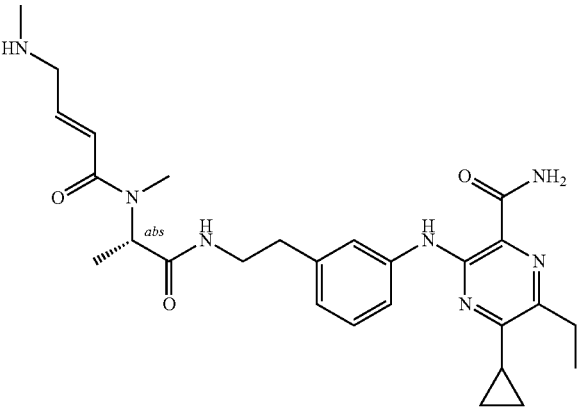 [SMILES: CCc1nc(C(N)=O)c(Nc2cccc(CCNC(=O)[C@H](C)N(C)C(=O)/C=C/CNC)c2)nc1C1CC1] | 507.63 | ** | *** | * |
| 225 | 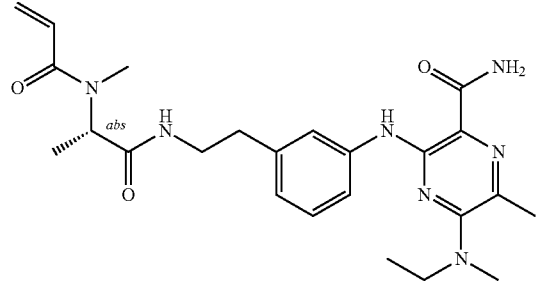 [SMILES: C=CC(=O)N(C)[C@@H](C)C(=O)NCCc1cccc(Nc2nc(N(C)CC)c(C)nc2C(N)=O)c1] | 467.56 | * | ** | * |
| 226 | 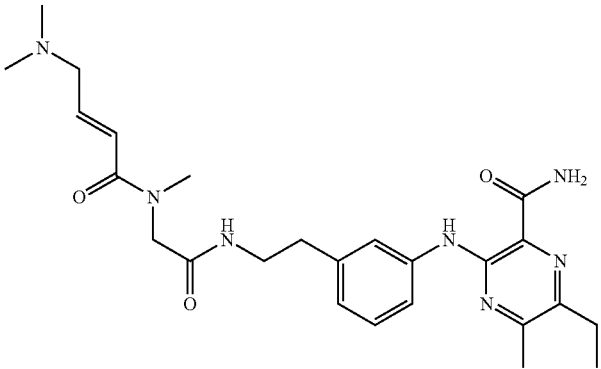 [SMILES: CCc1nc(C(N)=O)c(Nc2cccc(CCNC(=O)CN(C)C(=O)/C=C/CN(C)C)c2)nc1C] | 481.59 | ** | *** | * |
| 227 | 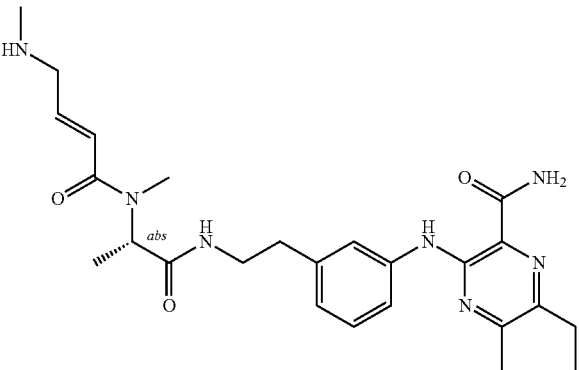 [SMILES: CCc1nc(C(N)=O)c(Nc2cccc(CCNC(=O)[C@H](C)N(C)C(=O)/C=C/CNC)c2)nc1C] | 481.59 | ** | ** | * |

TABLE 2A-continued

Representative compounds and their IC$_{50}$ values

| Compd ID | Structure | MW | MOLM-13 | MV-4:11 | K-562 |
|---|---|---|---|---|---|
| 228 | 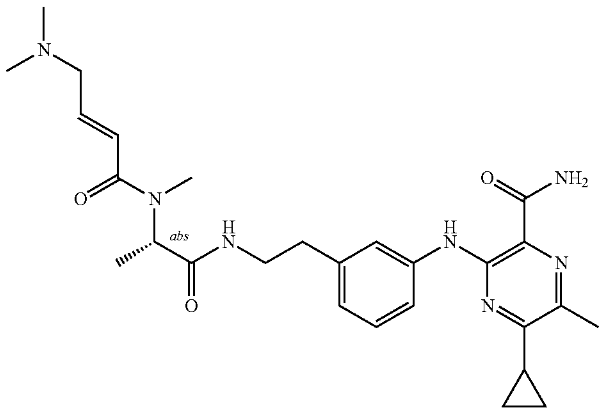 | 507.63 | ** | ** | * |
| 230 | 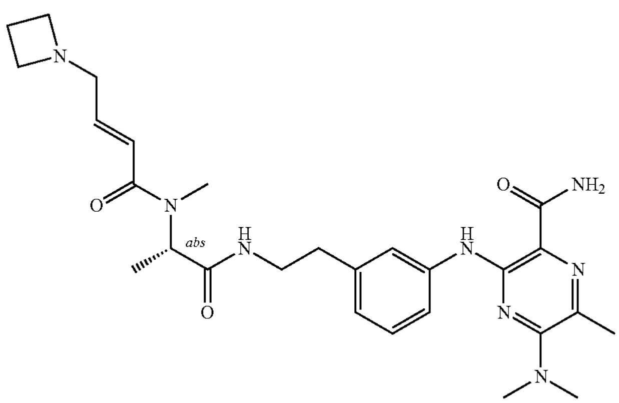 [SMILES: Cc1nc(C(N)=O)c(Nc2cccc(CCNC(=O)[C@H](C)N(C)C(=O)/C=C/CN3CCC3)c2)nc1N(C)C] | 522.64 | ** | *** | * |
| 231 | 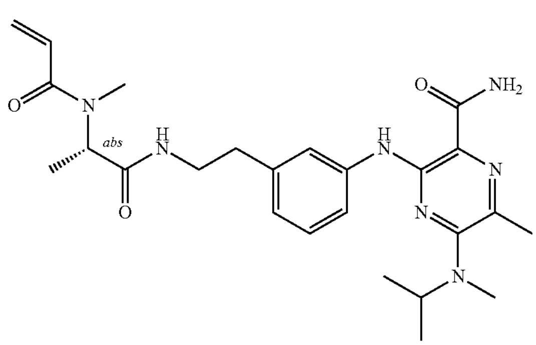 [SMILES: C=CC(=O)N(C)[C@@H](C)C(=O)NCCc1cccc(Nc2nc(N(C)C(C)C)c(C)nc2C(N)=O)c1] | 481.59 | * | ** | * |

TABLE 2A-continued
Representative compounds and their IC$_{50}$ values
| Compd ID | Structure | MW | MOLM-13 | MV-4:11 | K-562 |
|---|---|---|---|---|---|
| 232 | 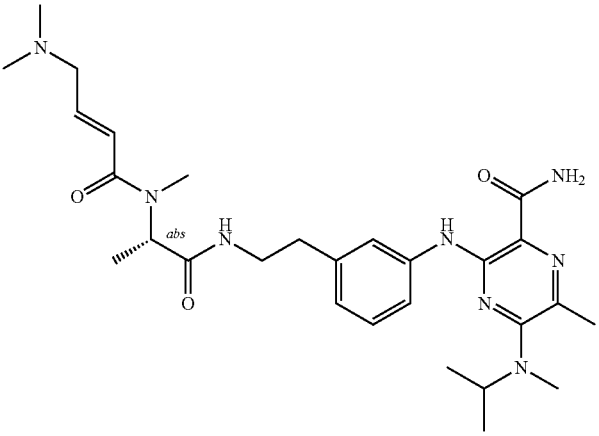 | 538.68 | ** | *** | * |
| 233 | 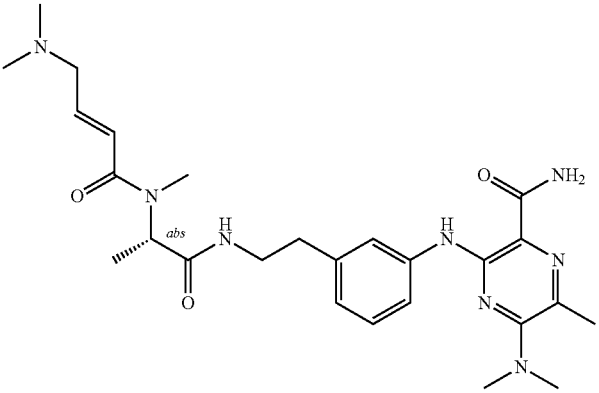 | 510.63 | ** | *** | * |
| 234 | 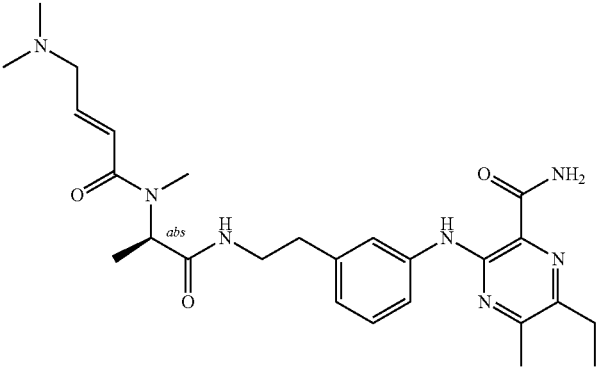 [SMILES: CCc1nc(C(N)=O)c(Nc2cccc(CCNC(=O)[C@@H](C)N(C)C(=O)/C=C/CN(C)C)c2)nc1C] | 495.62 | * | *** | * |
| 236 | 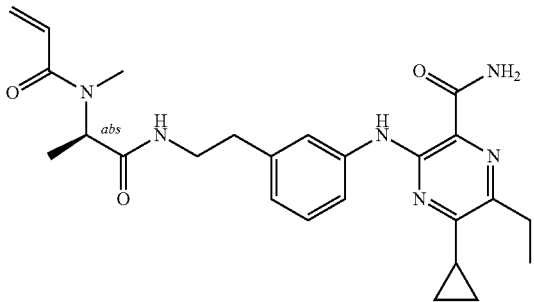 [SMILES: C=CC(=O)N(C)[C@H](C)C(=O)NCCc1cccc(Nc2nc(C3CC3)c(CC)nc2C(N)=O)c1] | 464.56 | * | * | * |

TABLE 2A-continued

Representative compounds and their IC$_{50}$ values

| Compd ID | Structure | MW | MOLM-13 | MV-4:11 | K-562 |
|---|---|---|---|---|---|
| 237 | 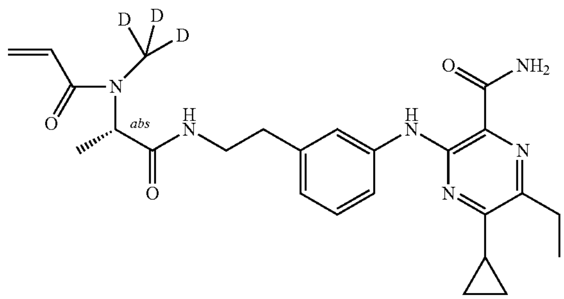 [SMILES: [2H]C([2H])([2H])N(C(=O)C=C)[C@@H](C)C(=O)NCCc1cccc(Nc2nc(C3CC3)c(CC)nc2C(N)=O)c1] | 467.58 | * | ** | * |
| 238 | 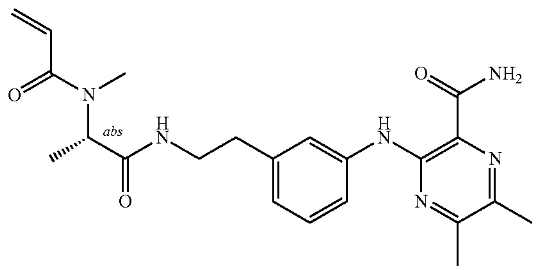 [SMILES: C=CC(=O)N(C)[C@@H](C)C(=O)NCCc1cccc(Nc2nc(C)c(C)nc2C(N)=O)c1] | 424.5 | * | * | * |
| 239 | 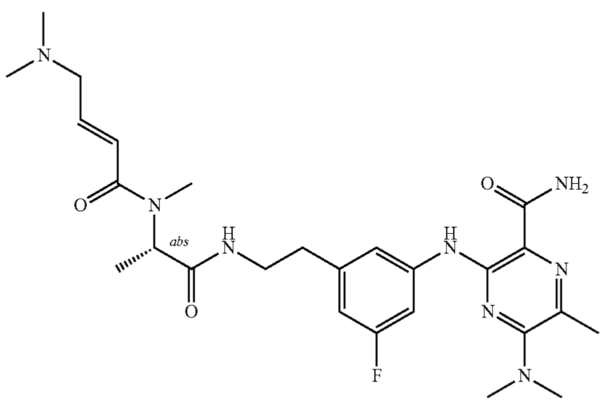 | 528.62 | * | ** | * |
| 240 | 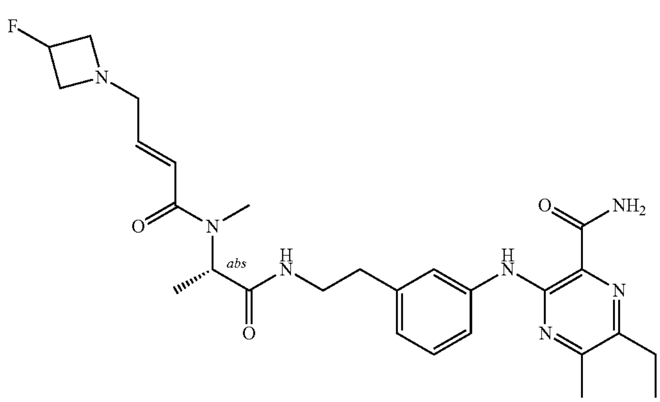 [SMILES: CCc1nc(C(N)=O)c(Nc2cccc(CCNC(=O)[C@H](C)N(C)C(=O)/C=C/CN3CC(F)C3)c2)nc1C] | 525.62 | * | *** | * |

TABLE 2A-continued
Representative compounds and their IC$_{50}$ values
| Compd ID | Structure | MW | MOLM-13 | MV-4:11 | K-562 |
|---|---|---|---|---|---|
| 241 | 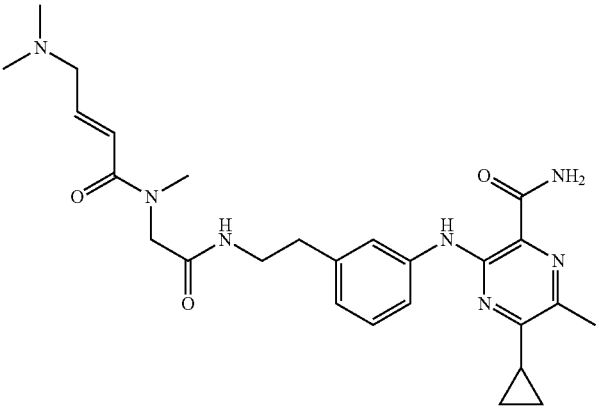 | 493.6 | ** | ** | * |
| 242 | 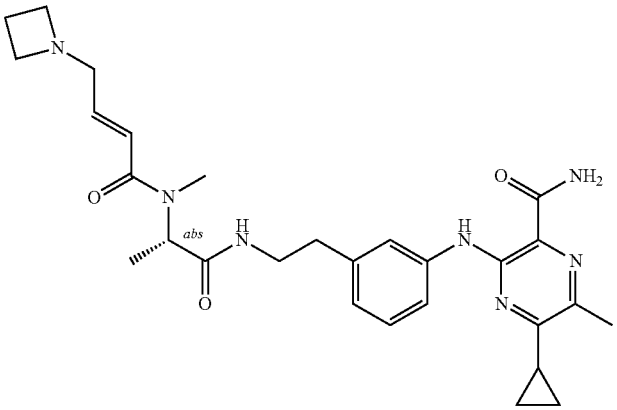 [SMILES: Cc1nc(C(N)=O)c(Nc2cccc(CCNC(=O)[C@H](C)N(C)C(=O)/C=C/CN3CCC3)c2)nc1C1CC1] | 519.64 | ** | ** | * |
| 243 | 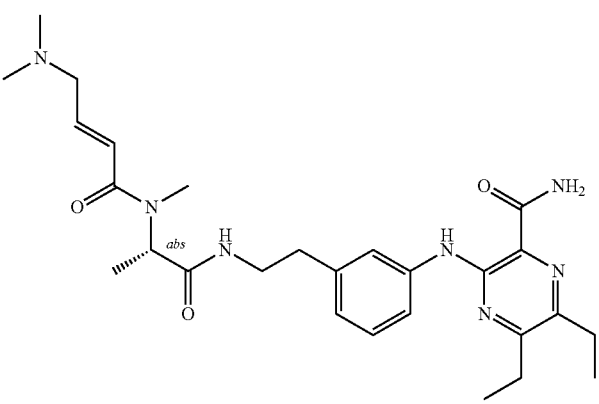 [SMILES: CCc1nc(Nc2cccc(CCNC(=O)[C@H](C)N(C)C(=O)/C=C/CN(C)C)c2)c(C(N)=O)nc1CC] | 509.64 | ** | *** | * |

TABLE 2A-continued
Representative compounds and their IC$_{50}$ values
| Compd ID | Structure | MW | MOLM-13 | MV-4:11 | K-562 |
|---|---|---|---|---|---|
| 244 | 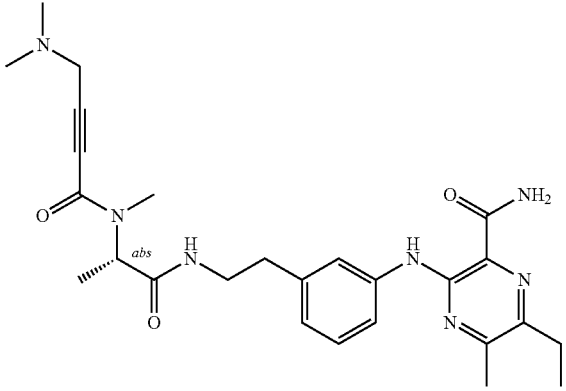 [SMILES: CCc1nc(C(N)=O)c(Nc2cccc(CCNC(=O)[C@H](C)N(C)C(=O)C#CCN(C)C)c2)nc1C] | 493.6 | ** | *** | * |
| 245 | 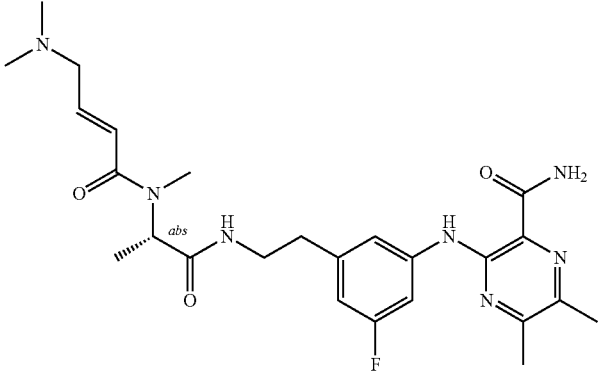 | 499.58 | * | ** | * |
| 246 | 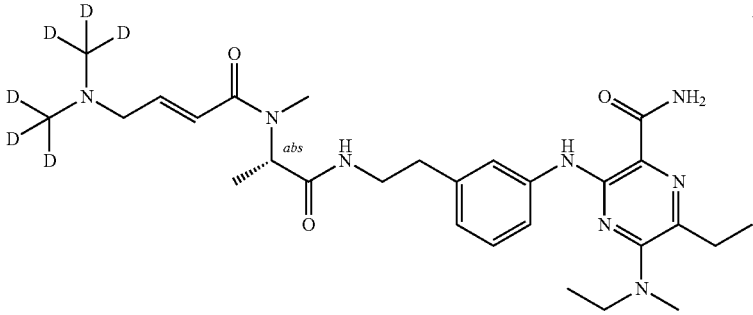 [SMILES: [2H]C([2H])([2H])N(C/C=C/C(=O)N(C)[C@@H](C)C(=O)NCCc1cccc(Nc2nc(N(C)CC)c(CC)nc2C(N)=O)c1)C([2H])([2H])[2H]] | 544.72 | *** | *** | * |
| 247 | 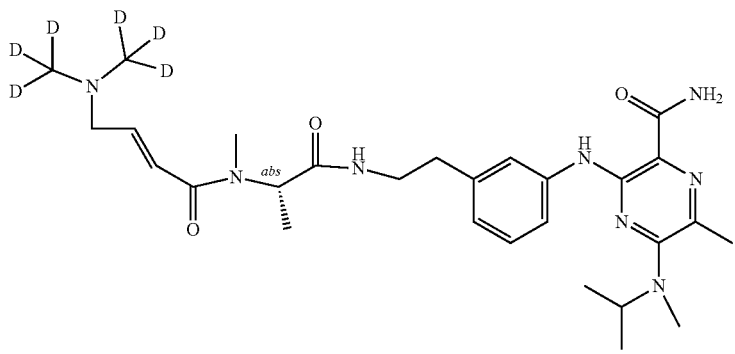 [SMILES: [2H]C([2H])([2H])N(C/C=C/C(=O)N(C)[C@@H](C)C(=O)NCCc1cccc(Nc2nc(N(C)C(C)C)c(C)nc2C(N)=O)c1)C([2H])([2H])[2H]] | 544.72 | ** | *** | * |

TABLE 2A-continued

Representative compounds and their IC₅₀ values

| Compd ID | Structure | MW | MOLM-13 | MV-4:11 | K-562 |
|---|---|---|---|---|---|
| 248 | 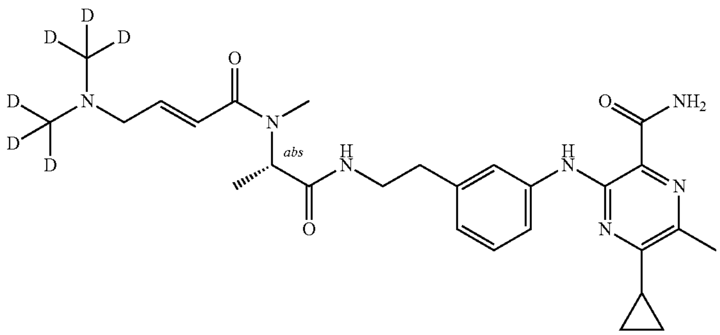 [SMILES: [2H]C([2H])([2H])N(C/C=C/C(=O)N(C)[C@@H](C)C(=O)NCCc1cccc(Nc2nc(C3CC3)c(C)nc2C(N)=O)c1)C([2H])([2H])[2H]] | 513.66 | ** | ** | * |
| 249 | 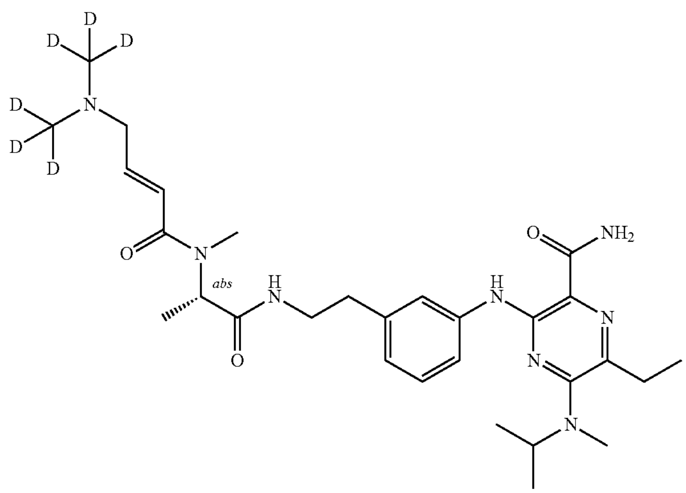 [SMILES: [2H]C([2H])([2H])N(C/C=C/C(=O)N(C)[C@@H](C)C(=O)NCCc1cccc(Nc2nc(N(C)C(C)C)c(CC)nc2C(N)=O)c1)C([2H])([2H])[2H]] | 558.75 | *** | *** | * |
| 250 | 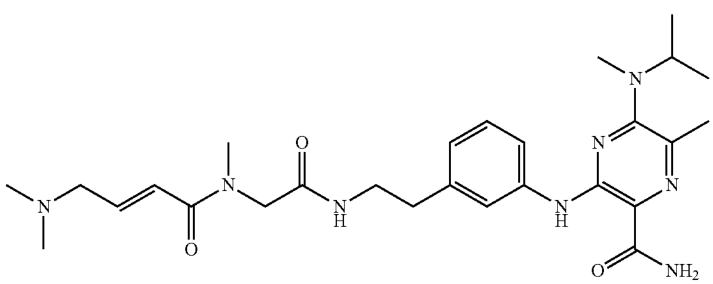 [SMILES: Cc1nc(C(N)=O)c(Nc2cccc(CCNC(=O)CN(C)C(=O)/C=C/CN(C)C)c2)nc1N(C)C(C)C] | 524.66 | ** | *** | * |
| 251 | 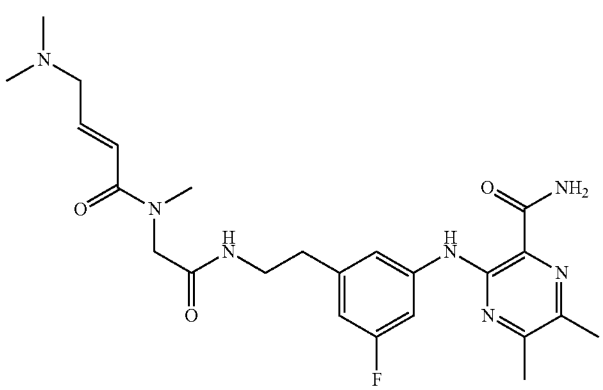 | 485.55 | * | ** | * |

TABLE 2A-continued

Representative compounds and their IC$_{50}$ values

| Compd ID | Structure | MW | MOLM-13 | MV-4:11 | K-562 |
|---|---|---|---|---|---|
| 252 | 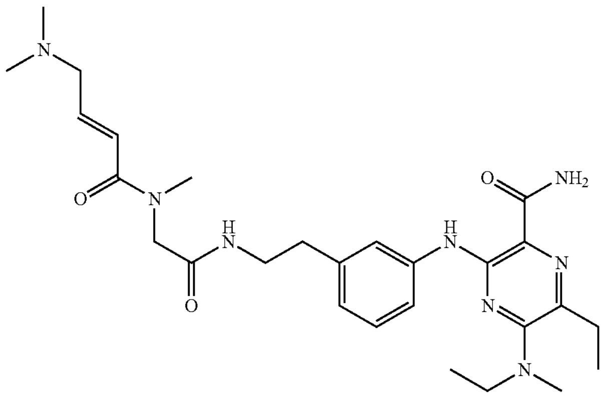 [SMILES: CCc1nc(C(N)=O)c(Nc2cccc(CCNC(=O)CN(C)C(=O)/C=C/CN(C)C)c2)nc1N(C)CC] | 524.66 | *** | *** | * |
| 253 | 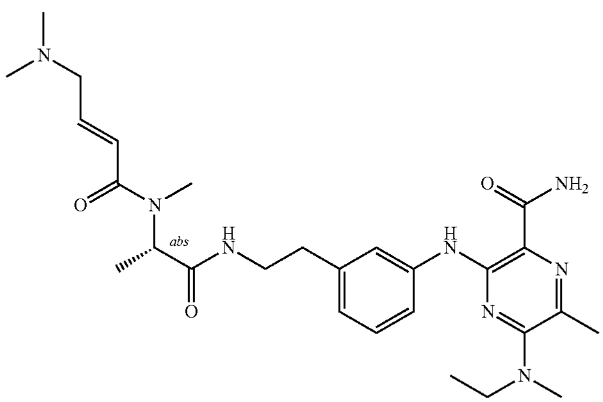 | 524.66 | ** | *** | * |
| 254 | 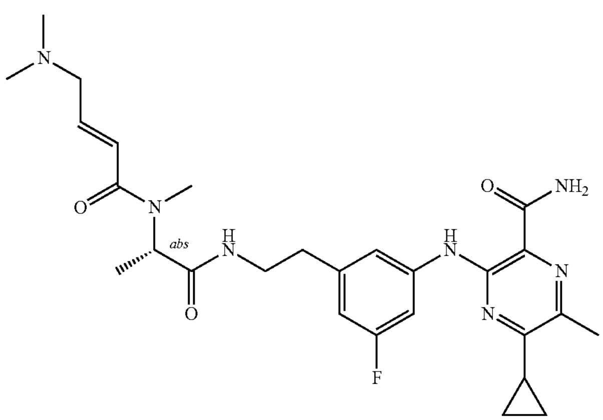 | 525.62 | ** | *** | * |

TABLE 2A-continued

Representative compounds and their IC$_{50}$ values

| Compd ID | Structure | MW | MOLM-13 | MV-4:11 | K-562 |
|---|---|---|---|---|---|
| 255 | 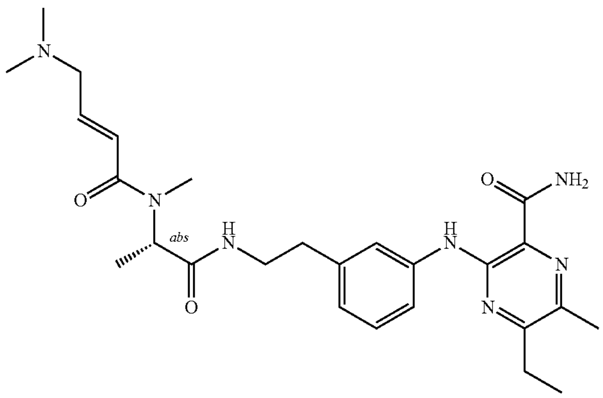 | 495.62 | * | ** | * |
| 301 | 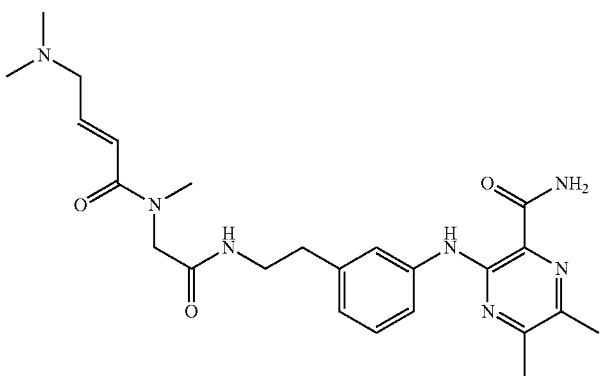 | 467.56 | * | * | * |
| 302 | 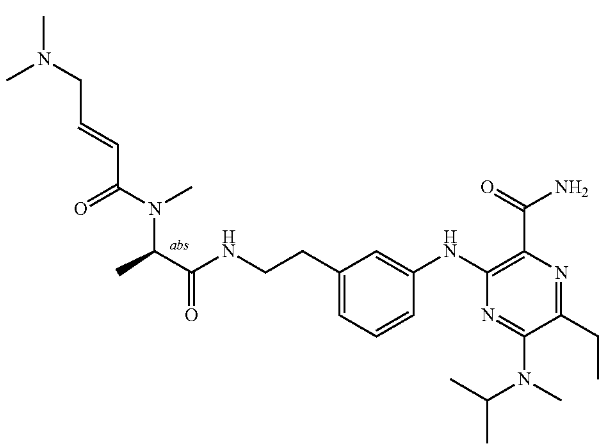 [SMILES: CCc1nc(C(N)=O)c(Nc2cccc(CCNC(=O)[C@@H](C)N(C)C(=O)/C=C/CN(C)C)c2)nc1N(C)C(C)C] | 552.71 | ** | *** | * |

TABLE 2A-continued

Representative compounds and their IC₅₀ values

| Compd ID | Structure | MW | MOLM-13 | MV-4:11 | K-562 |
|---|---|---|---|---|---|
| 303 | 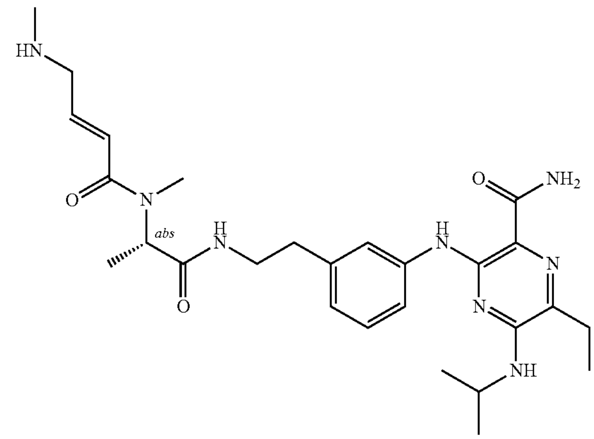 [SMILES: CCc1nc(C(N)=O)c(Nc2cccc(CCNC(=O)[C@H](C)N(C)C(=O)/C=C/CNC)c2)nc1NC(C)C] | 524.66 | *** | *** | * |
| 304 | 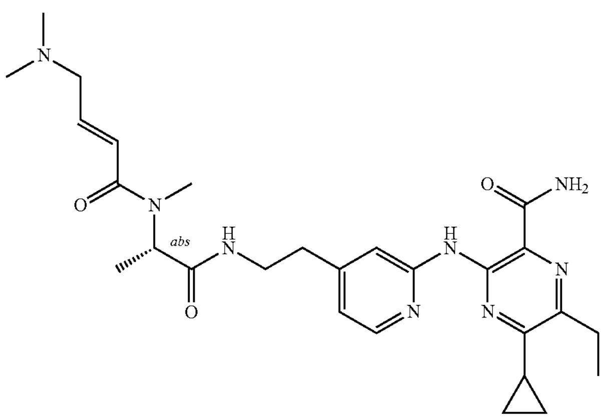 [SMILES: CCc1nc(C(N)=O)c(Nc2cc(CCNC(=O)[C@H](C)N(C)C(=O)/C=C/CN(C)C)ccn2)nc1C1CC1] | 522.64 |  |  | * |
| 305 | 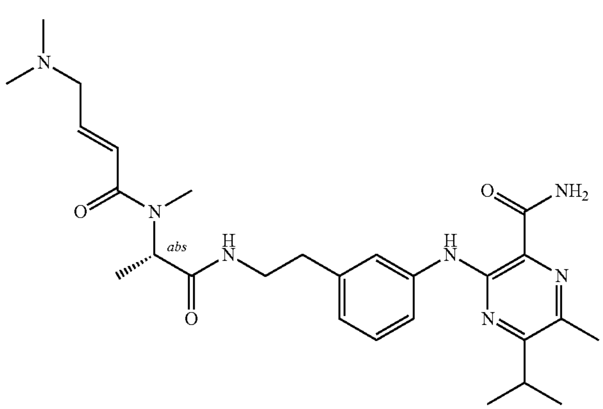 | 509.64 | ** | ** | * |

TABLE 2A-continued
Representative compounds and their IC$_{50}$ values
| Compd ID | Structure | MW | MOLM-13 | MV-4:11 | K-562 |
|---|---|---|---|---|---|
| 306 | 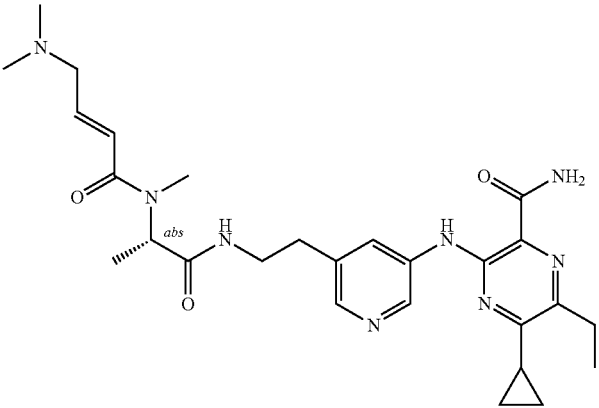 [SMILES: CCc1nc(C(N)=O)c(Nc2cncc(CCNC(=O)[C@H](C)N(C)C(=O)/C=C/CN(C)C)c2)nc1C1CC1] | 522.64 | ** | ** | |
| 307 | 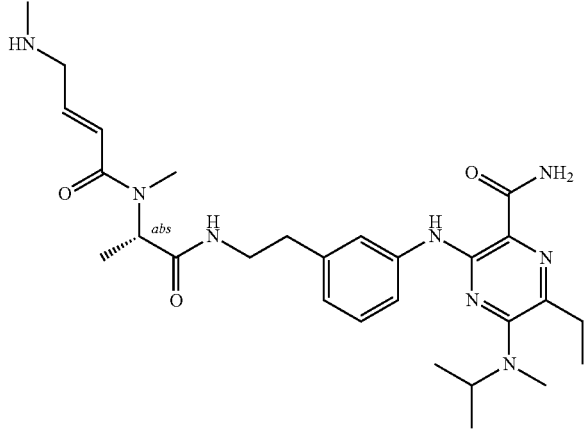 [SMILES: CCc1nc(C(N)=O)c(Nc2cccc(CCNC(=O)[C@H](C)N(C)C(=O)/C=C/CNC)c2)nc1N(C)C(C)C] | 538.68 | *** | *** | |
| 308 | 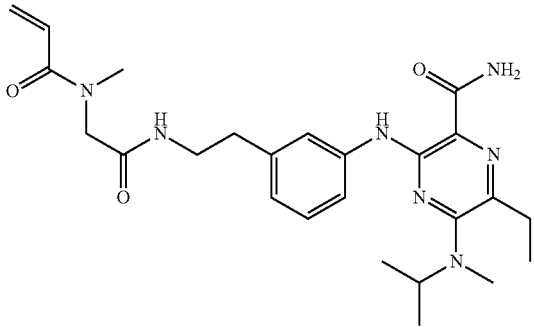 [SMILES: C=CC(=O)N(C)CC(=O)NCCc1cccc(Nc2nc(N(C)C(C)C)c(CC)nc2C(N)=O)c1] | 481.59 | ** | ** | * |
| 309 | 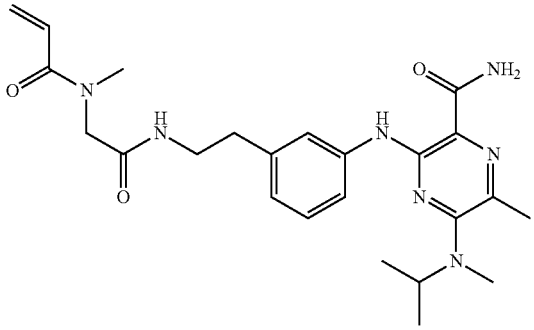 [SMILES: C=CC(=O)N(C)CC(=O)NCCc1cccc(Nc2nc(N(C)C(C)C)c(C)nc2C(N)=O)c1] | 467.56 |  | ** | * |

TABLE 2A-continued
Representative compounds and their IC$_{50}$ values
| Compd ID | Structure | MW | MOLM-13 | MV-4:11 | K-562 |
|---|---|---|---|---|---|
| 310 | 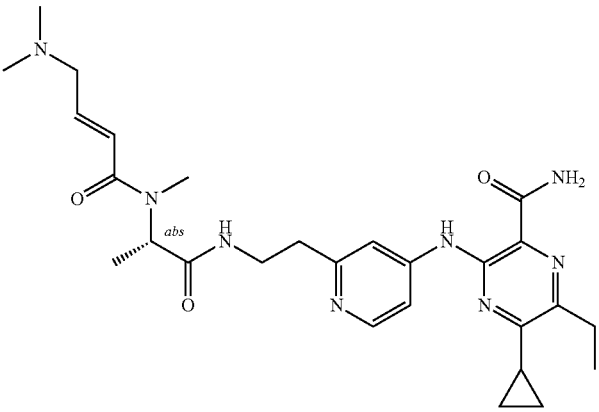 | 522.64 | ** | *** | * |
| 311 | 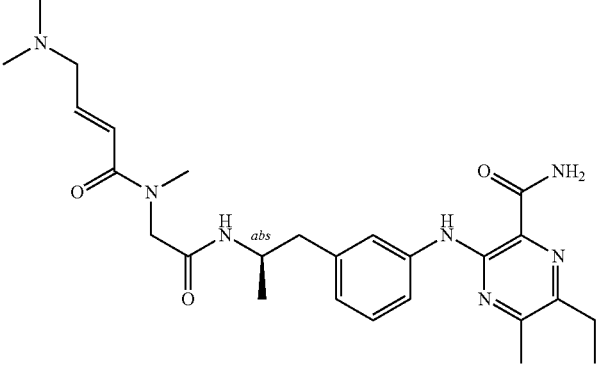 [SMILES: CCc1nc(C(N)=O)c(Nc2cccc(C[C@@H](C)NC(=O)CN(C)C(=O)/C=C/CN(C)C)c2)nc1C] | 495.62 |  | * | * |
| 312 | 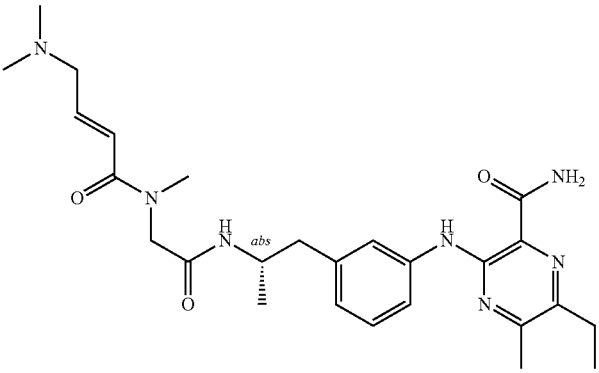 [SMILES: CCc1nc(C(N)=O)c(Nc2cccc(C[C@H](C)NC(=O)CN(C)C(=O)/C=C/CN(C)C)c2)nc1C] | 495.62 |  | * | * |

TABLE 2A-continued

Representative compounds and their IC₅₀ values

| Compd ID | Structure | MW | MOLM-13 | MV-4:11 | K-562 |
|---|---|---|---|---|---|
| 313 | 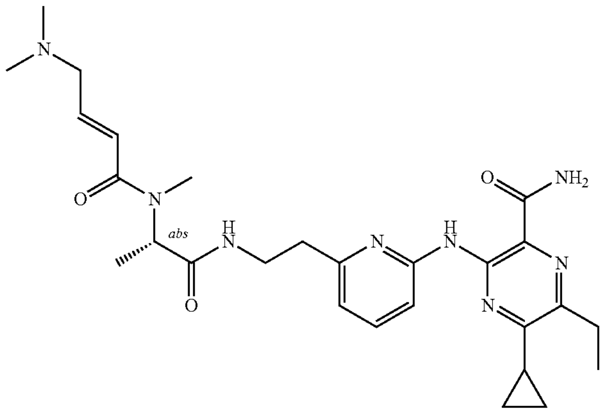 [SMILES: CCc1nc(C(N)=O)c(Nc2cccc(CCNC(=O)[C@H](C)N(C)C(=O)/C=C/CN(C)C)n2)nc1C1CC1] | 522.64 |  | * | * |
| 314 | 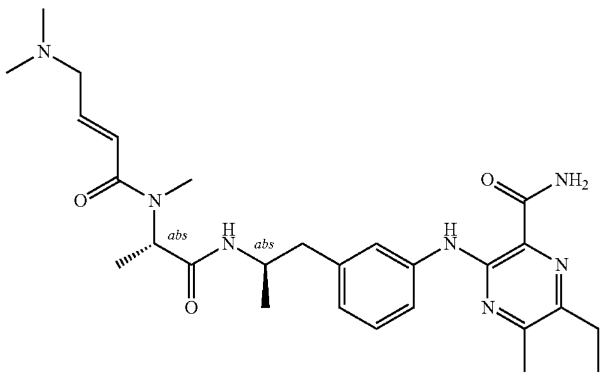 [SMILES: CCc1nc(C(N)=O)c(Nc2cccc(C[C@@H](C)NC(=O)[C@H](C)N(C)C(=O)/C=C/CN(C)C)c2)nc1C] | 509.64 |  | * | * |
| 315 | 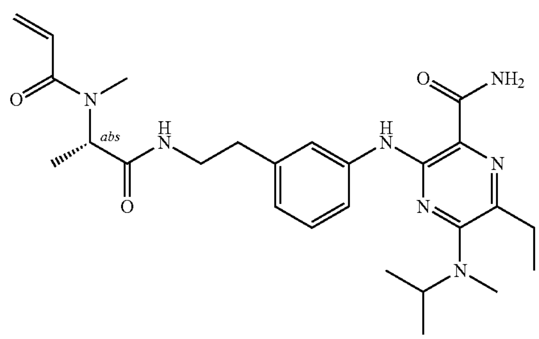 [SMILES: C=CC(=O)N(C)[C@@H](C)C(=O)NCCc1cccc(Nc2nc(N(C)C(C)C)c(CC)nc2C(N)=O)c1] | 495.62 | ** | ** | * |
| 316 | 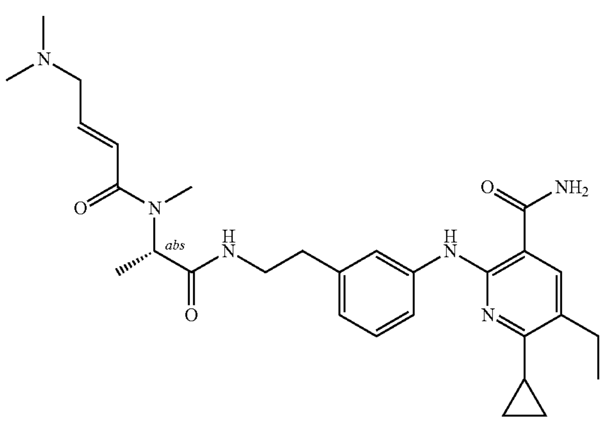 [SMILES: CCc1cc(C(N)=O)c(Nc2cccc(CCNC(=O)[C@H](C)N(C)C(=O)/C=C/CN(C)C)c2)nc1C1CC1] | 520.67 |  | * | * |

TABLE 2A-continued

Representative compounds and their IC$_{50}$ values

| Compd ID | Structure | MW | MOLM-13 | MV-4:11 | K-562 |
|---|---|---|---|---|---|
| 317 | 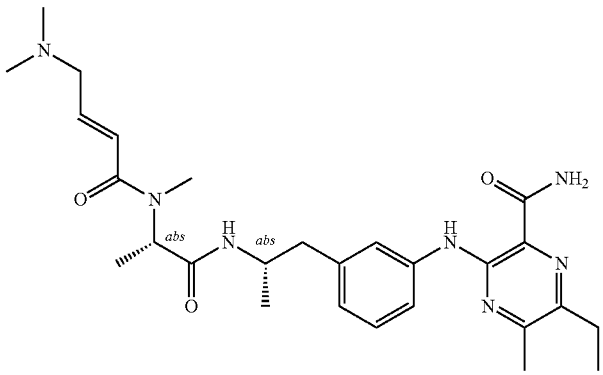 [SMILES: CCc1nc(C(N)=O)c(Nc2cccc(C[C@H](C)NC(=O)[C@H](C)N(C)C(=O)/C=C/CN(C)C)c2)nc1C] | 509.64 | * | ** | * |
| 318 | 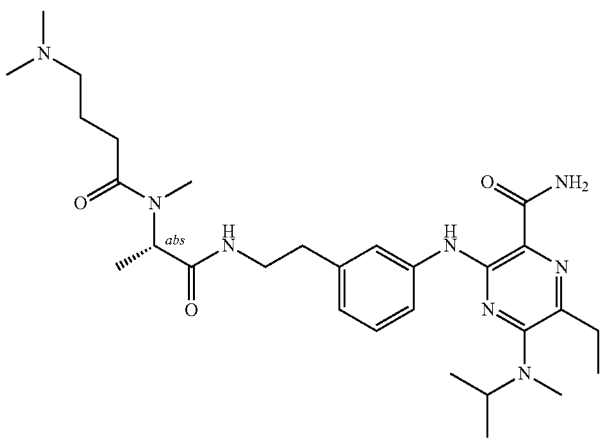 [SMILES: CCc1nc(C(N)=O)c(Nc2cccc(CCNC(=O)[C@H](C)N(C)C(=O)CCCN(C)C)c2)nc1N(C)C(C)C] | 554.73 | * | ** | * |
| 319 | 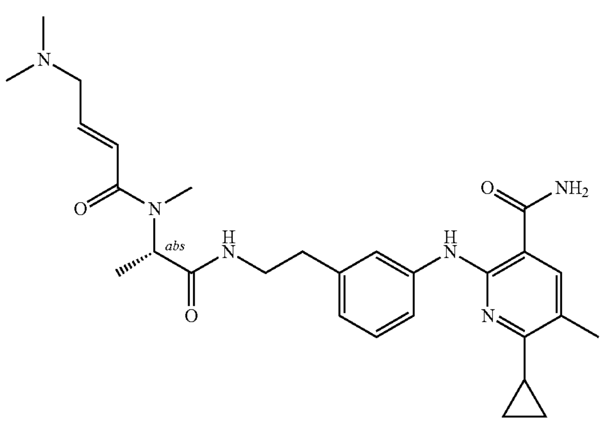 | 506.64 | * | * | * |

TABLE 2A-continued

Representative compounds and their IC$_{50}$ values

| Compd ID | Structure | MW | MOLM-13 | MV-4:11 | K-562 |
|---|---|---|---|---|---|
| 320 | 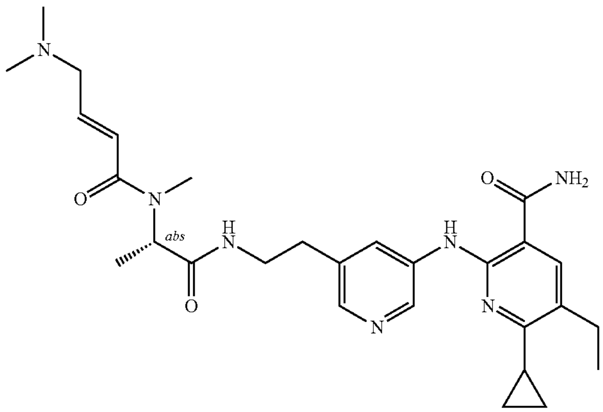 [SMILES: CCc1cc(C(N)=O)c(Nc2cncc(CCNC(=O)[C@H](C)N(C)C(=O)/C=C/CN(C)C)c2)nc1C1CC1] | 521.65 |  | * | * |
| 321 | 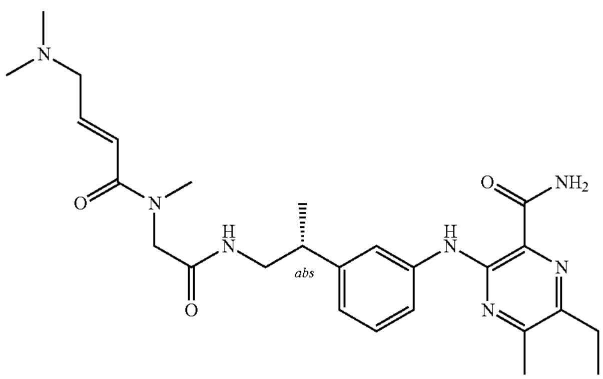 [SMILES: CCc1nc(C(N)=O)c(Nc2cccc([C@@H](C)CNC(=O)CN(C)C(=O)/C=C/CN(C)C)c2)nc1C] | 495.62 | ** | ** | * |
| 322 | 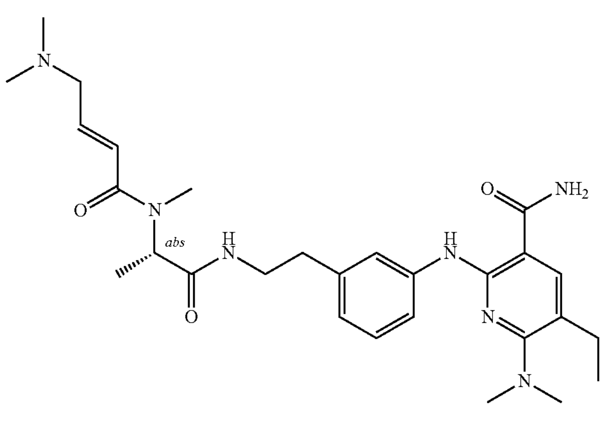 [SMILES: CCc1cc(C(N)=O)c(Nc2cccc(CCNC(=O)[C@H](C)N(C)C(=O)/C=C/CN(C)C)c2)nc1N(C)C] | 523.67 |  | * | * |

TABLE 2A-continued
Representative compounds and their IC$_{50}$ values
| Compd ID | Structure | MW | MOLM-13 | MV-4:11 | K-562 |
|---|---|---|---|---|---|
| 323 | 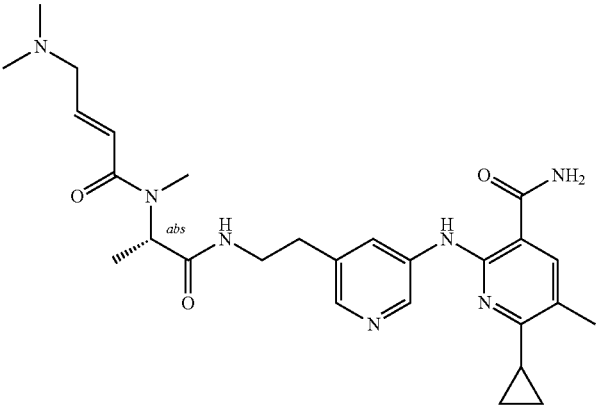 | 507.63 |  | * | |
| 324 | 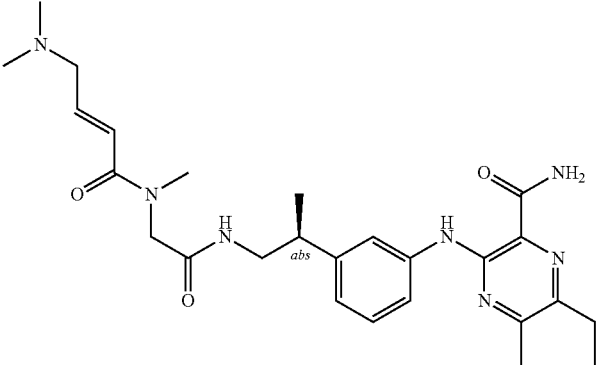 [SMILES: CCc1nc(C(N)=O)c(Nc2cccc([C@H](C)CNC(=O)CN(C)C(=O)/C=C/CN(C)C)c2)nc1C] | 495.62 |  | * | * |
| 325 | 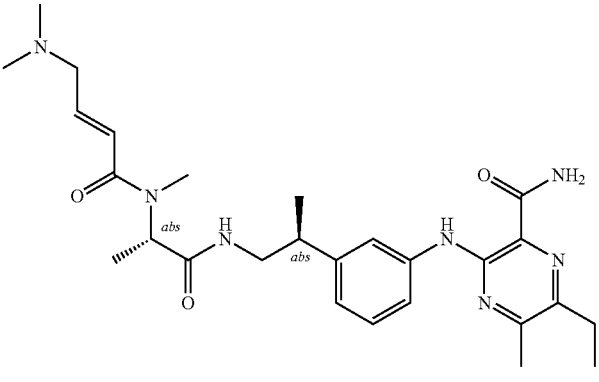 [SMILES: CCc1nc(C(N)=O)c(Nc2cccc([C@H](C)CNC(=O)[C@H](C)N(C)C(=O)/C=C/CN(C)C)c2)nc1C] | 509.64 |  |  | * |
| 326 | 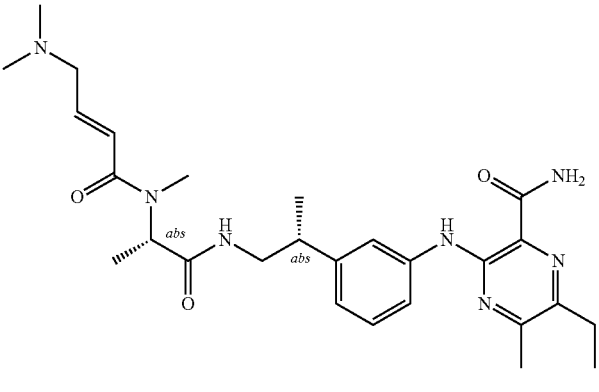 [SMILES: CCc1nc(C(N)=O)c(Nc2cccc([C@@H](C)CNC(=O)[C@H](C)N(C)C(=O)/C=C/CN(C)C)c2)nc1C] | 509.64 | * | * | * |

TABLE 2A-continued

Representative compounds and their IC$_{50}$ values

| Compd ID | Structure | MW | MOLM-13 | MV-4:11 | K-562 |
|---|---|---|---|---|---|
| 327 | 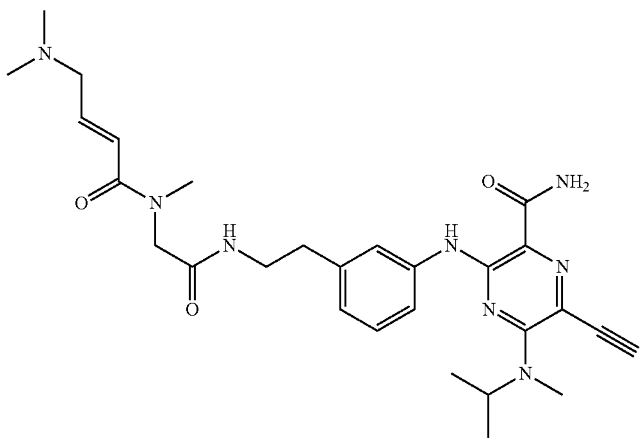 [SMILES: C#Cc1nc(C(N)=O)c(Nc2cccc(CCNC(=O)CN(C)C(=O)/C=C/CN(C)C)c2)nc1N(C)C(C)C] | 534.65 | ** | * | * |
| 328 | 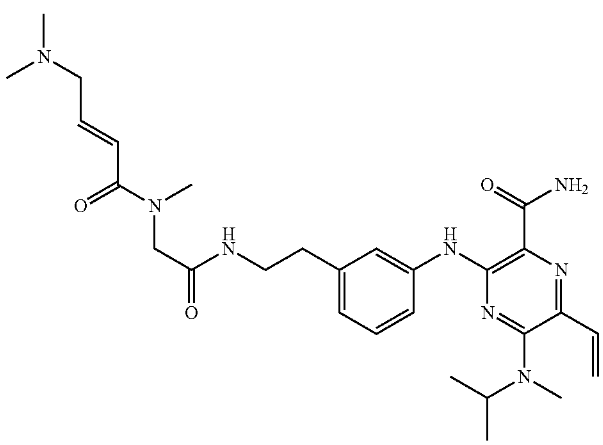 [SMILES: C=Cc1nc(C(N)=O)c(Nc2cccc(CCNC(=O)CN(C)C(=O)/C=C/CN(C)C)c2)nc1N(C)C(C)C] | 536.67 | * | *** | * |
| 501 | 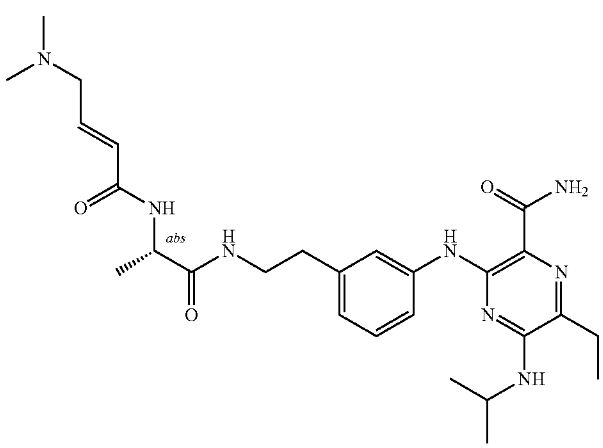 [SMILES: CCc1nc(C(N)=O)c(Nc2cccc(CCNC(=O)[C@H](C)NC(=O)/C=C/CN(C)C)c2)nc1NC(C)C] | 524.66 | *** | *** | * |

TABLE 2A-continued

Representative compounds and their IC$_{50}$ values

| Compd ID | Structure | MW | MOLM-13 | MV-4:11 | K-562 |
|---|---|---|---|---|---|
| 502 | 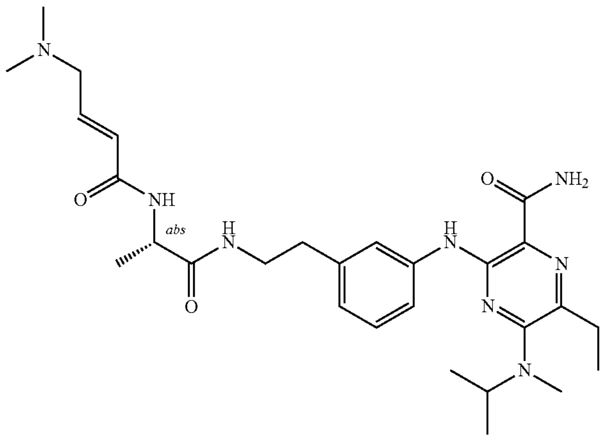 [SMILES: CCc1nc(C(N)=O)c(Nc2cccc(CCNC(=O)[C@H](C)NC(=O)/C=C/CN(C)C)c2)nc1N(C)C(C)C] | 538.68 | *** | *** | * |
| 503 | 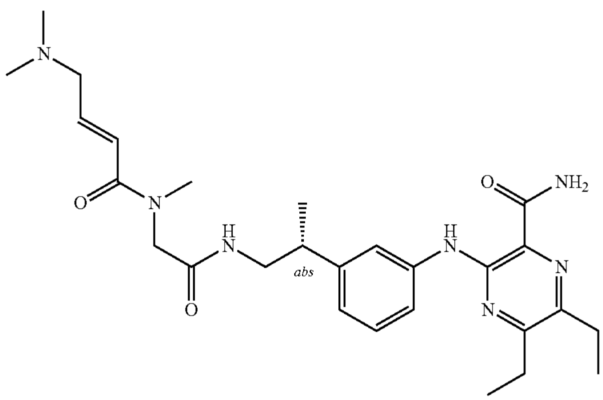 [SMILES: CCc1nc(Nc2cccc([C@@H](C)CNC(=O)CN(C)C(=O)/C=C/CN(C)C)c2)c(C(N)=O)nc1CC] | 509.64 | *** | *** | * |
| 504 | 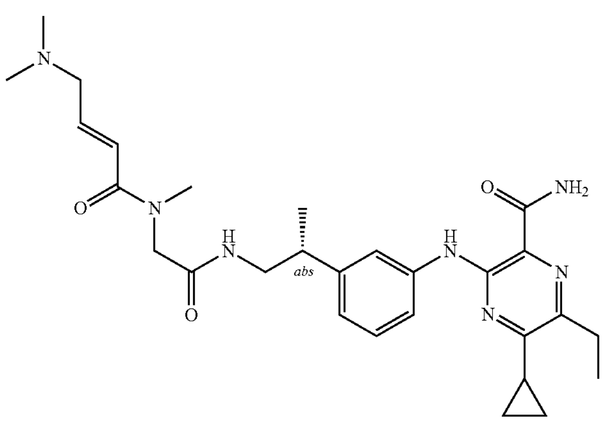 [SMILES: CCc1nc(C(N)=O)c(Nc2cccc([C@@H](C)CNC(=O)CN(C)C(=O)/C=C/CN(C)C)c2)nc1C1CC1] | 521.65 | *** | *** | * |

TABLE 2A-continued

Representative compounds and their IC₅₀ values

| Compd ID | Structure | MW | MOLM-13 | MV-4:11 | K-562 |
|---|---|---|---|---|---|
| 505 | 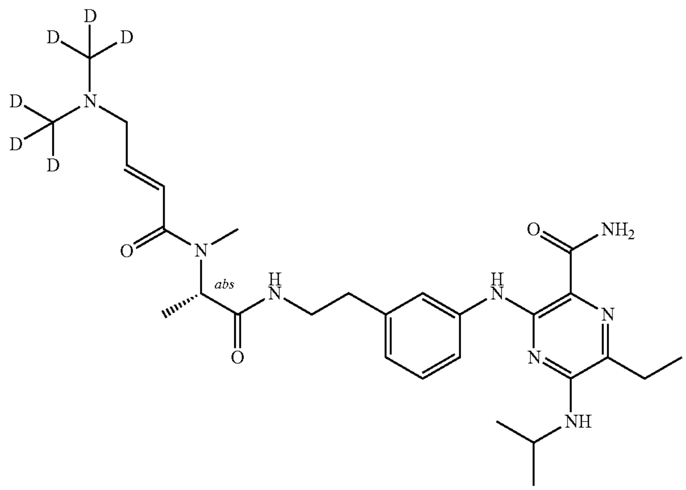 [SMILES: [2H]C([2H])([2H])N(C/C=C/C(=O)N(C)[C@@H](C)C(=O)NCCc1cccc(Nc2nc(NC(C)C)c(CC)nc2C(N)=O)c1)C([2H])([2H])[2H]] | 544.72 | | | * |
| 506 | 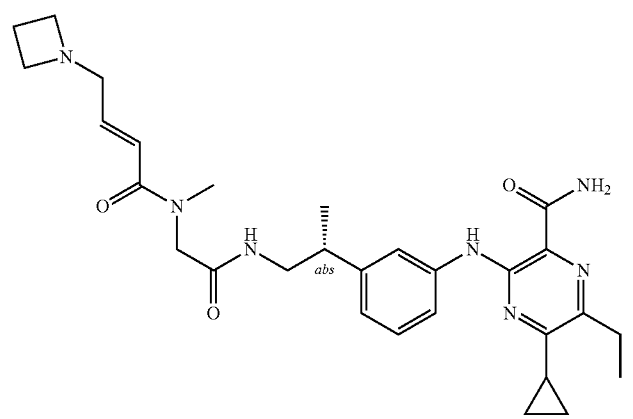 [SMILES: CCc1nc(C(N)=O)c(Nc2cccc([C@@H](C)CNC(=O)CN(C)C(=O)/C=C/CN3CCC3)c2)nc1C1CC1] | 533.67 | *** | ** | * |
| 507 | 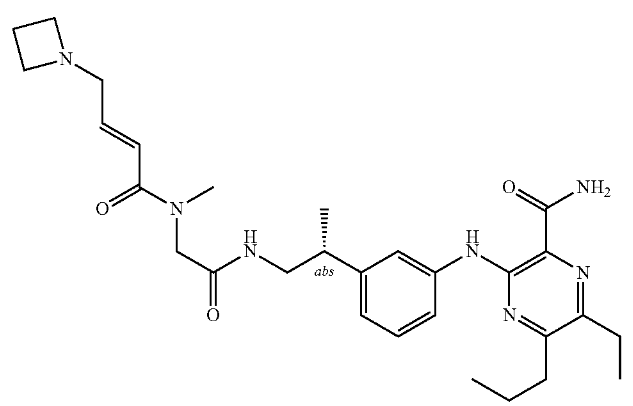 [SMILES: CCCc1nc(Nc2cccc([C@@H](C)CNC(=O)CN(C)C(=O)/C=C/CN3CCC3)c2)c(C(N)=O)nc1CC] | 535.68 | *** | ** | * |

TABLE 2A-continued

Representative compounds and their IC$_{50}$ values

| Compd ID | Structure | MW | MOLM-13 | MV-4:11 | K-562 |
|---|---|---|---|---|---|
| 508 | 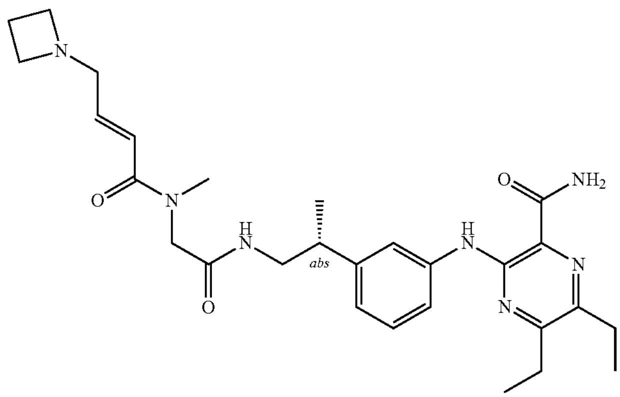 [SMILES: CCc1nc(Nc2cccc([C@@H](C)CNC(=O)CN(C)C(=O)/C=C/CN3CCC3)c2)c(C(N)=O)nc1CC] | 521.65 | * | * | * |
| 509 | 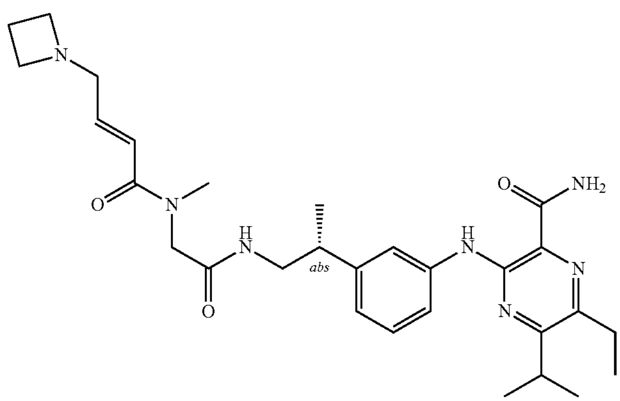 [SMILES: CCc1nc(C(N)=O)c(Nc2cccc([C@@H](C)CNC(=O)CN(C)C(=O)/C=C/CN3CCC3)c2)nc1C(C)C] | 535.68 | *** | ** | * |
| 510 | 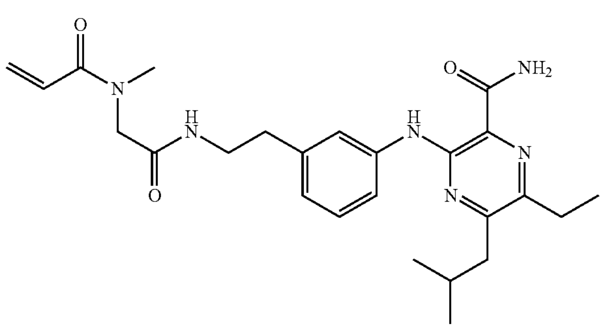 [SMILES: C=CC(=O)N(C)CC(=O)NCCc1cccc(Nc2nc(CC(C)C)c(CC)nc2C(N)=O)c1] | 466.58 | * | * | * |
| 511 | 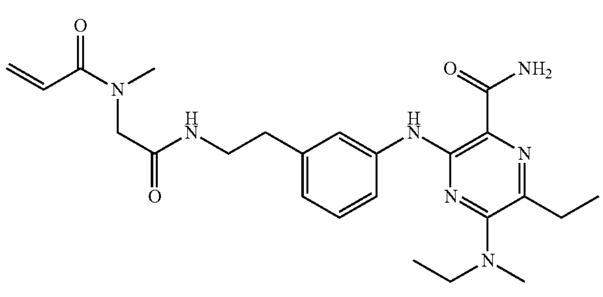 [SMILES: C=CC(=O)N(C)CC(=O)NCCc1cccc(Nc2nc(N(C)CC)c(CC)nc2C(N)=O)c1] | 467.56 | *** | ** | * |

TABLE 2A-continued

Representative compounds and their IC$_{50}$ values

| Compd ID | Structure | MW | MOLM-13 | MV-4:11 | K-562 |
|---|---|---|---|---|---|
| 512 | 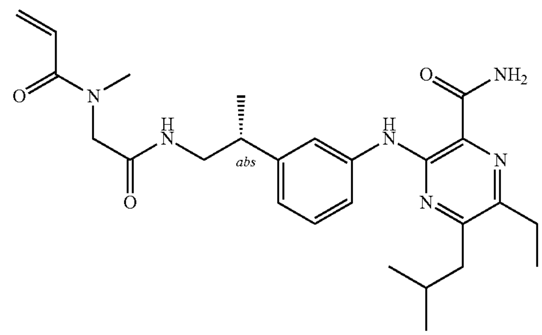 [SMILES: C=CC(=O)N(C)CC(=O)NC[C@H](C)c1cccc(Nc2nc(CC(C)C)c(CC)nc2C(N)=O)c1] | 480.6 | * | *** | * |
| 513 | 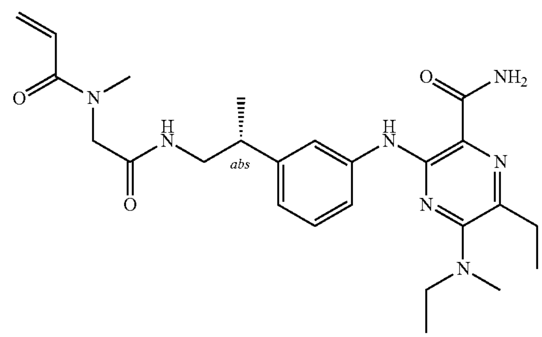 [SMILES: C=CC(=O)N(C)CC(=O)NC[C@H](C)c1cccc(Nc2nc(N(C)CC)c(CC)nc2C(N)=O)c1] | 481.59 | ** | * | * |
| 515 | 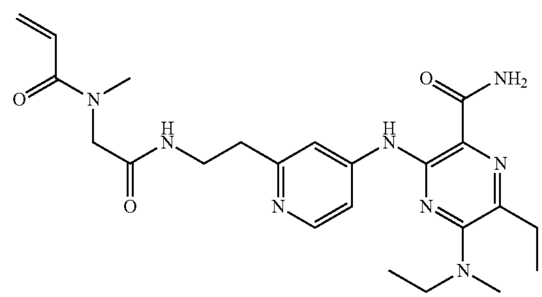 [SMILES: C=CC(=O)N(C)CC(=O)NCCc1cc(Nc2nc(N(C)CC)c(CC)nc2C(N)=O)ccn1] | 468.56 | ** | *** | * |
| 516 | 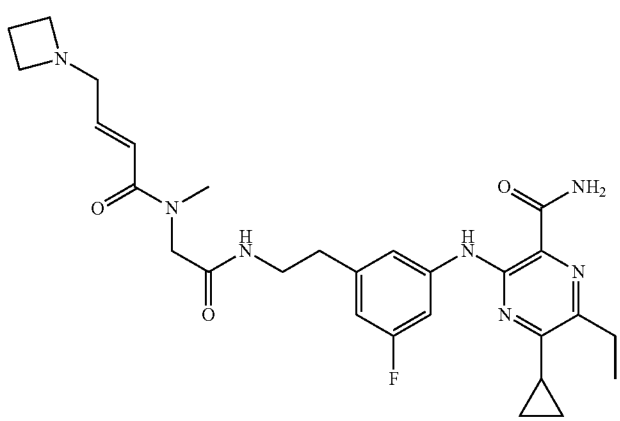 [SMILES: CCc1nc(C(N)=O)c(Nc2cc(F)cc(CCNC(=O)CN(C)C(=O)/C=C/CN3CCC3)c2)nc1C1CC1] | 537.64 | ** | ** | * |

TABLE 2A-continued
Representative compounds and their IC$_{50}$ values
| Compd ID | Structure | MW | MOLM-13 | MV-4:11 | K-562 |
|---|---|---|---|---|---|
| 516A | 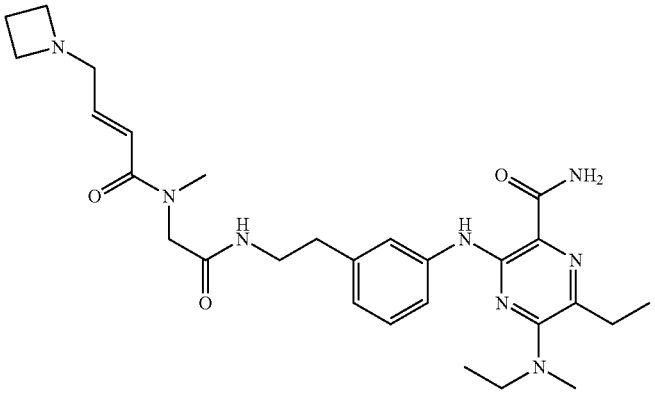 [SMILES: CCc1nc(C(N)=O)c(Nc2cccc(CCNC(=O)CN(C)C(=O)/C=C/CN3CCC3)c2)nc1N(C)CC] | 536.67 | *** | *** | * |
| 517 | 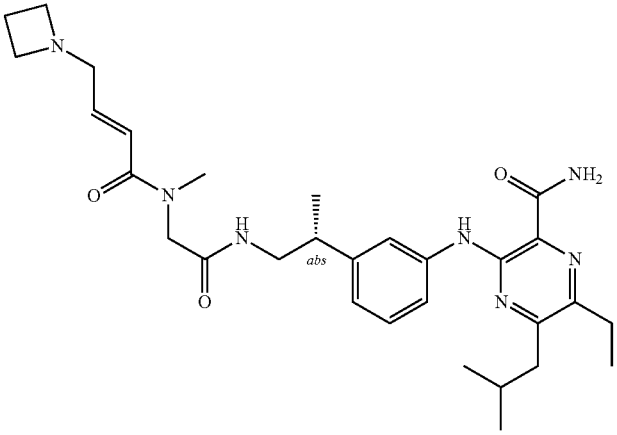 [SMILES: CCc1nc(C(N)=O)c(Nc2cccc([C@@H](C)CNC(=O)CN(C)C(=O)/C=C/CN3CCC3)c2)nc1CC(C)C] | 549.71 | ** | ** | * |
| 518 | 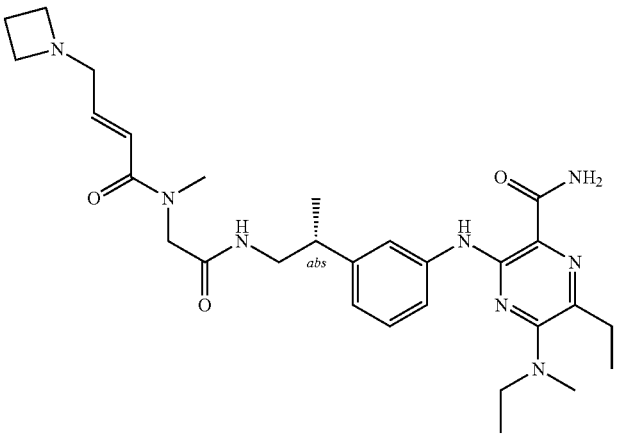 [SMILES: CCc1nc(C(N)=O)c(Nc2cccc([C@@H](C)CNC(=O)CN(C)C(=O)/C=C/CN3CCC3)c2)nc1N(C)CC] | 550.7 | *** | *** | * |

TABLE 2A-continued

Representative compounds and their IC$_{50}$ values

| Compd ID | Structure | MW | MOLM-13 | MV-4:11 | K-562 |
|---|---|---|---|---|---|
| 519 | 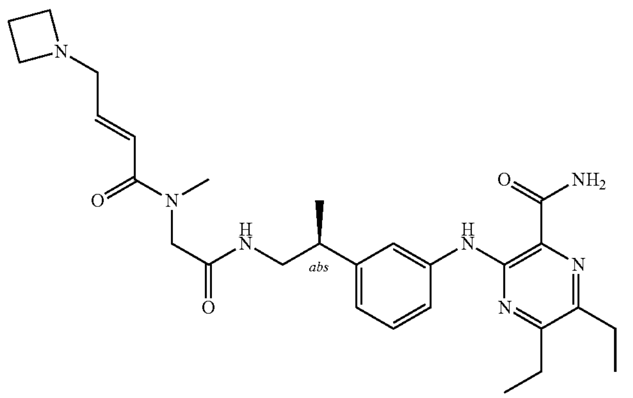 [SMILES: CCc1nc(Nc2cccc([C@H](C)CNC(=O)CN(C)C(=O)/C=C/CN3CCC3)c2)c(C(N)=O)nc1CC] | 521.65 | * | ** | * |
| 520 | 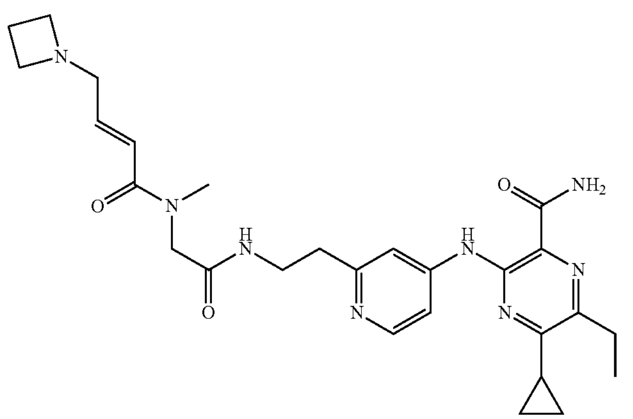 [SMILES: CCc1nc(C(N)=O)c(Nc2ccnc(CCNC(=O)CN(C)C(=O)/C=C/CN3CCC3)c2)nc1C1CC1] | 520.63 | ** | ** | * |
| 601 | 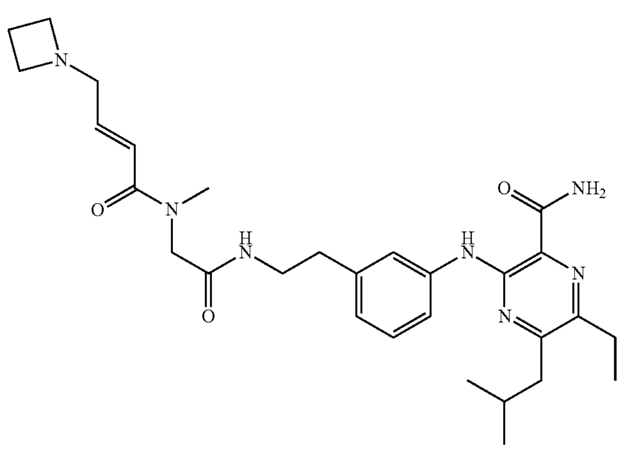 [SMILES: CCc1nc(C(N)=O)c(Nc2cccc(CCNC(=O)CN(C)C(=O)/C=C/CN3CCC3)c2)nc1CC(C)C] | 535.68 | ** | *** | * |

TABLE 2A-continued
Representative compounds and their IC$_{50}$ values
| Compd ID | Structure | MW | MOLM-13 | MV-4:11 | K-562 |
|---|---|---|---|---|---|
| 602 | 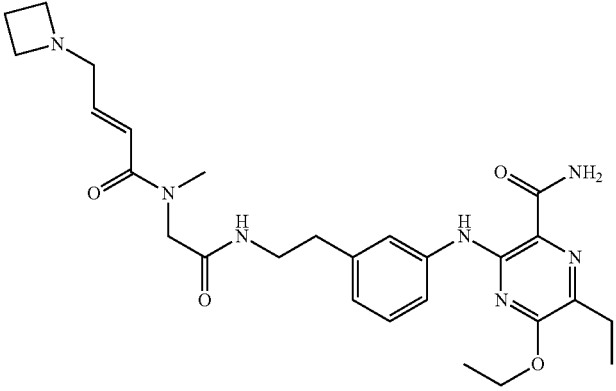 [SMILES: CCOc1nc(Nc2cccc(CCNC(=O)CN(C)C(=O)/C=C/CN3CCC3)c2)c(C(N)=O)nc1CC] | 523.63 | ** | *** | * |
| 603 | 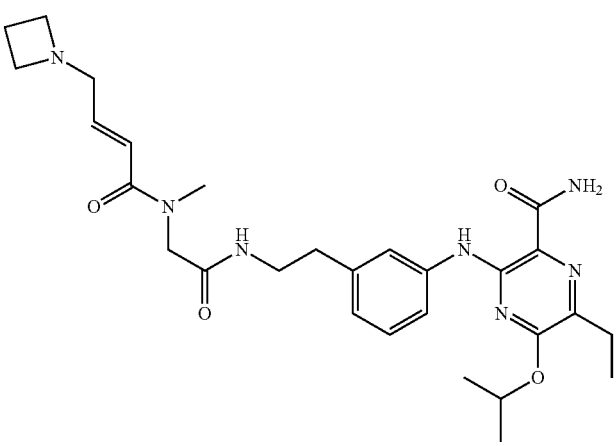 [SMILES: CCc1nc(C(N)=O)c(Nc2cccc(CCNC(=O)CN(C)C(=O)/C=C/CN3CCC3)c2)nc1OC(C)C] | 537.65 | ** | *** | * |
| 604 | 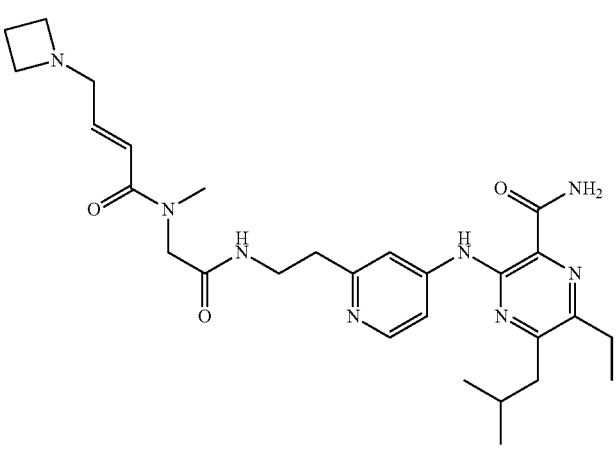 [SMILES: CCc1nc(C(N)=O)c(Nc2ccnc(CCNC(=O)CN(C)C(=O)/C=C/CN3CCC3)c2)nc1CC(C)C] | 536.67 | ** | *** | * |

TABLE 2A-continued
Representative compounds and their IC$_{50}$ values
| Compd ID | Structure | MW | MOLM-13 | MV-4:11 | K-562 |
|---|---|---|---|---|---|
| 605 | 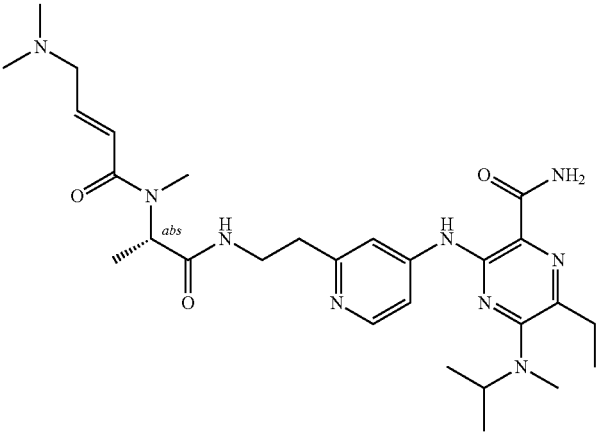 [SMILES: CCc1nc(C(N)=O)c(Nc2ccnc(CCNC(=O)[C@H](C)N(C)C(=O)/C=C/CN(C)C)c2)nc1N(C)C(C)C] | 553.7 | *** | *** | * |
| 606 | 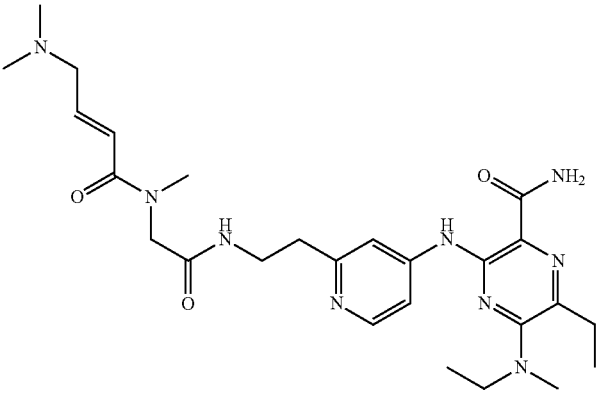 [SMILES: CCc1nc(C(N)=O)c(Nc2ccnc(CCNC(=O)CN(C)C(=O)/C=C/CN(C)C)c2)nc1N(C)CC] | 525.65 | ** | *** | * |
| 607 | 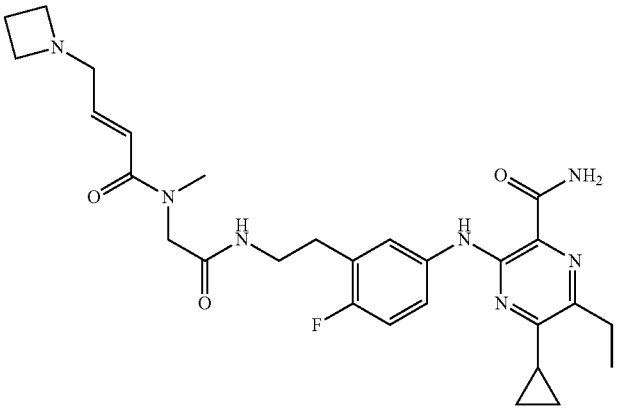 [SMILES: CCc1nc(C(N)=O)c(Nc2ccc(F)c(CCNC(=O)CN(C)C(=O)/C=C/CN3CCC3)c2)nc1C1CC1] | 537.63 | ** | ** | * |

TABLE 2A-continued

Representative compounds and their IC$_{50}$ values

| Compd ID | Structure | MW | MOLM-13 | MV-4:11 | K-562 |
|---|---|---|---|---|---|
| C-1 | 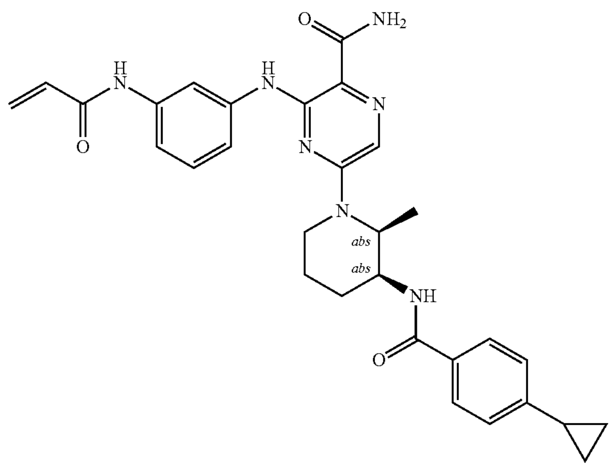 [SMILES: C=CC(=O)Nc1cccc(Nc2nc(N3CCC[C@H](NC(=O)c4ccc(C5CC5)cc4)[C@@H]3C)cnc2C(N)=O)c1] | 539.63 | * | * | * |
| C-2 | 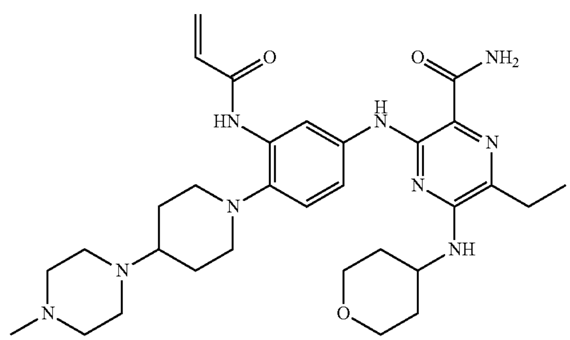 [SMILES: C=CC(=O)Nc1cc(Nc2nc(NC3CCOCC3)c(CC)nc2C(N)=O)ccc1N1CCC(N2CCN(C)CC2)CC1] | 591.75 | * |  | * |
| C-3 | 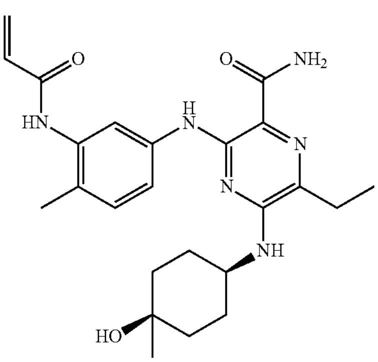 [SMILES: C=CC(=O)Nc1cc(Nc2nc(N[C@H]3CC[C@@](C)(O)CC3)c(CC)nc2C(N)=O)ccc1C] | 452.55 | * | * | * |
| Gilteritinib | 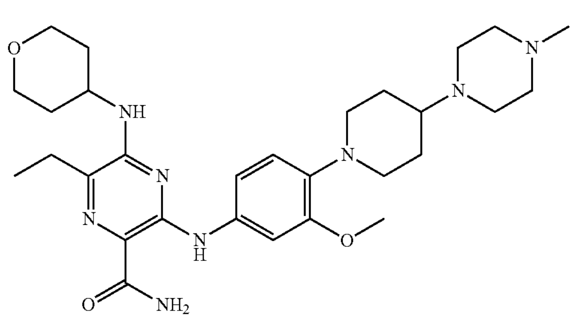 [SMILES: CCc1nc(C(N)=O)c(Nc2ccc(N3CCC(N4CCN(C)CC4)CC3)c(OC)c2)nc1NC1CCOCC1] | 552.71 | ** |  |  |

Example B2

WT FLT3 and FLT3-ITD Biochemical Assay

High throughput 384-well Lance Ultra TR-FRET based kinase assays were established for the WT FLT3 and FLT3-ITD enzymes and employed a ULight-labeled peptide (donor) and FLT3 proteins labelled with Eu-conjugated antibody (acceptor) (WuXi Aptec). The principle of TR-FRET is based on transfer of energy between a donor and acceptor fluorophore that results when the fluorophores are within close proximity (~100 Å) of each other. Recombinant WT FLT3 (#PR4666C, M.W. 48.6 kDa) was purchased from Invitrogen and FLT3-ITD (FLT3-ITD-W51, #F-12-12CG-10, M.W. 76 kDa) was purchased from Signalchem. Optimal assay conditions for the WT FLT3 enzyme assay were as follows: 0.5 nM FLT3 protein, 50 nM ULight-JAK-1 (Tyr1023) substrate peptide (PerkinElmer #TRF0121), 100 μM ATP, 60 min reaction time. Optimal assay conditions for the FLT3-ITD enzyme assay were as follows: 0.0625 nM FLT3-ITD protein, 50 nM ULight-JAK-1 (Tyr1023) substrate peptide, 50 μM ATP, 90 min reaction time. Briefly, 11 dose 3× serial dilutions were prepared for the test compounds and the reference compound and 100 nanoliters transferred to appropriate wells of 384-well assay plates. Five microliters of 2× enzyme/peptide were added into assay wells, assay plates centrifuged at 1000 rpm for about 30 seconds, sealed with sealing film and incubated for 30 min at 23° C. Assay buffer comprised 50 mM HEPES (pH 7.5), 1 mM EDTA, 0.01% Brij-35, 10 mM $MgCl_2$ and 2 mM DTT. Next 5 μl of a 2×ATP mixture were added into the assay wells and the plates centrifuged at 1000 rpm about 30 seconds, sealed with sealing film and incubated at 23° C. for appropriate duration. Following assay incubation (30 min for WT FLT3 and 60 min for FLT3-ITD) 10 μl 2× Detection Mixture (Eu-W1024 Anti-phosphotyrosine (PT66) 2 nM and EDTA 10 mM) was added to assay wells, assay plates centrifuge at 1000 rpm about 1 minutes, sealed with sealing film and incubated at 23° C. for 60 minutes. Assay plates were read on a Perkin Elmer Envision reader at two wavelengths (665/615) and the ratio of 615 nm to 665 nm calculated.

Data was expressed as % of inhibition relative to the vehicle control and calculated as follows: (100% inhibition−Well data)/(100% inhibition−0% inhibition)*100.

Results were analyzed by XLFIT5 as % inhibition vs. log [compound concentration] and $IC_{50}$ values were calculated by non-linear regression using four parameter-logistic equation. Fit=(A+((B−A)/(1+((C/x)^D)))). Res=(y−fit). Relative $IC_{50}$ values measured are reported in the Table 2B below: *** ≤0.1 nM,  0.101-0.200 nM, * 0.201-0.500 nM, ** 0.501-1.000 nM, * >1 nM.

Figure 3C:
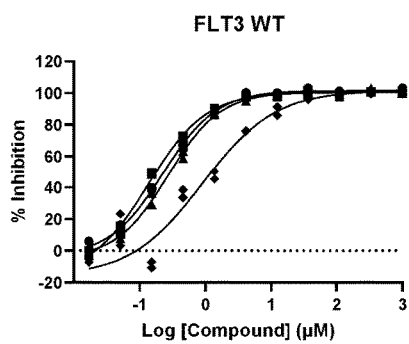
FIG. 3C depicts cell-based and biochemical activity of compounds 204, 205, 307, and 232 in FLT3-WT cells.
Figure 3D:
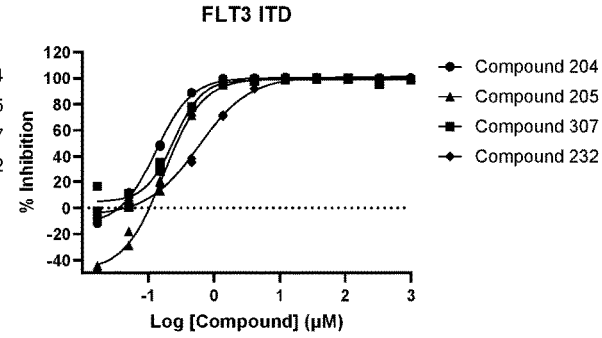
FIG. 3D depicts cell-based and biochemical activity of compounds 204, 205, 307, and 232 in FLT3-ITD enzymes.
Figure 4C:
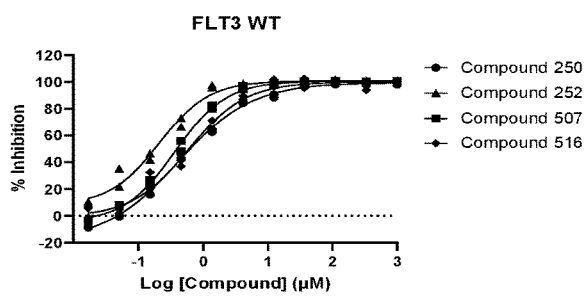
FIG. 4C depicts cell-based and biochemical activity of compounds 250, 252, 507, and 516 in FLT3-WT cells.
Figure 4D:
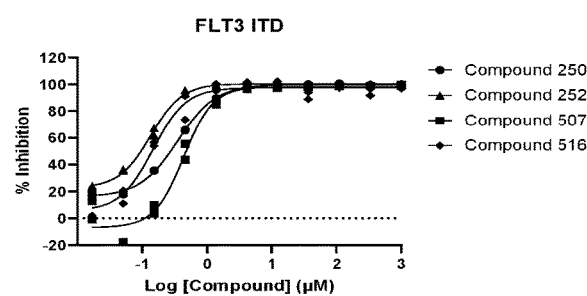
FIG. 4D depicts cell-based and biochemical activity of compounds 250, 252, 507, and 516 in FLT3-ITD enzymes.
Figure 5C:
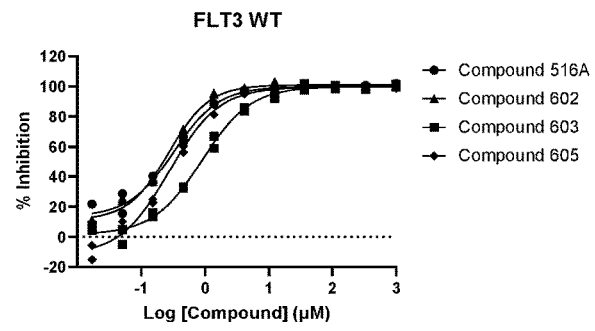
FIG. 5C depicts cell-based and biochemical activity of compounds 516A, 602, 603, and 605 in FLT3-WT cells.
Figure 5D:
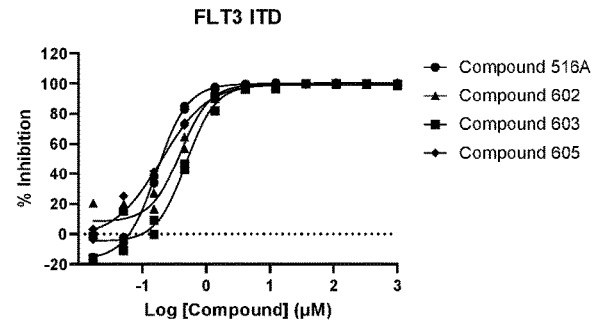
FIG. 5D depicts cell-based and biochemical activity of compounds 516A, 602, 603, and 605 in FLT3-ITD enzymes.

FIGS. 2c, 2d, 3c, 3d, 4c, 4d, 5c, and 5d depict biochemical activity of representative compounds in FLT3-WT, and FLT3-ITD enzymes.

Compounds of the disclosure provided the following $IC_{50}$ values:

TABLE 2B

Representative compounds and their $IC_{50}$ values

| Compd ID | FLT3 WT $IC_{50}$ | FLT3 ITD $IC_{50}$ |
|---|---|---|
| 137 | ** | *** |
| 138 | *** | *** |
| 143 | **** | **** |
| 144 | *** | *** |
| 156 | *** | *** |
| 158 | **** | **** |
| 159 | ** | *** |
| 203 | ** | *** |
| 204 | **** | **** |
| 205 | **** | **** |
| 213 | ** | **** |
| 221 | ** | **** |
| 232 | ** | ** |
| 239 | ** | **** |
| 241 | * | *** |
| 250 | *** | *** |
| 252 | *** | **** |
| 253 | ** | *** |
| 254 | ** | ** |
| 302 | * | * |
| 303 | *** | *** |
| 305 | * | * |
| 306 | ** | * |
| 307 | *** | *** |
| 308 | *** | **** |
| 310 | ** | ** |
| 315 | * | ** |
| 321 | ** | * |
| 327 | ** | *** |
| 328 | *** | *** |
| 501 | ** | ** |
| 502 | **** | *** |
| 503 | *** | ** |
| 506 | **** | *** |
| 507 | *** | *** |
| 508 | ** | ** |
| 509 | *** | ** |
| 510 | * | * |
| 511 | *** | ***** |
| 513 | ** | *** |
| 515 | ** | **** |
| 516 | *** | **** |
| 516A | ** | **** |
| 517 | ** | ** |
| 518 | *** | **** |
| 519 | * | * |
| 520 | * | ** |
| 601 | * | ** |
| 602 | *** | *** |
| 603 | *** | *** |
| 605 | *** | *** |
| 606 | ** | *** |
| C-1 | * | * |
| C-2 | ** | ** |
| C-3 | * | * |
| Gilteritinib | * | ** |

Example B3

FLT3 Mutant Assay

Multiple FLT3 kinase inhibitors are currently in the clinic, either approved or in developed, including midostaurin, sorafenib, quizartinib (AC220) and gilteritinib. Despite good potency, survival benefits, monotherapy of these targeted FLT3 inhibitors is limited by treatment-emergent resistance, thus leading to relapse and poor overall survival (Smith C C et al. Nature. 2012; 485(7397):260-U153, Smith et al. Blood. 2017; 130(1):48-58). Acquired mutations in the TKD and the F691L "gatekeeper" mutation confer resistance to most currently available FLT3 inhibitors (Eguchi et al. Biomedicines. 2020; 8(8):245; Smith C C et al. Cancer Discov. 2015; 5(6):668-79). Therefore, drugs that can overcome these drug resistance mutations confers selective advantages and is highly desired.

Activity of compounds on FLT3 activating mutations were assessed using Ba/F3 cell lines (mouse pro-B cell line) stably expressing human FLT3-ITD, FLT3-ITD-D835Y or FLT3-ITD-F691L. Briefly the human FLT3-ITD/FLT3-ITD-D835Y/FLT3-ITD-D691L expression plasmids were transfected into 293FT cells with lentivirus packaging plasmids to generate the lentiviruses. The supernatant collected were concentrated with PEG8000 and used to infect Ba/F3 cells at 1-5 MOI in serum-free media with polybrene. Infected Ba/F3 cells were selected in presence of puromycin, and surviving cells verified by sequencing and/or protein detection assay. Constitutive expression of the activating kinase transforms the Ba/F3 cells into IL-3-independent growth allowing them to be cultured in the absence of IL-3. The transformed cell lines thus generated were maintained in culture media (90% RPMI 1640+10% heat inactiate FBS+ 1× Pen-Strep/Antibiotic-Antimycotic) in the absence in IL-3 at 37° C. in an atmosphere of 5% $CO_2$ in air and routinely sub-cultured. For use in compound testing, cells in exponential growth phase were harvested, counted, and resuspended at the required cell density. Cell viability assays were performed in 96-well assay plates and 90 μL of cell suspension seeded per well. Serial dilutions of the test compounds and assay controls and were freshly prepared for the assay. Nine-point 3× serial dilutions were prepared in 100% DMSO (400× stock) and subsequently diluted in cell culture media to obtain 10× stocks. Ten microliters of the 10× stock serial dilutions were added to the appropriate wells (triplicate wells per condition) in the assay plate. The final DMSO concentration in the assay was 0.25%. Assay plates were incubated for 3 days in at 37° C. in a humidified incubator with 5% $CO_2$. At the end of 3 days, cell viability was assessed using the Promega CellTiter-Glo Luminescent Cell Viability Assay Kit (Promega-G7573) following manufacturer's protocol and the luminescence signal produced by ATP molecules in living cells was measured using the 2104 Envision plate reader (PerkinElmer).

Inhibition rate (IR) of the tested compounds was determined by the following formula: IR (%)=(1−(RLU compound−RLU blank)/(RLU control−RLU blank))*100%. The inhibitions of different dose of compound were calculated in Excel file, and the dose responses were analysed using GraphPad Prism to evaluate related parameters, such as Bottom, Top and IC50. For the IC50 analysis by GraphPad Prism, the equation below was used to fit curve: Y=Bottom+ (Top−Bottom)/(1+10^((Log IC50−X)*HillSlope))

Representative compounds provided herein showed potent antileukemic activity ($IC_{50}$<10 nM) when tested against the engineered Ba/F3 cell line stably expressing the human FLT3-ITD mutation, with top compounds showing higher potency than gilteritinib (Table 2C). Compounds were also tested against Ba/F3 cell lines stably expressing the TKD mutation, FLT3-ITD-D835Y, or the gatekeeper mutation, FLT3-ITD-F691L. Consistent with published data, FLT3-ITD-D835Y and FLT3-ITD-F691L mutants showed reduced sensitivity to quizartinib (50 to 100-fold increase in IC50) compared to FLT3-ITD. Gilteritinib retained high activity against FLT3-ITD and FLT3-ITD-D835Y mutant but was less active against the FLT3 gatekeeper mutation FLT3-ITD-F691L (—15-fold increase in IC50 versus FLT3-ITD). In comparison, the profile of several representative compounds provided herein stand out in that they retain good activity (<10-fold shift in $IC_{50}$) against both mutants. Of particular note FLT3-ITD-F691L was highly sensitivity to the majority of compounds of the invention. In conclusion, representative compounds of the invention show a superior profile given the ability to inhibit both the TKD mutation D835Y as well as the gatekeeper mutation F691L.

$IC_{50}$ values measured on day 3 (3 days) are reported in the Table 2C below: *** ≤1 nM, 1-10 nM, * 10-100 nM, ** 100-500 nM, * >500 nM.

Compounds of the disclosure provided the following $IC_{50}$ (3 days) values:

TABLE 2C

Representative compounds and their Relative $IC_{50}$ values

| Compd ID | Ba/F3-FLT3-ITD | Ba/F3-FLT3-ITD-D835Y | Ba/F3-FLT3-ITD-F691L |
|---|---|---|---|
| gilteritinib | **** | *** | *** |
| AC220 (quizartinib) | **** | ** | ** |
| 204 | **** | **** | **** |
| 205 | ***** | **** | **** |
| 219 | **** | *** | **** |
| 232 | **** | *** | **** |
| 250 | **** | *** | **** |
| 252 | ***** | **** | **** |
| 307 | **** | *** | *** |
| 310 | **** | *** | *** |
| 504 | **** | *** | **** |
| 506 | **** | *** | **** |
| 507 | **** | *** | **** |
| 508 | **** | *** | **** |
| 516 | **** | *** | *** |
| 516A | **** | *** | **** |
| 518 | **** | *** | **** |
| 602 | **** | *** | **** |
| 603 | **** | *** | *** |
| 605 | **** | *** | *** |

Gilteritinib - a known FLT3 inhibitor approved for approved for treatment of adult patients with relapsed or refractory acute myeloid leukemia (AML) with a FLT3 mutation.
Quizartinib - a known FLT3 inhibitor currently under development for the treatment of acute myeloid leukemia.

Example B34: Pharmaceutical Compositions

The compositions described below are presented with a compound of Formula (I) for illustrative purposes.

Example B32a: Parenteral Composition

To prepare a parenteral pharmaceutical composition suitable for administration by injection, 100 mg of a water-soluble salt of a compound of Formula (I) is dissolved in DMSO and then mixed with 10 mL of 0.9% sterile saline. The mixture is incorporated into a dosage unit form suitable for administration by injection.

Example B32b: Oral Composition

To prepare a pharmaceutical composition for oral delivery, 100 mg of a compound of Formula (I) is mixed with 750 mg of starch. The mixture is incorporated into an oral dosage unit for, such as a hard gelatin capsule, which is suitable for oral administration.

Example B2c: Sublingual (Hard Lozenge) Composition

To prepare a pharmaceutical composition for buccal delivery, such as a hard lozenge, mix 100 mg of a compound of Formula (I) with 420 mg of powdered sugar mixed, with 1.6 mL of light corn syrup, 2.4 mL distilled water, and 0.42 mL mint extract. The mixture is gently blended and poured into a mold to form a lozenge suitable for buccal administration.

Example B2d: Inhalation Composition

To prepare a pharmaceutical composition for inhalation delivery, 20 mg of a compound of Formula (I) is mixed with 50 mg of anhydrous citric acid and 100 mL of 0.9% sodium chloride solution.

The mixture is incorporated into an inhalation delivery unit, such as a nebulizer, which is suitable for inhalation administration.

Example B2e: Rectal Gel Composition

To prepare a pharmaceutical composition for rectal delivery, 100 mg of a compound of Formula (I) is mixed with 2.5 g of methylcelluose (1500 mPa), 100 mg of methylparapen, 5 g of glycerin and 100 mL of purified water. The resulting gel mixture is then incorporated into rectal delivery units, such as syringes, which are suitable for rectal administration.

Example B2f: Topical Gel Composition

To prepare a pharmaceutical topical gel composition, 100 mg of a compound of Formula (I) is mixed with 1.75 g of hydroxypropyl cellulose, 10 mL of propylene glycol, 10 mL of isopropyl myristate and 100 mL of purified alcohol USP. The resulting gel mixture is then incorporated into containers, such as tubes, which are suitable for topical administration.

Example B2 g: Ophthalmic Solution Composition

To prepare a pharmaceutical ophthalmic solution composition, 100 mg of a compound of Formula (I) is mixed with 0.9 g of NaCl in 100 mL of purified water and filtered using a 0.2 micron filter. The resulting isotonic solution is then incorporated into ophthalmic delivery units, such as eye drop containers, which are suitable for ophthalmic administration.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

At least some of the chemical names of compounds provided herein as given and set forth in this application, may have been generated on an automated basis by use of a commercially available chemical naming software program, and have not been independently verified. In the instance where the indicated chemical name and the depicted structure differ, the depicted structure will control. In the chemical structures where a chiral center exists in a structure, but no specific stereochemistry is shown for the chiral center, both enantiomers associated with the chiral structure are encompassed by the structure.

What is claimed is:
1. A compound according to Formula (P6-I):

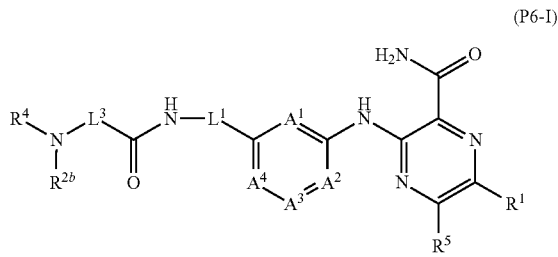

(P6-I)

or a stereoisomer thereof, or a pharmaceutically acceptable salt thereof,
wherein: each $A^1$, $A^2$, $A^3$, and $A^4$ is independently —C($R^7$);
each $L^1$ and $L^3$ is independently substituted or unsubstituted $C_1$-$C_4$ alkylene; and the substituents on each of $C_1$-$C_4$ alkylene are independently selected from one or more halo, CN, $C_{1-4}$ alkyl, hydroxy, and $C_{1-4}$ alkoxy;
$R^1$ is H, halo, CN, substituted or unsubstituted $C_{1-6}$ alkyl, substituted or unsubstituted alkoxy, substituted or unsubstituted alkenyl, substituted or unsubstituted alkynyl, substituted or unsubstituted cycloalkyl, or substituted or unsubstituted heterocycloalkyl, having 1-2 heteroatoms independently selected from nitrogen, oxygen, and sulfur; and the substituents on each of $C_{1-6}$ alkyl, alkoxy, alkenyl, alkynyl, cycloalkyl and heterocycloalkyl are selected from one or more halo, CN, $C_{1-4}$ alkyl, hydroxy, and $C_{1-4}$ alkoxy;
$R^{2b}$ is independently H or $C_1$-$C_4$ alkyl;
$R^4$ is —C(O)—C($R^{6a}$)=C($R^{6b}$)($R^{6c}$);
$R^5$ is H, cycloalkyl, heterocycloalkyl, CN, halo, $C_{1-6}$ alkyl, $C_{1-6}$ alkoxy, or $C_{1-6}$ alkylamino;
wherein
each of cycloalkyl, heterocycloalkyl, $C_{1-6}$ alkyl, $C_{1-6}$ alkoxy, and $C_{1-6}$ alkylamino is unsubstituted or substituted with
one or more halo, CN, $C_{1-4}$ alkyl, hydroxy, amino, alkylamino, dialkylamino, substituted or unsubstituted cycloalkyl, substituted or unsubstituted heterocycloalkyl, having 1-2 heteroatoms independently selected from nitrogen, oxygen, and sulfur; substituted or unsubstituted aryl, substituted or unsubstituted heteroaryl, or $C_{1-4}$ alkoxy; and
and the substituents on each of cycloalkyl, heterocycloalkyl, aryl, and heteroaryl are selected from one or more halo, CN, $C_{1-4}$ alkyl, hydroxy, and $C_{1-4}$ alkoxy;
each $R^{6a}$ and $R^{6b}$ is independently H, halo, CN, or $C_{1-6}$ alkyl; or $R^{6a}$ and $R^{6b}$ are joined together to form a bond; $R^{6c}$ is H, halo, CN, or $C_{1-6}$ alkyl, wherein the $C_{1-6}$ alkyl is unsubstituted or substituted with one or more groups selected from substituted or unsubstituted amino, hydroxy, substituted or unsubstituted $C_{1-6}$ alkoxy, and substituted or unsubstituted heterocycloalkyl having 1-2 heteroatoms independently selected from nitrogen, oxygen, and sulfur; and the substituents on each of amino, $C_{1-6}$ alkoxy and heterocycloalkyl are selected from one or more halo, CN, $C_{1-4}$ alkyl, hydroxy, and $C_{1-4}$ alkoxy;
each $R^7$ is independently H, halo, CN, substituted or unsubstituted $C_{1-6}$ alkyl, substituted or unsubstituted alkoxy, or substituted or unsubstituted heterocycloalkyl, having 1-2 heteroatoms independently selected from nitrogen, oxygen, and sulfur; and the substituents on each of $C_{1-6}$ alkyl, alkoxy and heterocycloalkyl are selected from one or more halo, CN, $C_{1-4}$ alkyl, hydroxy, and $C_{1-4}$ alkoxy.

2. The compound according to claim 1, wherein the compound is according to Formula (P6-IIa):

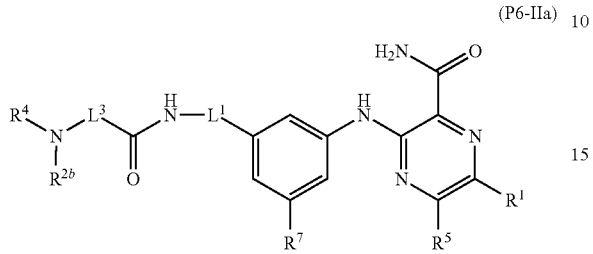

(P6-IIa)

or a stereoisomer thereof, or a pharmaceutically acceptable salt thereof.

3. The compound according to claim 1, wherein $L^1$ is —$CH_2$—$CH_2$—, —C(Me)H—$CH_2$—, or —$CH_2$—C(Me)H—.

4. The compound according to claim 1, wherein the compound is according to Formula (P6-IIIa):

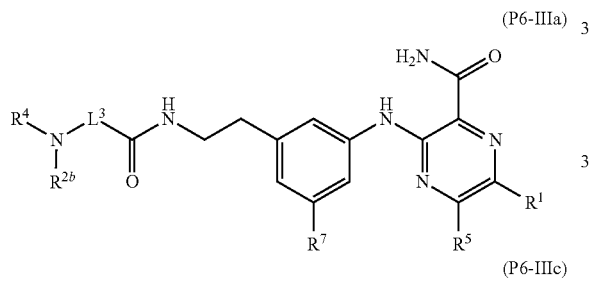

(P6-IIIa)

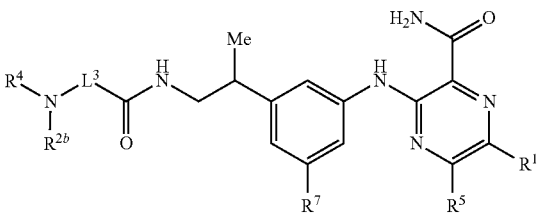

(P6-IIIc)

or a stereoisomer thereof, or a pharmaceutically acceptable salt thereof.

5. The compound according to claim 1, wherein $R^1$ is H, Me, or Et.

6. The compound according to claim 1, wherein the compound is according to Formula (P6-IVa) or (P6-IVc):

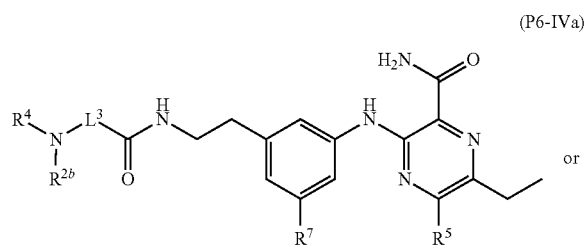

(P6-IVa)

or

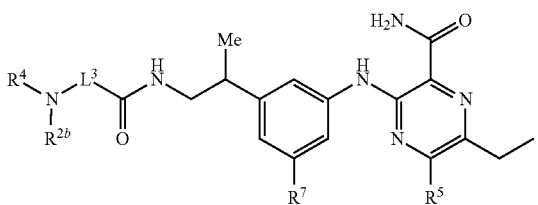

(P6-IVc)

or a stereoisomer thereof, or a pharmaceutically acceptable salt thereof.

7. The compound according to claim 1, wherein $L^3$ is —$CH_2$—, or —C(Me)H—.

8. The compound according to claim 1, wherein $R^{2b}$ is H or Me.

9. The compound according to claim 1, wherein $R^7$ is H, F, Me, Et, Cl, $CF_3$, or OMe.

10. The compound according to claim 1, wherein $R^5$ is unsubstituted or substituted $C_{1-6}$ alkyl, unsubstituted or substituted $C_{1-6}$ alkoxy, or unsubstituted or substituted $C_{1-6}$ alkylamino; wherein each of $C_{1-6}$ alkyl, $C_{1-6}$ alkoxy, and $C_{1-6}$ alkylamino is unsubstituted or substituted with one or more halo, CN, $C_{1-4}$ alkyl, hydroxy, amino, alkylamino, dialkylamino, substituted or unsubstituted cycloalkyl, substituted or unsubstituted heterocycloalkyl, having 1-2 heteroatoms independently selected from nitrogen, oxygen, and sulfur; substituted or unsubstituted aryl, substituted or unsubstituted heteroaryl, or $C_{1-4}$ alkoxy; and the substituents on each of cycloalkyl, heterocycloalkyl, aryl, and heteroaryl are selected from one or more halo, CN, $C_{1-4}$ alkyl, hydroxy, and $C_{1-4}$ alkoxy.

11. The compound according to claim 1, wherein $R^5$ is Me, Et, i-Pr, n-Pr, n-Bu, i-Bu, t-Bu, sec-Bu, substituted or unsubstituted cyclopropyl, substituted or unsubstituted cyclobutyl, substituted or unsubstituted cyclopentyl, substituted or unsubstituted cyclohexyl, Cl, F, CN, $CF_3$, OMe, OEt, O-i-Pr, —$OCF_3$, N,N-dimethylamino, N,N-diethylamino, N,N-diisopropylamino, N-ethyl-N-methylamino, N-iso-propyl-N-methylamino, N-iso-propyl-N-ethylamino, N-isopropylamino, N-ethylamino, N-methylamino, N-n-propylamino, substituted or unsubstituted 1-azetidinyl, substituted or unsubstituted 1-pyrrolidinyl, substituted or unsubstituted 1-piperidinyl, or substituted or unsubstituted 1-morpholinyl; and the substituents on each of cyclopropyl, cyclobutyl, cyclopentyl, cyclohexyl, azetidinyl, pyrrolidinyl, piperidinyl, and morpholinyl are selected from one or more halo, CN, $C_{1-4}$ alkyl, hydroxy, and $C_{1-4}$ alkoxy.

12. The compound according to claim 1, wherein $R^5$ is Me, Et, n-Pr, i-Pr, i-Bu, cyclopropyl, N,N-dimethyl, N-ethyl-N-methyl, N-isopropylamino, N-isopropyl-N-methylamino, methoxy, ethoxy, or i-propyloxy.

13. The compound according to claim 1, wherein each of $R^{6a}$, $R^{6b}$, and $R^{6c}$ is H.

14. The compound according to claim 1, wherein each of $R^{6a}$ and $R^{6b}$ is H; and $R^{6c}$ is $C_{1-6}$ alkyl substituted with amino, alkylamino or dialkylamino.

15. The compound according to claim 1, wherein $R^{6a}$ and $R^{6b}$ form a bond; and $R^{6c}$ is Me.

16. The compound according to claim 1, wherein each of $R^{6a}$ and $R^{6b}$ is H; and $R^{6c}$ is —$(CH_2)_q$-heterocycloalkyl; and q is 1.

17. The compound according to claim 1, wherein $R^4$ is —C(O)—CH=$CH_2$, —C(O)—CH=CH—$CH_2$—NHMe, —C(O)—CH=CH—$CH_2$—$NMe_2$, —C(O)—CH=CH—

CH₂-azetidin-1-yl, —C(O)—CH=CH—CH₂—(3-fluoro-azetidin-1-yl), —C(O)—CH=CH—CH₂—(3,3-difluoro-azetidin-1-yl), —C(O)—C≡CH, —C(O)—C≡C-Me, or —C(O)—C—C≡CH₂—NMe₂.
18. The compound according to claim 1, wherein the compound is selected from any one of the compounds listed in the following table, or a pharmaceutically acceptable salt or stereoisomer thereof
| Compd ID | Structure |
|---|---|
| 137 | 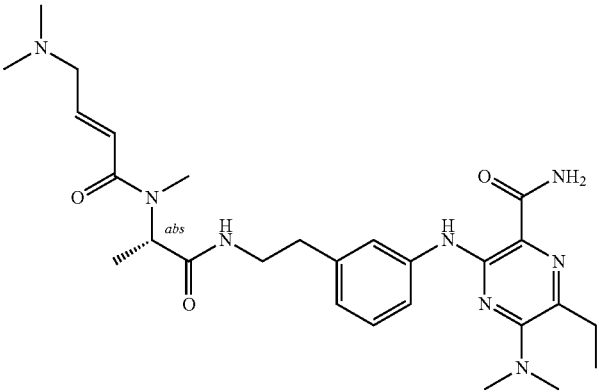 [SMILES: CCc1nc(C(N)=O)c(Nc2cccc(CCNC(=O)[C@H](C)N(C)C(=O)/C=C/CN(C)C)c2)nc1N(C)C] |
| 138 | 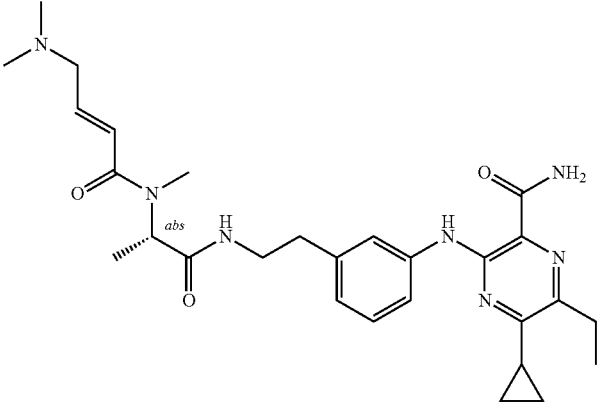 [SMILES: CCc1nc(C(N)=O)c(Nc2cccc(CCNC(=O)[C@H](C)N(C)C(=O)/C=C/CN(C)C)c2)nc1C1CC1] |
| 142A | 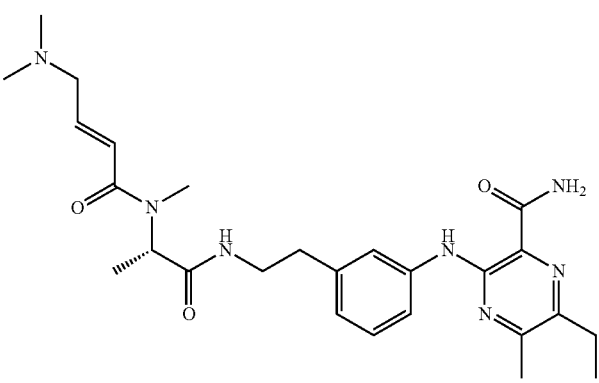 [SMILES: CCc1nc(C(N)=O)c(Nc2cccc(CCNC(=O)[C@H](C)N(C)C(=O)/C=C/CN(C)C)c2)nc1C] |

-continued

| Compd ID | Structure |
|---|---|
| 143 | 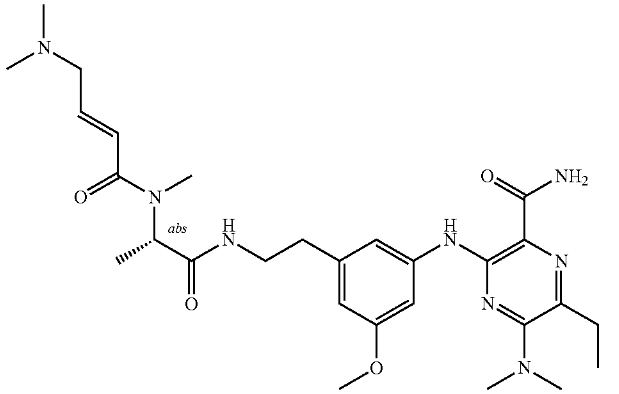 [SMILES: CCc1nc(C(N)=O)c(Nc2cc(CCNC(=O)[C@H](C)N(C)C(=O)/C=C/CN(C)C)cc(OC)c2)nc1N(C)C] |
| 144 | 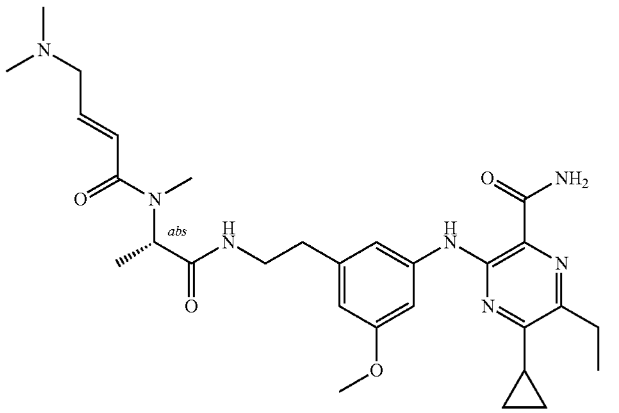 [SMILES: CCc1nc(C(N)=O)c(Nc2cc(CCNC(=O)[C@H](C)N(C)C(=O)/C=C/CN(C)C)cc(OC)c2)nc1C1CC1] |
| 156 | 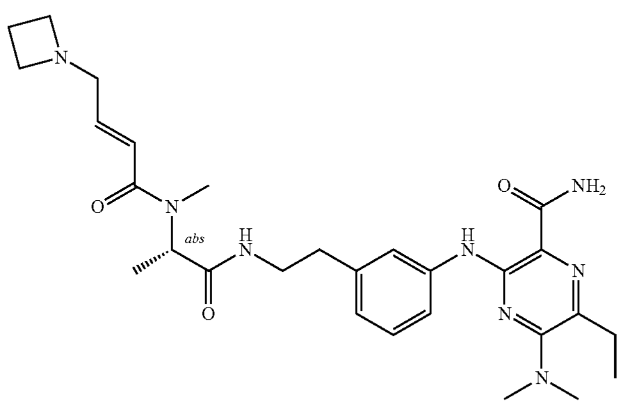 [SMILES: CCc1nc(C(N)=O)c(Nc2cccc(CCNC(=O)[C@H](C)N(C)C(=O)/C=C/CN3CCC3)c2)nc1N(C)C] |
| 158 | 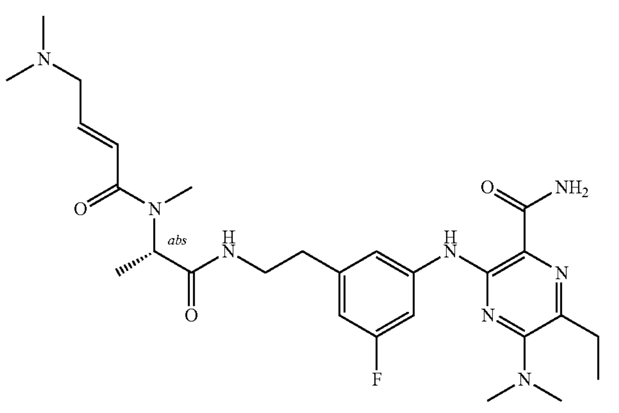 [SMILES: CCc1nc(C(N)=O)c(Nc2cc(F)cc(CCNC(=O)[C@H](C)N(C)C(=O)/C=C/CN(C)C)c2)nc1N(C)C] |

| Compd ID | Structure |
|---|---|
| 159 | 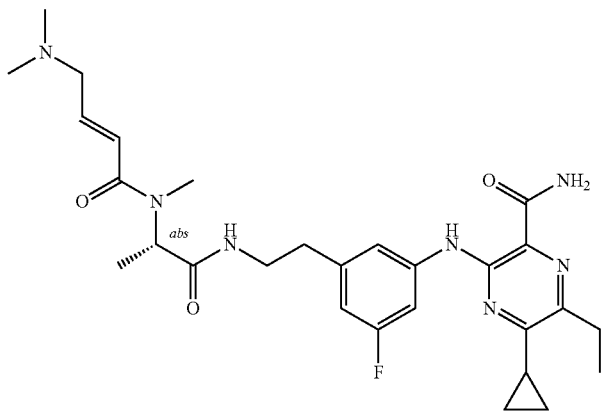 [SMILES: CCc1nc(C(N)=O)c(Nc2cc(F)cc(CCNC(=O)[C@H](C)N(C)C(=O)/C=C/CN(C)C)c2)nc1C1CC1] |
| 160 | 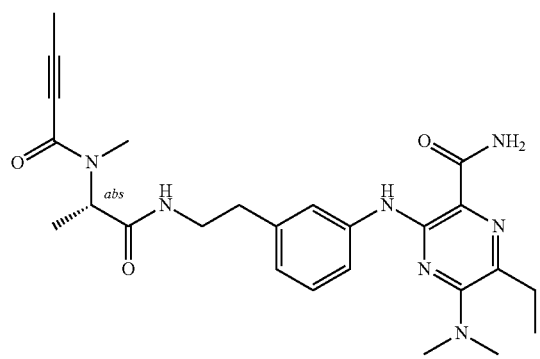 [SMILES: CC#CC(=O)N(C)[C@@H](C)C(=O)NCCc1cccc(Nc2nc(N(C)C)c(CC)nc2C(N)=O)c1] |
| 162 | 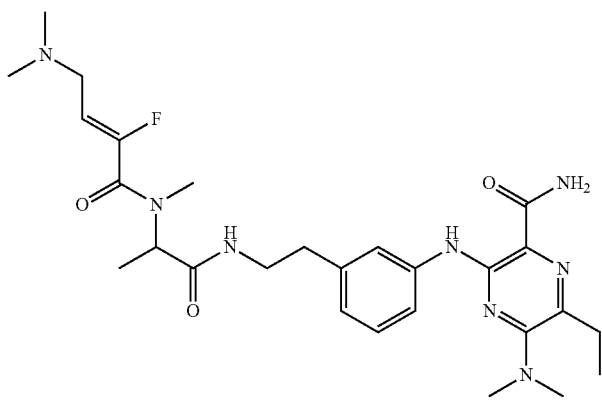 [SMILES: CCc1nc(C(N)=O)c(Nc2cccc(CCNC(=O)C(C)N(C)C(=O)/C(F)=C/CN(C)C)c2)nc1N(C)C] |
| 163 | 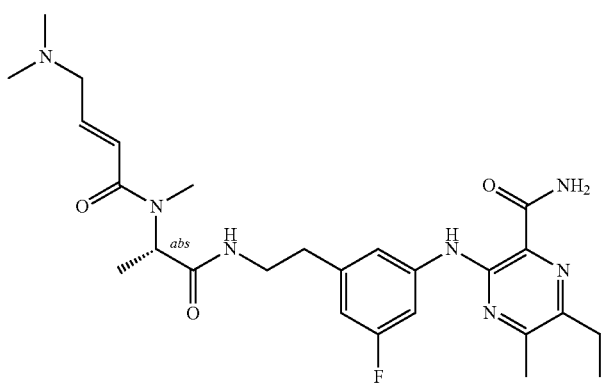 [SMILES: CCc1nc(C(N)=O)c(Nc2cc(F)cc(CCNC(=O)[C@H](C)N(C)C(=O)/C=C/CN(C)C)c2)nc1C] |

| Compd ID | Structure |
|---|---|
| 164 | 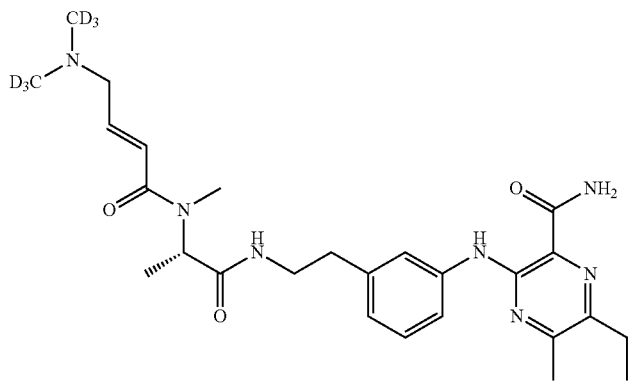 [SMILES: [2H]C([2H])([2H])N(C/C=C/C(=O)N(C)[C@@H](C)C(=O)NCCc1cccc(Nc2nc(C)c(CC)nc2C(N)=O)c1)C([2H])([2H])[2H]] |
| 202 | 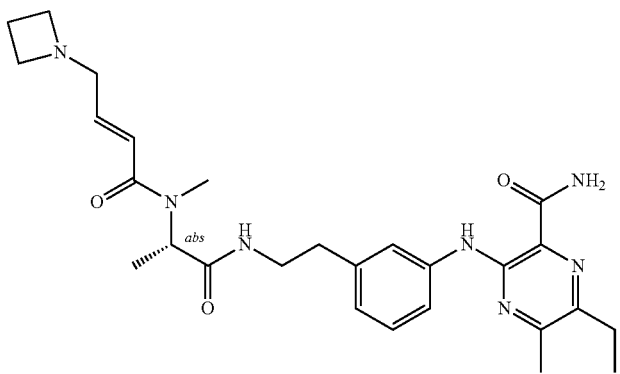 [SMILES: CCc1nc(C(N)=O)c(Nc2cccc(CCNC(=O)[C@H](C)N(C)C(=O)/C=C/CN3CCC3)c2)nc1C] |
| 203 | 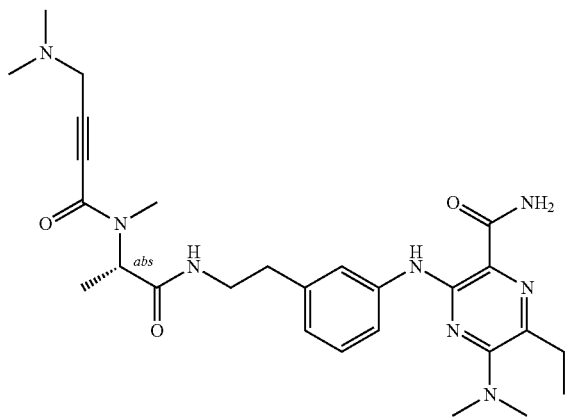 [SMILES: CCc1nc(C(N)=O)c(Nc2cccc(CCNC(=O)[C@H](C)N(C)C(=O)C#CCN(C)C)c2)nc1N(C)C] |
| 204 | 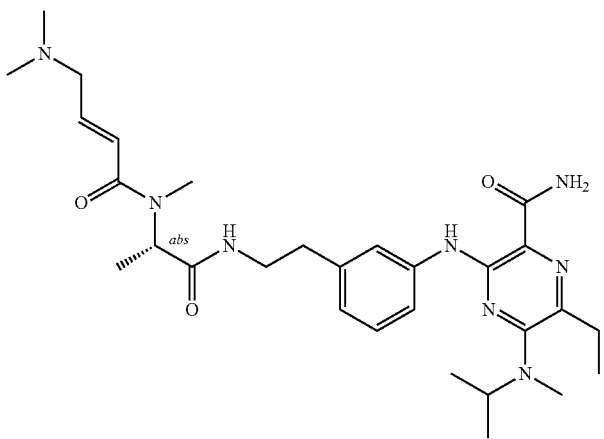 |

| Compd ID | Structure |
|---|---|
| 205 | 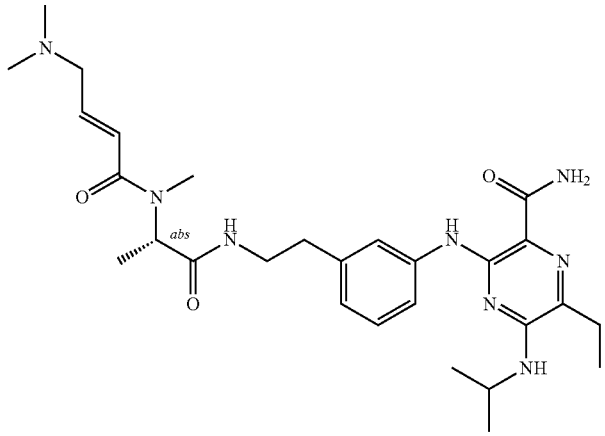 [SMILES: CCc1nc(C(N)=O)c(Nc2cccc(CCNC(=O)[C@H](C)N(C)C(=O)/C=C/CN(C)C)c2)nc1NC(C)C] |
| 207 | 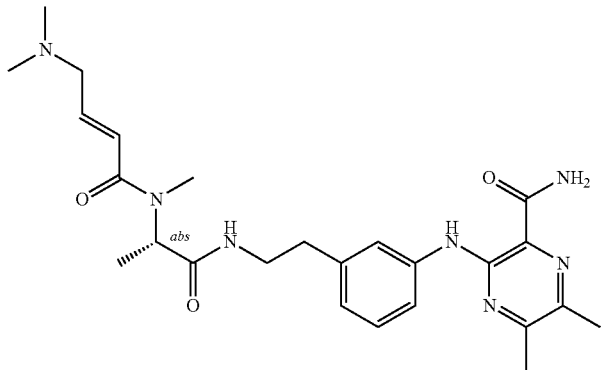 |
| 208 | 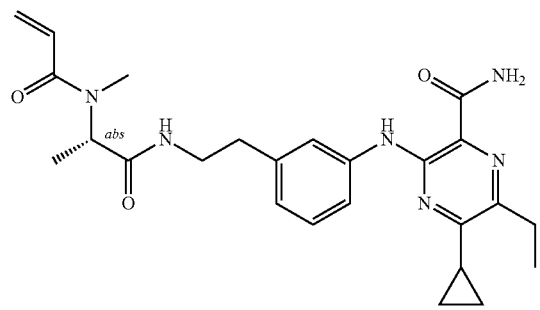 [SMILES: C=CC(=O)N(C)[C@@H](C)C(=O)NCCc1cccc(Nc2nc(C3CC3)c(CC)nc2C(N)=O)c1] |
| 209 | 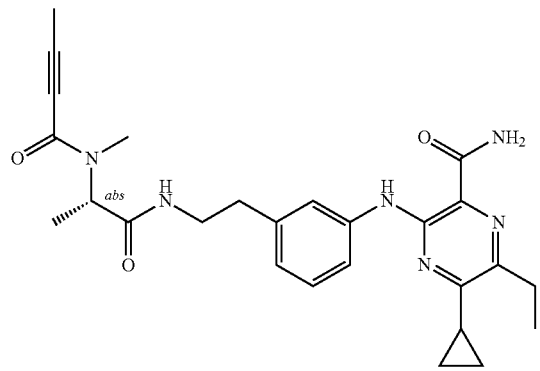 [SMILES: CC#CC(=O)N(C)[C@@H](C)C(=O)NCCc1cccc(Nc2nc(C3CC3)c(CC)nc2C(N)=O)c1] |

| Compd ID | Structure |
|---|---|
| 211 | 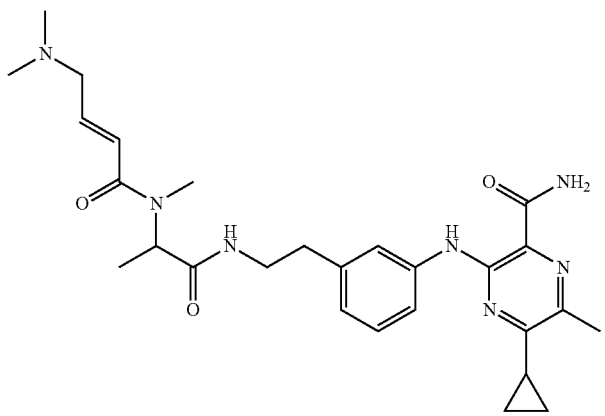 |
| 213 | 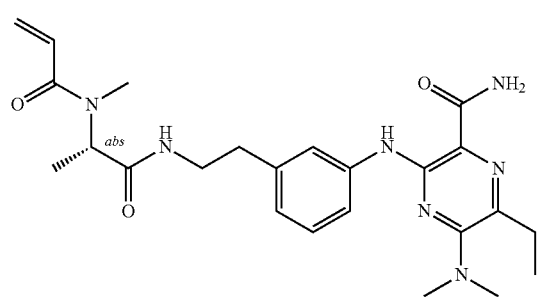 [SMILES: C=CC(=O)N(C)[C@@H](C)C(=O)NCCc1cccc(Nc2nc(N(C)C)c(CC)nc2C(N)=O)c1] |
| 214 | 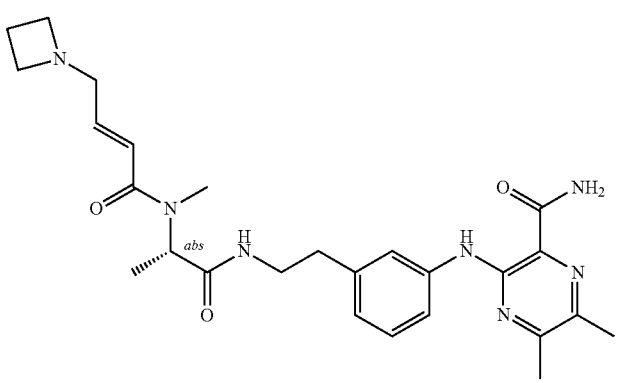 [SMILES: Cc1nc(Nc2cccc(CCNC(=O)[C@H](C)N(C)C(=O)/C=C/CN3CCC3)c2)c(C(N)=O)nc1C] |
| 215 | 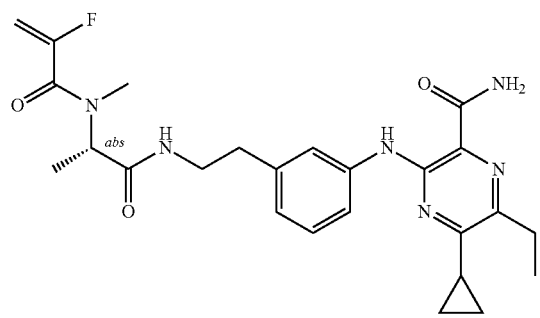 [SMILES: C=C(F)C(=O)N(C)[C@@H](C)C(=O)NCCc1cccc(Nc2nc(C3CC3)c(CC)nc2C(N)=O)c1] |

| Compd ID | Structure |
|---|---|
| 216 | 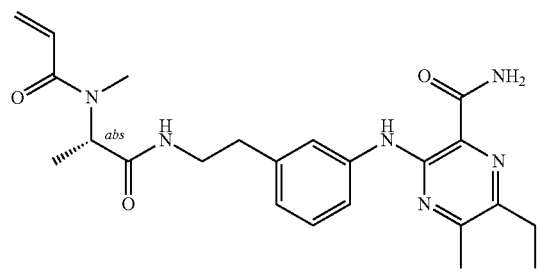 [SMILES: C=CC(=O)N(C)[C@@H](C)C(=O)NCCc1cccc(Nc2nc(C)c(CC)nc2C(N)=O)c1] |
| 217 | 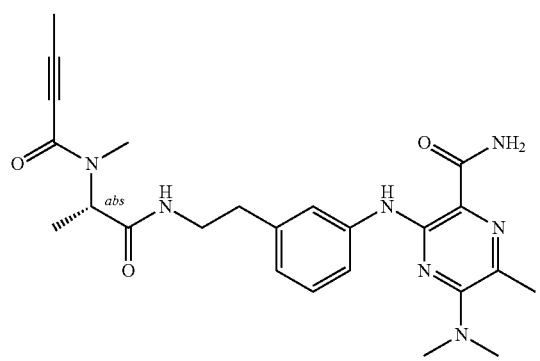 [SMILES: CC#CC(=O)N(C)[C@@H](C)C(=O)NCCc1cccc(Nc2nc(N(C)C)c(C)nc2C(N)=O)c1] |
| 218 | 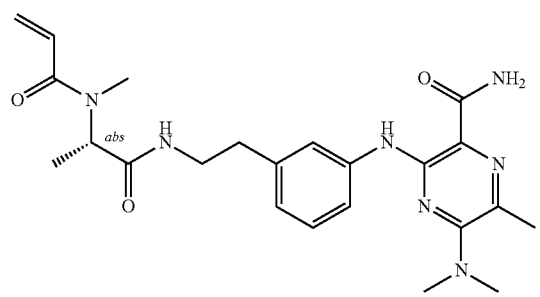 |
| 219 | 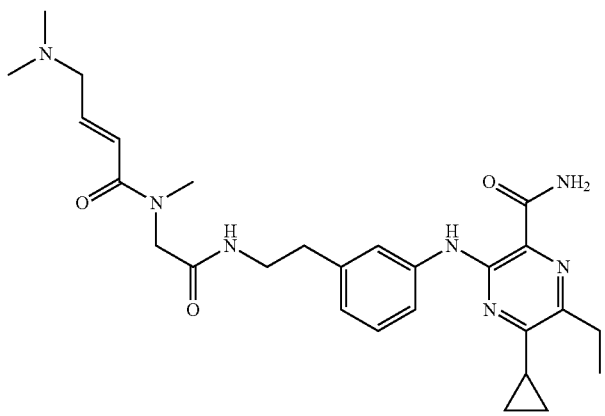 [SMILES: CCc1nc(C(N)=O)c(Nc2cccc(CCNC(=O)CN(C)C(=O)/C=C/CN(C)C)c2)nc1C1CC1] |

| Compd ID | Structure |
|---|---|
| 220 | 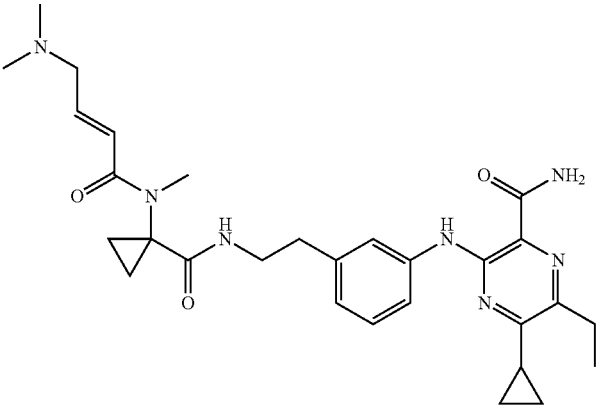 [SMILES: CCc1nc(C(N)=O)c(Nc2cccc(CCNC(=O)C3(N(C)C(=O)/C=C/CN(C)C)CC3)c2)nc1C1CC1] |
| 221 | 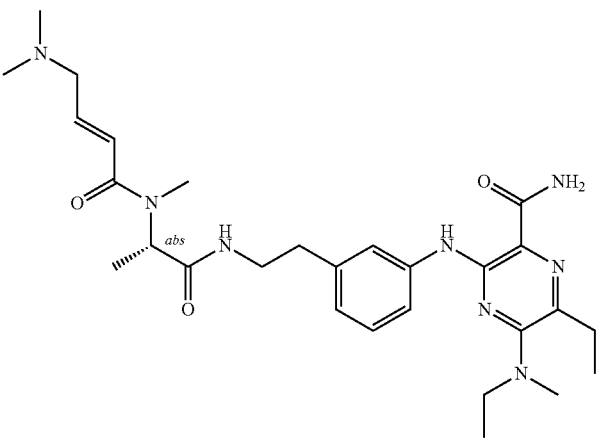 [SMILES: CCc1nc(C(N)=O)c(Nc2cccc(CCNC(=O)[C@H](C)N(C)C(=O)/C=C/CN(C)C)c2)nc1N(C)CC] |
| 222 | 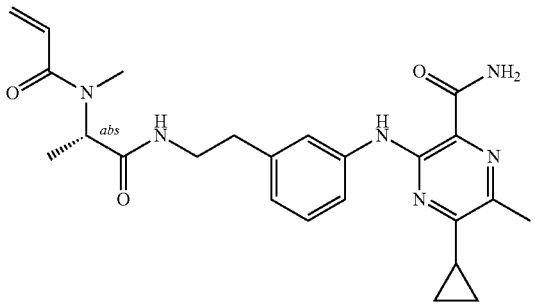 [SMILES: C=CC(=O)N(C)[C@@H](C)C(=O)NCCc1cccc(Nc2nc(C3CC3)c(C)nc2C(N)=O)c1] |
| 223 | 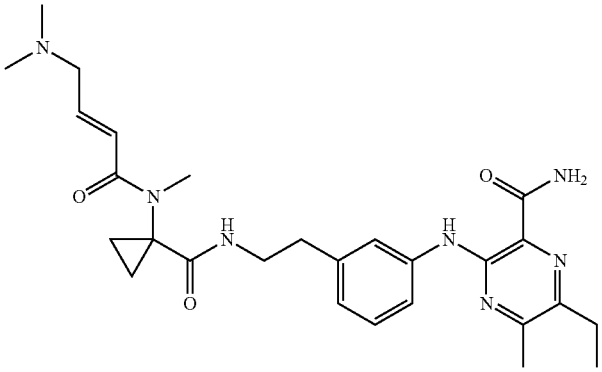 [SMILES: CCc1nc(C(N)=O)c(Nc2cccc(CCNC(=O)C3(N(C)C(=O)/C=C/CN(C)C)CC3)c2)nc1C] |

| Compd ID | Structure |
|---|---|
| 224 | 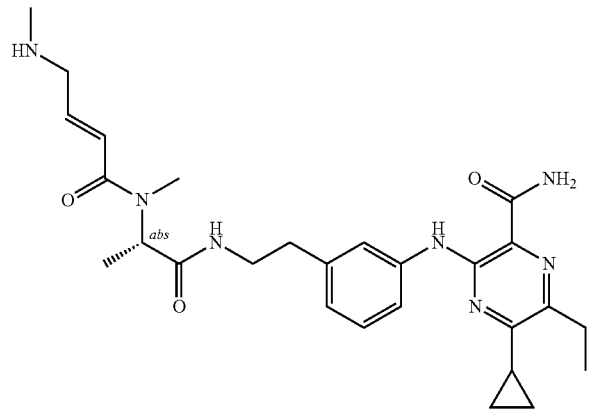 [SMILES: CCc1nc(C(N)=O)c(Nc2cccc(CCNC(=O)[C@H](C)N(C)C(=O)/C=C/CNC)c2)nc1C1CC1] |
| 225 | 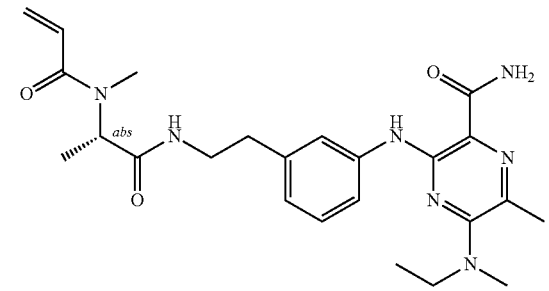 [SMILES: C=CC(=O)N(C)[C@@H](C)C(=O)NCCc1cccc(Nc2nc(N(C)CC)c(C)nc2C(N)=O)c1] |
| 226 | 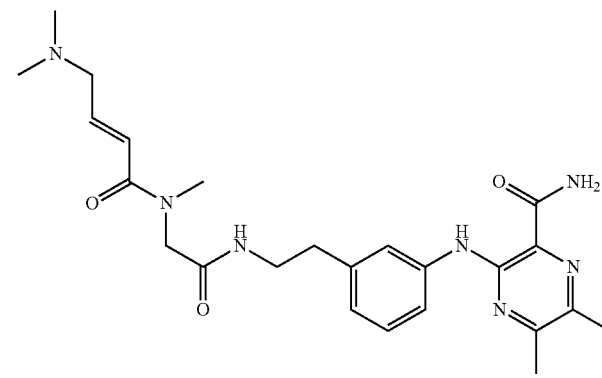 |
| 227 | 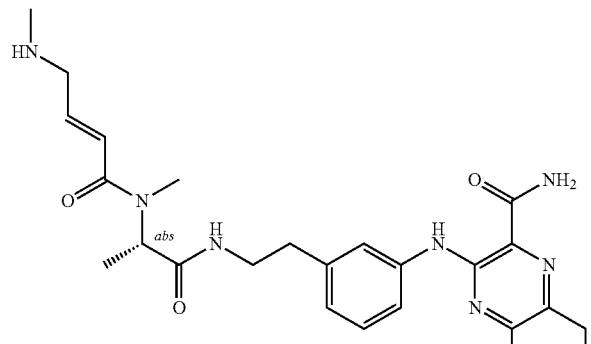 |

| Compd ID | Structure |
|---|---|
| 228 | 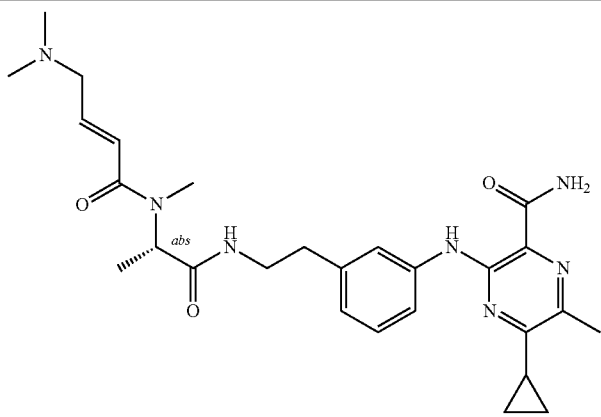 |
| 230 | 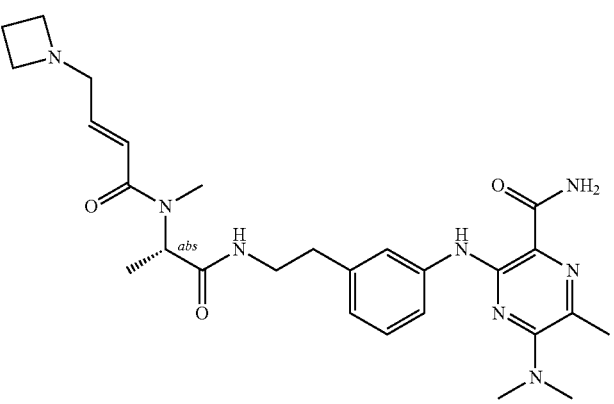 [SMILES: Cc1nc(C(N)=O)c(Nc2cccc(CCNC(=O)[C@H](C)N(C)C(=O)/C=C/CN3CCC3)c2)nc1N(C)C] |
| 231 | 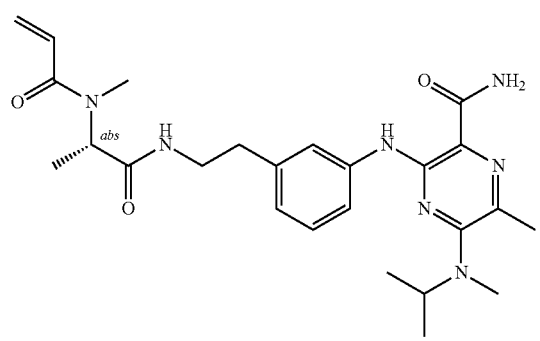 [SMILES: C=CC(=O)N(C)[C@@H](C)C(=O)NCCc1cccc(Nc2nc(N(C)C(C)C)c(C)nc2C(N)=O)c1] |
| 232 | 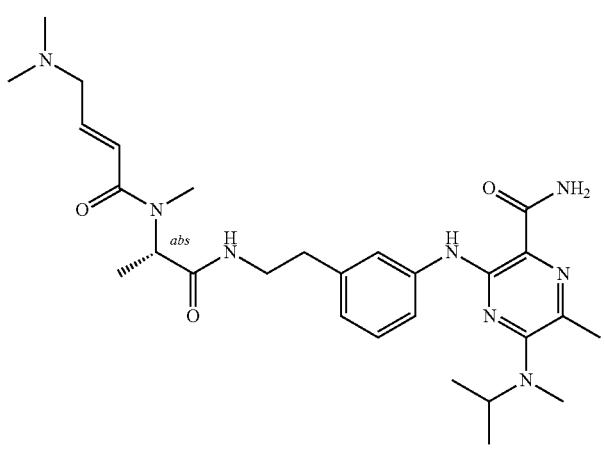 |

US 11,945,785 B2
467                                                                    468
-continued
| Compd ID | Structure |
|---|---|
| 233 | 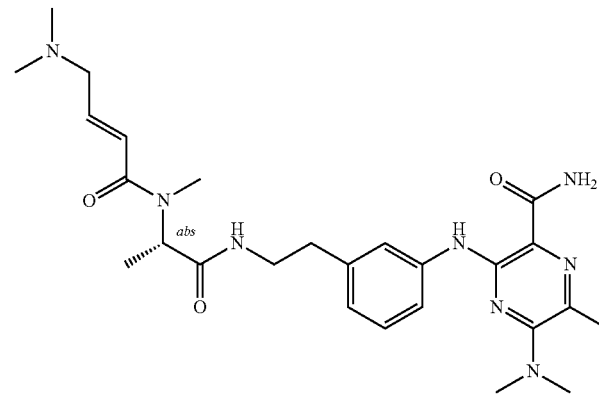 |
| 234 | 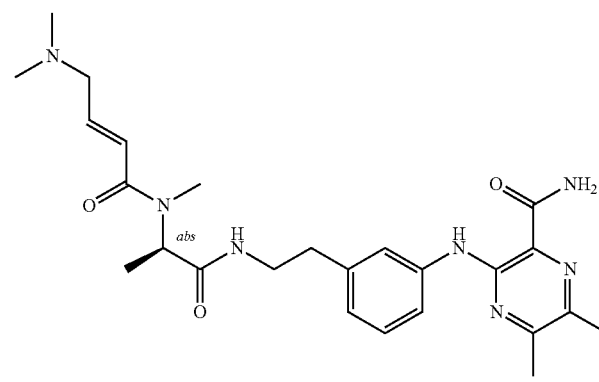 |
| 236 | 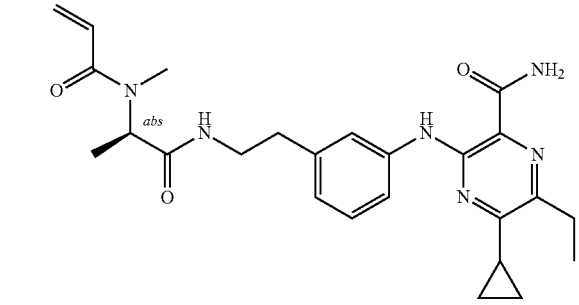 [SMILES: C=CC(=O)N(C)[C@H](C)C(=O)NCCc1cccc(Nc2nc(C3CC3)c(CC)nc2C(N)=O)c1] |
| 237 | 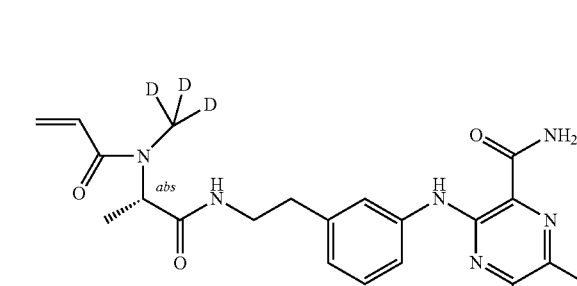 |

-continued
| Compd ID | Structure |
|---|---|
| 238 | 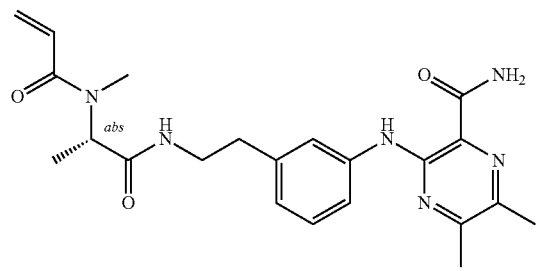 [SMILES: C=CC(=O)N(C)[C@@H](C)C(=O)NCCc1cccc(Nc2nc(C)c(C)nc2C(N)=O)c1] |
| 239 | 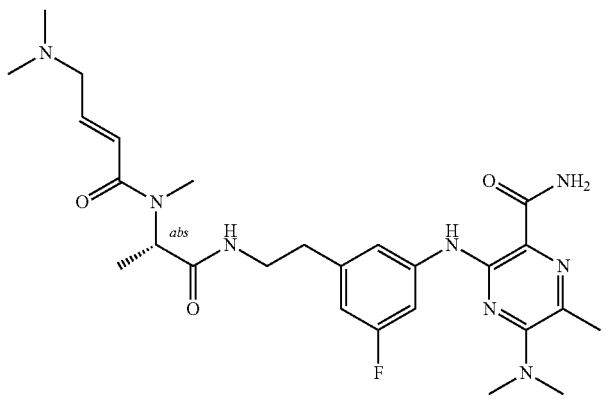 |
| 240 | 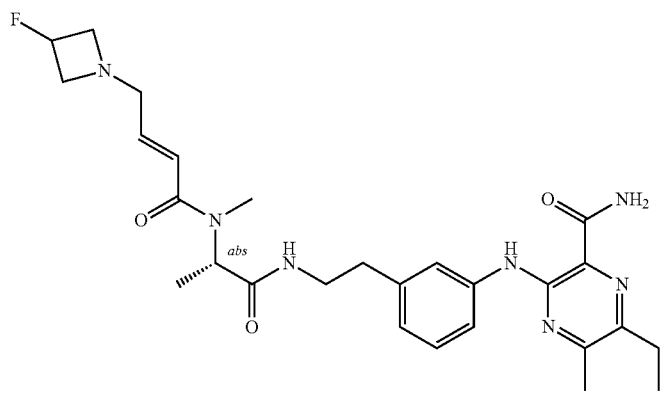 [SMILES: CCc1nc(C(N)=O)c(Nc2cccc(CCNC(=O)[C@H](C)N(C)C(=O)/C=C/CN3CC(F)C3)c2)nc1C] |
| 241 | 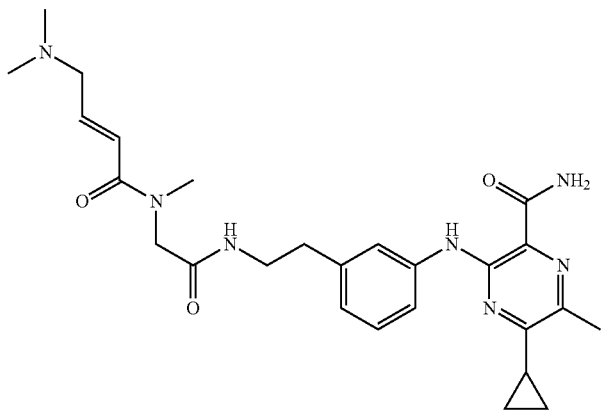 |

US 11,945,785 B2
471                                                                                                           472
-continued
| Compd ID | Structure |
|---|---|
| 242 | 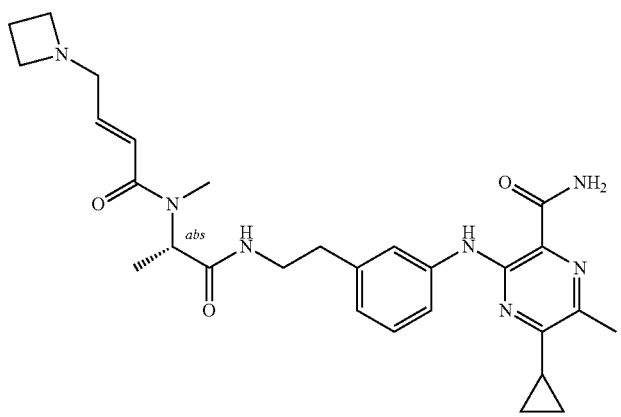 [SMILES: Cc1nc(C(N)=O)c(Nc2cccc(CCNC(=O)[C@H](C)N(C)C(=O)/C=C/CN3CCC3)c2)nc1C1CC1] |
| 243 | 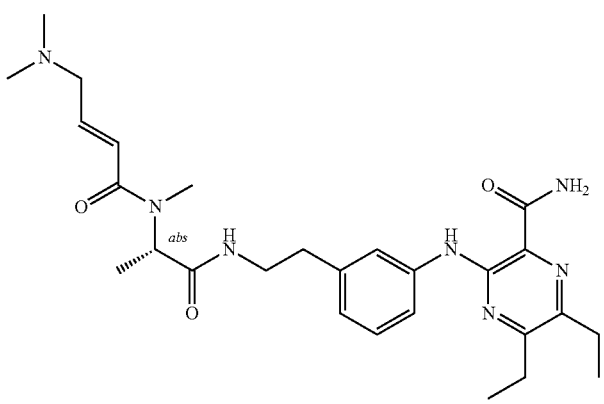 [SMILES: CCc1nc(Nc2cccc(CCNC(=O)[C@H](C)N(C)C(=O)/C=C/CN(C)C)c2)c(C(N)=O)nc1CC] |
| 244 | 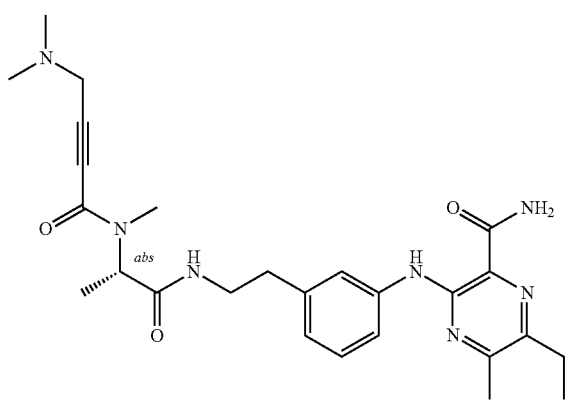 [SMILES: CCc1nc(C(N)=O)c(Nc2cccc(CCNC(=O)[C@H](C)N(C)C(=O)C#CCN(C)C)c2)nc1C] |
| 245 | 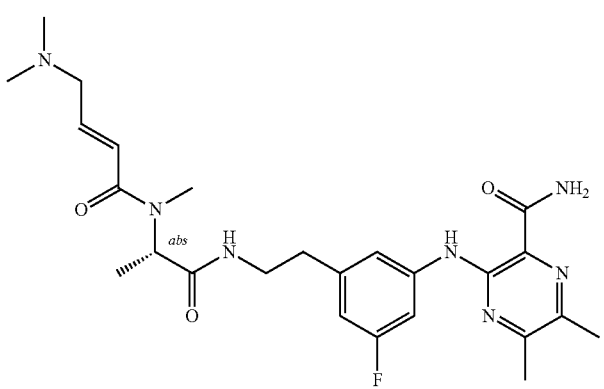 |

| Compd ID | Structure |
|---|---|
| 246 | 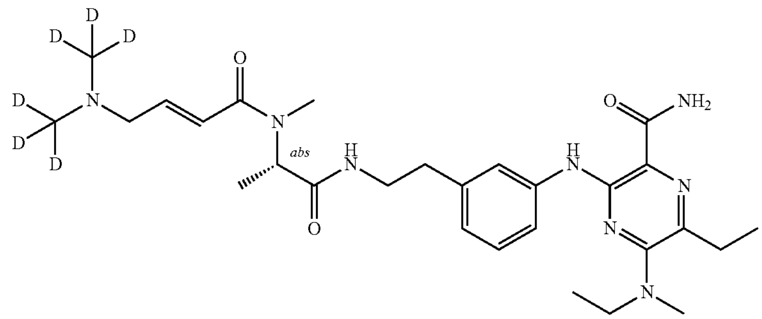 [SMILES: [2H]C([2H])([2H])N(C/C=C/C(=O)N(C)[C@@H](C)C(=O)NCCc1cccc(Nc2nc(N(C)CC)c(CC)nc2C(N)=O)c1)C([2H])([2H])[2H]] |
| 247 | 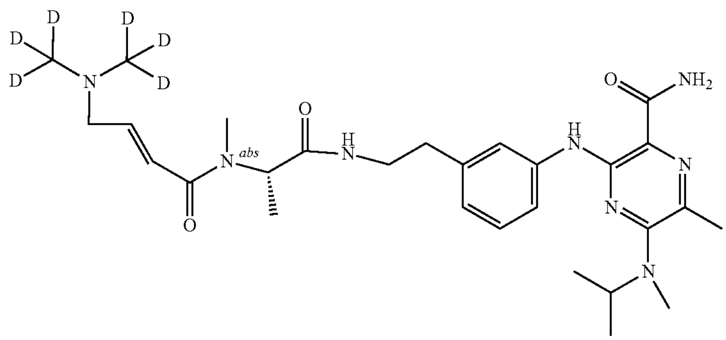 [SMILES: [2H]C([2H])([2H])N(C/C=C/C(=O)N(C)[C@@H](C)C(=O)NCCc1cccc(Nc2nc(N(C)C(C)C)c(C)nc2C(N)=O)c1)C([2H])([2H])[2H]] |
| 248 | 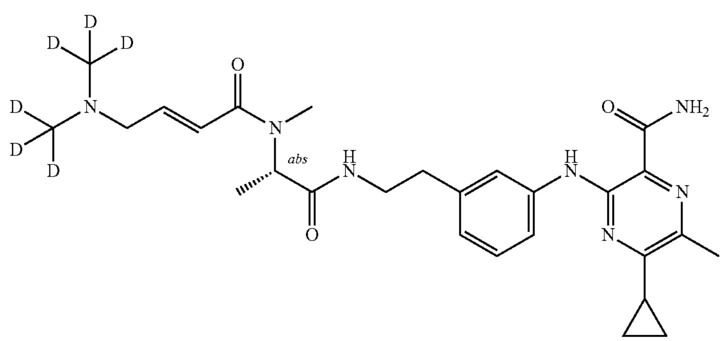 [SMILES: [2H]C([2H])([2H])N(C/C=C/C(=O)N(C)[C@@H](C)C(=O)NCCc1cccc(Nc2nc(C3CC3)c(C)nc2C(N)=O)c1)C([2H])([2H])[2H]] |
| 249 | 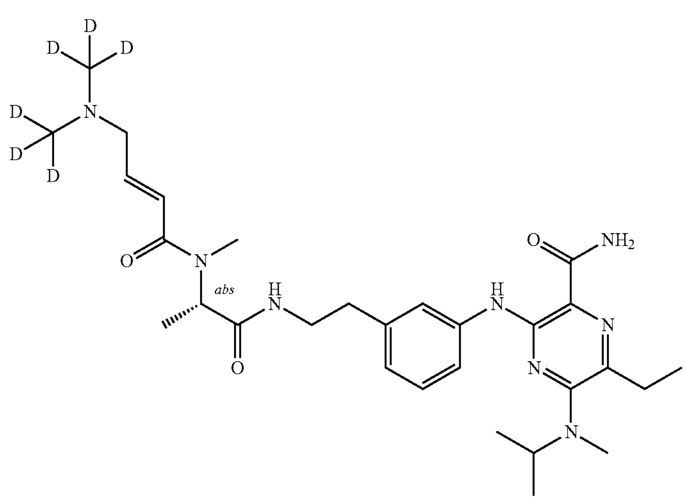 [SMILES: [2H]C([2H])([2H])N(C/C=C/C(=O)N(C)[C@@H](C)C(=O)NCCc1cccc(Nc2nc(N(C)C(C)C)c(CC)nc2C(N)=O)c1)C([2H])([2H])[2H]] |

-continued
| Compd ID | Structure |
|---|---|
| 250 | 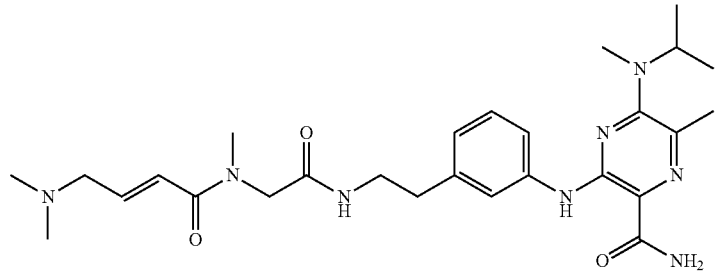 |
| 251 | 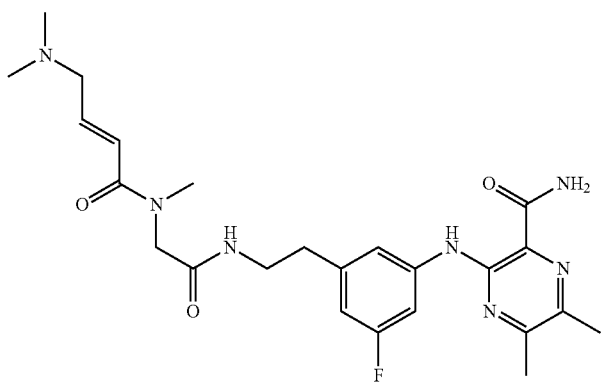 |
| 252 | 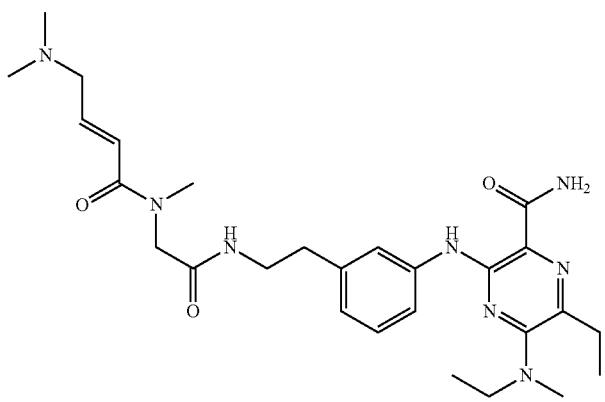 [SMILES: CCc1nc(C(N)=O)c(Nc2cccc(CCNC(=O)CN(C)C(=O)/C=C/CN(C)C)c2)nc1N(C)CC] |
| 253 | 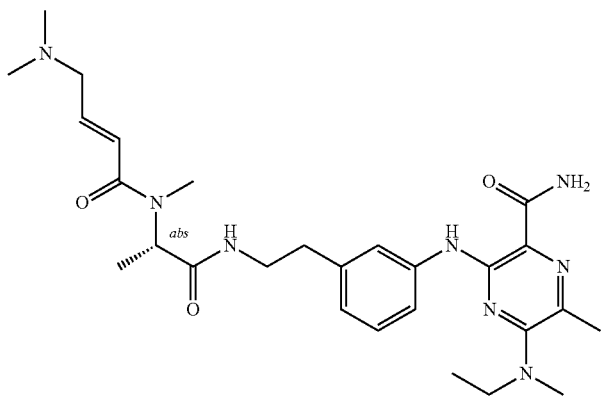 |

| Compd ID | Structure |
|---|---|
| 254 | 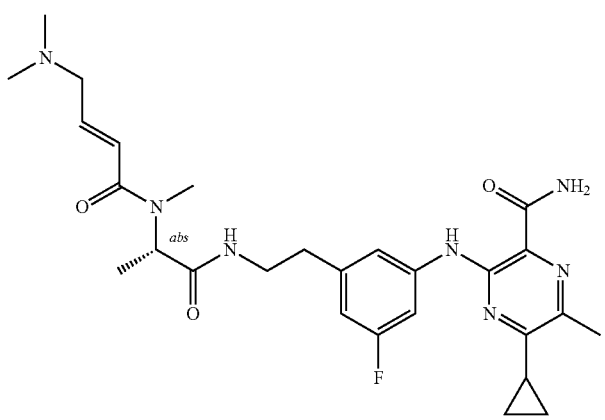 |
| 255 | 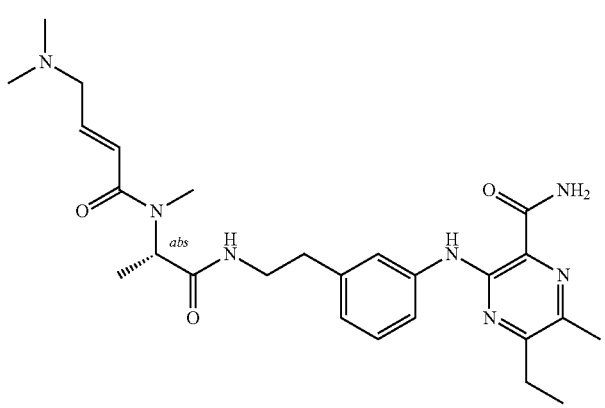 |
| 301 | 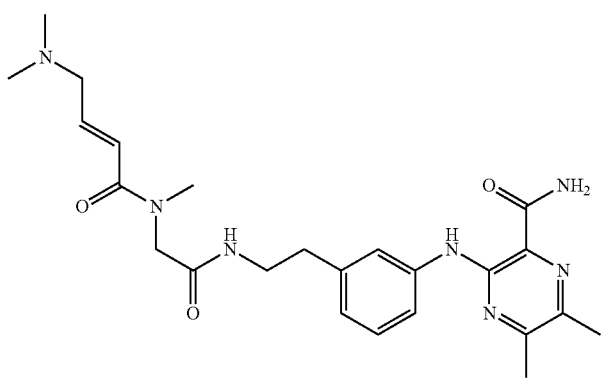 |

| Compd ID | Structure |
|---|---|
| 302 | 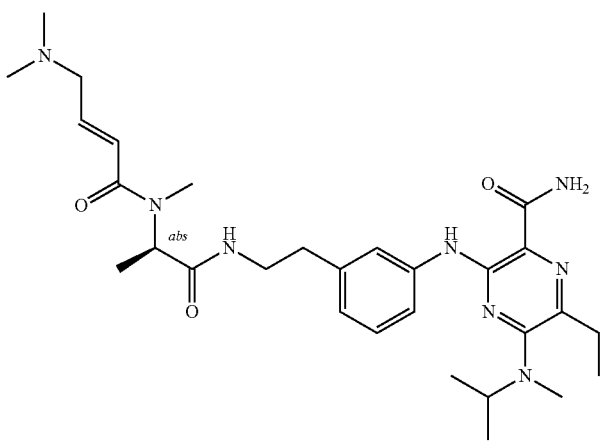 [SMILES: CCc1nc(C(N)=O)c(Nc2cccc(CCNC(=O)[C@@H](C)N(C)C(=O)/C=C/CN(C)C)c2)nc1N(C)C(C)C] |
| 303 | 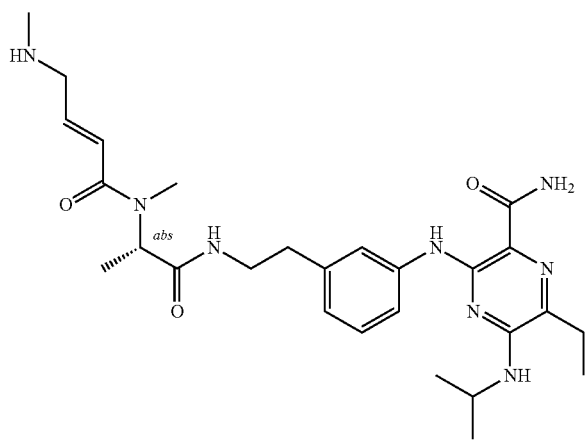 [SMILES: CCc1nc(C(N)=O)c(Nc2cccc(CCNC(=O)[C@H](C)N(C)C(=O)/C=C/CNC)c2)nc1NC(C)C] |
| 305 | 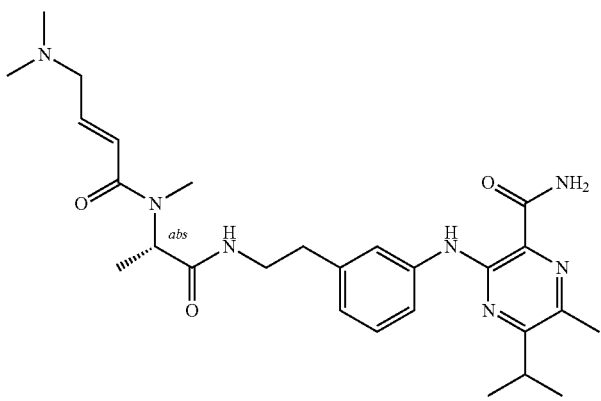 |

| Compd ID | Structure |
|---|---|
| 307 | 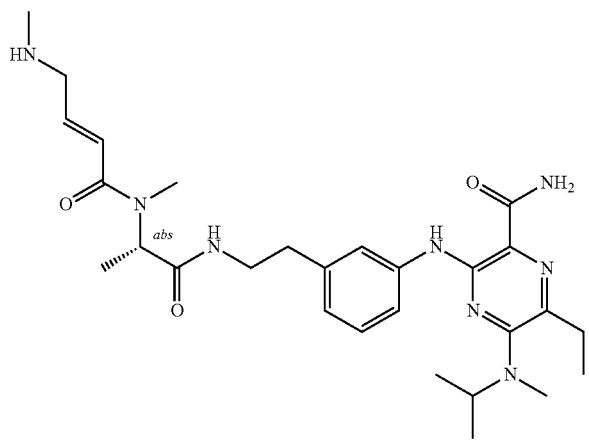 [SMILES: CCc1nc(C(N)=O)c(Nc2cccc(CCNC(=O)[C@H](C)N(C)C(=O)/C=C/CNC)c2)nc1N(C)C(C)C] |
| 308 | 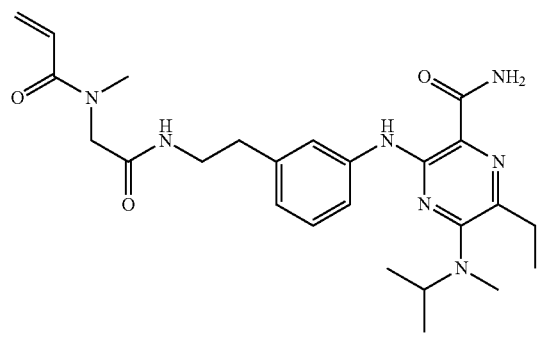 [SMILES: C=CC(=O)N(C)CC(=O)NCCc1cccc(Nc2nc(N(C)C(C)C)c(CC)nc2C(N)=O)c1] |
| 309 | 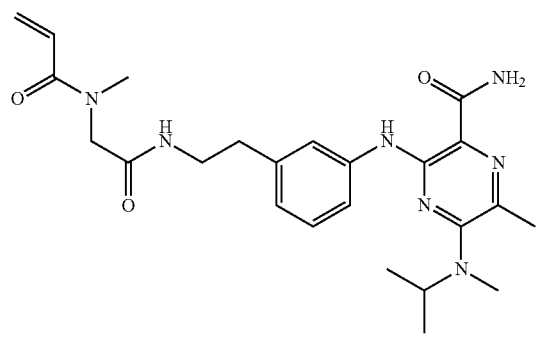 [SMILES: C=CC(=O)N(C)CC(=O)NCCc1cccc(Nc2nc(N(C)C(C)C)c(C)nc2C(N)=O)c1] |
| 311 | 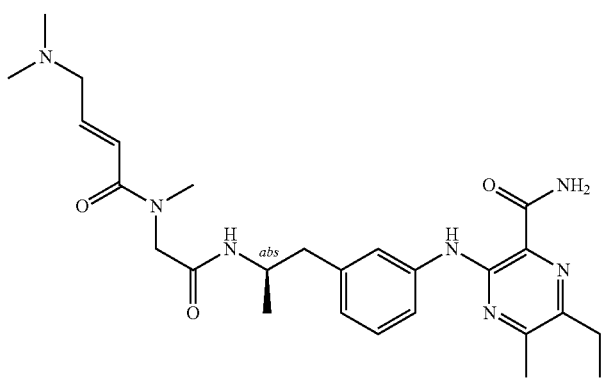 [SMILES: CCc1nc(C(N)=O)c(Nc2cccc(C[C@@H](C)NC(=O)CN(C)C(=O)/C=C/CN(C)C)c2)nc1C] |

| Compd ID | Structure |
|---|---|
| 312 | 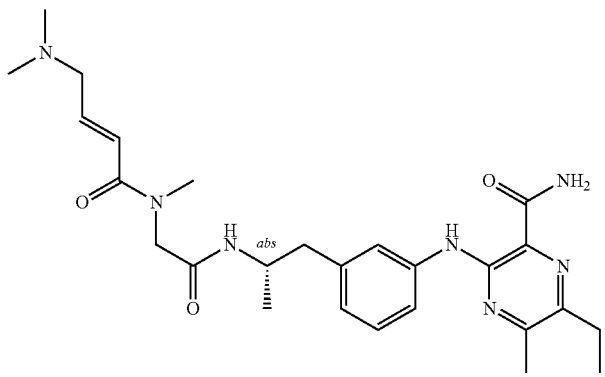 [SMILES: CCc1nc(C(N)=O)c(Nc2cccc(C[C@H](C)NC(=O)CN(C)C(=O)/C=C/CN(C)C)c2)nc1C] |
| 314 | 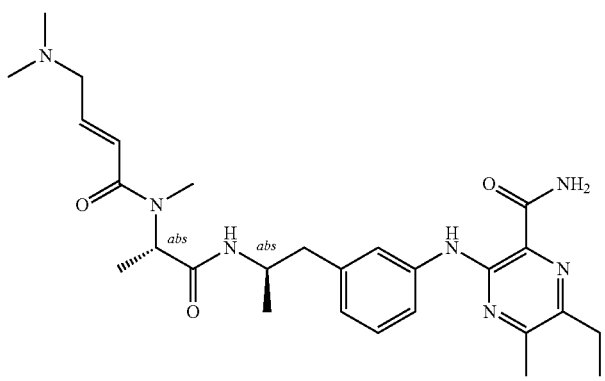 [SMILES: CCc1nc(C(N)=O)c(Nc2cccc(C[C@@H](C)NC(=O)[C@H](C)N(C)C(=O)/C=C/CN(C)C)c2)nc1C] |
| 315 | 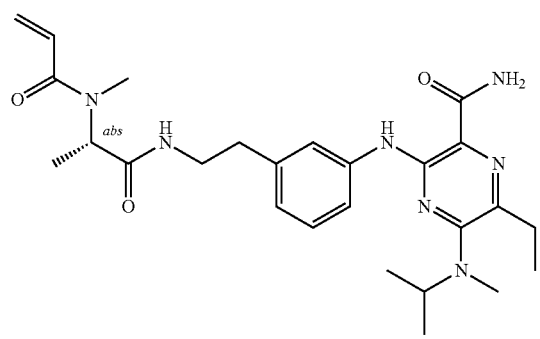 [SMILES: C=CC(=O)N(C)[C@@H](C)C(=O)NCCc1cccc(Nc2nc(N(C)C(C)C)c(CC)nc2C(N)=O)c1] |
| 316 | 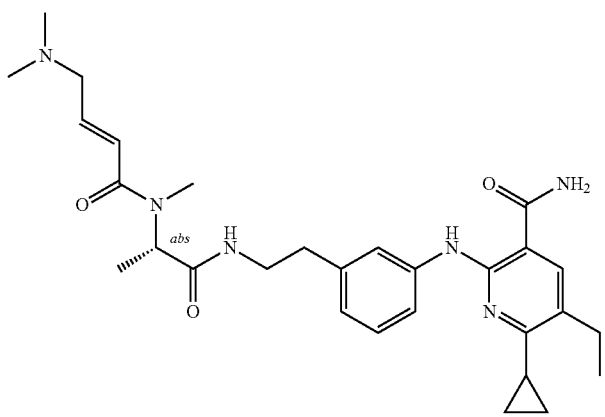 [SMILES: CCc1cc(C(N)=O)c(Nc2cccc(CCNC(=O)[C@H](C)N(C)C(=O)/C=C/CN(C)C)c2)nc1C1CC1] |

| Compd ID | Structure |
|---|---|
| 317 | 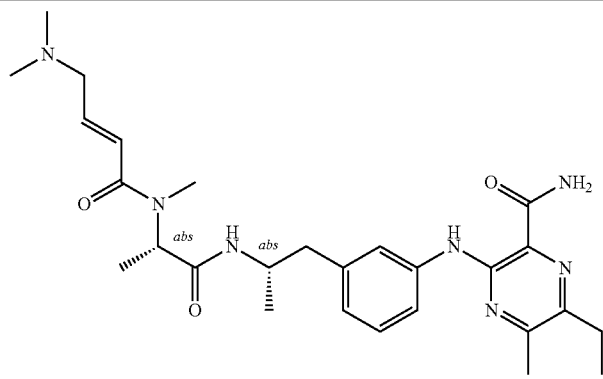 [SMILES: CCc1nc(C(N)=O)c(Nc2cccc(C[C@H](C)NC(=O)[C@H](C)N(C)C(=O)/C=C/CN(C)C)c2)nc1C] |
| 318 | 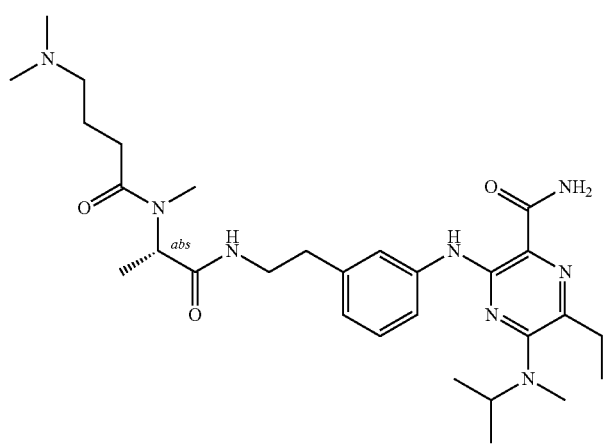 [SMILES: CCc1nc(C(N)=O)c(Nc2cccc(CCNC(=O)[C@H](C)N(C)C(=O)CCCN(C)C)c2)nc1N(C)C(C)C] |
| 319 | 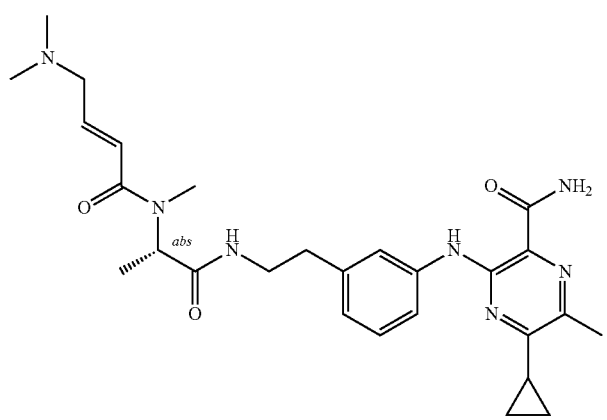 |
| 321 | 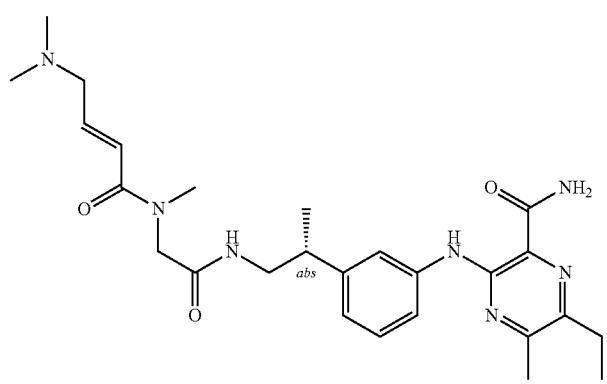 [SMILES: CCc1nc(C(N)=O)c(Nc2cccc([C@@H](C)CNC(=O)CN(C)C(=O)/C=C/CN(C)C)c2)nc1C] |

| Compd ID | Structure |
|---|---|
| 322 | 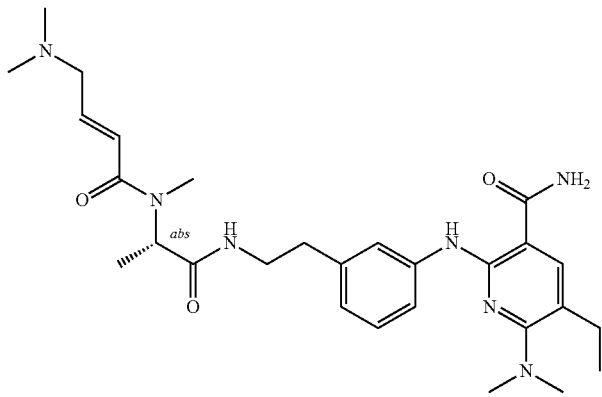 [SMILES: CCc1cc(C(N)=O)c(Nc2cccc(CCNC(=O)[C@H](C)N(C)C(=O)/C=C/CN(C)C)c2)nc1N(C)C] |
| 324 | 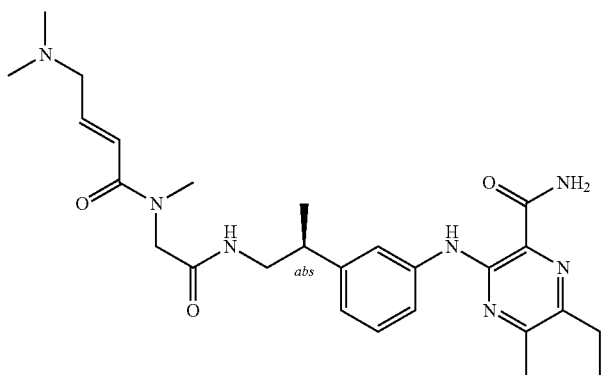 [SMILES: CCc1nc(C(N)=O)c(Nc2cccc([C@H](C)CNC(=O)CN(C)C(=O)/C=C/CN(C)C)c2)nc1C] |
| 325 | 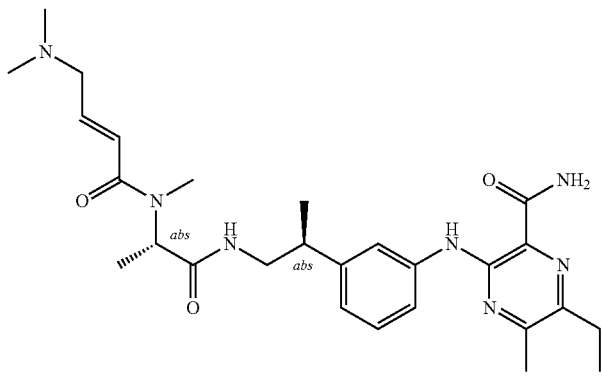 [SMILES: CCc1nc(C(N)=O)c(Nc2cccc([C@H](C)CNC(=O)[C@H](C)N(C)C(=O)/C=C/CN(C)C)c2)nc1C] |
| 326 | 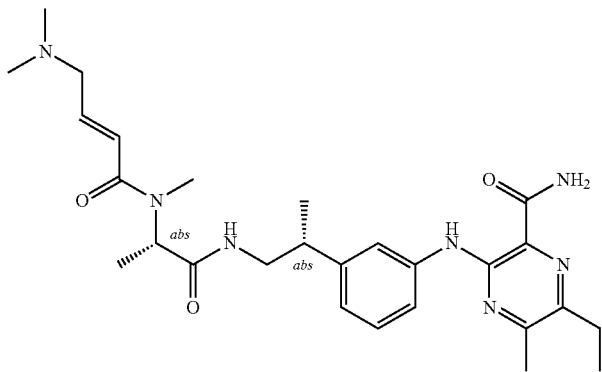 [SMILES: CCc1nc(C(N)=O)c(Nc2cccc([C@@H](C)CNC(=O)[C@H](C)N(C)C(=O)/C=C/CN(C)C)c2)nc1C] |

| Compd ID | Structure |
|---|---|
| 327 | 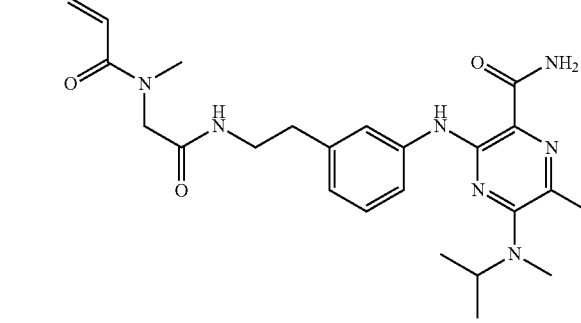 |
| 328 | 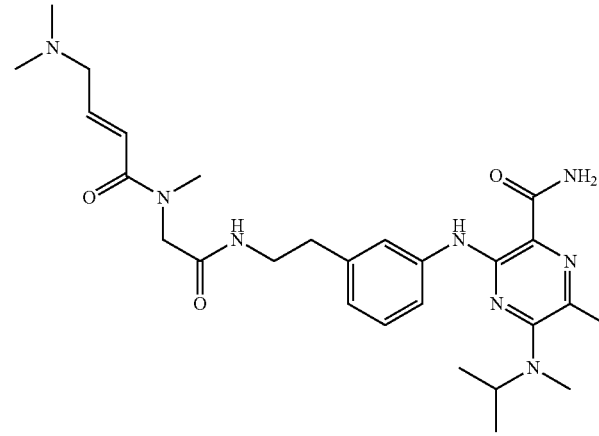 |
| 501 | 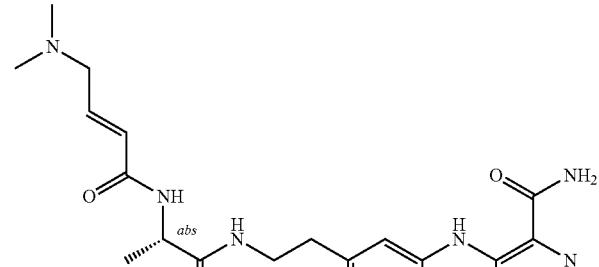 |

| Compd ID | Structure |
|---|---|
| 502 | 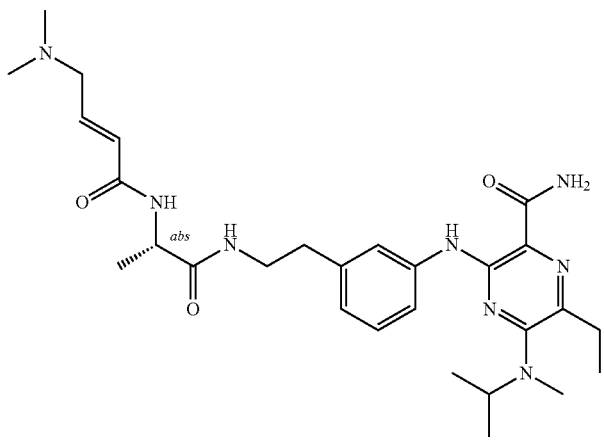 [SMILES: CCc1nc(C(N)=O)c(Nc2cccc(CCNC(=O)[C@H](C)NC(=O)/C=C/CN(C)C)c2)nc1N(C)C(C)C] |
| 503 | 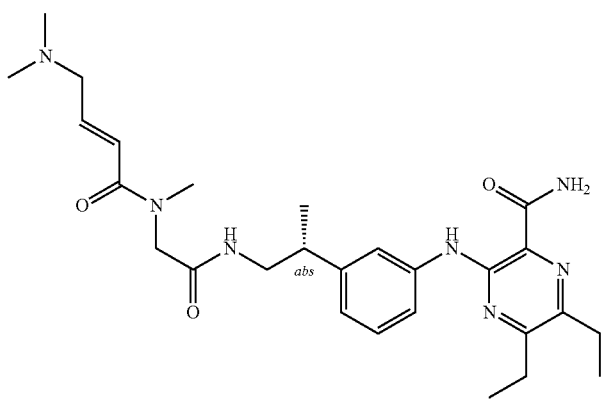 [SMILES: CCc1nc(Nc2cccc([C@@H](C)CNC(=O)CN(C)C(=O)/C=C/CN(C)C)c2)c(C(N)=O)nc1CC] |
| 504 | 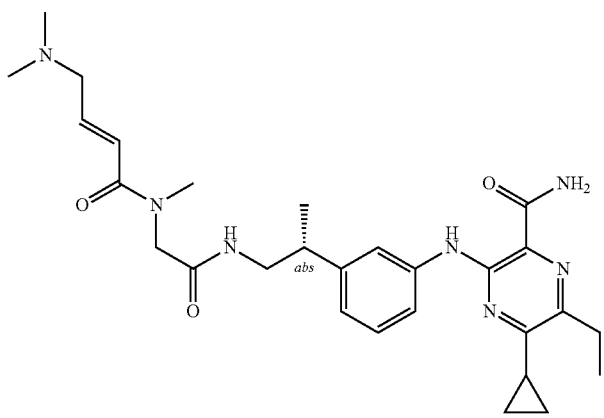 [SMILES: CCc1nc(C(N)=O)c(Nc2cccc([C@@H](C)CNC(=O)CN(C)C(=O)/C=C/CN(C)C)c2)nc1C1CC1] |

| Compd ID | Structure |
|---|---|
| 505 | 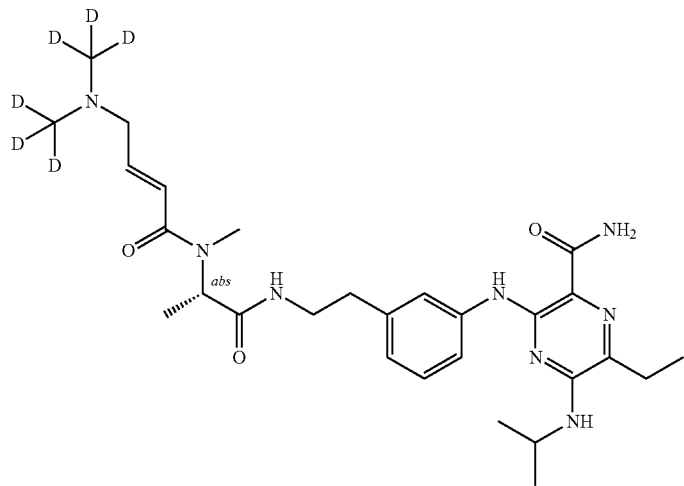 [SMILES: [2H]C([2H])([2H])N(C/C=C/C(=O)N(C)[C@@H](C)C(=O)NCCc1cccc(Nc2nc(NC(C)C)c(CC)nc2C(N)=O)c1)C([2H])([2H])[2H]] |
| 506 | 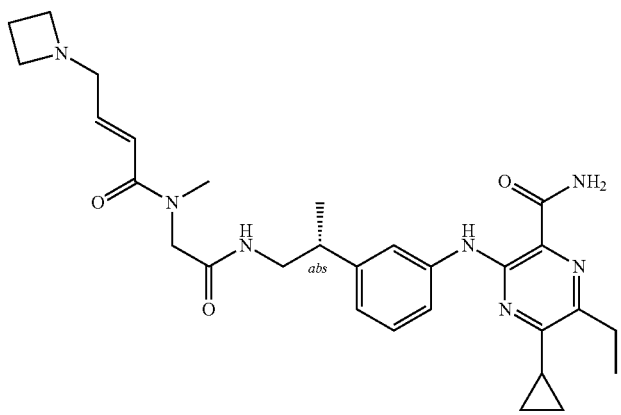 [SMILES: CCc1nc(C(N)=O)c(Nc2cccc([C@@H](C)CNC(=O)CN(C)C(=O)/C=C/CN3CCC3)c2)nc1C1CC1] |
| 507 | 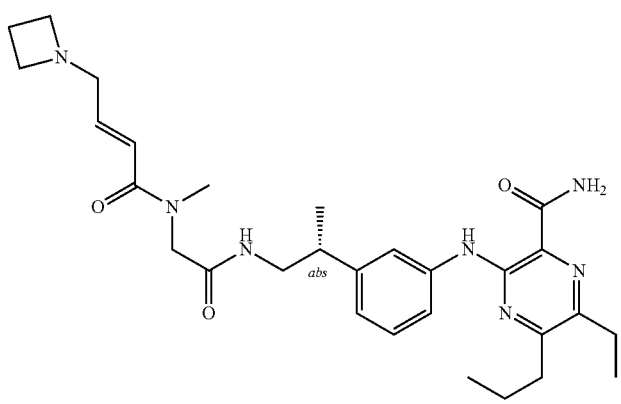 [SMILES: CCCc1nc(Nc2cccc([C@@H](C)CNC(=O)CN(C)C(=O)/C=C/CN3CCC3)c2)c(C(N)=O)nc1CC] |

-continued
| Compd ID | Structure |
|---|---|
| 508 | 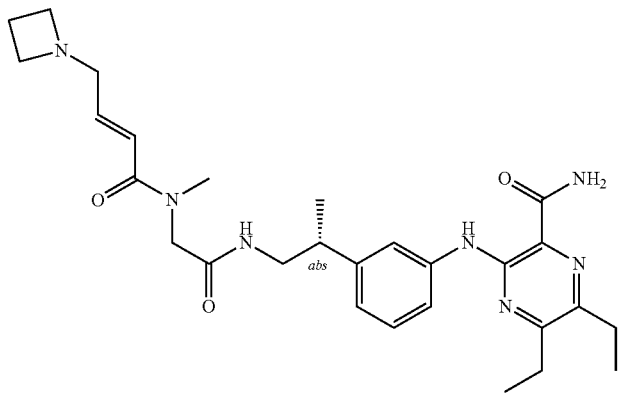 [SMILES: CCc1nc(Nc2cccc([C@@H](C)CNC(=O)CN(C)C(=O)/C=C/CN3CCC3)c2)c(C(N)=O)nc1CC] |
| 509 | 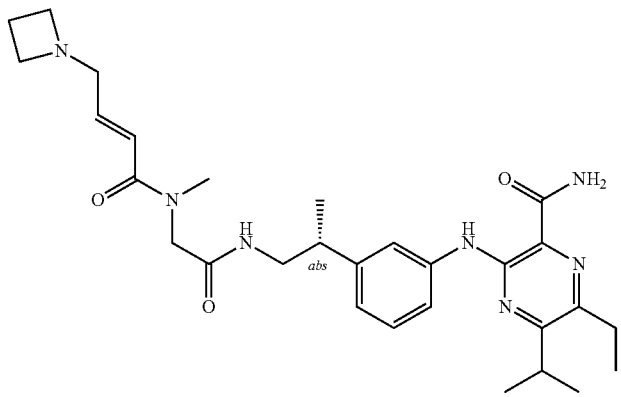 [SMILES: CCc1nc(C(N)=O)c(Nc2cccc([C@@H](C)CNC(=O)CN(C)C(=O)/C=C/CN3CCC3)c2)nc1C(C)C] |
| 510 | 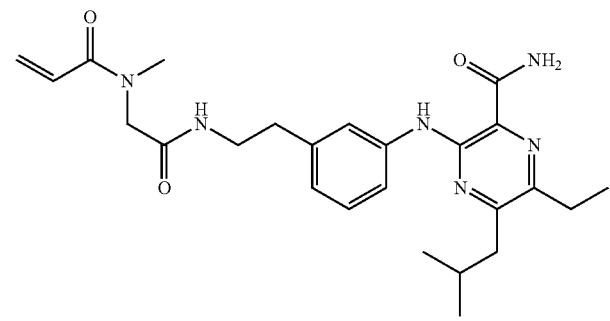 [SMILES: C=CC(=O)N(C)CC(=O)NCCc1cccc(Nc2nc(CC(C)C)c(CC)nc2C(N)=O)c1] |
| 511 | 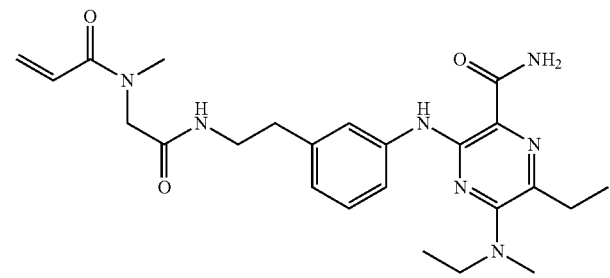 [SMILES: C=CC(=O)N(C)CC(=O)NCCc1cccc(Nc2nc(N(C)CC)c(CC)nc2C(N)=O)c1] |

-continued

| Compd ID | Structure |
|---|---|
| 512 | 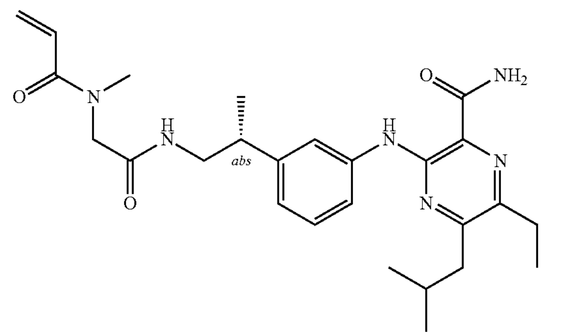 [SMILES: C=CC(=O)N(C)CC(=O)NC[C@H](C)c1cccc(Nc2nc(CC(C)C)c(CC)nc2C(N)=O)c1] |
| 513 | 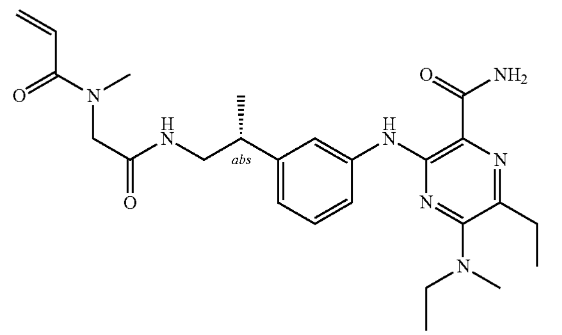 [SMILES: C=CC(=O)N(C)CC(=O)NC[C@H](C)c1cccc(Nc2nc(N(C)CC)c(CC)nc2C(N)=O)c1] |
| 515 | 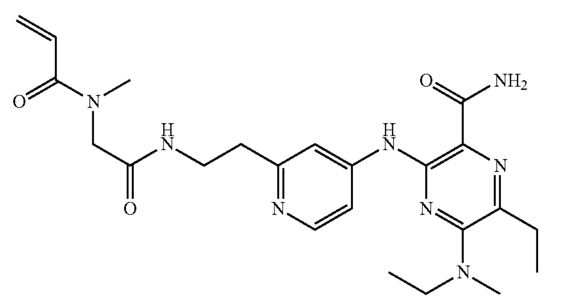 [SMILES: C=CC(=O)N(C)CC(=O)NCCc1cc(Nc2nc(N(C)CC)c(CC)nc2C(N)=O)ccn1] |
| 516 | 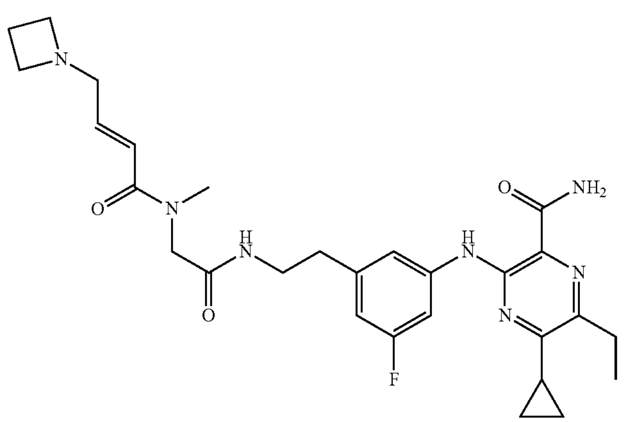 [SMILES: CCc1nc(C(N)=O)c(Nc2cc(F)cc(CCNC(=O)CN(C)C(=O)/C=C/CN3CCC3)c2)nc1C1CC1] |

| Compd ID | Structure |
|---|---|
| 516A | 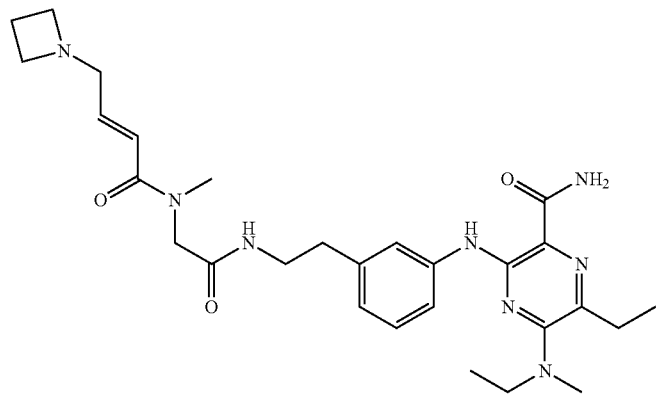 [SMILES: CCc1nc(C(N)=O)c(Nc2cccc(CCNC(=O)CN(C)C(=O)/C=C/CN3CCC3)c2)nc1N(C)CC] |
| 517 | 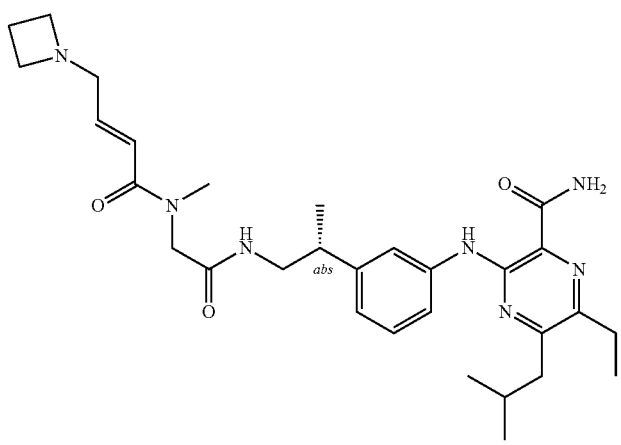 [SMILES: CCc1nc(C(N)=O)c(Nc2cccc([C@@H](C)CNC(=O)CN(C)C(=O)/C=C/CN3CCC3)c2)nc1CC(C)C] |
| 518 | 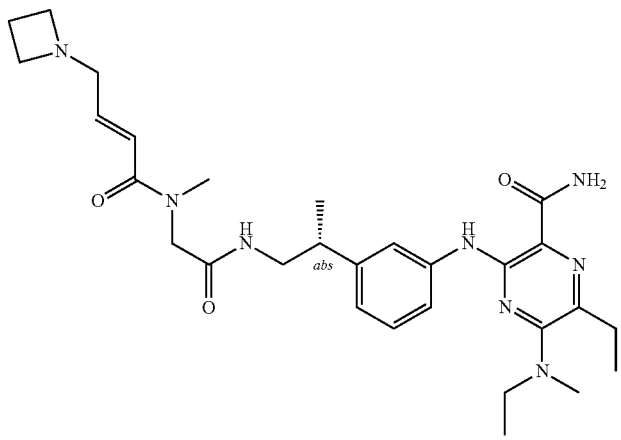 [SMILES: CCc1nc(C(N)=O)c(Nc2cccc([C@@H](C)CNC(=O)CN(C)C(=O)/C=C/CN3CCC3)c2)nc1N(C)CC] |

| Compd ID | Structure |
|---|---|
| 519 | 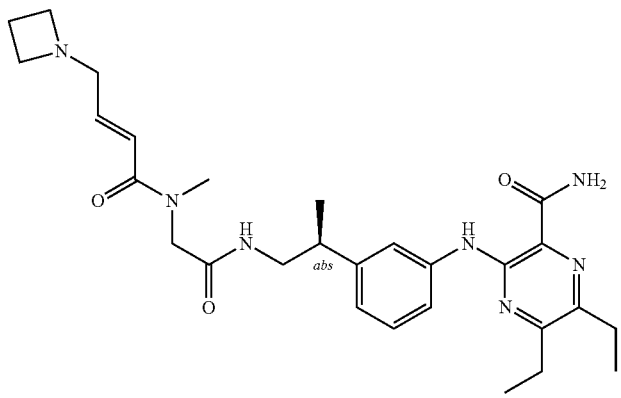 [SMILES: CCc1nc(Nc2cccc([C@H](C)CNC(=O)CN(C)C(=O)/C=C/CN3CCC3)c2)c(C(N)=O)nc1CC] |
| 520 | 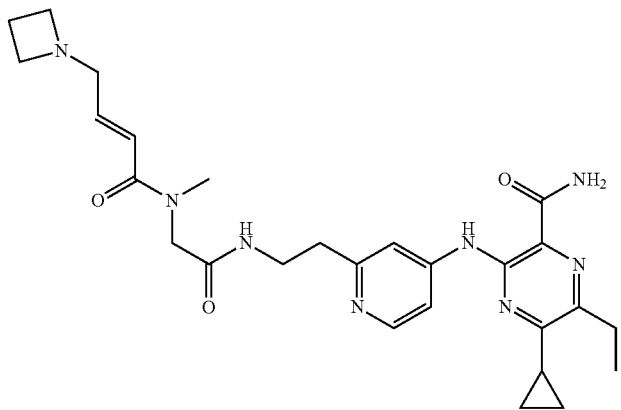 [SMILES: CCc1nc(C(N)=O)c(Nc2ccnc(CCNC(=O)CN(C)C(=O)/C=C/CN3CCC3)c2)nc1C1CC1] |
| 601 | 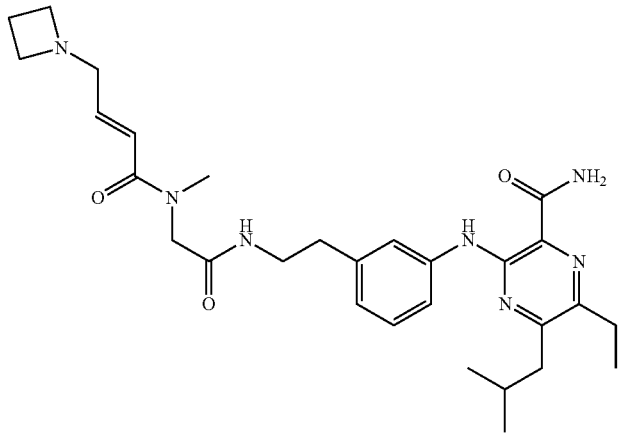 |

-continued
| Compd ID | Structure |
|---|---|
| 602 | 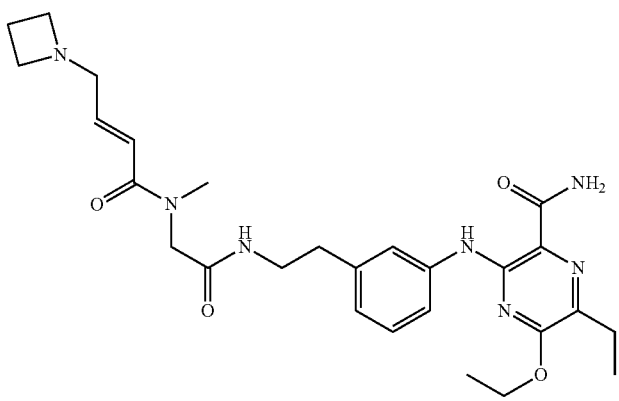 [SMILES: CCOc1nc(Nc2cccc(CCNC(=O)CN(C)C(=O)/C=C/CN3CCC3)c2)c(C(N)=O)nc1CC] |
| 603 | 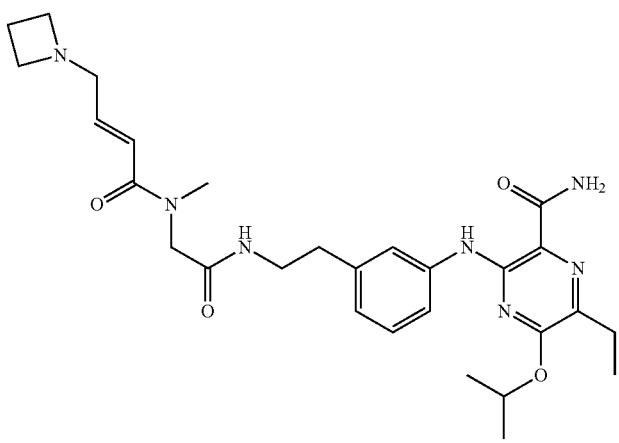 [SMILES: CCc1nc(C(N)=O)c(Nc2cccc(CCNC(=O)CN(C)C(=O)/C=C/CN3CCC3)c2)nc1OC(C)C] |
| 607 | 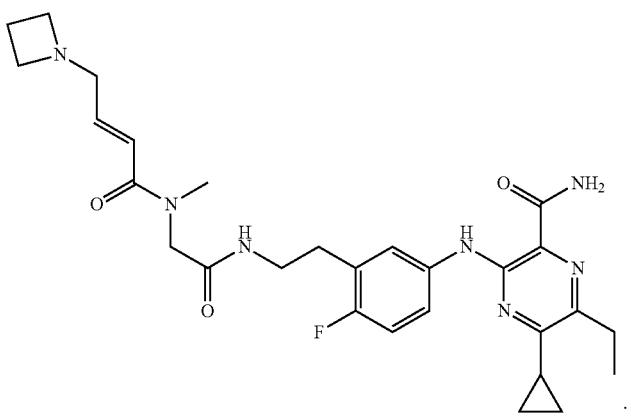 [SMILES: CCc1nc(C(N)=O)c(Nc2ccc(F)c(CCNC(=O)CN(C)C(=O)/C=C/CN3CCC3)c2)nc1C1CC1] |

19. The compound according to claim 1, wherein the compound is selected from
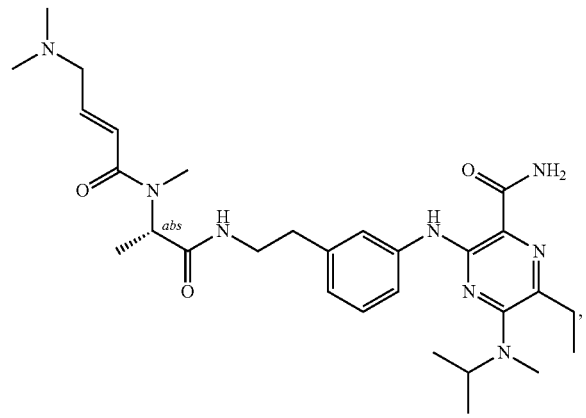 [SMILES: CCc1nc(C(N)=O)c(Nc2cccc(CCNC(=O)[C@H](C)N(C)C(=O)/C=C/CN(C)C)c2)nc1N(C)C(C)C]
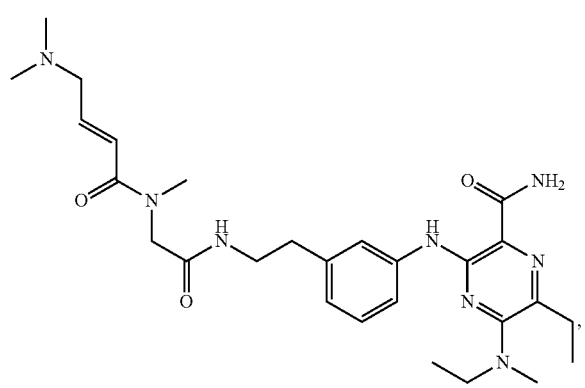
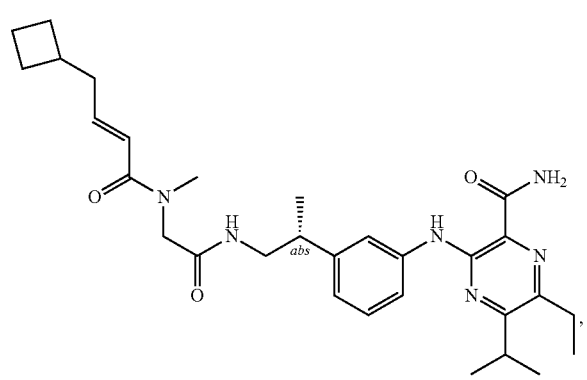
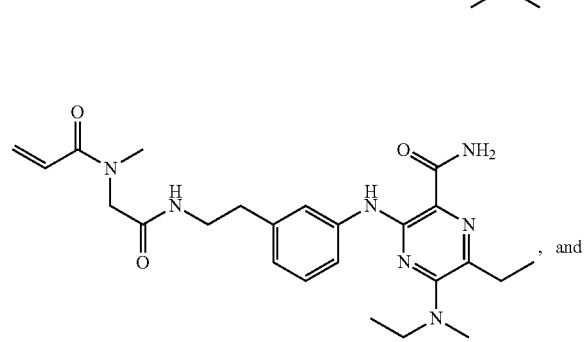
, and
-continued
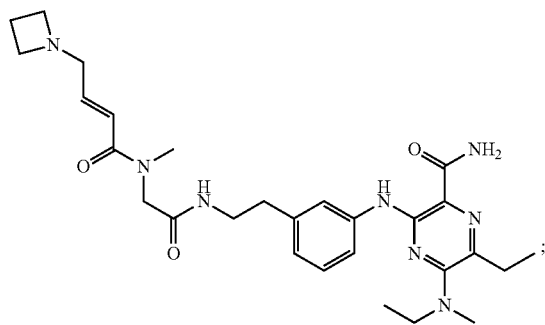
or a pharmaceutically acceptable salt or stereoisomer thereof.
20. The compound according to claim 1, wherein the compound is selected from
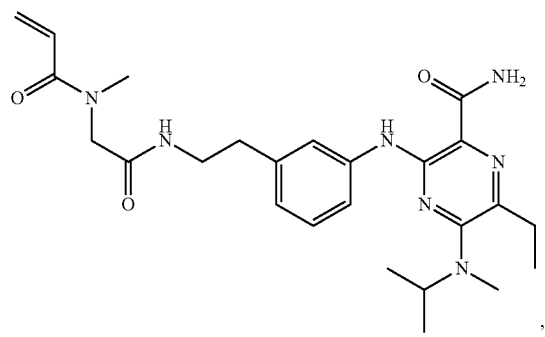
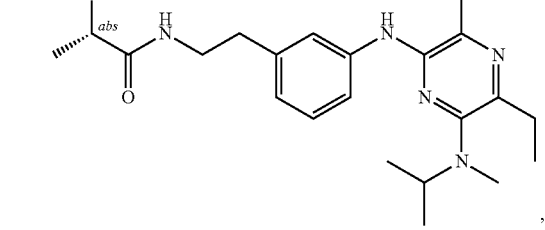
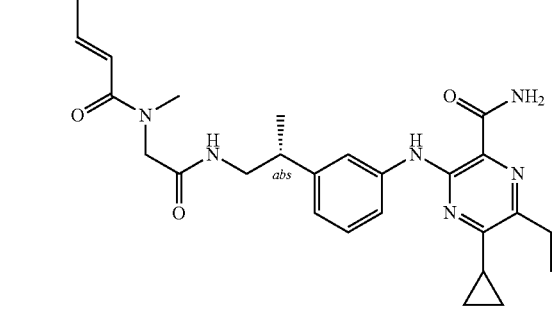

-continued
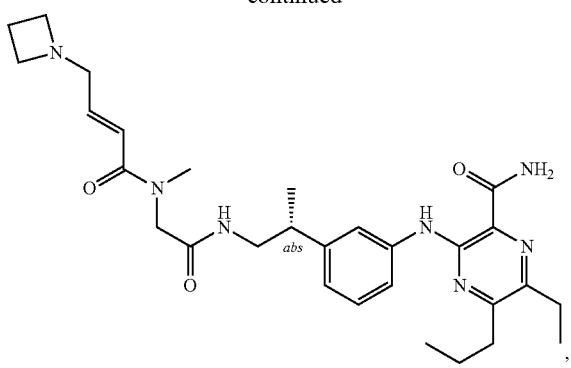
,
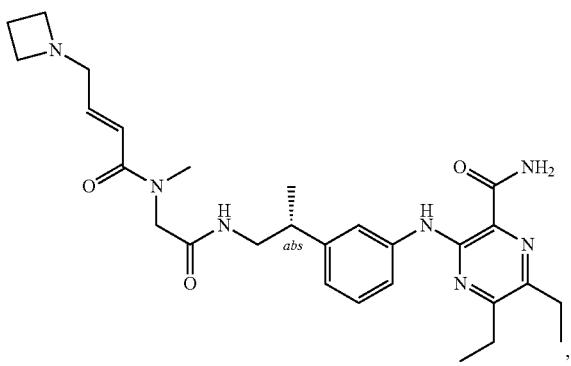
,
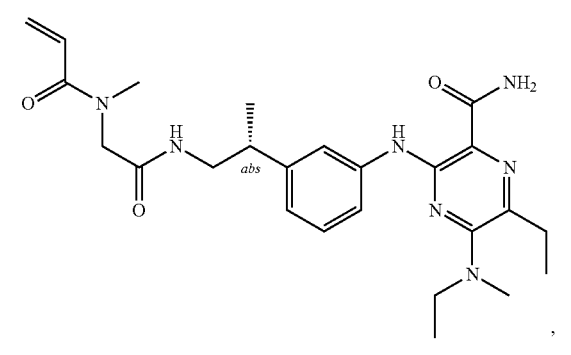
,
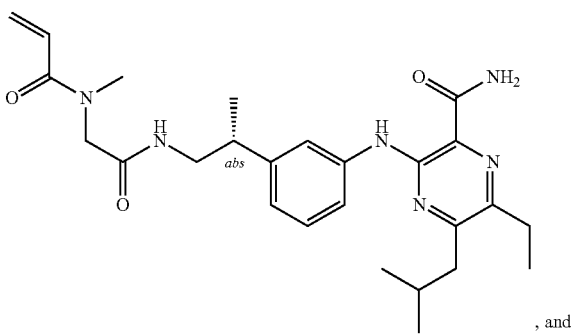
, and
-continued
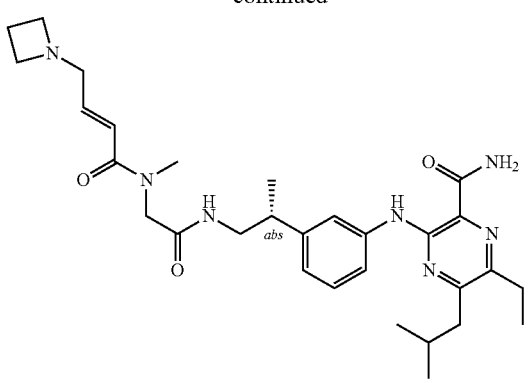
;
or a pharmaceutically acceptable salt or stereoisomer thereof.
21. The compound according to claim 1, wherein the compound is selected from
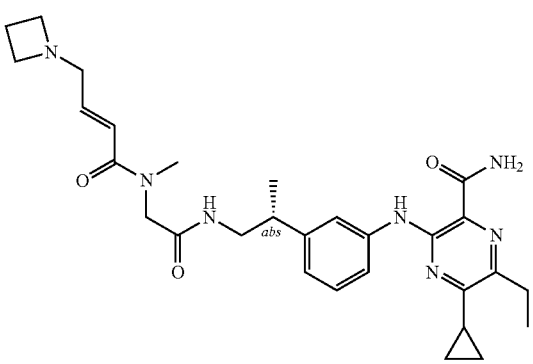
and
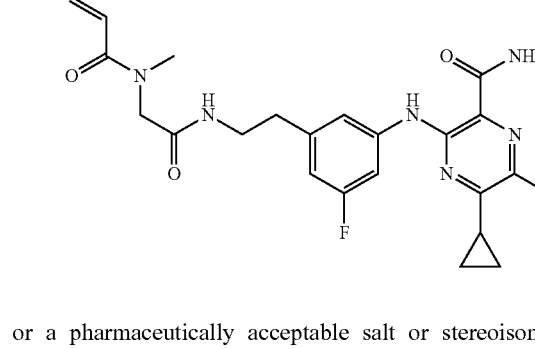
;
or a pharmaceutically acceptable salt or stereoisomer thereof.

22. The compound according to claim 1, wherein the compound is Compound ID 204

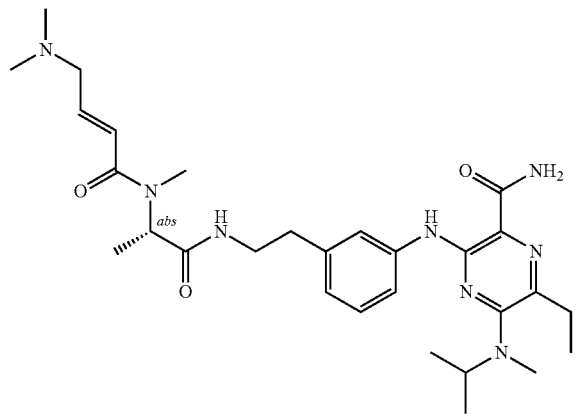

or a pharmaceutically acceptable salt or stereoisomer thereof.

23. The compound according to claim 1, wherein the compound is Compound ID 516A

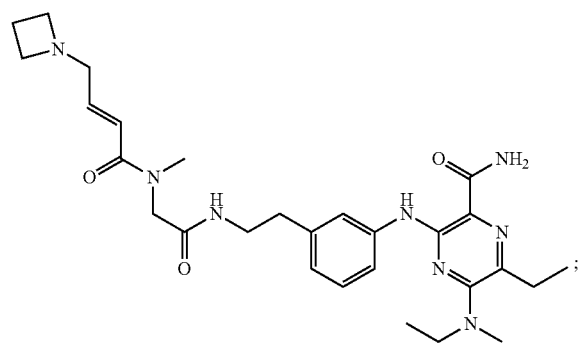 [SMILES: CCc1nc(C(N)=O)c(Nc2cccc(CCNC(=O)CN(C)C(=O)/C=C/CN3CCC3)c2)nc1N(C)CC]

or a pharmaceutically acceptable salt or stereoisomer thereof.

24. The compound according to claim 1, wherein the compound is Compound ID 252 or a pharmaceutically acceptable salt or stereoisomer thereof.

25. The compound according to claim 1, wherein the compound is Compound ID 506

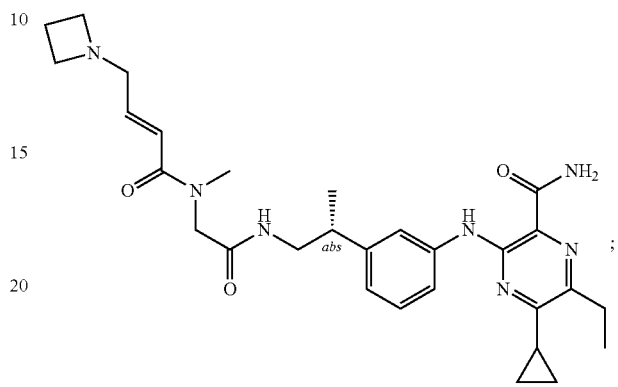

or a pharmaceutically acceptable salt or stereoisomer thereof.

26. The compound according to claim 1, wherein the compound is Compound ID 511

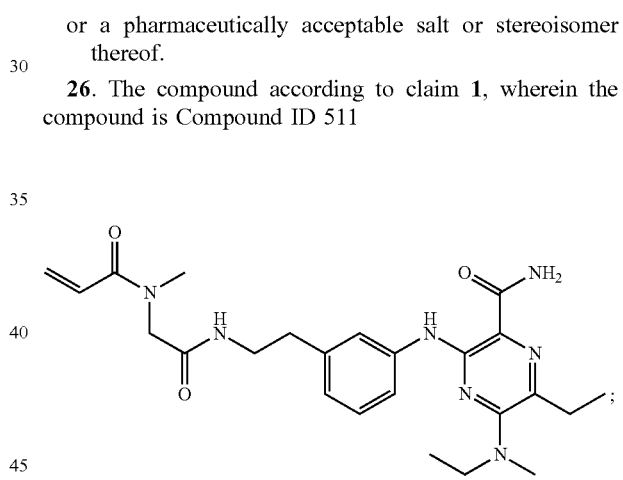

or a pharmaceutically acceptable salt or stereoisomer thereof.

27. A pharmaceutical composition comprising a therapeutically effective amount of a compound of claim 1; or a pharmaceutically acceptable salt or stereoisomer thereof; and a pharmaceutically acceptable excipient.

28. The pharmaceutical composition of claim 27 that is formulated for a route of administration selected from oral administration, parenteral administration, buccal administration, nasal administration, topical administration, or rectal administration.

* * * * *